US009812653B2

(12) United States Patent
Jung et al.

(10) Patent No.: US 9,812,653 B2
(45) Date of Patent: Nov. 7, 2017

(54) CARBAZOLE COMPOUND AND ORGANIC LIGHT-EMITTING DEVICE INCLUDING THE SAME

(71) Applicants: Samsung Electronics Co., Ltd., Suwon-si, Gyeonggi-do (KR); SAMSUNG SDI CO., LTD., Yongin-si, Gyeonggi-do (KR)

(72) Inventors: Yongsik Jung, Seoul (KR); Jhunmo Son, Yongin-si (KR); Seungjae Lee, Uiwang-si (KR); Youngkwon Kim, Uiwang-si (KR); Hyungsun Kim, Uiwang-si (KR); Yeonsook Chung, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 247 days.

(21) Appl. No.: 14/550,518

(22) Filed: Nov. 21, 2014

(65) Prior Publication Data

US 2015/0171342 A1 Jun. 18, 2015

(30) Foreign Application Priority Data

Nov. 28, 2013 (KR) ........................ 10-2013-0146413

(51) Int. Cl.
*H01L 51/50* (2006.01)
*H01L 51/00* (2006.01)
(Continued)

(52) U.S. Cl.
CPC ........ *H01L 51/0071* (2013.01); *C07D 401/14* (2013.01); *C07D 403/10* (2013.01);
(Continued)

(58) Field of Classification Search
None
See application file for complete search history.

(56) References Cited

U.S. PATENT DOCUMENTS 7,585,573 B2 9/2009 Lee et al.
7,846,763 B2 12/2010 Bold et al.
(Continued)

FOREIGN PATENT DOCUMENTS

JP 2010-135467 A 6/2010
JP 5338184 B2 8/2013
(Continued)

OTHER PUBLICATIONS

Extended European Search Report dated Apr. 8, 2015 issued by the European Patent Office for Application No. 14195105.3.

*Primary Examiner* — Gregory Clark
(74) *Attorney, Agent, or Firm* — Cantor Colburn LLP

(57) ABSTRACT

A carbazole compound represented by Formula 1:

Formula 1

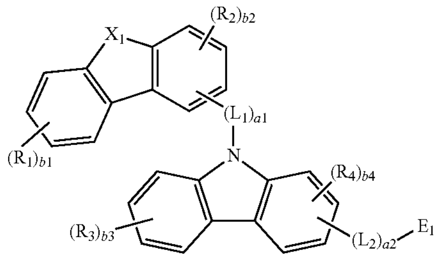

wherein in Formula 1, groups and variables are the same as defined in the specification.

23 Claims, 3 Drawing Sheets

(51) Int. Cl.

| | |
|---|---|
| ***C07D 405/14*** | (2006.01) |
| ***C07D 403/10*** | (2006.01) |
| ***C07D 403/14*** | (2006.01) |
| ***C07D 409/14*** | (2006.01) |
| ***C09K 11/06*** | (2006.01) |
| ***C07F 5/02*** | (2006.01) |
| ***C07F 7/08*** | (2006.01) |
| ***C07D 401/14*** | (2006.01) |

(52) U.S. Cl.

CPC ......... *C07D 403/14* (2013.01); *C07D 405/14* (2013.01); *C07D 409/14* (2013.01); *C07F 5/025* (2013.01); *C07F 7/0812* (2013.01); *C09K 11/06* (2013.01); *C09K 2211/1416* (2013.01); *C09K 2211/1466* (2013.01); *C09K 2211/1475* (2013.01); *C09K 2211/1483* (2013.01); *C09K 2211/1491* (2013.01); *H01L 51/5016* (2013.01)

(56) References Cited

U.S. PATENT DOCUMENTS

| | | | | |
|---|---|---|---|---|
| 7,915,414 | B2 | 3/2011 | Chi et al. | |
| 8,367,224 | B2 | 2/2013 | Katakura et al. | |
| 2007/0190359 | A1 | 8/2007 | Knowles et al. | |
| 2009/0284138 | A1 | 11/2009 | Yasukawa et al. | |
| 2010/0207105 | A1* | 8/2010 | Katakura ............. | C07D 209/86 257/40 |
| 2013/0270540 | A1* | 10/2013 | Numata ................. | C09K 11/06 257/40 |

FOREIGN PATENT DOCUMENTS

| | | | |
|---|---|---|---|
| JP | 2013-206649 | A | 10/2013 |
| KR | 10-2013-0051807 | A | 5/2013 |
| KR | 10-2012-0144602 | A | 6/2014 |
| WO | 0202714 | A2 | 1/2002 |
| WO | 2005-019373 | A2 | 3/2005 |
| WO | 2005-123873 | A1 | 12/2005 |
| WO | 2010-079051 | A1 | 7/2010 |
| WO | 2011004639 | A1 | 1/2011 |
| WO | 2011049325 | A2 | 4/2011 |
| WO | 2011-081286 | A2 | 7/2011 |
| WO | 2012-090967 | A1 | 7/2012 |
| WO | 2012105310 | A1 | 8/2012 |
| WO | 2012141499 | A1 | 10/2012 |
| WO | 2013-0073356 | A1 | 5/2013 |
| WO | 2014054912 | A1 | 4/2014 |

* cited by examiner

CARBAZOLE COMPOUND AND ORGANIC LIGHT-EMITTING DEVICE INCLUDING THE SAME

CROSS-REFERENCE TO RELATED APPLICATIONS

This application claims priority to Korean Patent Application No. 10-2013-0146413, filed on Nov. 28, 2013, and all the benefits accruing therefrom under 35 U.S.C. §119, the content of which is incorporated herein in its entirety by reference.

BACKGROUND

1. Field

One or more embodiments relate to a carbazole compound and an organic light-emitting device including the same.

2. Description of the Related Art

Organic light emitting devices (OLEDs) are self-emission devices that have wide viewing angles, high contrast ratios, and short response times. In addition, OLEDs have excellent brightness, driving voltage, and response speed characteristics, and produce full-color images.

As an example, a typical organic light-emitting device includes an anode, a cathode, and an emission layer that is disposed between the anode and the cathode. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, are recombined in the emission layer to produce excitons. These excitons change from an excited state to a ground state, thereby generating light.

Different types of organic light emitting devices are known. However, there still remains a need in OLEDs having low driving voltage, high efficiency, high brightness, and long lifespan.

SUMMARY

One or more embodiments relate to a novel carbazole compound and an organic light-emitting device including the same.

An aspect provides a carbazole compound represented by Formula 1:

Formula 1

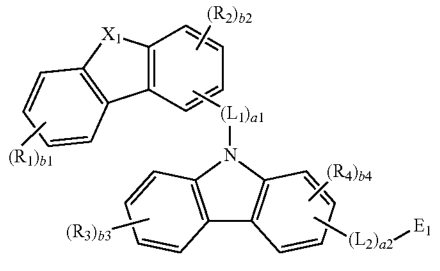

wherein in Formula 1, $X_1$ is selected from N-[$(L_{11})_{a11}$-$(R_{11})_{b11}$], S, O, S(=O), S(=O)$_2$, C($R_{12}$)($R_{13}$), and Si($R_{12}$)($R_{13}$);

$L_1$, $L_2$, and $L_{11}$ are each independently selected from a substituted or unsubstituted $C_1$-$C_{60}$ alkylene group, a substituted or unsubstituted $C_2$-$C_{60}$ alkenylene group, a substituted or unsubstituted $C_2$-$C_{60}$ alkynylene group, a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic hetero-condensed polycyclic group;

a1 and a2 are each independently an integer selected from 1 to 5;

a11 is an integer selected from 0 to 5;

$R_1$ is selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(=O)—O-$Q_1$, —C(=O)-$Q_2$, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; and a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group, —C(=O)—O-$Q_3$, —C(=O)-$Q_4$, a sulfonic acid group or a salt thereof, and a phosphoric acid group or a salt thereof;

$R_2$ to $R_4$ and $R_{11}$ to $R_{13}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(=O)—O-$Q_{11}$, —C(=O)-$Q_{12}$, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, and a substituted or unsubstituted monovalent non-aromatic heterocondensed polycyclic group, —N($Q_{13}$)($Q_{14}$), —Si($Q_{15}$)($Q_{16}$)($Q_{17}$), and —B($Q_{18}$)($Q_{19}$);

b1 and b3 are each independently an integer selected from 1 to 4;

b2, b4, and b11 are each independently an integer selected from 1 to 3;

$E_1$ is an electron transporting-cyclic group containing at least one nitrogen as a ring-forming atom and substituted with at least one $Ar_1$, wherein $Ar_1$ is selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, and a substituted or unsubstituted monovalent non-aromatic heterocondensed polycyclic group; and at least one substituent of the substituted $C_1$-$C_{60}$ alkylene group, the substituted $C_2$-$C_{60}$ alkenylene group, the substituted $C_2$-$C_{60}$ alkynylene group, the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic hetero-condensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, a substituted or unsubstituted $C_7$-$C_{60}$ arylalkyl group, the substituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, the substituted monovalent non-aromatic condensed polycyclic group, and the substituted monovalent non-aromatic heterocondensed polycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, a monovalent non-aromatic heterocondensed polycyclic group, —$N(Q_{21})(Q_{22})$, —$Si(Q_{23})(Q_{24})(Q_{25})$, and —$B(Q_{26})(Q_{27})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic heterocondensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic heterocondensed polycyclic group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, a monovalent non-aromatic heterocondensed polycyclic group, —$N(Q_{31})(Q_{32})$, —$Si(Q_{33})(Q_{34})(Q_{35})$, and —$B(Q_{36})(Q_{37})$; and —$N(Q_{41})(Q_{42})$, —$Si(Q_{43})(Q_{44})(Q_{45})$, and —$B(Q_{46})(Q_{47})$; wherein $Q_1$ to $Q_4$ are each independently selected from a hydrogen, a $C_1$-$C_{60}$ alkyl group, a $C_2$-$C_{60}$ alkenyl group, and a $C_2$-$C_{60}$ alkynyl group; and $Q_{11}$ to $Q_{19}$, $Q_{21}$ to $Q_{27}$, $Q_{31}$ to $Q_{37}$ and $Q_{41}$ to $Q_{47}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic heterocondensed polycyclic group.

Another aspect provides an organic light-emitting device including: a first electrode; a second electrode; and an organic layer disposed between the first electrode and the second electrode, wherein the organic layer includes an emission layer and at least one of the carbazole compounds represented by Formula 1.

The carbazole compound may be included in the emission layer, and the emission layer may further include a dopant, and the carbazole compound included in the emission layer may be a host.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
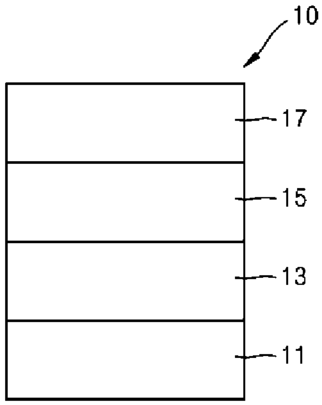
FIG. 1 is a schematic view of an organic light-emitting device according to an embodiment.
Figure 2:
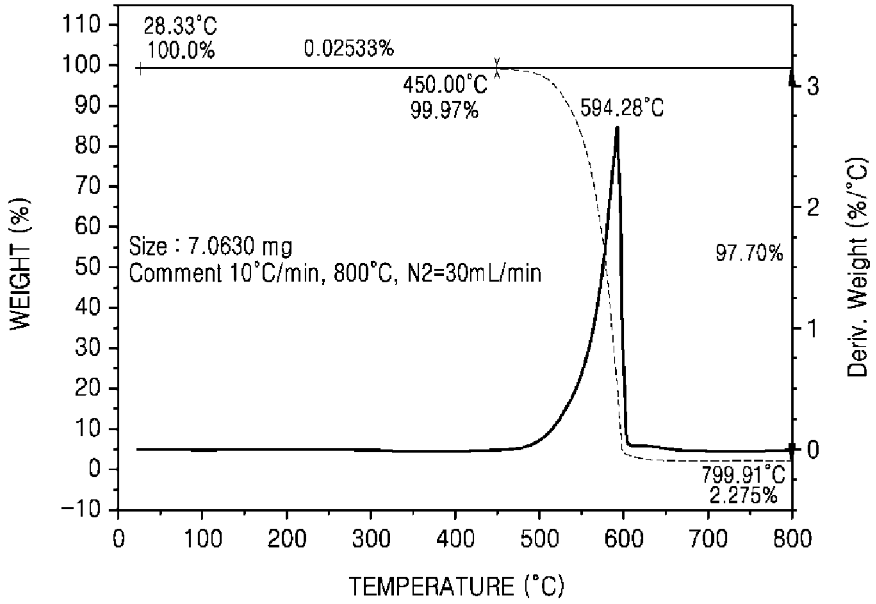
FIG. 2 is a graph of weight (percent, %) versus temperature (degree Centigrade, ° C.) and derivative weight (percent per degree Centigrade, %/° C.) versus temperature (° C.) showing thermal gravimetry analysis (TGA) data of Compound 1.
Figure 3:
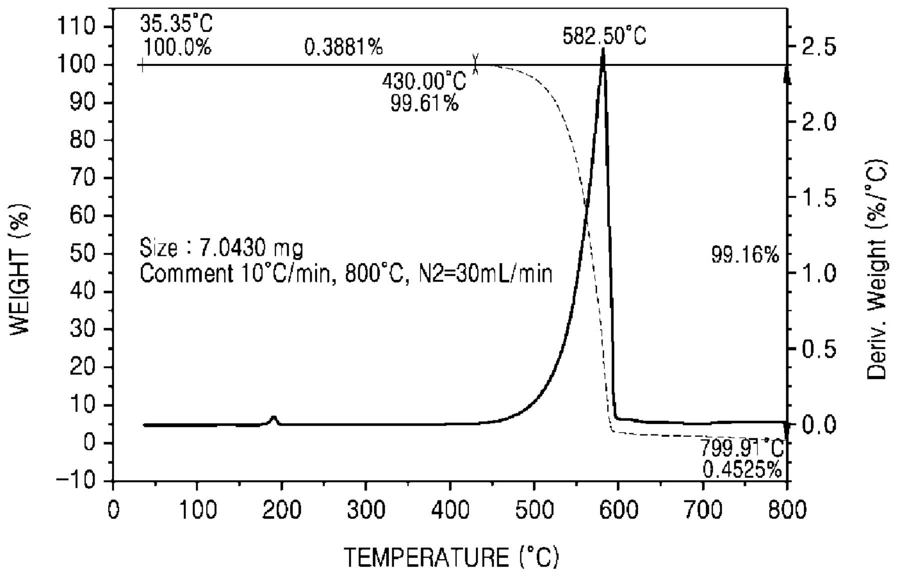
FIG. 3 is a graph of weight (%) versus temperature (° C.) and derivative weight (%/° C.) versus temperature (° C.) showing TGA data of Compound 4.
Figure 4:
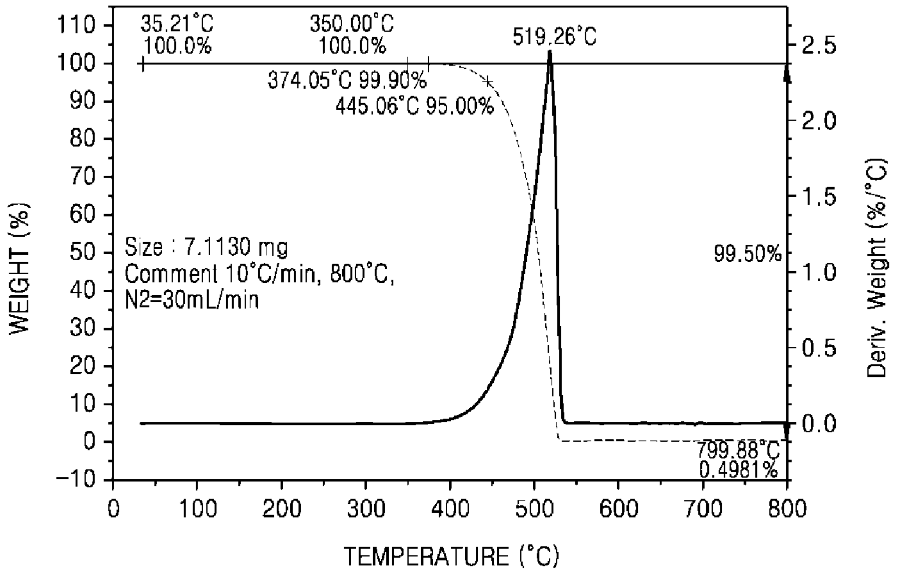
FIG. 4 is a graph of weight (%) versus temperature (° C.) and derivative weight (%/° C.) versus temperature (° C.) showing TGA data of Compound A.
Figure 5:
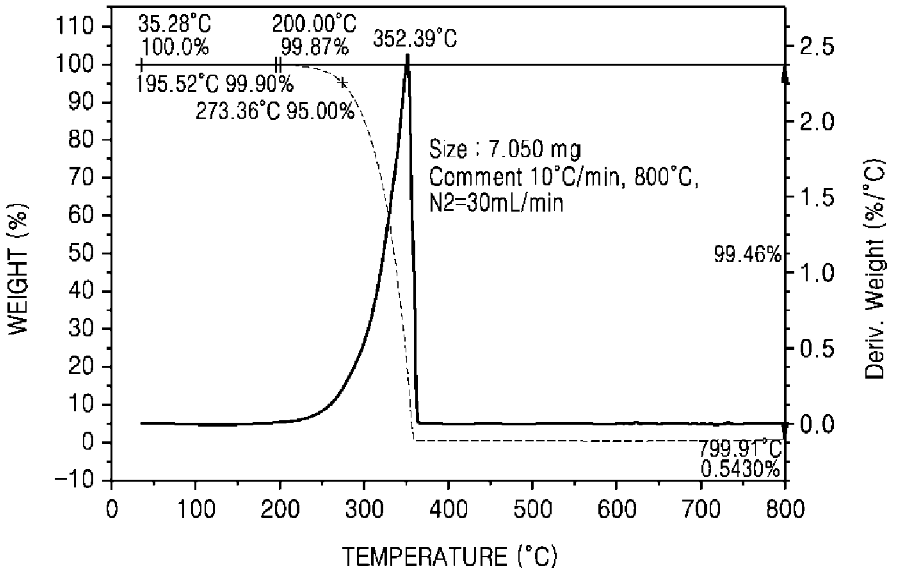
FIG. 5 is a graph of weight (percent, %) versus temperature (° C.) and derivative weight (%/° C.) versus temperature (° C.) showing TGA data of Compound B.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

A carbazole compound according to an embodiment is represented by Formula 1 below:

Formula 1

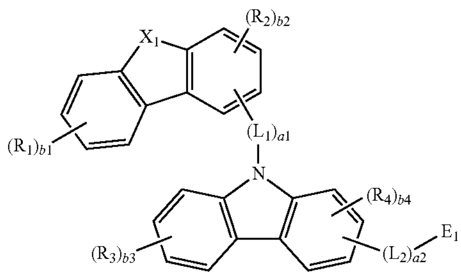

Group $X_1$ in Formula 1 is selected from N-$[(L_{11})_{a11}$-$(R_{11})_{b11}]$, S, O, S(=O), $S(=O)_2$, $C(R_{12})(R_{13})$, and $Si(R_{12})(R_{13})$. Herein, $L_{11}$, a11, $R_{11}$, b11, $R_{12}$, and $R_{13}$ may be understood by referring to corresponding description presented herein.

According to an embodiment, $X_1$ in Formula 1 may be N-$[(L_{11})_{a11}$-$(R_{11})_{b11}]$, S, O, or $C(R_{12})(R_{13})$, but is not limited thereto.

Groups $L_1$, $L_2$, and $L_{11}$ in Formula 1 may be each independently a substituted or unsubstituted $C_1$-$C_{60}$ alkylene group, a substituted or unsubstituted $C_2$-$C_{60}$ alkenylene group, a substituted or unsubstituted $C_2$-$C_{60}$ alkynylene group, a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic hetero-condensed polycyclic group.

According to an embodiment, $L_1$, $L_2$, and $L_{11}$ may be each independently selected from a $C_1$-$C_{20}$ alkylene group, a $C_2$-$C_{20}$ alkenylene group, and a $C_2$-$C_{20}$ alkynylene group;

a $C_1$-$C_{20}$ alkylene group, a $C_2$-$C_{20}$ alkenylene group, and a $C_2$-$C_{20}$ alkynylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, a oxadiazolylene group, a triazinylene group, a dibenzofuranylene group, a dibenzothiophenylene group, a benzocarbazolyl group, a dibenzocarbazolyl group, an imidazopyrimidinylene group, and an imidazopyridinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, a oxadiazolylene group, a triazinylene group, a dibenzofuranylene group, a dibenzothiophenylene group, a benzocarbazolyl group, a dibenzocarbazolyl group, an imidazopyrimidinylene group, and an imidazopyridinylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{20}$ aryl group, and a $C_2$-$C_{60}$ heteroaryl group.

According to another embodiment, $L_1$, $L_2$, and $L_{11}$ in Formula 1 may be each independently selected from a $C_1$-$C_{20}$ alkylene group, a $C_2$-$C_{20}$ alkenylene group, and a $C_2$-$C_{20}$ alkynylene group;

a $C_1$-$C_{20}$ alkylene group, a $C_2$-$C_{20}$ alkenylene group, and a $C_2$-$C_{20}$ alkynylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenylene group, a naphthylene group, a phenalenylene group, a phenanthrenylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group; and a phenylene group, a naphthylene group, a phenalenylene group, a phenanthrenylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group.

According to another embodiment, $L_1$, $L_2$, and $L_{11}$ in Formula 1 may be each independently a $C_1$-$C_{10}$ alkylene group, a $C_2$-$C_{10}$ alkenylene group, a $C_2$-$C_{10}$ alkynylene group, and one of Formulae 2-1 to 2-45, but are not limited thereto:

-continued
Formula 2-1
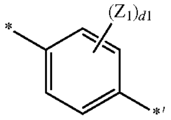
Formula 2-2
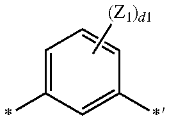
Formula 2-3
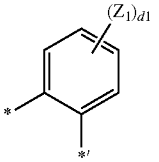
Formula 2-4
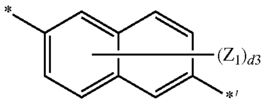
Formula 2-5
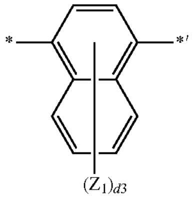
Formula 2-6
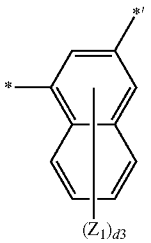
Formula 2-7
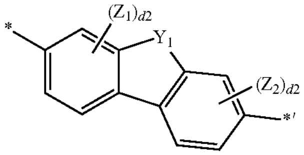
Formula 2-8
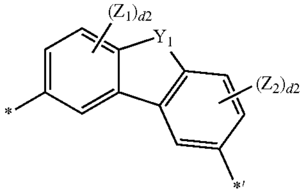
Formula 2-9
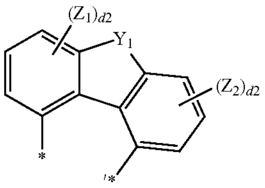
Formula 2-10
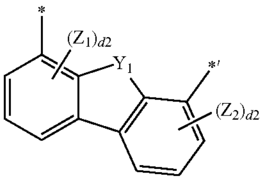
Formula 2-11
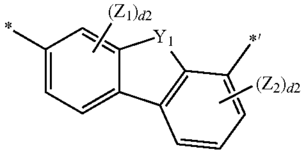
Formula 2-12
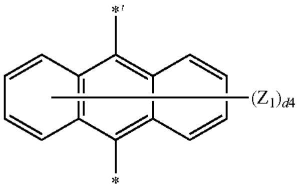
Formula 2-13
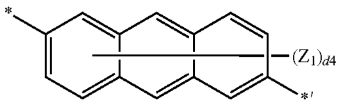
Formula 2-14
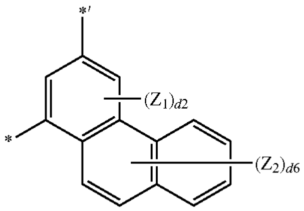
Formula 2-15
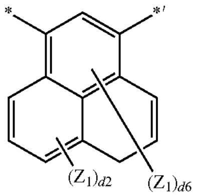
Formula 2-16
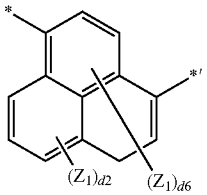
Formula 2-17
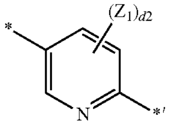
Formula 2-18
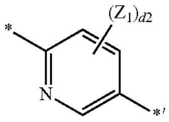

-continued
Formula 2-19
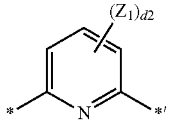
Formula 2-20
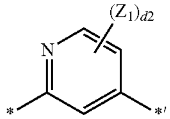
Formula 2-21
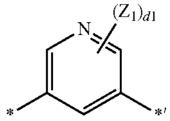
Formula 2-22
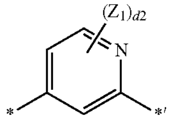
Formula 2-23
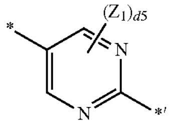
Formula 2-24
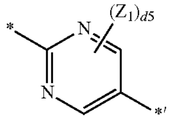
Formula 2-25
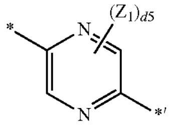
Formula 2-26
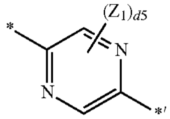
Formula 2-27
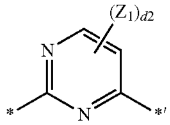
Formula 2-28
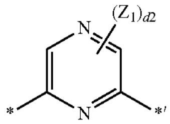
Formula 2-29
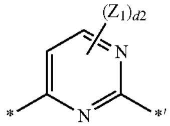
Formula 2-30
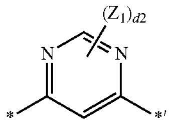
-continued
Formula 2-31
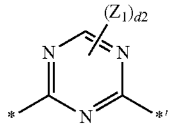
Formula 2-32
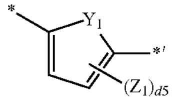
Formula 2-33
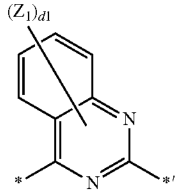
Formula 2-34
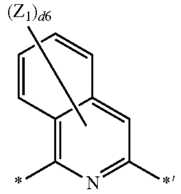
Formula 2-35
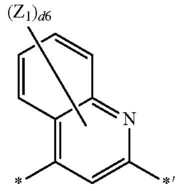
Formula 2-36
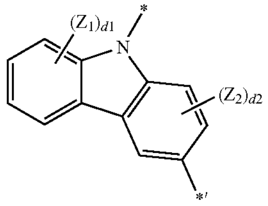
Formula 2-37
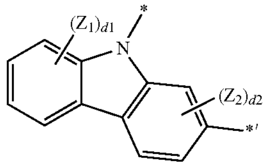
Formula 2-38
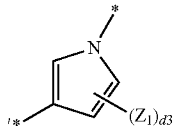
Formula 2-39
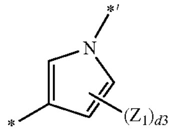

-continued

Formula 2-40

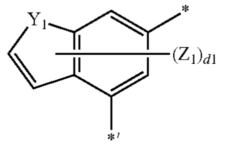

Formula 2-41

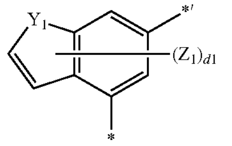

Formula 2-42

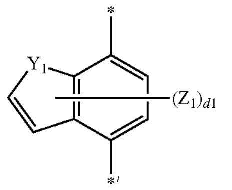

Formula 2-43

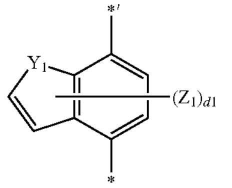

Formula 2-44

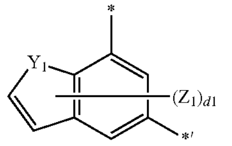

Formula 2-45

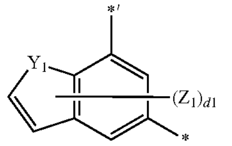

wherein in Formulae 2-1 to 2-45, $Y_1$ may be 0, S, $C(Z_2)(Z_3)$, $N(Z_5)$, or $Si(Z_6)(Z_7)$;

$Z_1$ to $Z_7$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, a monovalent non-aromatic heterocondensed polycyclic group, —$N(Q_{41})(Q_{42})$, and —$Si(Q_{43})(Q_{44})(Q_{45})$ ($Q_{41}$ to $Q_{45}$ may be understood by referring to corresponding description provided herein); and d1 may be an integer of 1 to 4; d2 may be an integer of 1 to 3; d3 may be an integer of 1 to 6; d4 may be an integer of 1 to 8; d5 may be an integer of 1 or 2; d6 may be an integer of 1 to 5; and each of * and *' may indicate a binding site to a neighboring atom.

For example, $Z_1$ to $Z_7$ in Formula 2-1 to 2-45 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group, but are not limited thereto.

Variable a1 in Formula 1 indicates the number of $L_1$, and may be 1, 2, 3, 4, or 5, for example, 1 or 2, or for example, 1. That is, Formula 1 has at least one $L_1$. When a1 is 2 or more, a plurality of $L_1$ may be identical or different.

Variable a2 in Formula 1 indicates the number of $L_2$, and may be 1, 2, 3, 4, or 5, for example, 1 or 2, or for example, 1. That is, Formula 1 has at least one $L_1$. When a2 is 2 or more, groups $L_2$ may be identical or different.

Variable a11 in Formula 1 indicates the number of $L_{11}$, and may be 0, 1, 2, 3, 4 or 5, for example, 0, 1 or 2, or for example, 0 or 1. When a11 is 0, $R_{11}$ in $N-[(L_{11})_{a11}-(R_{11})_{b11}]$ may directly link to N. When a11 is 2 or more, groups $L_{11}$ may be identical or different.

According to an embodiment, a1 and a2 in Formula 1 may both be 1.

Group $R_1$ in Formula 1 may be selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(═O)—O-$Q_1$, —C(═O)-$Q_2$, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; and a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group, —C(═O)—O-$Q_3$, —C(═O)-$Q_4$, a sulfonic acid group or a salt thereof, and a phosphoric acid group or a salt thereof. Herein, $Q_1$ to $Q_4$ may be each independently selected from a hydrogen, a $C_1$-$C_{60}$ alkyl group, a $C_2$-$C_{60}$ alkenyl group, and a $C_2$-$C_{60}$ alkynyl group.

According to an embodiment, $R_1$ in Formula 1 may be selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(═O)—O-$Q_1$, —C(═O)-$Q_2$, a sulfonic acid group or a salt thereof, a phosphoric acid group or a salt thereof, a $C_1$-$C_{20}$ alkyl group, and a $C_1$-$C_{20}$ alkoxy group, wherein $Q_1$ and $Q_2$ may be each independently selected from a hydrogen and a $C_1$-$C_{20}$ alkyl group, but is not limited thereto.

Group $R_2$ to $R_4$ and $R_{11}$ to $R_{13}$ in Formula 1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(=O)—O-$Q_{11}$, —C(=O)-$Q_{12}$, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, and a substituted or unsubstituted monovalent non-aromatic heterocondensed polycyclic group, —N($Q_{13}$)($Q_{14}$), —Si($Q_{15}$)($Q_{16}$)($Q_{17}$), and —B($Q_{18}$)($Q_{19}$).

According to an embodiment, $R_2$ to $R_4$ and $R_{11}$ to $R_{13}$ in Formula 1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(=O)—O-$Q_{11}$, —C(=O)-$Q_{12}$, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, and a $C_1$-$C_{20}$ alkoxy group;

a $C_1$-$C_{20}$ alkyl group, a $C_2$-$C_{20}$ alkenyl group, a $C_2$-$C_{20}$ alkynyl group, and a $C_1$-$C_{20}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolylene group, a triazinyl group, a dibenzofuranyl group, a dibenzothiophenyl group, a benzocarbazolyl group, a dibenzocarbazolyl group, an imidazopyridimidinyl group, and an imidazopyridinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolylene group, a triazinyl group, a dibenzofuranyl group, a dibenzothiophenyl group, a benzocarbazolyl group, a dibenzocarbazolyl group, an imidazopyridimidinyl group, and an imidazopyridinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group; and —N($Q_{13}$)($Q_{14}$) and —Si($Q_{15}$)($Q_{16}$)($Q_{17}$), wherein $Q_{11}$ to $Q_{17}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cynolinyl group, and a quinazolinyl group.

According to another embodiment, $R_2$ to $R_4$ and $R_{11}$ to $R_{13}$ in Formula 1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(=O)—O-$Q_{11}$, —C(=O)-$Q_{12}$, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, and a $C_1$-$C_{20}$ alkoxy group;

a phenyl group, a naphthyl group, a pyridinyl group, and a naphthyridinyl group;

a phenyl group, a naphthyl group, a pyridinyl group, and a naphthyridinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group; and —$Si(Q_{15})(Q_{16})(Q_{17})$, wherein $Q_{11}$, $Q_{12}$, and $Q_{15}$ to $Q_{17}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cynolinyl group, and a quinazolinyl group, but they are not limited thereto.

According to another embodiment, $R_1$ to $R_4$ in Formula 1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group.

According to another embodiment, $R_1$ and $R_4$ in Formula 1 may both be a hydrogen.

Variable b1 in Formula 1 indicates the number of $R_1$, and may be an integer of 1 to 4, for example, an integer of 1 or 2. When b1 is 2 or more, groups $R_1$ may be identical or different.

Variable b2 in Formula 1 indicates the number of $R_2$, and may be an integer of 1 to 3, for example, an integer of 1 or 2. When b2 is 2 or more, groups $R_2$ may be identical or different.

Variable b3 in Formula 1 indicates the number of $R_3$, and may be an integer of 1 to 4, for example, an integer of 1 or 2. When b3 is 2 or more, groups $R_3$ may be identical or different.

Variable b4 in Formula 1 indicates the number of $R_4$, and may be an integer of 1 to 3, for example, an integer of 1 or 2. When b4 is 2 or more, groups $R_4$ may be identical or different.

Variable b11 in Formula 1 indicates the number of $R_{11}$, and may be an integer of 1 to 3, for example, an integer of 1 or 2. When b11 is 2 or more, groups $R_{11}$ may be identical or different.

Group $E_1$ in Formula 1 is an electron transporting-cyclic group containing at least one nitrogen (N) as a ring-forming atom and substituted with at least one $Ar_1$. That is, $E_1$ includes at least one $Ar_1$ as a substituent thereof. $E_1$ may include as a substituent, in addition to at least one $Ar_1$, optionally, any substituent described herein. However, $E_1$ cannot be "a substituted or unsubstituted carbazole", "a substituted or unsubstituted dibenzofuran," and "a substituted or unsubstituted dibenzothiophene."

According to an embodiment, $E_1$ in Formula 1 is an electron transporting-cyclic group containing at least one N as a ring-forming atom and substituted with at least one $Ar_1$, wherein the electron transporting-cyclic group may be a 6-membered-cyclic group (for example, see Formulae 11-1 to 11-8), a 10-membered-cyclic group (for example, see Formulae 11-9 to 11-17) in which two 6-membered rings are condensed to each other, or a 9-membered-cyclic group (for example, see Formulae 11-18 to 11-21) in which one 5-membered ring is condensed to one 6-membered ring.

$Ar_1$ may be selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, and a substituted or unsubstituted monovalent non-aromatic heterocondensed polycyclic group.

According to an embodiment, $E_1$ in Formula 1 may be selected from a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cynolinyl group, a phenanthridinyl group, an acridinyl group, a phenanthrolinyl group, a phenazinyl group, a benzoimidazolyl group, a thiazolyl group, an isothiazolyl group, a benzothiazolyl group, an isooxazolyl group, an oxazolyl group, a triazolyl group, a tetrazolyl group, an oxadiazolyl group, a triazinyl group, an imidazopyrimidinyl group, and an imidazopyridinyl group; and a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cynolinyl group, a phenanthridinyl group, an acridinyl group, a phenanthrolinyl group, a phenazinyl group, a benzoimidazolyl group, a thiazolyl group, an isothiazolyl group, a benzothiazolyl group, an isooxazolyl group, an oxazolyl group, a triazolyl group, a tetrazolyl group, an oxadiazolyl group, a triazinyl group, an imidazopyrimidinyl group, and an imidazopyridinyl group, each substituted with at least one $Ar_1$, and $Ar_1$ may be selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cynolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isooxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolylene group, a triazinyl group, a dibenzofuranyl group, a dibenzothiophenyl group, a benzocarbazolyl group, a dibenzocarbazolyl group, an imidazopyridimidinyl group, and an imidazopyridinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group, but is not limited thereto.

According to another embodiment, $E_1$ in Formula 1 may be selected from Formulae 11-1 to 11-21 below, but are not limited thereto:

Formula 11-1

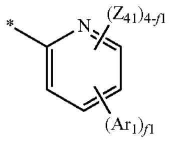

-continued

Formula 11-2

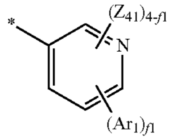

Formula 11-3

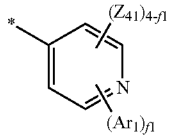

Formula 11-4

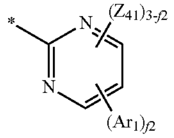

Formula 11-5

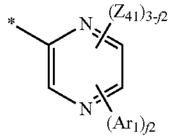

Formula 11-6

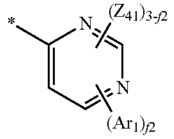

Formula 11-7

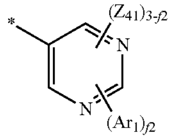

Formula 11-8

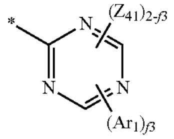

Formula 11-9

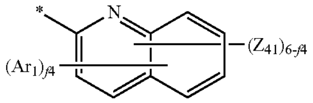

Formula 11-10

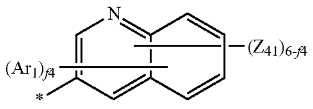

Formula 11-11

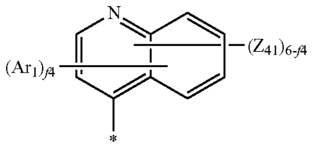

Formula 11-12

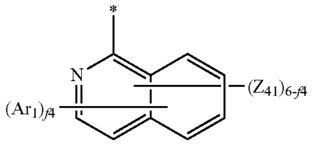

-continued

Formula 11-13

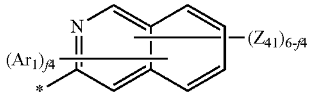

Formula 11-14

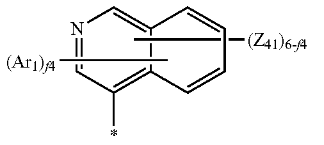

Formula 11-15

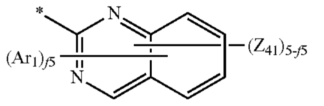

Formula 11-16

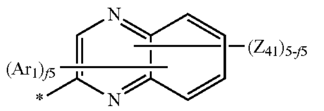

Formula 11-17

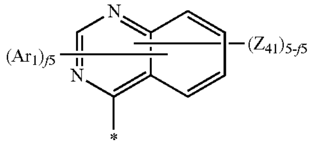

Formula 11-18

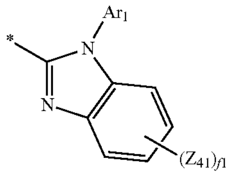

Formula 11-19

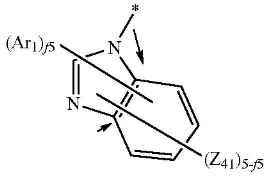

Formula 11-20

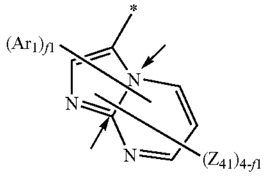

Formula 11-21

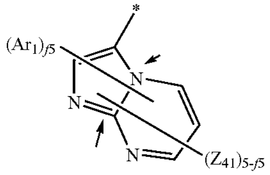

wherein in Formulae 11-1 to 11-21, $Z_{41}$ and $Z_{42}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group;

f1 may be an integer of 1 to 4;

f2 may be an integer of 1 to 3;

f3 may be an integer of 1 or 2;

f4 may be an integer of 1 to 6; and f5 may be an integer of 1 to 5; and $Ar_1$ may be selected from a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group.

For example, $E_1$ in Formula 1 may be selected from Formulae 11-1 to 11-8 below, but are not limited thereto.

Groups $L_1$ and $L_2$ in Formula 1 may be each independently linked to $1^{st}$, $2^{nd}$, $3^{rd}$, or $4^{th}$ carbon of a benzo group. Accordingly, the carbazole compound represented by Formula 1 may be represented by any one of Formulae 1(1) to 1(4), 2(1) to 2(4), 3(1) to 3(4), and 4(1) to 4(4).

Formula 1(1)

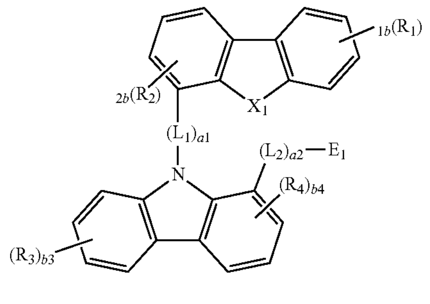

Formula 1(2)

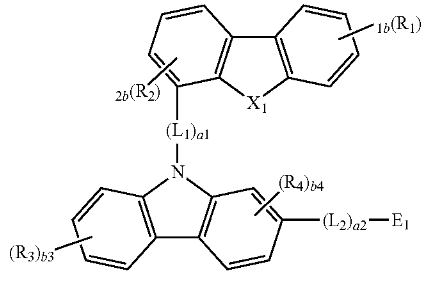

Formula 1(3)

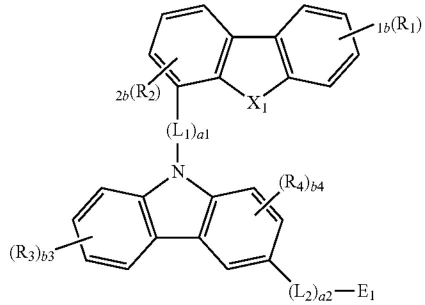

-continued
Formula 1(4)
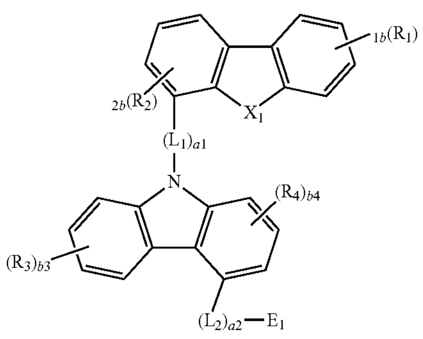
Formula 2(1)
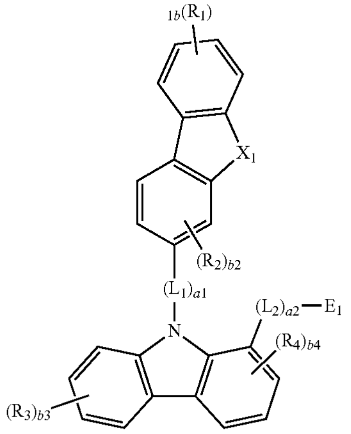
Formula 2(2)
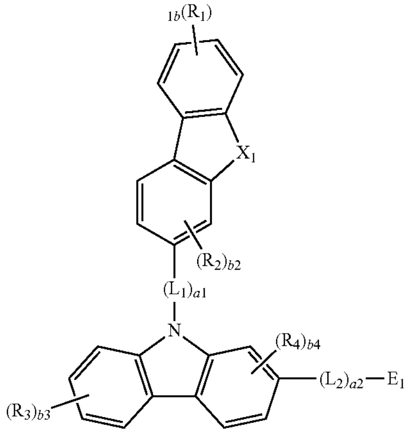
-continued
Formula 2(3)
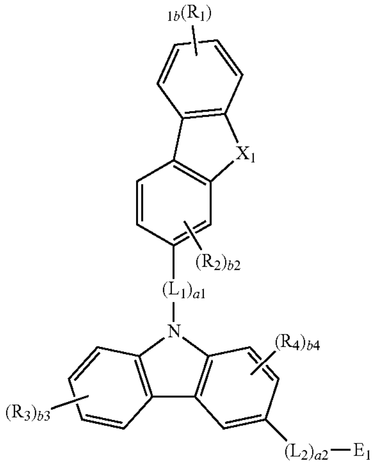
Formula 2(4)
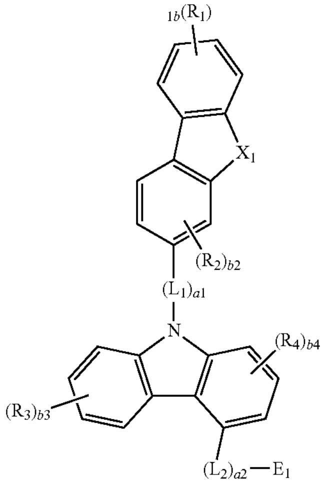
Formula 3(1)
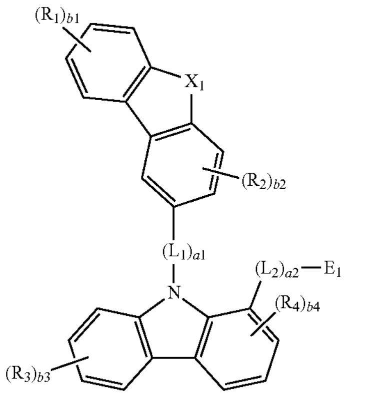

-continued

Formula 3(2)

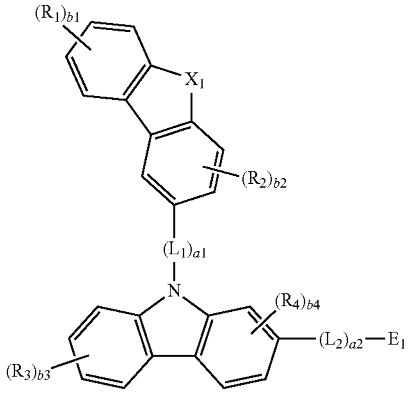

Formula 3(3)

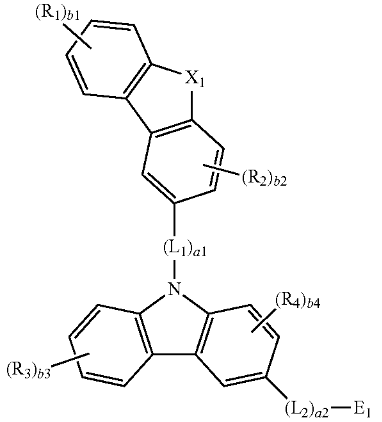

Formula 3(4)

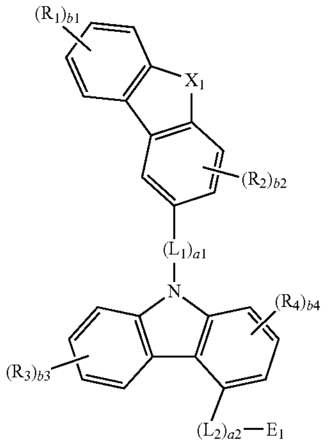

Formula 4(1)

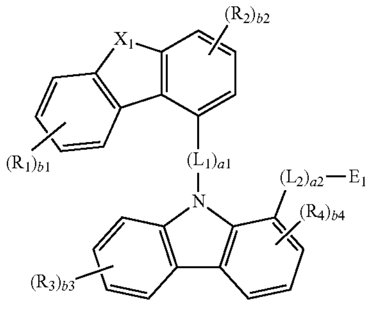

-continued

Formula 4(2)

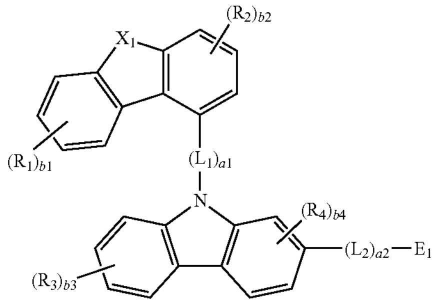

Formula 4(3)

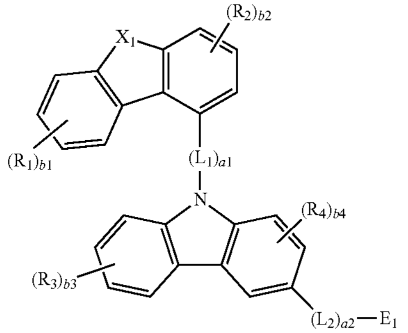

Formula 4(4)

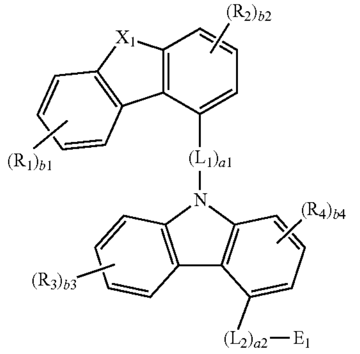

Groups $X_1$, $L_1$, $L_2$, $L_{11}$, $R_1$ to $R_4$, $R_{11}$ to $R_{13}$, a1, a2, a11, b1, b2, b3, b4, b11, and $E_1$ in Formulae 1(1) to 1(4), 2(1) to 2(4), 3(1) to 3(4), and 4(1) to 4(4) may be understood by referring to description provided herein.

According to another embodiment, the carbazole compound represented by Formula 1 may be represented by any one of Formulae 1A, 1B, 1C, and 1D below:

Formula 1A

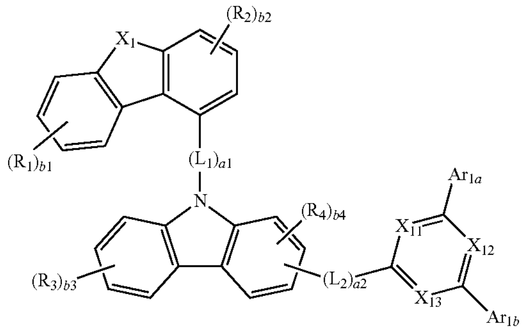

-continued

Formula 1B

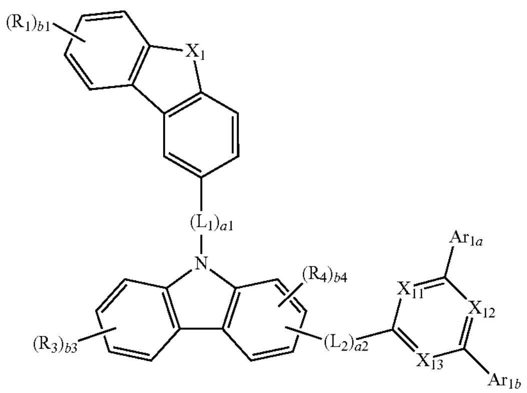

Formula 1C

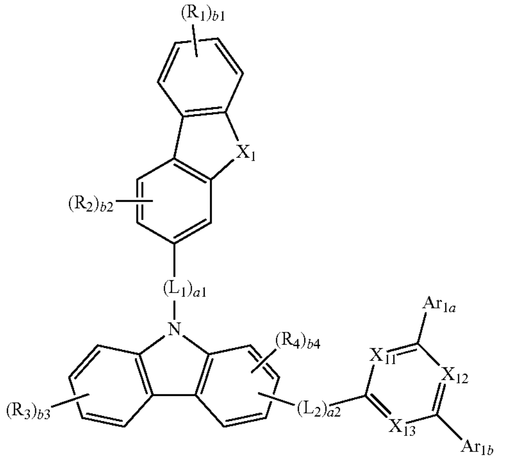

Formula 1D

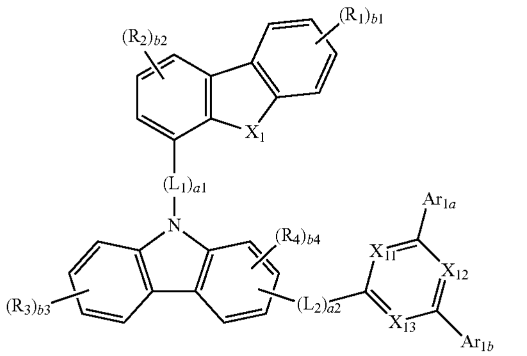

Groups $X_1$, $L_1$, $L_2$, $L_{11}$, $R_1$ to $R_4$, $R_{11}$ to $R_{13}$, a1, a2, a11, b1, b2, b3, b4, and b11 in Formulae 1A, 1B, 1C, and 1D may be understood by referring to description provided herein.

In Formulae 1A, 1B, 1C, and 1D, $X_{11}$ may be N or $C(R_{21})$, $X_{12}$ may be N or $C(R_{22})$, and $X_{13}$ may be N or $C(R_{23})$, and at least one of $X_{11}$ to $X_{13}$ may be N.

The $R_{21}$ to $R_{23}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(═O)—O-$Q_{11}$, —C(═O)-$Q_{12}$, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, and a substituted or unsubstituted monovalent non-aromatic heterocondensed polycyclic group, —N($Q_{13}$)($Q_{14}$), —Si($Q_{15}$)($Q_{16}$)($Q_{17}$), and —B($Q_{18}$)($Q_{19}$). Groups $R_{21}$ to $R_{23}$ in Formulae 1A, 1B, 1C, and 1D may be understood by referring to the description provided in connection with $R_2$.

Groups $Ar_{1a}$ and $Ar_{1b}$ may be selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, and a substituted or unsubstituted monovalent non-aromatic heterocondensed polycyclic group. $Ar_{1a}$ and $Ar_{1b}$ in Formulae 1A, 1B, 1C, and 1D may be understood by referring to the description provided in connection with $Ar_1$.

According to an embodiment, in Formulae 1A, 1B, 1C, and 1D, $L_1$, $L_2$, and $L_{11}$ may be each independently selected from a $C_1$-$C_{20}$ alkylene group, a $C_2$-$C_{20}$ alkenylene group, and a $C_2$-$C_{20}$ alkynylene group;

a $C_1$-$C_{20}$ alkylene group, a $C_2$-$C_{20}$ alkenylene group, and a $C_2$-$C_{20}$ alkynylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenylene group, a naphthylene group, a phenalenylene group, a phenanthrenylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group; and a phenylene group, a naphthylene group, a phenalenylene group, a phenanthrenylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group and a quinazolinyl group (for example, $L_1$, $L_2$, and $L_{11}$ may be each independently selected from a $C_1$-$C_{10}$ alkylene group, a $C_2$-$C_{10}$ alkenylene group, a $C_2$-$C_{10}$ alkynylene group, and Formulae 2-1 to 2-45);

a1 and a2 may be each independently 1 or 2;

a11 may be 0 or 1;

$R_1$ may be selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(=O)—O-$Q_1$, —C(=O)-$Q_2$, a sulfonic acid group or a salt thereof, a phosphoric acid group or a salt thereof, a $C_1$-$C_{20}$ alkyl group, and a $C_1$-$C_{20}$ alkoxy group, and Q1 and $Q_2$ may be each independently selected from a hydrogen and a $C_1$-$C_{20}$ alkyl group;

$R_2$ to $R_4$, $R_{11}$ to $R_{13}$, and $R_{21}$ to $R_{23}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(=O)—O-$Q_{11}$, —C(=O)-$Q_{12}$, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, and a $C_1$-$C_{20}$ alkoxy group;

a phenyl group, a naphthyl group, a pyridinyl group, and a naphthyridinyl group;

a phenyl group, a naphthyl group, a pyridinyl group, and a naphthyridinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group; and —Si($Q_{15}$)($Q_{16}$)($Q_{17}$), wherein $Q_{11}$, $Q_{12}$, and $Q_{15}$ to $Q_{17}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cynolinyl group, and a quinazolinyl group;

b1 and b3 are each independently an integer selected from 1 to 4;

b2, b4, and b11 are each independently an integer selected from 1 to 3; and $Ar_{1a}$ and $Ar_{1b}$ may be each independently selected from a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group.

According to another embodiment, the carbazole compound represented by Formula 1 may be represented by any one of Formulae 1A-1, 1B-1, 1C-1, and 1 D-1 below:

Formula 1A-1

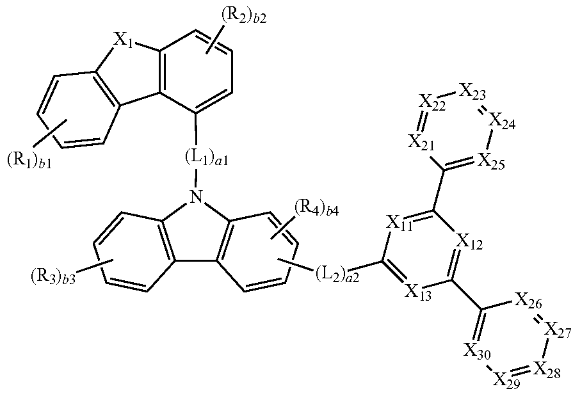

Formula 1B-1

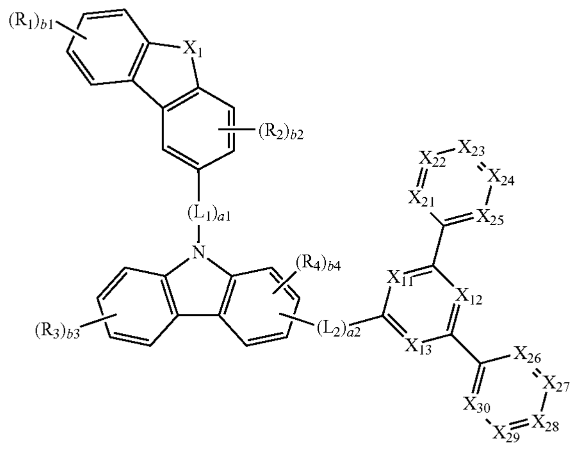

-continued

Formula 1C-1

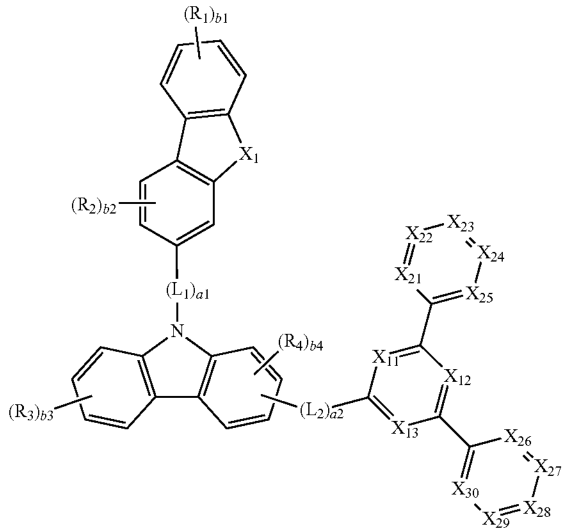

Formula 1D-1

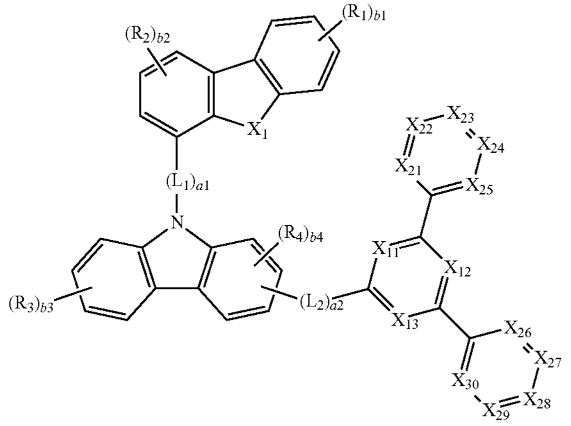

Groups $X_1$, $L_1$, $L_2$, $L_{11}$, $R_1$ to $R_4$, $R_{11}$ to $R_{13}$, a1, a2, a11, b1, b2, b3, b4, and b11 in Formulae 1A-1, 1B-1, 1C-1, and 1D-1 may be understood by referring to description provided herein.

In Formulae 1A-1, 1B-1, 1C-1, and 1D-1, $X_{11}$ may be N or $C(R_{21})$, $X_{12}$ may be N or $C(R_{22})$, $X_{13}$ may be N or $C(R_{23})$, $X_{21}$ may be N or $C(R_{31})$, $X_{22}$ may be N or $C(R_{32})$, $X_{23}$ may be N or $C(R_{33})$, $X_{24}$ may be N or $C(R_{34})$, $X_{25}$ may be N or $C(R_{35})$, $X_{26}$ may be N or $C(R_{36})$, $X_{27}$ may be N or $C(R_{37})$, $X_{28}$ may be N or $C(R_{38})$, $X_{29}$ may be N or $C(R_{39})$, and $X_{30}$ may be N or $C(R_{40})$, wherein at least one of $X_{11}$ to $X_{13}$ may be N.

Groups $R_{21}$ to $R_{23}$ and $R_{31}$ to $R_{40}$ in Formulae 1A-1, 1B-1, 1C-1, and 1D-1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(═O)—O-$Q_{11}$, —C(═O)-$Q_{12}$, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, and a substituted or unsubstituted monovalent non-aromatic heterocondensed polycyclic group, —N($Q_{13}$)($Q_{14}$), —Si($Q_{15}$)($Q_{16}$)($Q_{17}$), and —B($Q_{18}$)($Q_{19}$).

For example, in Formulae 1A-1, 1B-1, 1C-1, and 1D-1, $L_1$, $L_2$, and $L_{11}$ may be each independently selected from a $C_1$-$C_{20}$ alkylene group, a $C_2$-$C_{20}$ alkenylene group, and a $C_2$-$C_{20}$ alkynylene group;

a $C_1$-$C_{20}$ alkylene group, a $C_2$-$C_{20}$ alkenylene group, and a $C_2$-$C_{20}$ alkynylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenylene group, a naphthylene group, a phenalenylene group, a phenanthrenylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group; and a phenylene group, a naphthylene group, a phenalenylene group, a phenanthrenylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group and a quinazolinyl group (for example, $L_1$, $L_2$, and $L_{11}$ may be each independently selected from a $C_1$-$C_{10}$ alkylene group, a $C_2$-$C_{10}$ alkenylene group, a $C_2$-$C_{10}$ alkynylene group, and Formulae 2-1 to 2-45);

a1 and a2 may be each independently 1 or 2;

a11 may be 0 or 1;

$R_1$ may be selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(═O)—O-$Q_1$, —C(═O)-$Q_2$, a sulfonic acid group or a salt thereof, a phosphoric acid group or a salt thereof, a $C_1$-$C_{20}$ alkyl group, and a $C_1$-$C_{20}$ alkoxy group, and $Q_1$ and $Q_2$ may be each independently selected from a hydrogen and a $C_1$-$C_{20}$ alkyl group;

$R_2$ to $R_4$, $R_{11}$ to $R_{13}$, $R_{21}$ to $R_{23}$, and $R_{31}$ to $R_{40}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(═O)—O-$Q_{11}$, —C(═O)-$Q_{12}$, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, and a $C_1$-$C_{20}$ alkoxy group;

a phenyl group, a naphthyl group, a pyridinyl group, and a naphthyridinyl group;

a phenyl group, a naphthyl group, a pyridinyl group, and a naphthyridinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group; and —Si($Q_{15}$)($Q_{16}$)($Q_{17}$), wherein $Q_{11}$, $Q_{12}$, and $Q_{15}$ to $Q_{17}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cynolinyl group, and a quinazolinyl group;

b1 and b3 are each independently an integer selected from 1 to 4;

b2, b4, and b11 are each independently an integer selected from 1 to 3;

$Ar_{1a}$ and $Ar_{1b}$ may be each independently selected from a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group.

In the present specification, at least one substituent of the substituted $C_1$-$C_{60}$ alkylene group, the substituted $C_2$-$C_{60}$ alkenylene group, the substituted $C_2$-$C_{60}$ alkynylene group, the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic hetero-condensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, a substituted or unsubstituted $C_7$-$C_{60}$ arylalkyl group, the substituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, the substituted monovalent non-aromatic condensed polycyclic group, and the substituted monovalent non-aromatic heterocondensed polycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, a monovalent non-aromatic heterocondensed polycyclic group, —N($Q_{21}$)($Q_{22}$), —Si($Q_{23}$)($Q_{24}$)($Q_{25}$), and —B($Q_{26}$)($Q_{27}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic heterocondensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic heterocondensed polycyclic group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, a monovalent non-aromatic heterocondensed polycyclic group, —$N(Q_{31})(Q_{32})$, —$Si(Q_{33})(Q_{34})(Q_{35})$, and —$B(Q_{36})(Q_{37})$; and —$N(Q_{41})(Q_{42})$, —$Si(Q_{43})(Q_{44})(Q_{45})$, and —$B(Q_{46})(Q_{47})$.

$Q_1$ to $Q_4$ used herein are each independently selected from a hydrogen, a $C_1$-$C_{60}$ alkyl group, a $C_2$-$C_{60}$ alkenyl group, and a $C_2$-$C_{60}$ alkynyl group; and $Q_{11}$ to $Q_{19}$, $Q_{21}$ to $Q_{27}$, $Q_{31}$ to $Q_{37}$ and $Q_{41}$ to $Q_{47}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic heterocondensed polycyclic group.

According to another embodiment, in the present specification, at least one substituent of the substituted $C_1$-$C_{60}$ alkylene group, the substituted $C_2$-$C_{60}$ alkenylene group, the substituted $C_2$-$C_{60}$ alkynylene group, the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic hetero-condensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, a substituted or unsubstituted $C_7$-$C_{60}$ arylalkyl group, the substituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, the substituted monovalent non-aromatic condensed polycyclic group, and the substituted monovalent non-aromatic heterocondensed polycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a cyclopentyl group, a cyclohexyl group, a cycloheptyl group, a cyclopentenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cynolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, $N(Q_{21})(Q_{22})$, —$Si(Q_{23})(Q_{24})(Q_{25})$, and —$B(Q_{26})(Q_{27})$;

a cyclopentyl group, a cyclohexyl group, a cycloheptyl group, a cyclopentenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cynolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclopentenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cynolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, —$N(Q_{31})(Q_{32})$, —$Si(Q_{33})(Q_{34})(Q_{35})$, and —$B(Q_{36})(Q_{37})$; and —$N(Q_{41})(Q_{42})$, —$Si(Q_{43})(Q_{44})(Q_{45})$, and —$B(Q_{46})(Q_{47})$; and $Q_{11}$ to $Q_{19}$, $Q_{21}$ to $Q_{27}$, $Q_{31}$ to $Q_{37}$, and $Q_{41}$ to $Q_{47}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cynolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group.

The carbazole compound represented by Formula 1 may be one of Compounds 1 to 351 below, but is not limited thereto.

1

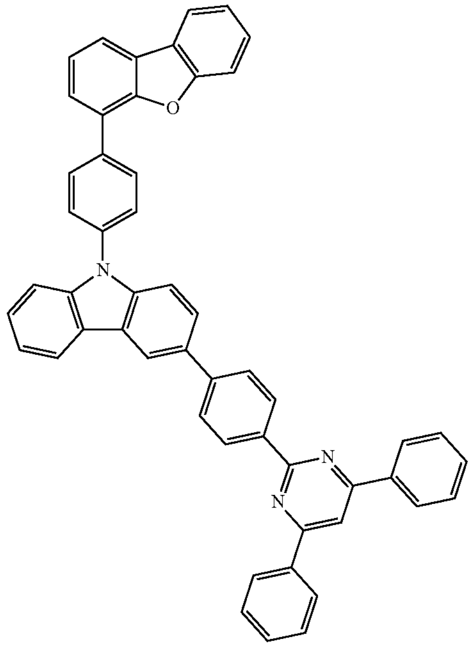

2

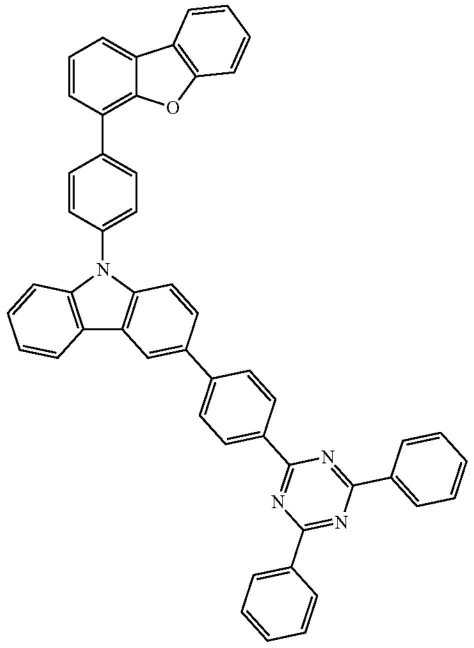

-continued
3
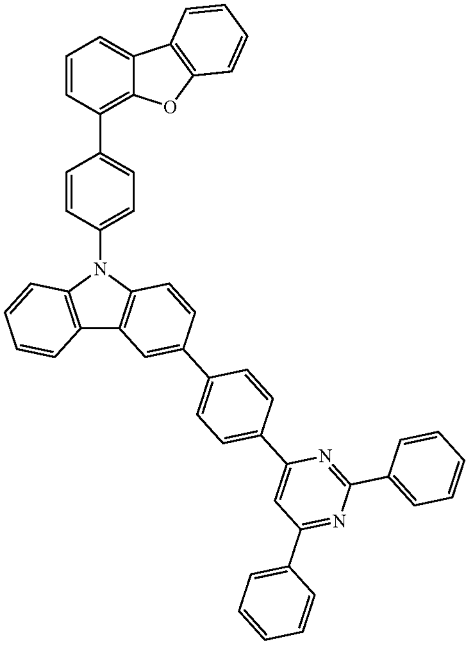
4
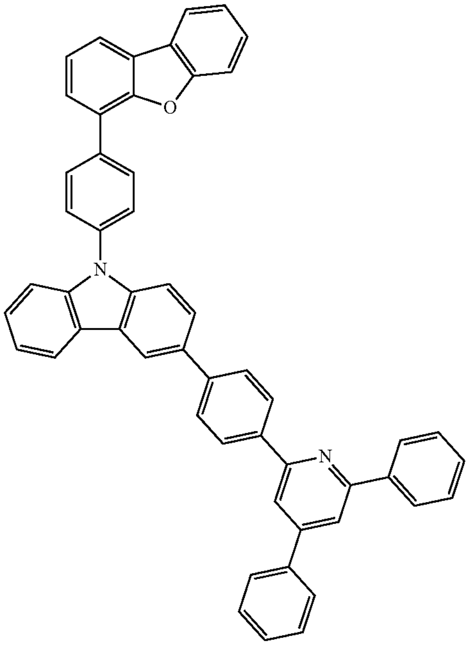
-continued
5
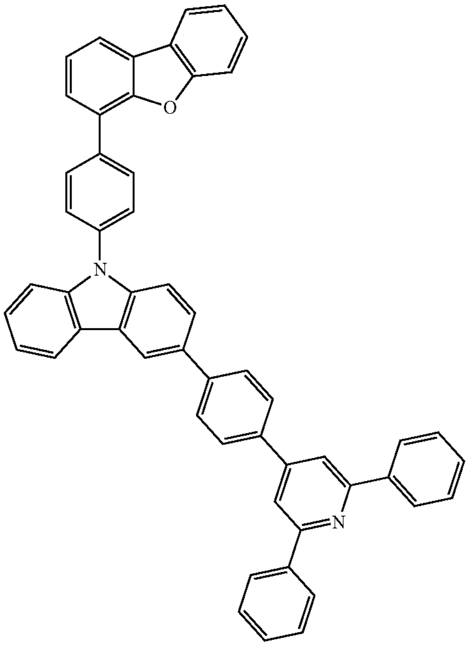
6
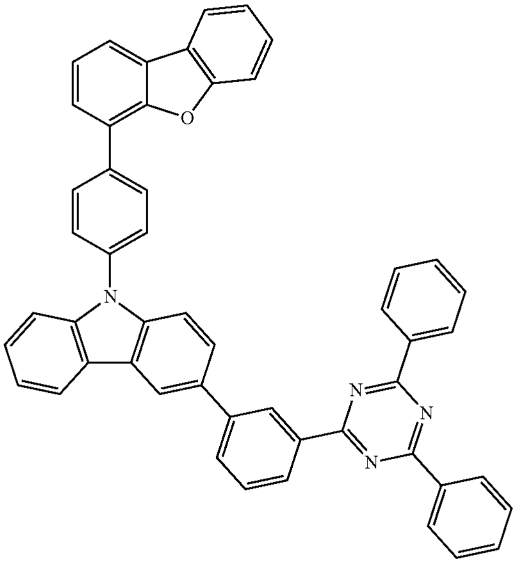

-continued
7
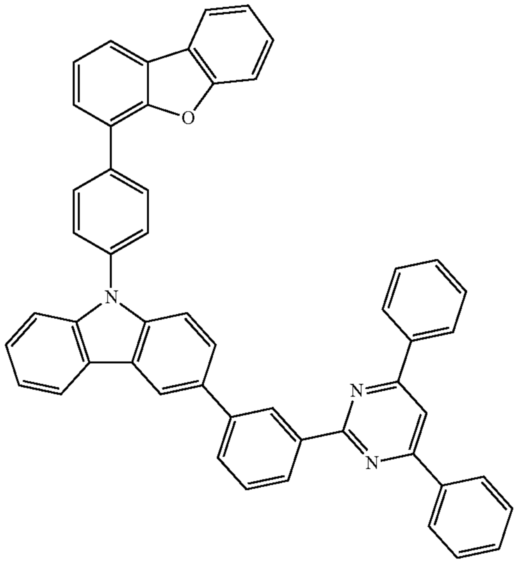
8
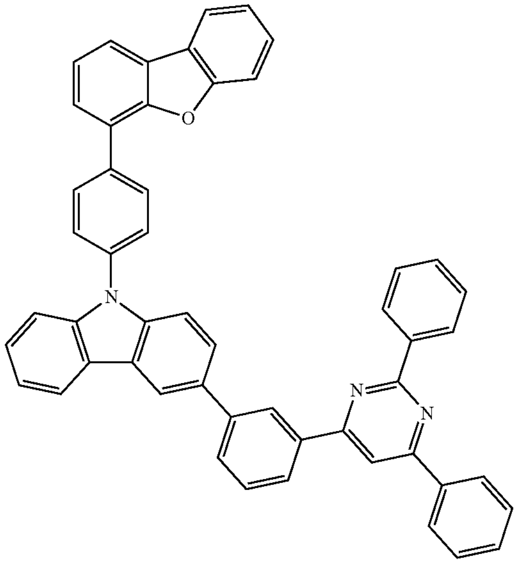
-continued
9
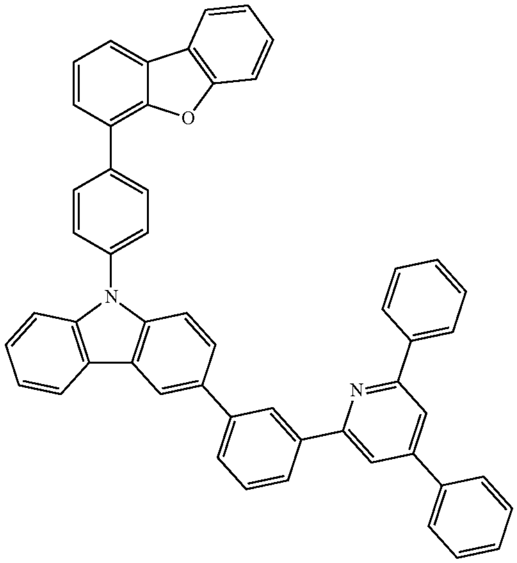
10
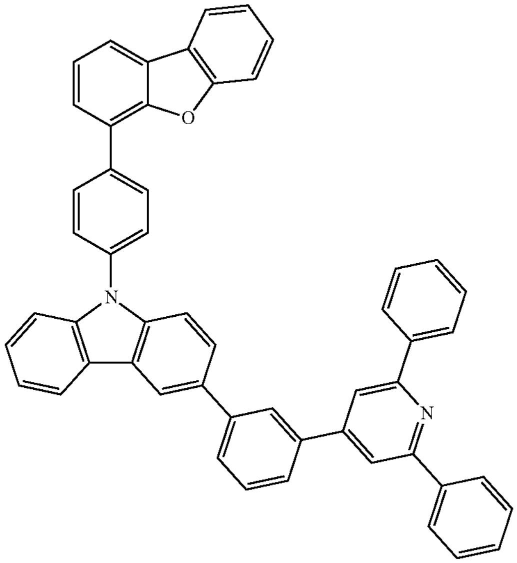

-continued
11
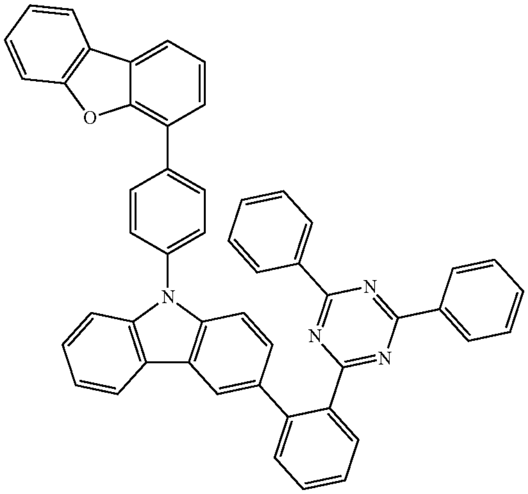
12
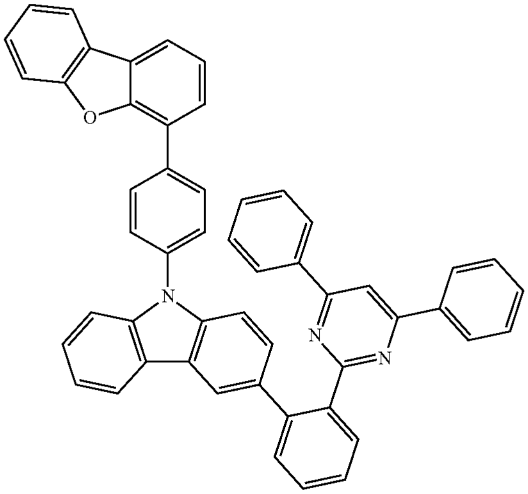
13
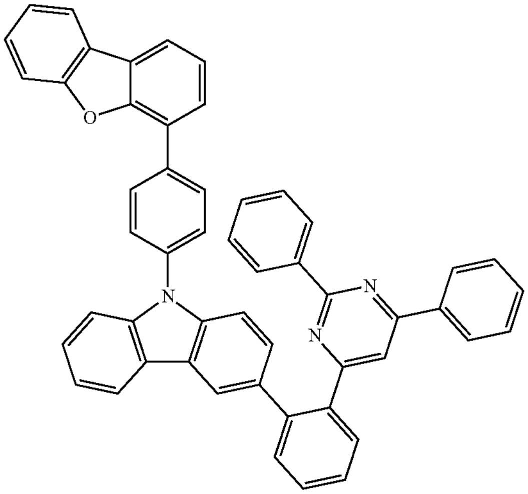
-continued
14
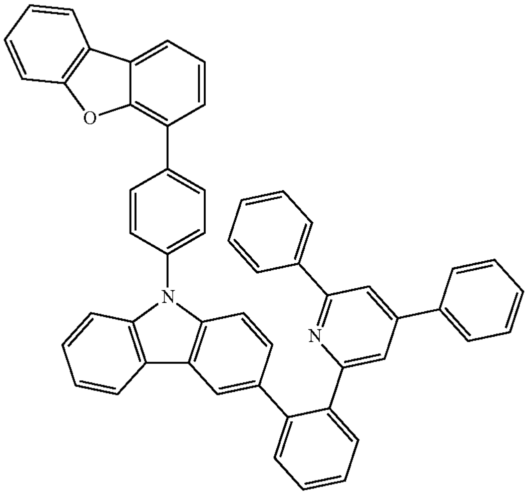
15
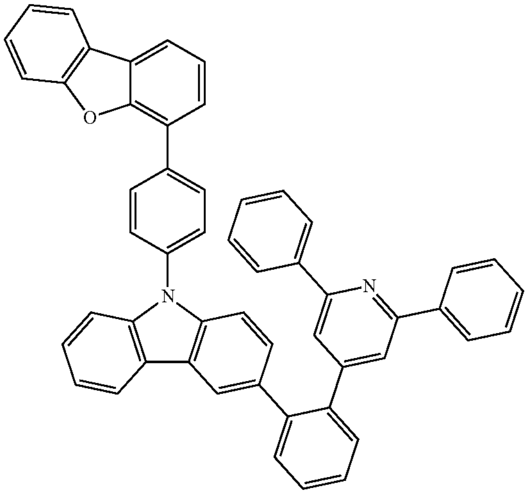

-continued
16
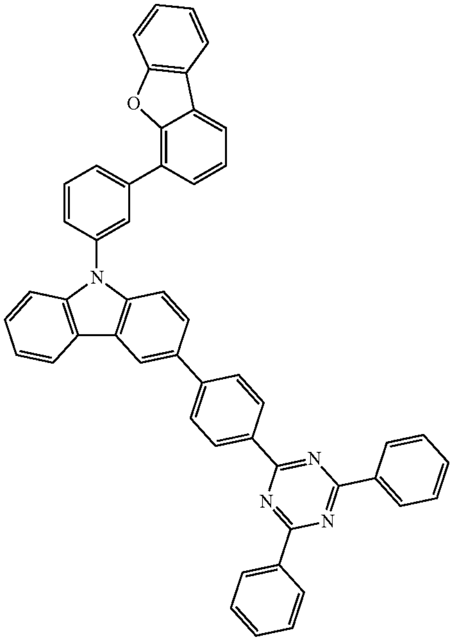
17
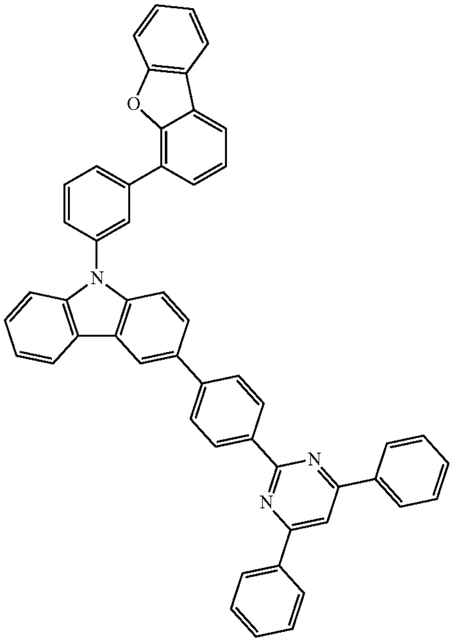
-continued
18
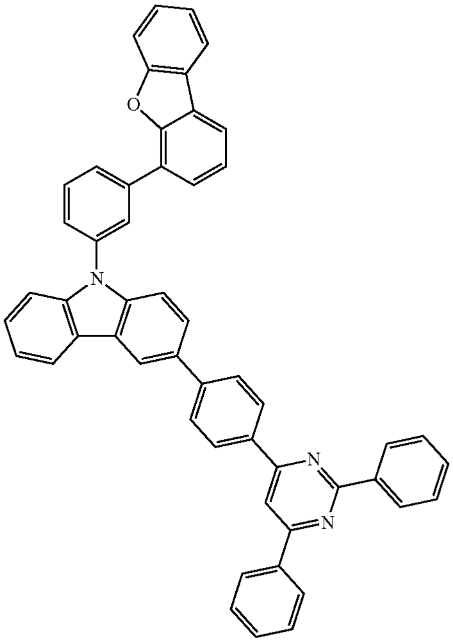
19
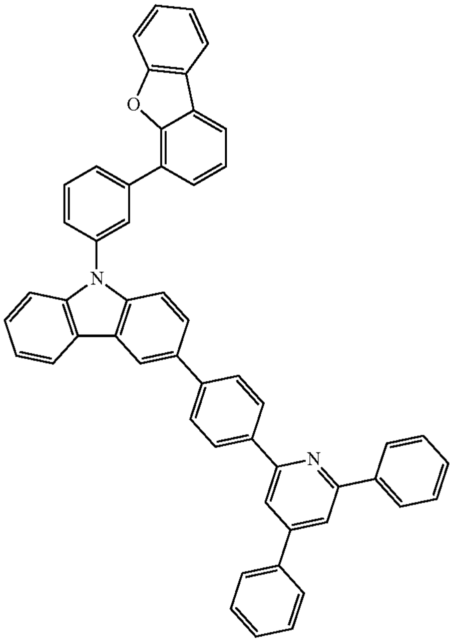

-continued
20
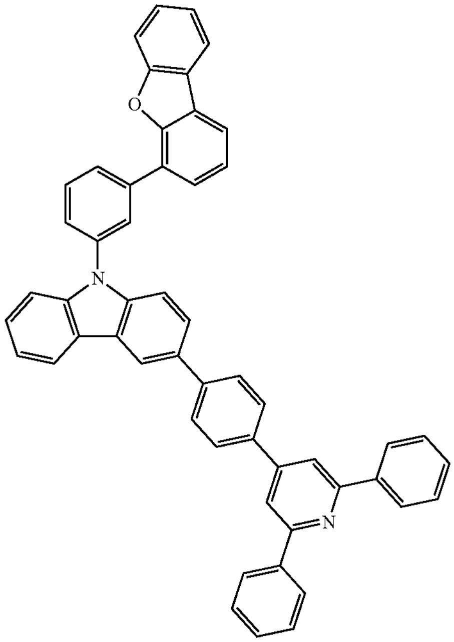
21
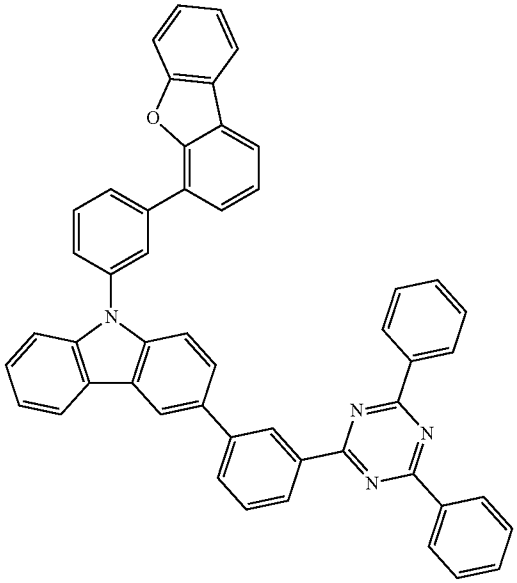
-continued
22
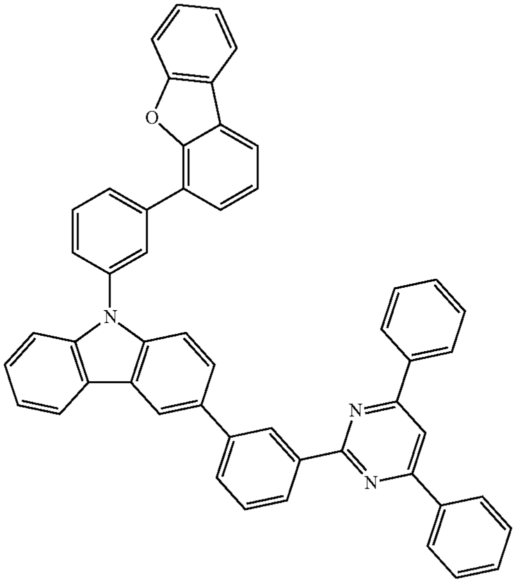
23
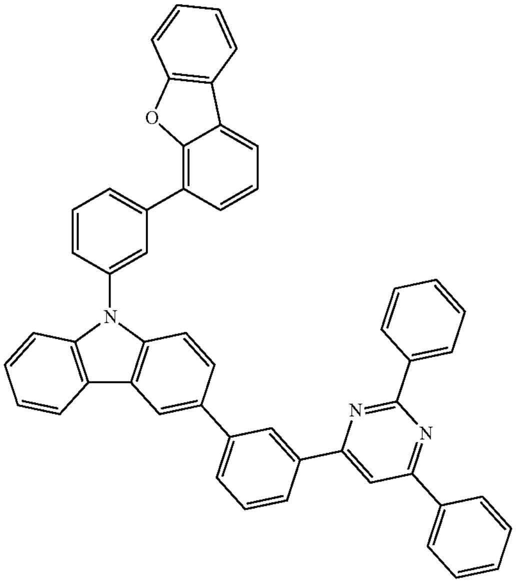

-continued
24
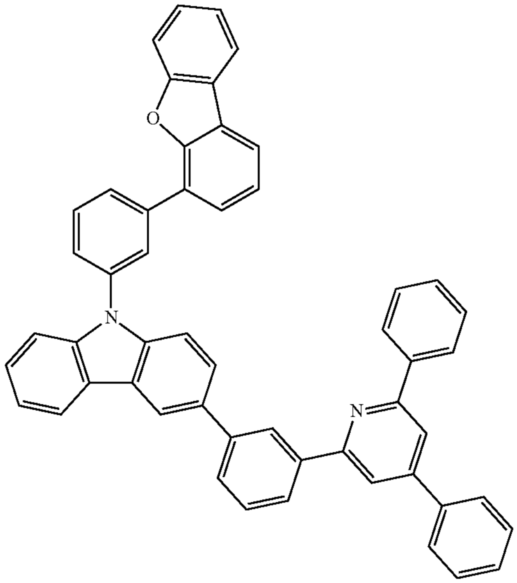
25
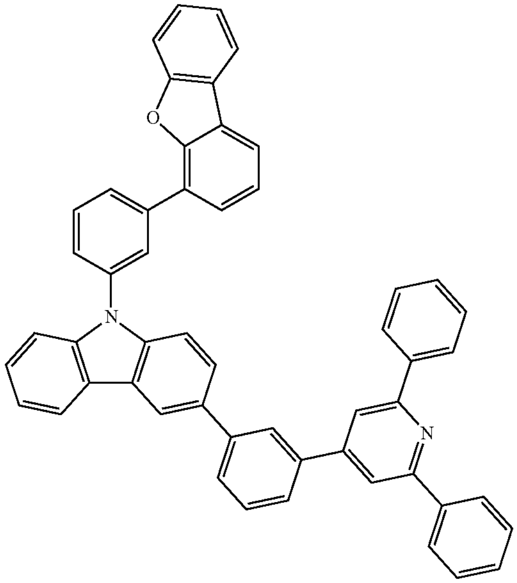
-continued
26
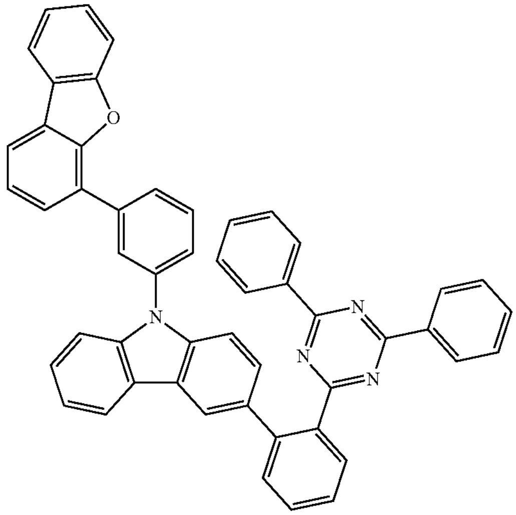
27
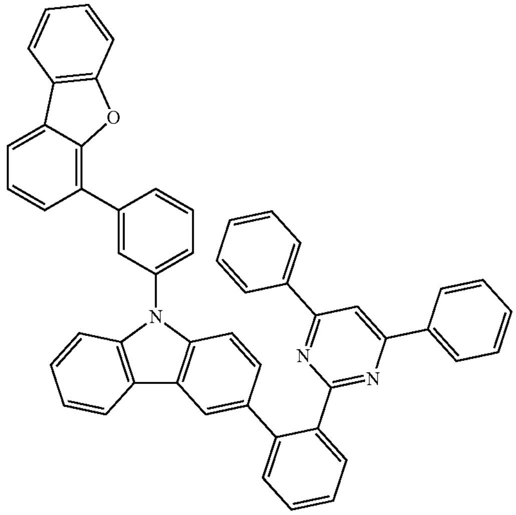
28
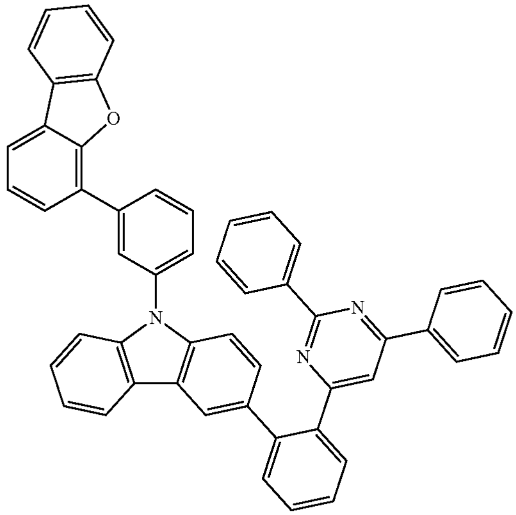

-continued
29
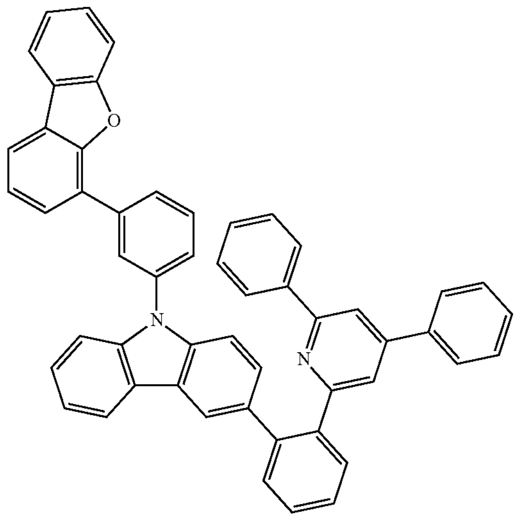
30
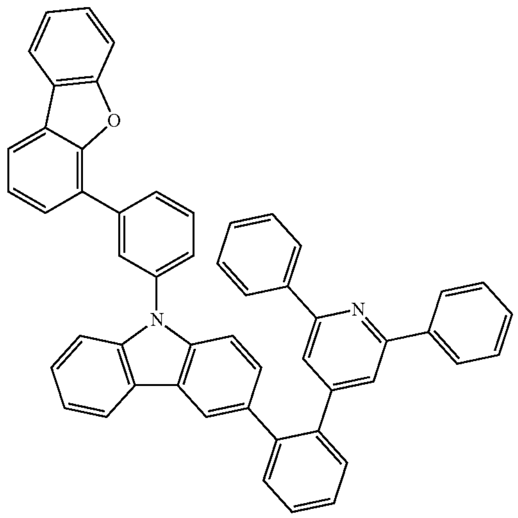
31
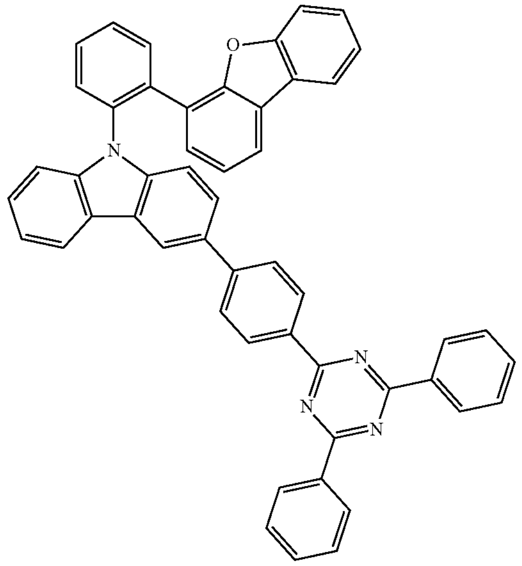
-continued
32
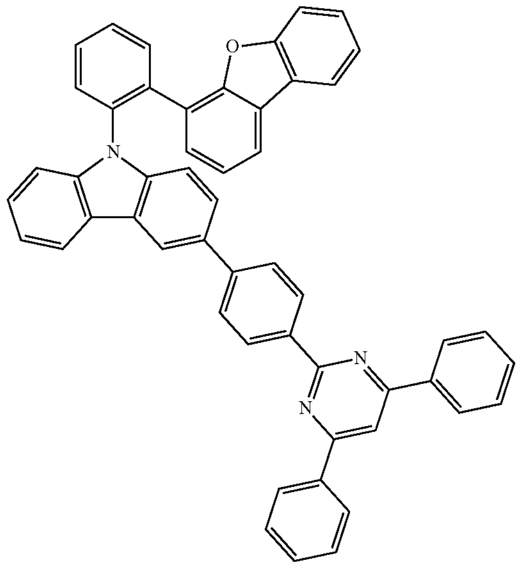
33
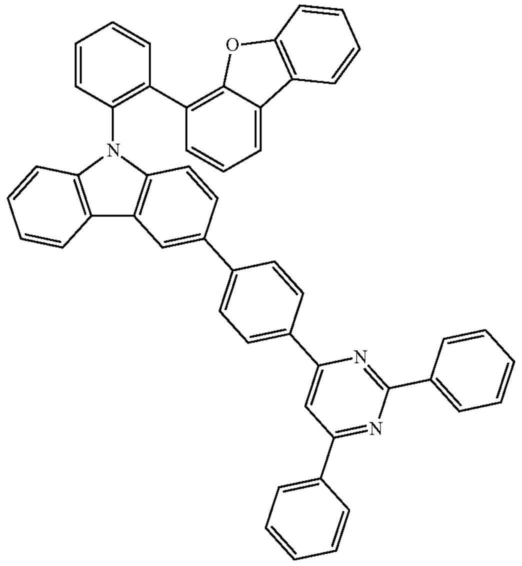

-continued
34
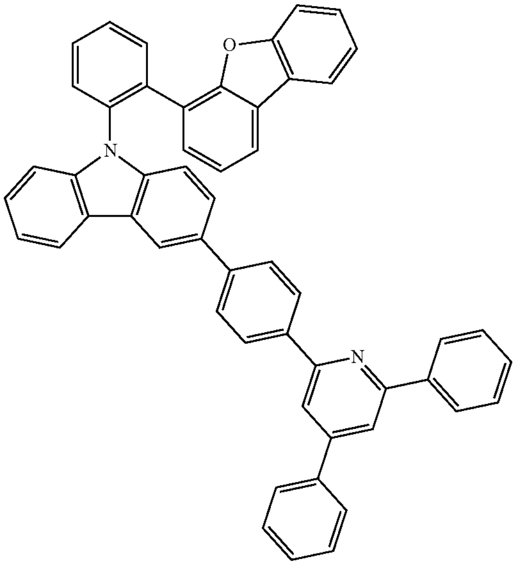
35
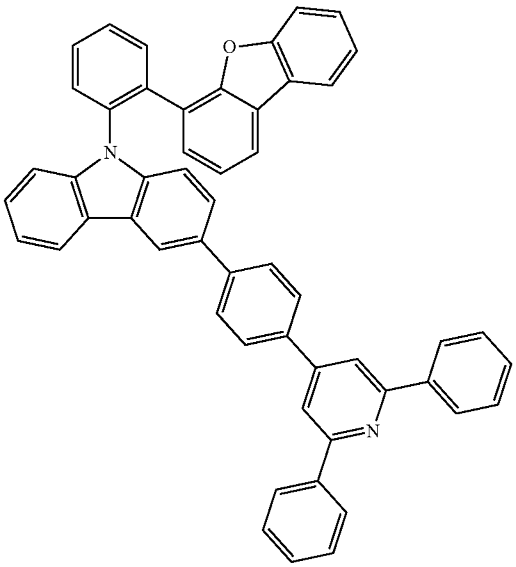
36
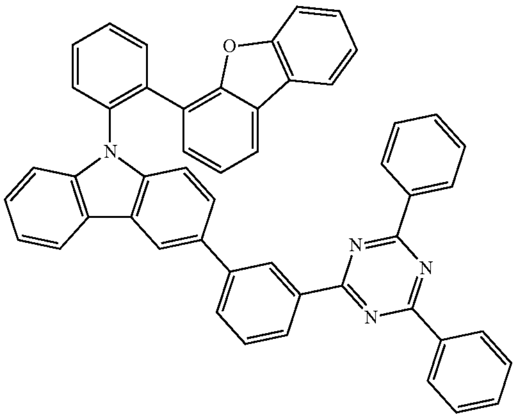
-continued
37
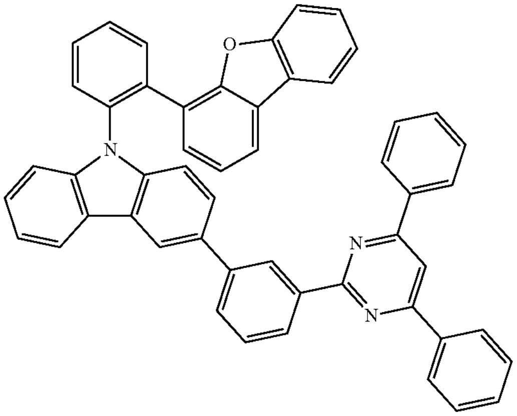
38
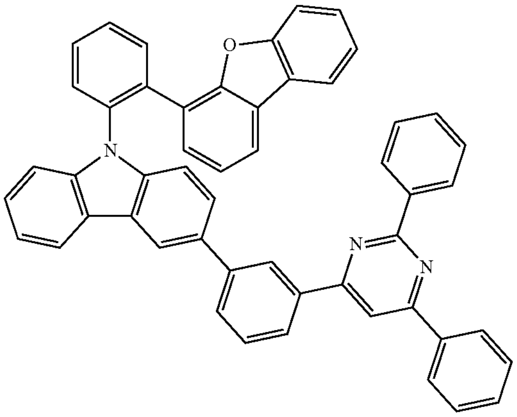
39
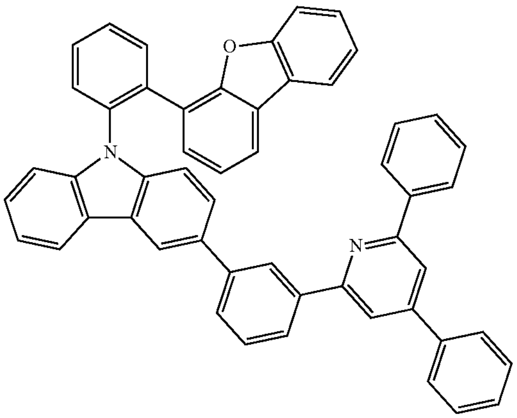

-continued
40
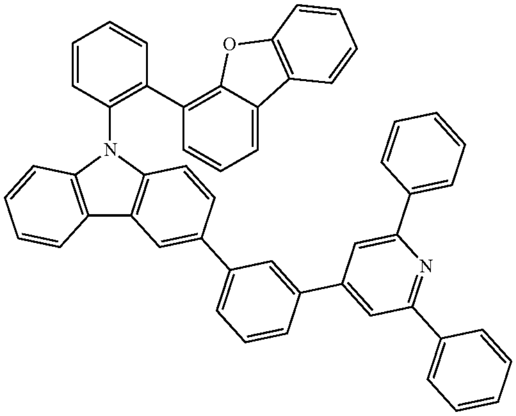
41
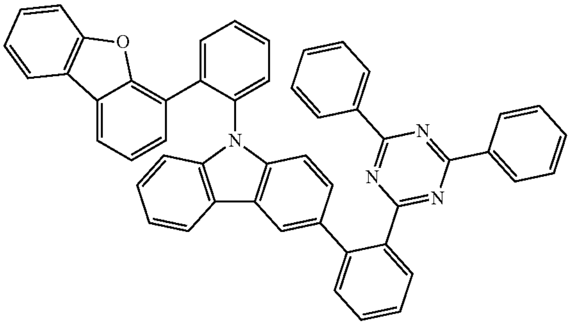
42
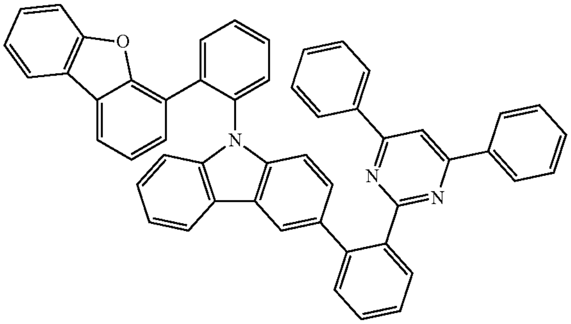
43
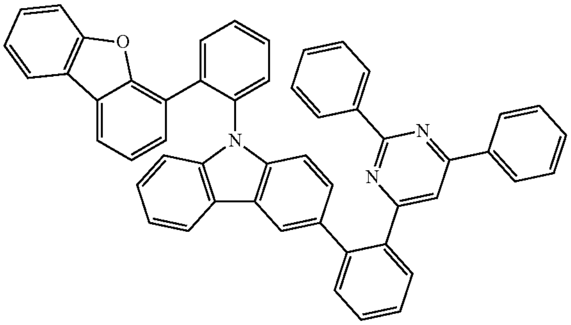
-continued
44
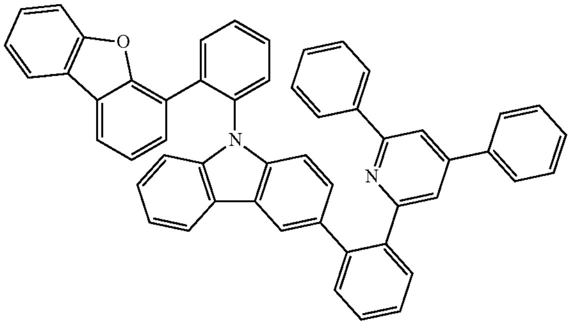
45
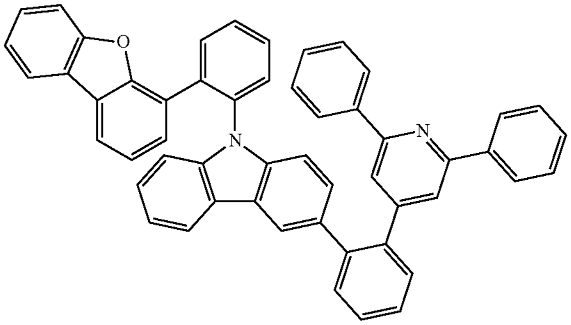
46
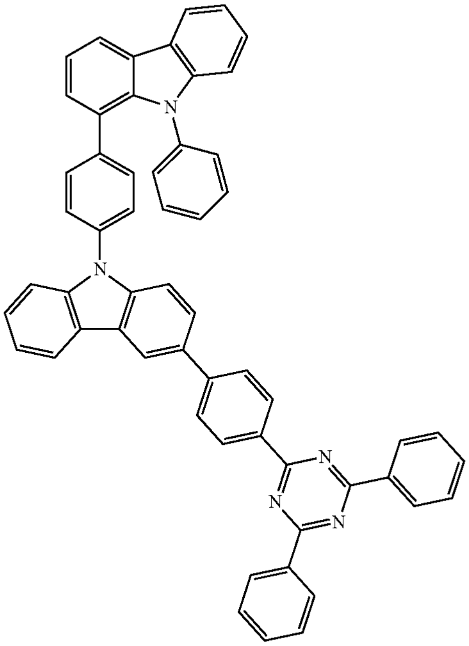

-continued
47
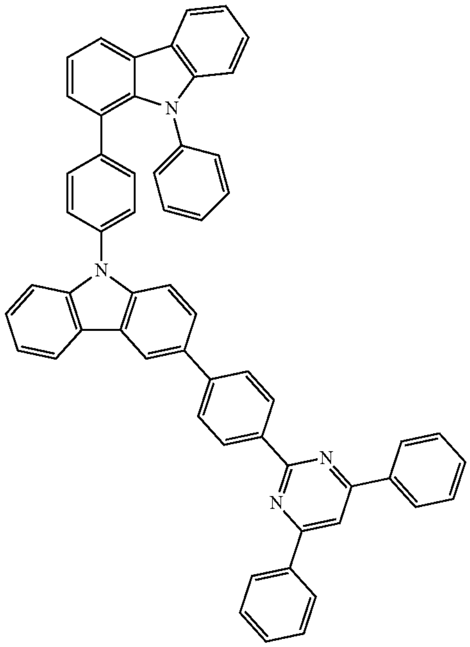
48
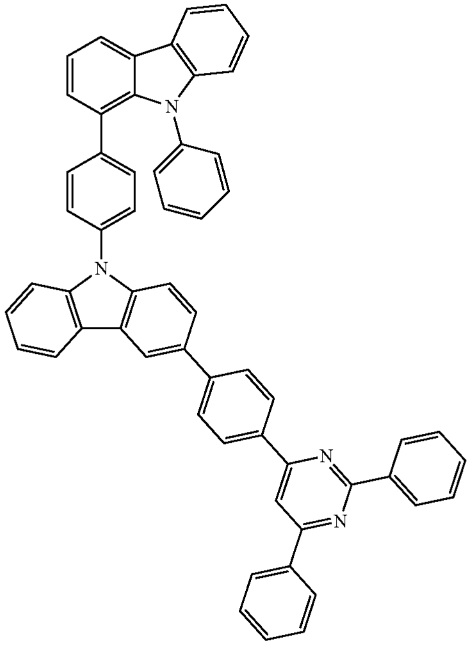
-continued
49
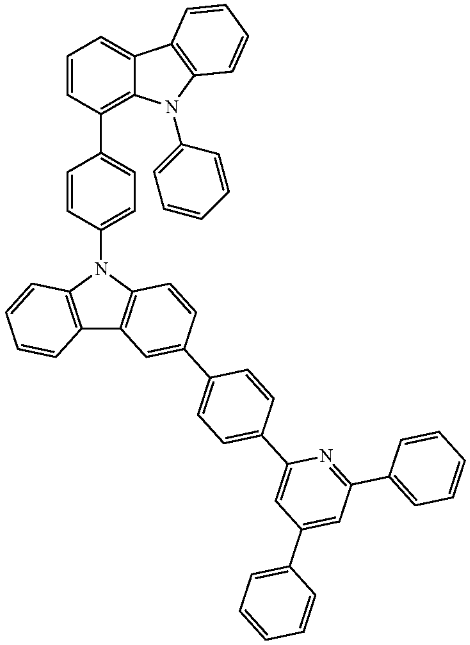
50
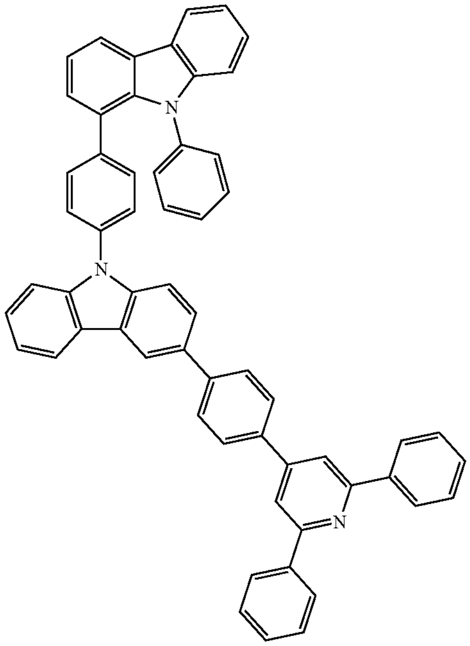

-continued
51
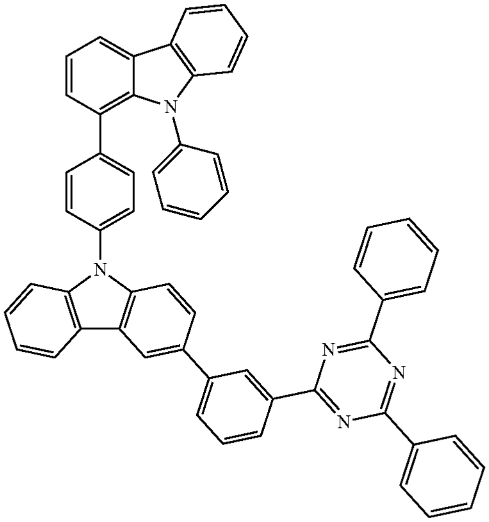
52
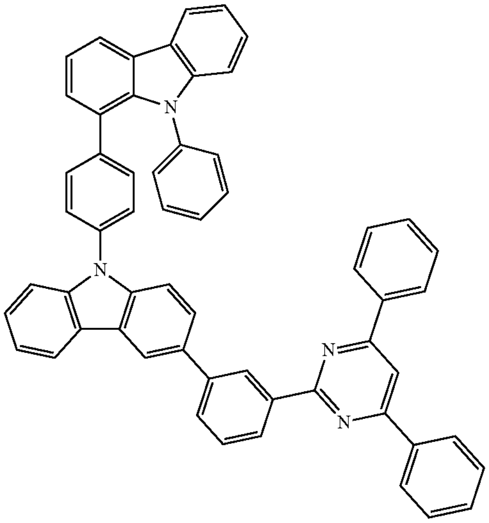
53
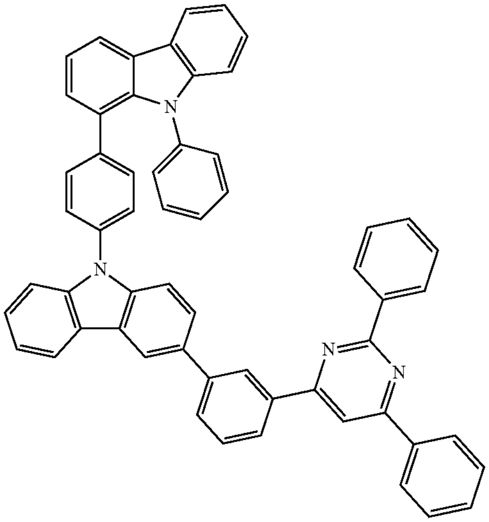
-continued
54
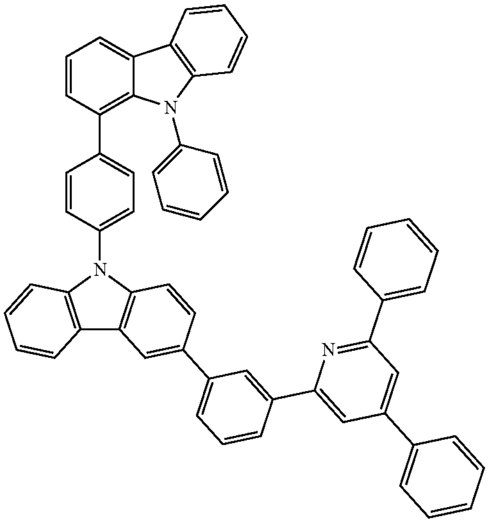
55
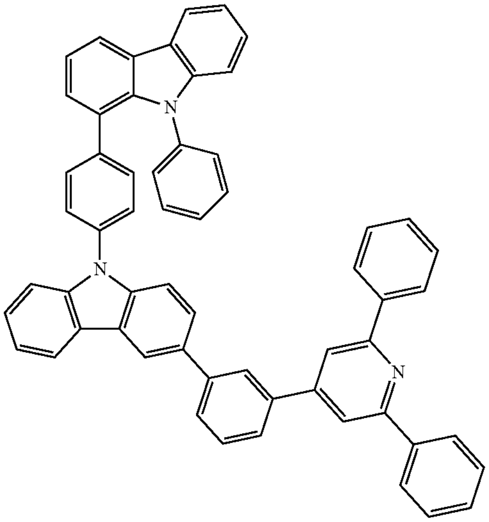
56
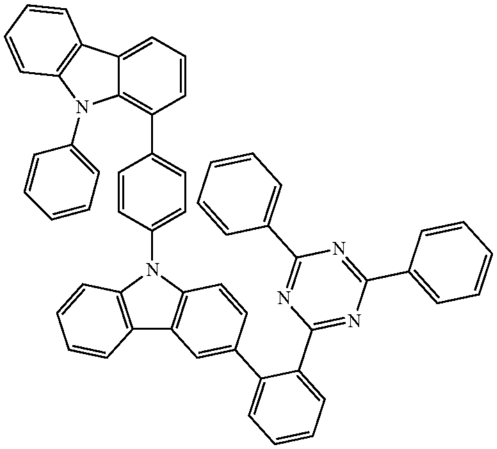

-continued
57
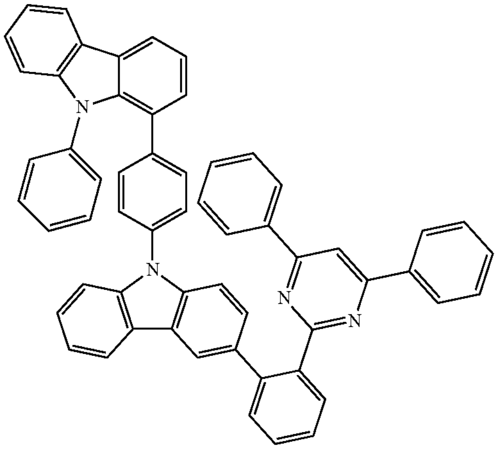
58
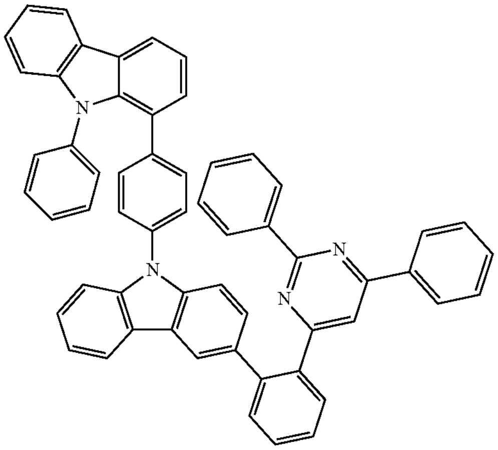
59
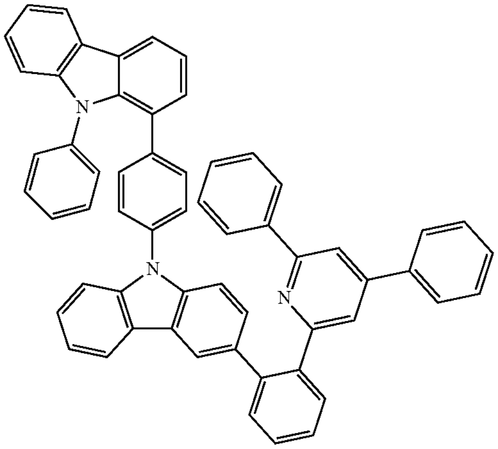
-continued
60
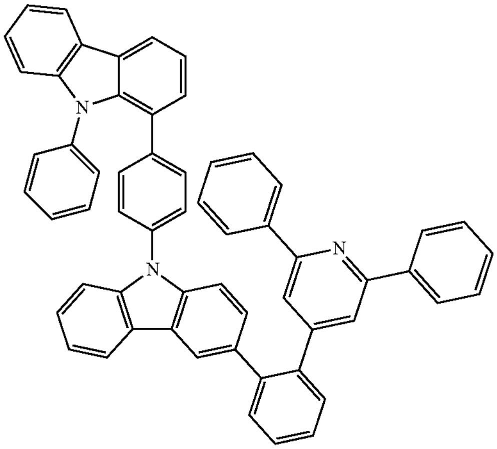
61
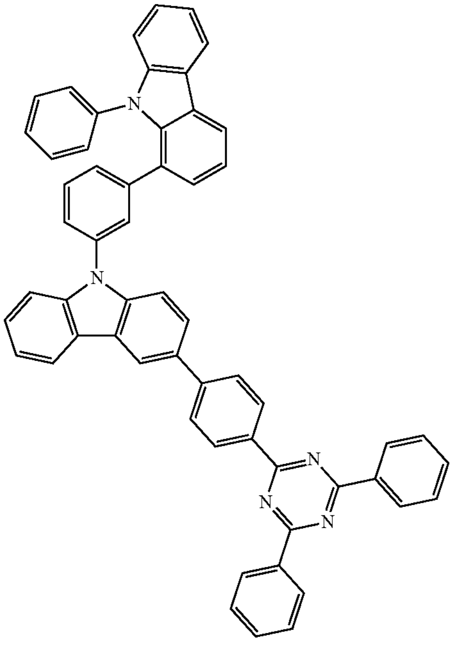

-continued
62
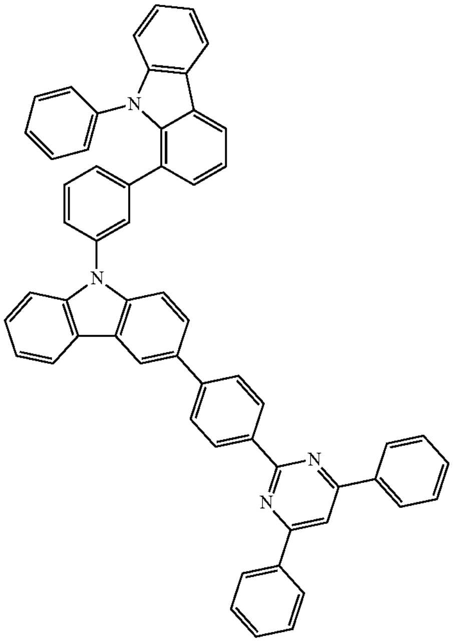
63
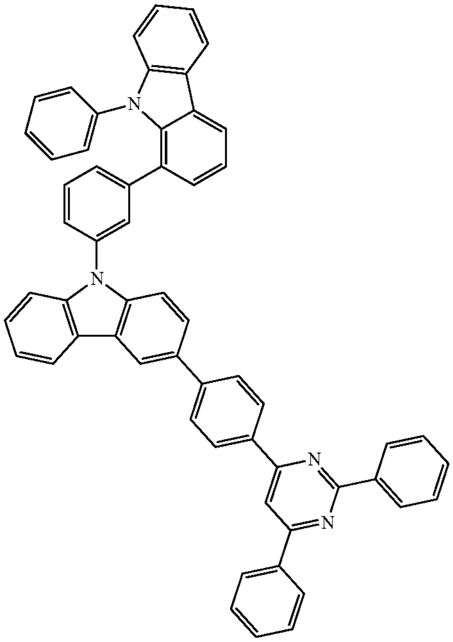
-continued
64
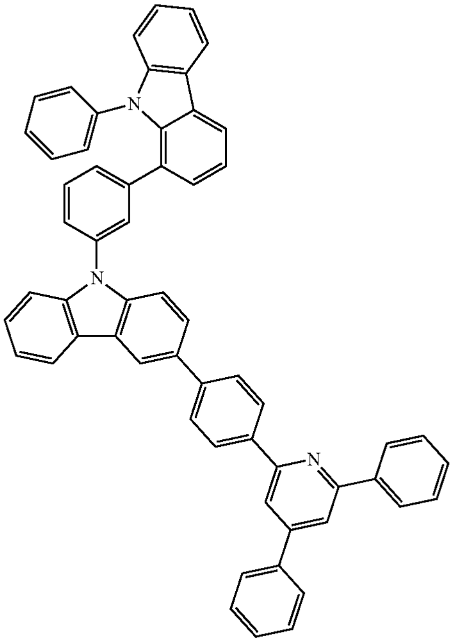
65
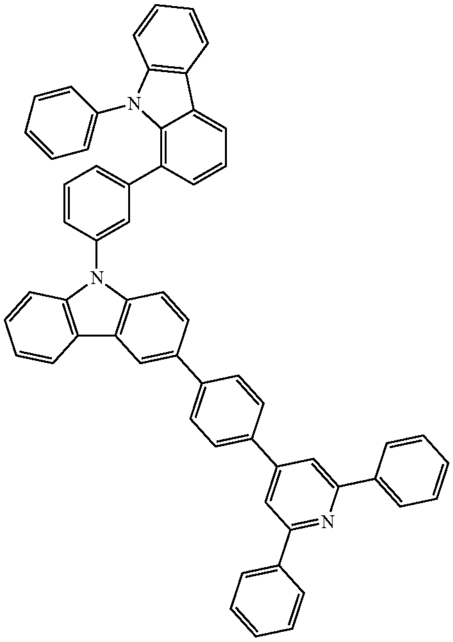

-continued
66
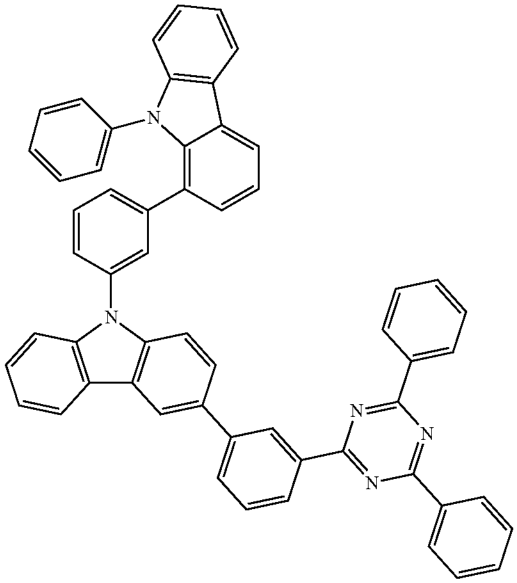
67
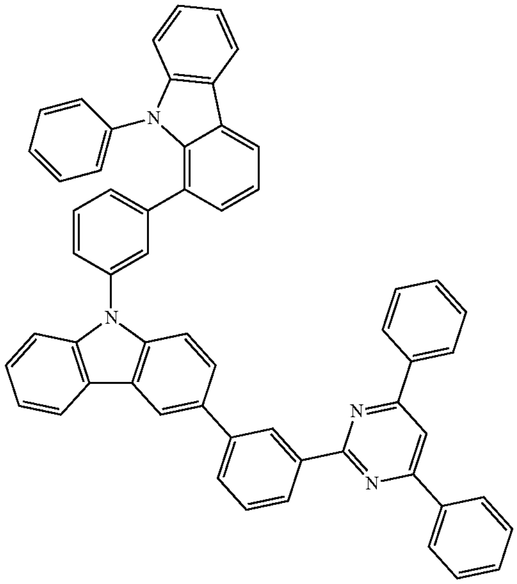
-continued
68
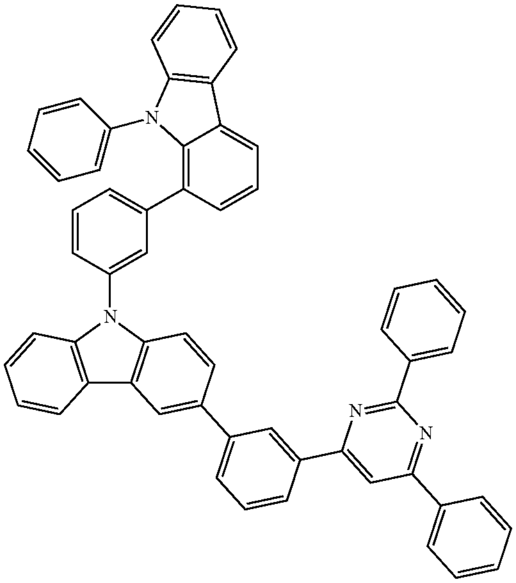
69
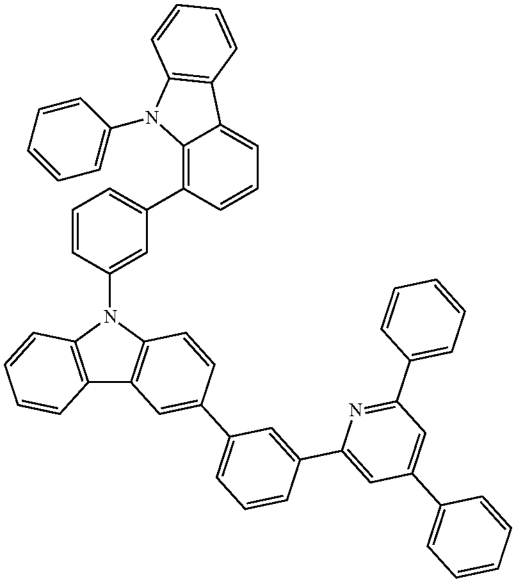

-continued
70
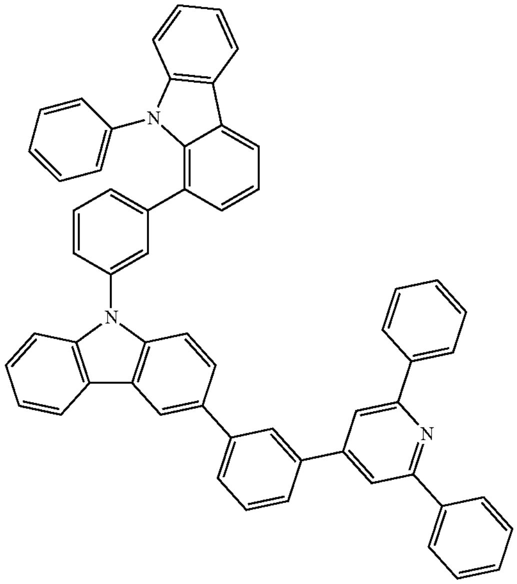
71
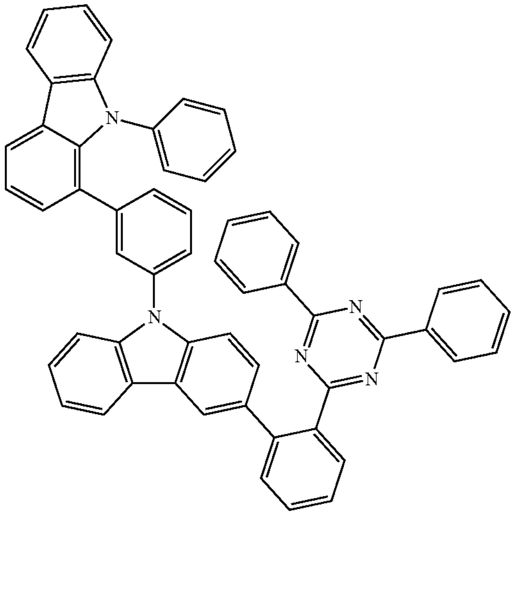
-continued
72
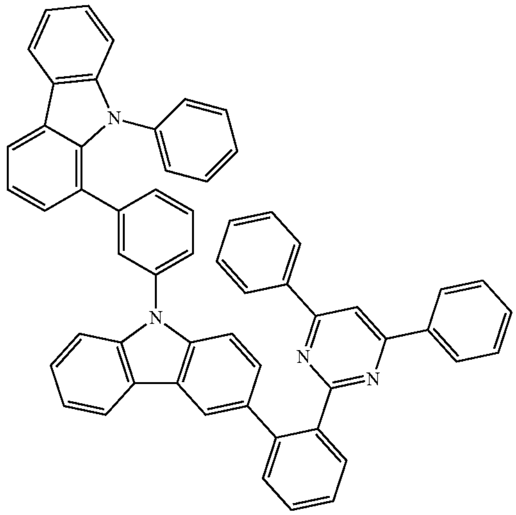
73
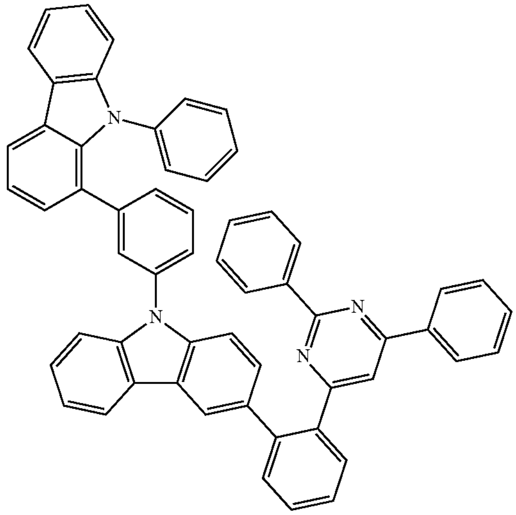
74
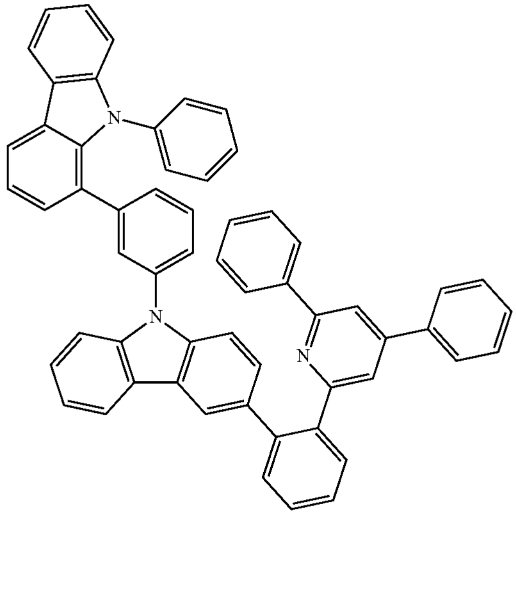

-continued
75
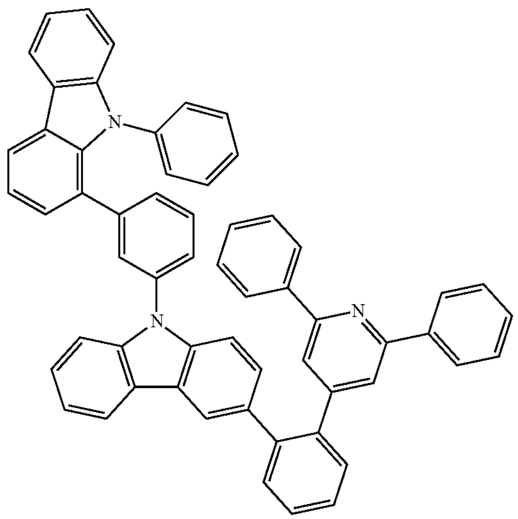
-continued
77
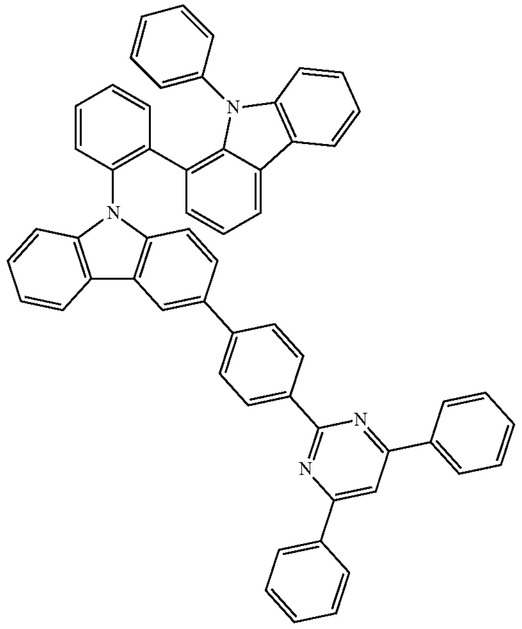
76
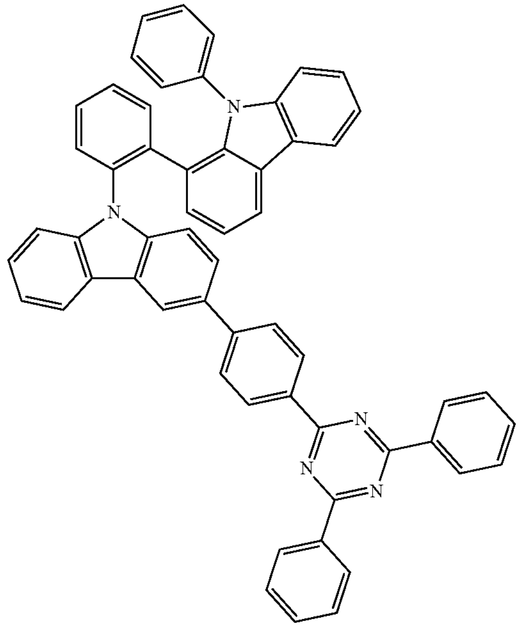
78
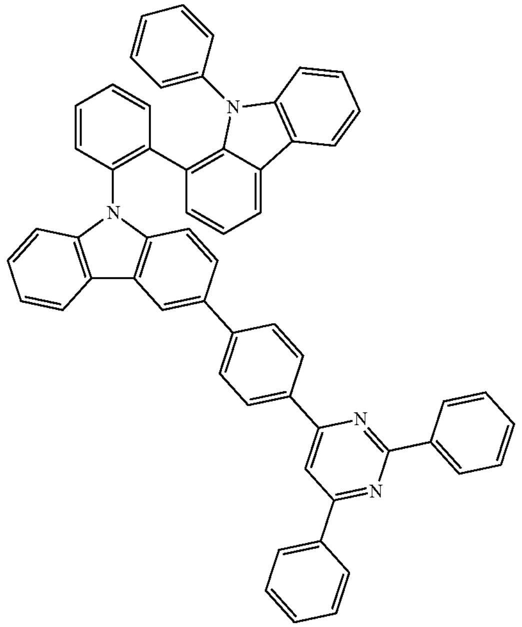

-continued
79
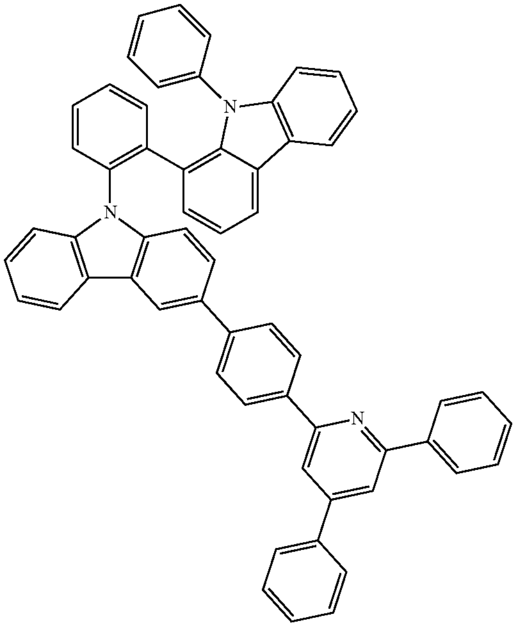
80
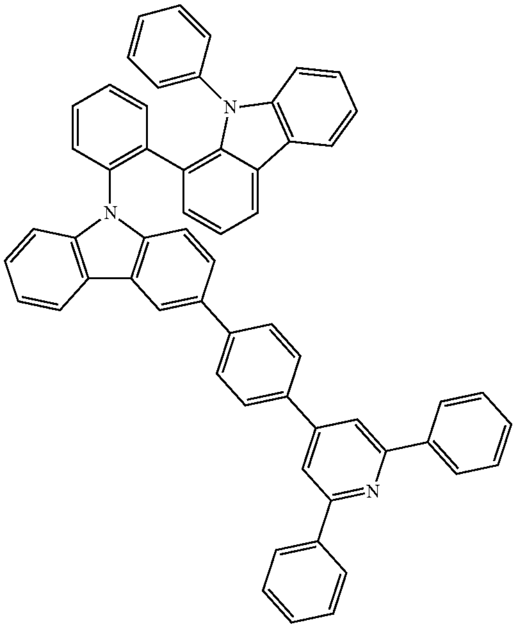
-continued
81
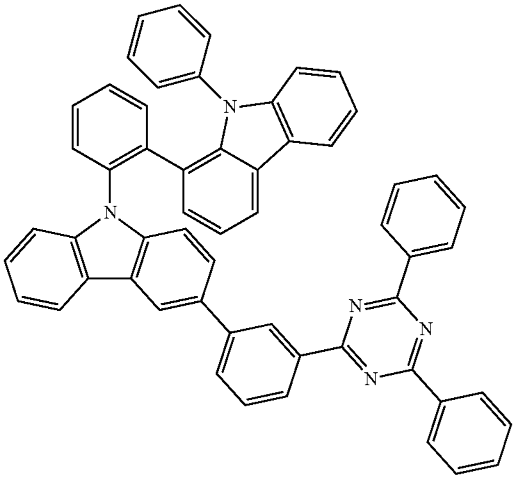
82
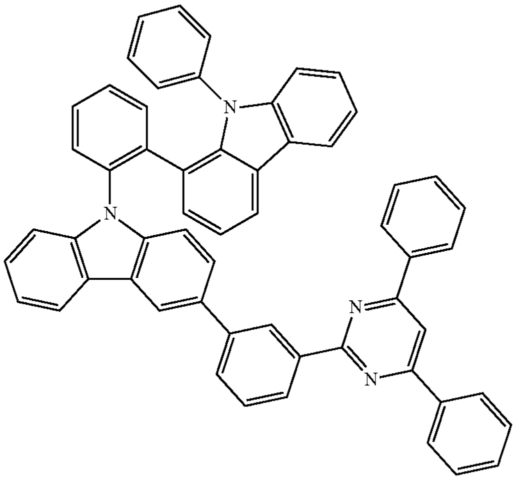
83
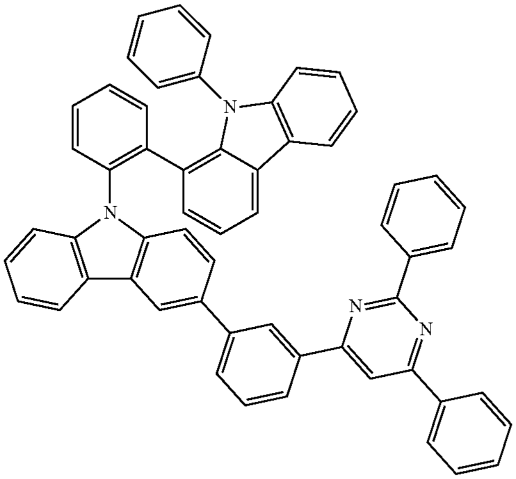

-continued
84
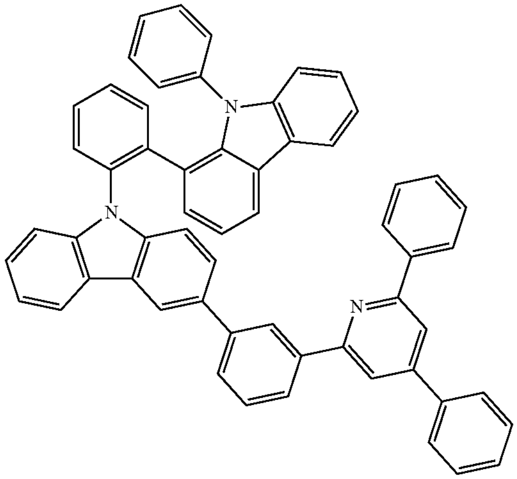
85
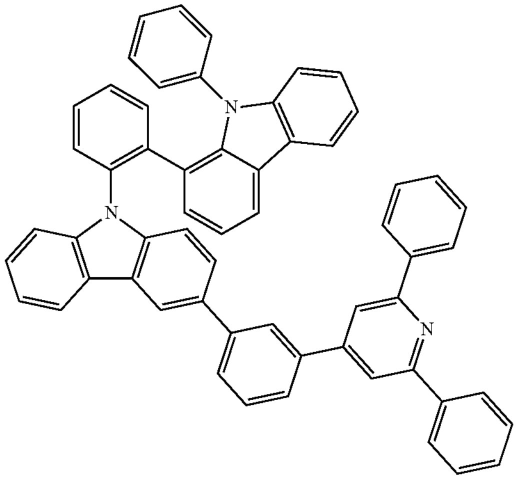
86
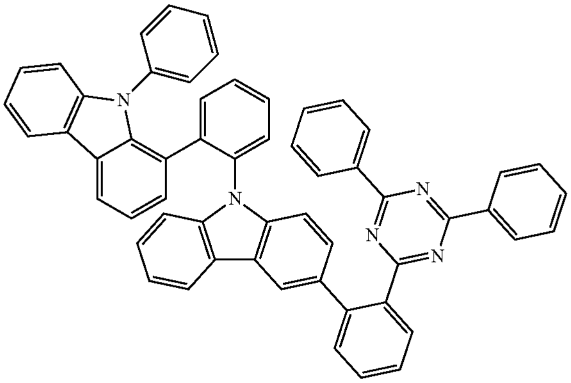
-continued
87
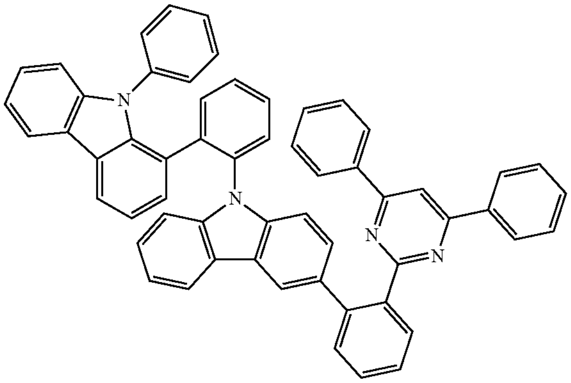
88
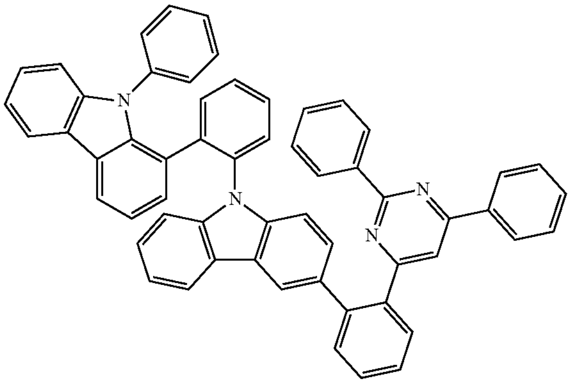
89
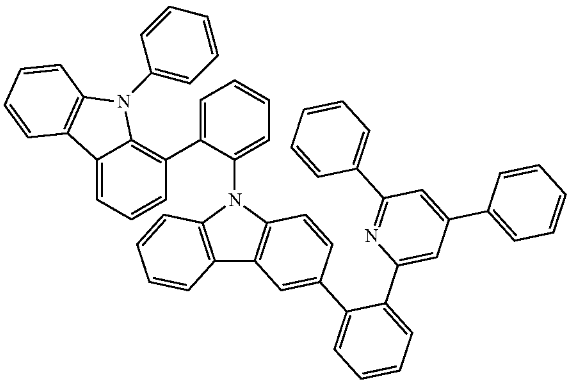
90
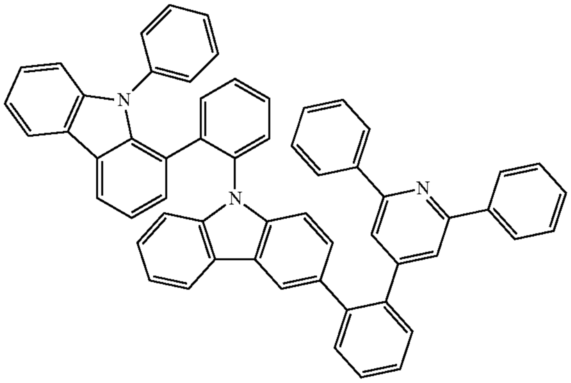

-continued
91
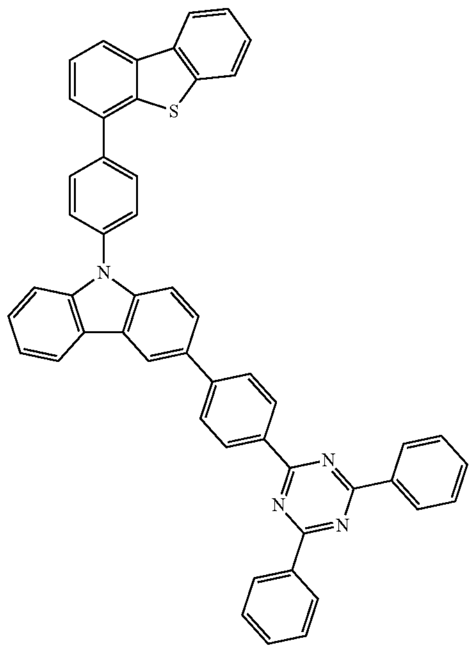
92
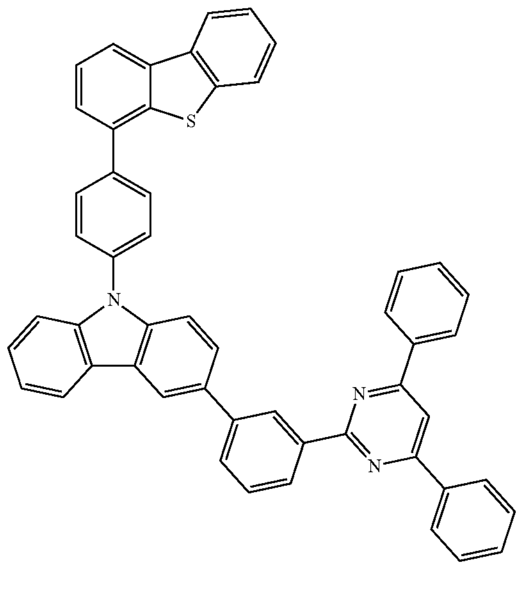
-continued
93
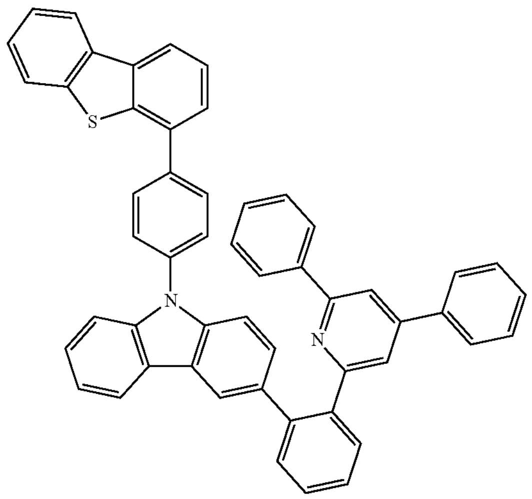
94
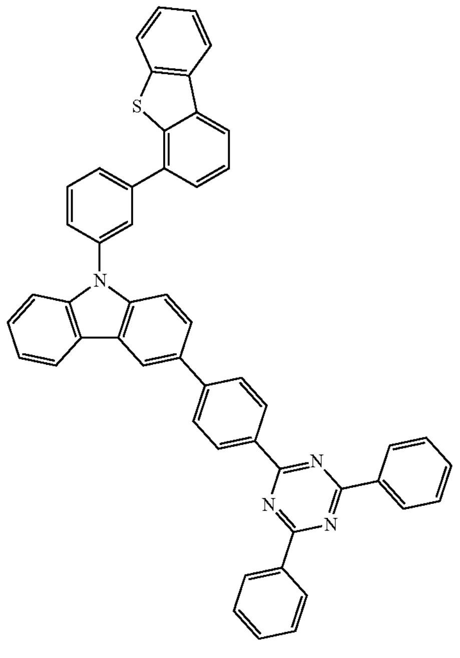

-continued
95
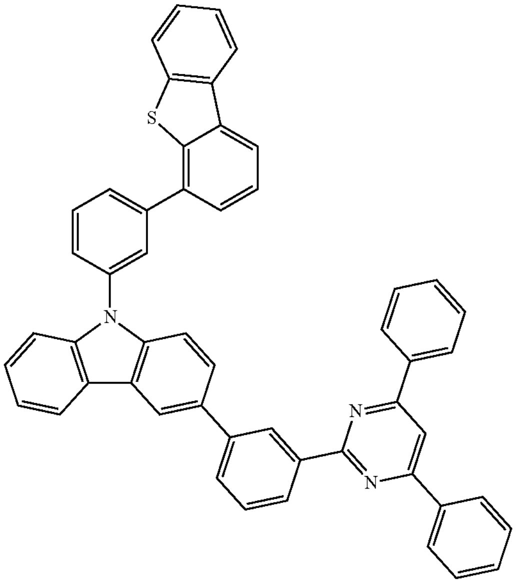
96
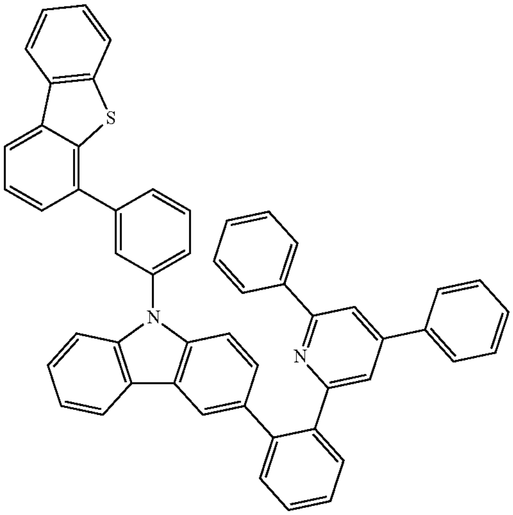
-continued
97
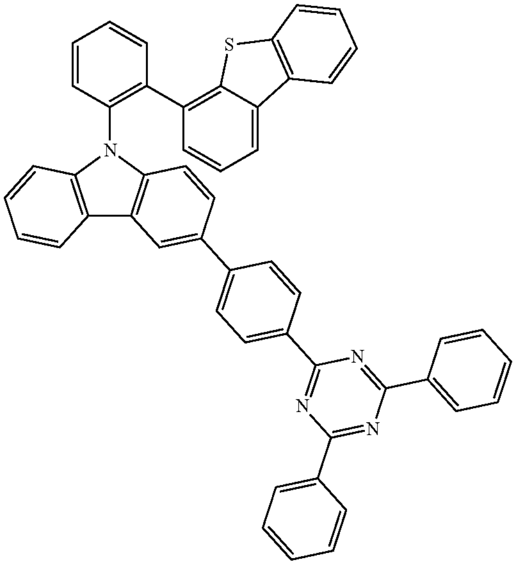
98
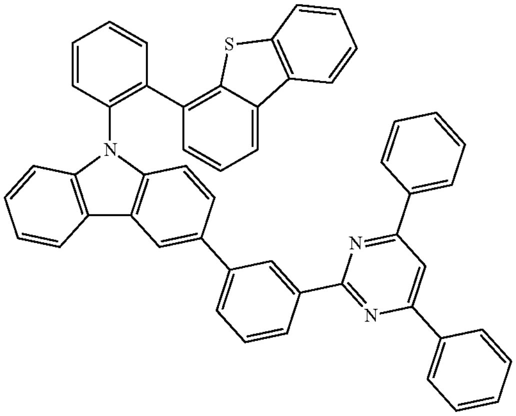
99
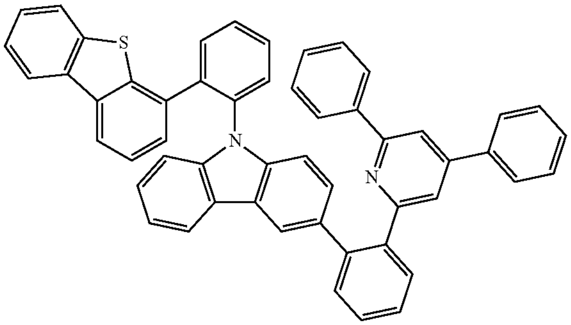

-continued
100
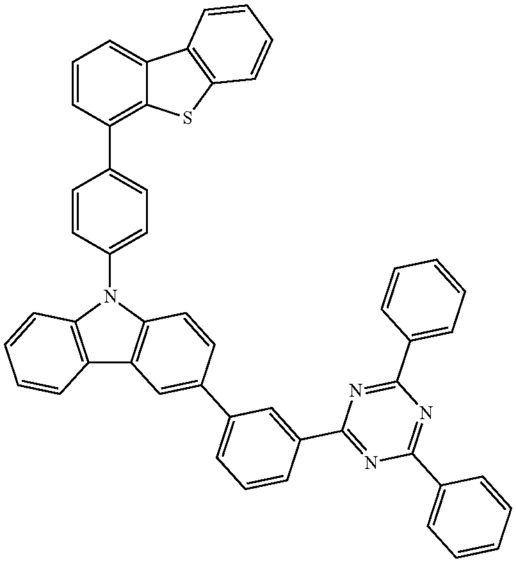
101
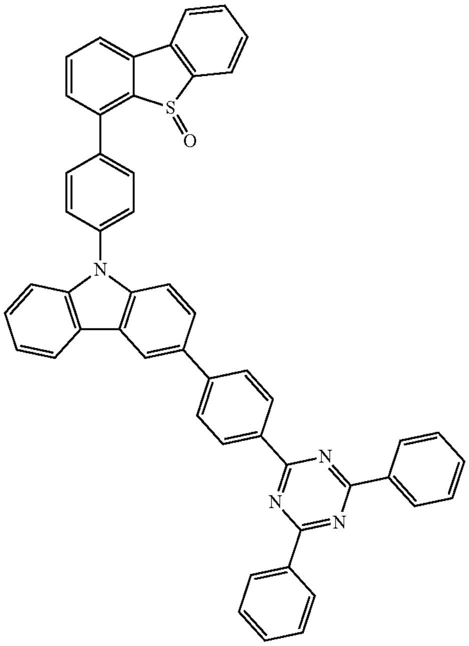
-continued
102
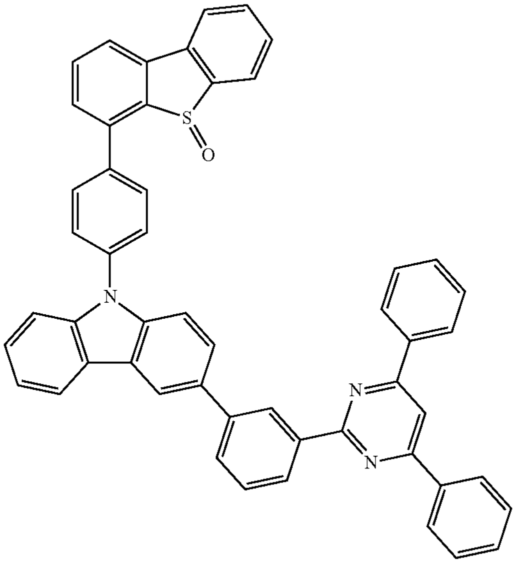
103
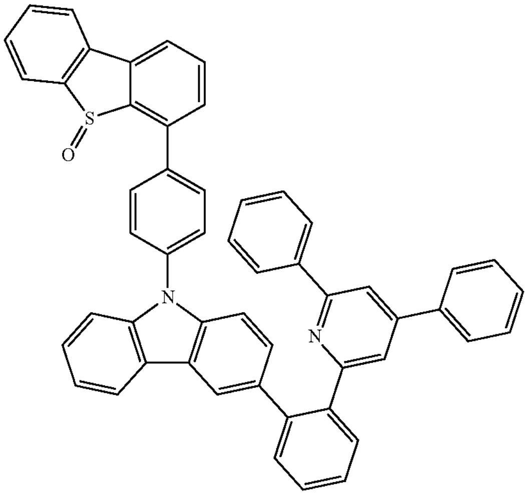

-continued
104
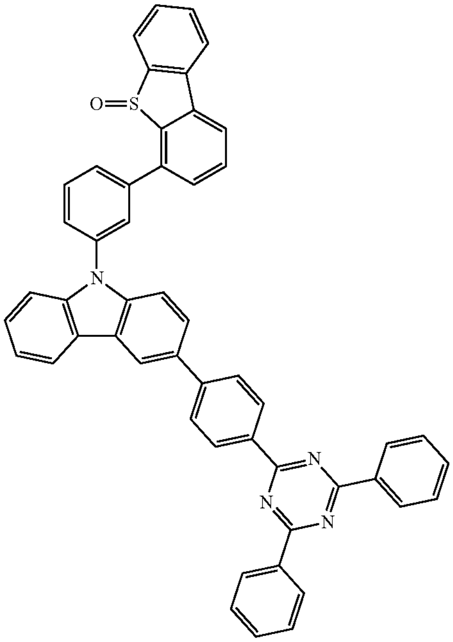
105
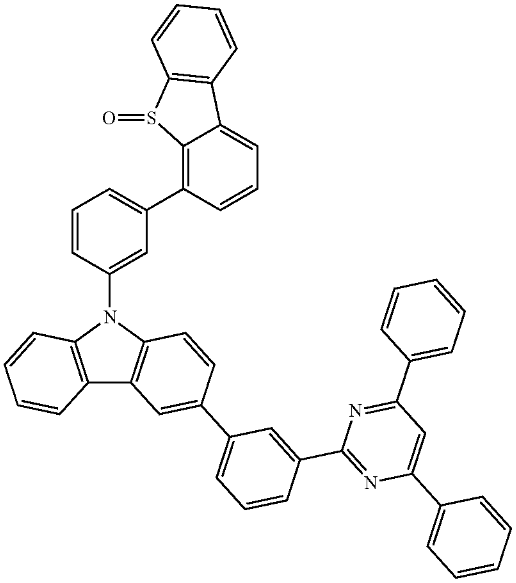
-continued
106
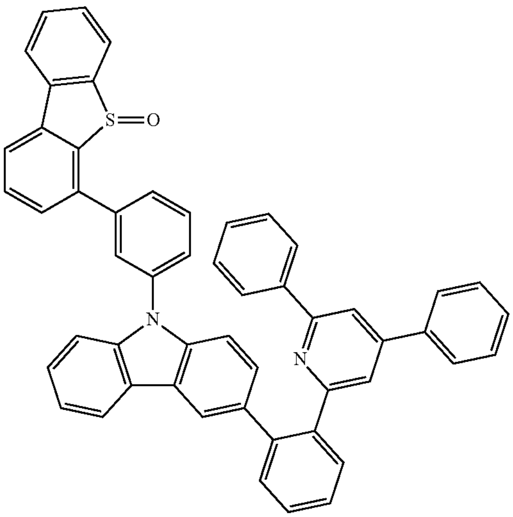
107
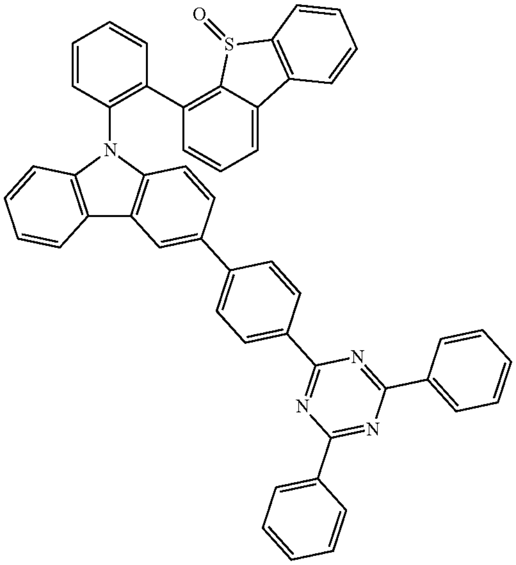
108
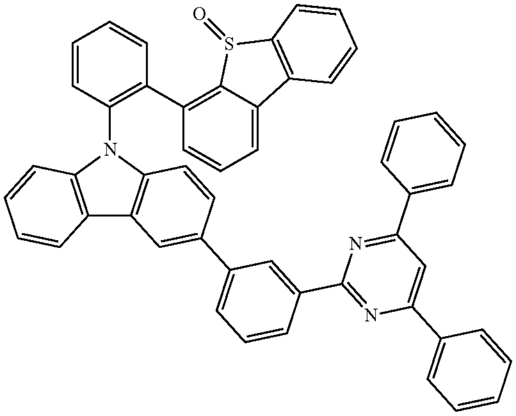

-continued
109
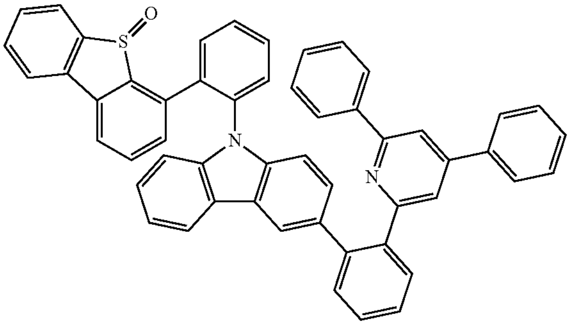
110
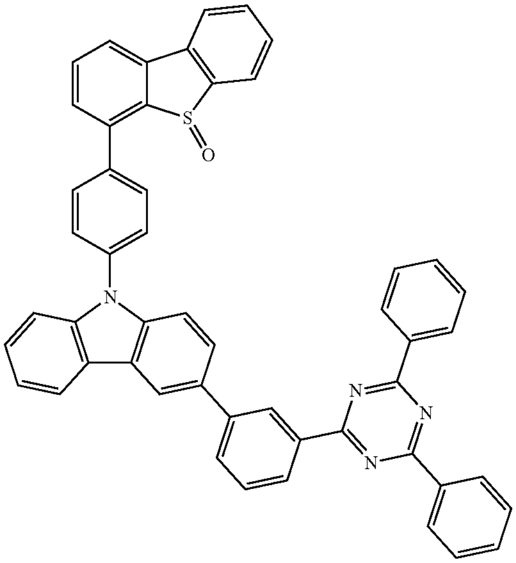
111
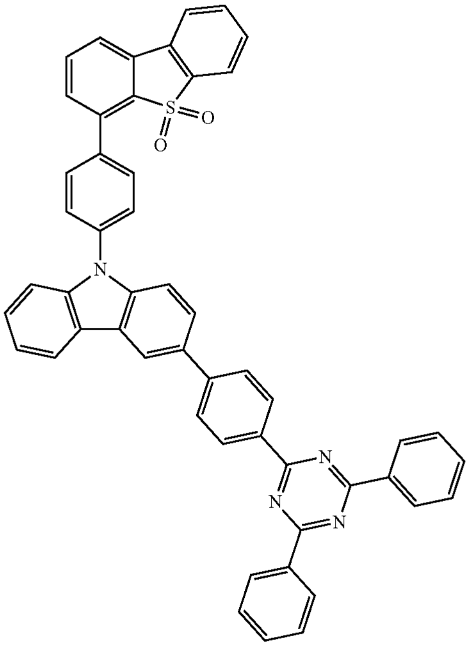
-continued
112
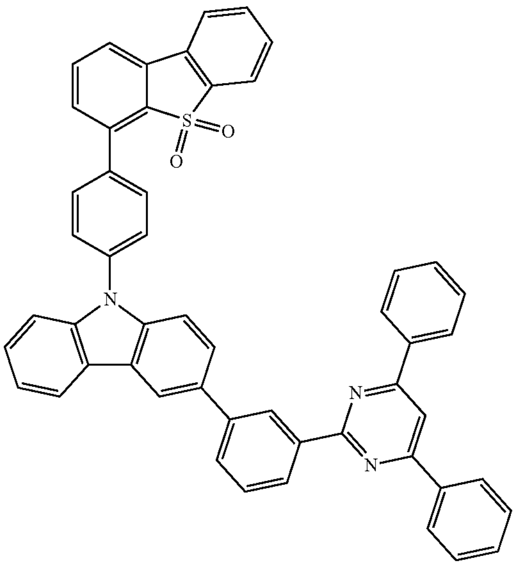
113
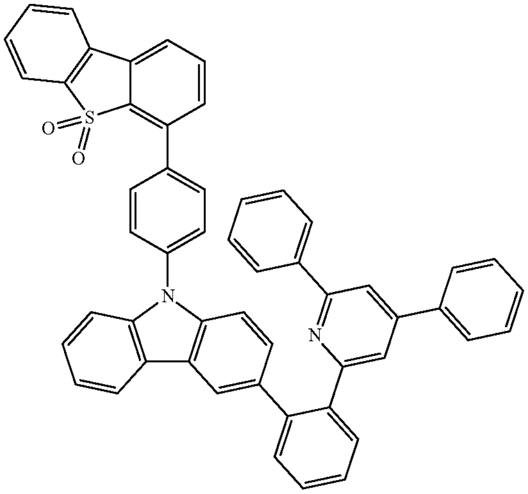

114
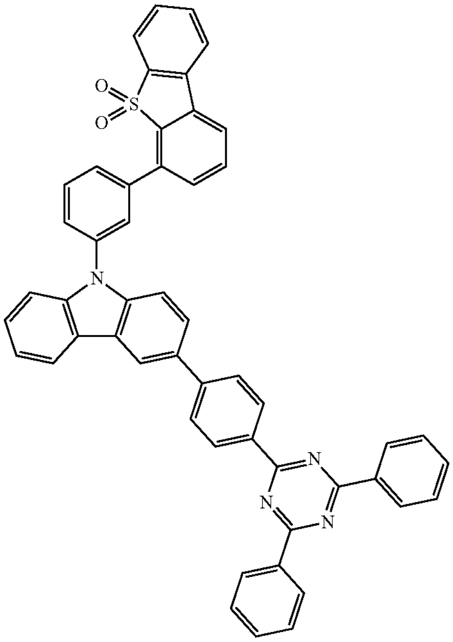
115
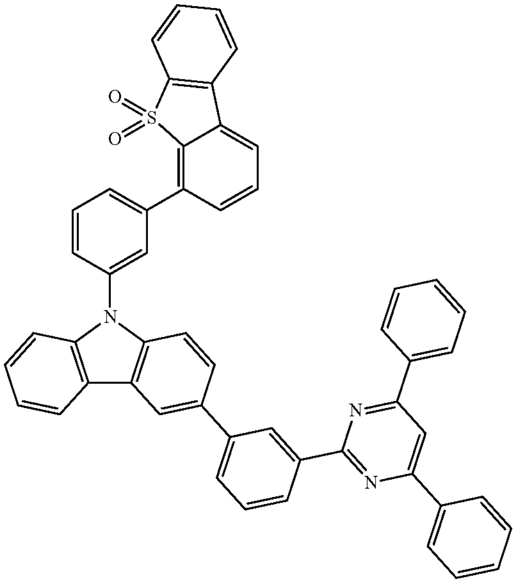
116
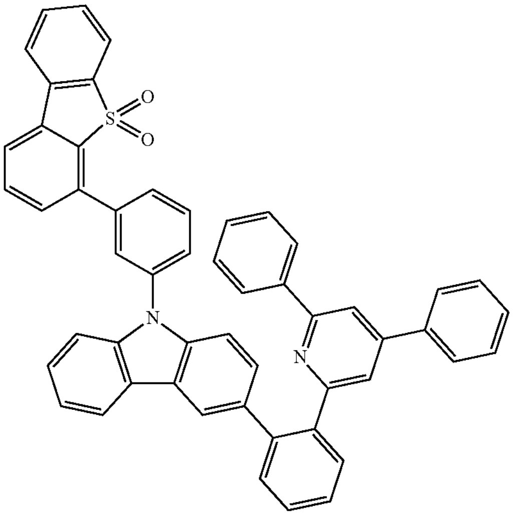
117
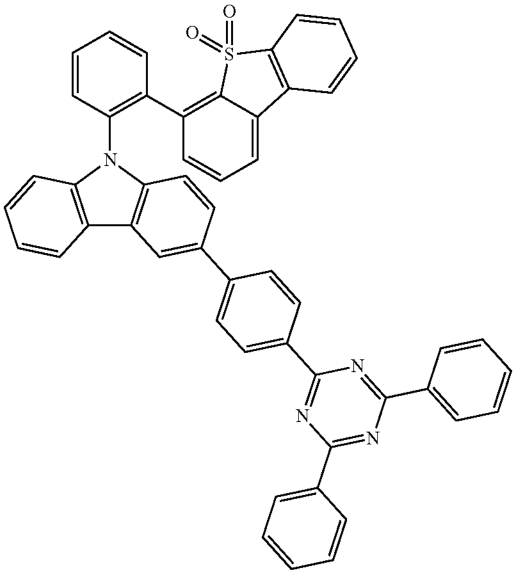
118
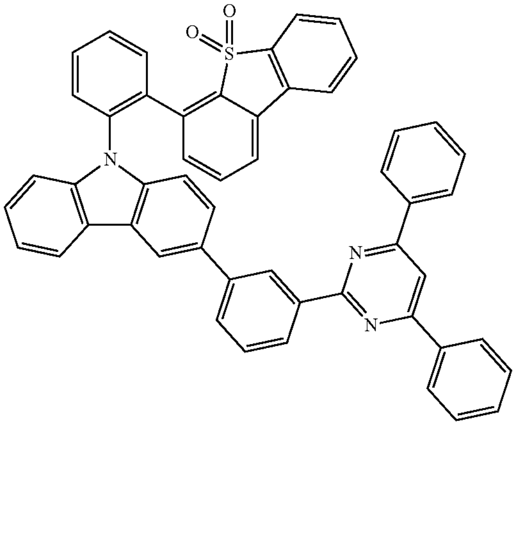

-continued
119
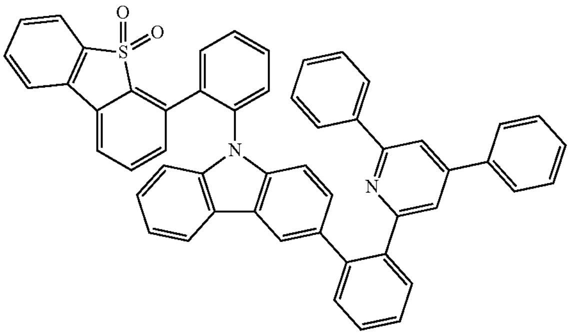
120
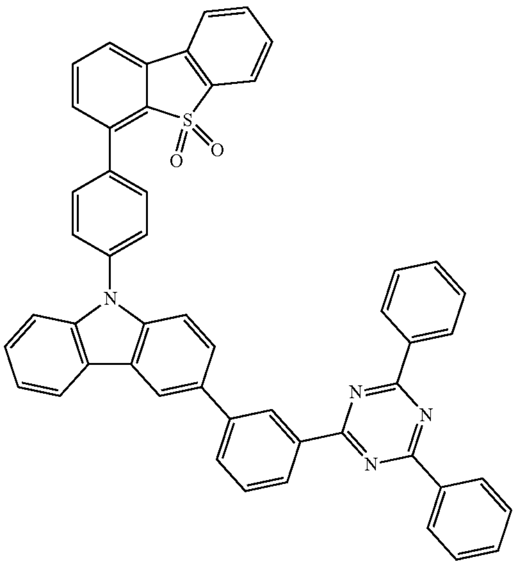
121
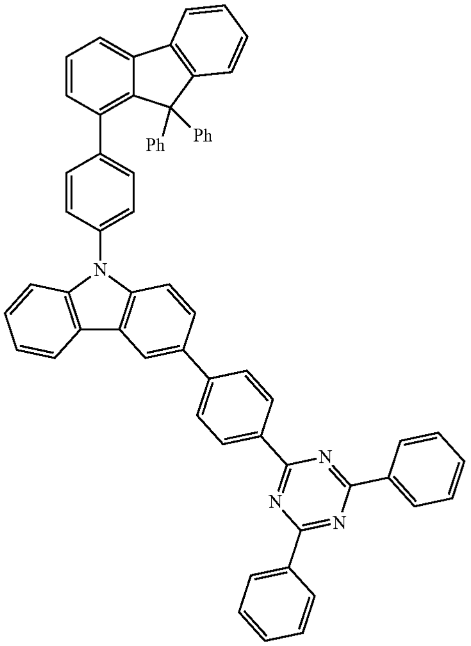
-continued
122
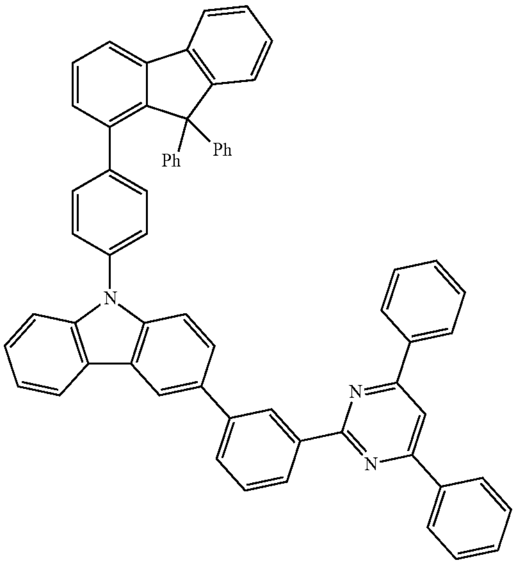
123
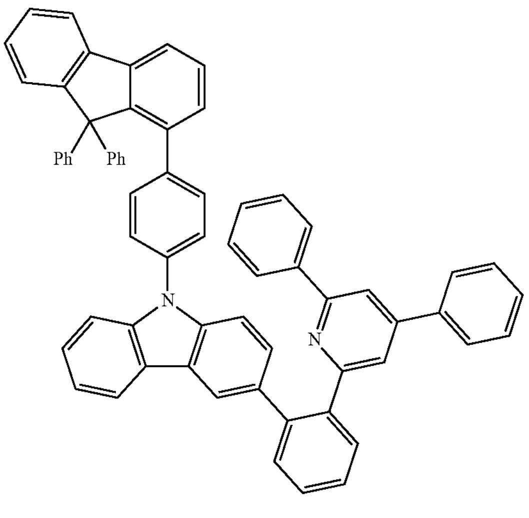

-continued
124
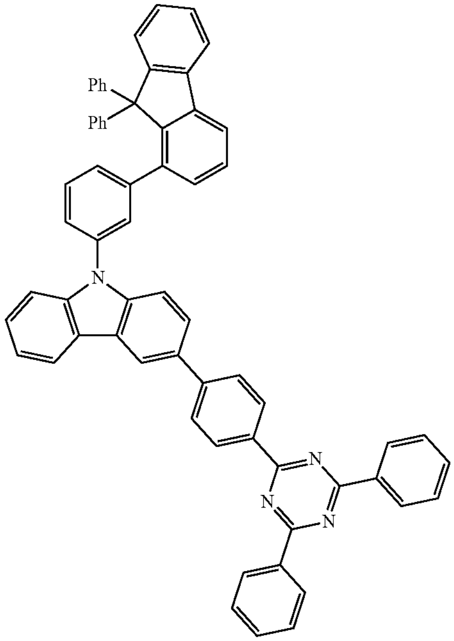
125
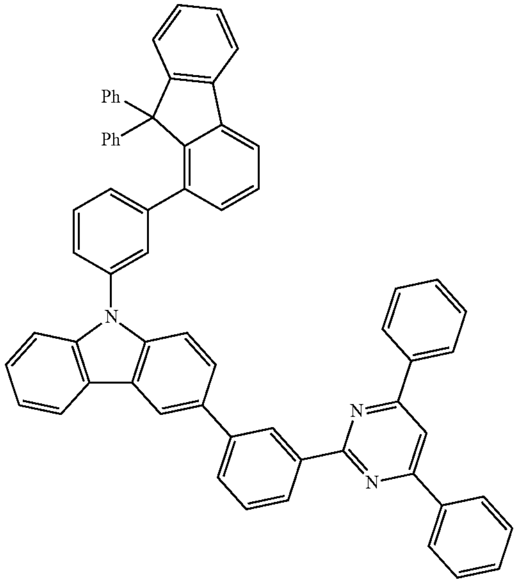
-continued
126
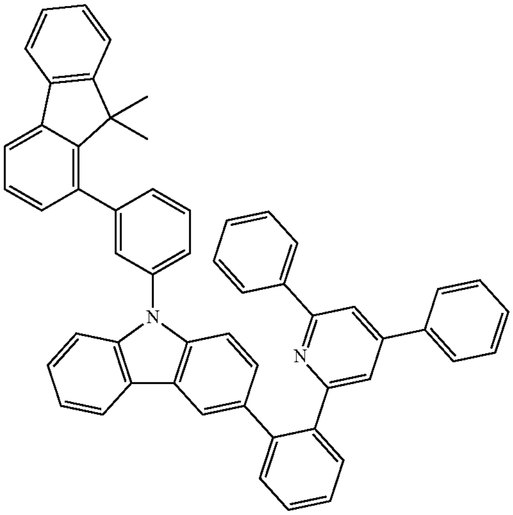
127
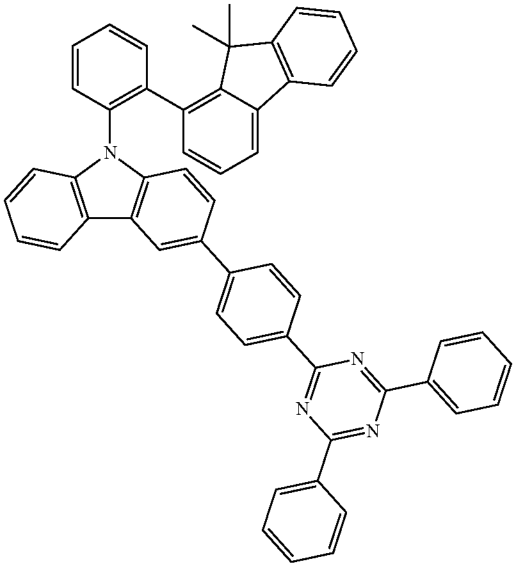
128
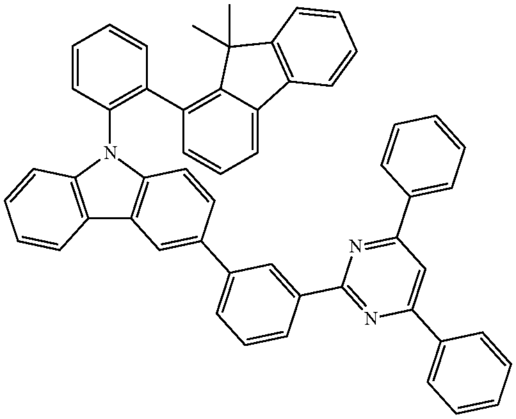

-continued
129
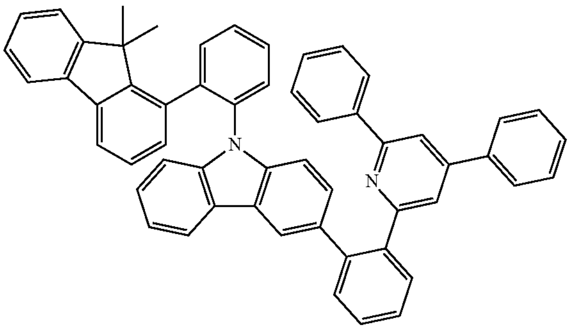
130
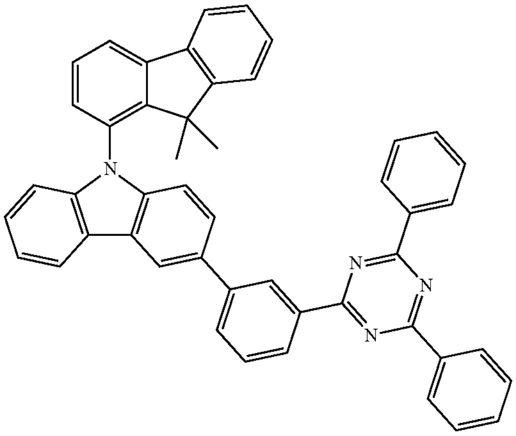
131
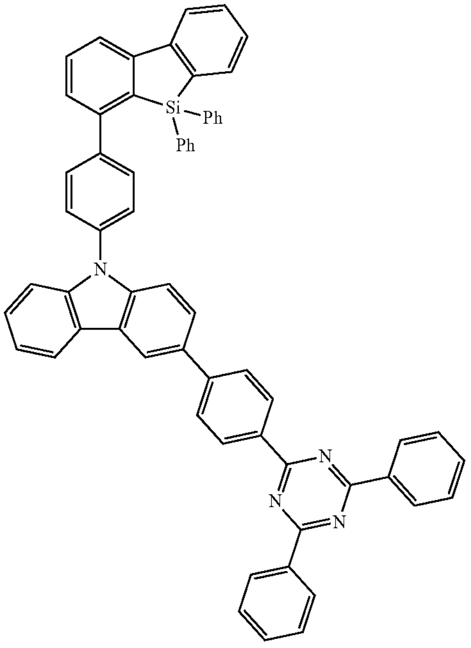
-continued
132
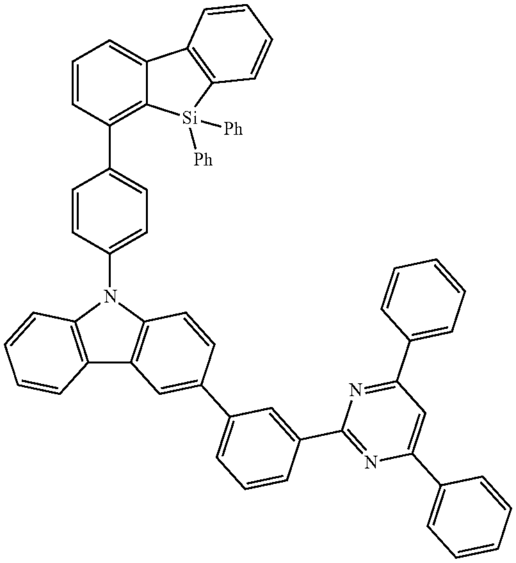
133
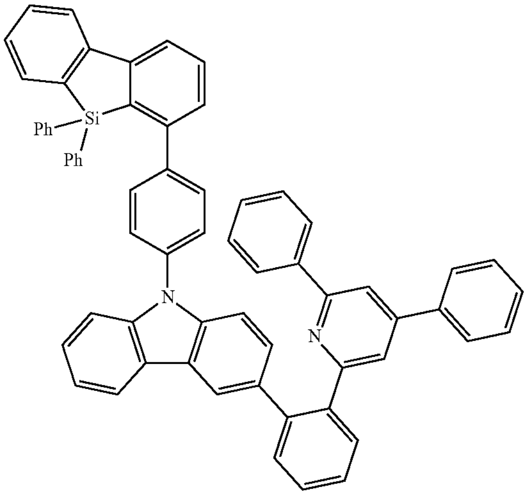

-continued
134
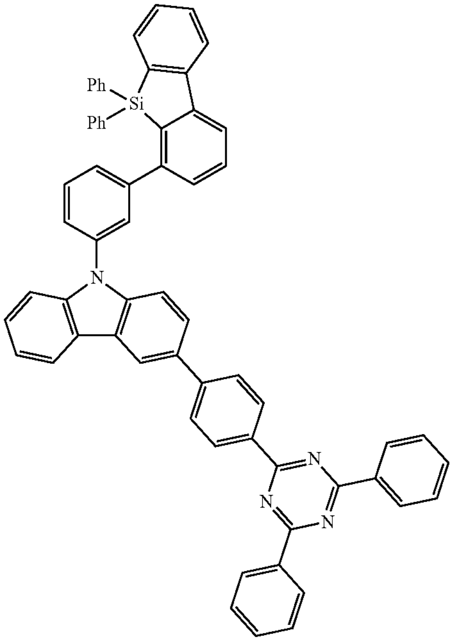
135
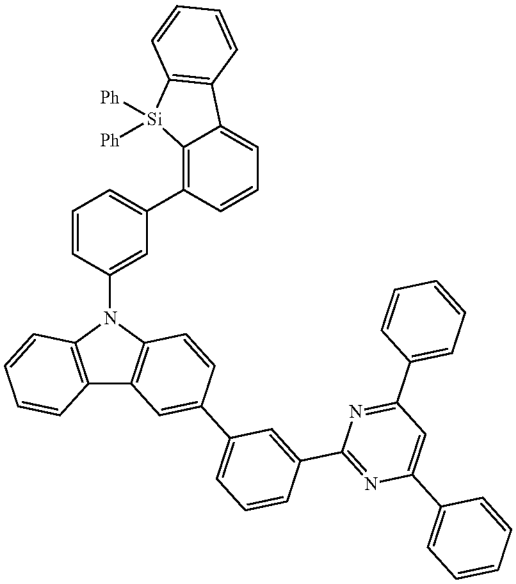
-continued
136
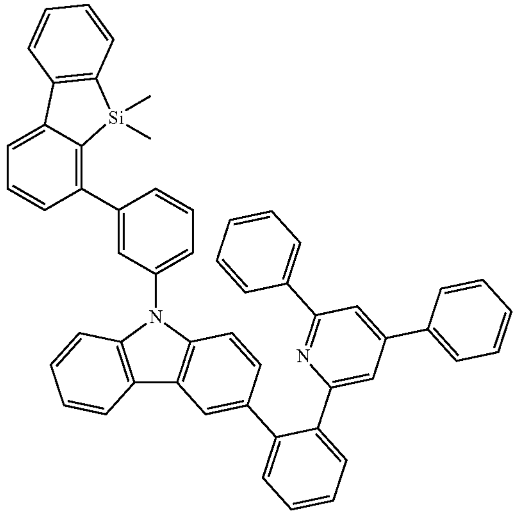
137
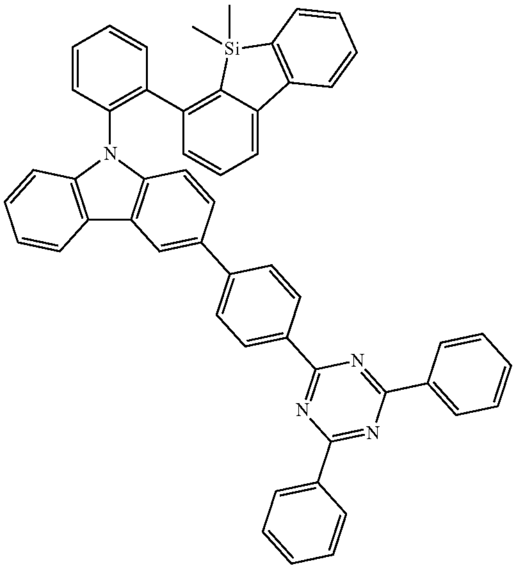
138
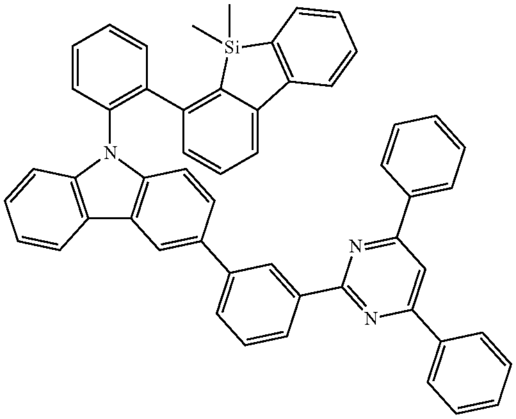

-continued
139
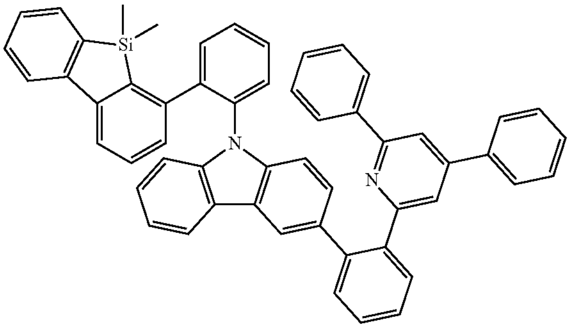
140
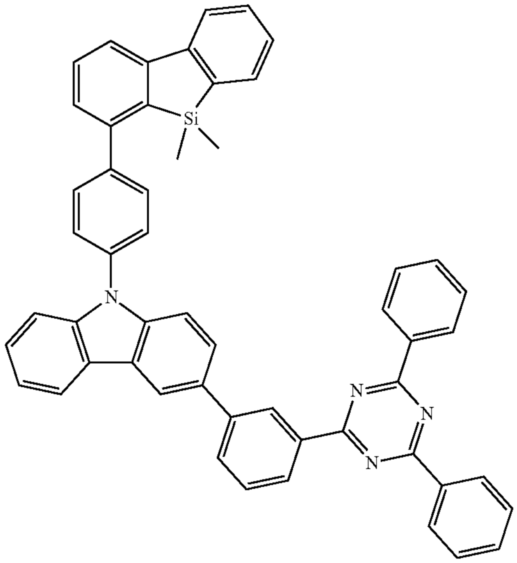
141
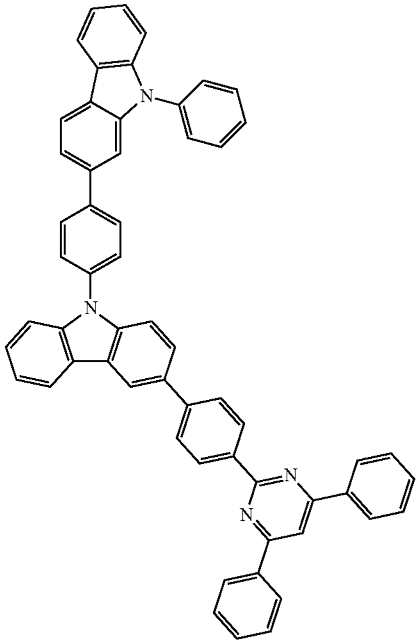
-continued
142
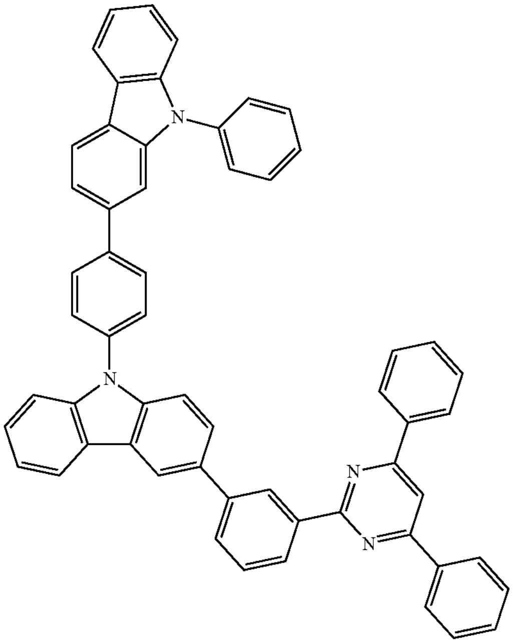
143
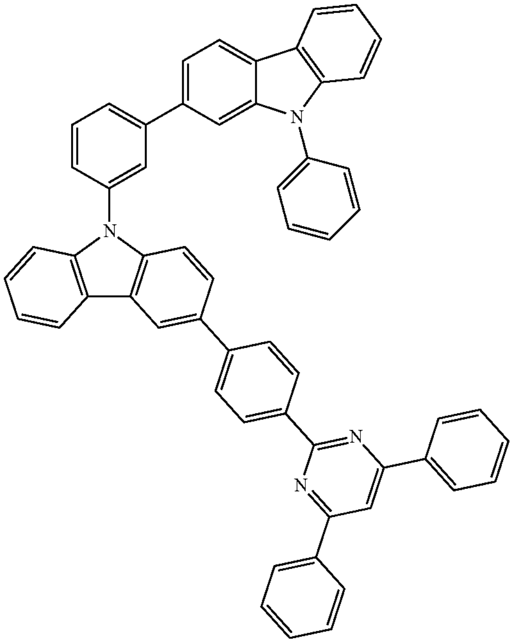

-continued
144
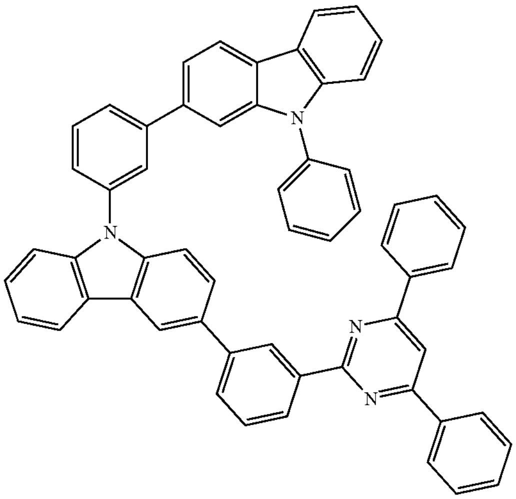
145
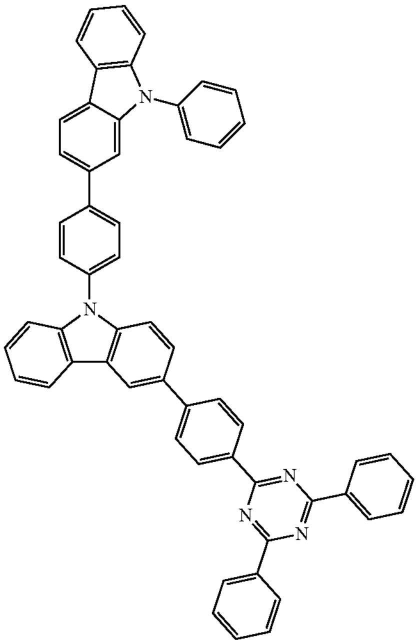
-continued
146
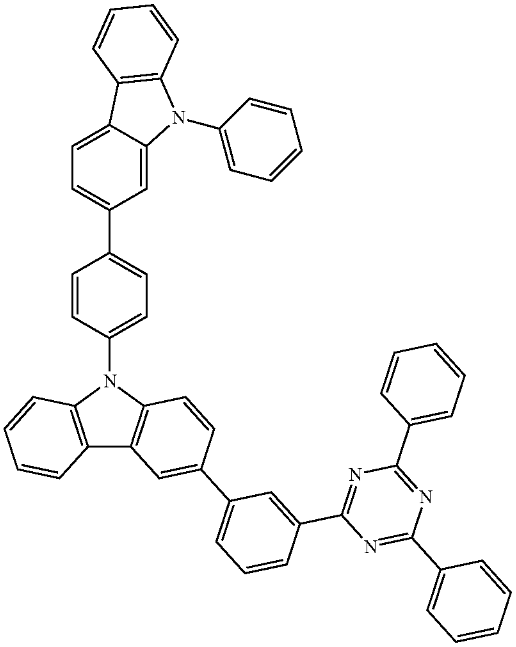
147
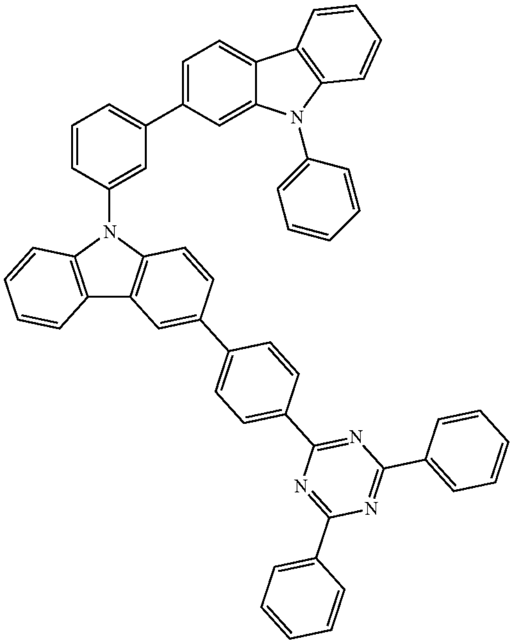

-continued
148
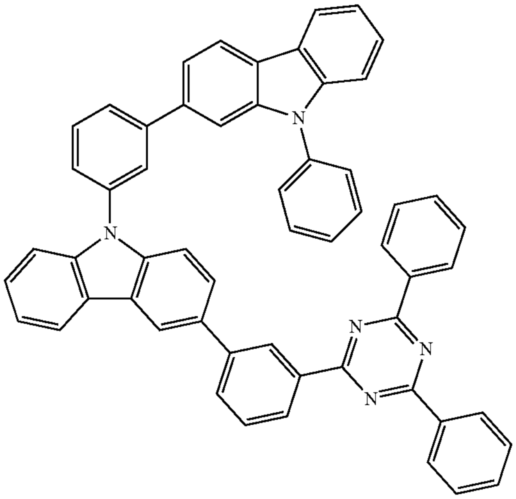
149
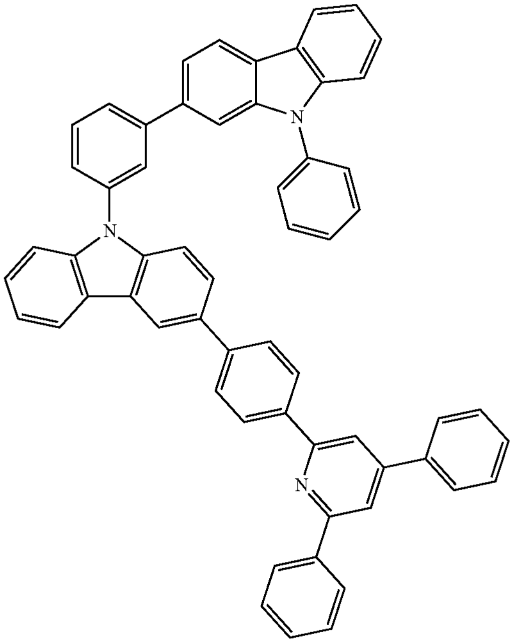
-continued
150
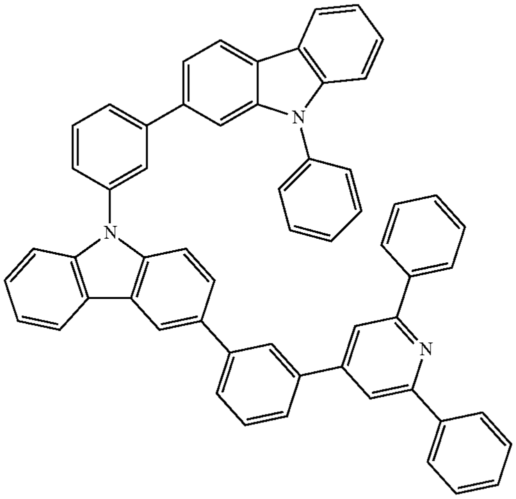
151
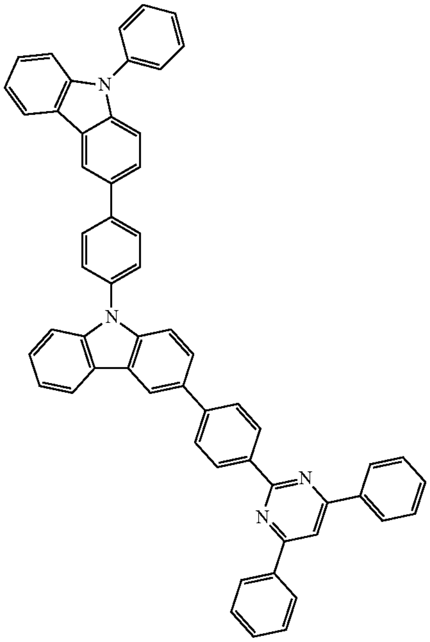

-continued
152
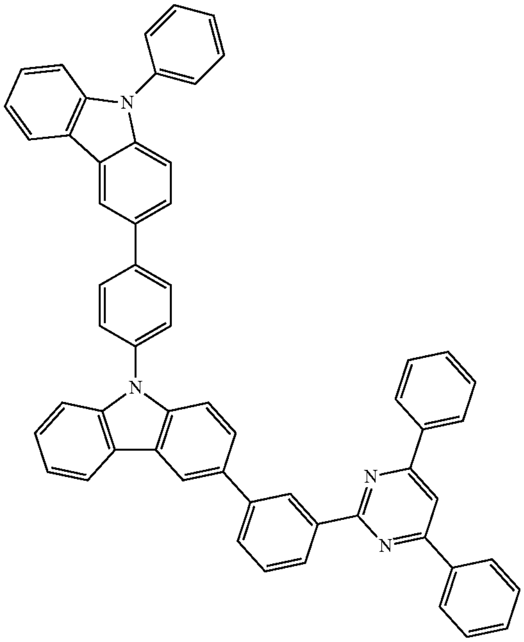
153
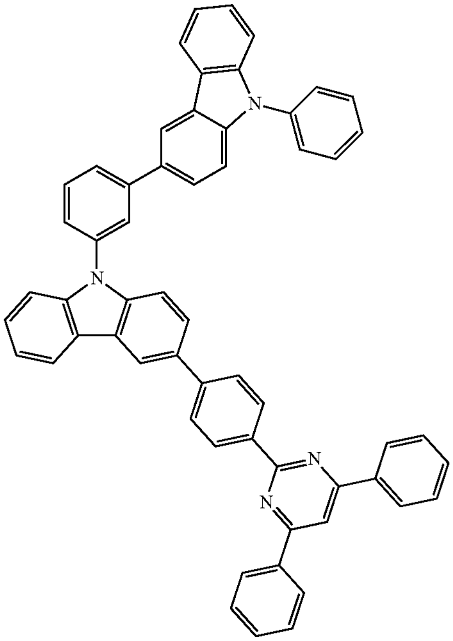
-continued
154
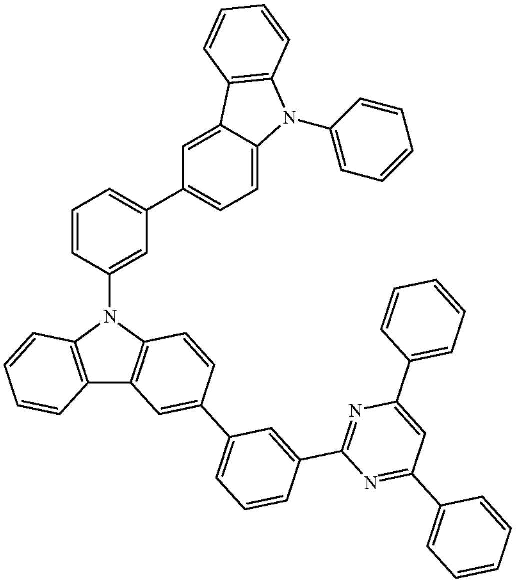
155
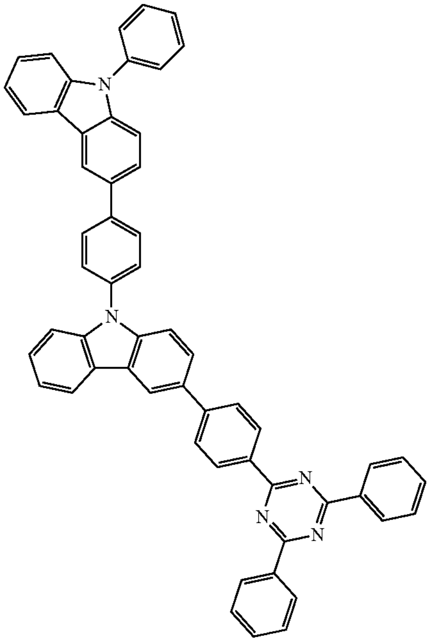

-continued
156
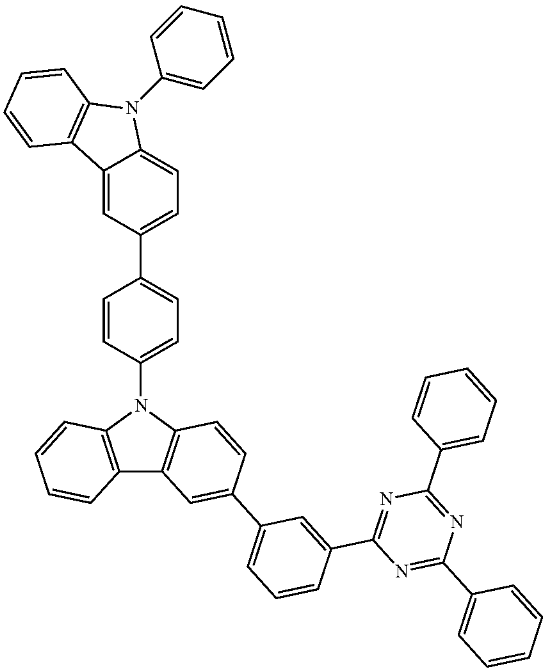
157
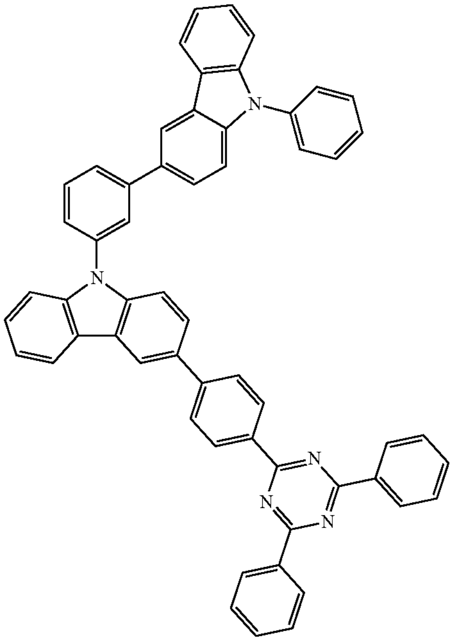
-continued
158
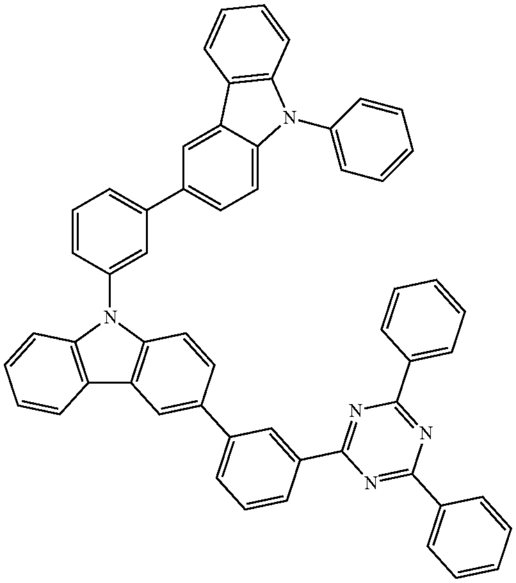
159
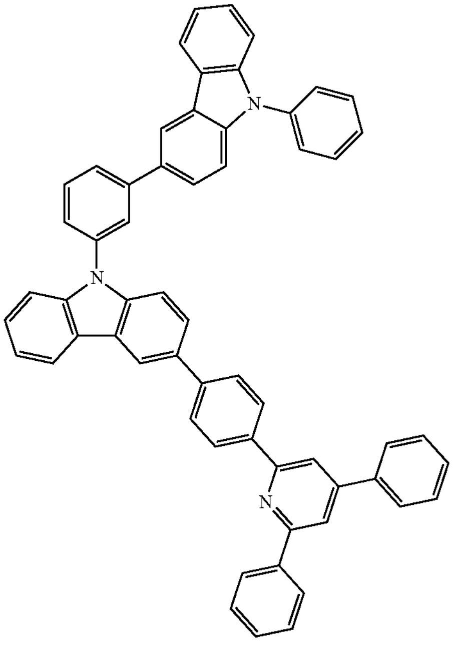

-continued
160
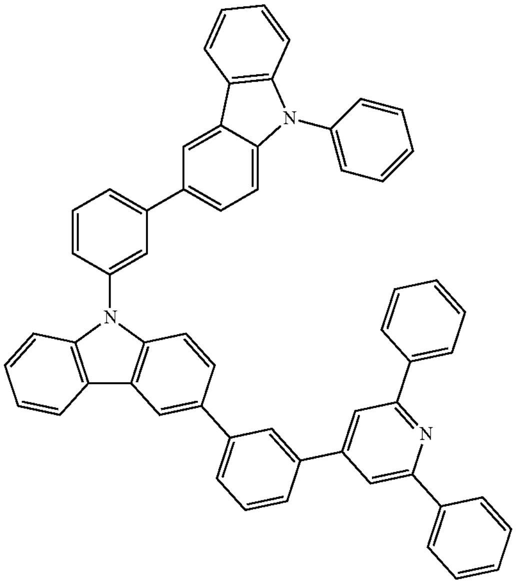
161
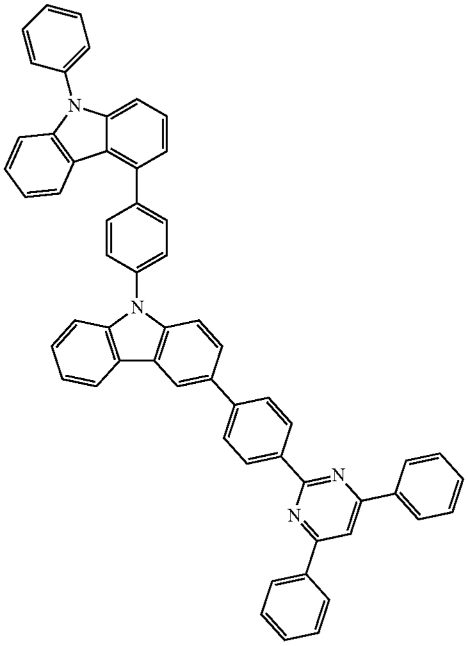
-continued
162
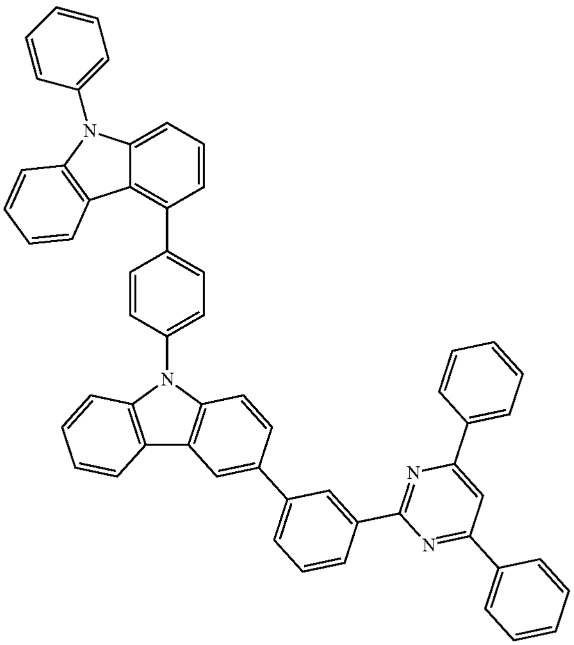
163
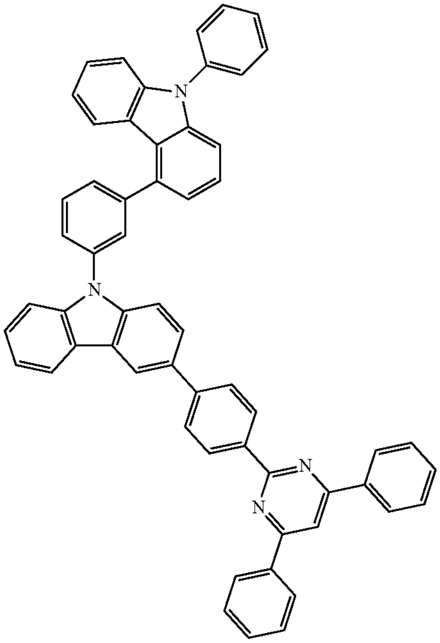

-continued
164
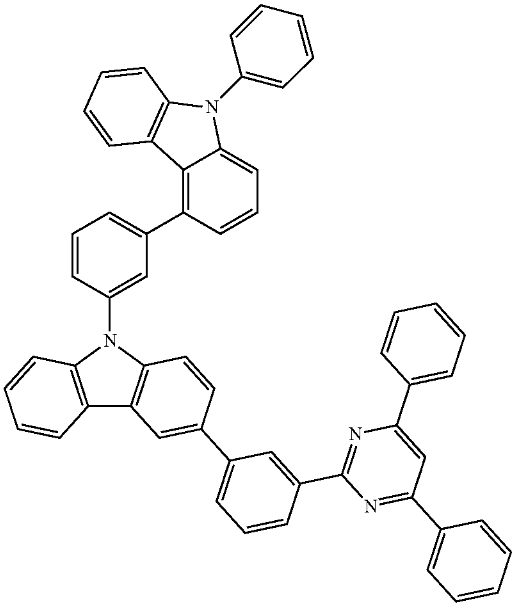
165
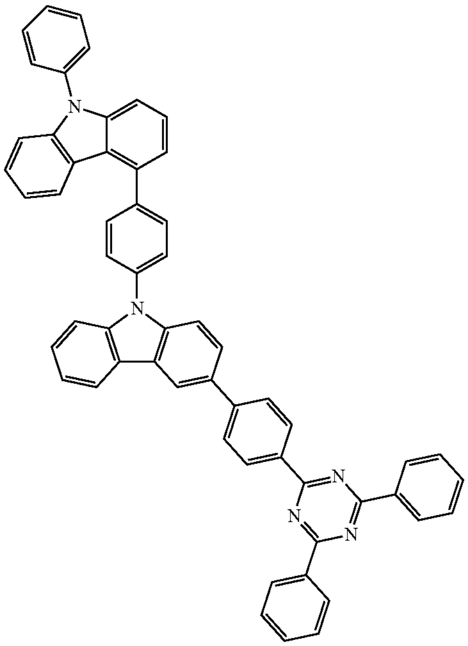
-continued
166
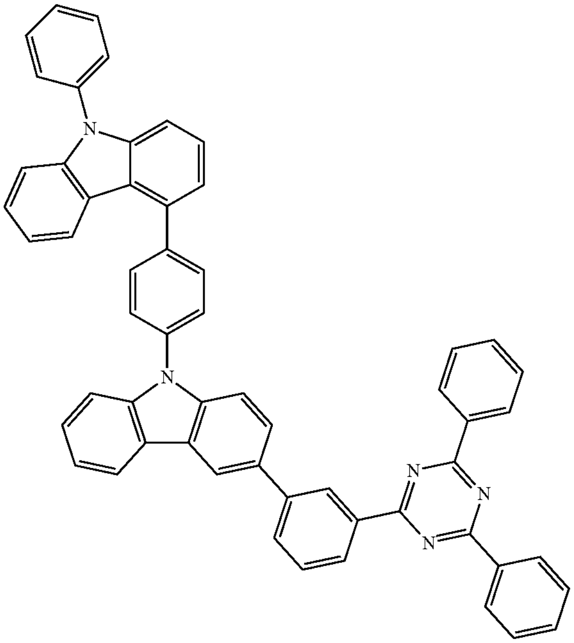
167
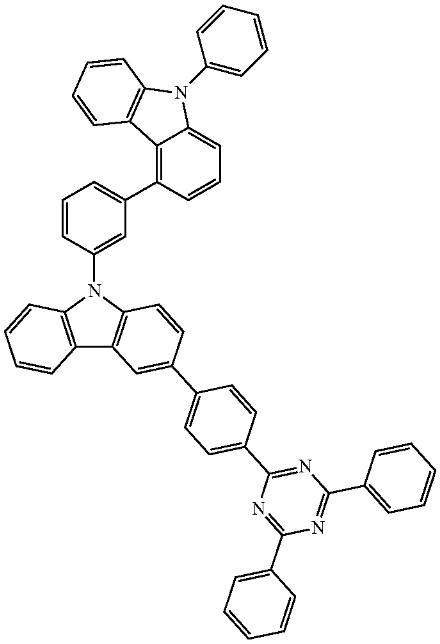

-continued
168
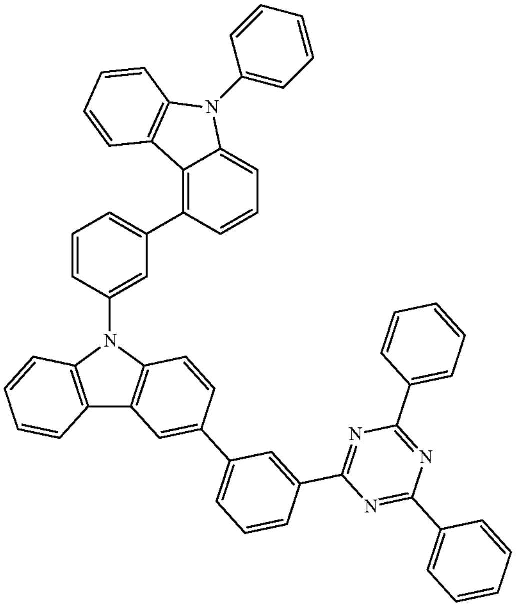
169
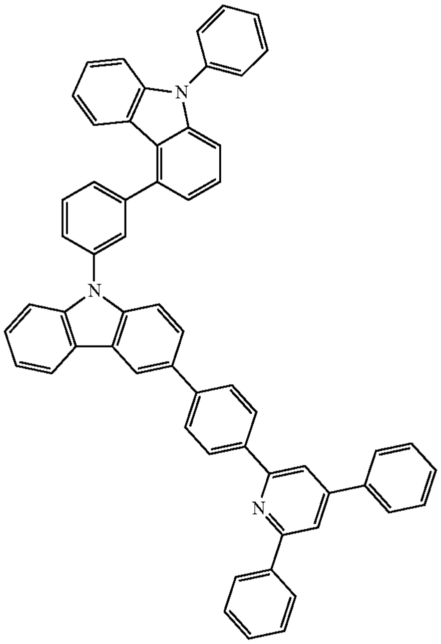
-continued
170
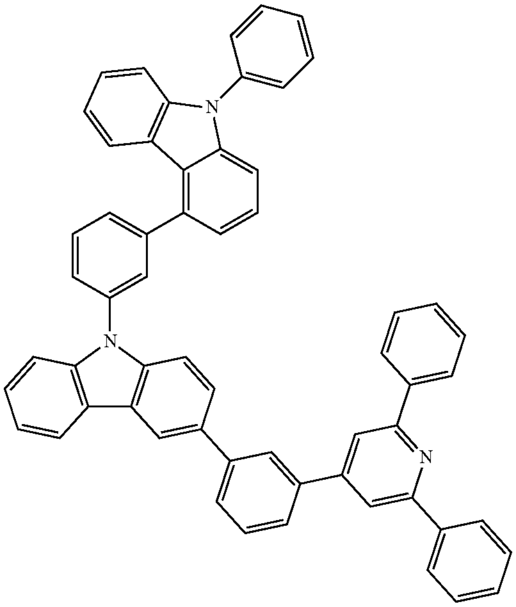
171
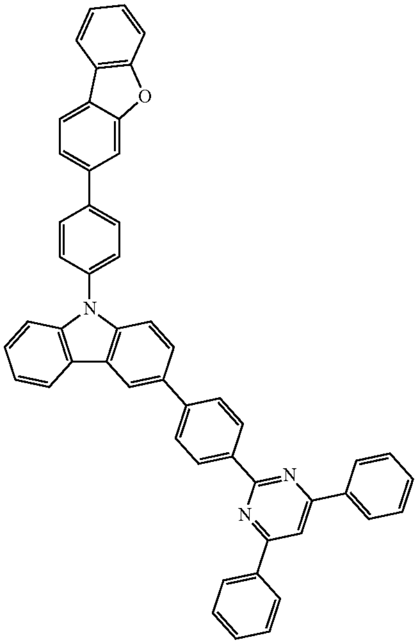

-continued
172
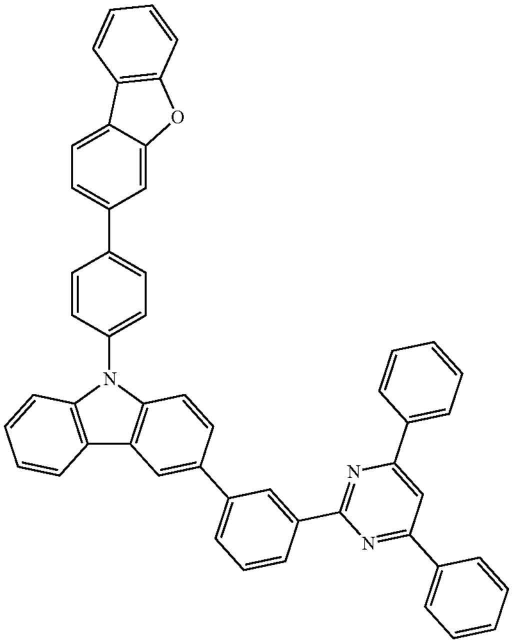
173
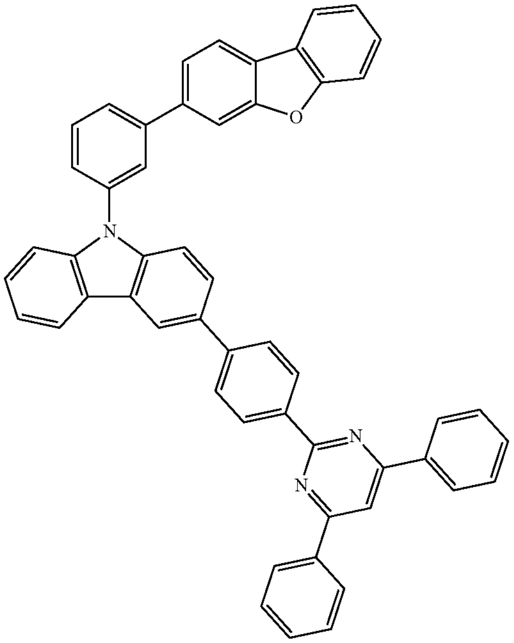
-continued
174
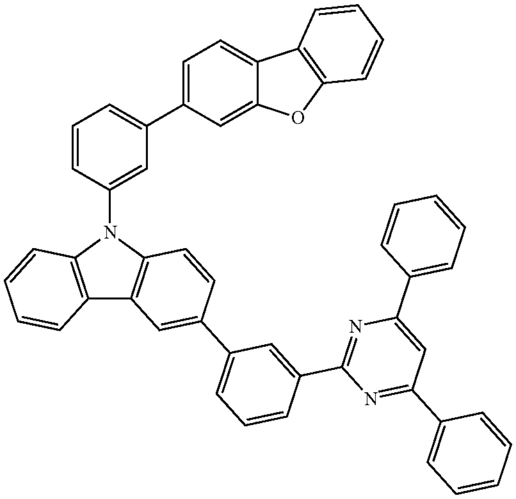
175
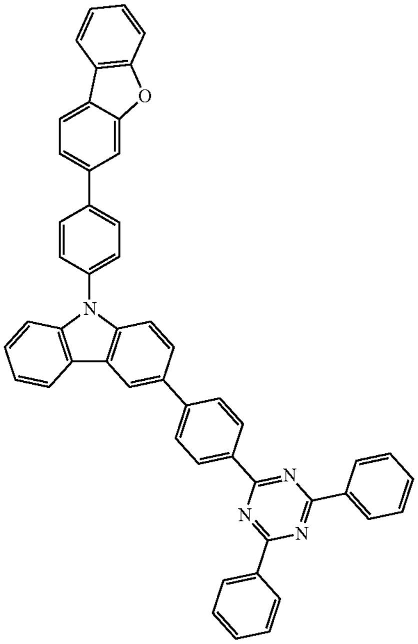

176
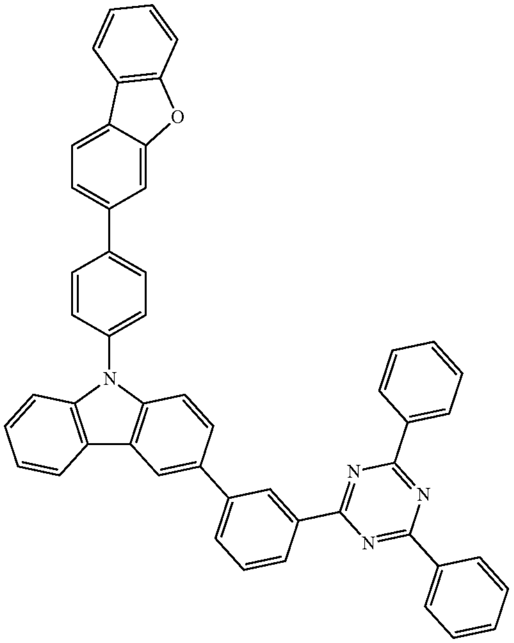
177
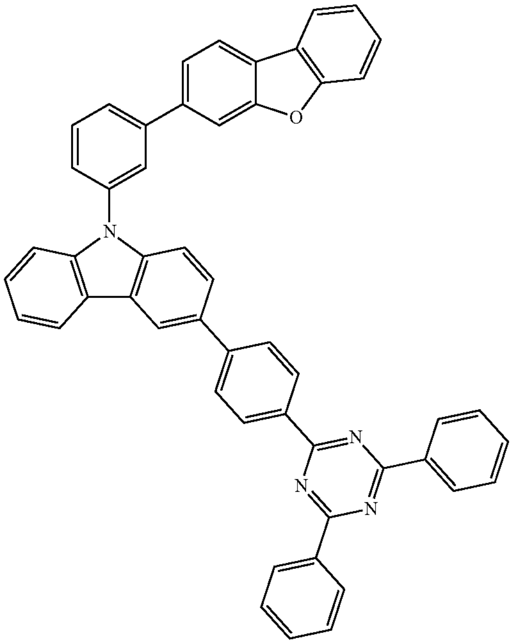
178
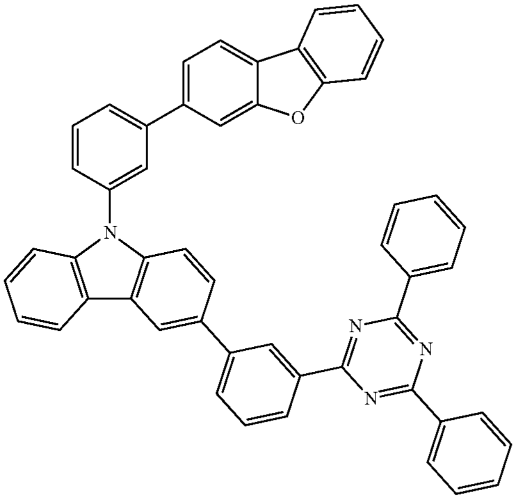
179
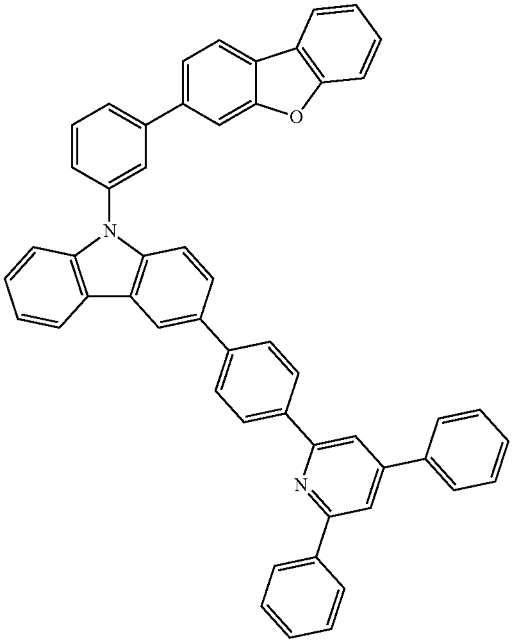

180
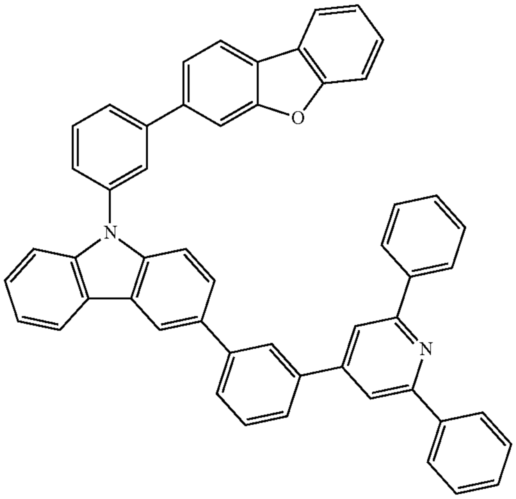
181
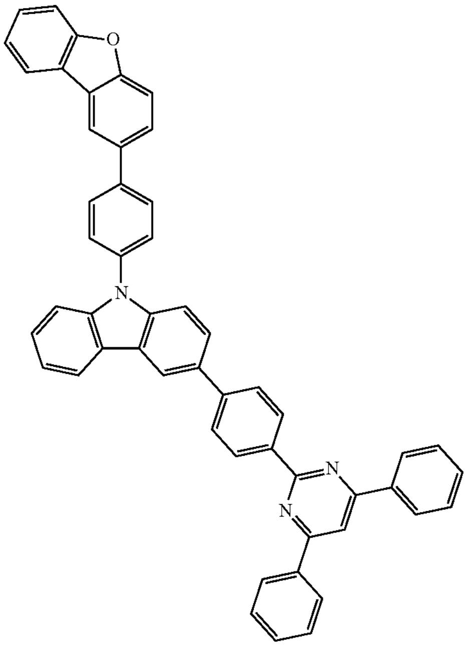
182
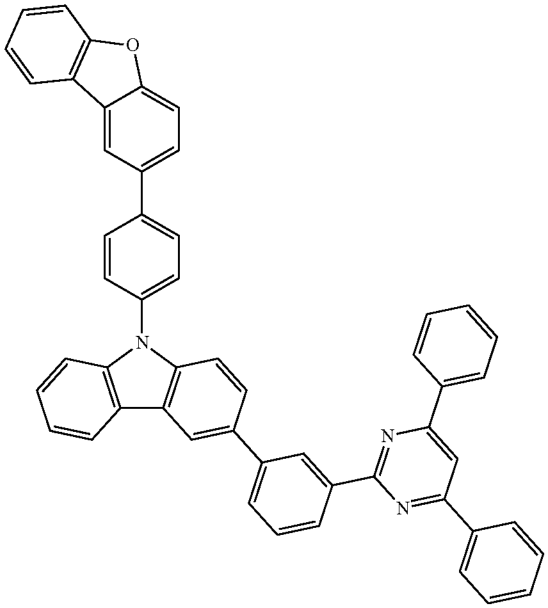
183
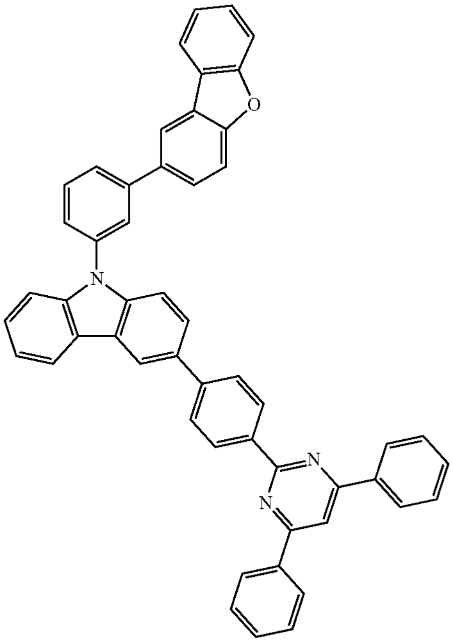

-continued
184
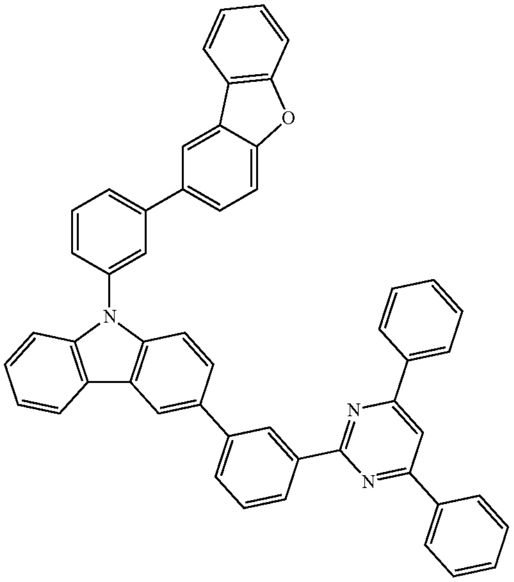
185
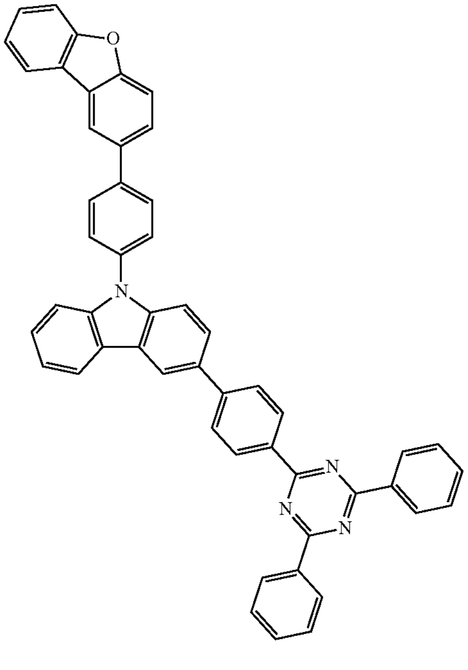
-continued
186
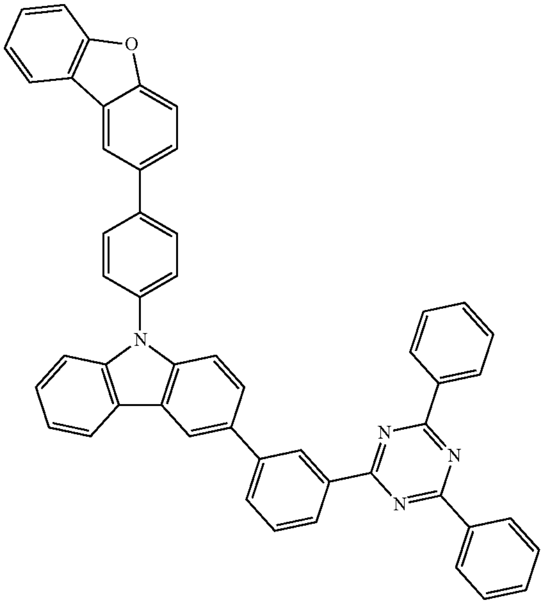
187
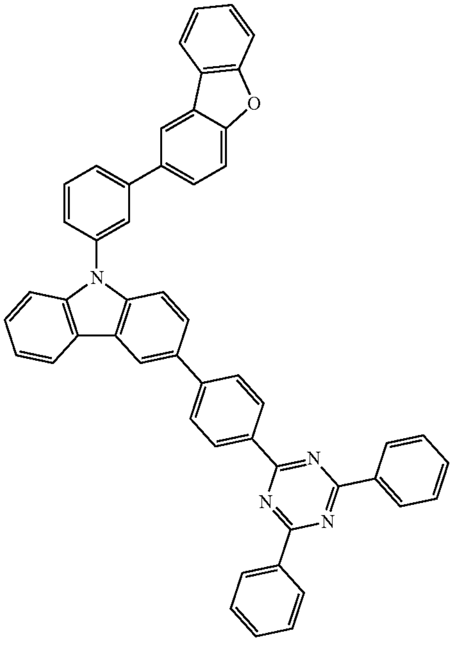

-continued
188
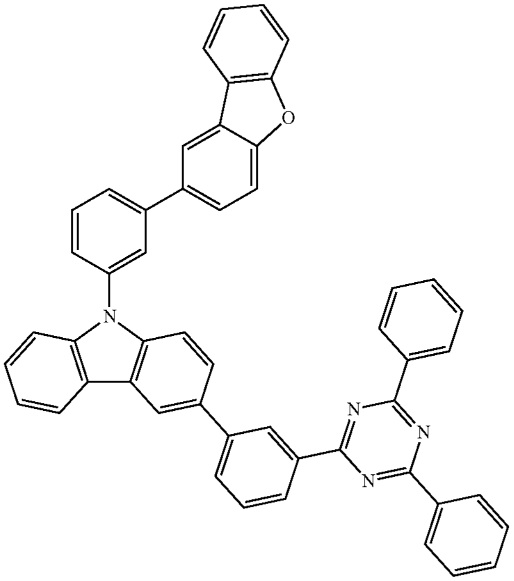
190
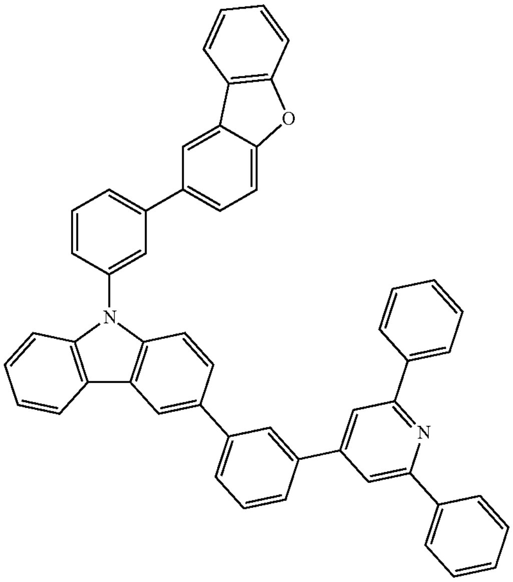
189
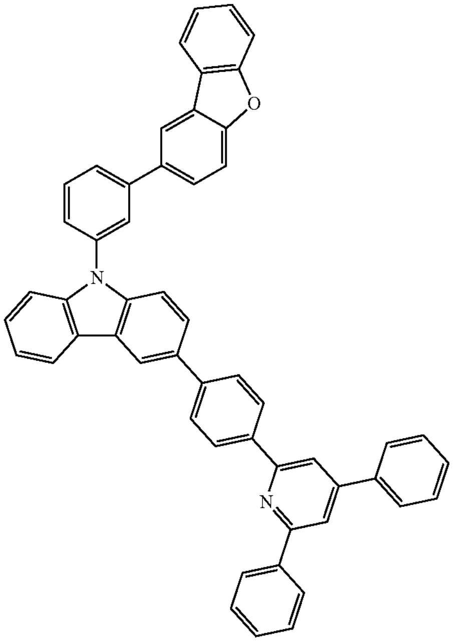
191
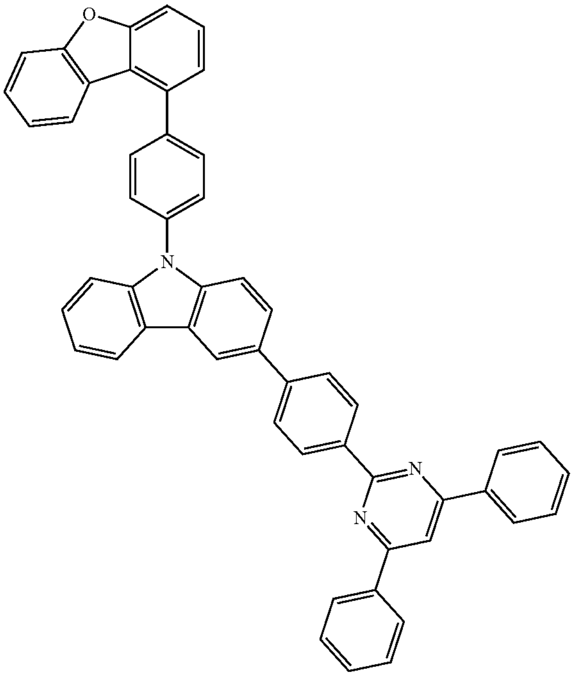

-continued
192
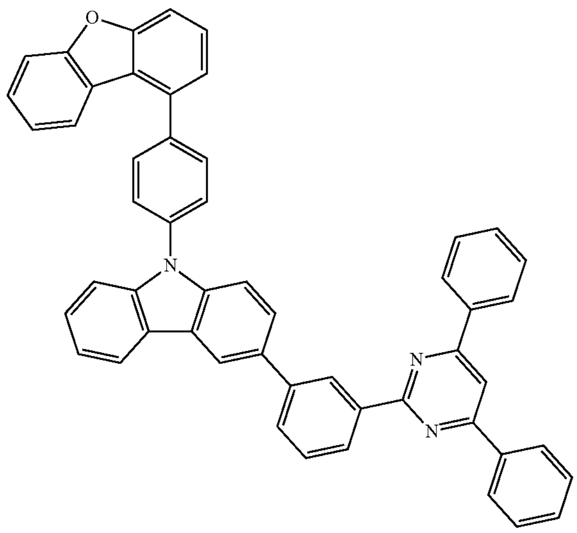
193
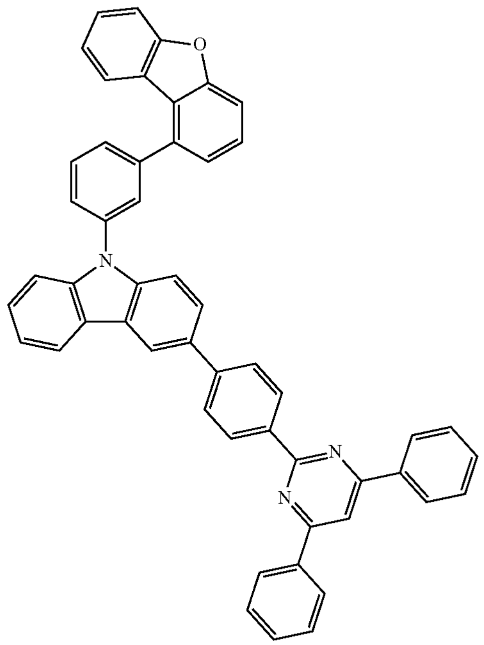
-continued
194
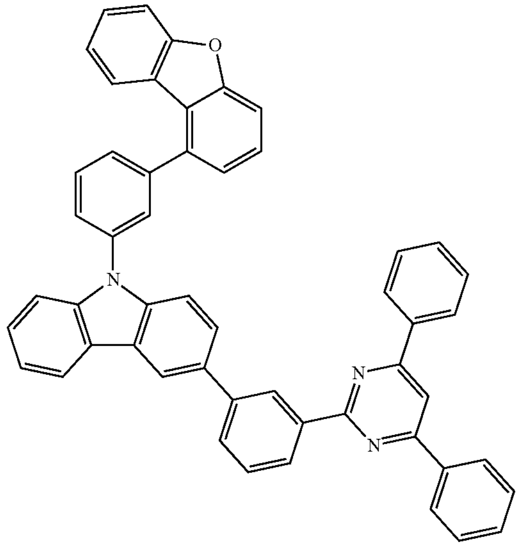
195
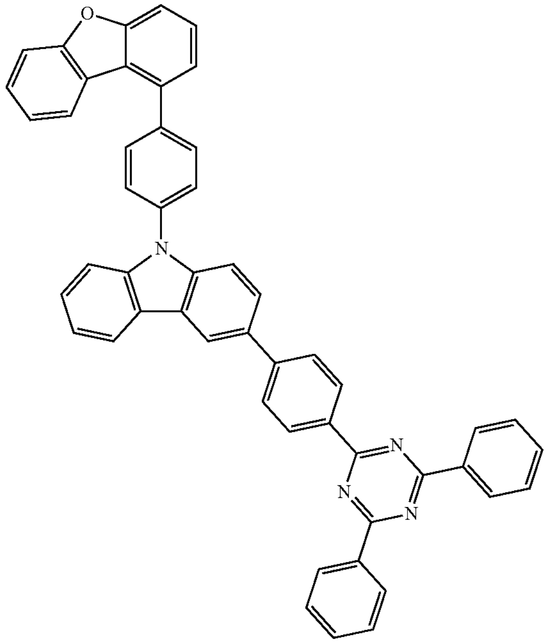

196
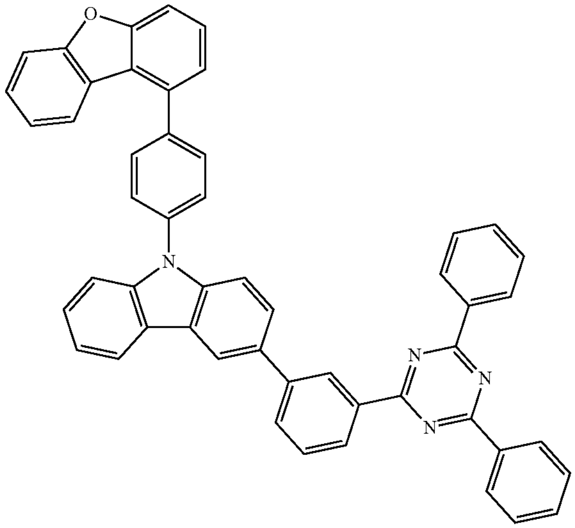
197
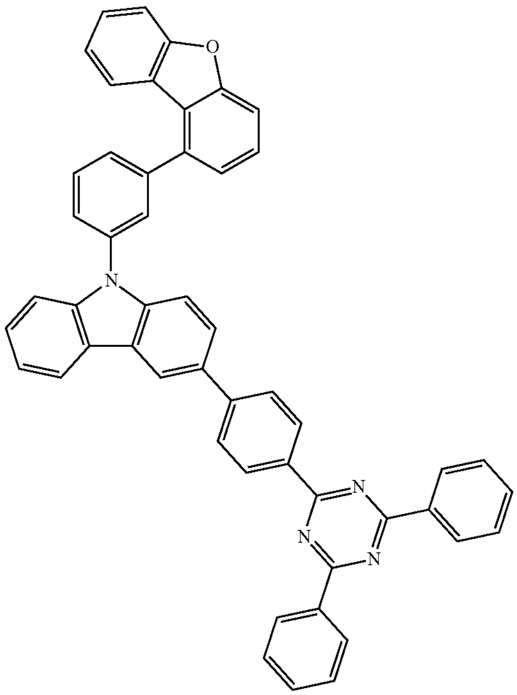
198
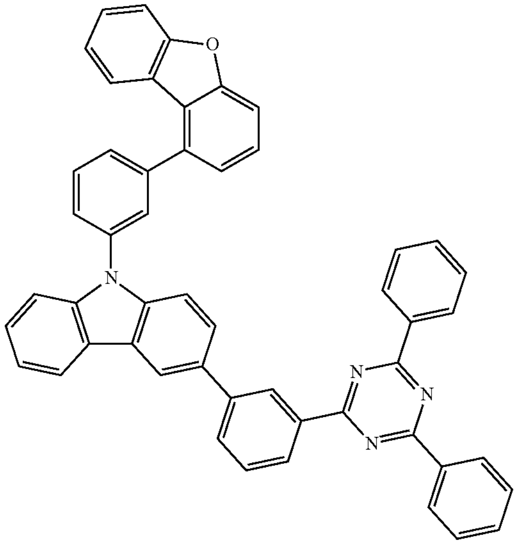
199
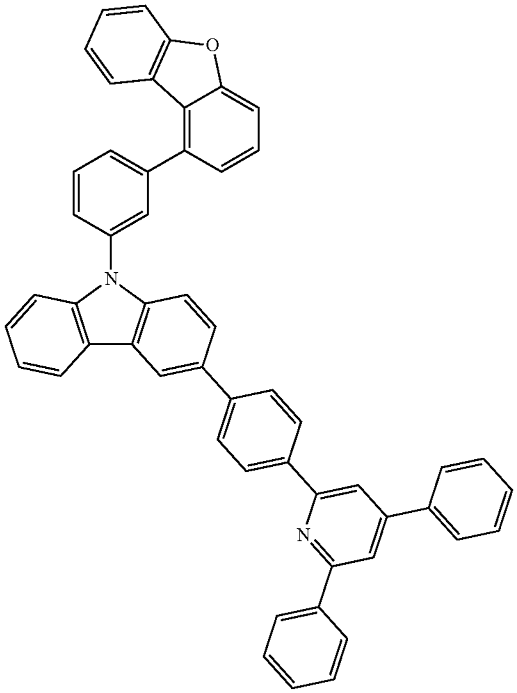

-continued
200
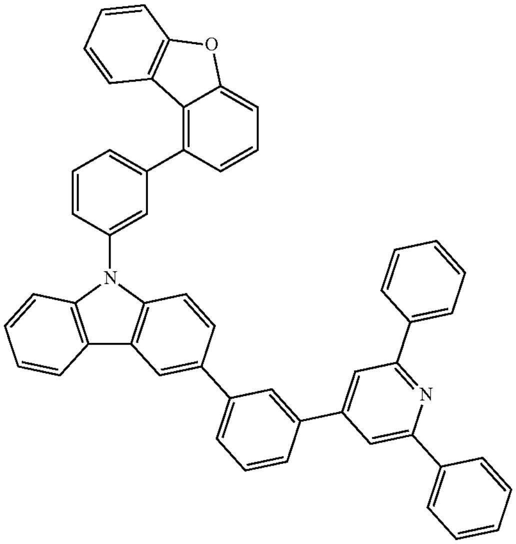
201
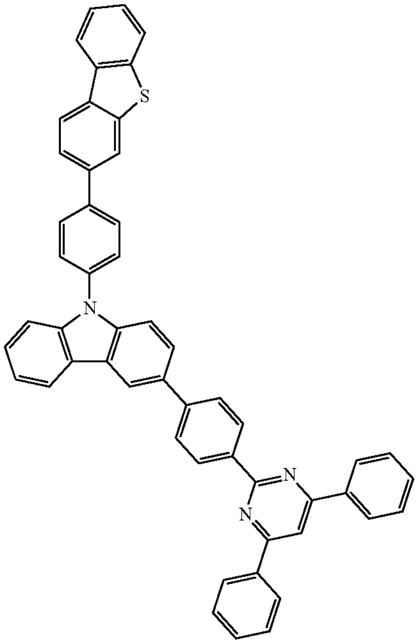
-continued
202
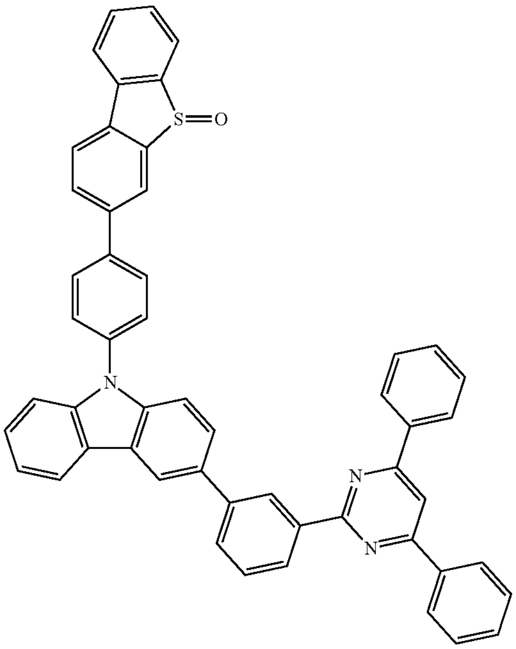
203
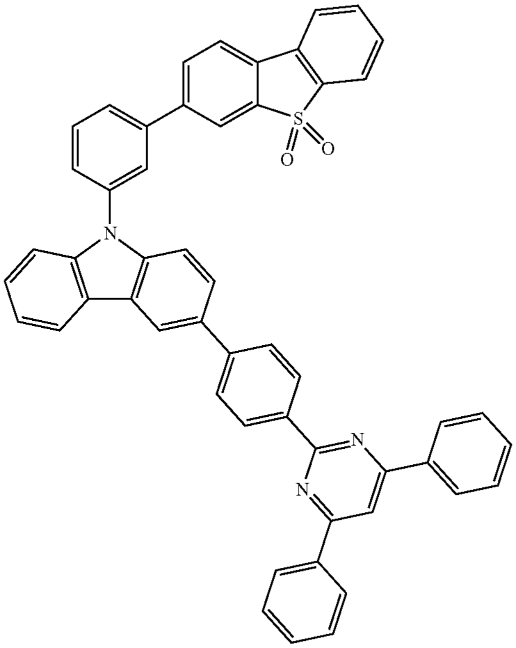

-continued
204
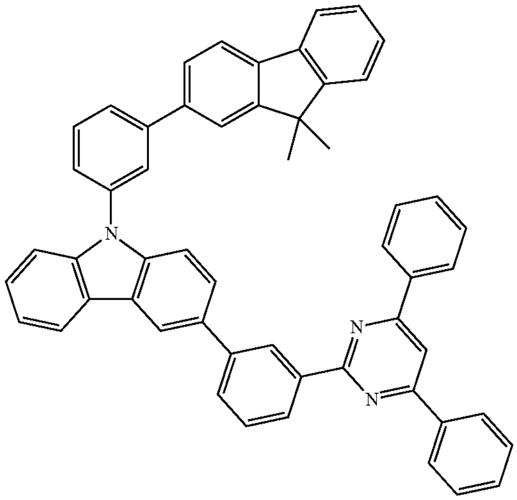
205
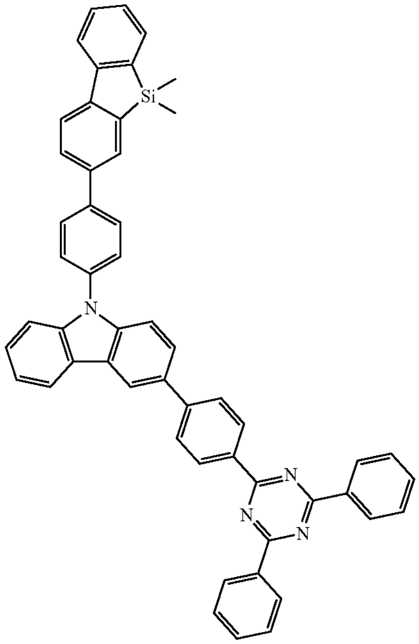
-continued
206
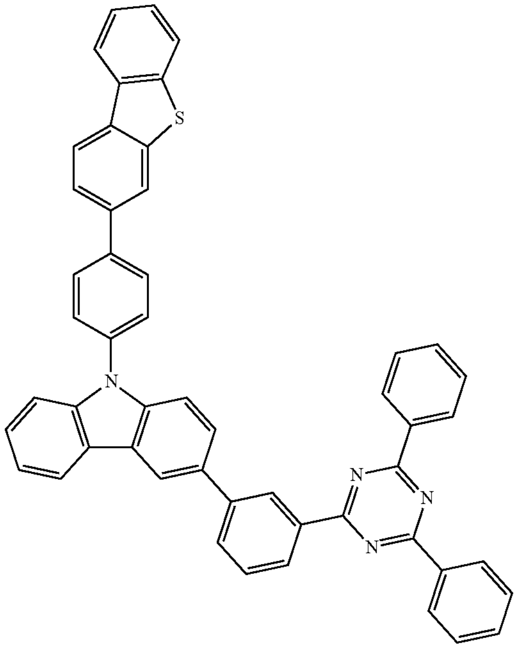
207
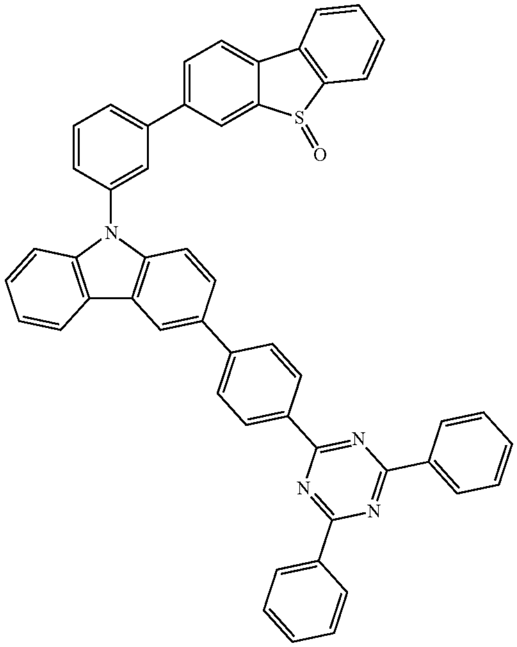

-continued
208
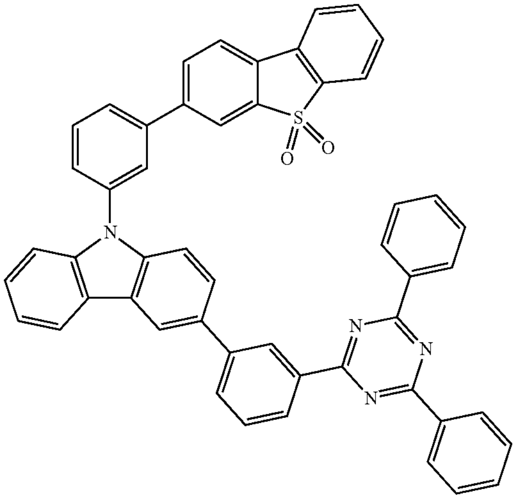
209
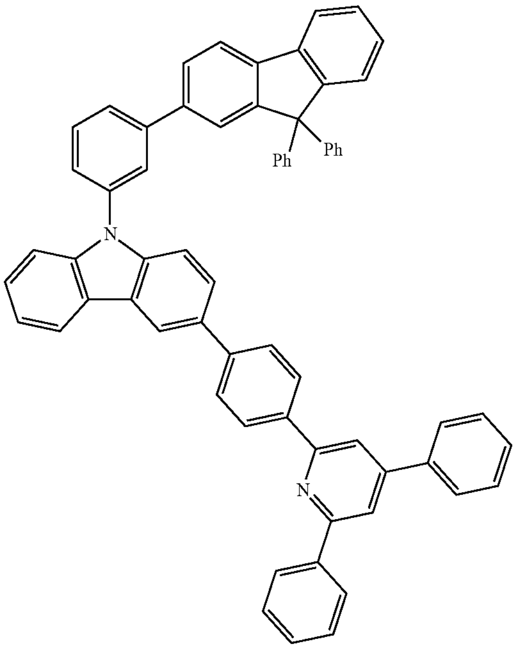
-continued
210
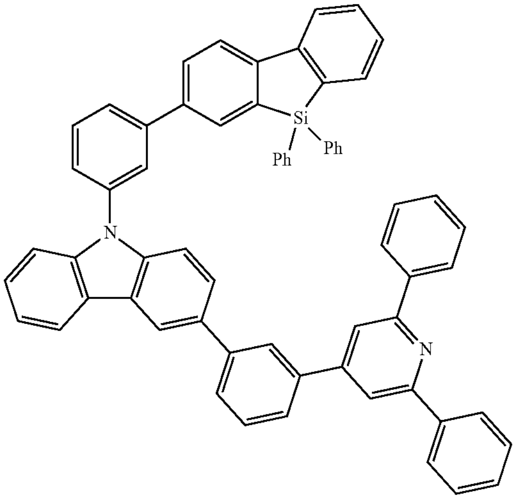
211
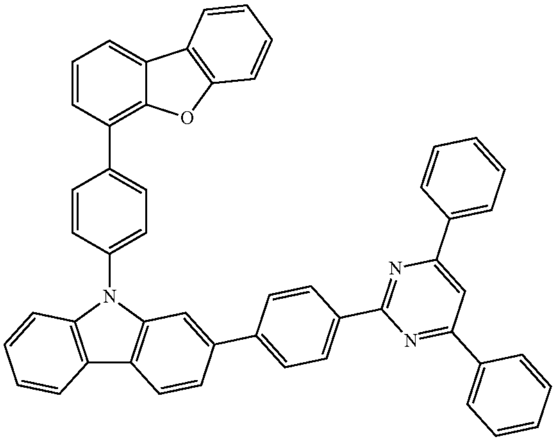
212
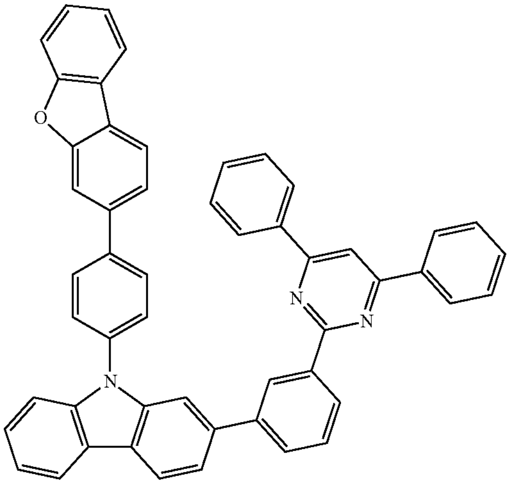

-continued
213
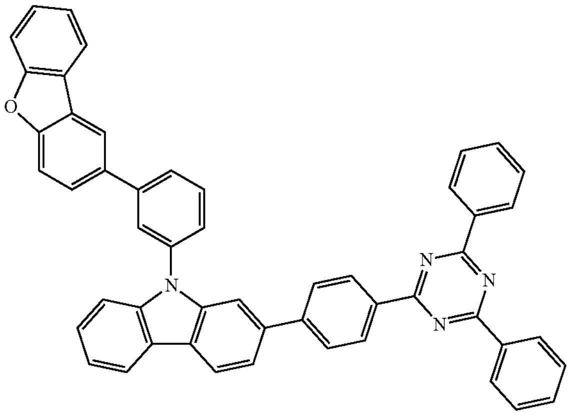
214
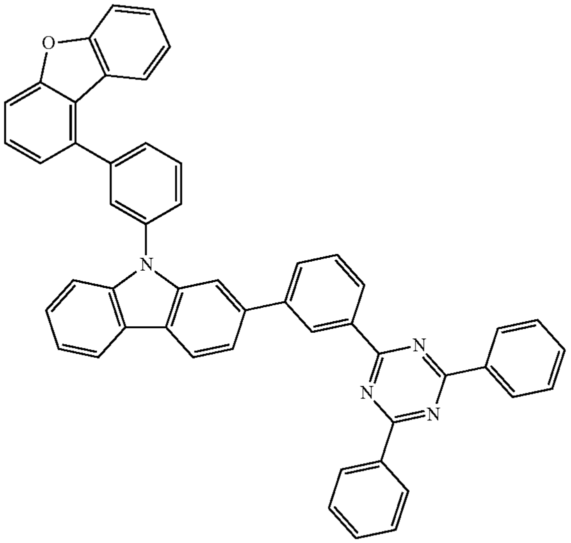
215
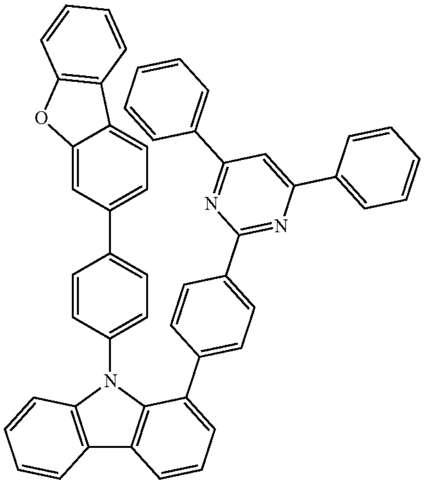
-continued
216
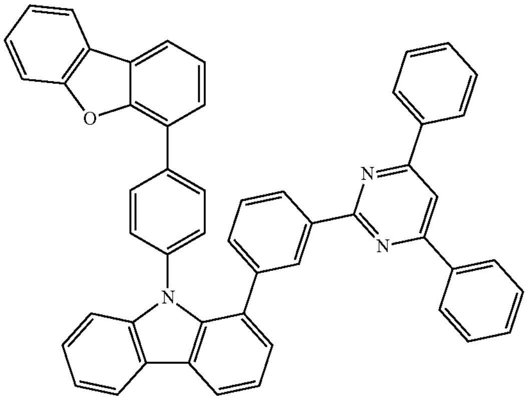
217
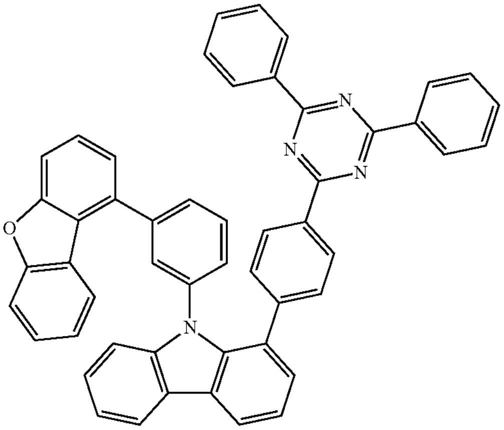
218
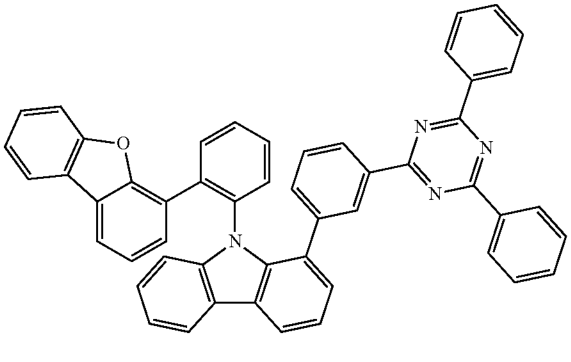

-continued
219
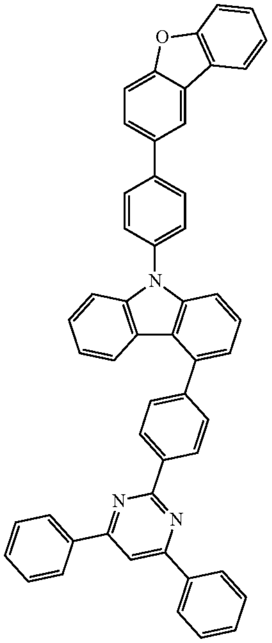
221
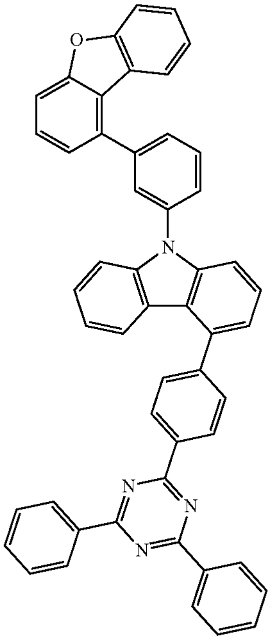
220
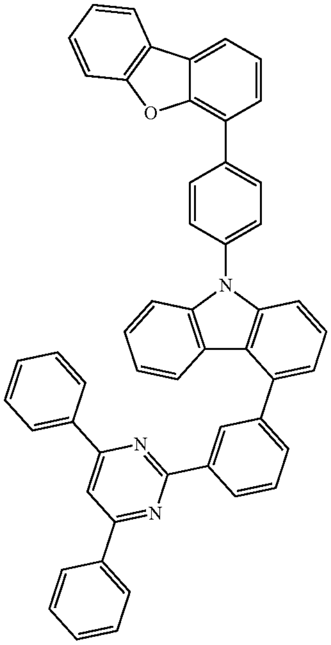
222
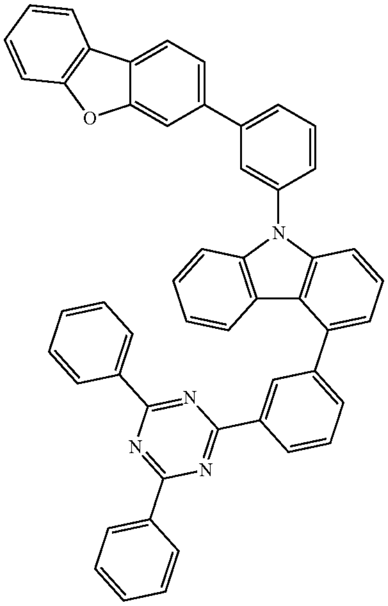

-continued
223
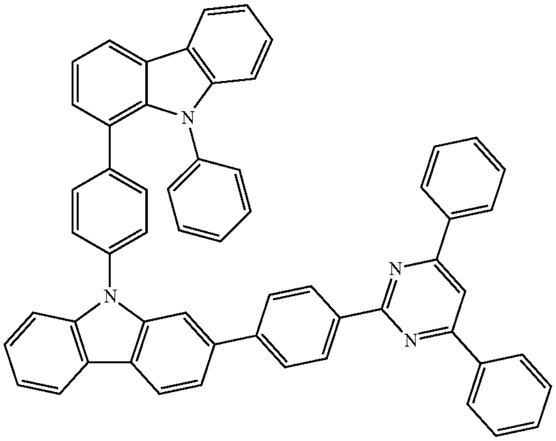
224
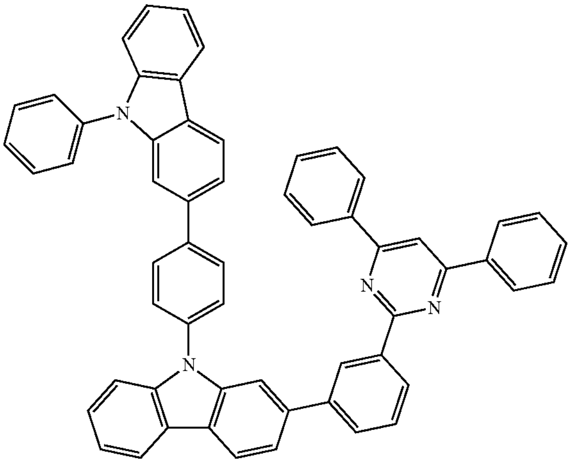
225
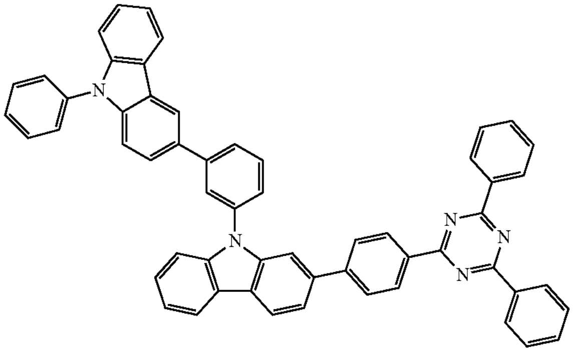
-continued
226
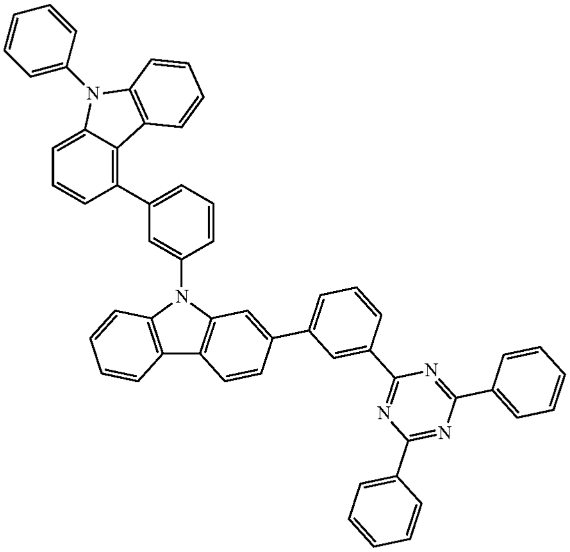
227
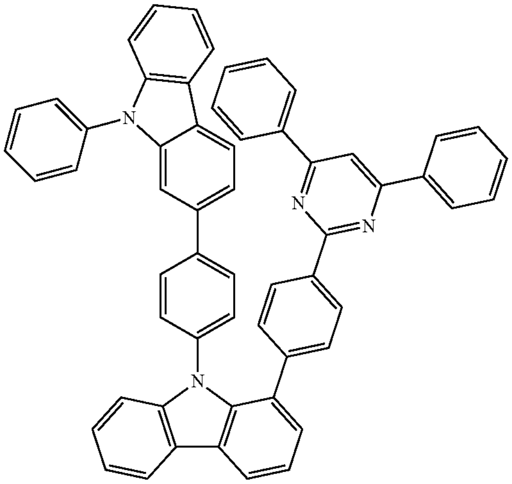
228
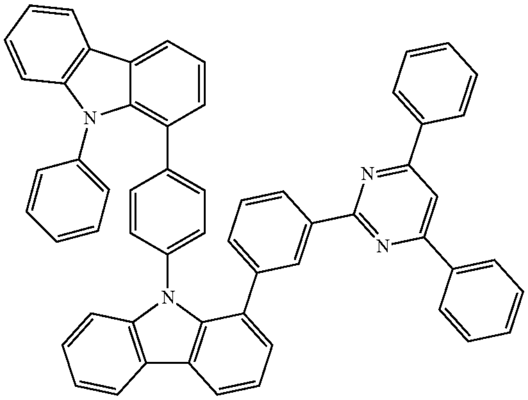

229
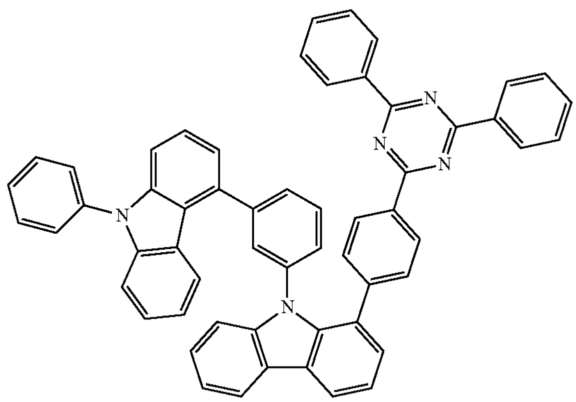
230
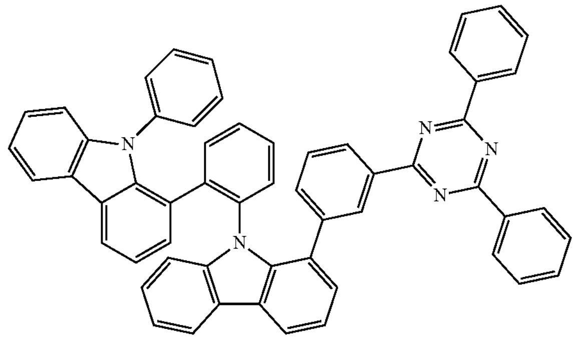
231
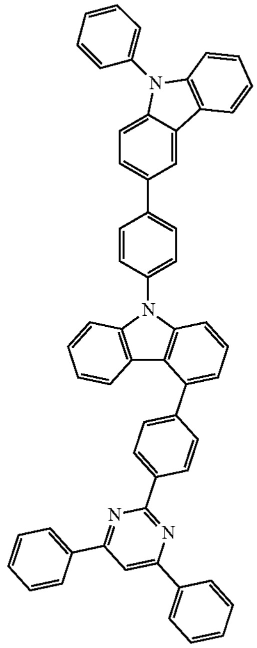
232
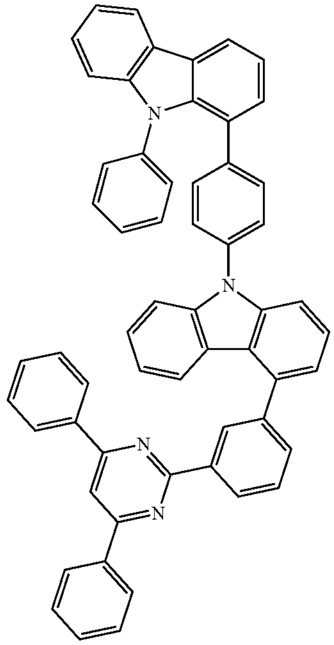
233
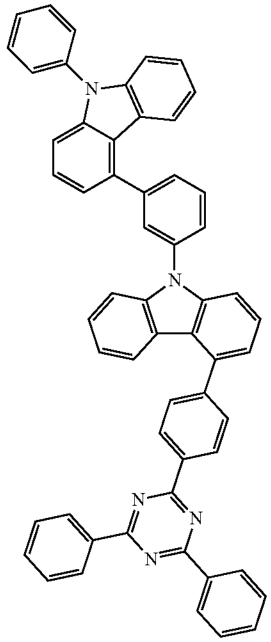

-continued
234
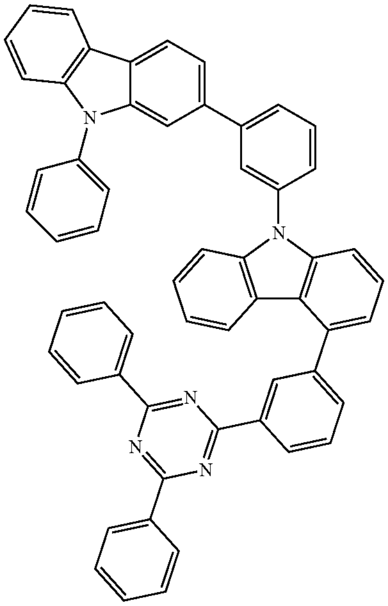
235
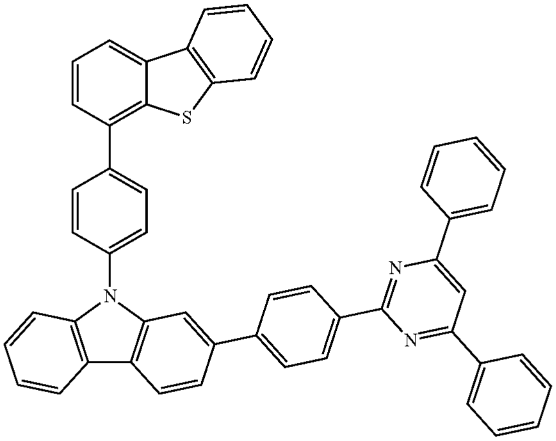
236
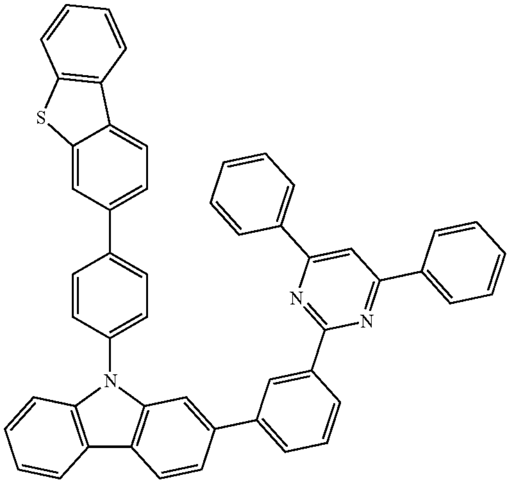
-continued
237
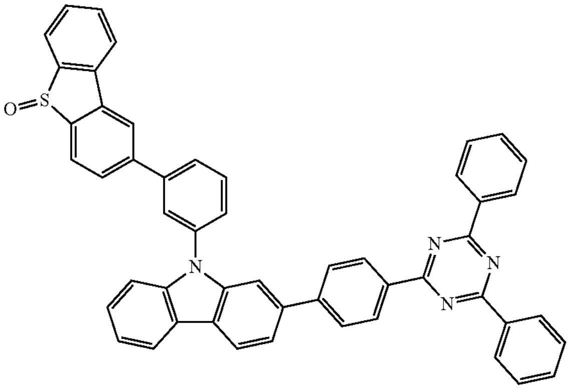
238
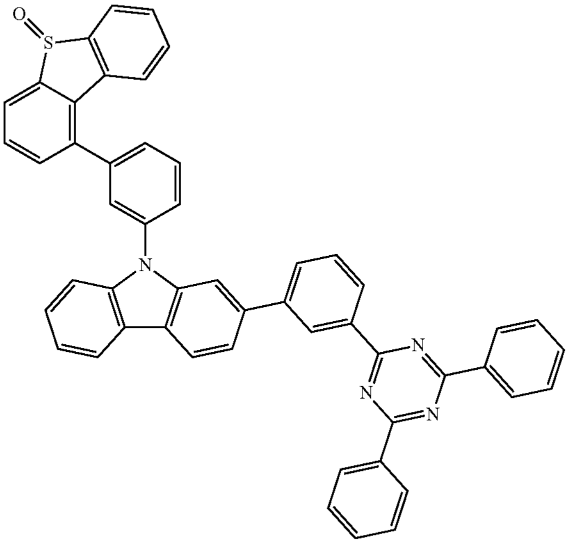
239
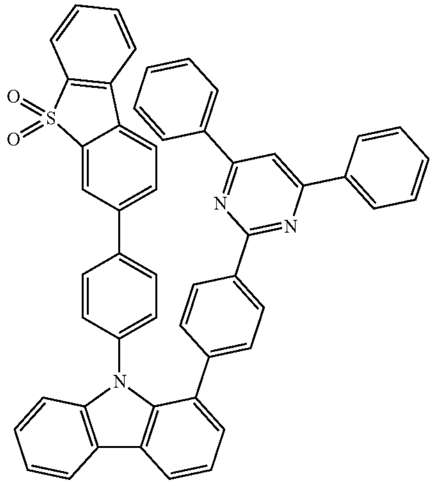

-continued
240
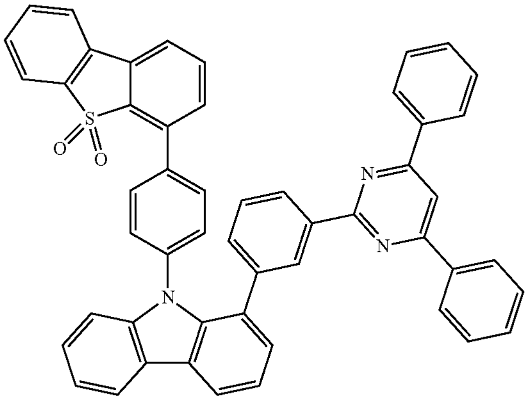
241
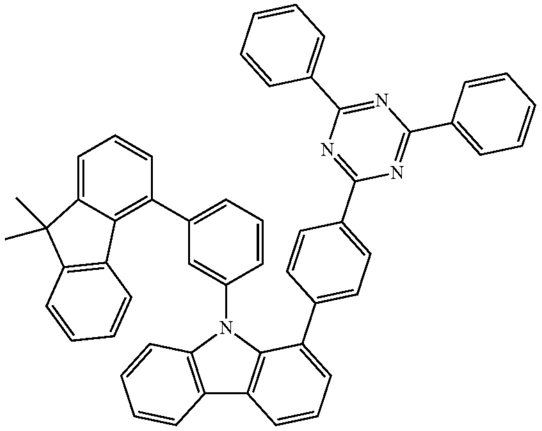
242
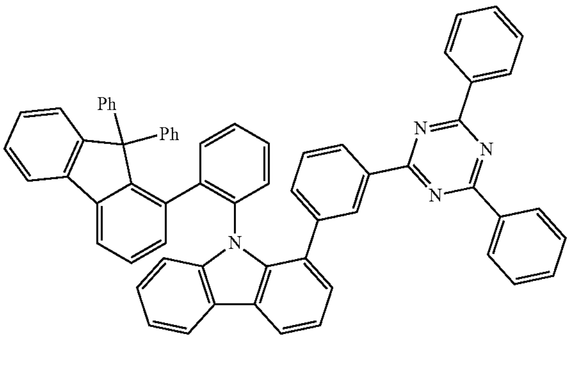
-continued
243
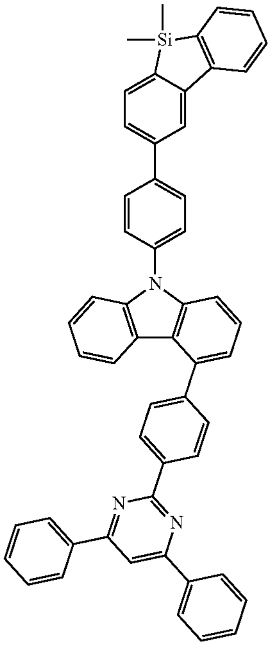
244
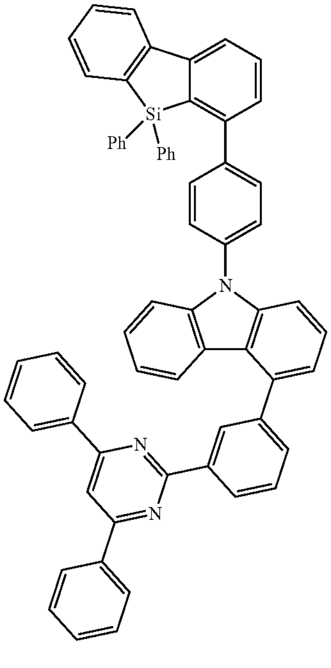

-continued
245
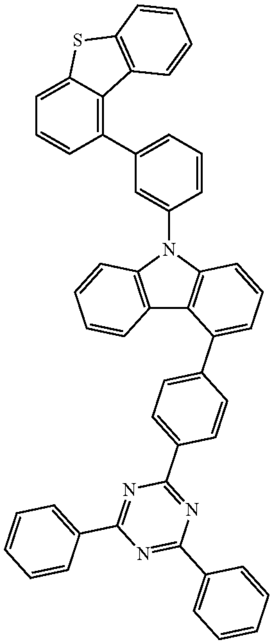
246
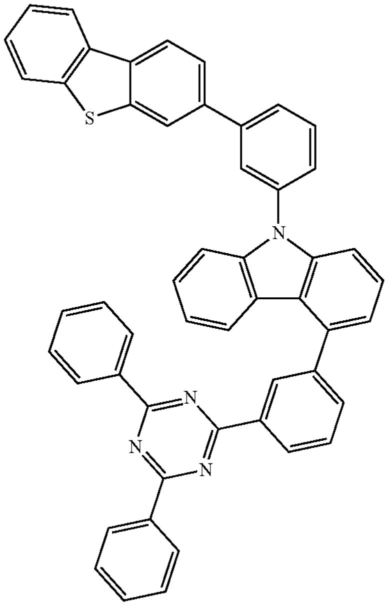
-continued
247
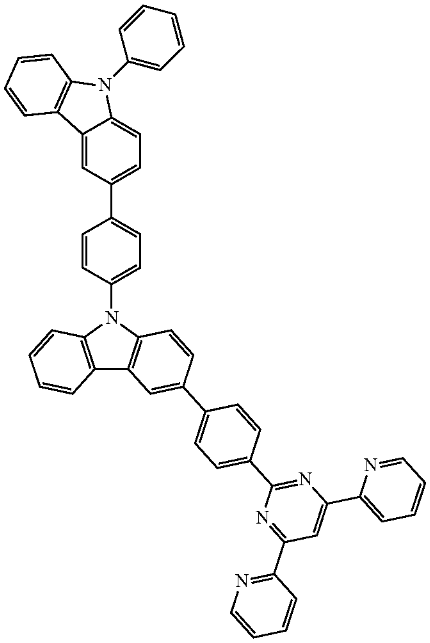
248
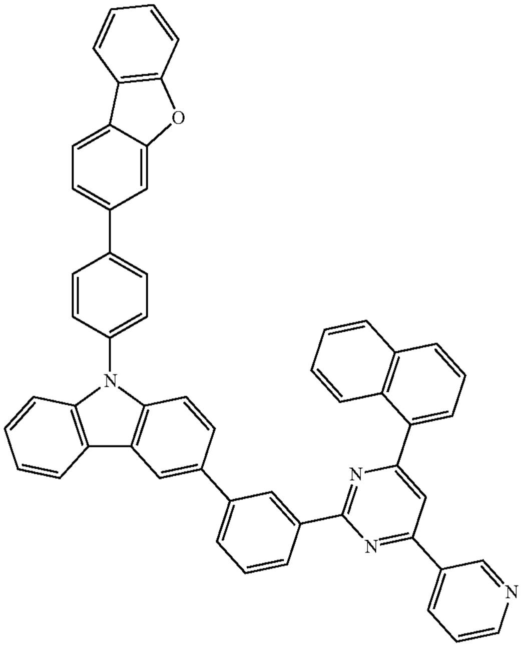

-continued
249
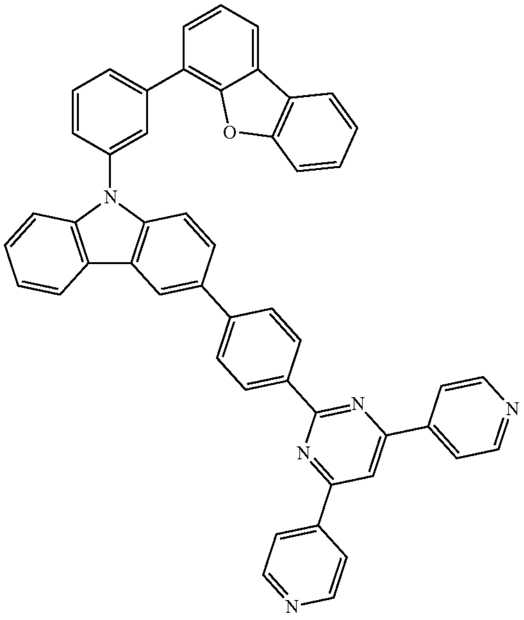
-continued
251
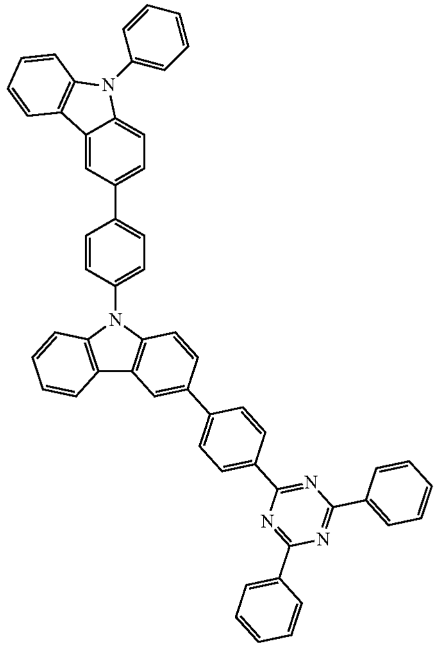
250
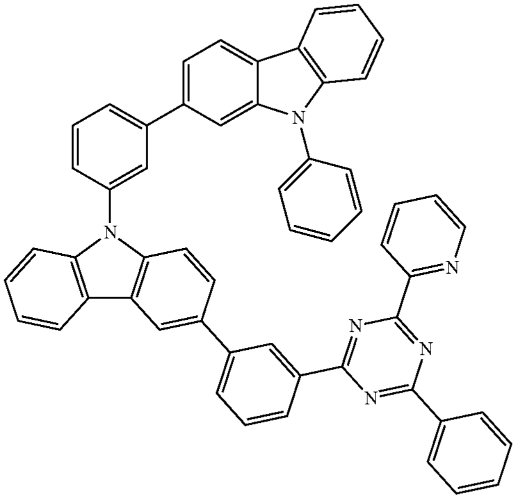
252
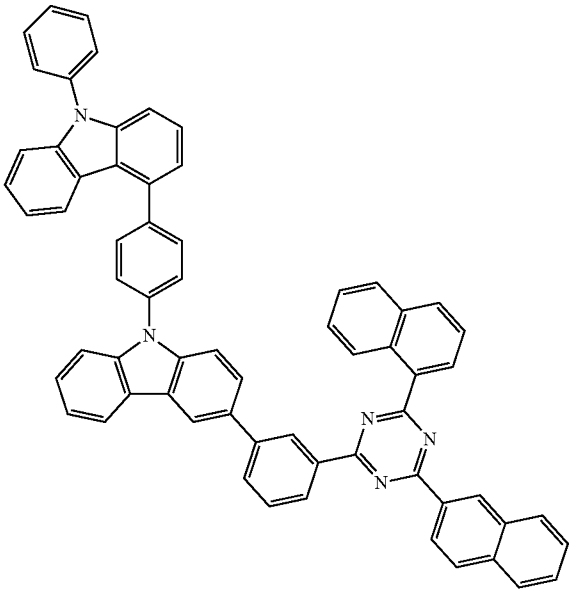

-continued
253
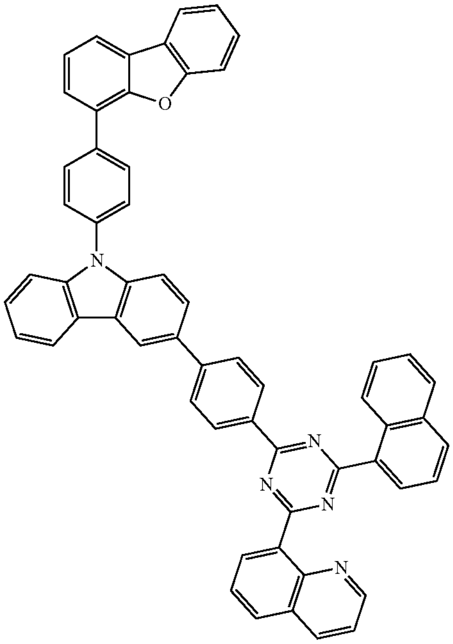
254
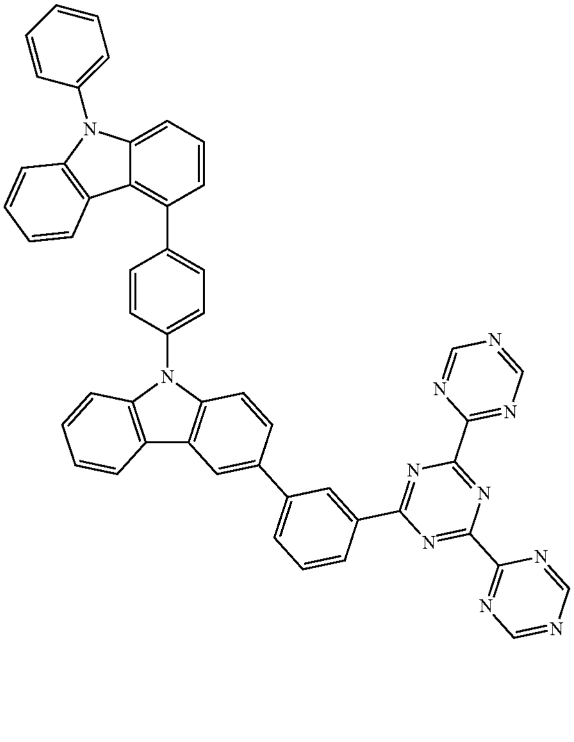
-continued
255
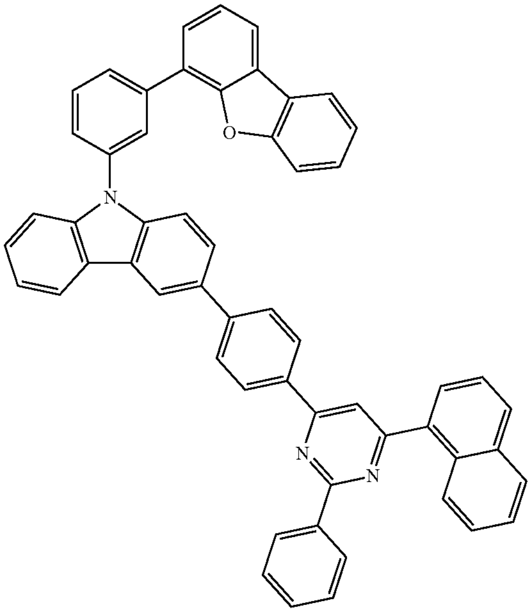
256
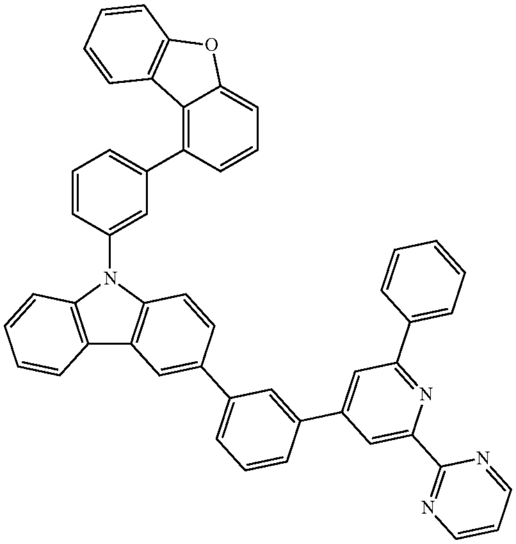

-continued
257
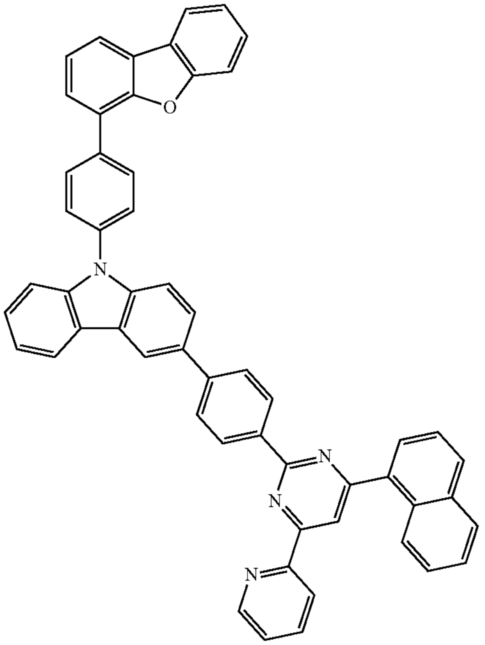
258
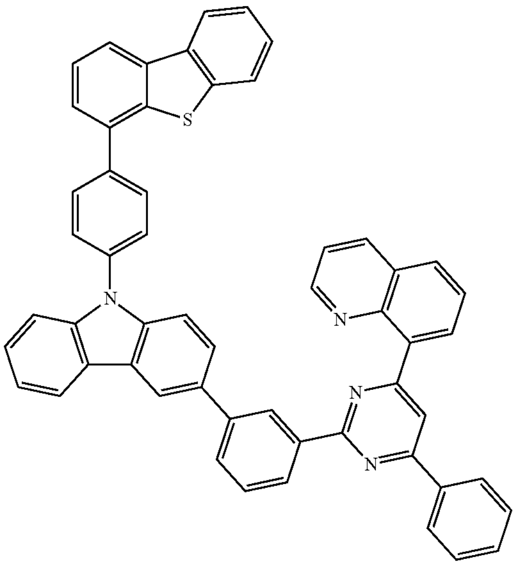
-continued
259
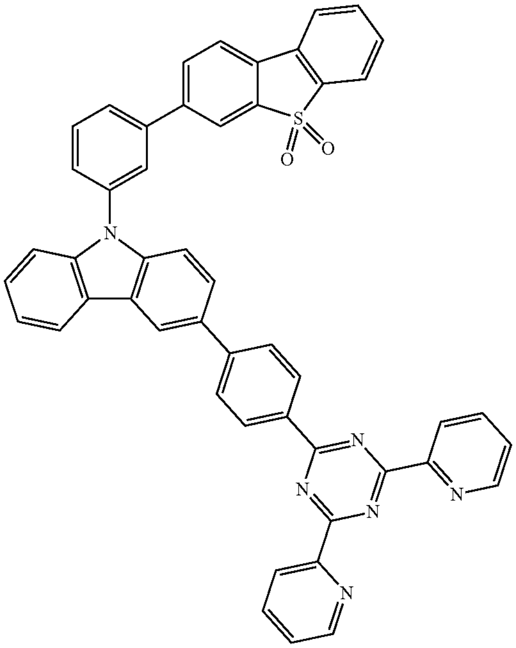
260
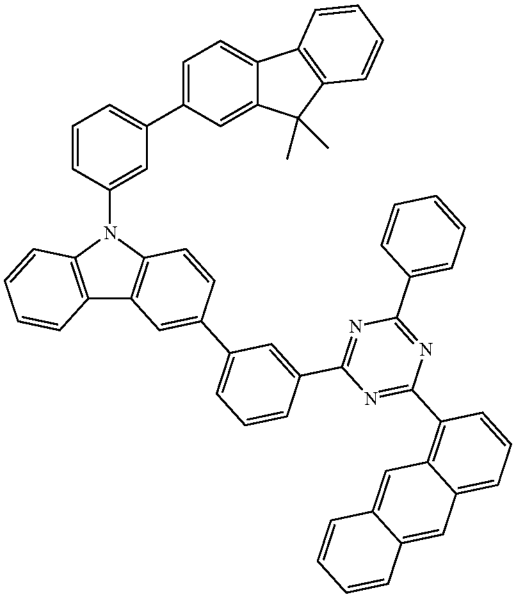

-continued
261
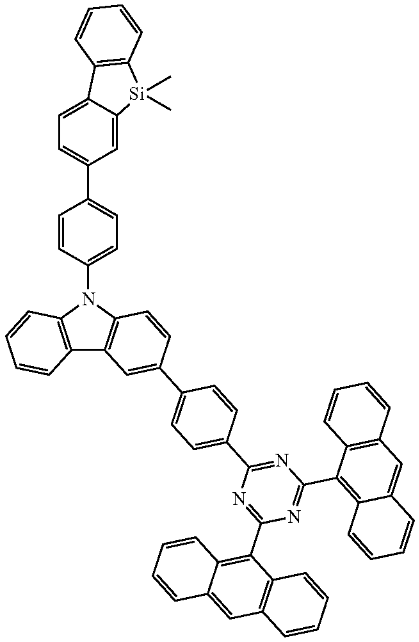
262
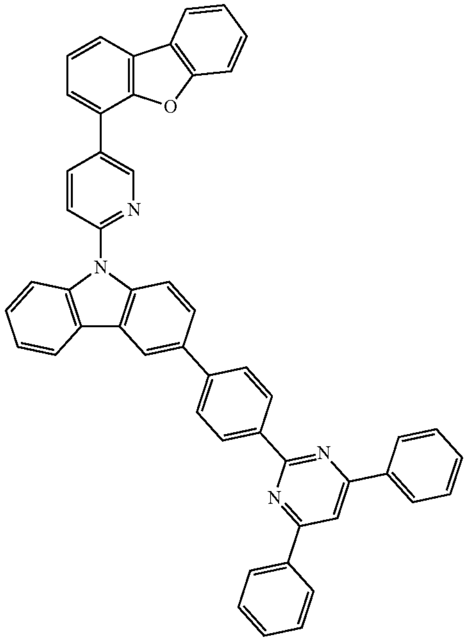
-continued
263
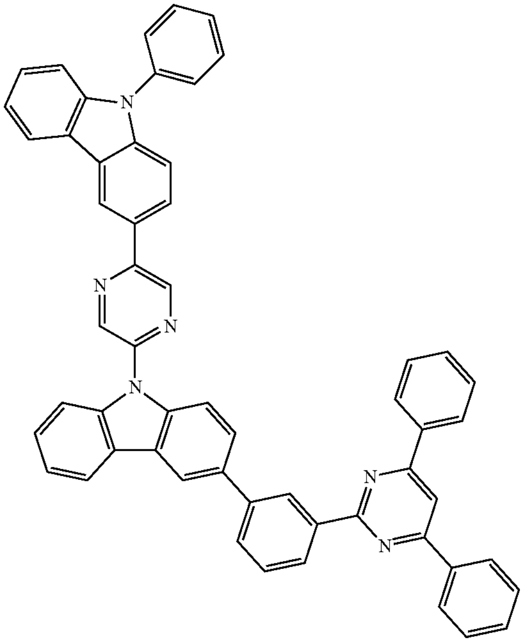
264
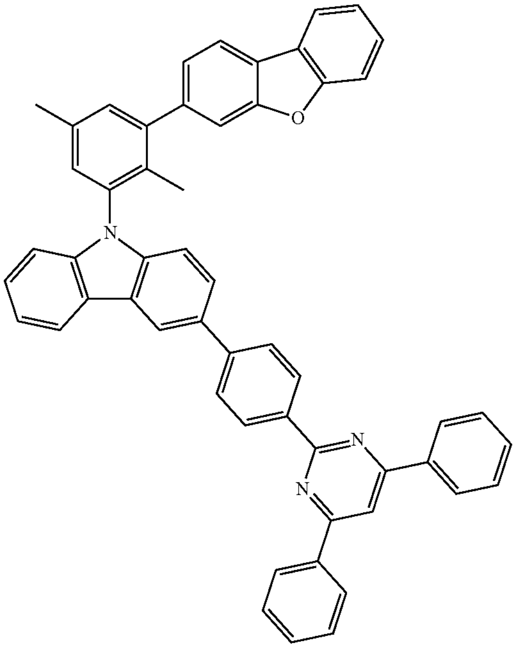

-continued
265
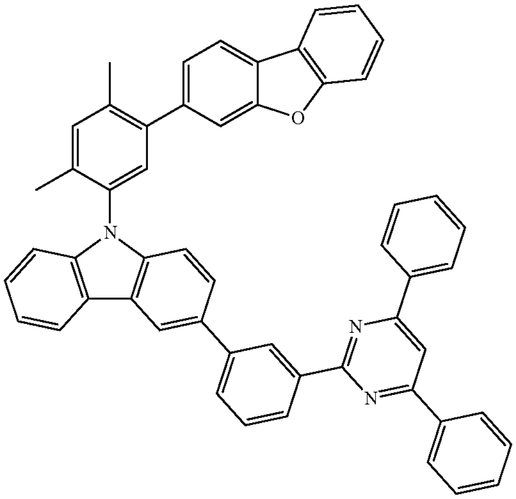
266
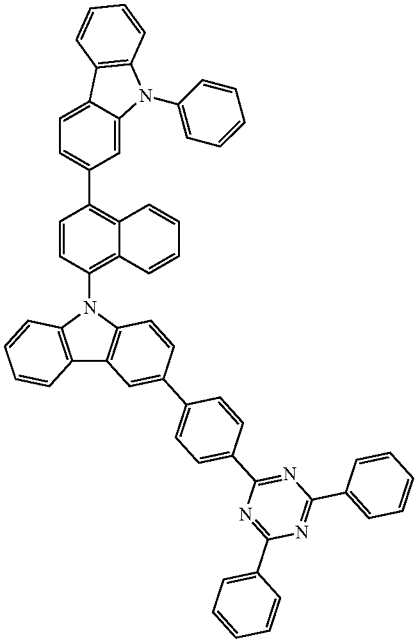
-continued
267
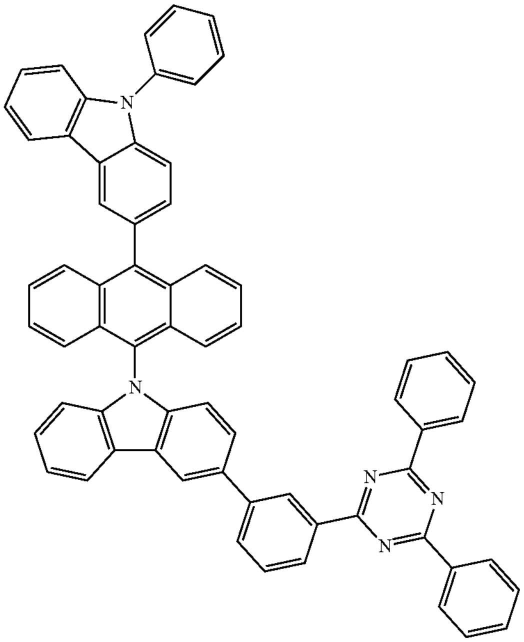
268
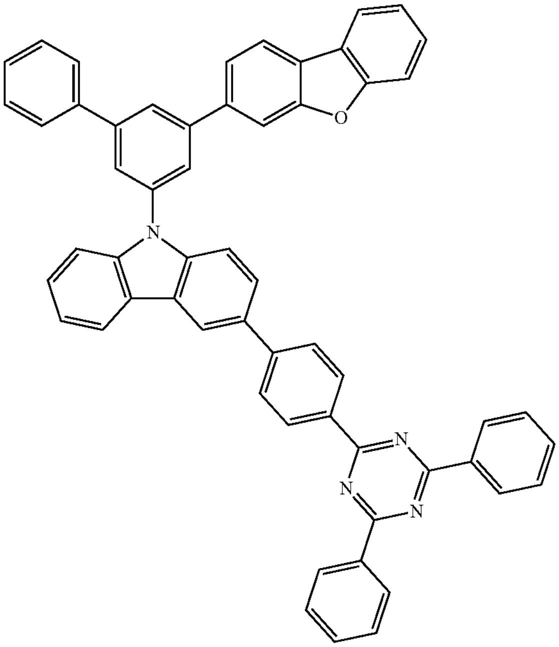

-continued
269
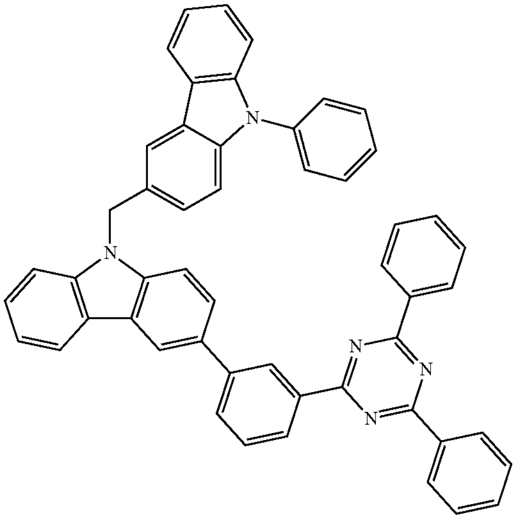
270
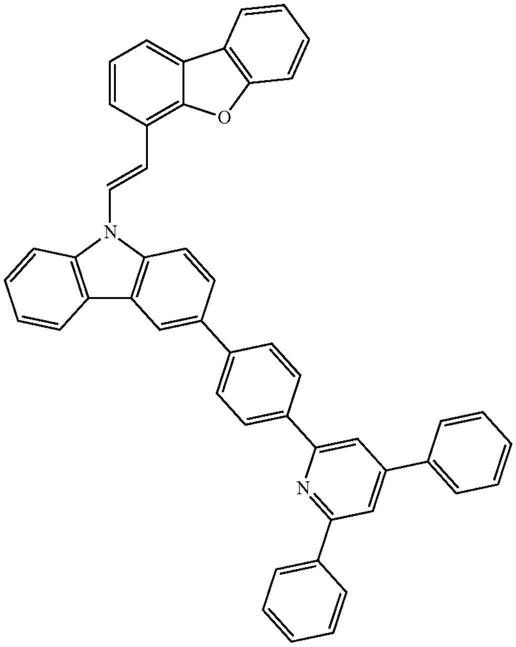
-continued
271
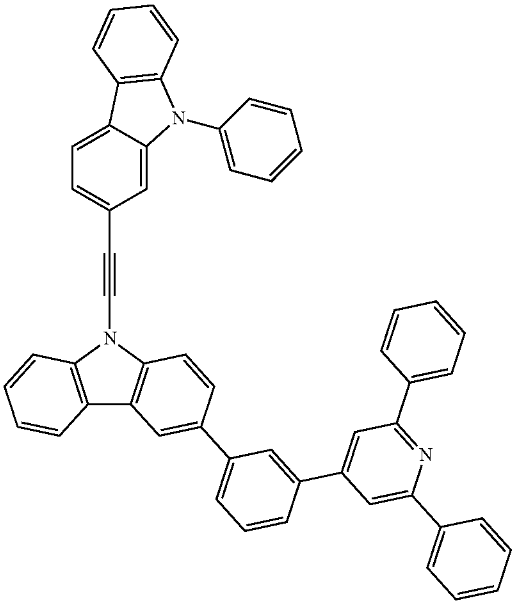
272
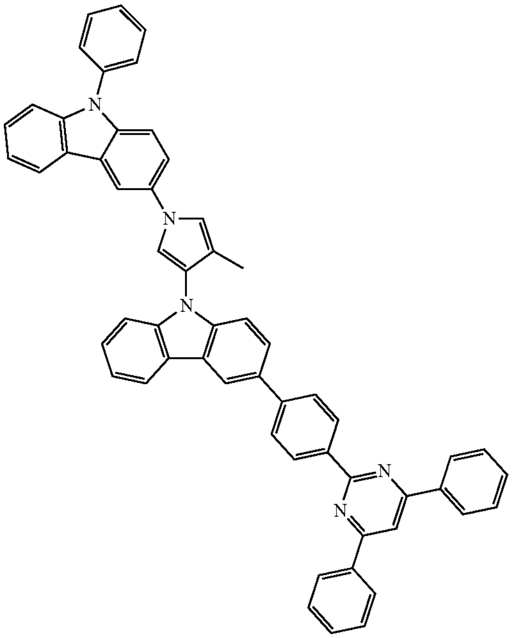

-continued
273
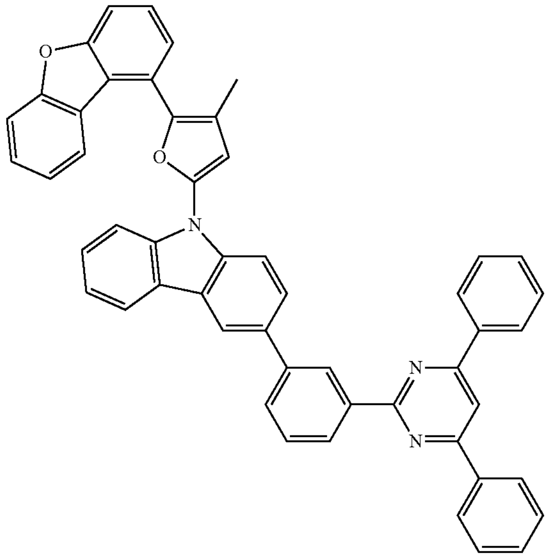
275
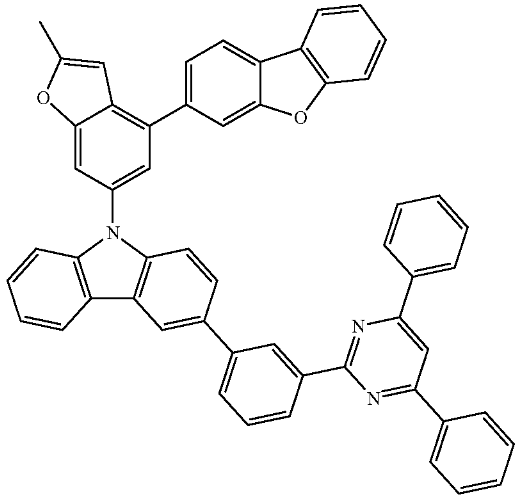
274
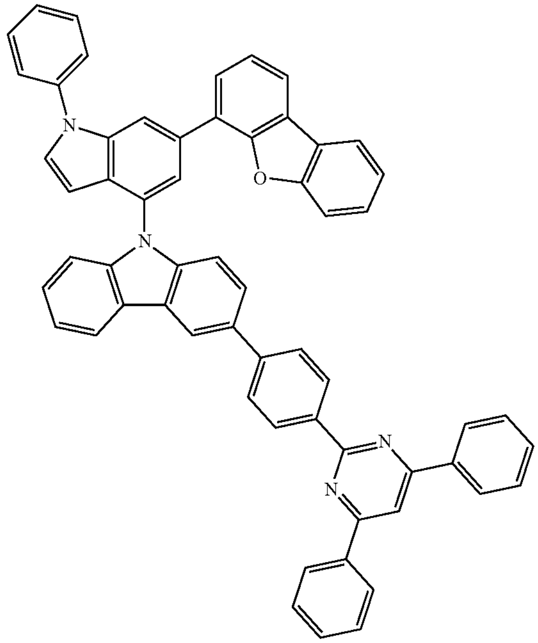
276
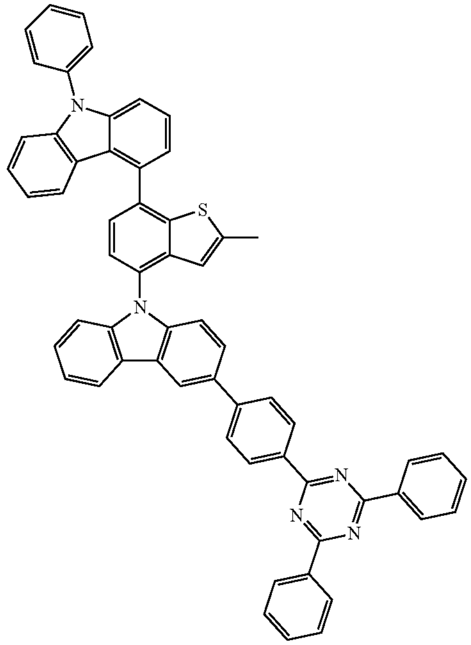

-continued
277
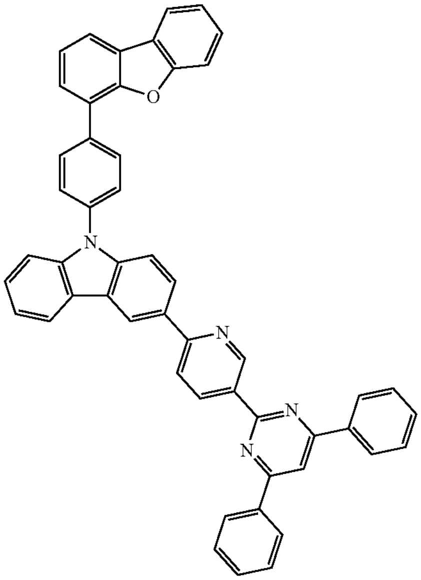
278
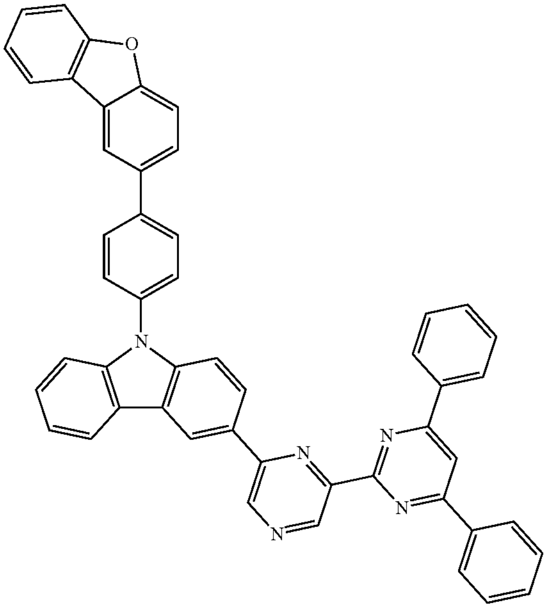
-continued
279
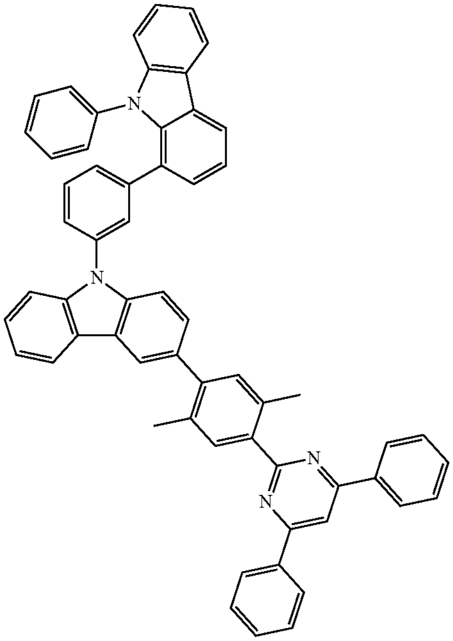
280
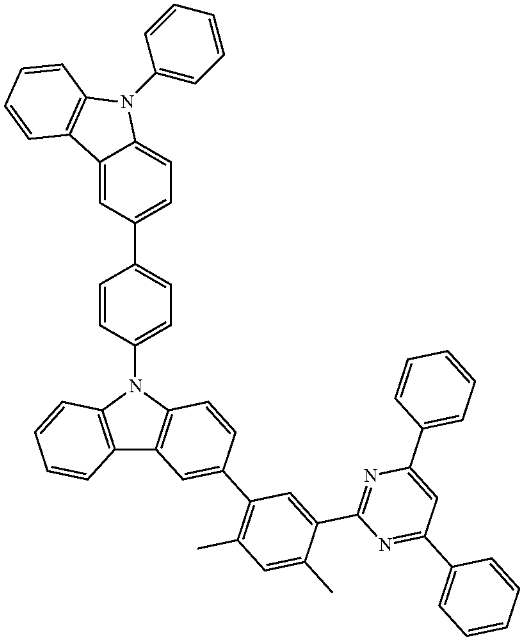

-continued
281
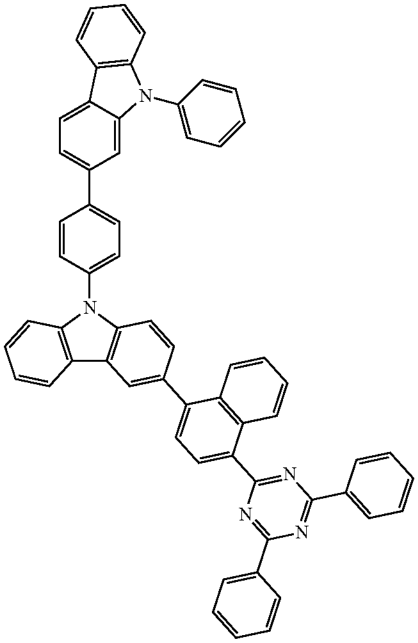
282
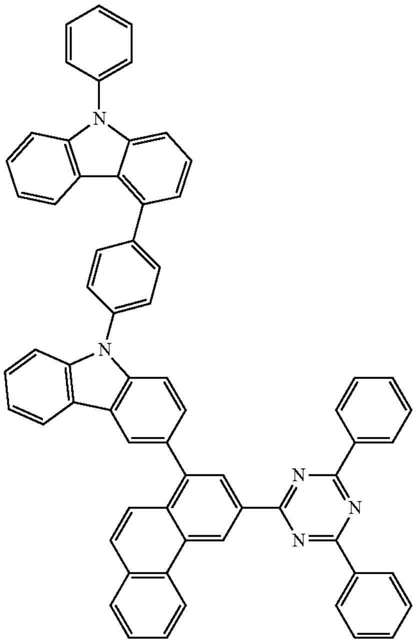
-continued
283
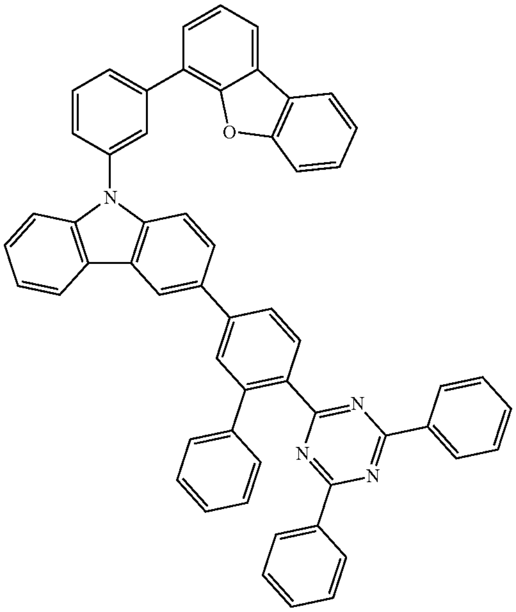
284
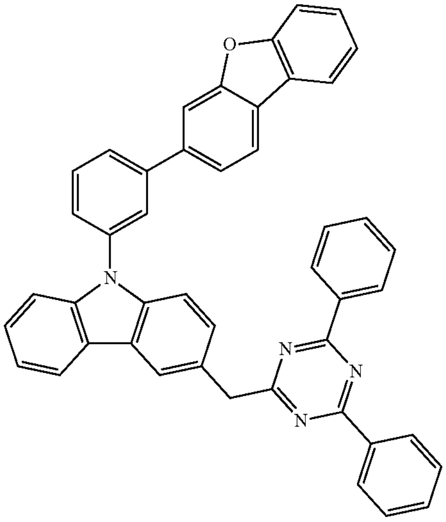

-continued
285
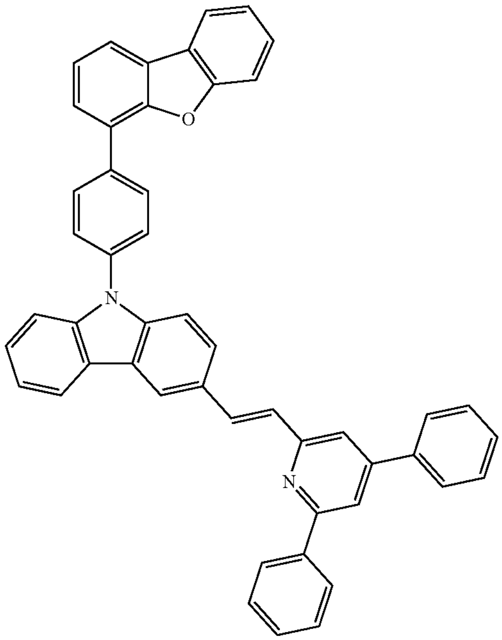
286
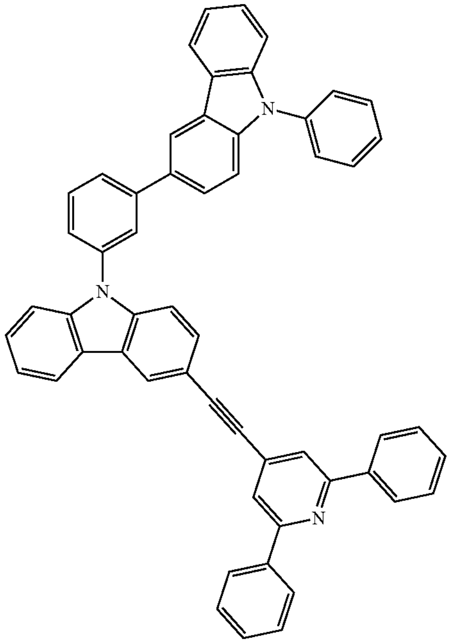
-continued
287
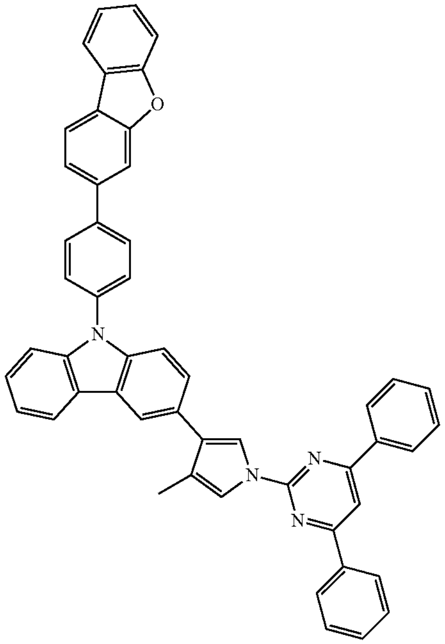
288
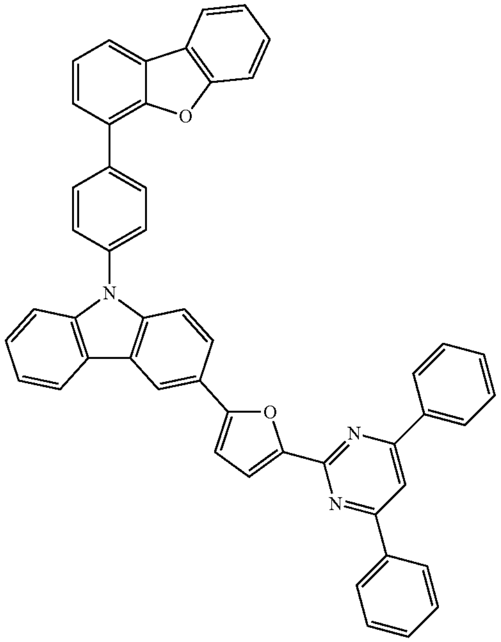

-continued
289
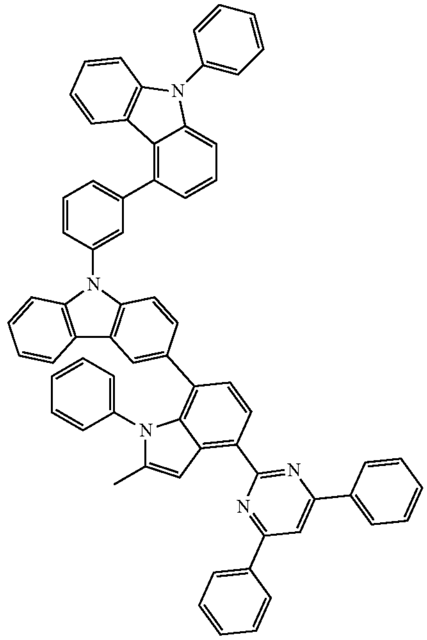
290
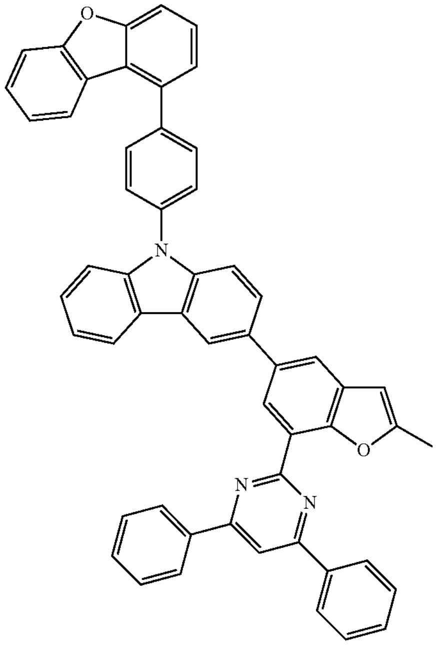
-continued
291
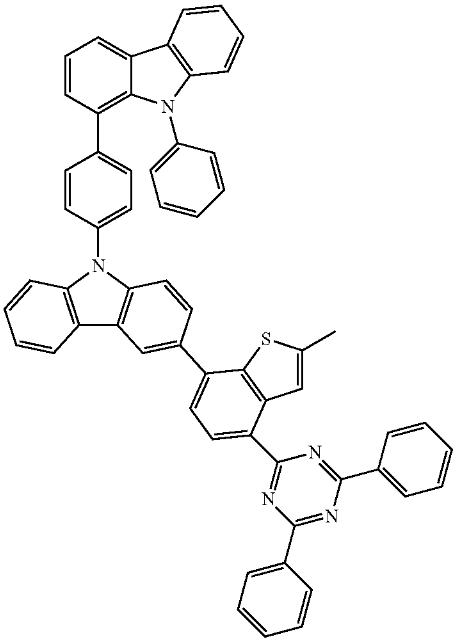
292
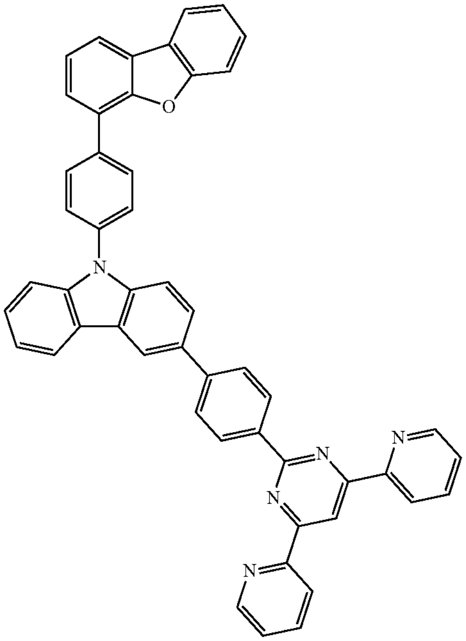

293
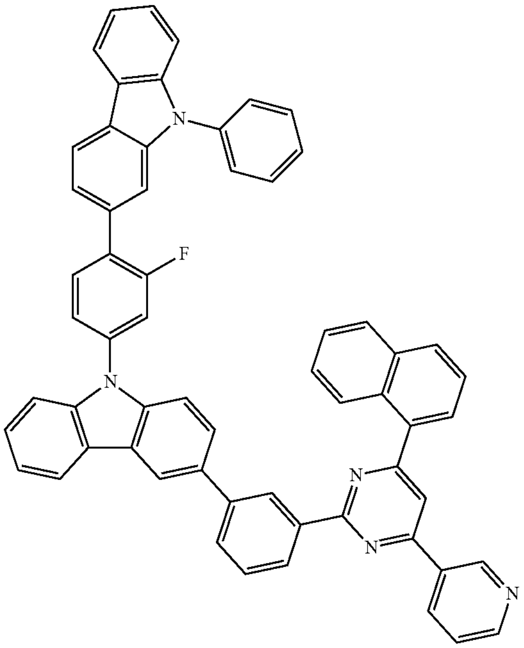
294
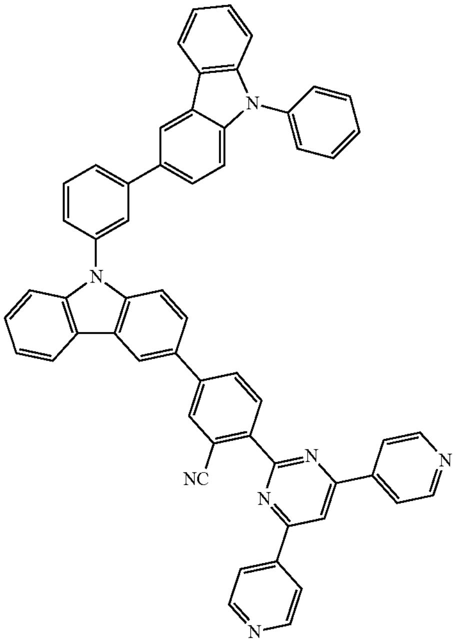
295
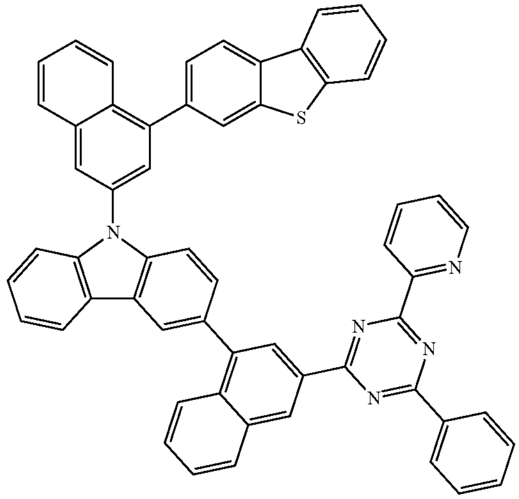
296
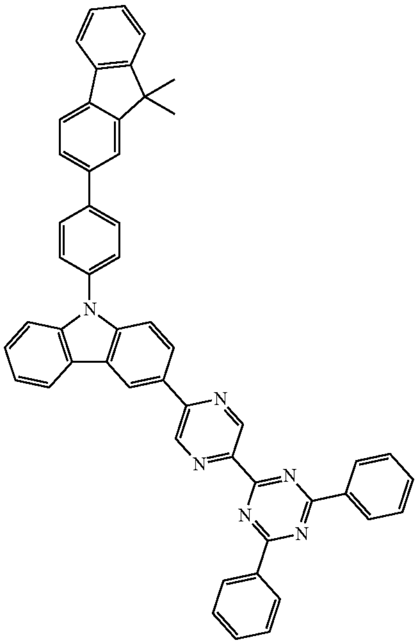

-continued
297
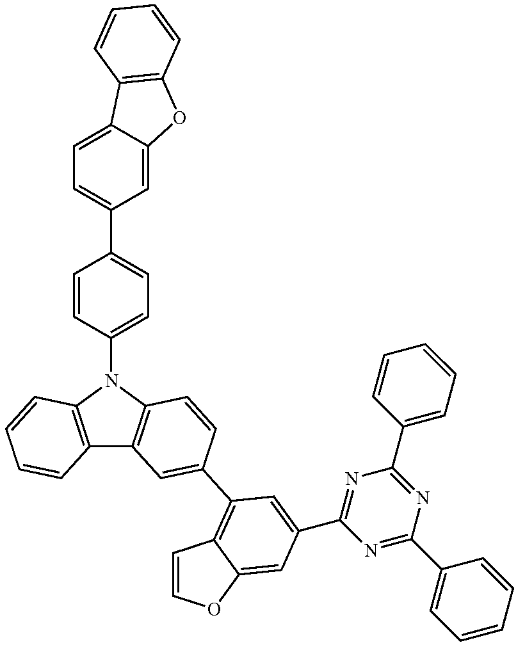
298
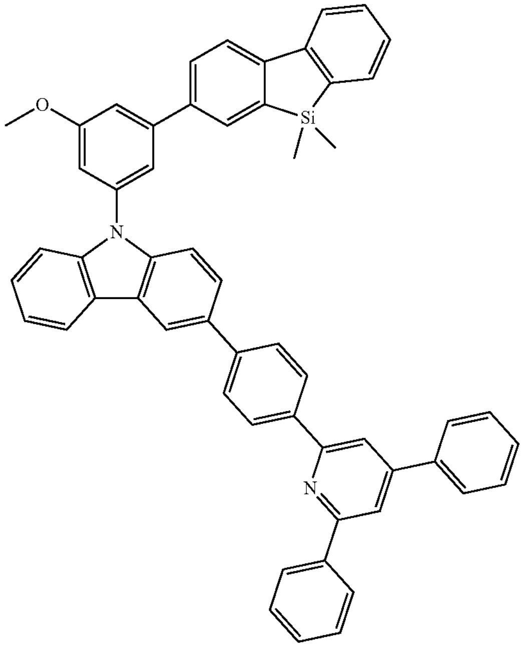
-continued
299
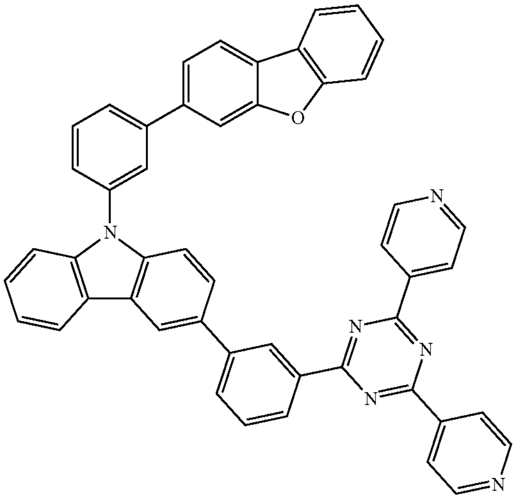
300
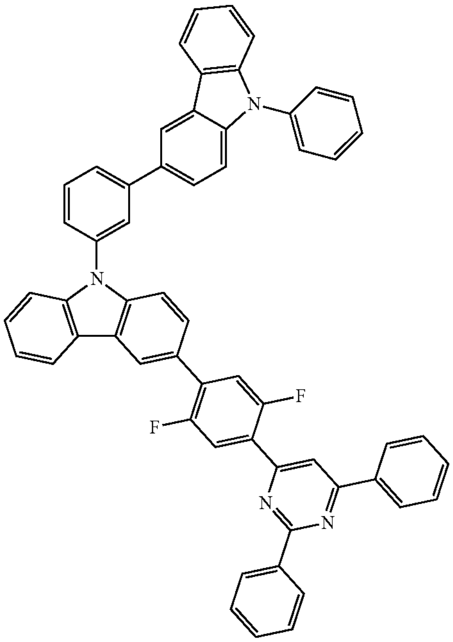

-continued
301
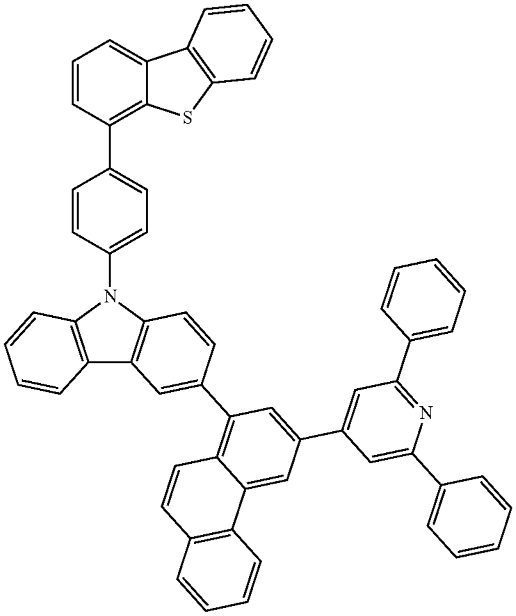
302
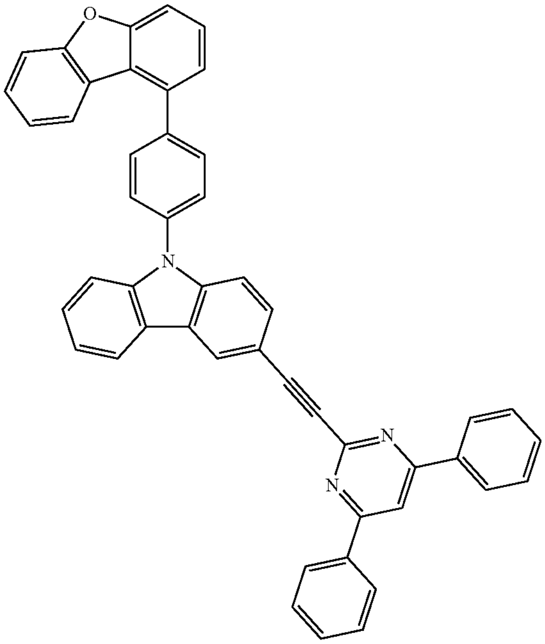
-continued
303
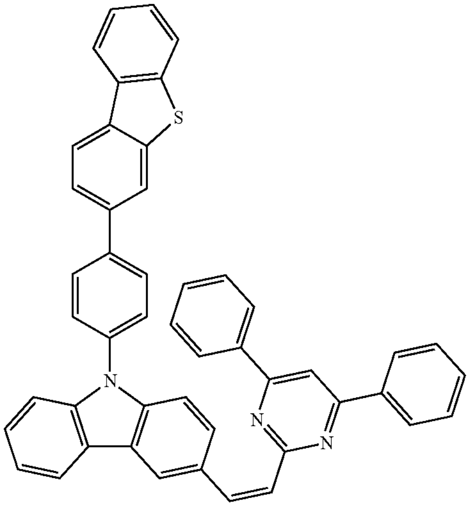
304
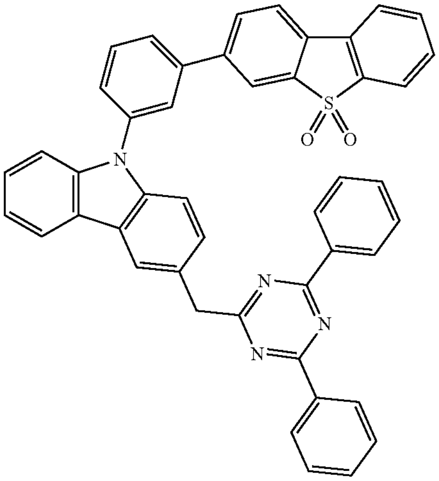
305
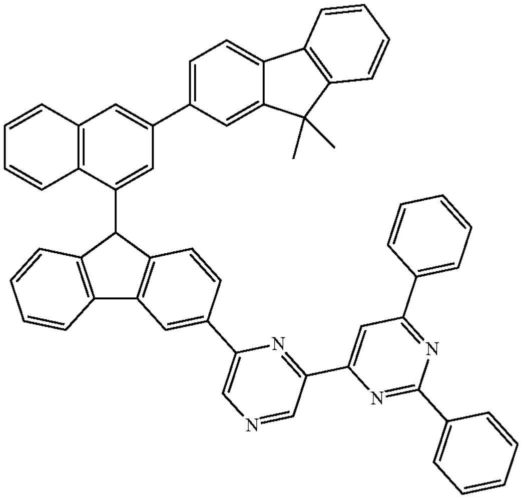

-continued
306
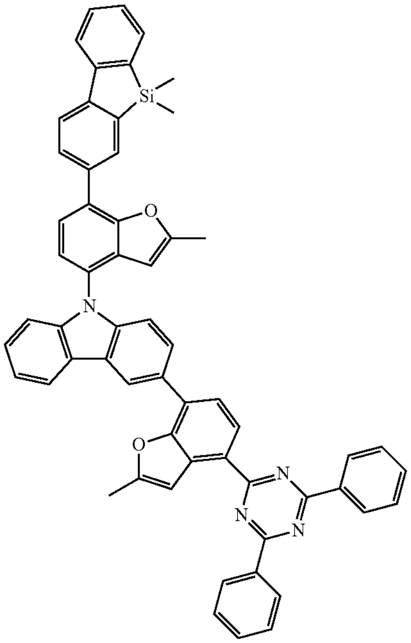
307
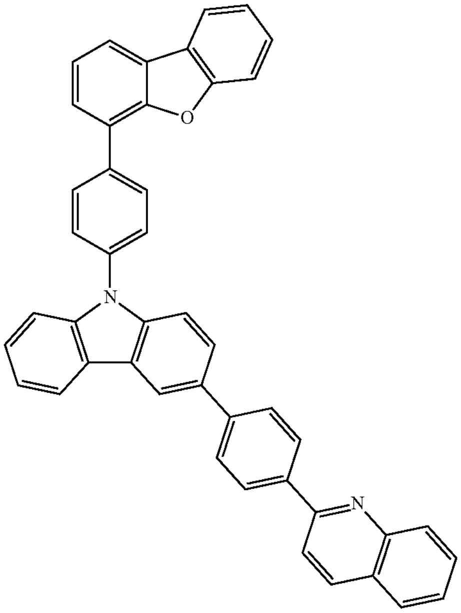
-continued
308
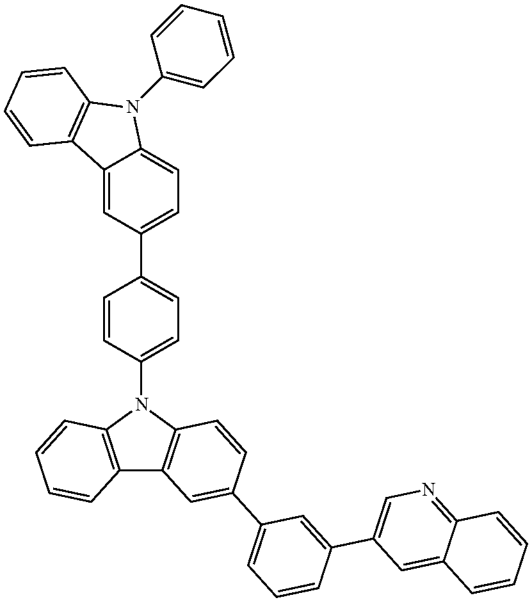
309
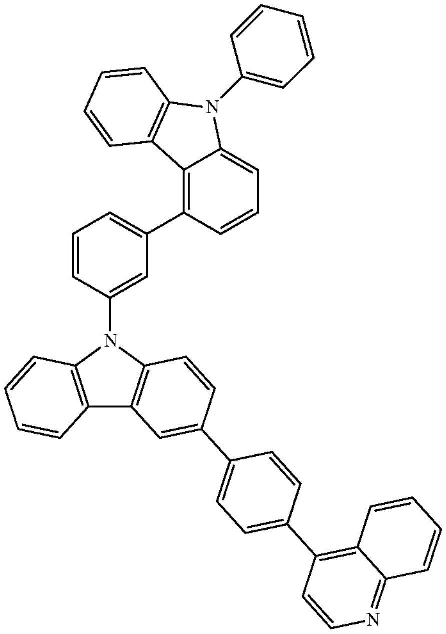

-continued
310
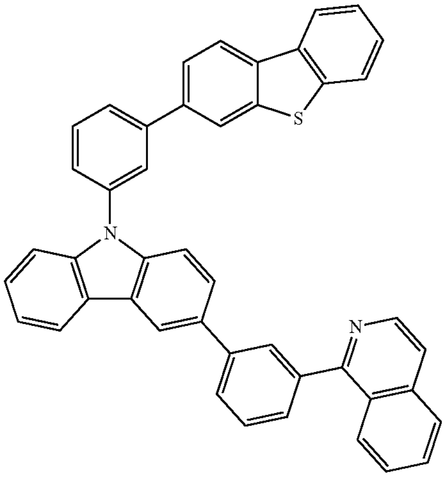
311
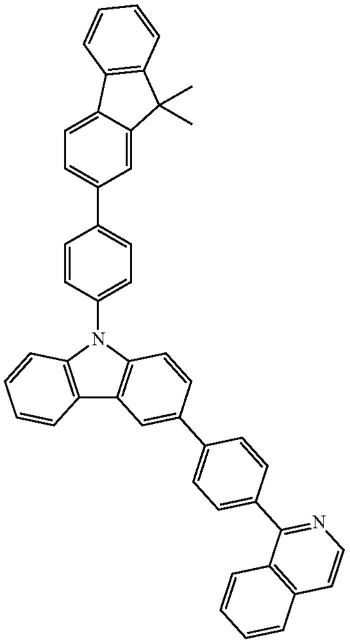
312
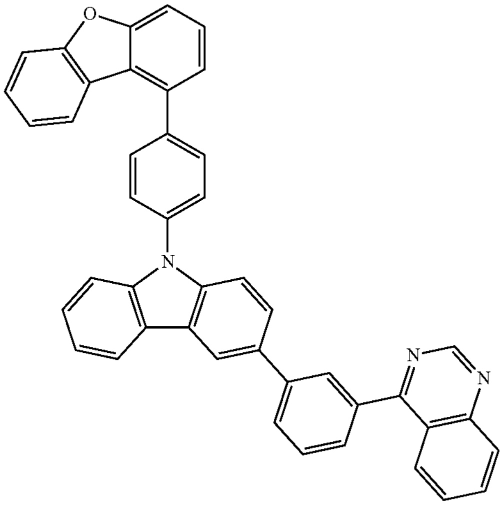
-continued
313
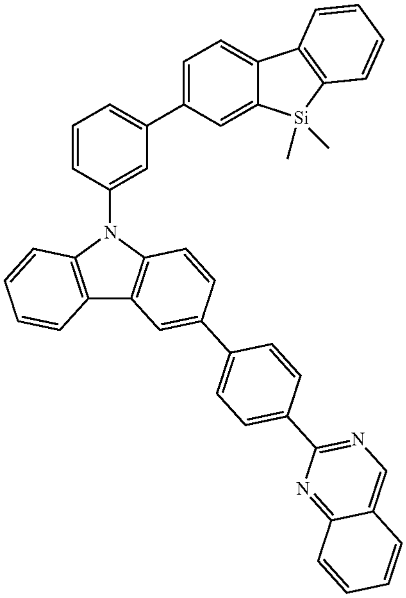
314
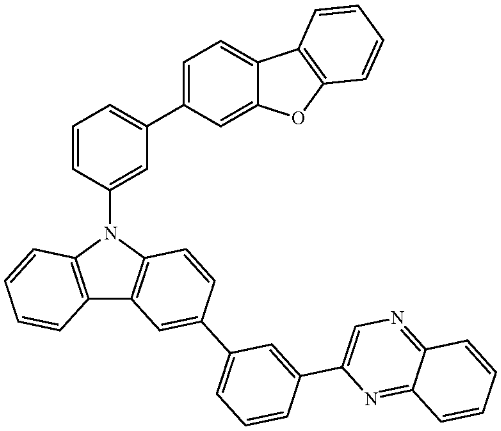
315
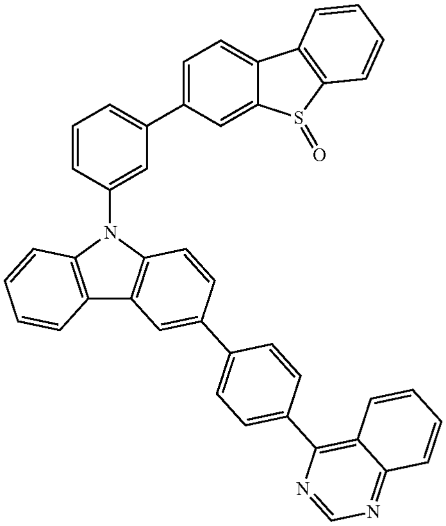

-continued
316
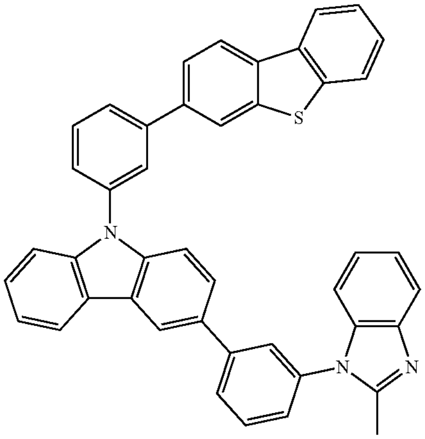
317
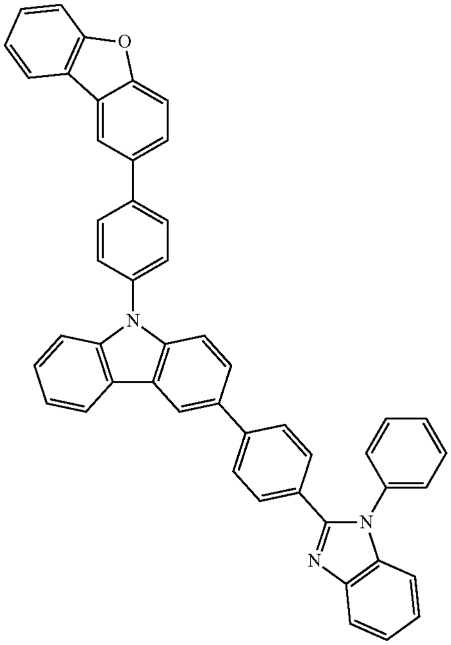
-continued
318
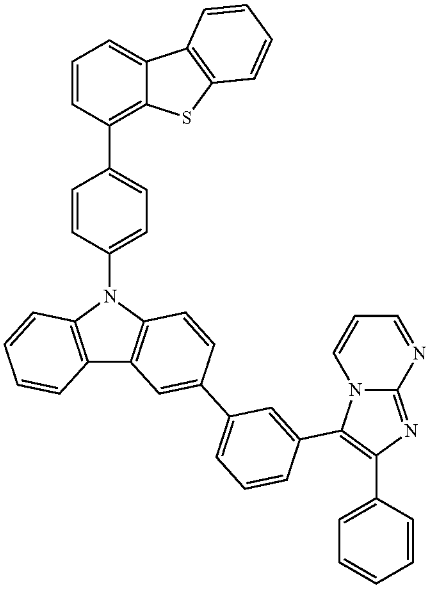
319
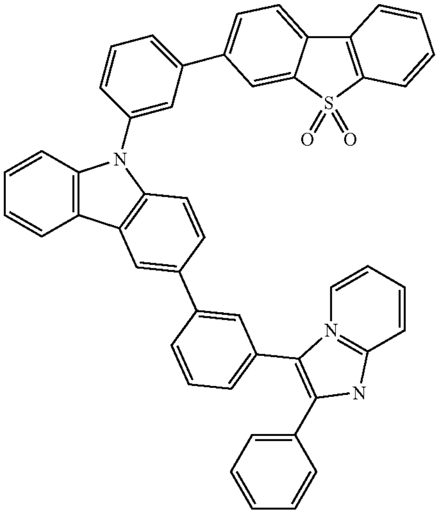
320
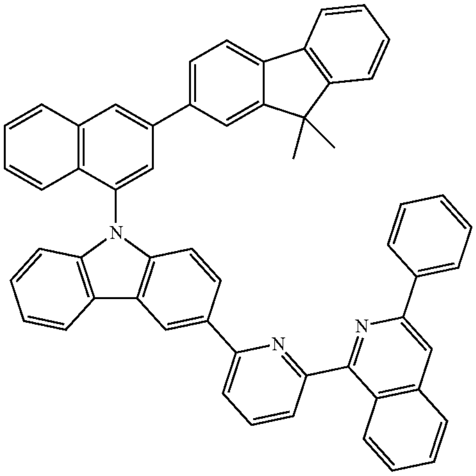

321
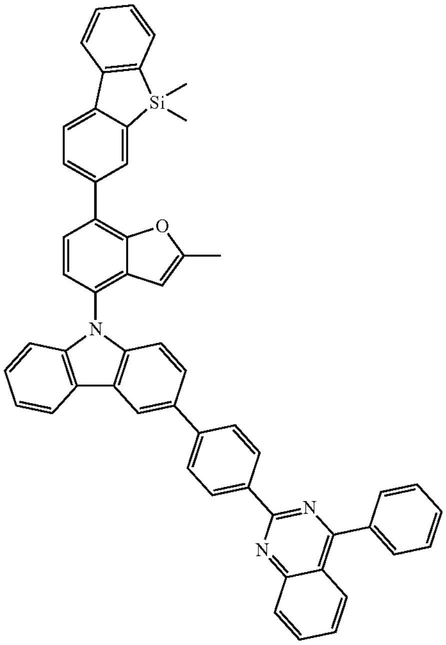
322
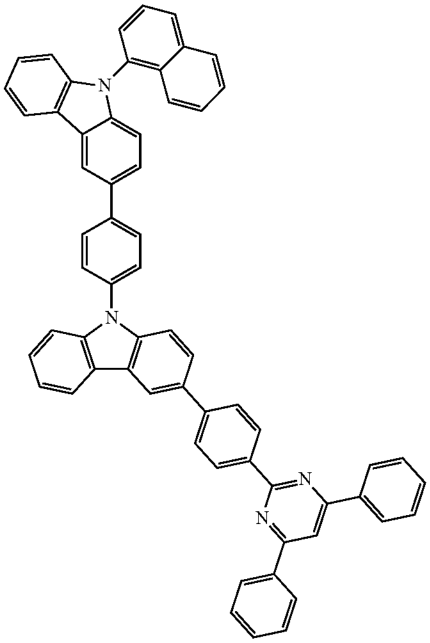
323
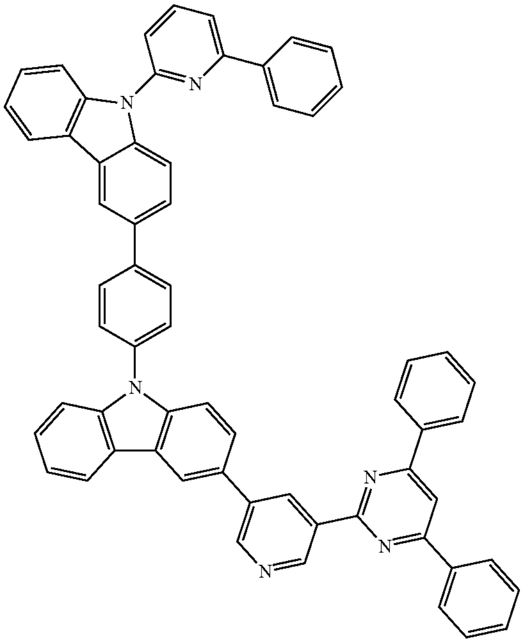
324
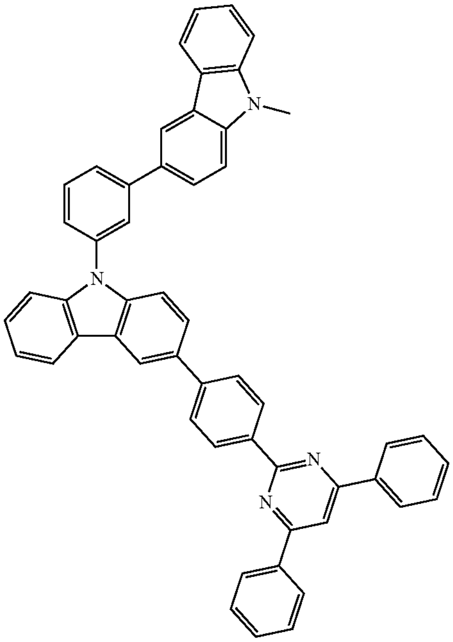

-continued
325
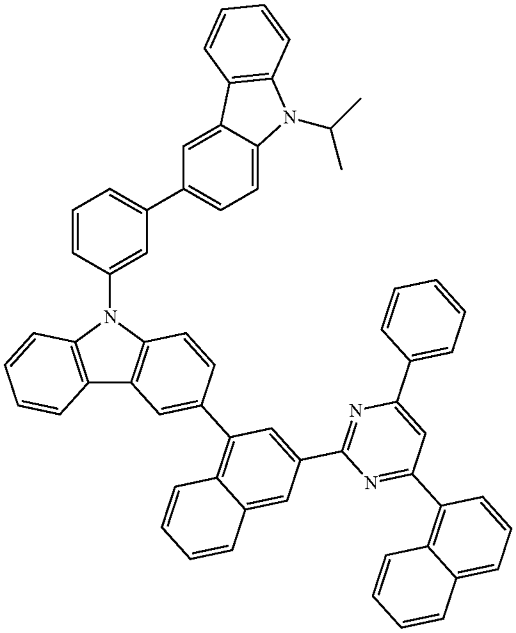
327
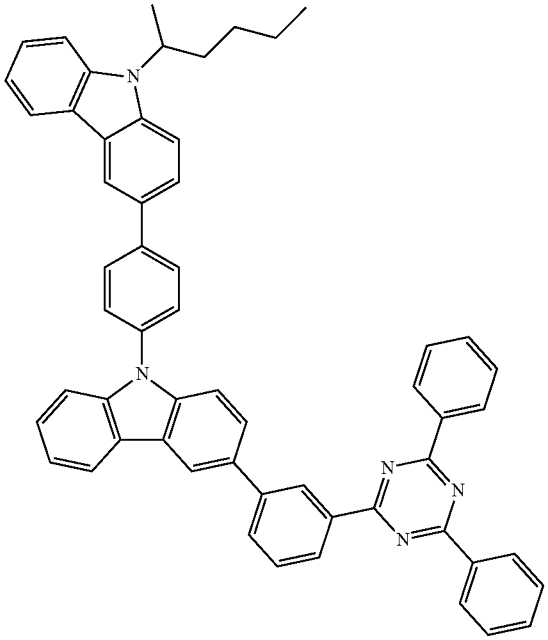
326
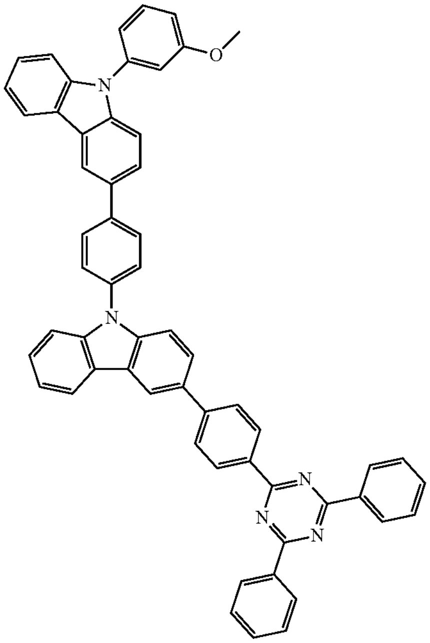
328
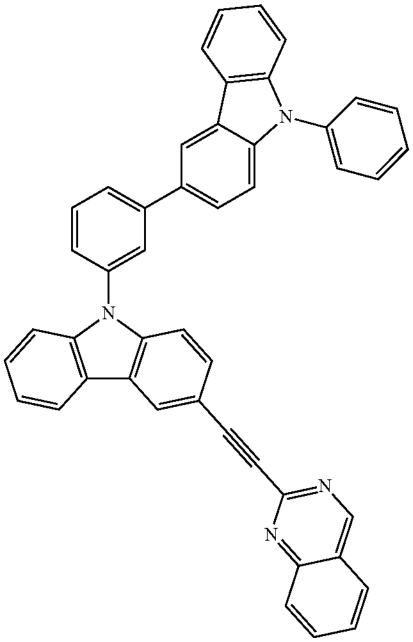

-continued
329
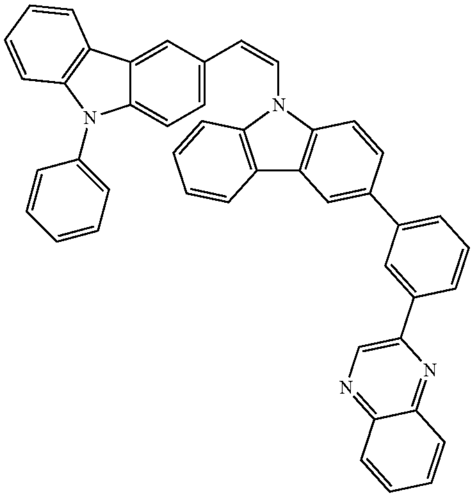
330
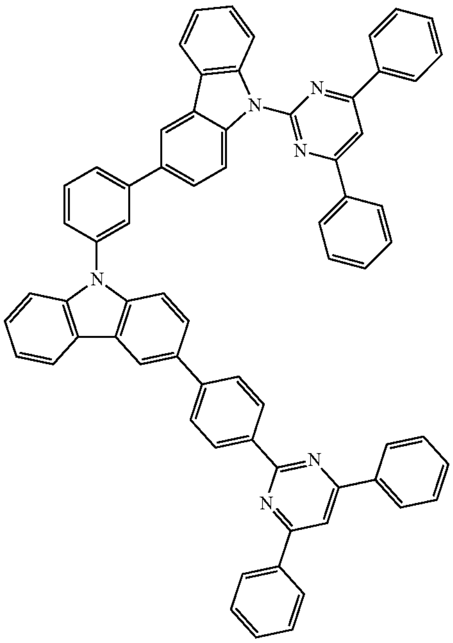
-continued
331
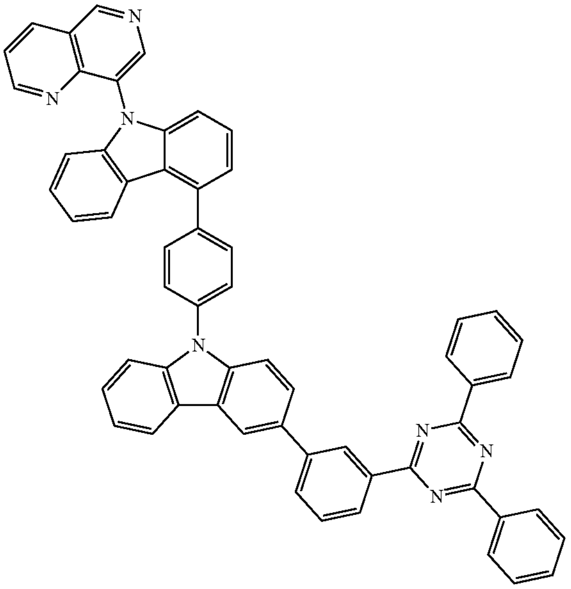
332
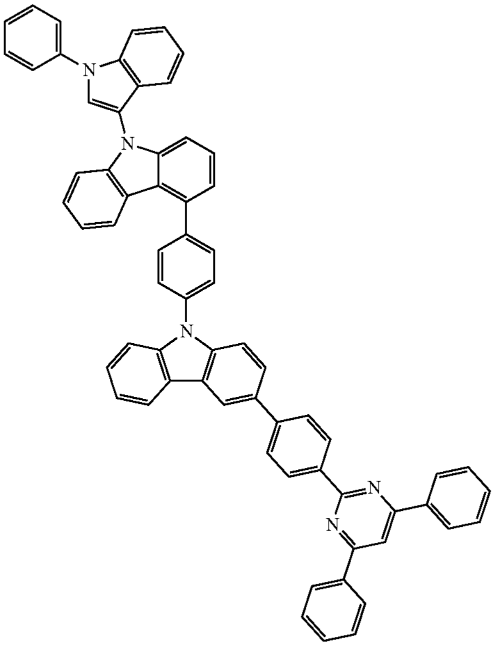

-continued
333
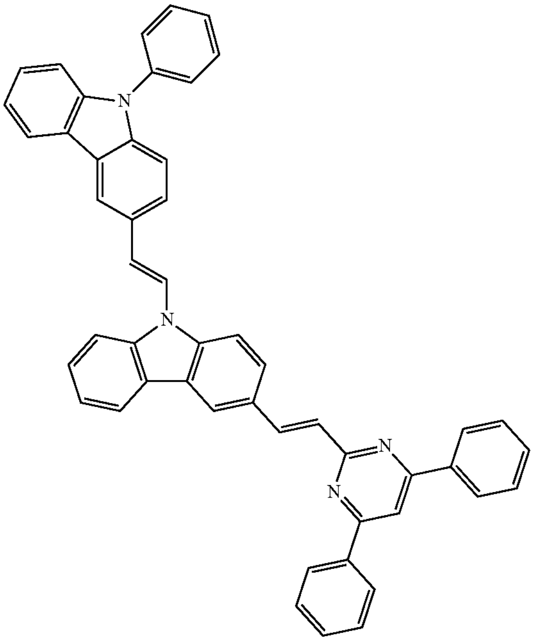
-continued
335
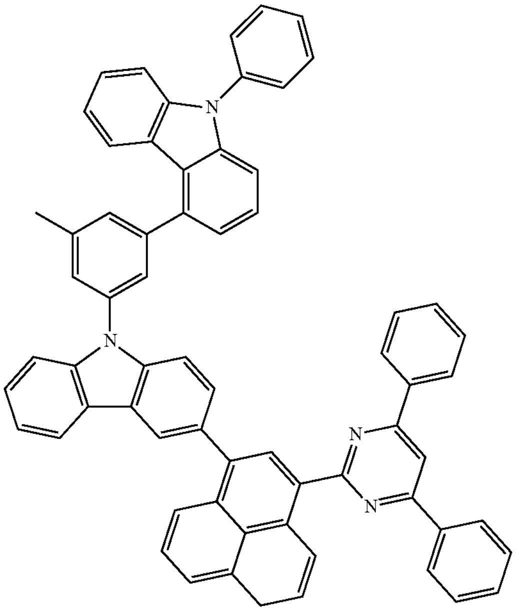
334
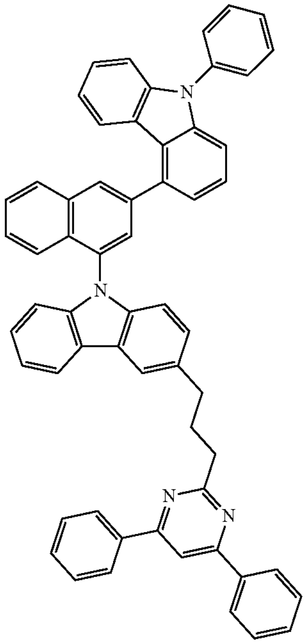
336
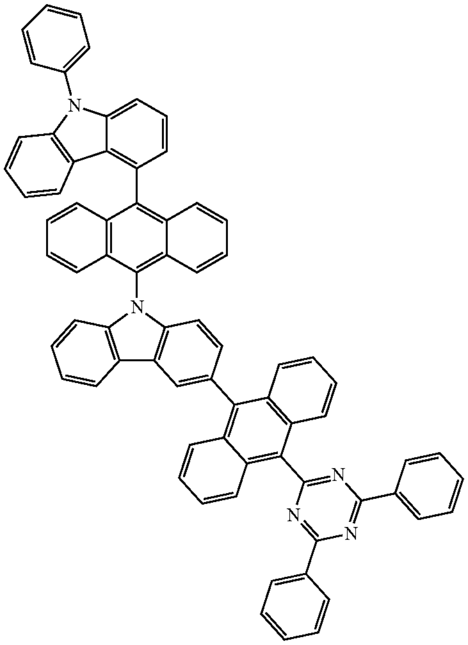

-continued
337
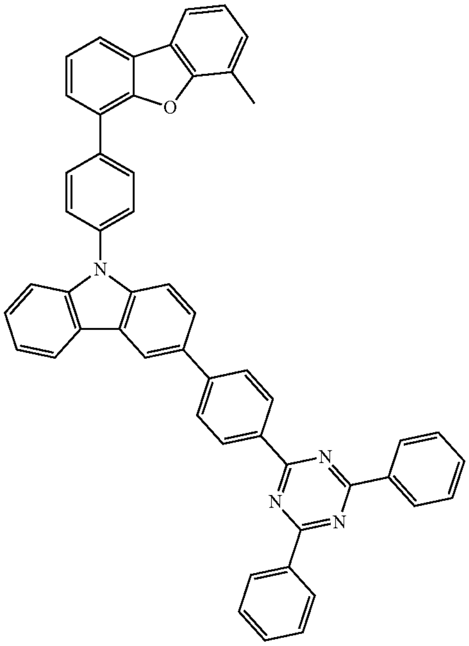
338
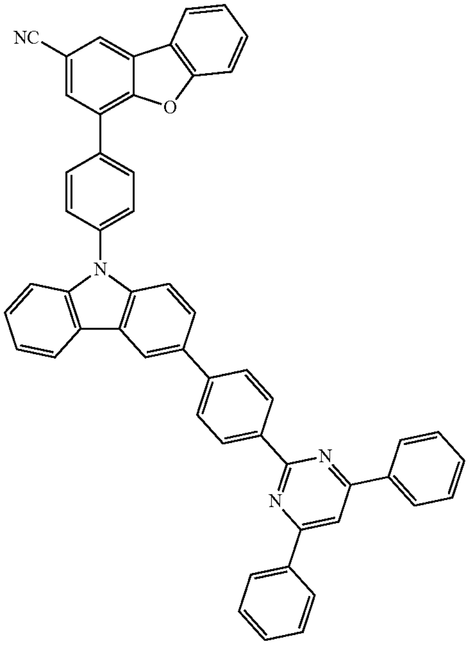
-continued
339
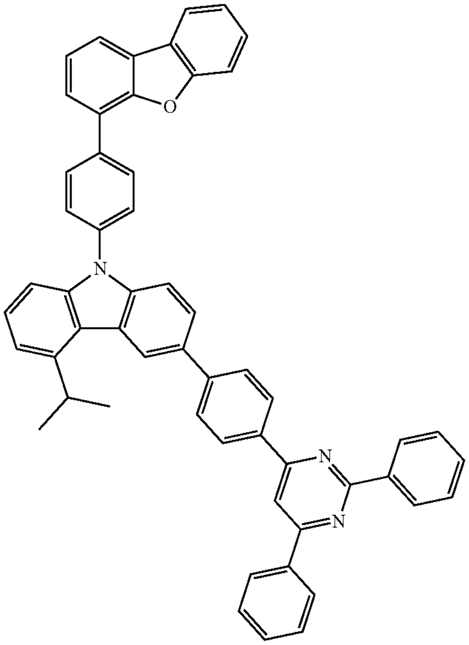
340
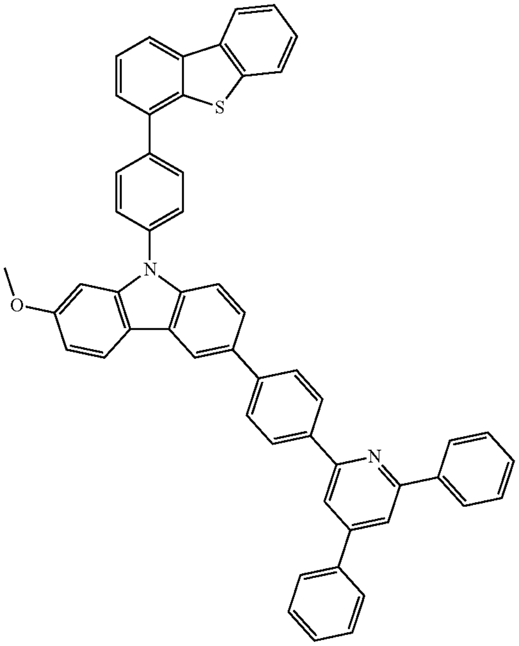

-continued
341
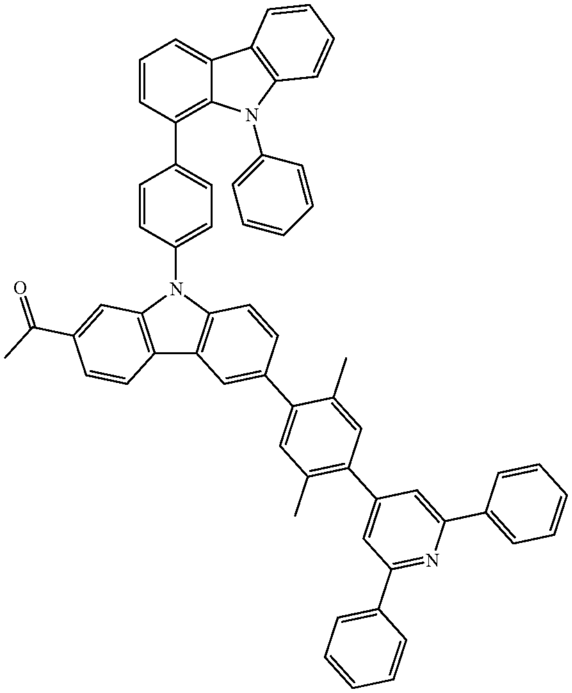
342
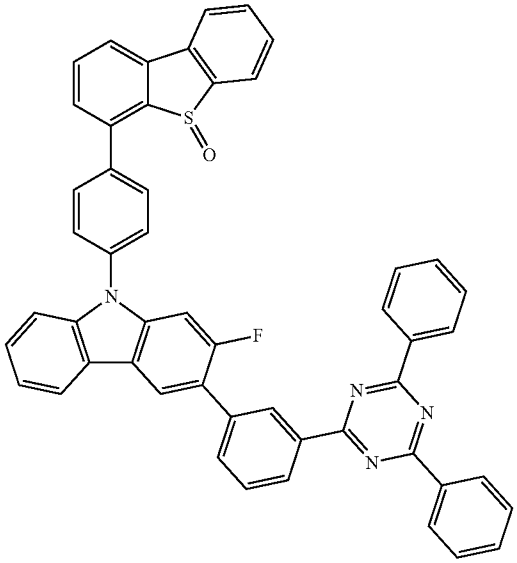
-continued
343
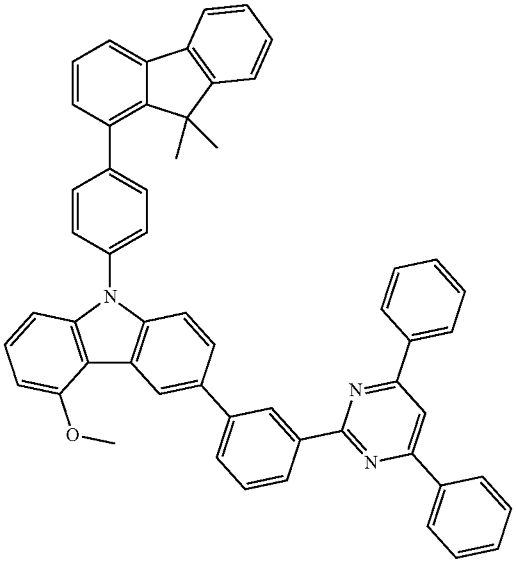
344
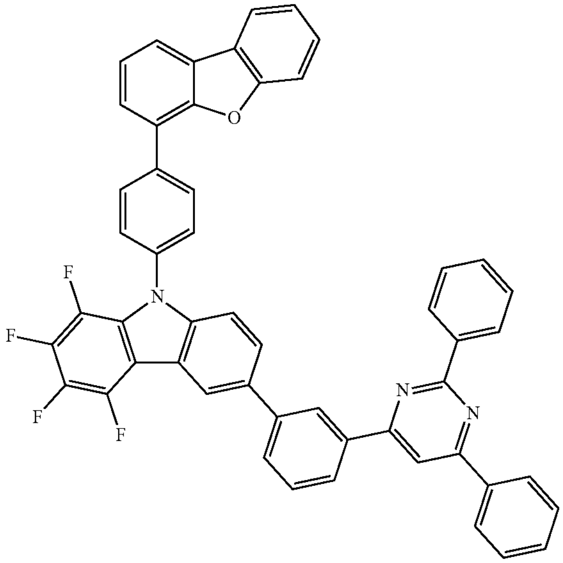

-continued
345
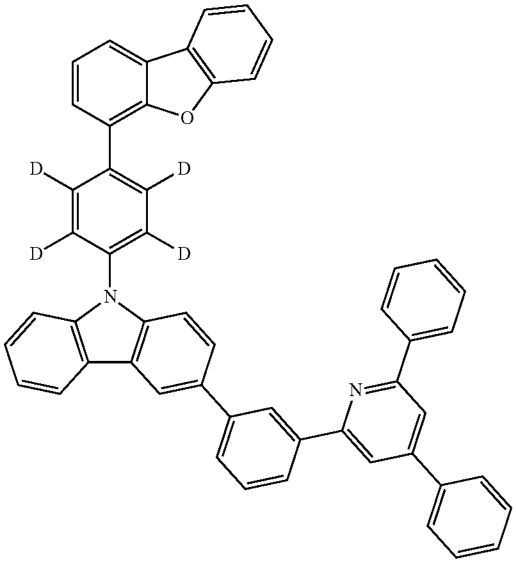
346
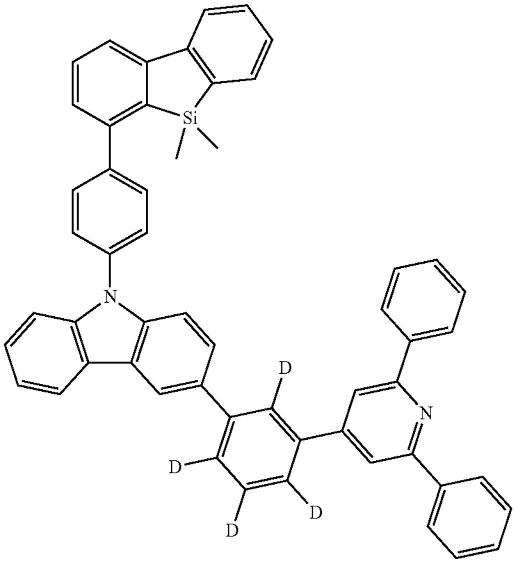
-continued
347
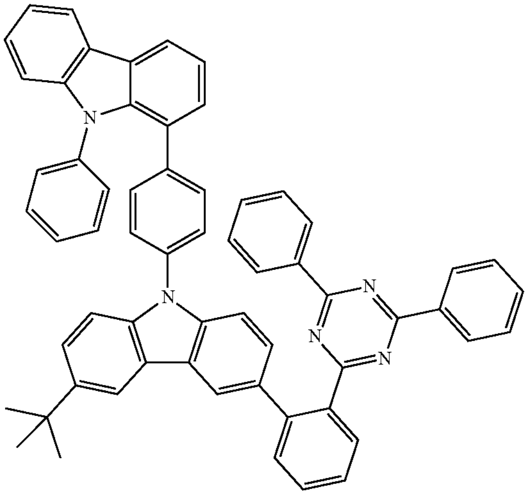
348
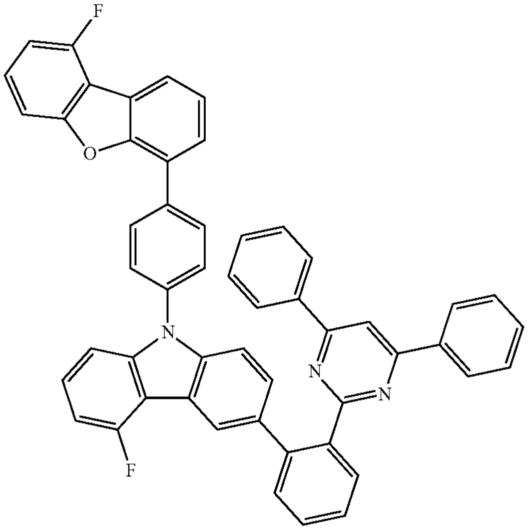
349
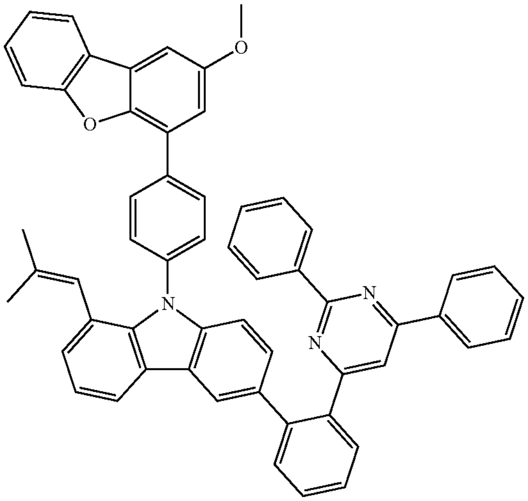

-continued

350

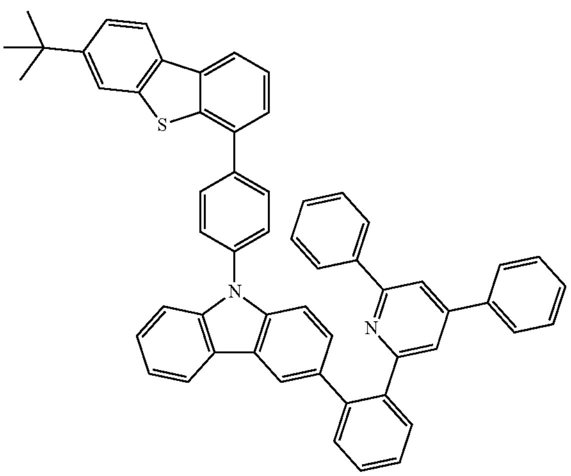

351

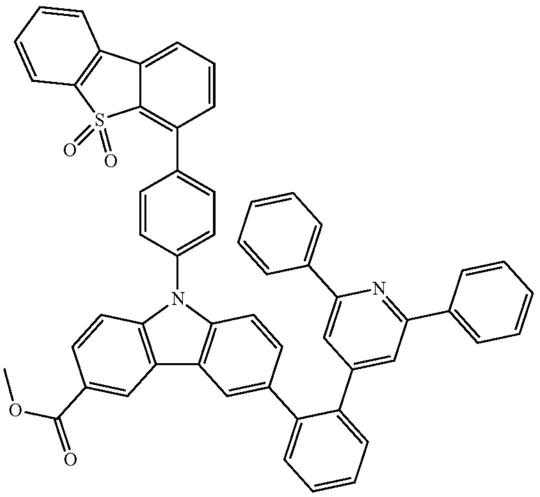

Group $R_1$ in Formula 1 may be selected from "a hydrogen, a deuterium, —F, —Cl, —Br, —I, a hydroxyl group, a cyano group, a nitro group, an amino group, an amidino group, a hydrazine group, a hydrazone group, a carboxylic acid group, —C(=O)—O-$Q_1$, —C(=O)-$Q_2$, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; and a $C_1$-$C_{60}$ alkyl group, a $C_2$-$C_{60}$ alkenyl group, a $C_2$-$C_{60}$ alkynyl group, and a $C_1$-$C_{60}$ alkoxy group", each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group, —C(=O)—O-$Q_3$, —C(=O)-$Q_4$, a sulfonic acid group or a salt thereof, and a phosphoric acid group or a salt thereof. That is, $R_1$ in Formula 1 is not a cyclic group.

Group $E_1$ in Formula 1 may be substituted with at least one $Ar_1$, and $Ar_1$ may be selected from "a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, and a substituted or unsubstituted monovalent non-aromatic heterocondensed polycyclic group". That is, $E_1$ in Formula 1 may be substituted with at least one cyclic group.

Furthermore, a "nitrogen" of a "carbazole" in Formula 1 may be linked to a "carbon" of the benzo group of the a "carbazole ring" with -$(L_1)_{a1}$-located therebetween (see Formula 1' below).

Formula 1'

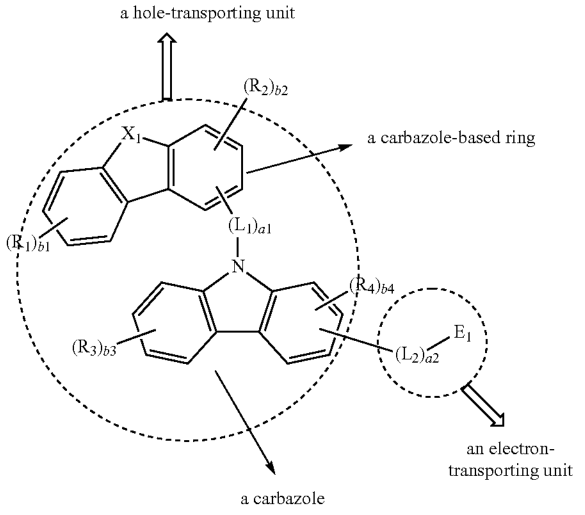

The carbazole compound represented by Formula 1 has, as represented by Formula 1', a bipolar structure having a hole-transporting unit and an electron-transporting unit. Due to the bipolar structure, the carbazole compound may have excellent electric characteristics.

The carbazole compound represented by Formula 1 includes two linking groups represented by -$(L_1)_{a1}$- and -$(L_2)_{a2}$-, and $R_1$ in Formula 1 is not a cyclic group, as described above. These two linking groups and $R_1$ may provide the carbazole compound represented by Formula 1 with a molecular structure that enables the carbazole compound to have high decomposition temperature. Thus, the carbazole compound represented by Formula 1 may have excellent thermal stability. For example, the carbazole compound represented by Formula 1 may have a decomposition temperature that is higher than a sublimation temperature thereof at a vacuum degree of about $10^{-8}$ torr to about $10^{-3}$ torr. According to an embodiment, the decomposition temperature of the carbazole compound represented by Formula 1 may be higher than the sublimation temperature of the carbazole compound represented by Formula 1 at the vacuum degree of about $10^{-8}$ torr to about $10^{-3}$ torr by 30° C. or more. Accordingly, the carbazole compound represented by Formula 1 may have excellent process stability, excellent film-formation characteristics, and when included in an organic light-emitting device (OLED), improvement in stability and longer lifespan of the OLED may be achieved.

The carbazole compound represented by Formula 1 has an electron-transporting cyclic group $E_1$ as defined herein. The electron-transporting cyclic group $E_1$ has at least one $Ar_1$ defined herein as a substituent, and two linking groups represented by $-(L_1)_{a1}-$ and $-(L_2)_{a2}-$. Accordingly, the carbazole compound represented by Formula 1 may have a HOMO energy level, a LUMO energy level, and a triplet energy level, suitable for use as a material for an emission layer of an organic light-emitting device.

A synthesis method of the carbazole compound represented by Formula 1 may be apparent to one of ordinary skill in the art by referring to Synthesis Examples 1 to 17.

The carbazole compound represented by Formula 1 is suitable for use in an organic layer of an organic light-emitting device, for example, for use as a host in an emission layer of the organic layer. Thus, another aspect provides an organic light-emitting device that includes: a first electrode; a second electrode; and an organic layer disposed between the first electrode and the second electrode, wherein the organic layer includes an emission layer and at least one of the carbazole compounds represented by Formula 1.

The organic light-emitting device may have, due to the inclusion of an organic layer including the carbazole compound represented by Formula 1, low driving voltage, high efficiency, high brightness, and long lifespan.

The carbazole compound of Formula 1 may be used between a pair of electrodes of an organic light-emitting device. For example, the carbazole compound may be included in at least one group selected from i) the emission layer, ii) a hole transport region (including, for example, at least one layer selected from a hole injection layer, a hole transport layer, a buffer layer, and an electron blocking layer) disposed between the first electrode and the emission layer, and iii) an electron transport region (including, for example, at least one layer selected from a hole blocking layer, an electron transport layer, and an electron injection layer) disposed between the emission layer and the second electrode. For example, the carbazole compound represented by Formula 1 may be included in the emission layer. In this regard, the carbazole compound may further include a dopant, and the carbazole compound included in the emission layer may act as a host. The emission layer may be a blue emission layer emitting blue light or a green emission layer emitting green light, and the dopant may be a phosphorescent dopant.

The expression "(an organic layer) includes at least one of the carbazole compounds" used herein may be applicable when (an organic layer) includes one carbazole compound of Formula 1 and when (an organic layer) includes two or more different carbazole compounds of Formula 1.

For example, the organic layer may include, as the carbazole compound, only Compound 1. In this regard, Compound 1 may exist in an emission layer of the organic light-emitting device. In another embodiment, the organic layer may include, as the carbazole compound, Compound 1 and Compound 2. In this regard, Compound 1 and Compound 2 may be situated in either an identical layer (for example, Compound 1 and Compound 2 all may exist in an emission layer), or different layers.

The first electrode may be an anode, which is a hole injection electrode, and the second electrode may be a cathode, which is an electron injection electrode, or the first electrode may be a cathode, which is an electron injection electrode, or the second electrode may be an anode, which is a hole injection electrode.

For example, the first electrode is an anode, and the second electrode is a cathode, and the organic layer includes i) a hole transport region disposed between the first electrode and the emission layer, wherein the hole transport region includes at least one of a hole injection layer, a hole transport layer, and an electron blocking layer, and ii) an electron transport region disposed between the emission layer and the second electrode, wherein the electron transport region includes at least one layer selected from a hole blocking layer, an electron transport layer, and an electron injection layer.

The term "organic layer" used herein refers to a single layer and/or a plurality of layers disposed between the first electrode and the second electrode of an organic light-emitting device. The "organic layer" may include, in addition to an organic compound, an organometallic complex including metal.

FIG. 1 is a schematic view of an organic light-emitting device 10 according to an embodiment. Hereinafter, the structure of an organic light-emitting device according to an embodiment and a method of manufacturing an organic light-emitting device according to an embodiment will be described in connection with FIG. 1. The organic light-emitting device 10 includes a first electrode 11, an organic layer 15, and a second electrode 19, which are sequentially stacked.

In FIG. 1, a substrate may be additionally disposed under the first electrode 11 or above the second electrode 19. For use as the substrate, any substrate that is used in general organic light-emitting devices may be used, and the substrate may be a glass substrate or transparent plastic substrate, each with excellent mechanical strength, thermal stability, transparency, surface smoothness, ease of handling, and water repellency.

The first electrode 11 may be formed by depositing or sputtering a material for forming the first electrode on the substrate. The first electrode 11 may be an anode. The material for the first electrode 11 may be selected from materials with a high work function to make holes be easily injected. The first electrode 13 may be a reflective electrode or a transmissive electrode. The material for the first electrode 11 may be an indium tin oxide (ITO), indium zinc oxide (IZO), tin oxide ($SnO_2$), or zinc oxide (ZnO). According to another embodiment, the material for the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layer structure or a multi-layer structure including two or more layers.

An organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one of a hole injection layer, a hole transport layer, an electron blocking layer, and a buffer layer.

The hole transport region may include only either a hole injection layer or a hole transport layer. According to another embodiment, the hole transport region may have a structure of hole injection layer/hole transport layer or hole injection layer/hole transport layer/electron blocking layer, which are sequentially stacked in this stated order from the first electrode 11.

When the hole injection layer (HIL) includes a hole injection layer, the hole injection layer may be formed on the first electrode 11 by using any one of various methods, for example, vacuum deposition, spin coating, casting, or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 to about 500° C., for example about 100 to about 350° C., a vacuum pressure of about $10^{-8}$ to about $10^{-3}$ torr, and a deposition rate of about 0.01 to about 100 Angstrom per second (Å/sec), for example about 0.1 to about 100 Angstrom per second (Å/sec). However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 rpm to about 5,000 rpm, and a temperature at which a heat treatment is performed to remove a solvent after coating may be from about 80° C. to about 200° C., for example about 130° C. to about 200° C. However, the coating conditions are not limited thereto.

Conditions for a hole transport layer and an electron blocking layer may be understood by referring to conditions for forming the hole injection layer.

The hole transport region may include at least one compound selected from m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202 below:

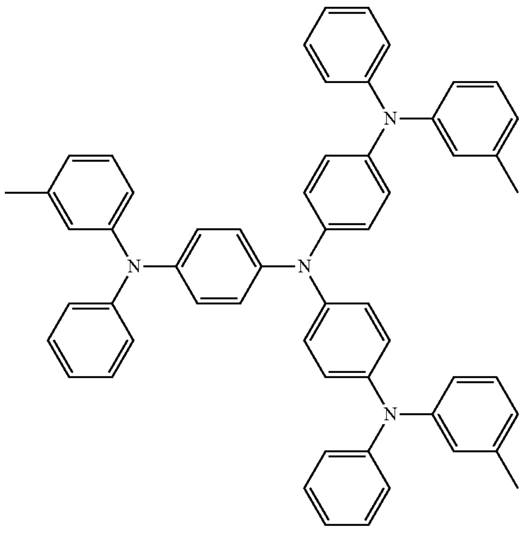

m-MTDATA

-continued

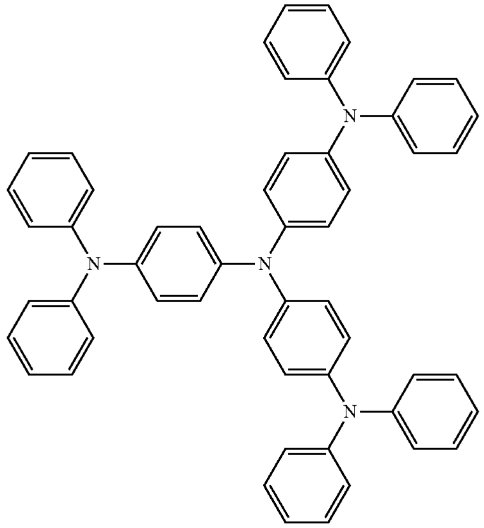

TDATA

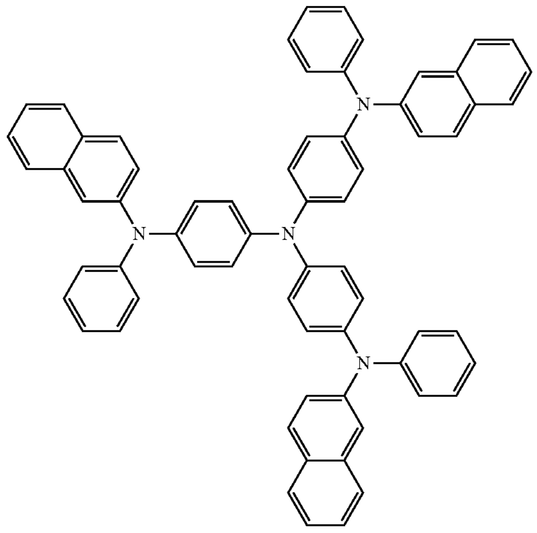

2-TNATA

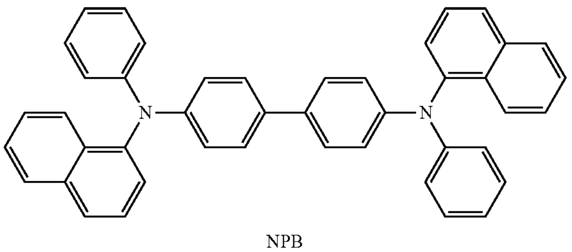

NPB

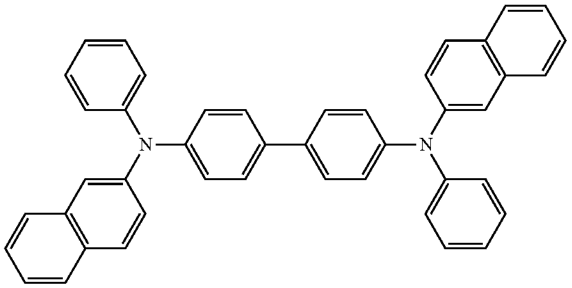

β-NPB

-continued

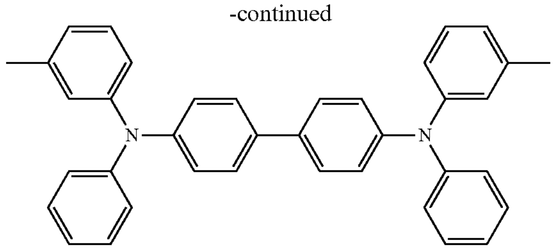

TPD

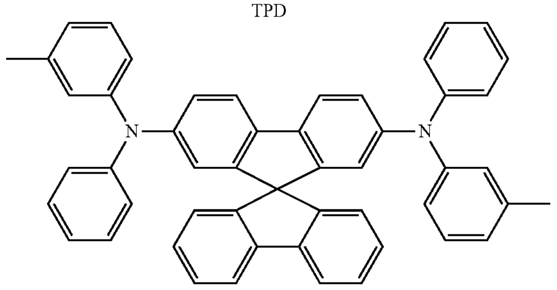

Spiro-TPD

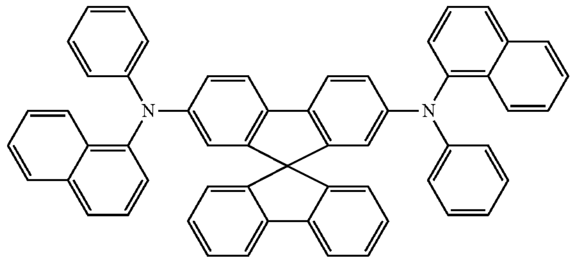

Spiro-NPB

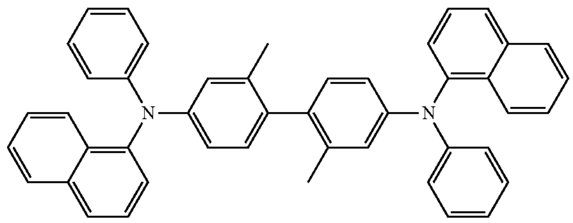

α-NPB

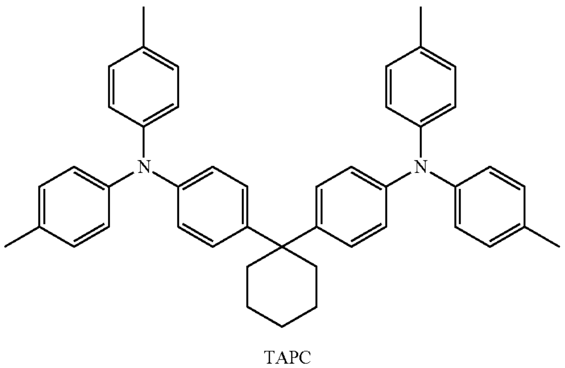

TAPC

-continued

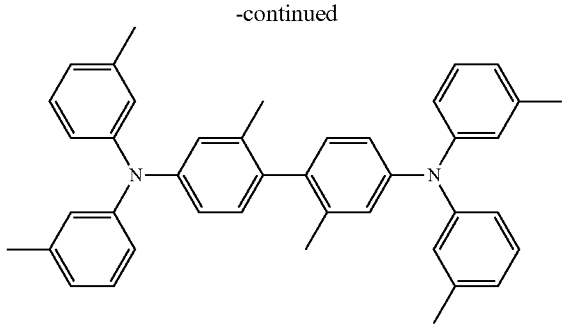

HMTPD

Formula 201

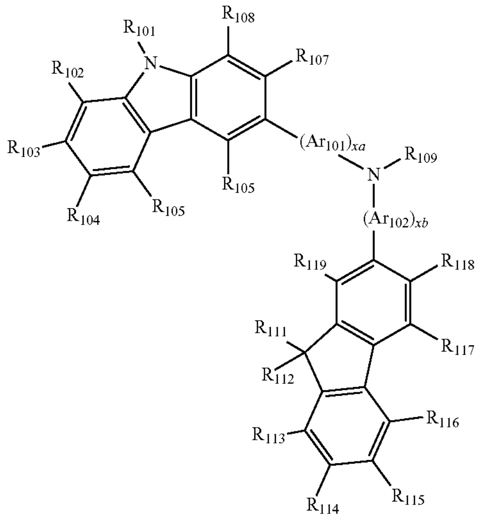

Formula 202

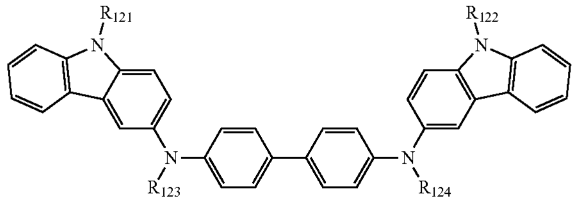

Groups $Ar_{101}$ to $Ar_{102}$ in Formula 201 may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthrenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthrenylene group, a triphenylenylene group, a pyrenylene group, a chrysenylenylene group, a naphthacenylene group, a picenylene group, a perylenylene group, and a pentacenylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic heterocondensed polycyclic group.

xa and xb in Formula 201 may be each independently an integer of 0 to 5, or 0, 1 or 2. For example, xa may be 1 and xb may be 0, but xa and xb are not limited thereto.

Groups $R_{101}$ to $R_{108}$, $R_{111}$ to $R_{119}$, and $R_{121}$ to $R_{124}$ in Formulae 201 and 202 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and so on), and a $C_1$-$C_{10}$ alkoxy group (for example, a methoxy group, an ethoxy group, a propoxy group, a butoxy group, a pentoxy group, and so on);

a $C_1$-$C_{10}$ alkyl group and a $C_1$-$C_{10}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one group selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group and a $C_1$-$C_{10}$ alkoxy group, but they are not limited thereto.

Group $R_{109}$ in Formula 201 may be selected from a phenyl group, a naphthyl group, an anthracenyl group, and a pyridinyl group, each substituted with at least one group selected from a phenyl group, a naphthyl group, an anthracenyl group and a pyridinyl group; and a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group.

According to an embodiment, the compound represented by Formula 201 may be represented by Formula 201A below, but is not limited thereto:

Formula 201A

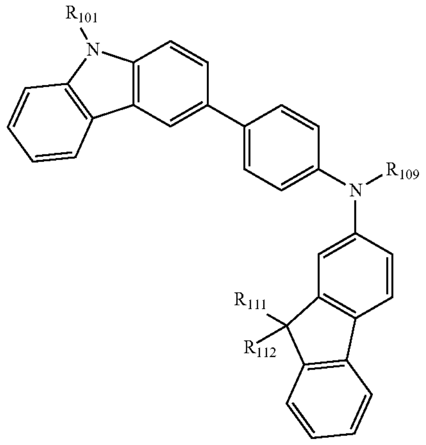

Detailed description about $R_{101}$, $R_{111}$, $R_{112}$, and $R_{109}$ in Formula 201A are already described above.

For example, the compound represented by Formula 201, and the compound represented by Formula 202 may include compounds HT1 to HT20 illustrated below, but are not limited thereto.

HT1

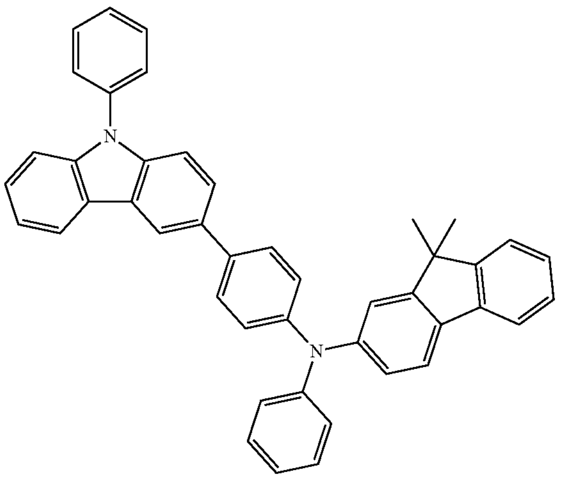

-continued
HT2
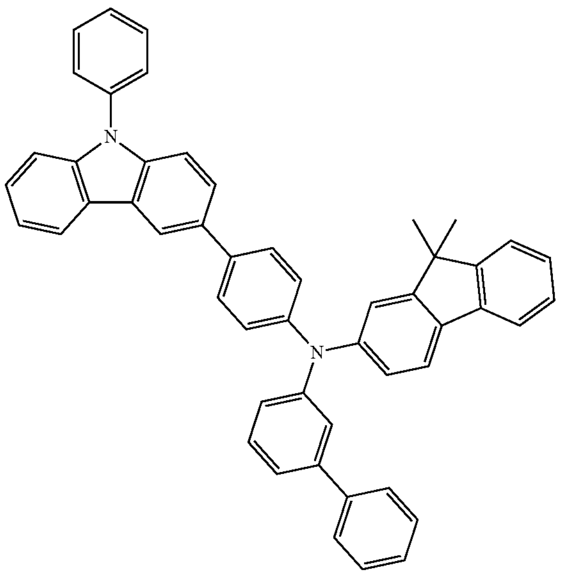
-continued
HT4
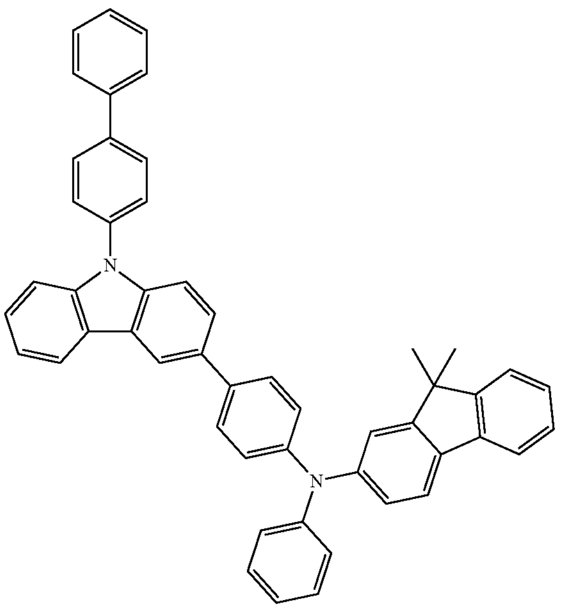
HT3
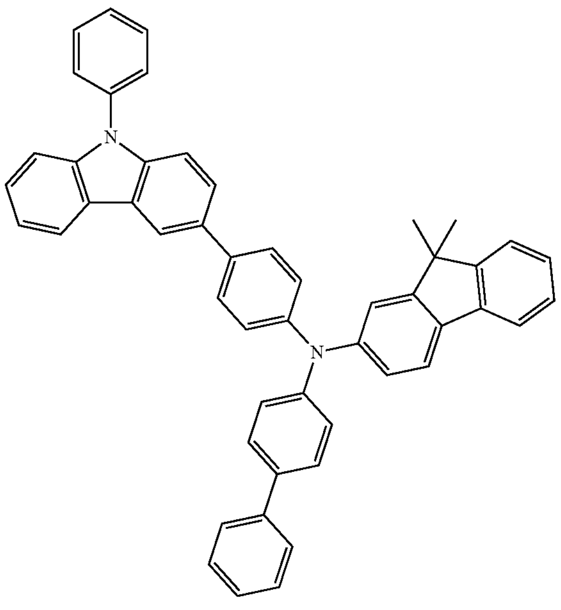
HT5
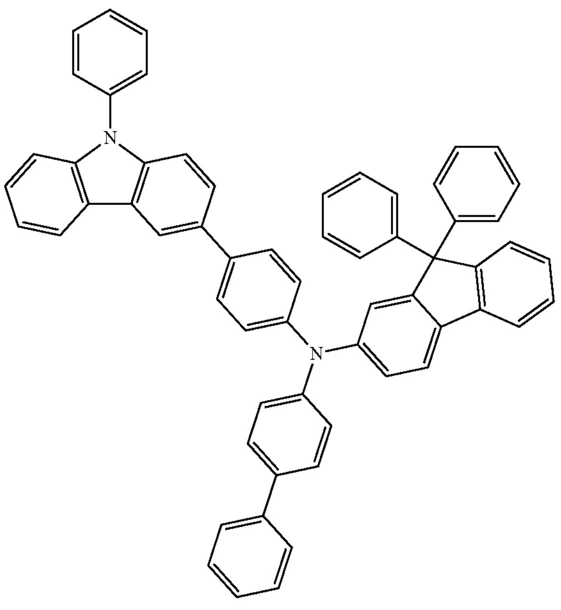

-continued
HT6
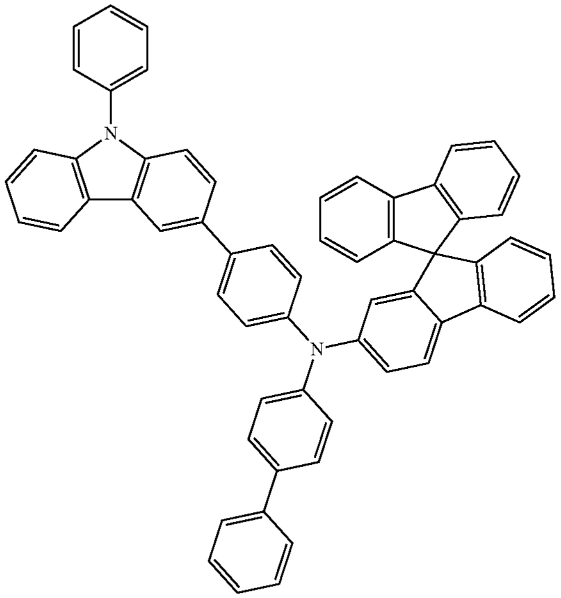
HT7
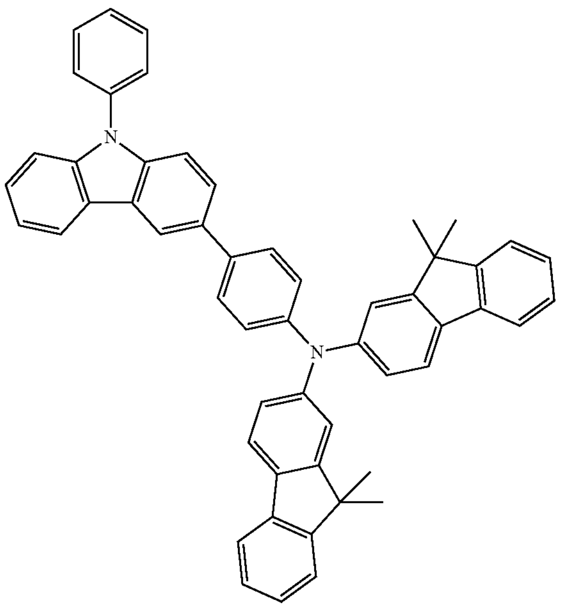
-continued
HT8
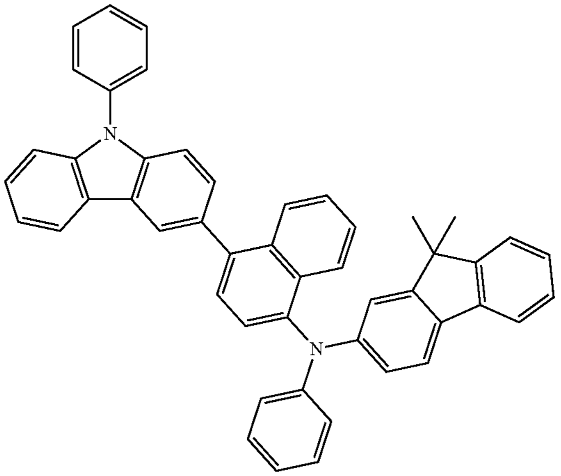
HT9
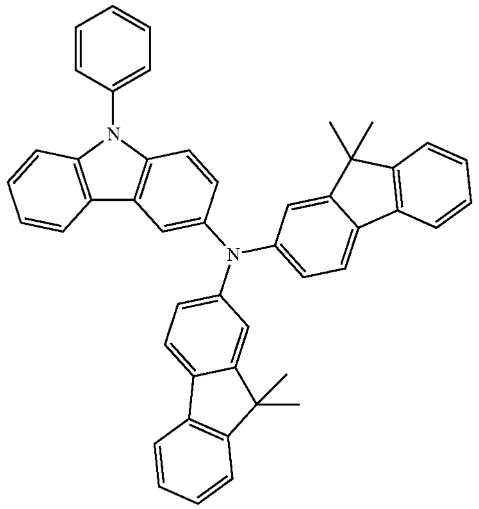
HT10
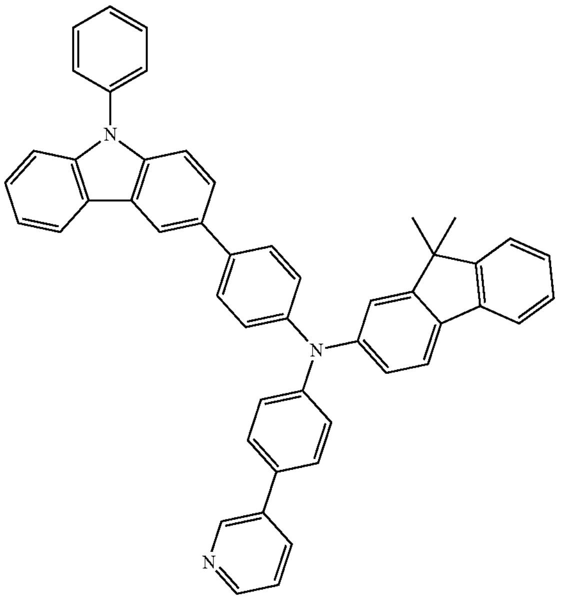

-continued
HT11
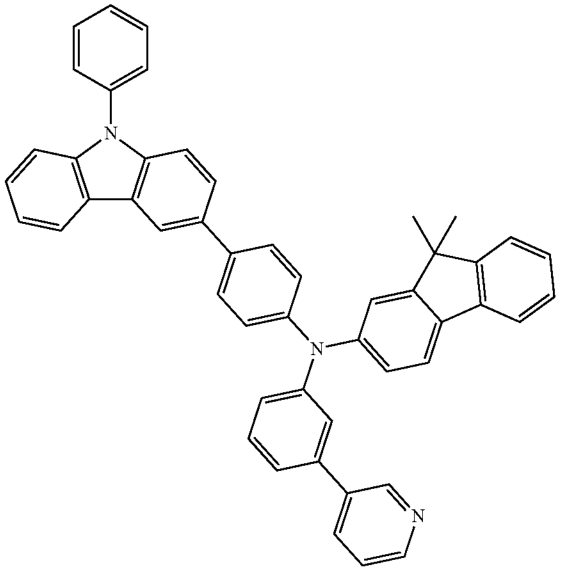
HT12
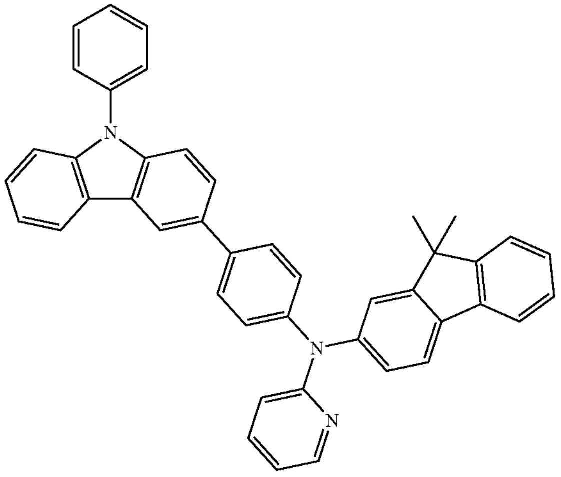
HT13
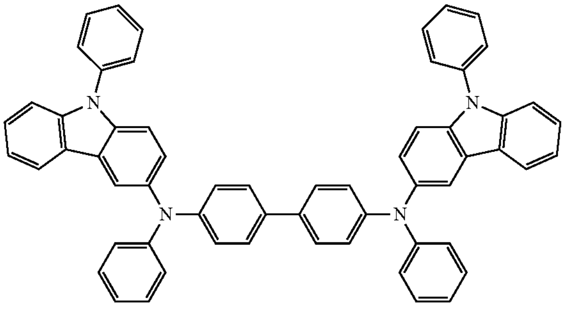
-continued
HT14
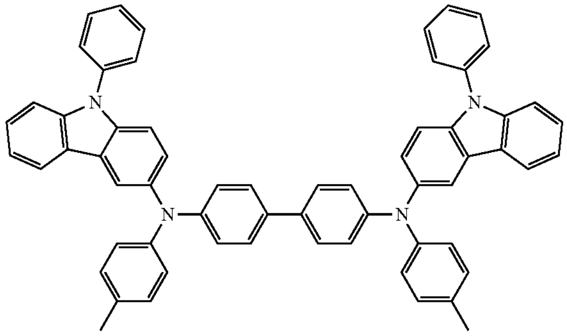
HT15
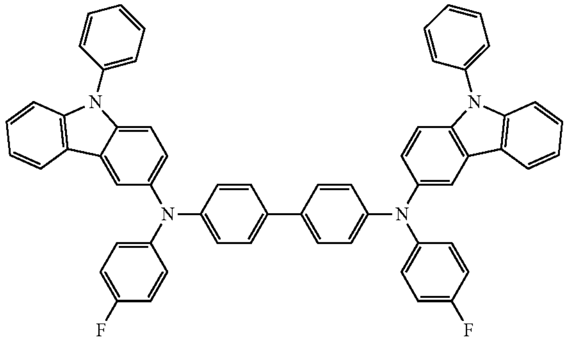
HT16
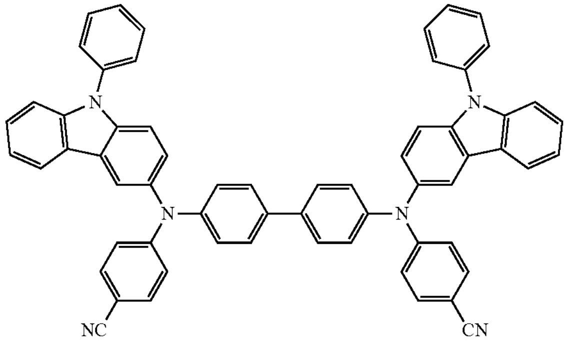
HT17
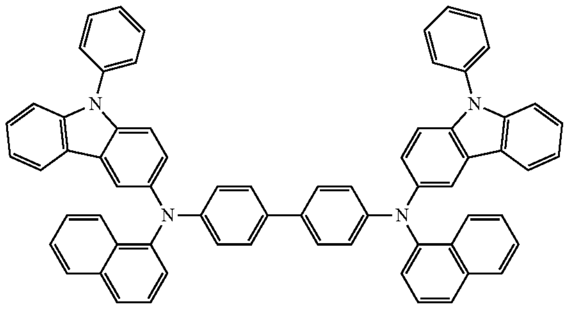

-continued

HT18

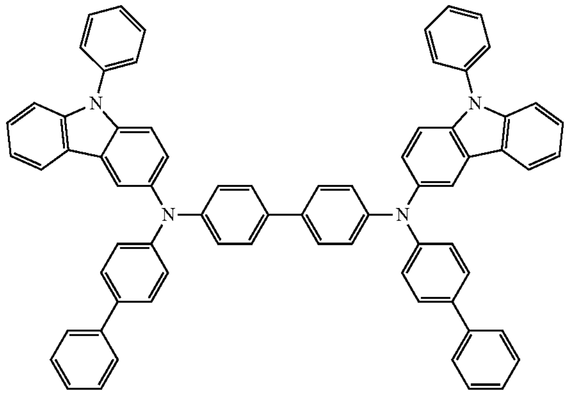

HT19

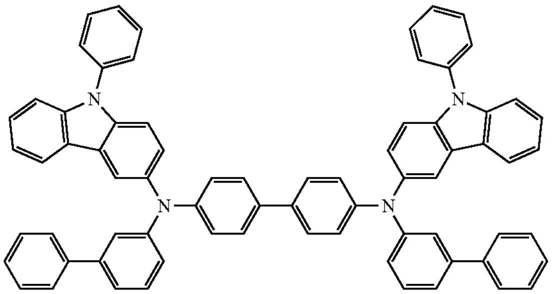

HT20

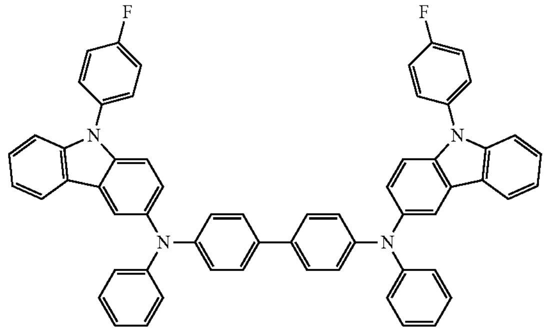

A thickness of the hole transport region may be in a range of about 100 Angstrom (Å) to about 10,000 Å, for example, about 100 Å to about 1,000 Å. When the hole transport region includes both a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one of a quinone derivative, a metal oxide, and a cyano group-containing compound, but is not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 below, but are not limited thereto.

Compound HT-D1

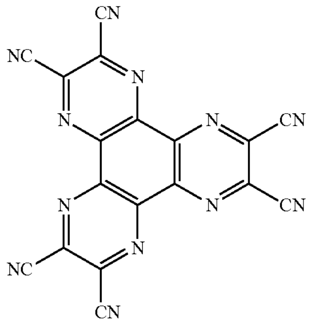

F4-TCNQ

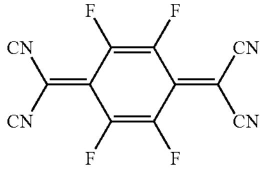

The hole transport region may include a buffer layer.

Also, the buffer layer may compensate for an optical resonance distance according to a wavelength of light emitted from the emission layer, and thus, efficiency of a formed organic light-emitting device may be improved.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

The emission layer may include a host and a dopant. The host may include at least one carbazole compound represented by Formula 1.

The host may further include, in addition to the carbazole compound represented by Formula 1, at least one of TPBi, TBADN, AND (also referred to as "DNA"), CBP, CDBP, and TCP.

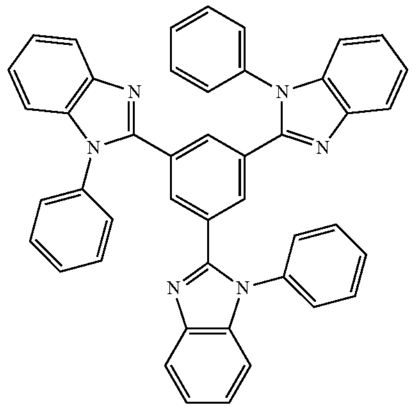

TPBi

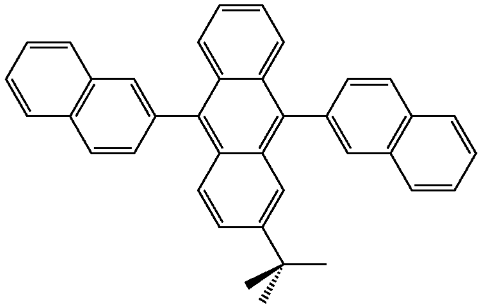

TBADN

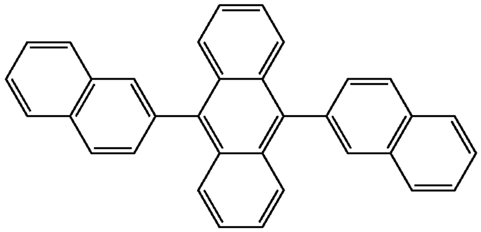

ADN

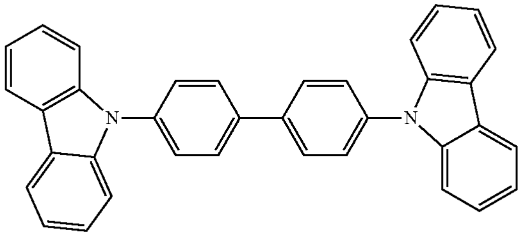

CBP

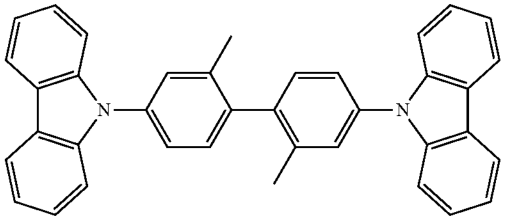

CDBP

-continued

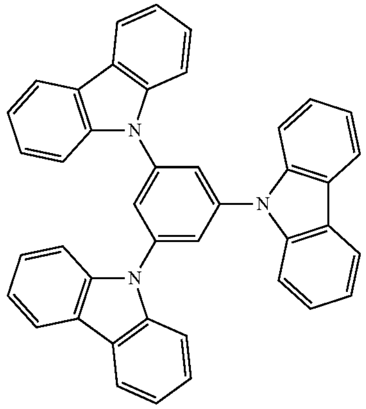

TCP

According to another embodiment, the host may further include, the carbazole compound represented by Formula 1, a compound represented by Formula 301 below:

Formula 301

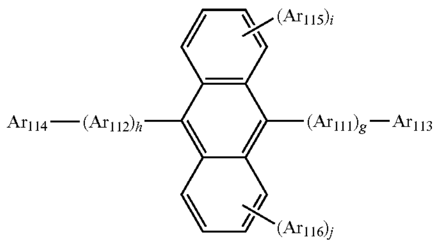

$Ar_{111}$ and $Ar_{112}$ in Formula 301 may be each independently selected from a phenylene group, a naphthylene group, a phenanthrenylene group, a fluorenyl group, and a pirenylene group, each substituted with at least one group selected from a phenylene group, a naphthylene group, a phenanthrenylene group, and a pirenylene group; and a phenyl group, a naphthyl group and an anthracenyl group.

$Ar_{113}$ to $Ar_{116}$ in Formula 301 may be each independently selected from a C1-C10 alkyl group; a phenyl group, a naphthyl group, a phenanthrenyl group and a pyrenyl group; and a phenyl group, a naphthyl group, a phenanthrenyl group, a fluorenyl group and a pyrenyl group, each substituted with at least one group selected from a phenyl group, a naphthyl group, and an anthracenyl group.

Variables g, h, I, and j in Formula 301 may be each independently an integer of 0 to 4, for example, an integer of 0, 1, or 2.

Groups $Ar_{113}$ to $Ar_{116}$ in Formula 301 may be each independently selected from a $C_1$-$C_{10}$ alkyl group substituted with at least one group selected from a phenyl group, a naphthyl group, and an anthracenyl group;

a phenyl group, a naphthyl group, an anthracenyl group, a pyrenyl, a phenanthrenyl group, and a fluorenyl group;

a phenyl group, a naphthyl group, an anthracenyl group, a pyrenyl group, a phenanthrenyl group, and a fluorenyl group, each substituted with at least one group selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, and a fluorenyl group; and

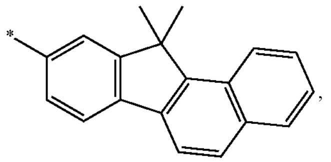 [SMILES: *c1ccc2c(c1)C(C)(C)c1c-2ccc2ccccc12]

but they are not limited thereto.

According to another embodiment, the host may further include, in addition to the carbazole compound represented by Formula 1, a compound represented by Formula 302 below:

Formula 302

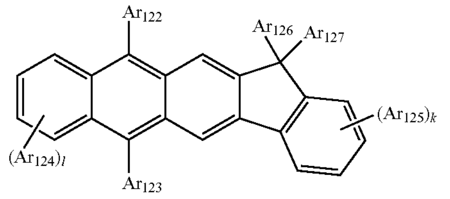

Groups $Ar_{122}$ to $Ar_{125}$ in Formula 302 are the same as described in detail in connection with $Ar_{113}$ in Formula 301.

Groups $Ar_{126}$ and $Ar_{127}$ in Formula 302 may be each independently a $C_1$-$C_{10}$ alkyl group (for example, a methyl group, an ethyl group, or a propyl group).

Variables k and l in Formula 302 may be each independently an integer of 0 to 4. For example, k and l may be 0, 1, or 2.

The compound represented by Formula 301 and the compound represented by Formula 302 may include Compounds H1 to H42 illustrated below, but are not limited thereto.

H1

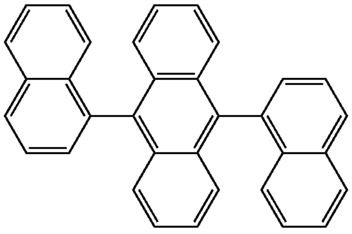

H2

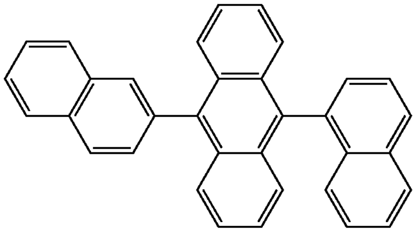

-continued

H3

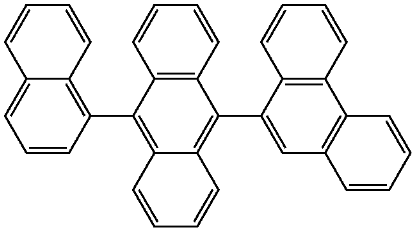

H4

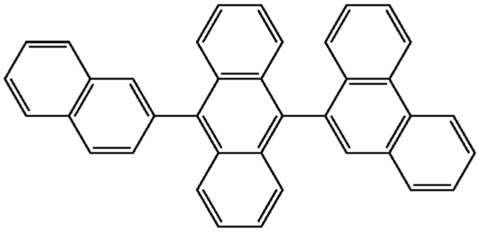

H5

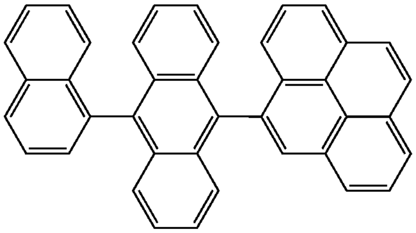

H6

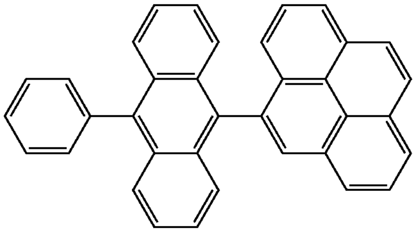

H7

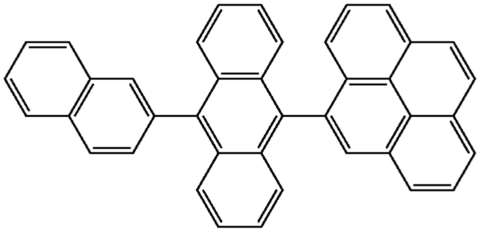

H8

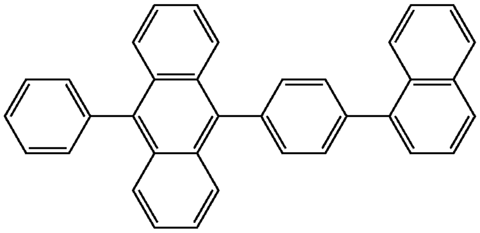

-continued
H9
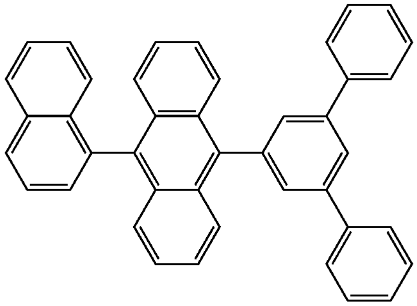
H10
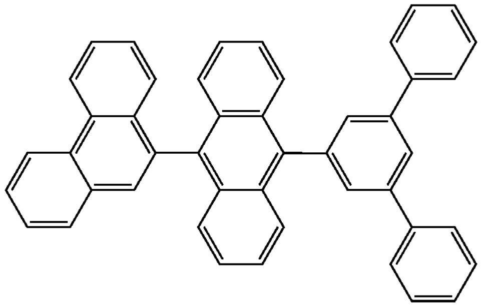
H11
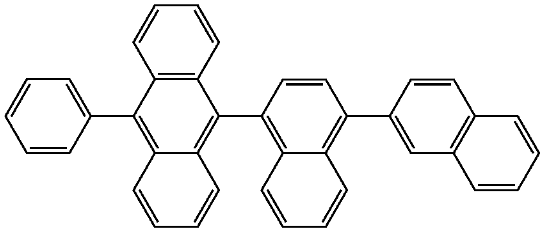
H12
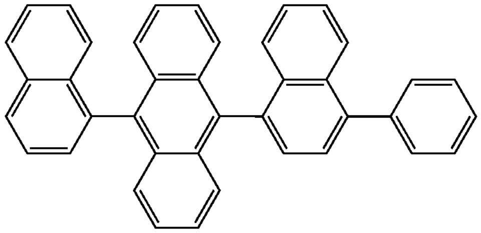
H13
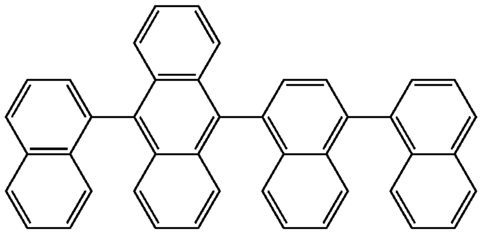
H14
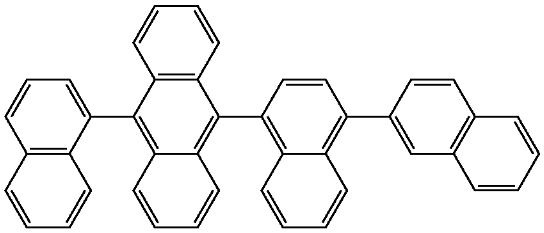
-continued
H15
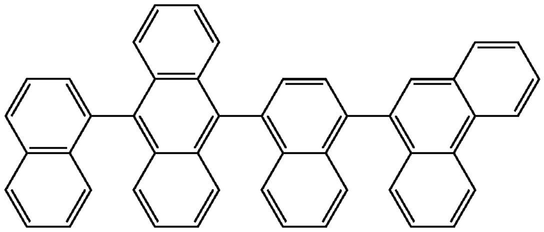
H16
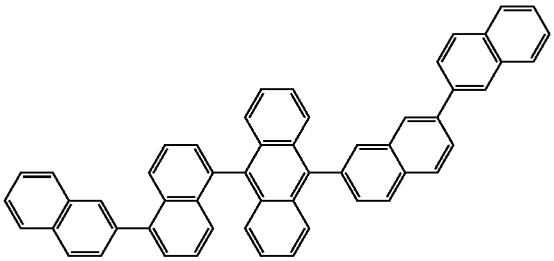
H17
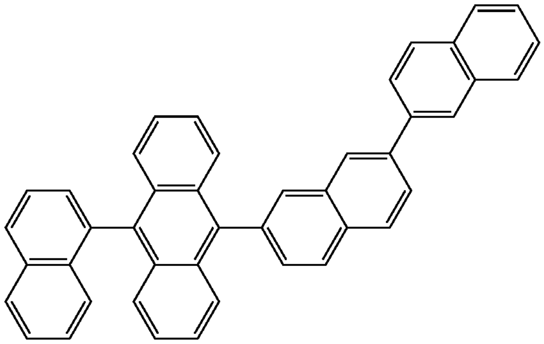
H18
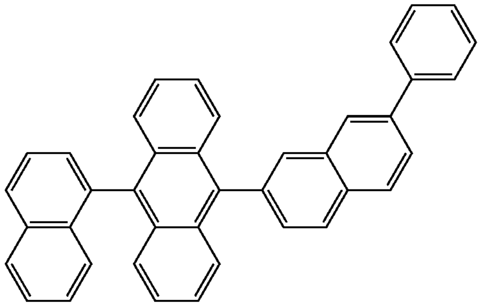
H19
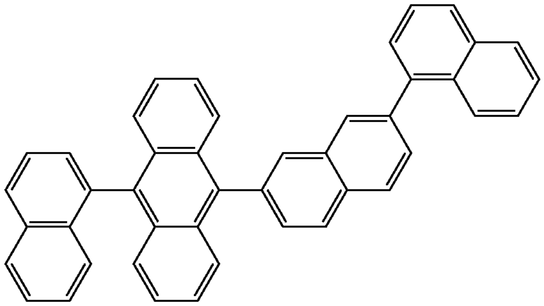

-continued
H20
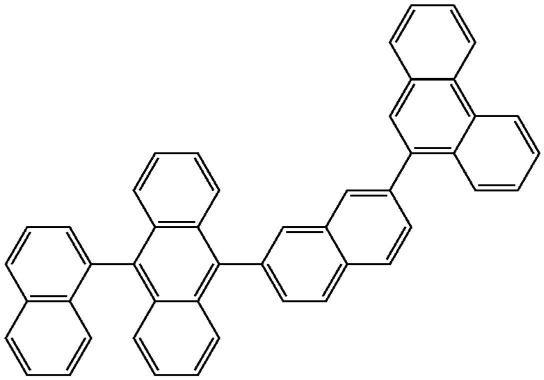
H21
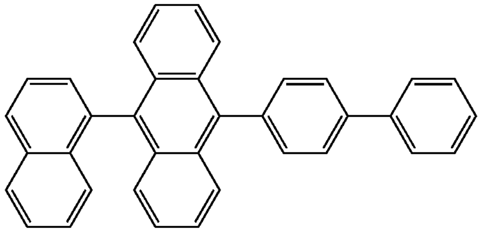
H22
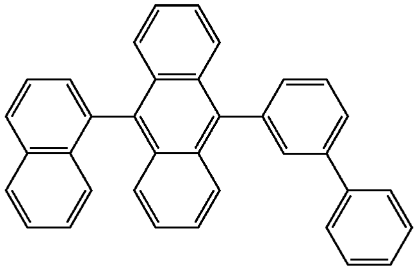
H23
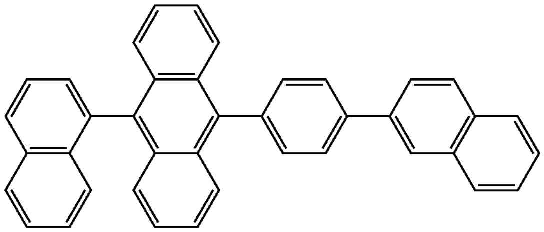
H24
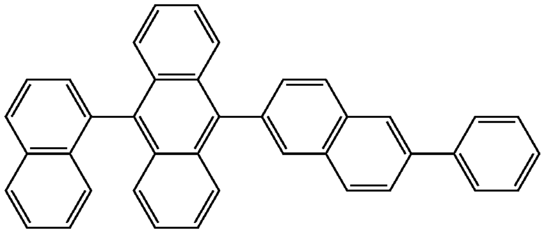
-continued
H25
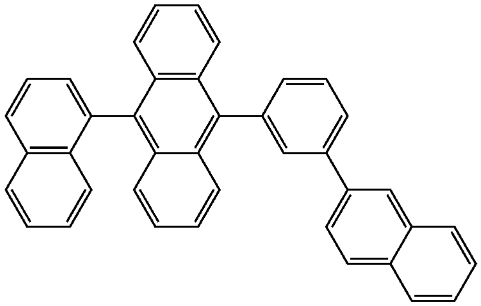
H26
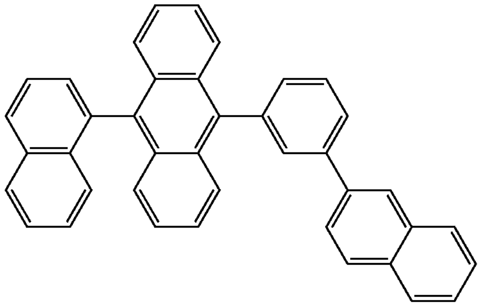
H27
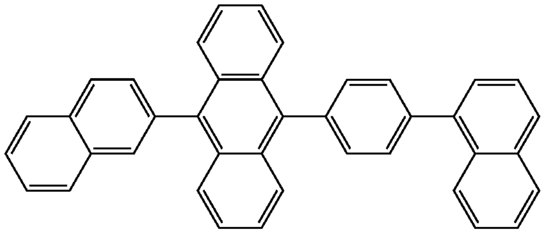
H28
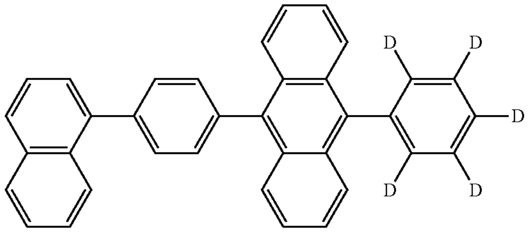
H29
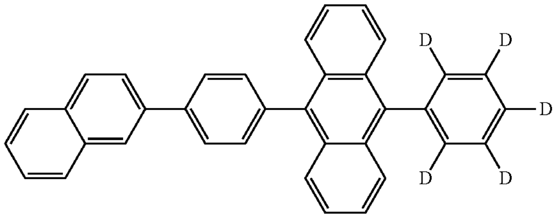
H30
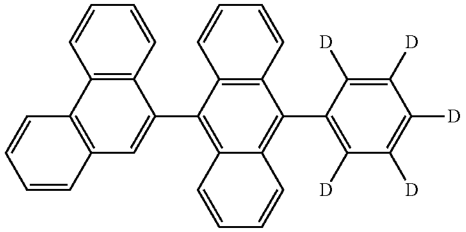

-continued
H31
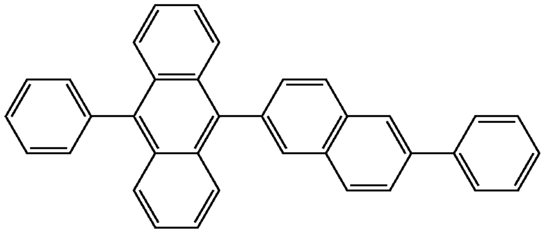
H32
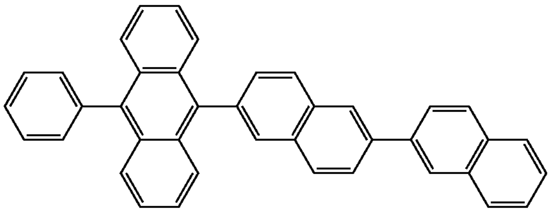
H33
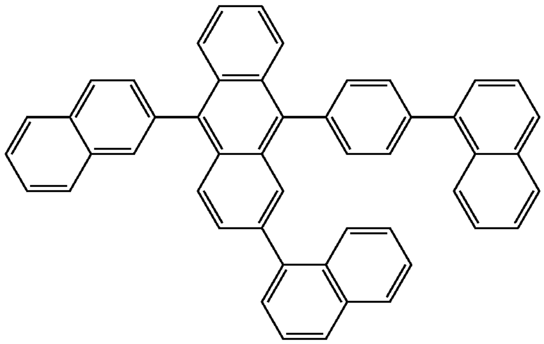
H34
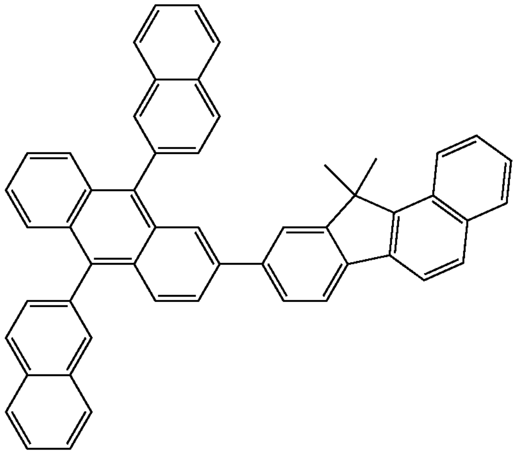
-continued
H35
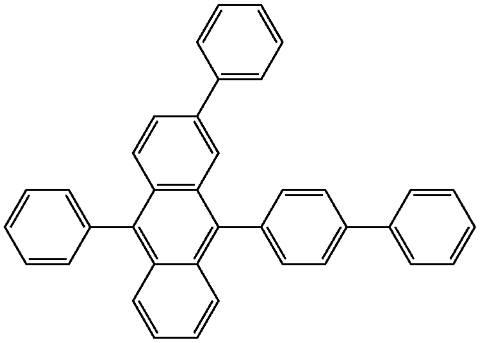
H36
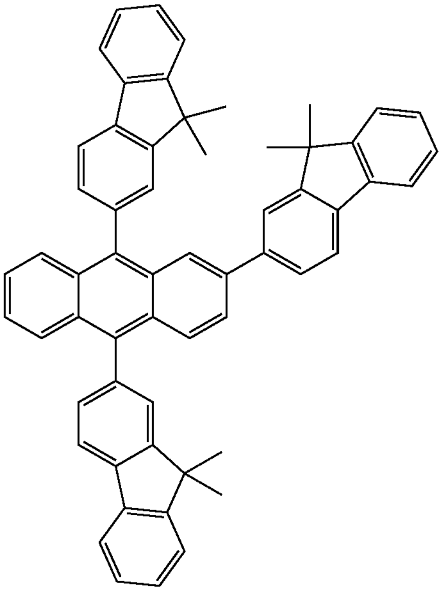
H37
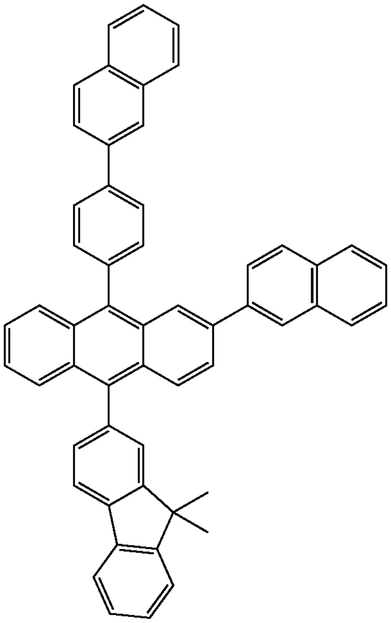

-continued
H38
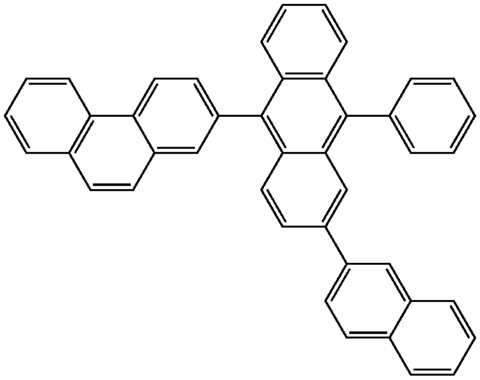
H39
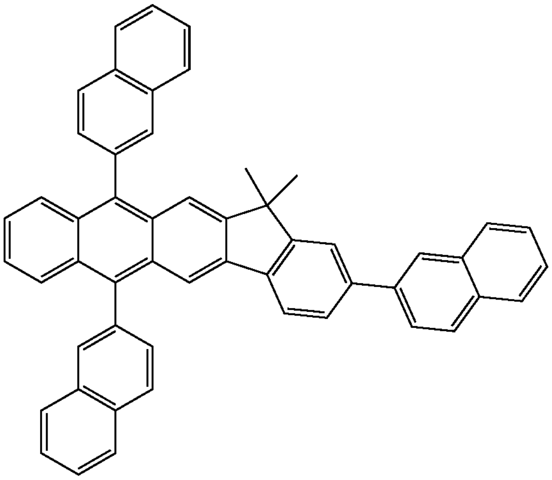
H40
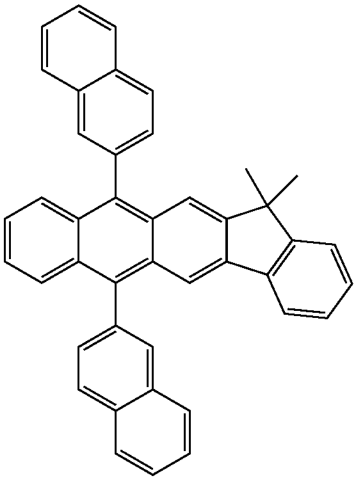
-continued
H41
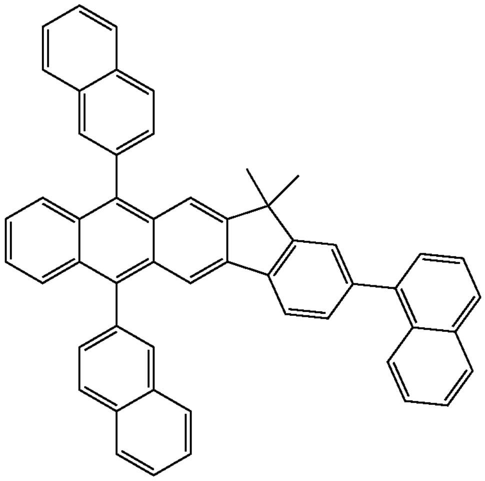
H42
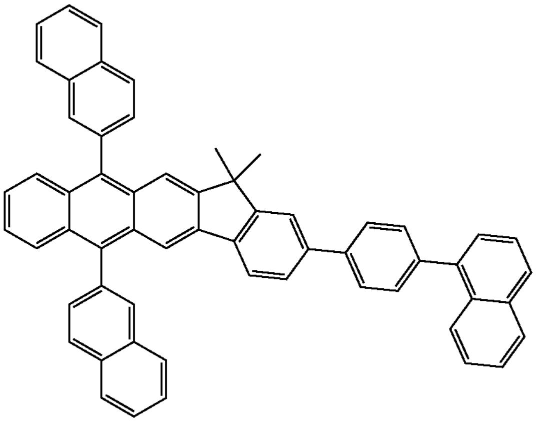
According to another embodiment, the host may include, in addition to the carbazole compound represented by Formula 1, at least one of Compounds H43 to H49 below, but is not limited thereto:
H43
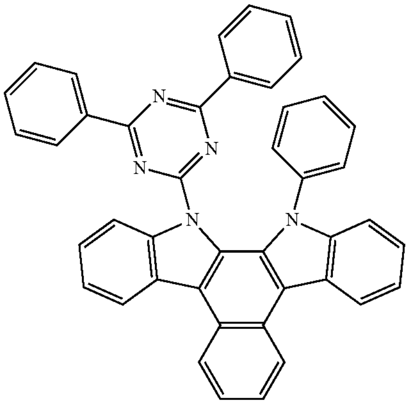

-continued

H44

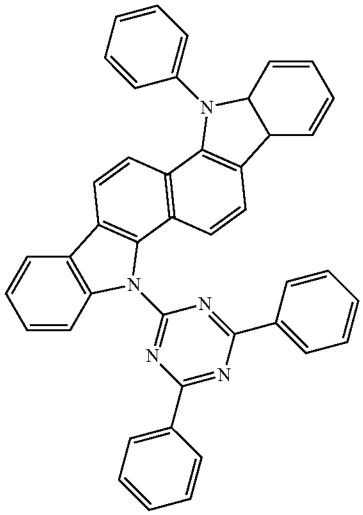

H45

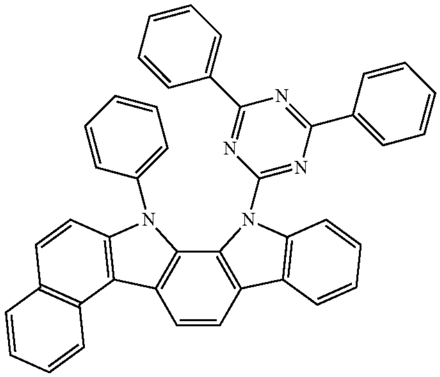

H46

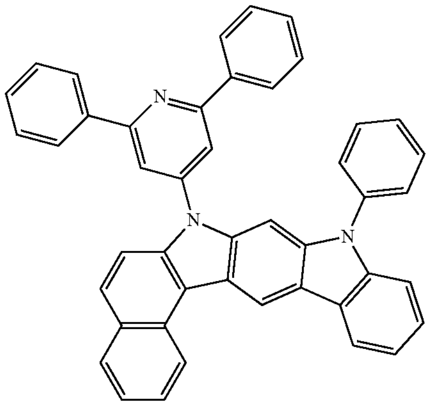

-continued

H47

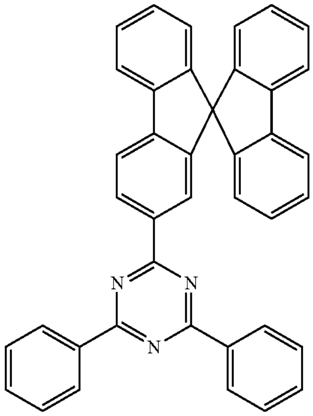

H48

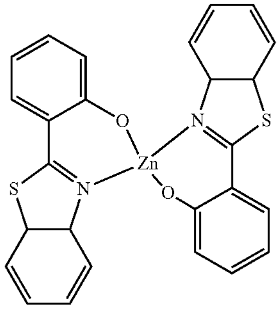

H49

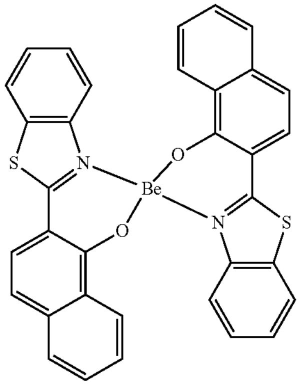

When the organic light-emitting device is a full color organic light-emitting device, the emission layer may be patterned into a red emission layer, a green emission layer, and a blue emission layer. According to another embodiment, due to a stack structure including a red emission layer, a green emission layer, and/or a blue emission layer, the emission layer may emit white light. A host in the red emission layer, the green emission layer, and the blue emission layer may include the carbazole compound represented by Formula 1. According to an embodiment, the host in the green emission layer may include the carbazole compound represented by Formula 1.

A dopant in the emission layer may be a fluorescent dopant that emits light according to a fluorescent emission mechanism or a phosphorescent dopant that emits light according to a phosphorescent emission mechanism.

According to an embodiment, the emission layer may include a host including the carbazole compound represented by Formula 1 and a phosphorescent dopant. The phosphorescent dopant may include an organometallic complex including a transition metal (for example, iridium (Ir), platinum (Pt), osmium (Os), or rhodium (Rh)).

The phosphorescent dopant may include an organometallic complex represented by Formula 81 below:

Formula 81

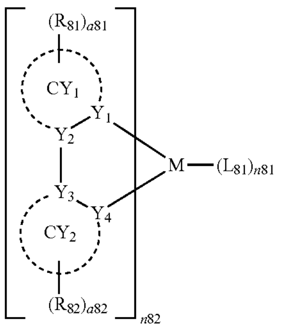

wherein in Formula 81,

M may be selected from iridium (Ir), platinum (Pt), osmium (Os), titanium (Ti), zirconium (Zr), hafnium (Hf), europium (Eu), terbium (Tb), and thulium (Tm);

$Y_1$ to $Y_4$ are each independently selected from carbon (C) or nitrogen (N);

$CY_1$ and $CY_2$ are each independently selected from a benzene, a naphthalene, a fluorene, a spiro-fluorene, an indene, a pyrrole, a thiophene, a furan, an imidazole, a pyrazole, a thiazole, an isothiazole, an oxazole, an isooxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzooxazole, an isobenzooxazole, a triazole, a tetrazole, an oxadiazole, a triazine, a dibenzofuran, and a dibenzothiophene, and $CY_1$ and $CY_2$ are optionally linked to each other through a single bond or an organic linking group;

$R_{81}$ and $R_{82}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, $—SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, a substituted or unsubstituted monovalent non-aromatic heterocondensed polycyclic group, $—N(Q_1)(Q_2)$, $—Si(Q_3)(Q_4)(Q_5)$, and $—B(Q_6)(Q_7)$;

a81 and a82 are each independently an integer of 1 to 5;

n81 is an integer of 0 to 4;

n82 is 1, 2, or 3;

$L_{81}$ is selected from a monovalent organic ligand, a divalent organic ligand, and a trivalent organic ligand; and in Formula 81, the bond between $Y_1$ and $Y_2$ and the bond between $Y_3$ and $Y_4$ are each independently a single bond or a double bond.

The phosphorescent dopant may include at least one of Compounds PD1 to PD74 below, but is not limited thereto (Compound PD1 below is $Ir(ppy)_3$):

PD1

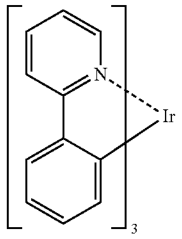

PD2

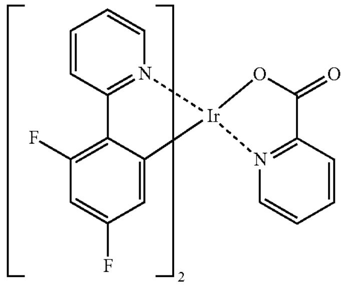

PD3

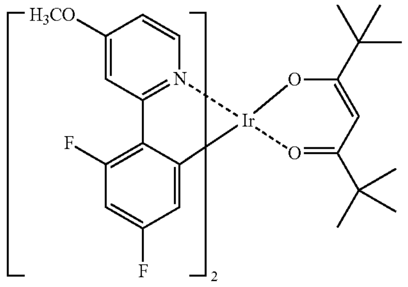

PD4

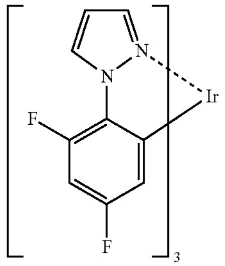

PD5

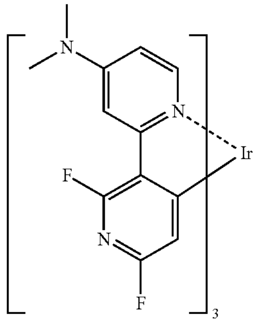

-continued
PD6
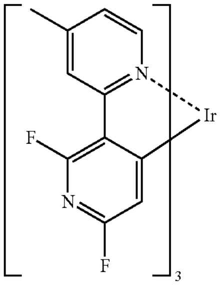
PD7
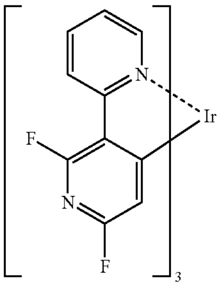
PD8
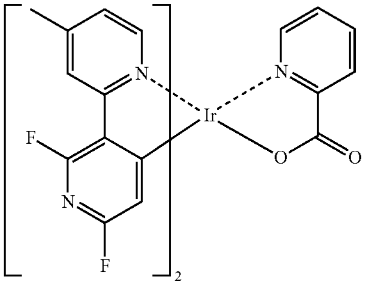
PD9
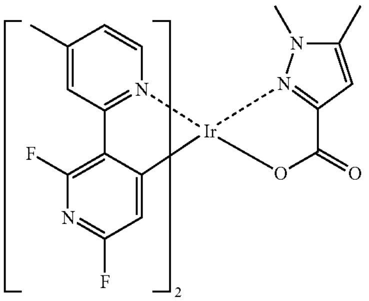
PD10
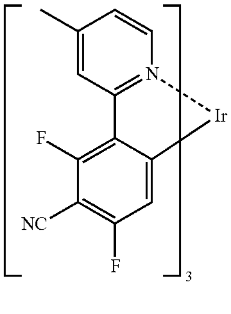
-continued
PD11
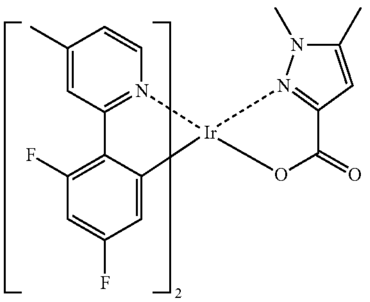
PD12
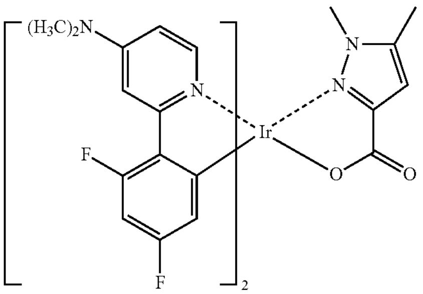
PD13
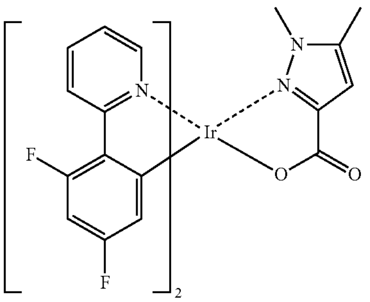
PD14
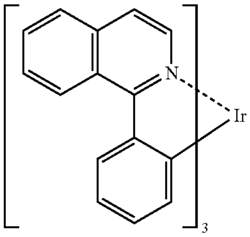
PD15
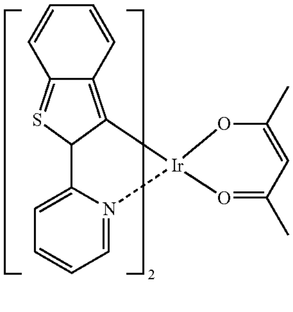

-continued
PD16
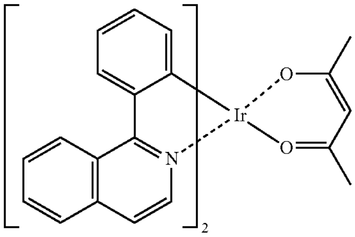
PD17
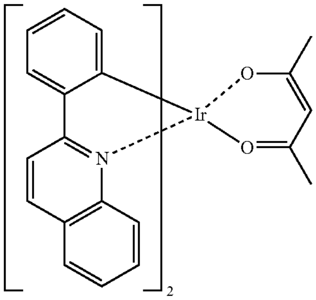
PD18
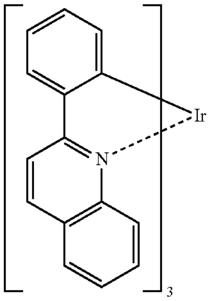
PD19
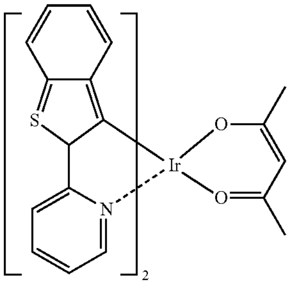
PD20
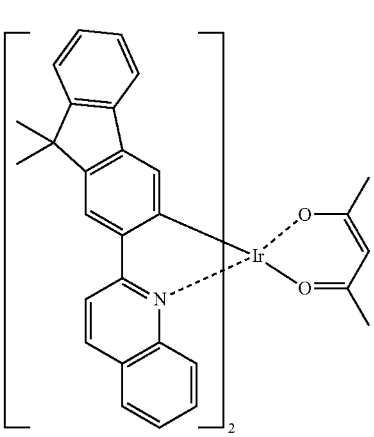
-continued
PD21
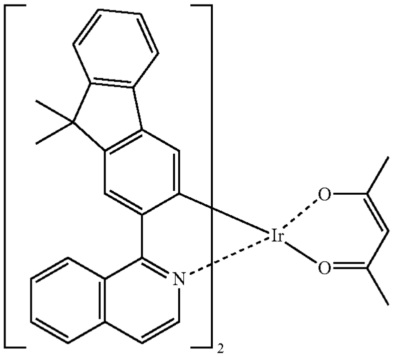
PD22
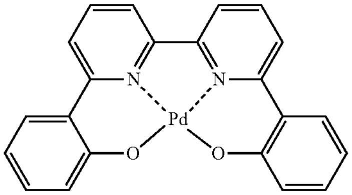
PD23
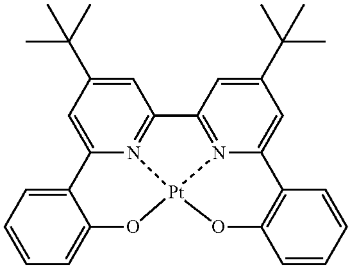
PD24
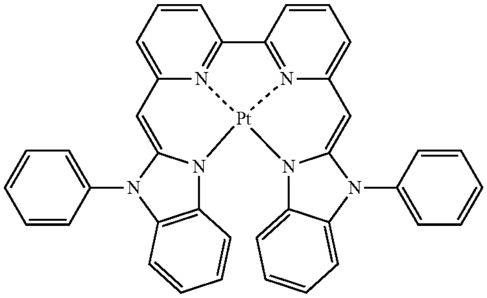
PD25
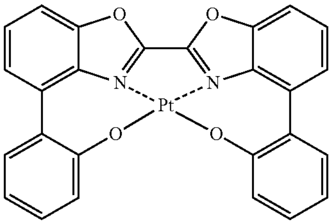
PD26
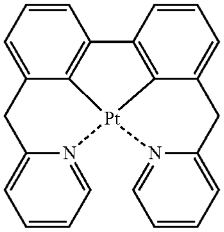

-continued
PD27
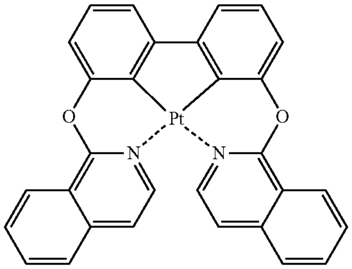
PD28
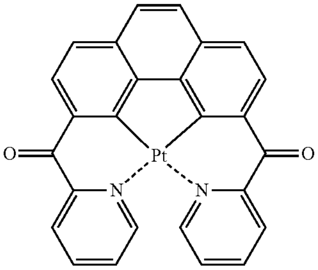
PD29
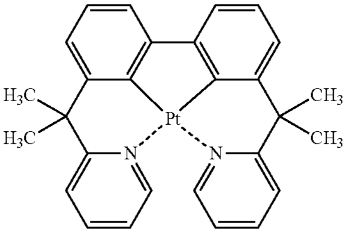
PD30
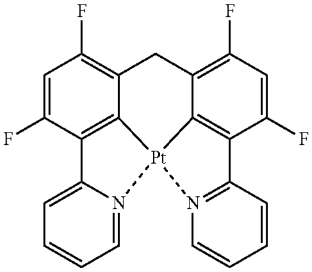
PD31
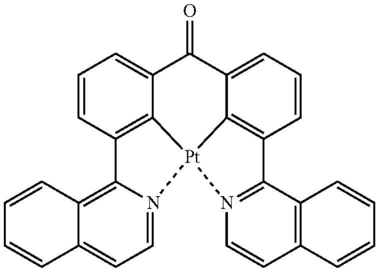
PD32
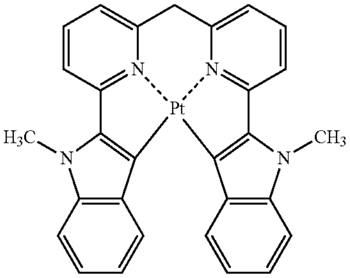
-continued
PD33
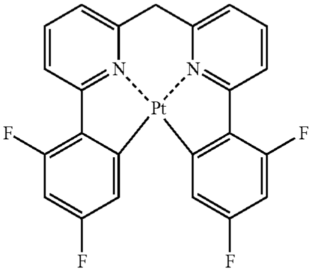
PD34
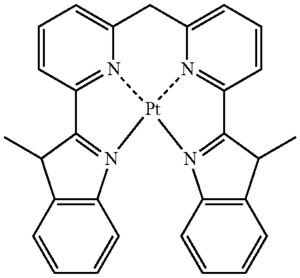
PD35
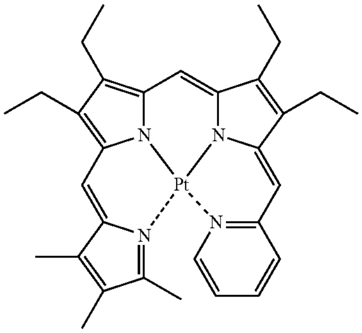
PD36
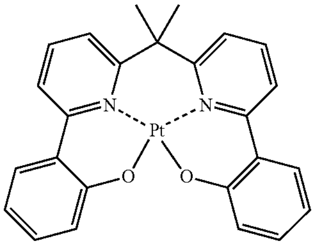
PD37
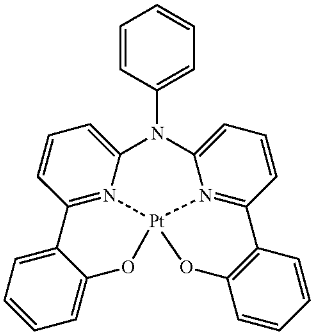

-continued
PD38
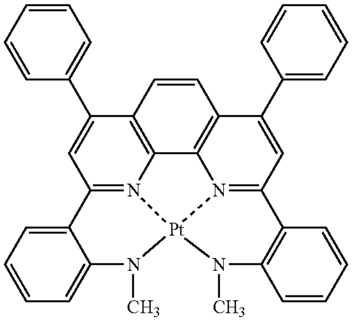
PD39
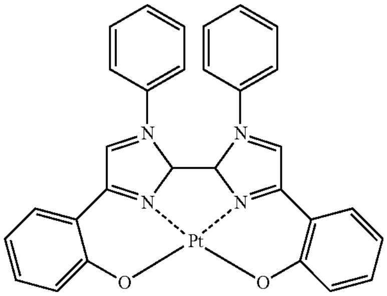
PD40
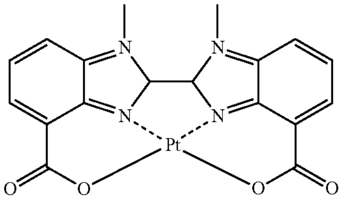
PD41
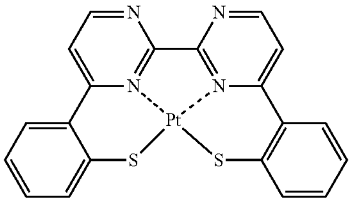
PD42
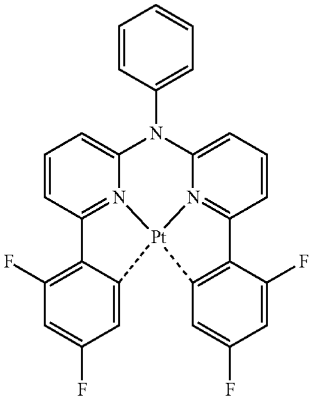
-continued
PD43
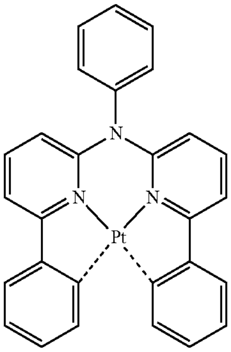
PD44
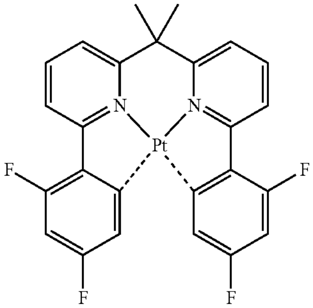
PD45
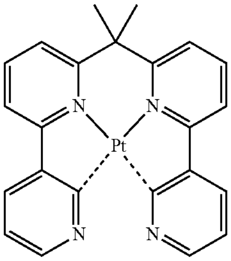
PD46
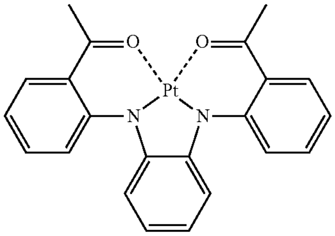
PD47
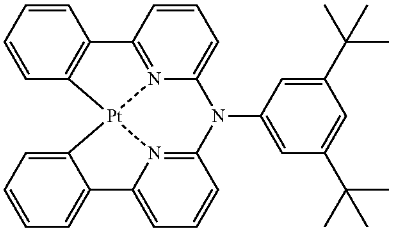

-continued
PD48
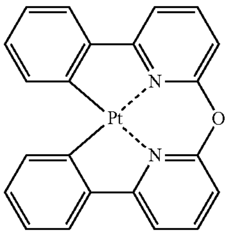
PD49
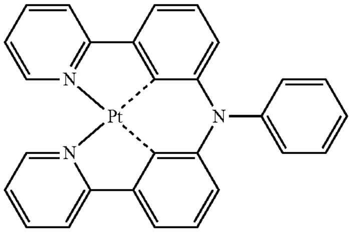
PD50
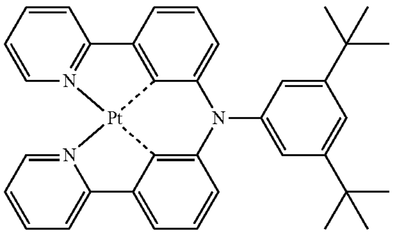
PD51
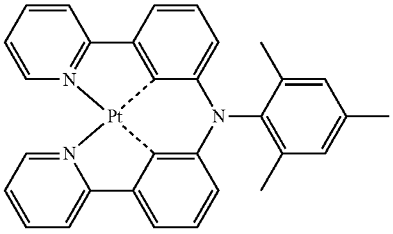
PD52
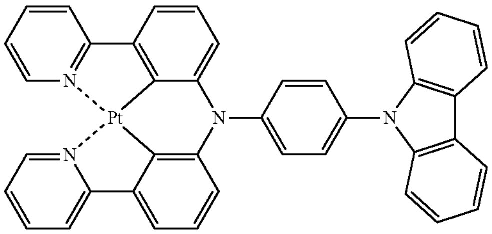
PD53
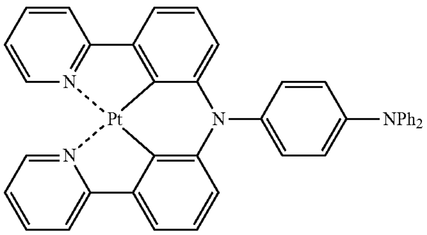
-continued
PD54
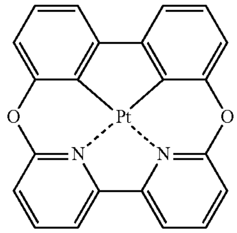
PD55
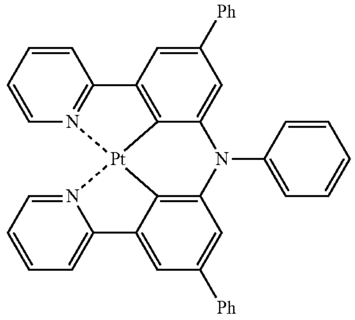
PD56
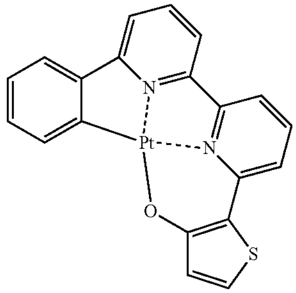
PD57
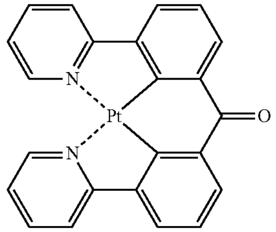
PD58
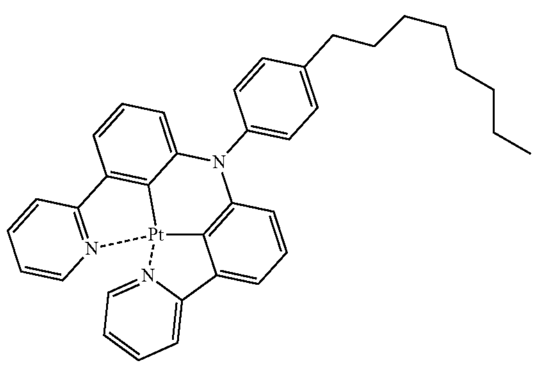

-continued
PD59
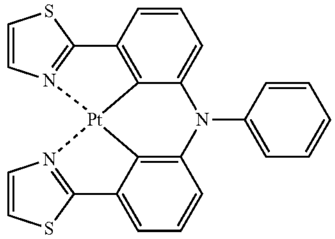
PD60
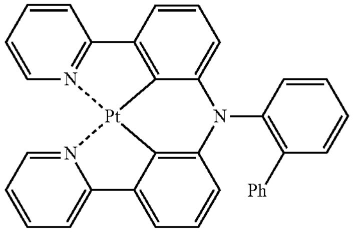
PD61
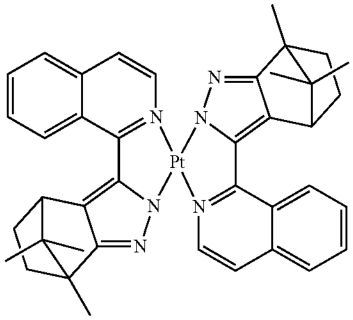
PD62
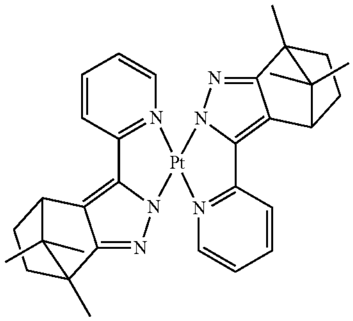
PD63
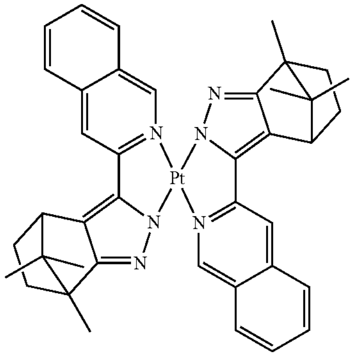
-continued
PD64
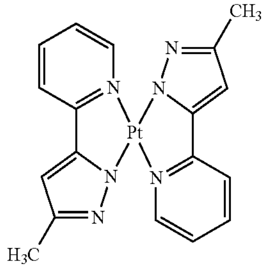
PD65
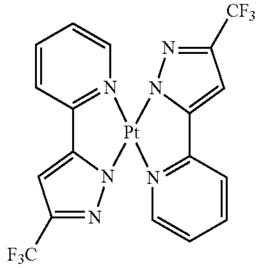
PD66
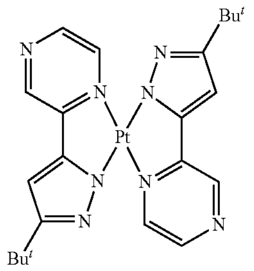
PD67
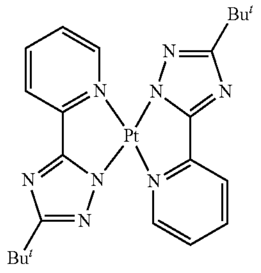
PD68
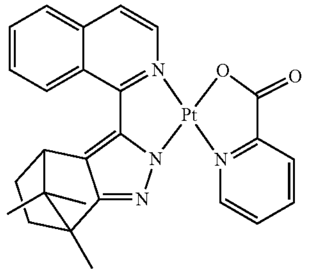
PD69
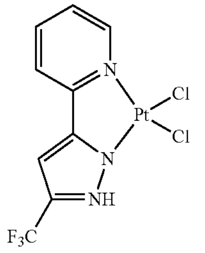

-continued
PD70
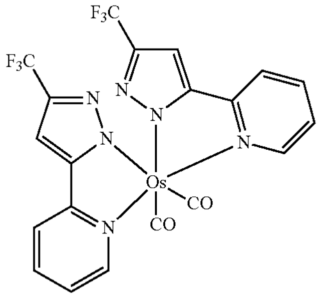
PD71
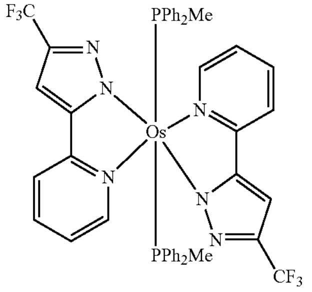
PD72
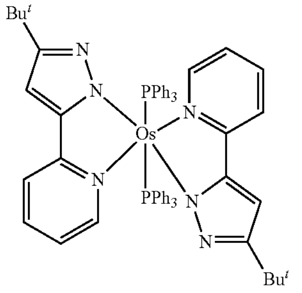
PD73
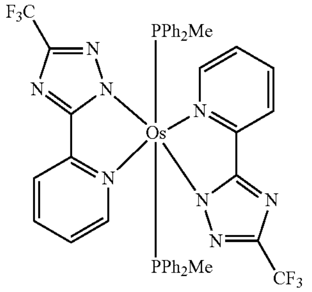
-continued
PD74
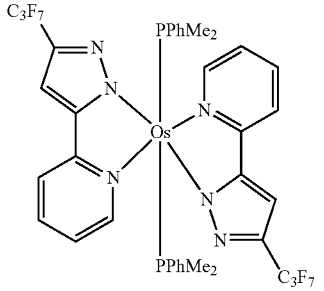
According to another embodiment, the phosphorescent dopant may include PtOEP or Compound PhGD illustrated below:
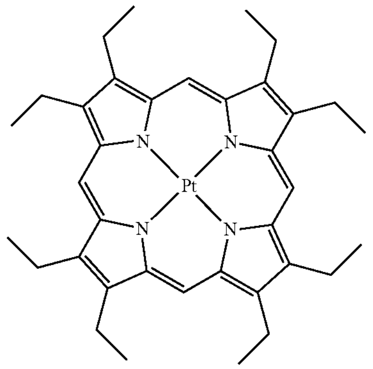
PtOEP
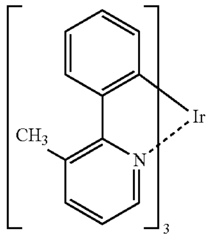
PhGD
The fluorescent dopant may include at least one compound selected from DPAVBi, BDAVBi, TBPe, DCM, DCJTB, Coumarin 6, and C545T.

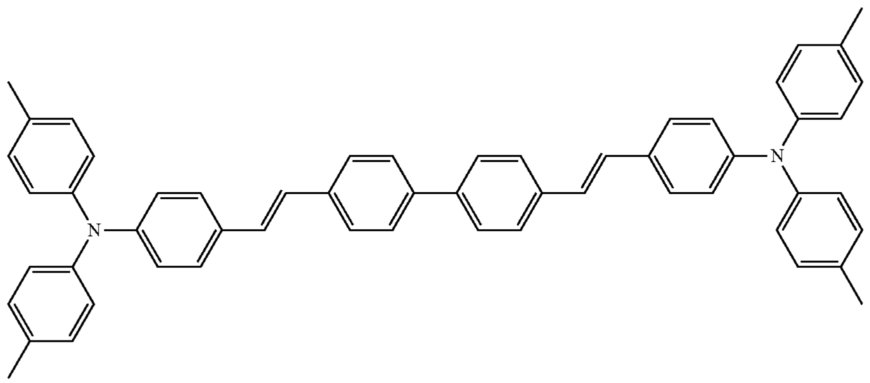
DPAVBi
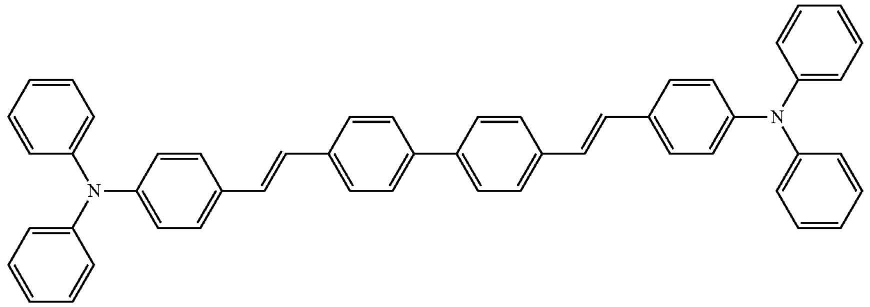
BDAVBi
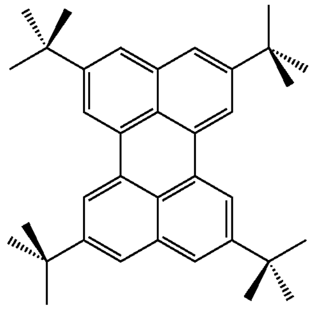
TBPe
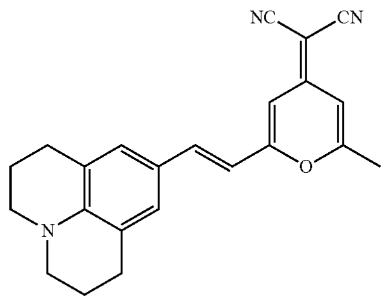
DCM
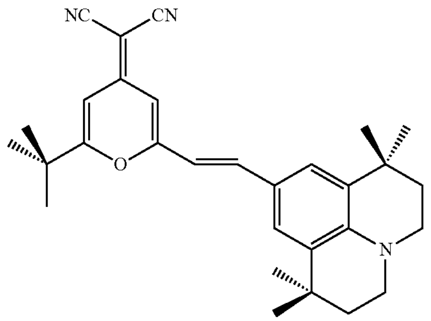
DCJTB
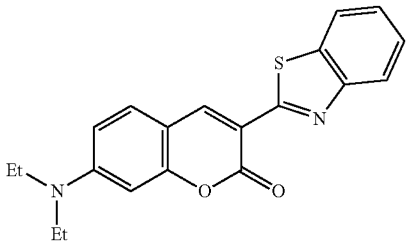
Coumarin 6

-continued

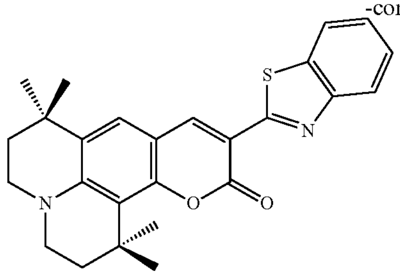

C545T

When the emission layer includes a host and a dopant, an amount of the dopant may be in a range of about 0.01 to about 15 parts by weight based on 100 parts by weight of the host, but is not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one layer selected from a hole blocking layer, an electron transport layer, and an electron injection layer.

For example, the electron transport region may have a structure of hole blocking layer/electron transport layer/electron injection layer or electron transport layer/electron injection layer, but the structure of the electron transport region is not limited thereto. The electron transport layer may have a single-layered structure or a multi-layer structure including two or more different materials.

Conditions for forming the hole blocking layer, the electron transport layer, and the electron injection layer which constitute the electron transport region may be understood by referring to the conditions for forming the hole injection layer.

When the electron transport layer includes a hole blocking layer, the hole blocking layer may include, for example, at least one of BCP, Bphen, and BAlq but is not limited thereto.

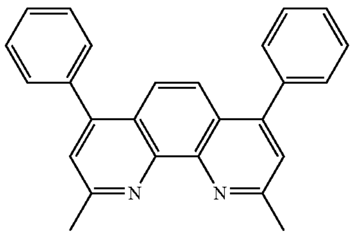

BCP

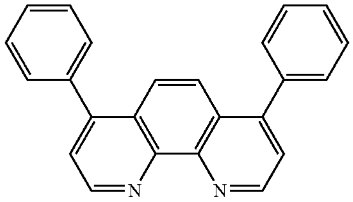

Bphen

A thickness of the hole blocking layer may be in a range of about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport layer may further include at least one compound selected from BCP, Bphen, $Alq_3$, Balq, TAZ, and NTAZ.

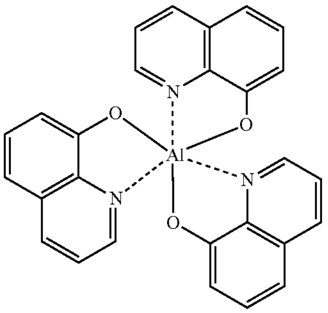

$Alq_3$

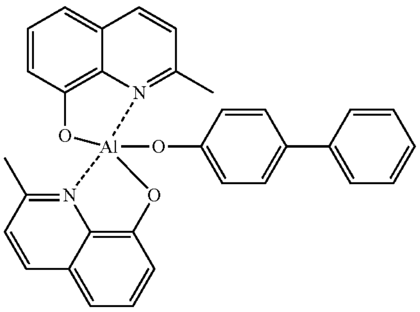

Balq

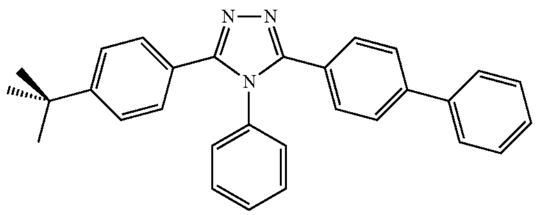

TAZ

-continued

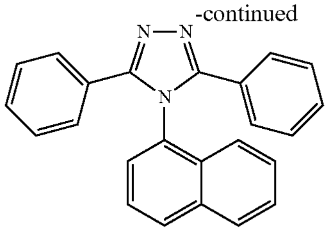

NTAZ

According to another embodiment, the electron transport layer may include at least one of ET1 and ET2, but are not limited thereto:

ET1

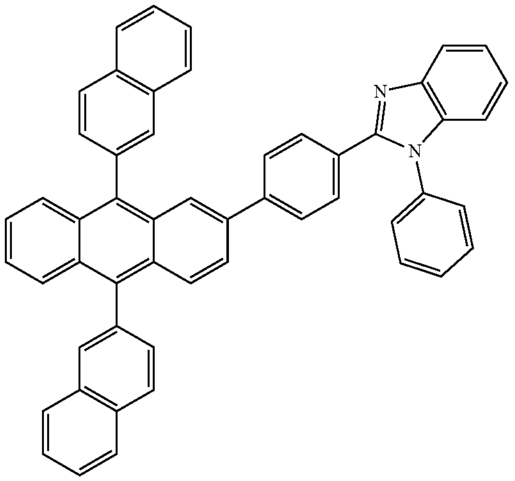

ET2

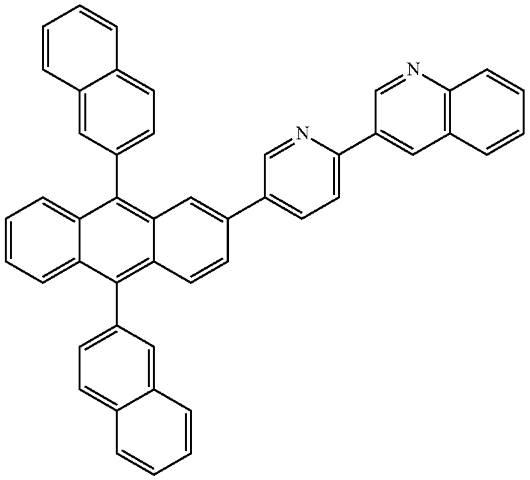

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2.

ET-D1

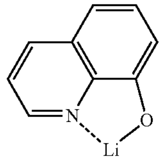

ET-D2

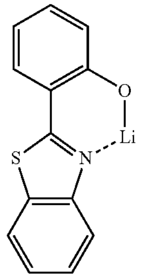

The electron transport region may include an electron injection layer (EIL) that allows electrons to be easily provided from a second electrode 19.

The electron injection layer may include at least one compound selected from, LiF, NaCl, CsF, $Li_2O$, BaO, and LiQ.

A thickness of the electron injection layer may be in a range of about 1 Å to about 100 Å, for example, about 3 Å to about 90 Å. When the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top emission type light-emitting device, a transmissive electrode formed using ITO or IZO may be used as the second electrode 19.

Hereinbefore, the organic light-emitting device has been described with reference to FIG. 1, but is not limited thereto.

A $C_1$-$C_{60}$ alkyl group used herein refers to a linear or branched aliphatic hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group used herein refers to a divalent group having the same structure as the $C_1$-$C_{60}$ alkyl group.

A $C_1$-$C_{60}$ alkoxy group used herein refers to a monovalent group represented by —$OA_{101}$ (wherein $A_{101}$ is the $C_1$-$C_{60}$ alkyl group). Detailed examples thereof are a methoxy group, an ethoxy group, and an isopropyloxy group.

A $C_2$-$C_{60}$ alkenyl group used herein refers to a hydrocarbon group formed by substituting at least one carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene group used herein refers to a divalent group having the same structure as the $C_2$-$C_{60}$ alkenyl group.

A $C_2$-$C_{60}$ alkynyl group used herein refers to a hydrocarbon group formed by substituting at least one carbon trip bond in the middle or at the terminal of the $C_2$-$C_{60}$ alkyl group. Detailed examples thereof are an ethynyl group, and a propynyl group. A $C_2$-$C_{60}$ alkynylene group used herein refers to a divalent group having the same structure as the $C_2$-$C_{60}$ alkynyl group.

A $C_3$-$C_{10}$ cycloalkyl group used herein refers to a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_2$-$C_{10}$ heterocycloalkyl group used herein refers to a monovalent monocyclic group having at least one hetero atom selected from N, O, P, and S as a ring-forming atom and 2 to 10 carbon atoms. Detailed examples thereof are a tetrahydrofuranyl group, and a tetrahydrothiophenyl group. A $C_2$-$C_{10}$ heterocycloalkylene group used herein refers to a divalent group having the same structure as the $C_2$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof and does not have aromaticity. Detailed examples thereof are a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_2$-$C_{10}$ heterocycloalkenyl group used herein refers to a monovalent monocyclic group that has at least one hetero atom selected from N, O, P, and S as a ring-forming atom, 2 to 10 carbon atoms, and at least one double bond in its ring. Detailed examples of the $C_2$-$C_{10}$ heterocycloalkenyl group are a 2,3-dihydrofuranyl group and a 2,3-dihydrothiophenyl group. A $C_2$-$C_{10}$ heterocycloalkenylene group used herein refers to a divalent group having the same structure as the $C_2$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_2$-$C_{60}$ heteroaryl group used herein refers to a monovalent group having a carbocyclic aromatic system that has at least one hetero atom selected from N, O, P, and S as a ring-forming atom, and 2 to 60 carbon atoms. A $C_2$-$C_{60}$ heteroarylene group used herein refers to a divalent group having a carbocyclic aromatic system that has at least one hetero atom selected from N, O, P, and S as a ring-forming atom, and 2 to 60 carbon atoms. Examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ heteroarylene group each include two or more rings, the rings may be fused to each other.

A $C_6$-$C_{60}$ aryloxy group used herein indicates —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group), and the $C_7$-$C_{60}$ arylalkyl indicates -$A_{104}A_{105}$ (wherein $A_{104}$ is the $C_6$-$C_{60}$ aryl group and $A_{105}$ is the $C_1$-$C_{60}$ alkyl group).

The $C_2$-$C_{60}$ heteroaryloxy used herein indicates —$OA_{106}$ (wherein $A_{106}$ is the $C_2$-$C_{60}$ heteroaryl group), the $C_2$-$C_{60}$ heteroarylthio indicates —$SA_{107}$ (wherein $A_{107}$ is the $C_2$-$C_{60}$ heteroaryl group), and the $C_3$-$C_{60}$ heteroarylalkyl indicates -$A_{108}A_{109}$ (wherein $A_{108}$ is the $C_2$-$C_{60}$ heteroaryl group and $A_{109}$ is the $C_1$-$C_{60}$ alkyl group).

A monovalent non-aromatic condensed polycyclic group used herein refers to a monovalent group that has two or more rings condensed to each other, only carbon atoms (for example, the number of carbon atoms may be in a range of 8 to 60) as a ring forming atom, wherein the molecular structure as a whole is non-aromatic. An example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group used herein refers to a monovalent group that has two or more rings condensed to each other, has a heteroatom selected from N, O P, and S, other than carbon atoms (for example, the number of carbon atoms may be in a range of 2 to 60), as a ring forming atom, wherein the molecular structure as a whole is non-aromatic. An example of the monovalent non-aromatic condensed heteropolycyclic group is a carbazolyl group. A divalent non-aromatic condensed heteropolycyclic group used herein refers to a divalent group having the same structure as the monovalent non-aromatic condensed heteropolycyclic group.

Hereinafter, a compound and an organic light-emitting device according to embodiments is described in detail with reference to Synthesis Example and Examples. However, the organic light-emitting device is not limited thereto. The wording "B was used instead of A" used in describing Synthesis Examples means that a molar equivalent of A was identical to a molar equivalent of B.

EXAMPLE

Synthesis Example 1

Synthesis of Compound 1

Compound 1 was synthesized according to Reaction Scheme below:

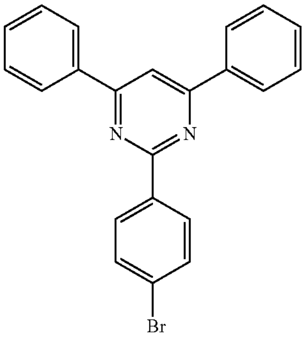

+

-continued

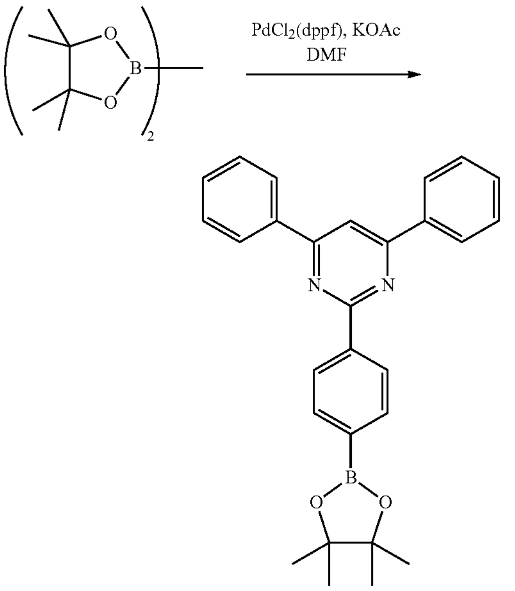

(A)

(A) +

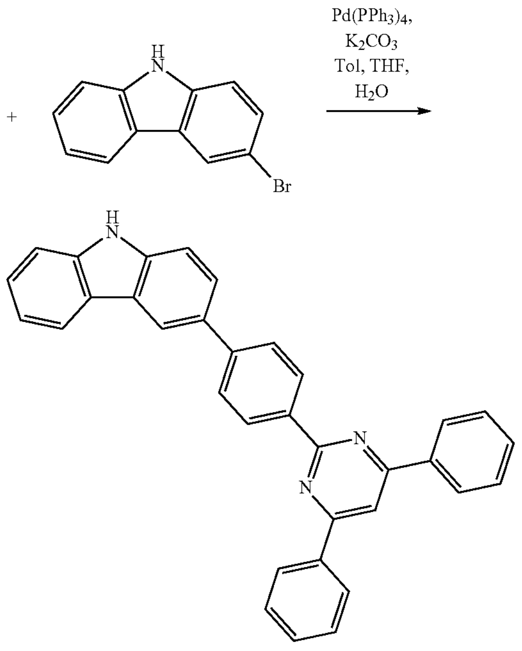

(B)

(B) +

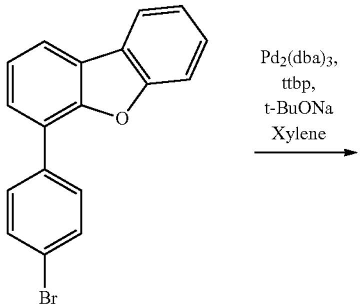

-continued

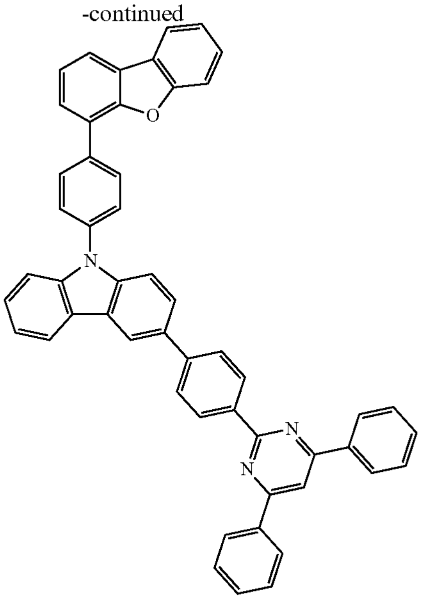

Compound 1

Synthesis of Intermediate (A)

5.00 g (12.9 mmol) of 2-(4-bromophenyl)-4,6-diphenylpyrimidine, 3.94 g (15.5 mmol) of bis(pinacolato)diboron, 527 mg (0.645 mmol) of $PdCl_2(dppf).CH_2Cl_2$, and 3.80 g (38.7 mmol) of potassium acetate were added to 100 mL of DMF, and then, the mixture was heated at a temperature of 100° C. while stirring. When the reaction stopped, the reaction product was cooled to room temperature and then subjected to silica gel to perform filtering under a reduced pressure, and the filtration solution was concentrated under a reduced pressure. The product was refined by performing recrystallization using ethyl acetate/toluene to obtain 4.19 g (yield of 75%) of Intermediate (A) as a target compound.

LC-Mass (calculated: 434.22 g/mol. found: M+1=435 g/mol)

Synthesis of Intermediate (B)

1.80 g (4.14 mmol) of Intermediate (A), 1.02 g (4.14 mmol) of 3-bromocarbazole, 478 mg (0.414 mmol) of tetrakistriphenylphosphine palladium (0)($Pd(PPh_3)_4$), and 1.72 g (12.4 mmol) of potassium carbonate were added to a mixed solution including 8 mL of toluene, 8 mL of tetrahydrofuran, and 8 mL of water, and then, the mixture was refluxed while stirring. When the reaction stopped, the reaction solution was cooled to room temperature, and then, an aqueous solution layer was removed by extraction, and then, the remaining product was subjected to silica gel to perform filtering under a reduced pressure. The filtration solution was concentrated under a reduced pressure. The product was subjected to silica gel column chromatography (ethylacetate:n-hexane)=1:5, volume to volume) to obtain 1.45 g (yield of 72%) of Intermediate (B) as a target compound.

LC-Mass (calculated: 473.19 g/mol. found: M+1=474 g/mol)

Synthesis of Compound 1

475 mg (1.00 mmol) of Intermediate (B), 388 mg (1.20 mmol) of 4-(4-bromophenyl)dibenzo[b,d]furan, 91.6 mg (0.100 mmol) of $Pd_2(dba)_3$, 100 μL (50% in toluene, 0.200 mmol) of tri-tert-butylphosphine (ttbp), and 192 mg (2.00 mmol) of sodium tert-butoxide were added to 10 mL of xylene, and then, the mixture was heated at a temperature of 145° C. while stirring. When the reaction stopped, the reaction product was cooled to room temperature and then subjected to silica gel to perform filtering under a reduced pressure, and the filtration solution was concentrated under a reduced pressure. The product was subjected to silica gel column chromatography (ethylacetate:n-hexane=1:4 volume to volume). The product was refined by recrystallization using toluene/methanol to obtain 465 mg (yield of 65%) of Compound 1 as a target compound.

LC-Mass (calculated: 715.26 g/mol. found: M+1=716 g/mol)

Synthesis Example 2

Synthesis of Compound 2

Compound 2 was synthesized according to Reaction Scheme below:

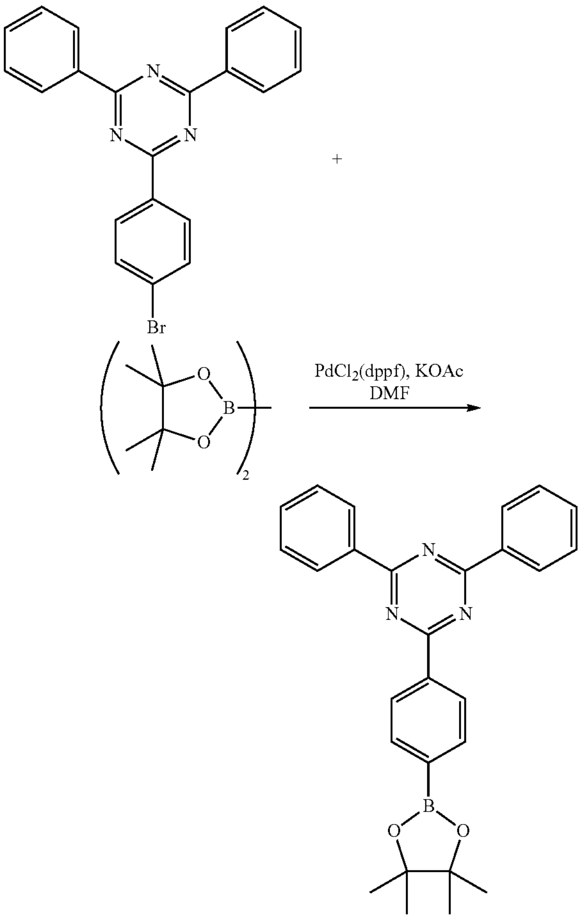

(C)

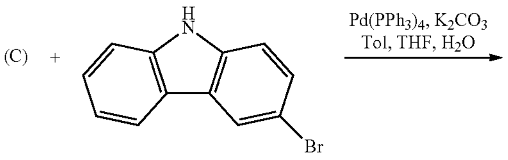

-continued

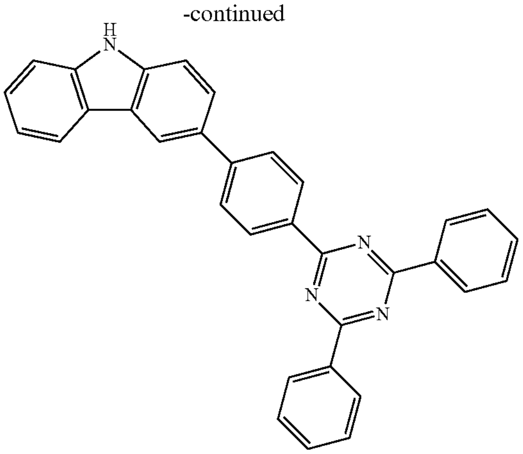

(D)

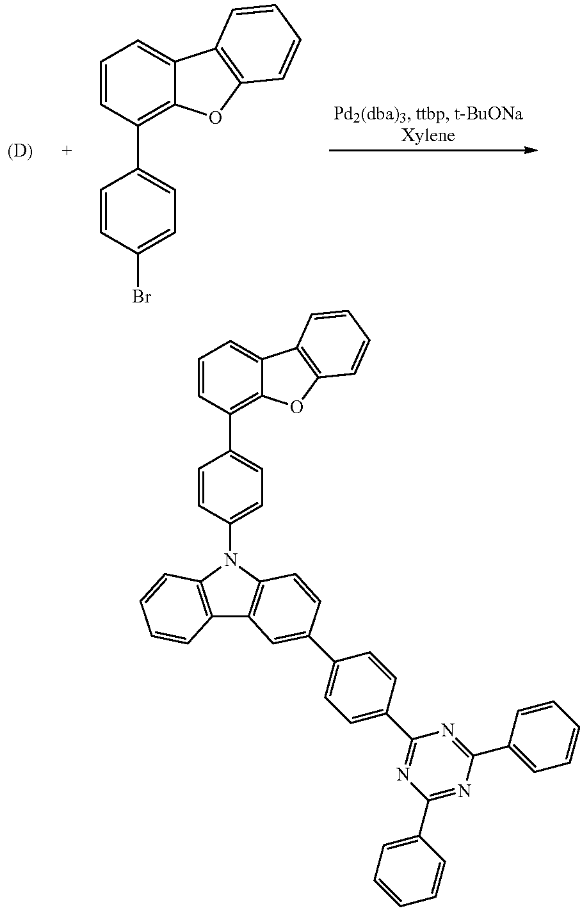

Compound 2

Synthesis of Intermediate (C)

5.00 g (12.9 mmol) of 2-(4-bromophenyl)-4,6-diphenyl-1,3,5-triazine, 3.94 g (15.5 mmol) of bis(pinacolato)diboron, 527 mg (0.645 mmol) of $PdCl_2(dppf).CH_2Cl_2$, and 3.80 g (38.7 mmol) of potassium acetate were added to 100 mL of DMF, and then, the mixture was heated at a temperature of 100° C. while stirring. When the reaction stopped, the reaction product was cooled to room temperature and then subjected to silica gel to perform filtering under a reduced pressure, and the filtration solution was concentrated a reduced pressure. The product was refined by performing recrystallization using ethyl acetate/toluene to obtain 4.81 g (yield of 86%) of Intermediate (C) as a target compound.

LC-Mass (calculated: 435.21 g/mol. found: M+1=436 g/mol)

Synthesis of Intermediate (D)

1.80 g (4.14 mmol) of Intermediate (C), 1.02 g (4.14 mmol) of 3-bromocarbazole, 478 mg (0.414 mmol) of tetrakistriphenylphosphine palladium (0)(Pd($PPh_3$)$_4$), and 1.72 g (12.4 mmol) of potassium carbonate were added to a mixed solution including 8 mL of toluene, 8 mL of tetrahydrofuran, and 8 mL of water, and then, the mixture was refluxed while stirring. When the reaction stopped, the reaction solution was cooled to room temperature, and then, an aqueous solution layer was removed by extraction, and then, the remaining product was subjected to silica gel to perform filtering under a reduced pressure. The filtration solution was concentrated under a reduced pressure. The product was subjected to silica gel column chromatography (ethylacetate:n-hexane)=1:5 volume to volume) to obtain 1.51 g (yield of 77%) of Intermediate (D) as a target compound.

LC-Mass (calculated: 474.18 g/mol. found: M+1=475 g/mol)

Synthesis of Compound 2

474 mg (1.00 mmol) of Intermediate (D), 388 mg (1.20 mmol) of 4-(4-bromophenyl)dibenzo[b,d]furan, 91.6 mg (0.100 mmol) of $Pd_2(dba)_3$, 100 μL (50% in toluene, 0.200 mmol) of tri-tert-butylphosphine (ttbp), and 192 mg (2.00 mmol) of sodium tert-butoxide were added to 10 mL of xylene, and then, the mixture was heated at a temperature of 145° C. while stirring. When the reaction stopped, the reaction product was cooled to room temperature and then subjected to silica gel to perform filtering under a reduced pressure, and the filtration solution was concentrated under a reduced pressure. The product was subjected to silica gel column chromatography (ethylacetate:n-hexane=1:4 volume to volume). The product was refined by recrystallization using toluene/methanol to obtain 494 mg (yield of 69%) of Compound 2 as a target compound.

LC-Mass (calculated: 716.26 g/mol. found: M+1=717 g/mol)

Synthesis Example 3

Synthesis of Compound 3

Compound 3 was synthesized according to Reaction Scheme below:

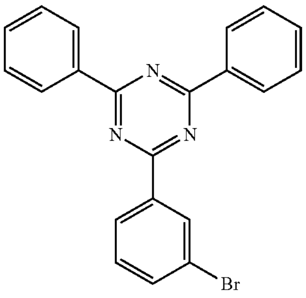

+

-continued

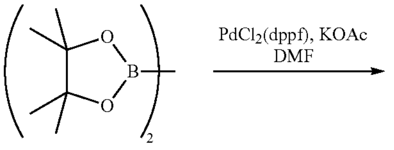

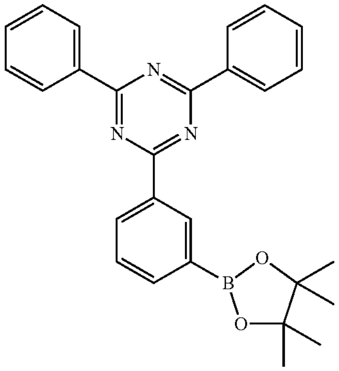

(E)

(E) +

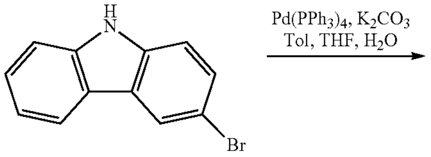

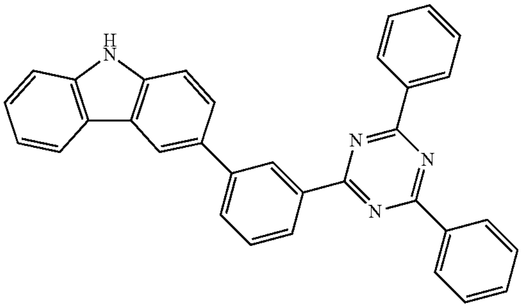

(F)

(F) +

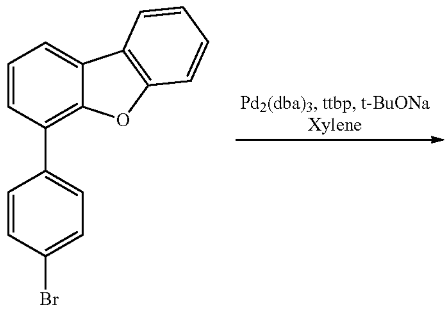

-continued

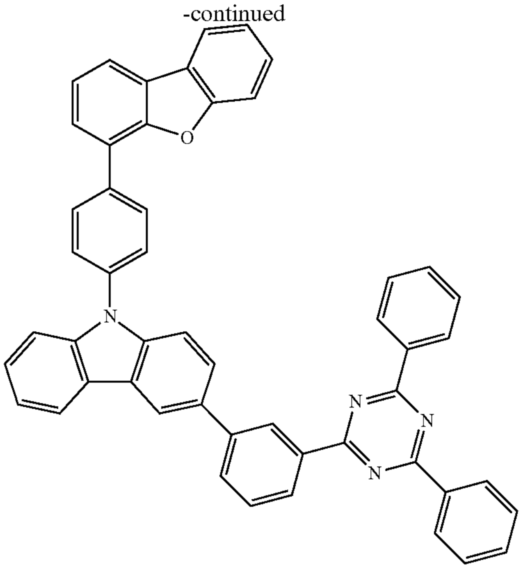

Compound 3

Synthesis of Intermediate (E)

5.00 g (12.9 mmol) of 2-(3-bromophenyl)-4,6-diphenyl-1,3,5-triazine, 3.94 g (15.5 mmol) of bis(pinacolato)diboron, 527 mg (0.645 mmol) of $PdCl_2(dppf).CH_2Cl_2$, and 3.80 g (38.7 mmol) of potassium acetate were added to 100 mL of DMF, and then, the mixture was heated at a temperature of 100° C. while stirring. When the reaction stopped, the reaction product was cooled to room temperature and then subjected to silica gel to perform filtering under a reduced pressure, and the filtration solution was concentrated under a reduced pressure. The product was refined by performing recrystallization using ethyl acetate/toluene to obtain 4.92 g (yield of 88%) of Intermediate (E) as a target compound.

LC-Mass (calculated: 435.21 g/mol. found: M+1=436 g/mol)

Synthesis of Intermediate (F)

1.80 g (4.14 mmol) of Intermediate (E), 1.02 g (4.14 mmol) of 3-bromocarbazole, 478 mg (0.414 mmol) of tetrakistriphenylphosphine palladium (0)($Pd(PPh_3)_4$), and 1.72 g (12.4 mmol) of potassium carbonate were added to a mixed solution including 8 mL of toluene, 8 mL of tetrahydrofuran, and 8 mL of water, and then, the mixture was refluxed while stirring. When the reaction stopped, the reaction solution was cooled to room temperature, and then, an aqueous solution layer was removed by extraction, and then, the remaining product was subjected to silica gel to perform filtering under a reduced pressure. The filtration solution was concentrated under a reduced pressure. The product was subjected to silica gel column chromatography (ethylacetate:n-hexane)=1:5 volume to volume) to obtain 1.61 g (yield of 82%) of Intermediate (F) as a target compound.

LC-Mass (calculated: 474.18 g/mol. found: M+1=475 g/mol)

Synthesis of Compound 3

474 mg (1.00 mmol) of Intermediate (F), 388 mg (1.20 mmol) of 4-(4-bromophenyl)dibenzo[b,d]furan, 91.6 mg (0.100 mmol) of $Pd_2(dba)_3$, 100 μL (50% in toluene, 0.200 mmol) of tri-tert-butylphosphine (ttbp), and 192 mg (2.00 mmol) of sodium tert-butoxide were added to 10 mL of xylene, and then, the mixture was heated at a temperature of 145° C. while stirring. When the reaction stopped, the reaction product was cooled to room temperature and then subjected to silica gel to perform filtering under a reduced pressure, and the filtration solution was concentrated under a reduced pressure. The product was subjected to silica gel column chromatography (ethylacetate:n-hexane=1:4 volume to volume). The product was refined by recrystallization using toluene/methanol to obtain 537 mg (yield of 75%) of Compound 3 as a target compound.

LC-Mass (calculated: 716.26 g/mol. found: M+1=717 g/mol)

Synthesis Example 4

Synthesis of Compound 4

Compound 4 was synthesized according to Reaction Scheme below:

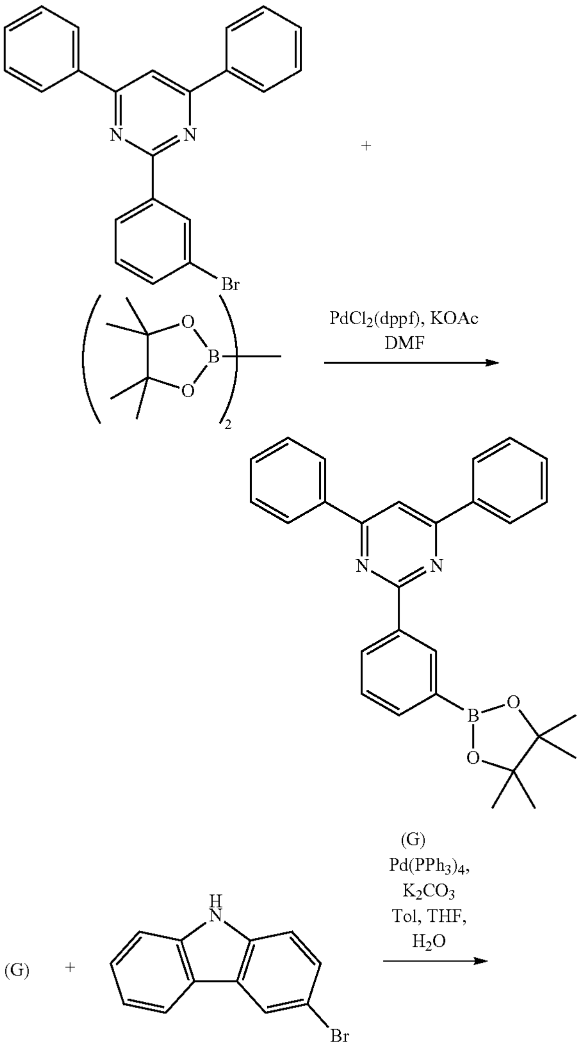

-continued

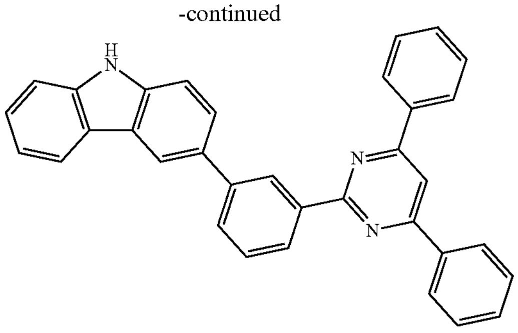

(H)

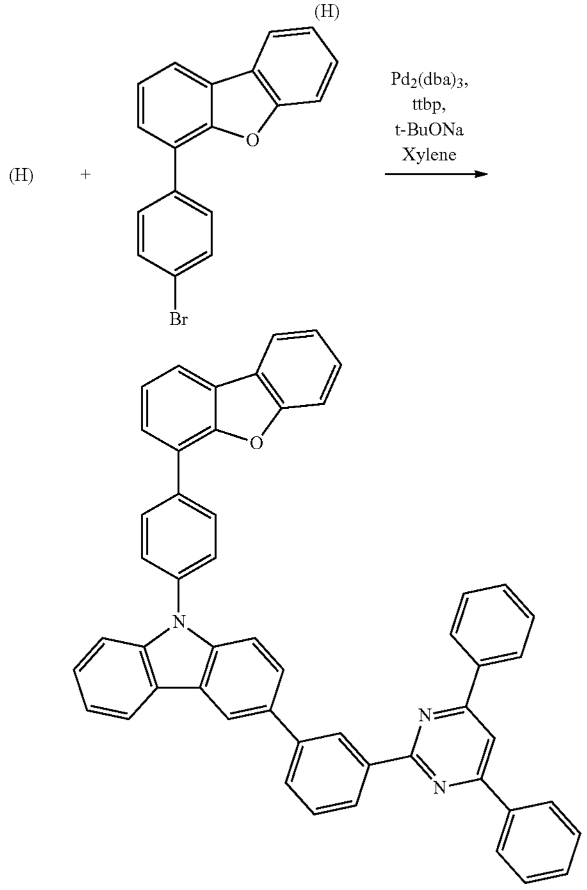

Compound 4

Synthesis of Intermediate (G)

5.00 g (12.9 mmol) of 2-(3-bromophenyl)-4,6-diphenylpyrimidine, 3.94 g (15.5 mmol) of bis(pinacolato)diboron, 527 mg (0.645 mmol) of $PdCl_2(dppf).CH_2Cl_2$, and 3.80 g (38.7 mmol) of potassium acetate were added to 100 mL of DMF, and then, the mixture was heated at a temperature of 100° C. while stirring. When the reaction stopped, the reaction product was cooled to room temperature and then subjected to silica gel to perform filtering under a reduced pressure, and the filtration solution was concentrated under a reduced pressure. The product was refined by performing recrystallization using ethyl acetate/toluene to obtain 4.25 g (yield of 76%) of Intermediate (G) as a target compound.

LC-Mass (calculated: 434.22 g/mol. found: M+1=435 g/mol)

Synthesis of Intermediate (H)

1.80 g (4.14 mmol) of Intermediate (G), 1.02 g (4.14 mmol) of 3-bromocarbazole, 478 mg (0.414 mmol) of tetrakistriphenylphosphine palladium $(0)(Pd(PPh_3)_4)$, and 1.72 g (12.4 mmol) of potassium carbonate were added to a mixed solution including 8 mL of toluene, 8 mL of tetrahydrofuran, and 8 mL of water, and then, the mixture was refluxed while stirring. When the reaction stopped, the reaction solution was cooled to room temperature, and then, an aqueous solution layer was removed by extraction, and then, the remaining product was subjected to silica gel to perform filtering under a reduced pressure. The filtration solution was concentrated under a reduced pressure. The product was subjected to silica gel column chromatography (ethylacetate:n-hexane)=1:5 volume to volume) to obtain 1.49 g (yield of 74%) of Intermediate (H) as a target compound.

LC-Mass (calculated: 473.19 g/mol. found: M+1=474 g/mol)

Synthesis of Compound 4

475 mg (1.00 mmol) of Intermediate (H), 388 mg (1.20 mmol) of 4-(4-bromophenyl)dibenzo[b,d]furan, 91.6 mg (0.100 mmol) of $Pd_2(dba)_3$, 100 μL (50% in toluene, 0.200 mmol) of tri-tert-butylphosphine (ttbp), and 192 mg (2.00 mmol) of sodium tert-butoxide were added to 10 mL of xylene, and then, the mixture was heated at a temperature of 145° C. while stirring. When the reaction stopped, the reaction product was cooled to room temperature and then subjected to silica gel to perform filtering under a reduced pressure, and the filtration solution was concentrated under a reduced pressure. The product was subjected to silica gel column chromatography (ethylacetate:n-hexane=1:4 volume to volume). The product was refined by recrystallization using toluene/methanol to obtain 508 mg (yield of 71%) of Compound 4 as a target compound.

LC-Mass (calculated: 715.26 g/mol. found: M+1=716 g/mol)

Synthesis Example 5

Synthesis of Compound 22

Compound 22 was synthesized according to Reaction Scheme below:

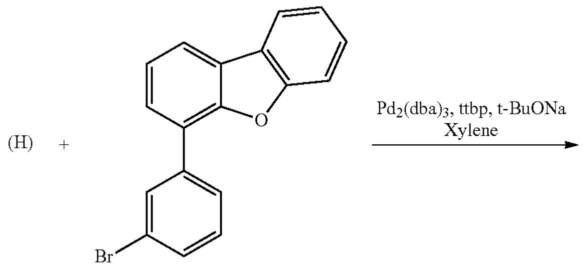

-continued

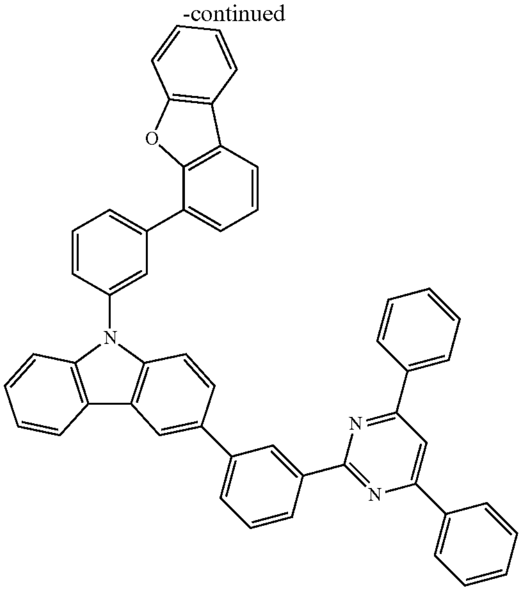

Compound 22

475 mg (1.00 mmol) of Intermediate (H), 388 mg (1.20 mmol) of 4-(3-bromophenyl)dibenzo[b,d]furan, 91.6 mg (0.100 mmol) of $Pd_2(dba)_3$, 100 μL (50% in toluene, 0.200 mmol) of tri-tert-butylphosphine (ttbp), and 192 mg (2.00 mmol) of sodium tert-butoxide were added to 10 mL of xylene, and then, the mixture was heated at a temperature of 145° C. while stirring. When the reaction stopped, the reaction product was cooled to room temperature and then subjected to silica gel to perform filtering under a reduced pressure, and the filtration solution was concentrated under a reduced pressure. The product was subjected to silica gel column chromatography (ethylacetate:n-hexane=1:4 volume to volume). The product was refined by recrystallization using toluene/methanol to obtain 465 mg (yield of 65%) of Compound 22 as a target compound.

LC-Mass (calculated: 716.26 g/mol. found: M+1=717 g/mol)

Synthesis Example 6

Synthesis of Compound 91

Compound 91 was synthesized according to Reaction Scheme below:

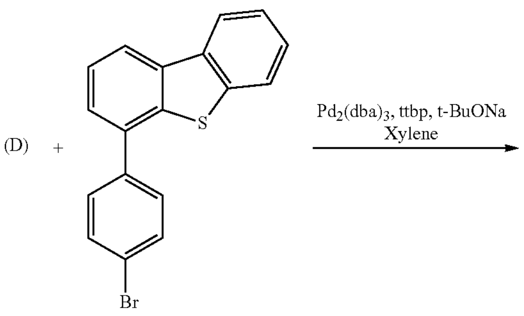

-continued

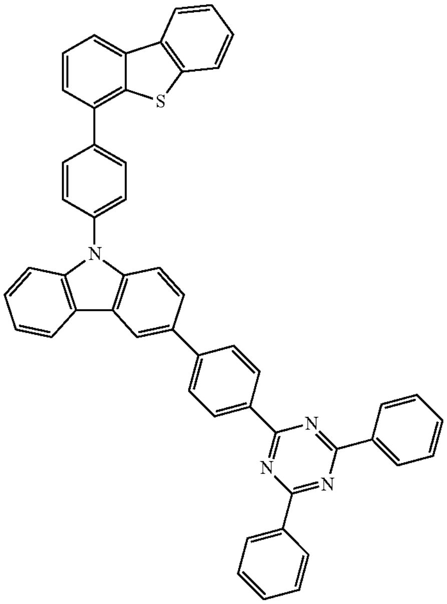

Compound 91

474 mg (1.00 mmol) of Intermediate (D), 407 mg (1.20 mmol) of 4-(4-bromophenyl)dibenzo[b,d]thiophene, 91.6 mg (0.100 mmol) of $Pd_2(dba)_3$, 100 μL (50% in toluene, 0.200 mmol) of tri-tert-butylphosphine (ttbp), and 192 mg (2.00 mmol) of sodium tert-butoxide were added to 10 mL of xylene, and then, the mixture was heated at a temperature of 145° C. while stirring. When the reaction stopped, the reaction product was cooled to room temperature and then subjected to silica gel to perform filtering under a reduced pressure, and the filtration solution was concentrated under a reduced pressure. The product was subjected to silica gel column chromatography (ethylacetate:n-hexane=1:4 volume to volume). The product was refined by recrystallization using toluene/methanol to obtain 381 mg (yield of 52%) of Compound 91 as a target compound.

LC-Mass (calculated: 732.23 g/mol. found: M+1=733 g/mol)

Synthesis Example 7

Synthesis of Compound 95

Compound 95 was synthesized according to Reaction Scheme below:

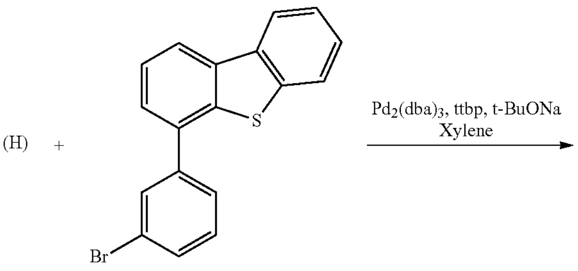

-continued

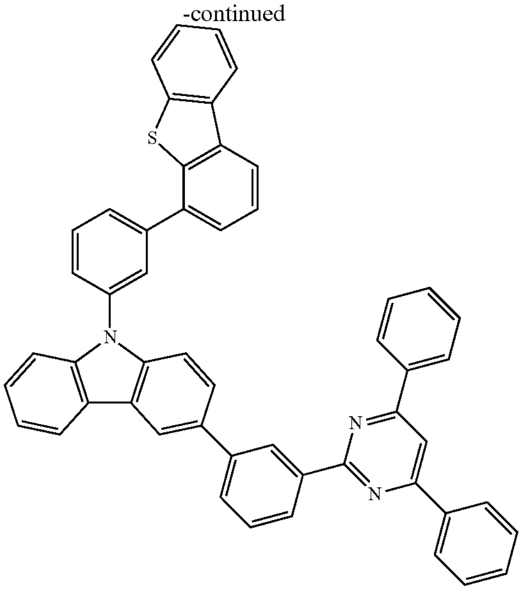

Compound 95

475 mg (1.00 mmol) of Intermediate (H), 407 mg (1.20 mmol) of 4-(3-bromophenyl)dibenzo[b,d]thiophene, 91.6 mg (0.100 mmol) of $Pd_2(dba)_3$, 100 μL (50% in toluene, 0.200 mmol) of tri-tert-butylphosphine (ttbp), and 192 mg (2.00 mmol) of sodium tert-butoxide were added to 10 mL of xylene, and then, the mixture was heated at a temperature of 145° C. while stirring. When the reaction stopped, the reaction product was cooled to room temperature and then subjected to silica gel to perform filtering under a reduced pressure, and the filtration solution was concentrated under a reduced pressure. The product was subjected to silica gel column chromatography (ethylacetate:n-hexane=1:4 volume to volume). The product was refined by recrystallization using toluene/methanol to obtain 352 mg (yield of 48%) of Compound 95 as a target compound.

LC-Mass (calculated: 731.24 g/mol. found: M+1=732 g/mol)

Synthesis Example 8

Synthesis of Compound 130

Compound 130 was synthesized according to Reaction Scheme below:

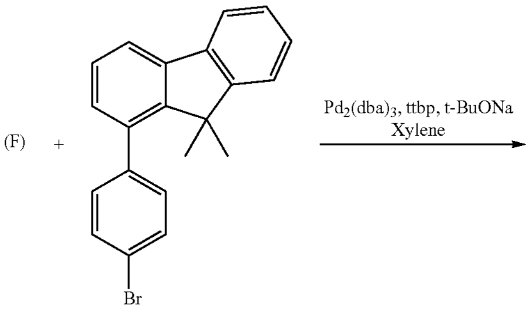

-continued

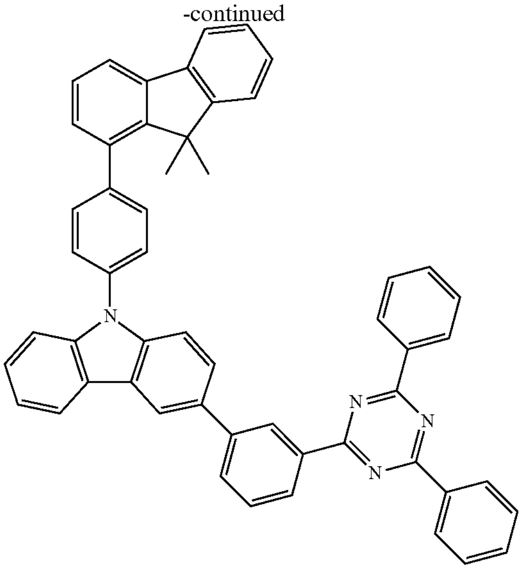

Compound 130

474 mg (1.00 mmol) of Intermediate (F), 419 mg (1.20 mmol) of 1-(4-bromophenyl)-9,9-dimethyl-9H-fluorene, 91.6 mg (0.100 mmol) of $Pd_2(dba)_3$, 100 μL (50% in toluene, 0.200 mmol) of tri-tert-butylphosphine (ttbp), and 192 mg (2.00 mmol) of sodium tert-butoxide were added to 10 mL of xylene, and then, the mixture was heated at a temperature of 145° C. while stirring. When the reaction stopped, the reaction product was cooled to room temperature and then subjected to silica gel to perform filtering under a reduced pressure, and the filtration solution was concentrated under a reduced pressure. The filtration solution was compression-filtered. The product was subjected to silica gel column chromatography (ethylacetate:n-hexane)=1:10 volume to volume) to obtain 608 mg (yield of 82%) of Compound 130 as a target compound.

LC-Mass (calculated: 742.31 g/mol. found: M+1=743 g/mol)

Synthesis Example 9

Synthesis of Compound 151

Compound 151 was synthesized according to Reaction Scheme below:

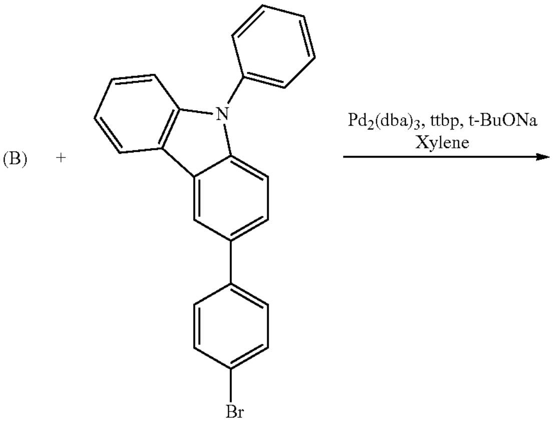

-continued

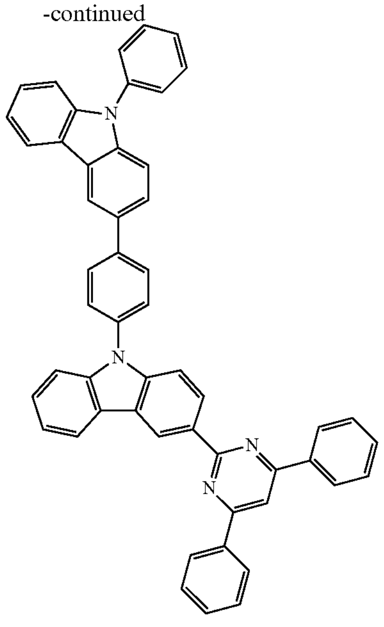

Compound 151

475 mg (1.00 mmol) of Intermediate (B), 478 mg (1.20 mmol) of 3-(4-bromophenyl)-9-phenyl-9H-carbazole, 91.6 mg (0.100 mmol) of $Pd_2(dba)_3$, 100 μL (50% in toluene, 0.200 mmol) of tri-tert-butylphosphine (ttbp), and 192 mg (2.00 mmol) of sodium tert-butoxide were added to 10 mL of xylene, and then, the mixture was heated at a temperature of 145° C. while stirring. When the reaction stopped, the reaction product was cooled to room temperature and then subjected to silica gel to perform filtering under a reduced pressure, and the filtration solution was concentrated under a reduced pressure. The product was subjected to silica gel column chromatography (ethylacetate:n-hexane=1:3 volume to volume). The product was refined by recrystallization using toluene/methanol to obtain 664 mg (yield of 84%) of Compound 151 as a target compound.

LC-Mass (calculated: 790.31 g/mol. found: M+1=791 g/mol)

Synthesis Example 10

Synthesis of Compound 152

Compound 152 was synthesized according to Reaction Scheme below:

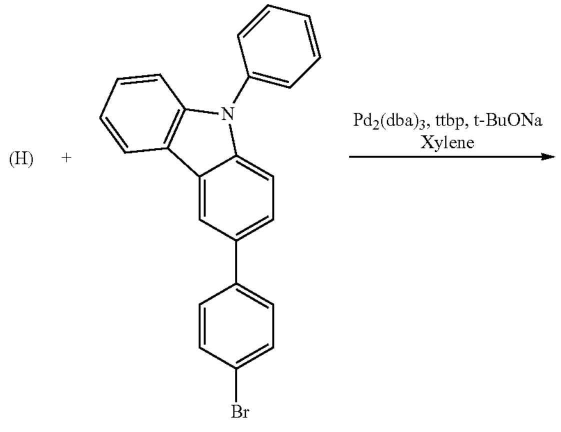

-continued

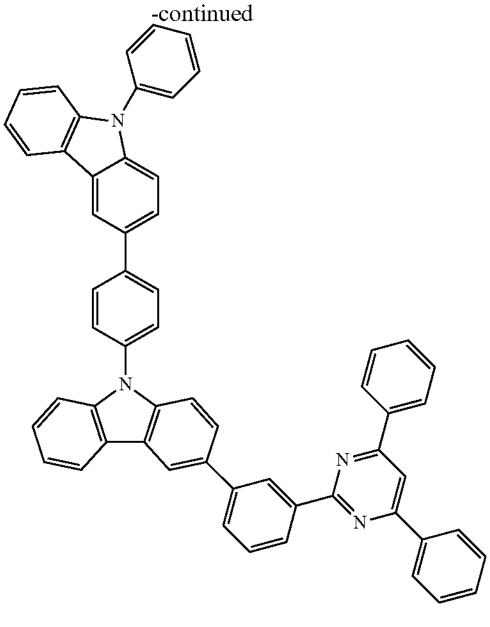

Compound 152

475 mg (1.00 mmol) of Intermediate (H), 478 mg (1.20 mmol) of 3-(4-bromophenyl)-9-phenyl-9H-carbazole, 91.6 mg (0.100 mmol) of $Pd_2(dba)_3$, 100 μL (50% in toluene, 0.200 mmol) of tri-tert-butylphosphine (ttbp), and 192 mg (2.00 mmol) of sodium tert-butoxide were added to 10 mL of xylene, and then, the mixture was heated at a temperature of 145° C. while stirring. When the reaction stopped, the reaction product was cooled to room temperature and then subjected to silica gel to perform filtering under a reduced pressure, and the filtration solution was concentrated under a reduced pressure. The product was subjected to silica gel column chromatography (ethylacetate:n-hexane=1:3 volume to volume). The product was refined by recrystallization using toluene/methanol to obtain 632 mg (yield of 80%) of Compound 152 as a target compound.

LC-Mass (calculated: 790.31 g/mol. found: M+1=791 g/mol)

Synthesis Example 11

Synthesis of Compound 158

Compound 158 was synthesized according to Reaction Scheme below:

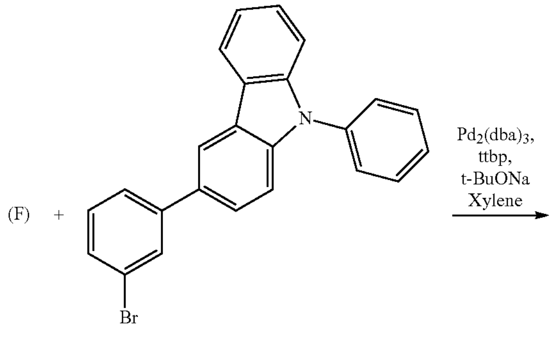

-continued

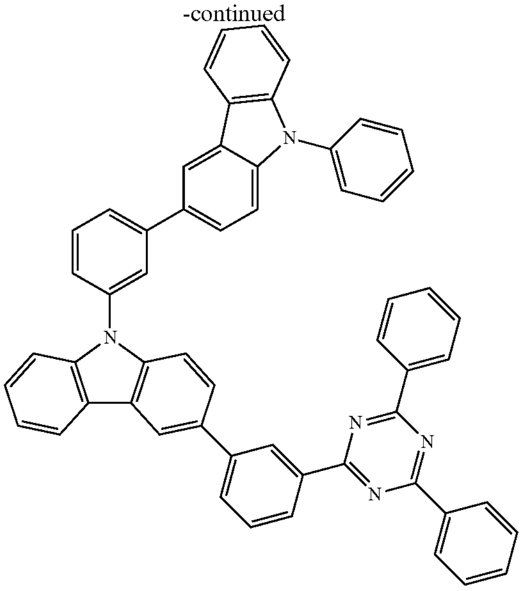

Compound 158

474 mg (1.00 mmol) of Intermediate (F), 478 mg (1.20 mmol) of 3-(3-bromophenyl)-9-phenyl-9H-carbazole, 91.6 mg (0.100 mmol) of $Pd_2(dba)_3$, 100 μL (50% in toluene, 0.200 mmol) of tri-tert-butylphosphine (ttbp), and 192 mg (2.00 mmol) of sodium tert-butoxide were added to 10 mL of xylene, and then, the mixture was heated at a temperature of 145° C. while stirring. When the reaction stopped, the reaction product was cooled to room temperature and then subjected to silica gel to perform filtering under a reduced pressure, and the filtration solution was concentrated under a reduced pressure. The product was subjected to silica gel column chromatography (ethylacetate:n-hexane=1:3 volume to volume). The product was refined by recrystallization using toluene/methanol to obtain 616 mg (yield of 78%) of Compound 158 as a target compound.

LC-Mass (calculated: 791.30 g/mol. found: M+1=792 g/mol)

Synthesis Example 12

Synthesis of Compound 166

Compound 166 was synthesized according to Reaction Scheme below:

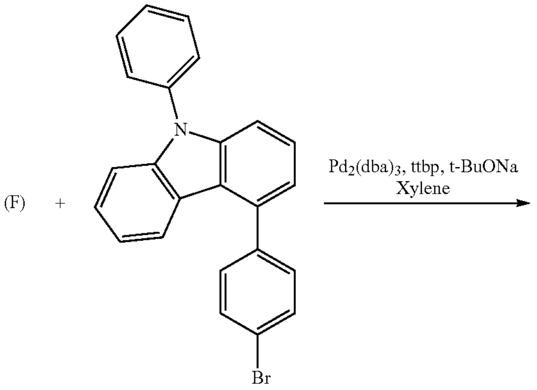

-continued

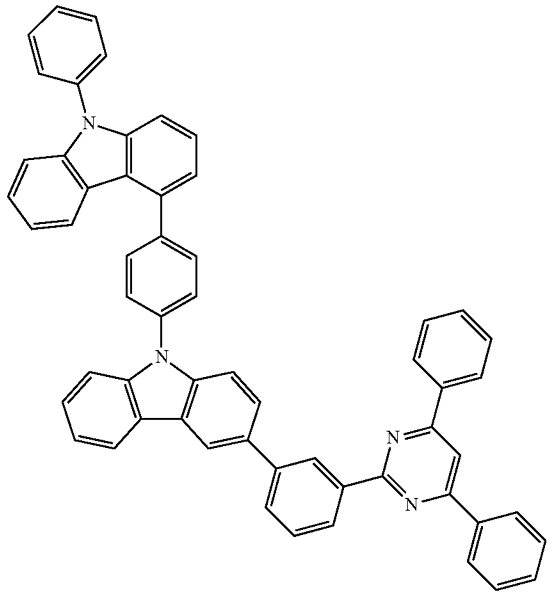

Compound 166

474 mg (1.00 mmol) of Intermediate (F), 478 mg (1.20 mmol) of 4-(4-bromophenyl)-9-phenyl-9H-carbazole, 91.6 mg (0.100 mmol) of $Pd_2(dba)_4$, 100 μL (50% in toluene, 0.200 mmol) of tri-tert-butylphosphine (ttbp), and 192 mg (2.00 mmol) of sodium tert-butoxide were added to 10 mL of xylene, and then, the mixture was heated at a temperature of 145° C. while stirring. When the reaction stopped, the reaction product was cooled to room temperature and then subjected to silica gel to perform filtering under a reduced pressure, and the filtration solution was concentrated under a reduced pressure. The product was subjected to silica gel column chromatography (ethylacetate:n-hexane=1:3 volume to volume). The product was refined by recrystallization using toluene/methanol to obtain 482 mg (yield of 61%) of Compound 166 as a target compound.

LC-Mass (calculated: 791.30 g/mol. found: M+1=792 g/mol)

Synthesis Example 13

Synthesis of Compound 173

Compound 173 was synthesized according to Reaction Scheme below:

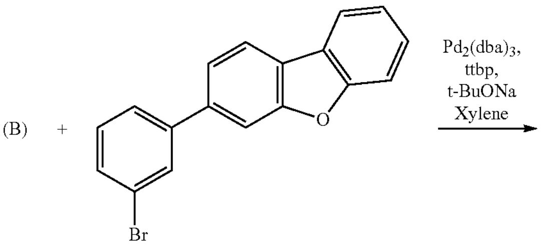

-continued

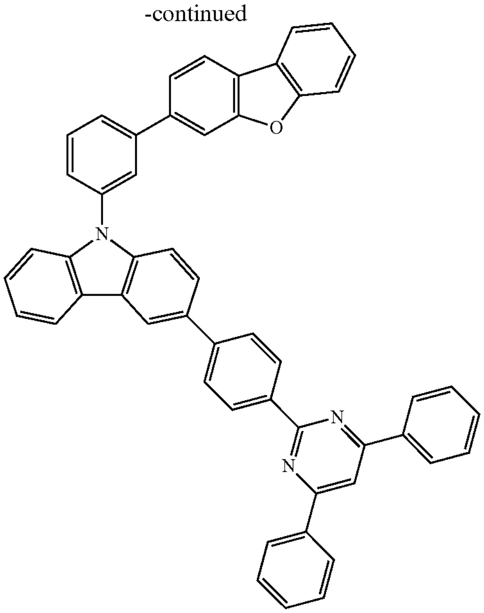

Compound 173

475 mg (1.00 mmol) of Intermediate (B), 388 mg (1.20 mmol) of 3-(3-bromophenyl)dibenzo[b,d]furan, 91.6 mg (0.100 mmol) of Pd2(dba)3, 100 μL (50% in toluene, 0.200 mmol) of tri-tert-butylphosphine (ttbp), and 192 mg (2.00 mmol) of sodium tert-butoxide were added to 10 mL of xylene, and then, the mixture was heated at a temperature of 145° C. while stirring. When the reaction stopped, the reaction product was cooled to room temperature and then subjected to silica gel to perform filtering under a reduced pressure, and the filtration solution was concentrated under a reduced pressure. The product was subjected to silica gel column chromatography (ethylacetate:n-hexane=1:4 volume to volume). The product was refined by recrystallization using toluene/methanol to obtain 508 mg (yield of 71%) of Compound 173 as a target compound.

LC-Mass (calculated: 715.26 g/mol. found: M+1=716 g/mol)

Synthesis Example 14

Synthesis of Compound 186

Compound 186 was synthesized according to Reaction Scheme below:

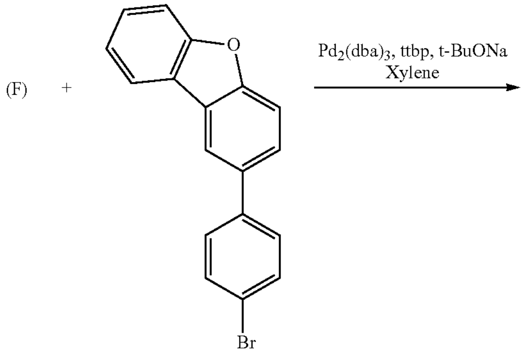

-continued

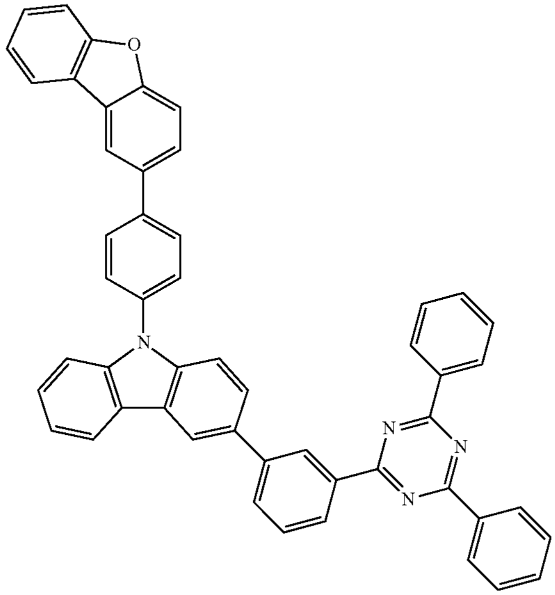

Compound 186

474 mg (1.00 mmol) of Intermediate (F), 388 mg (1.20 mmol) of 2-(4-bromophenyl)dibenzo[b,d]furan, 91.6 mg (0.100 mmol) of $Pd_2(dba)_3$, 100 μL (50% in toluene, 0.200 mmol) of tri-tert-butylphosphine (ttbp), and 192 mg (2.00 mmol) of sodium tert-butoxide were added to 10 mL of xylene, and then, the mixture was heated at a temperature of 145° C. while stirring. When the reaction stopped, the reaction product was cooled to room temperature and then subjected to silica gel to perform filtering under a reduced pressure, and the filtration solution was concentrated under a reduced pressure. The product was subjected to silica gel column chromatography (ethylacetate:n-hexane=1:4 volume to volume). The product was refined by recrystallization using toluene/methanol to obtain 551 mg (yield of 77%) of Compound 186 as a target compound.

LC-Mass (calculated: 716.26 g/mol. found: M+1=717 g/mol)

Synthesis Example 15

Synthesis of Compound 191

Compound 191 was synthesized according to Reaction Scheme below:

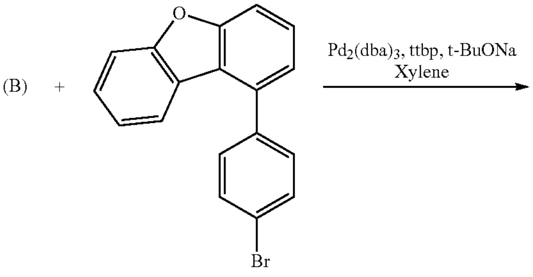

-continued

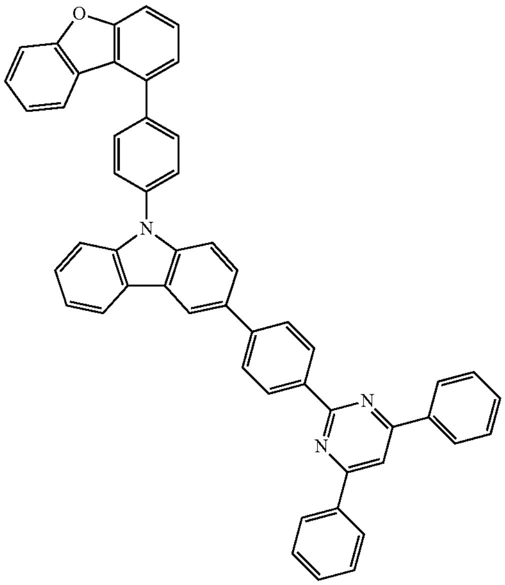

Compound 191

475 mg (1.00 mmol) of Intermediate (B), 388 mg (1.20 mmol) of 1-(4-bromophenyl)dibenzo[b,d]furan, 91.6 mg (0.100 mmol) of $Pd_2(dba)_3$, 100 μL (50% in toluene, 0.200 mmol) of tri-tert-butylphosphine (ttbp), and 192 mg (2.00 mmol) of sodium tert-butoxide were added to 10 mL of xylene, and then, the mixture was heated at a temperature of 145° C. while stirring. When the reaction stopped, the reaction product was cooled to room temperature and then subjected to silica gel to perform filtering under a reduced pressure, and the filtration solution was concentrated under a reduced pressure. The product was subjected to silica gel column chromatography (ethylacetate:n-hexane=1:4 volume to volume). The product was refined by recrystallization using toluene/methanol to obtain 537 mg (yield of 75%) of Compound 191 as a target compound.

LC-Mass (calculated: 715.26 g/mol. found: M+1=716 g/mol)

Synthesis Example 16

Synthesis of Compound 196

Compound 196 was synthesized according to Reaction Scheme below:

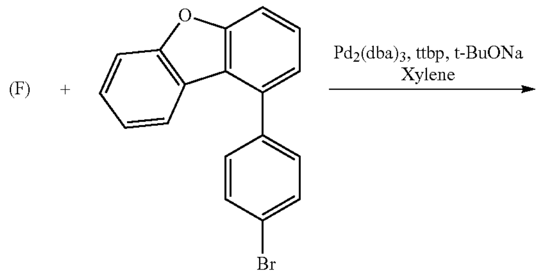

-continued

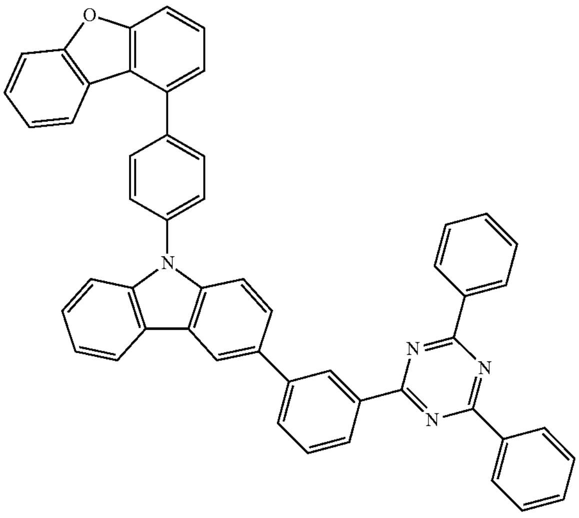

Compound 196

474 mg (1.00 mmol) of Intermediate (F), 388 mg (1.20 mmol) of 1-(4-bromophenyl)dibenzo[b,d]furan, 91.6 mg (0.100 mmol) of $Pd_1(dba)_3$, 100 μL (50% in toluene, 0.200 mmol) of tri-tert-butylphosphine (ttbp), and 192 mg (2.00 mmol) of sodium tert-butoxide were added to 10 mL of xylene, and then, the mixture was heated at a temperature of 145° C. while stirring. When the reaction stopped, the reaction product was cooled to room temperature and then subjected to silica gel to perform filtering under a reduced pressure, and the filtration solution was concentrated under a reduced pressure. The product was subjected to silica gel column chromatography (ethylacetate:n-hexane=1:4 volume to volume). The product was refined by recrystallization using toluene/methanol to obtain 408 mg (yield of 57%) of Compound 196 as a target compound.

LC-Mass (calculated: 716.26 g/mol. found: M+1=717 g/mol)

Synthesis Example 17

Synthesis of Compound 262

Compound 262 was synthesized according to Reaction Scheme below:

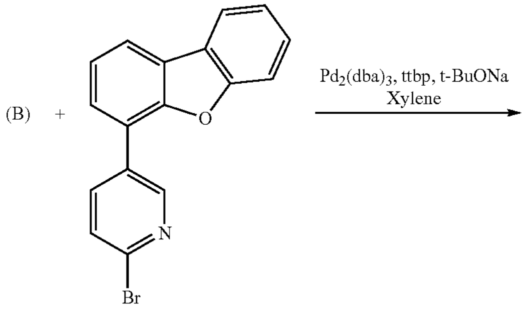

-continued

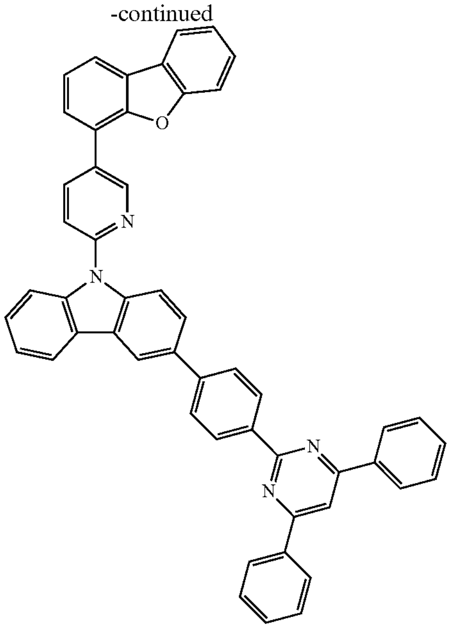

Compound 262

475 mg (1.00 mmol) of Intermediate (B), 389 mg (1.20 mmol) of 2-bromo-5-(dibenzo[b,d]furan-4-yl)pyridine, 91.6 mg (0.100 mmol) of $Pd_2(dba)_3$, 100 μL (50% in toluene, 0.200 mmol) of tri-tert-butylphosphine (ttbp), and 192 mg (2.00 mmol) of sodium tert-butoxide were added to 10 mL of xylene, and then, the mixture was heated at a temperature of 145° C. while stirring. When the reaction stopped, the reaction product was cooled to room temperature and then subjected to silica gel to perform filtering under a reduced pressure, and the filtration solution was concentrated under a reduced pressure. The product was subjected to silica gel column chromatography (ethylacetate:n-hexane=1:3 volume to volume). The product was refined by recrystallization using toluene/methanol to obtain 315 mg (yield of 44%) of Compound 262 as a target compound.

LC-Mass (calculated: 716.26 g/mol. found: M+1=717 g/mol)

Evaluation Example 1

HOMO, LUMO and triplet (T1) energy level evaluations of Compounds 1 to 4, 22, 91, 95, 130, 151, 152, 158, 166, 173, 186, 191, 196, and 262, and Compound C HOMO, LUMO and T1 energy levels of Compounds 1 to 4, 22, 91, 95, 130, 151, 152, 158, 166, 173, 186, 191, 196 and 262 and Compound C below (the synthesis method for Compound C may be understood by referring to JP publication 2010-135467) were evaluated according to the methods shown in Table 1 below, and results thereof are shown in Table 2.

Compound C

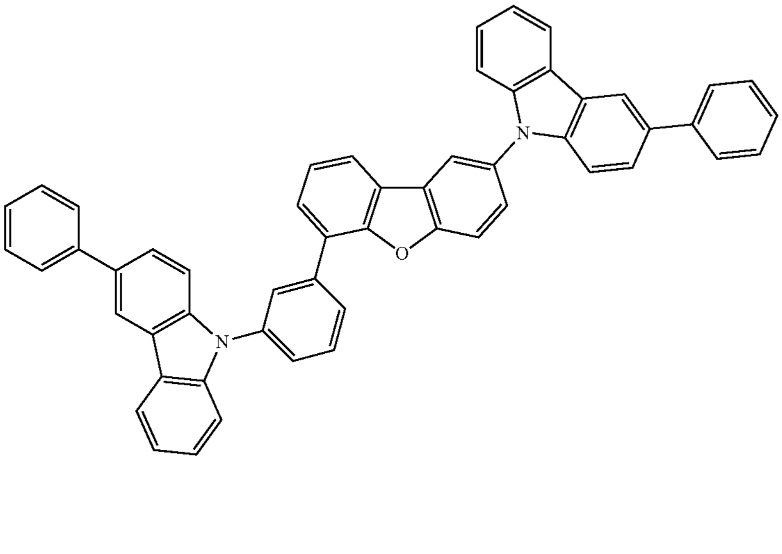

TABLE 1

| | |
|---|---|
| HOMO energy level evaluation method | Each compound was diluted in toluene to a concentration of 1 × $10^{-5}$M, and then, UV absorption spectrum thereof was measured at room temperature by using Varian Cary 5000 UV-Vis-NIR spectrophotometer. A HOMO energy level of the compound was calculated by using an optical band gap (Eg) measured using the edge of the absorption spectrum. |
| LUMO energy level evaluation method | Cyclic voltammetry (CV) (electrolyte: 0.1M $Bu_4NClO_4$/solvent: THF/electrode: 3 electrode system (working electrode: GC, reference electrode: Ag/AgCl, auxiliary electrode: Pt)) were used to obtain a potential (V)-current (A) graph of each compound, and then, from reduction onset of the graph, the LUMO energy level of each compound was calculated. |

TABLE 1-continued

| | |
|---|---|
| T1 energy level evaluation method | A mixture (each compound was dissolved in an amount of 1 mg in 3 cc of toluene) of 2-MeTHF and each compound was loaded into a quartz cell, and then, the resultant quartz cell was loaded into liquid nitrogen (77K) and a photoluminescence spectrum thereof was measured by using a device for measuring photoluminescence, and the obtained spectrum was compared with a photoluminescence spectrum measured at room temperature, and peaks appearing only at low temperature were analyzed to calculate T1 energy levels. |

TABLE 2

| Compound No. | HOMO(eV) (absolute value) | LUMO(eV) (absolute value) | T1 energy level (eV) |
|---|---|---|---|
| Compound 1 | 5.19 | 1.59 | 2.72 |
| Compound 2 | 5.30 | 1.78 | 2.70 |
| Compound 3 | 5.26 | 1.77 | 2.84 |
| Compound 4 | 5.18 | 1.62 | 2.88 |
| Compound 5 | 5.20 | 1.64 | 2.89 |
| Compound 91 | 5.34 | 1.79 | 2.68 |
| Compound 95 | 5.23 | 1.65 | 2.89 |
| Compound 130 | 5.33 | 1.79 | 2.85 |
| Compound 151 | 5.11 | 1.58 | 2.71 |
| Compound 152 | 5.09 | 1.61 | 2.89 |
| Compound 158 | 5.24 | 1.76 | 2.85 |
| Compound 166 | 5.24 | 1.76 | 2.84 |
| Compound 173 | 5.24 | 1.61 | 2.72 |
| Compound 186 | 5.29 | 1.78 | 2.85 |
| Compound 191 | 5.25 | 1.61 | 2.73 |
| Compound 196 | 5.34 | 1.80 | 2.86 |
| Compound 262 | 5.23 | 1.58 | 2.72 |
| Compound C | 5.18 | 1.92 | 2.64 |

From Table 2, it was confirmed that Compounds 1 to 4, 22, 91, 95, 130, 151, 152, 158, 166, 173, 186, 191, 196, and 262 have a higher triplet energy level and a wider band gap than Compound C, which means that these compounds have electric characteristics suitable for use as a material for an organic light-emitting device.

Evaluation Example 2

Thermal Characteristics Evaluation on Compounds 1 and 4 and Compounds A and B Like Compounds 1 and 4, Compounds A and B below (the synthesis methods for Compounds A and B may be understood by referring to WO2012-105310) were subjected to thermo gravimetric analysis (TGA) and differential scanning calorimetry (DSC) to perform thermal analysis ($N_2$ atmosphere, temperature range: from room temperature to 800° C. (10° C./min)-TGA, from room temperature to 400° C.-DSC, Pan Type: Pt Pan in disposable Al Pan(TGA), disposable Al pan (DSC)), and results thereof are shown in Tables 2 to 5, and from the results, decomposition temperature of Compounds 1 and 4 and Compounds A and B were evaluated and results thereof are shown in Table 3 below.

TABLE 3

| | Compound 1 | Compound 4 | Compound A | Compound B |
|---|---|---|---|---|
| Decomposition starting temperature | 450° C. | 430° C. | 374° C. | 200° C. |

Compound 1

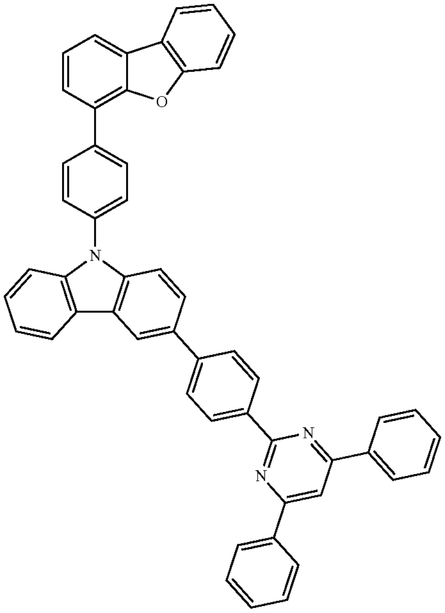

1

Compound 4

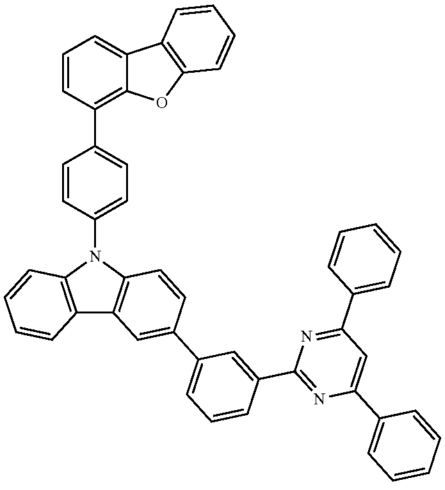

4

TABLE 3-continued

| | Compound 1 | Compound 4 | Compound A | Compound B |
|---|---|---|---|---|

Compound A

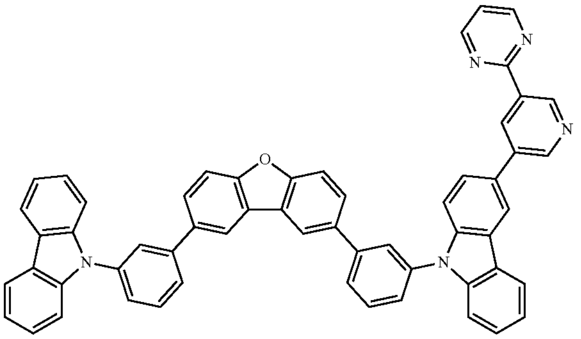 [SMILES: c1cnc(-c2cncc(-c3ccc4c(c3)c3ccccc3n4-c3cccc(-c4ccc5oc6ccc(-c7cccc(-n8c9ccccc9c9ccccc98)c7)cc6c5c4)c3)c2)nc1]

Compound B

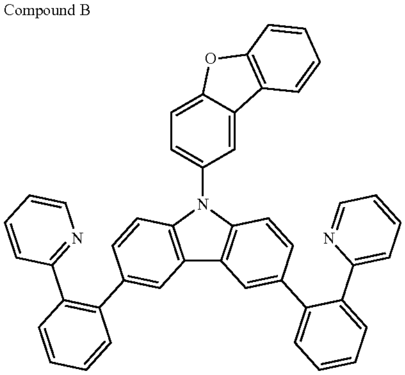

From FIGS. 2 to 5 and Table 3, it was confirmed that Compounds 1 and 4 have excellent thermal stability than Compounds A and B.

Example 1

ITO glass substrate (ITO layer acts as an anode) having a surface resistance of 15 ohms per square centimeter ($\Omega/cm^2$) was cut to a size of 50 mm×50 mm×0.7 mm, and then, sonicated with acetone, isopropylalcohol, and pure water, each for 15 minutes, and then, cleaned with UV ozone for 30 minutes.

On the ITO anode, N,N'-di(1-naphthyl)-N,N'-diphenylbenzidine (NPB) was deposited at a vacuum degree of $650\times10^{-7}$ pascals (Pa) and at a deposition speed of 0.1 to 0.3 nanometers per second (nm/s) to form a hole injection layer having a thickness of 70 nm. 4,4',4"-tri(N-carbazolyl)triphenylamine (TCTA) was deposited on the hole injection layer to form a hole transport layer having a thickness of 10 nanometers (nm), thereby forming a hole transport region having a total thickness of 80 nm.

Subsequently, Compound 1 (host) and $Ir(ppyy)_3$ (dopant) were co-deposited on the hole transport layer at a weight ratio of 90:10 to form an emission layer having a thickness of 300 Å, and then, bis(8-hydroxy-2-methylquinolinato)-aluminumbiphenoxide BAlq) was deposited on the emission layer to form a hole blocking layer having a thickness of 50 Å.

Then, $Alq_3$ was deposited on the hole blocking layer to from an electron transport layer having a thickness of 200 Å, and LiF was deposited on the electron transport layer to form an electron injection layer having a thickness of 1 nm, and an Al layer having a thickness of 100 nm was formed on the electron injection layer to form a cathode, thereby completing manufacturing of an organic light-emitting device having a structure of ITO/NPB (70 nm)/TCTA (10 nm)/EML (Compound 1 (90 weight %):$Ir(ppy)_3$(10 wt. %), 30 nm)/Balq (5 nm)/$Alq_3$(20 nm)/LiF (1 nm)/Al (100 nm).

Example 2

An organic light-emitting device was manufactured in the same manner as in Example 1, except that in forming an emission layer, as a host, Compound 2 was used instead of Compound 1.

Example 3

An organic light-emitting device was manufactured in the same manner as in Example 1, except that in forming an emission layer, as a host, Compound 3 was used instead of Compound 1.

Example 4

An organic light-emitting device was manufactured in the same manner as in Example 1, except that in forming an emission layer, as a host, Compound 4 was used instead of Compound 1.

Example 5

An organic light-emitting device was manufactured in the same manner as in Example 1, except that in forming an emission layer, as a host, Compound 22 was used instead of Compound 1.

Example 6

An organic light-emitting device was manufactured in the same manner as in Example 1, except that in forming an emission layer, as a host, Compound 91 was used instead of Compound 1.

Example 7

An organic light-emitting device was manufactured in the same manner as in Example 1, except that in forming an emission layer, as a host, Compound 95 was used instead of Compound 1.

Example 8

An organic light-emitting device was manufactured in the same manner as in Example 1, except that in forming an emission layer, as a host, Compound 130 was used instead of Compound 1.

Example 9

An organic light-emitting device was manufactured in the same manner as in Example 1, except that in forming an emission layer, as a host, Compound 151 was used instead of Compound 1.

Example 10

An organic light-emitting device was manufactured in the same manner as in Example 1, except that in forming an emission layer, as a host, Compound 152 was used instead of Compound 1.

Example 11

An organic light-emitting device was manufactured in the same manner as in Example 1, except that in forming an emission layer, as a host, Compound 158 was used instead of Compound 1.

Example 12

An organic light-emitting device was manufactured in the same manner as in Example 1, except that in forming an emission layer, as a host, Compound 166 was used instead of Compound 1.

Example 13

An organic light-emitting device was manufactured in the same manner as in Example 1, except that in forming an emission layer, as a host, Compound 173 was used instead of Compound 1.

Example 14

An organic light-emitting device was manufactured in the same manner as in Example 1, except that in forming an emission layer, as a host, Compound 186 was used instead of Compound 1.

Example 15

An organic light-emitting device was manufactured in the same manner as in Example 1, except that in forming an emission layer, as a host, Compound 191 was used instead of Compound 1.

Example 16

An organic light-emitting device was manufactured in the same manner as in Example 1, except that in forming an emission layer, as a host, Compound 196 was used instead of Compound 1.

Example 17

An organic light-emitting device was manufactured in the same manner as in Example 1, except that in forming an emission layer, as a host, Compound 262 was used instead of Compound 1.

Comparative Example 1

An organic light-emitting device was manufactured in the same manner as in Example 1, except that in forming an emission layer, as a host, Compound A was used instead of Compound 1.

Compound A

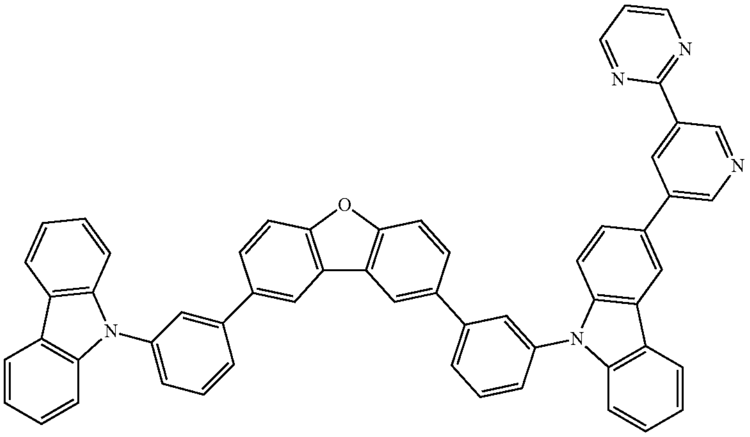

Comparative Example 2

An organic light-emitting device was manufactured in the same manner as in Example 1, except that in forming an emission layer, as a host, Compound B was used instead of Compound 1.

Compound B

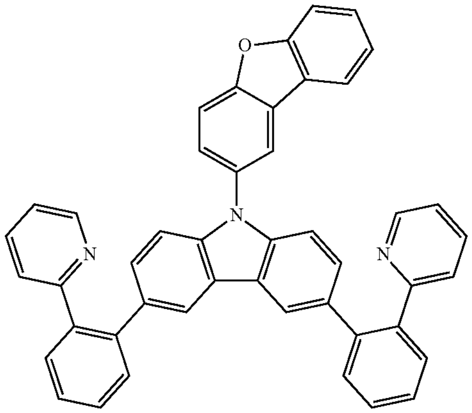 [SMILES: c1ccc(-c2ccccc2-c2ccc3c(c2)c2cc(-c4ccccc4-c4ccccn4)ccc2n3-c2ccc3oc4ccccc4c3c2)nc1]

Comparative Example 3

An organic light-emitting device was manufactured in the same manner as in Example 1, except that in forming an emission layer, as a host, Compound C was used instead of Compound 1.

Compound C

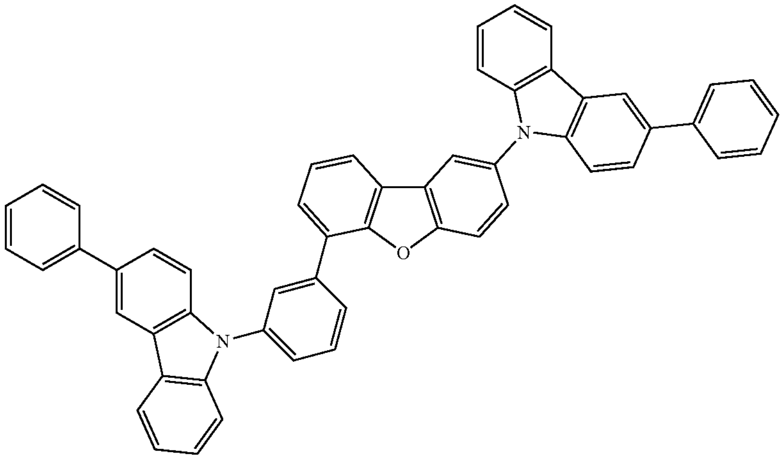

Evaluation Example 3

Evaluation on Characteristics of an Organic Light-Emitting Device

Figure 6:
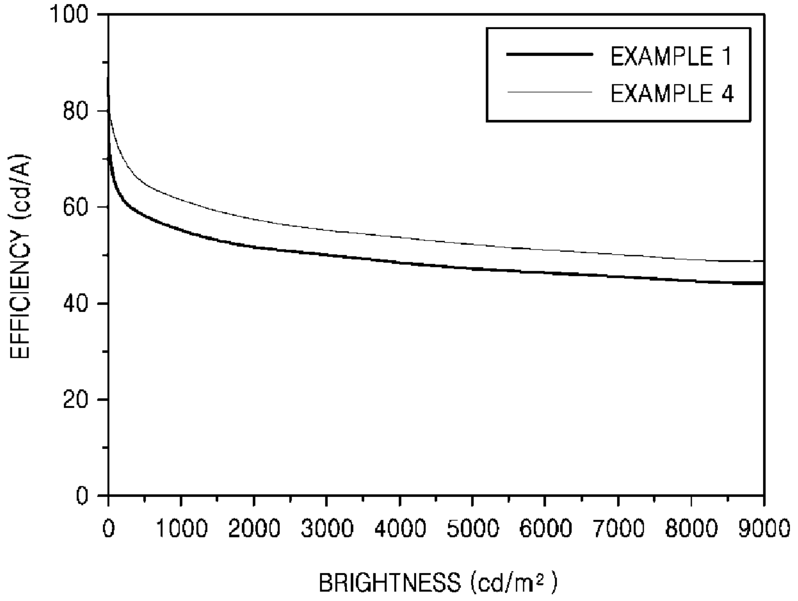
FIG. 6 is graph of efficiency (candelas per ampere, cd/A) versus brightness (candelas per square meter, $cd/m^2$) which is a brightness-efficiency graph of an organic light-emitting device manufactured according to Examples 1 and 4.

The current density, brightness, and emission efficiency of the organic light-emitting devices manufactured according to Examples 1 to 17 and Comparative Examples 1 to 3 were measured. Details of the measurement method are provided below, and Results thereof are shown in Table 4. FIG. 6 shows a brightness-efficiency graph of the organic light-emitting devices of Examples 1 to 4.

(1) Change in Current Density According to Voltage

Regarding the manufactured organic light-emitting device, a current flowing in a unit device was measured by using a current-voltage meter while a voltage was raised from 0 volts (V) to 10 V, and the measured current value was divided by an area (2) Change in Brightness According to Voltage Regarding the manufactured organic light-emitting device, brightness was measured by using Minolta Cs-1000A while a voltage was raised from 0 V to 10 V.

(3) Emission Efficiency Measurement

Current efficiency candelas per ampere (cd/A) was measured at the same current density (10 milliamperes per square centimeter ($mA/cm^2$)) by using brightness, current density, and voltage measured according to (1) and (2).

TABLE 4

| | Host | Driving voltage (V) | Current efficiency (cd/A) | Power efficiency (lm/W) | Color |
|---|---|---|---|---|---|
| Example 1 | Compound 1 | 4.6 | 44.1 | 30.1 | Green |
| Example 2 | Compound 2 | 4.8 | 42.5 | 27.8 | Green |
| Example 3 | Compound 3 | 5.1 | 46.2 | 28.4 | Green |
| Example 4 | Compound 4 | 5.8 | 48.5 | 26.3 | Green |
| Example 5 | Compound 22 | 4.9 | 38.5 | 24.7 | Green |
| Example 6 | Compound 91 | 5.3 | 35.9 | 21.3 | Green |
| Example 7 | Compound 95 | 4.7 | 40.2 | 26.9 | Green |
| Example 8 | Compound 130 | 5.3 | 33.7 | 20.0 | Green |
| Example 9 | Compound 151 | 5.9 | 41.1 | 21.9 | Green |
| Example 10 | Compound 152 | 6.0 | 37.0 | 19.4 | Green |
| Example 11 | Compound 158 | 4.6 | 41.0 | 28.0 | Green |
| Example 12 | Compound 166 | 4.8 | 44.5 | 29.1 | Green |
| Example 13 | Compound 173 | 5.0 | 34.4 | 21.6 | Green |
| Example 14 | Compound 186 | 5.2 | 37.8 | 22.8 | Green |

TABLE 4-continued

| | Host | Driving voltage (V) | Current efficiency (cd/A) | Power efficiency (lm/W) | Color |
|---|---|---|---|---|---|
| Example 15 | Compound 191 | 5.6 | 40.3 | 22.6 | Green |
| Example 16 | Compound 196 | 4.8 | 32.1 | 21.0 | Green |
| Example 17 | Compound 262 | 4.7 | 34.5 | 23.0 | Green |
| Comparative Example A | Compound A | 6.2 | 17.5 | 8.9 | Green |
| Comparative Example B | Compound B | 4.4 | 22.1 | 15.8 | Green |

TABLE 4-continued

| | Host | Driving voltage (V) | Current efficiency (cd/A) | Power efficiency (lm/W) | Color |
|---|---|---|---|---|---|
| Comparative Example C | Compound C | 5.0 | 25.0 | 15.7 | Green |

From Table 4 and FIG. 6, it was confirmed that the organic light-emitting devices of Examples 1 to 17 had a better emission efficiency than the organic light-emitting devices of Comparative Examples 1 to 3.

The carbazole compound according to embodiments has excellent electric characteristics and thermal stability. Accordingly, an organic light-emitting device including the carbazole compound may have a low driving voltage, high efficiency, high brightness, and a long lifespan.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:

1. A carbazole compound represented by Formula 1:

Formula 1

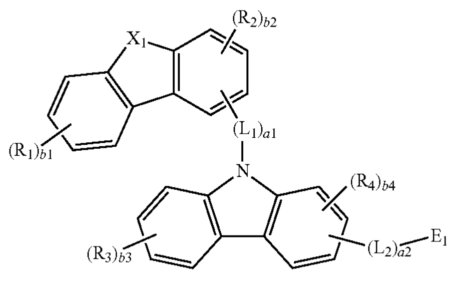

wherein in Formula 1, $X_1$ is selected from N-[$(L_{11})_{a11}$-$(R_{11})_{b11}$], S, O, S(=O), S(=O)$_2$, C($R_{12}$)($R_{13}$), and Si($R_{12}$)($R_{13}$);

$L_1$, $L_2$, and $L_{11}$ are each independently selected from a substituted or unsubstituted $C_1$-$C_{60}$ alkylene group, a substituted or unsubstituted $C_2$-$C_{60}$ alkenylene group, a substituted or unsubstituted $C_2$-$C_{60}$ alkynylene group, a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic hetero-condensed polycyclic group;

a1 and a2 are each independently an integer selected from 1 to 5;

a11 is an integer selected from 0 to 5;

$R_1$ is selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(=O)—O-$Q_1$, —C(=O)-$Q_2$, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; and a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group, —C(=O)—O-$Q_3$, —C(=O)-$Q_4$, a sulfonic acid group or a salt thereof, and a phosphoric acid group or a salt thereof;

$R_2$ to $R_4$ and $R_{11}$ to $R_{13}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(=O)—O-$Q_{11}$, —C(=O)-$Q_{12}$, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, and a substituted or unsubstituted monovalent non-aromatic heterocondensed polycyclic group, —N($Q_{13}$)($Q_{14}$), —Si($Q_{15}$)($Q_{16}$)($Q_{17}$), and —B($Q_{18}$)($Q_{19}$);

b1 and b3 are each independently an integer selected from 1 to 4;

b2, b4, and b11 are each independently an integer selected from 1 to 3;

$E_1$ is an electron transporting-cyclic group containing at least one nitrogen as a ring-forming atom and substituted with at least one $Ar_1$, wherein $Ar_1$ is selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, and a substituted or unsubstituted monovalent non-aromatic heterocondensed polycyclic group; and at least one substituent of the substituted $C_1$-$C_{60}$ alkylene group, the substituted $C_2$-$C_{60}$ alkenylene group, the substituted $C_2$-$C_{60}$ alkynylene group, the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic hetero-condensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, a substituted or unsubstituted $C_7$-$C_{60}$ arylalkyl group, the substituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, the substituted monovalent non-aromatic condensed polycyclic group, and the substituted monovalent non-aromatic heterocondensed polycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, a monovalent non-aromatic heterocondensed polycyclic group, —$N(Q_{21})(Q_{22})$, —$Si(Q_{23})(Q_{24})(Q_{25})$, and —$B(Q_{26})(Q_{27})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic heterocondensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic heterocondensed polycyclic group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a substituted or unsubstituted $C_7$-$C_{60}$ arylalkyl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, a monovalent non-aromatic heterocondensed polycyclic group, —$N(Q_{31})(Q_{32})$, —$Si(Q_{33})(Q_{34})(Q_{35})$, and —$B(Q_{36})(Q_{37})$; and —$N(Q_{41})(Q_{42})$, —$Si(Q_{43})(Q_{44})(Q_{45})$, and —$B(Q_{46})(Q_{47})$; wherein $Q_1$ to $Q_4$ are each independently selected from a hydrogen, a $C_1$-$C_{60}$ alkyl group, a $C_2$-$C_{60}$ alkenyl group, and a $C_2$-$C_{60}$ alkynyl group; and $Q_{11}$ to $Q_{19}$, $Q_{21}$ to $Q_{27}$, $Q_{31}$ to $Q_{37}$, and $Q_{41}$ to $Q_{47}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic heterocondensed polycyclic group.

2. The carbazole compound of claim 1, wherein $X_1$ is N-$[(L_{11})_{a11}$-$(R_{11})_{b11}]$, S, O, or $C(R_{12})(R_{13})$.

3. The carbazole compound of claim 1, wherein $L_1$, $L_2$, and $L_{11}$ are each independently selected from a $C_1$-$C_{20}$ alkylene group, a $C_2$-$C_{20}$ alkenylene group, and a $C_2$-$C_{20}$ alkynylene group;

a $C_1$-$C_{20}$ alkylene group, a $C_2$-$C_{20}$ alkenylene group, and a $C_2$-$C_{20}$ alkynylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, a oxadiazolylene group, a triazinylene group, a dibenzofuranylene group, a dibenzothiophenylene group, a benzocarbazolyl group, a dibenzocarbazolyl group, an imidazopyrimidinylene group, and an imidazopyridinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, a oxadiazolylene group, a triazinylene group, a dibenzofuranylene group, a dibenzothiophenylene group, a benzocarbazolyl group, a dibenzocarbazolyl group, an imidazopyrimidinylene group, and an imidazopyridinylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{20}$ aryl group, and a $C_2$-$C_{60}$ heteroaryl group.

4. The carbazole compound of claim 1, wherein $L_1$, $L_2$, and $L_{11}$ are each independently selected from a $C_1$-$C_{20}$ alkylene group, a $C_2$-$C_{20}$ alkenylene group, and a $C_2$-$C_{20}$ alkynylene group;

a $C_1$-$C_{20}$ alkylene group, a $C_2$-$C_{20}$ alkenylene group, and a $C_2$-$C_{20}$ alkynylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenylene group, a naphthylene group, a phenalenylene group, a phenanthrenylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group; and a phenylene group, a naphthylene group, a phenalenylene group, a phenanthrenylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group.

5. The carbazole compound of claim 1, wherein $L_1$, $L_2$, and $L_{11}$ in Formula 1 are each independently selected from a $C_1$-$C_{10}$ alkylene group, a $C_2$-$C_{10}$ alkenylene group, a $C_2$-$C_{10}$ alkynylene group, and one of Formulae 2-1 to 2-45:

Formula 2-1

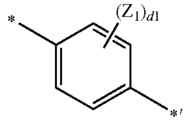

Formula 2-2

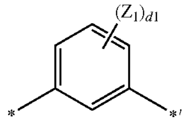

Formula 2-3
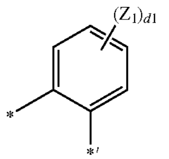
Formula 2-4
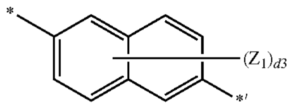
Formula 2-5
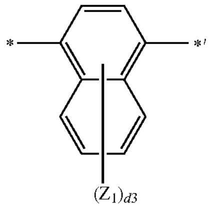
Formula 2-6
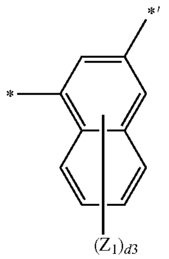
Formula 2-7
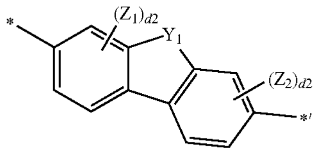
Formula 2-8
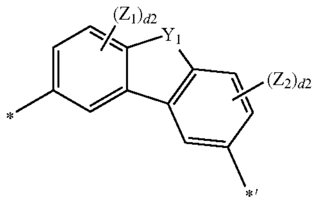
Formula 2-9
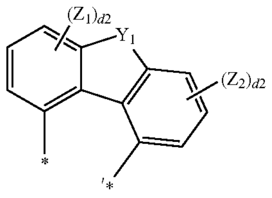
Formula 2-10
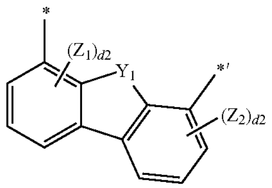
Formula 2-11
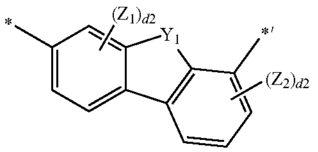
Formula 2-12
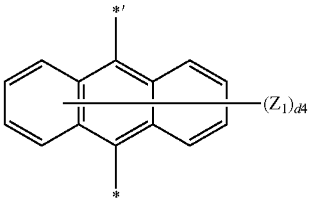
Formula 2-13
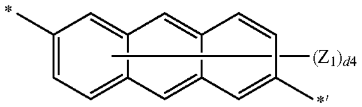
Formula 2-14
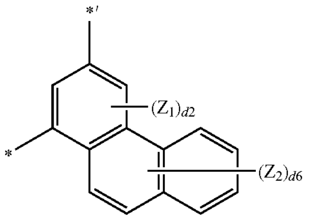
Formula 2-15
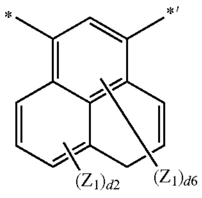
Formula 2-16
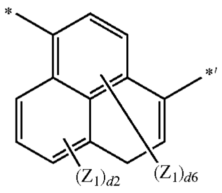
Formula 2-17
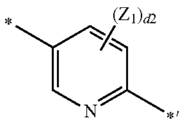
Formula 2-18
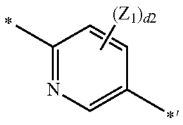
Formula 2-19
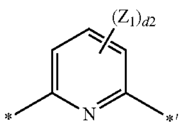

-continued
Formula 2-20
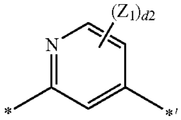
Formula 2-21
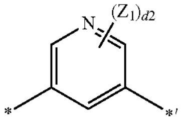
Formula 2-22
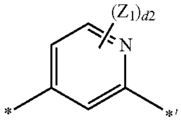
Formula 2-23
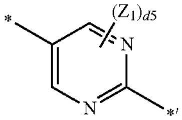
Formula 2-24
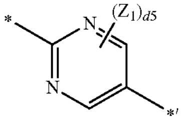
Formula 2-25
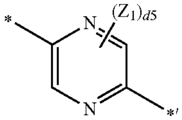
Formula 2-26
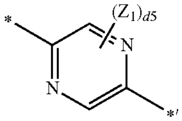
Formula 2-27
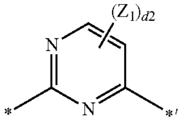
Formula 2-28
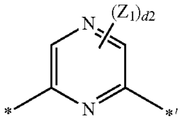
Formula 2-29
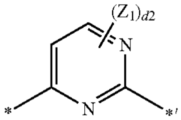
Formula 2-30
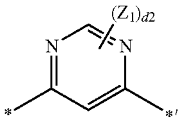
-continued
Formula 2-31
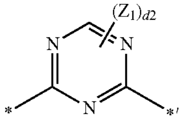
Formula 2-32
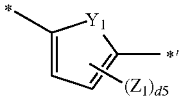
Formula 2-33
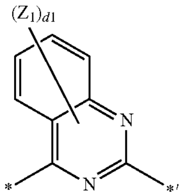
Formula 2-34
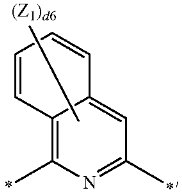
Formula 2-35
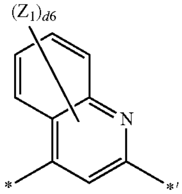
Formula 2-36
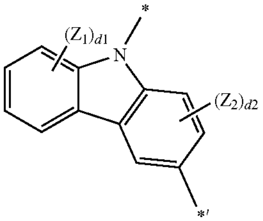
Formula 2-37
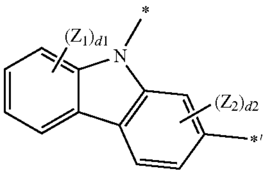
Formula 2-38
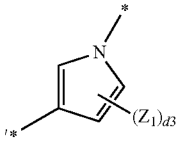

-continued

Formula 2-39

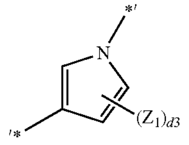

Formula 2-40

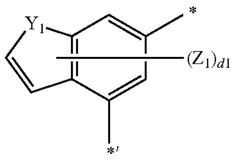

Formula 2-41

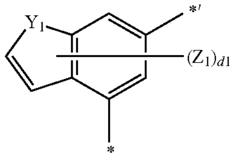

Formula 2-42

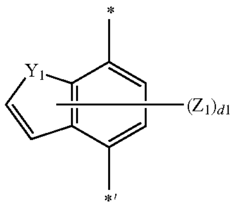

Formula 2-43

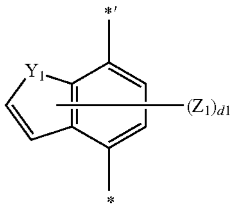

Formula 2-44

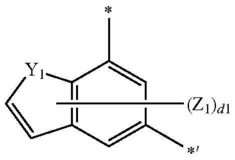

Formula 2-45

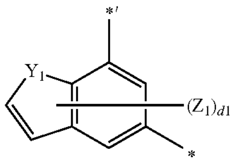

wherein in Formulae 2-1 to 2-45, $Y_1$ is O, S, $C(Z_2)(Z_3)$, $N(Z_5)$, or $Si(Z_6)(Z_7)$;

$Z_1$ to $Z_7$ in Formula 2-1 to 2-45 are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group;

d1 is an integer of 1 to 4;

d2 is an integer of 1 to 3;

d3 is an integer of 1 to 6;

d4 is an integer of 1 to 8;

d5 is 1 or 2;

d6 is an integer of 1 to 5; and each of * and *' indicates a binding site to a neighboring atom.

6. The carbazole compound of claim 1, wherein each of a1 and a2 is 1.

7. The carbazole compound of claim 1, wherein $R_1$ is selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(=O)—O-$Q_1$, —C(=O)-$Q_2$, a sulfonic acid group or a salt thereof, a phosphoric acid group or a salt thereof, a $C_1$-$C_{20}$ alkyl group, and a $C_1$-$C_{20}$ alkoxy group; and $Q_1$ and $Q_2$ are each independently selected from a hydrogen and a $C_1$-$C_{20}$ alkyl group.

8. The carbazole compound of claim 1, wherein $R_2$ to $R_4$ and $R_{11}$ to $R_{13}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(=O)—O-$Q_{11}$, —C(=O)-$Q_{12}$, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, and a $C_1$-$C_{20}$ alkoxy group;

a $C_1$-$C_{20}$ alkyl group, a $C_2$-$C_{20}$ alkenyl group, a $C_2$-$C_{20}$ alkynyl group, and a $C_1$-$C_{20}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolylene group, a triazinyl group, a dibenzofuranyl group, a dibenzothiophenyl group, a benzocarbazolyl group, a dibenzocarbazolyl group, an imidazopyridimidinyl group, and an imidazopyridinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolylene group, a triazinyl group, a dibenzofuranyl group, a dibenzothiophenyl group, a benzocarbazolyl group, a dibenzocarbazolyl group, an imidazopyridimidinyl group, and an imidazopyridinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group;

—N($Q_{13}$)($Q_{14}$) and —Si($Q_{15}$)($Q_{16}$)($Q_{17}$); wherein $Q_{11}$ to $Q_{17}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cynolinyl group, and a quinazolinyl group.

9. The carbazole compound of claim 1, wherein $R_2$ to $R_4$ and $R_{11}$ to $R_{13}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(═O)—O-$Q_{11}$, —C(═O)-$Q_{12}$, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, and a $C_1$-$C_{20}$ alkoxy group;

a phenyl group, a naphthyl group, a pyridinyl group, and a naphthyridinyl group;

a phenyl group, a naphthyl group, a pyridinyl group, and a naphthyridinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group; and —Si($Q_{15}$)($Q_{16}$)($Q_{17}$), wherein $Q_{11}$, $Q_{12}$, and $Q_{15}$ to $Q_{17}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cynolinyl group, and a quinazolinyl group.

10. The carbazole compound of claim 1, wherein each of $R_1$ to $R_4$ is a hydrogen.

11. The carbazole compound of claim 1, wherein $E_1$ is selected from a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cynolinyl group, a phenanthridinyl group, an acridinyl group, a phenanthrolinyl group, a phenazinyl group, a benzoimidazolyl group, a thiazolyl group, an isothiazolyl group, a benzothiazolyl group, an isooxazolyl group, an oxazolyl group, a triazolyl group, a tetrazolyl group, an oxadiazolyl group, a triazinyl group, an imidazopyrimidinyl group, and an imidazopyridinyl group; and a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cynolinyl group, a phenanthridinyl group, an acridinyl group, a phenanthrolinyl group, a phenazinyl group, a benzoimidazolyl group, a thiazolyl group, an isothiazolyl group, a benzothiazolyl group, an isooxazolyl group, an oxazolyl group, a triazolyl group, a tetrazolyl group, an oxadiazolyl group, a triazinyl group, an imidazopyrimidinyl group, and an imidazopyridinyl group, each substituted with at least one $Ar_1$, wherein $Ar_1$ is selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cynolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isooxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolylene group, a triazinyl group, a dibenzofuranyl group, a dibenzothiophenyl group, a benzocarbazolyl group, a dibenzocarbazolyl group, an imidazopyridimidinyl group, and an imidazopyridinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, triazinyl group, a quinolinyl group, an isoquinolinyl group, a phthalazinyl group, a quinoxalinyl group, a cynolinyl group, and a quinazolinyl group.

12. The carbazole compound of claim 1, wherein $E_1$ is selected from Formulae 11-1 to 11-21:

Formula 11-1

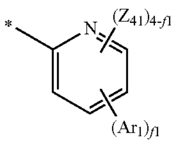

Formula 11-2

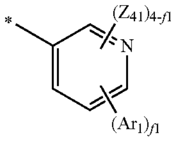

Formula 11-3

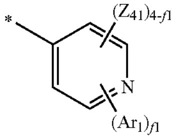

Formula 11-4

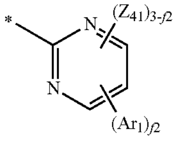

Formula 11-5

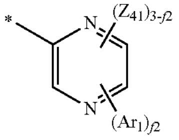

Formula 11-6

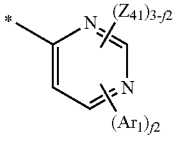

Formula 11-7

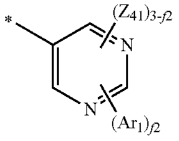

-continued

Formula 11-8

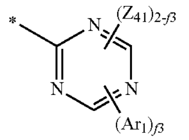

Formula 11-9

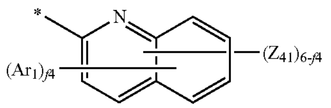

Formula 11-10

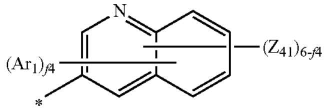

Formula 11-11

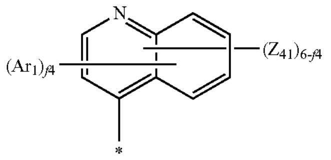

Formula 11-12

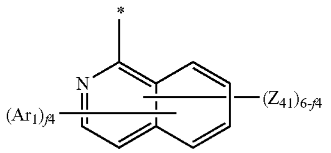

Formula 11-13

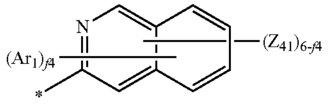

Formula 11-14

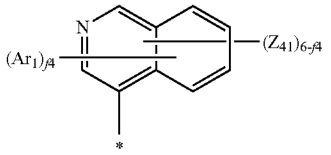

Formula 11-15

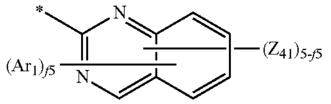

Formula 11-16

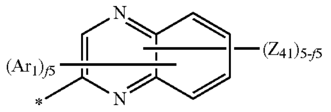

Formula 11-17

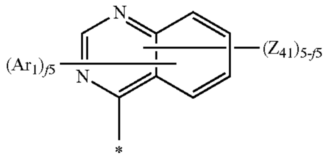

-continued

Formula 11-18

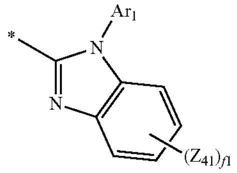

Formula 11-19

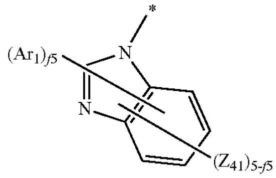

Formula 11-20

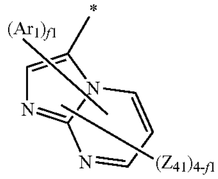

Formula 11-21

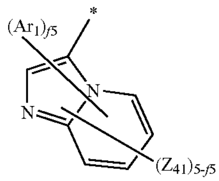

wherein in Formulae 11-1 to 11-21, $Z_{41}$ and $Z_{42}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group;

f1 is an integer of 1 to 4;

f2 is an integer of 1 to 3;

f3 is 1 or 2;

f4 is an integer of 1 to 6; and f5 is an integer of 1 to 5; and $Ar_1$ is selected from a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group.

13. The carbazole compound of claim 1, wherein the carbazole compound represented by Formula 1 is represented by any one of Formulae 1(1) to 1(4), 2(1) to 2(4), 3(1) to 3(4), and 4(1) to 4(4) below:

-continued
Formula 1(1)
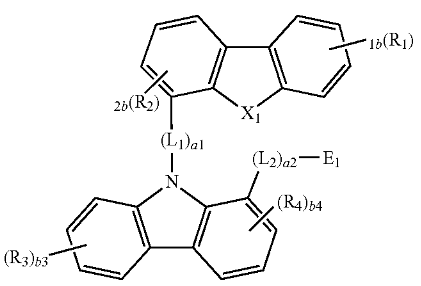
Formula 1(2)
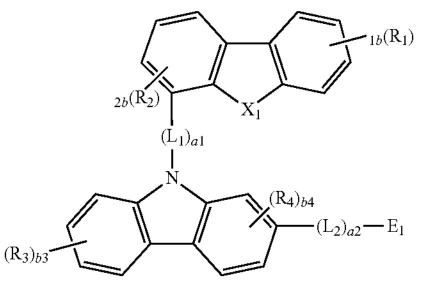
Formula 1(3)
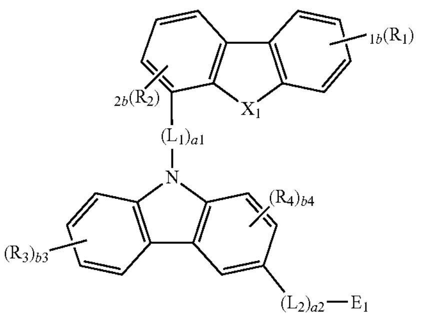
Formula 1(4)
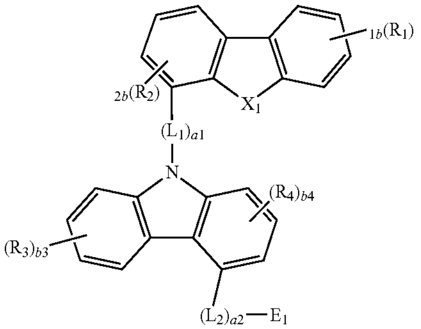
Formula 2(1)
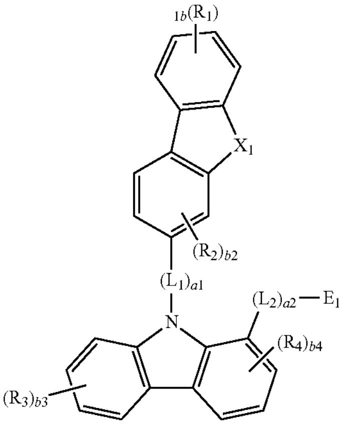
Formula 2(2)
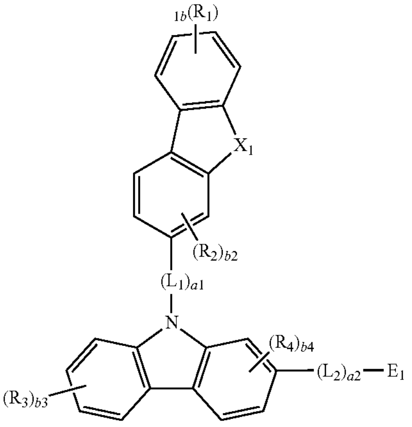
Formula 2(3)
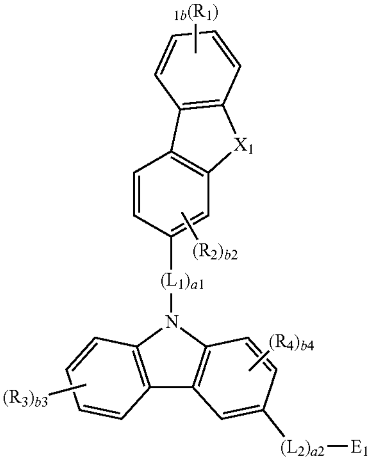

Formula 2(4)
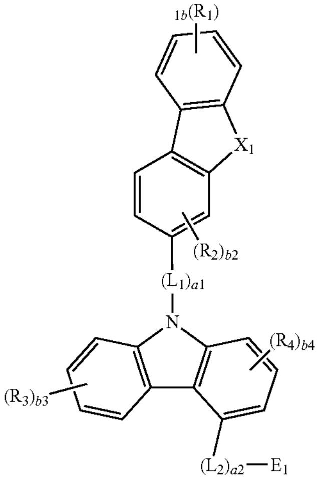
Formula 3(1)
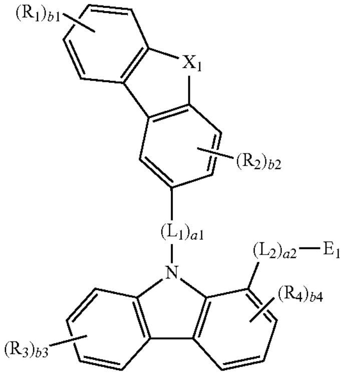
Formula 3(2)
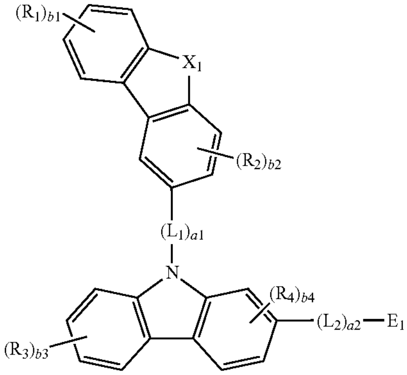
Formula 3(3)
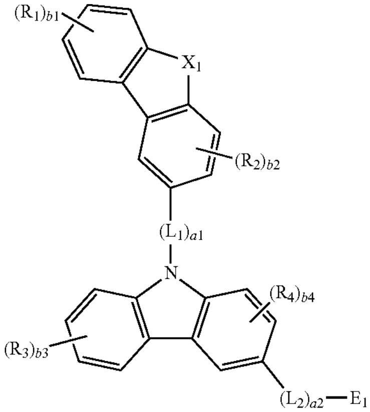
Formula 3(4)
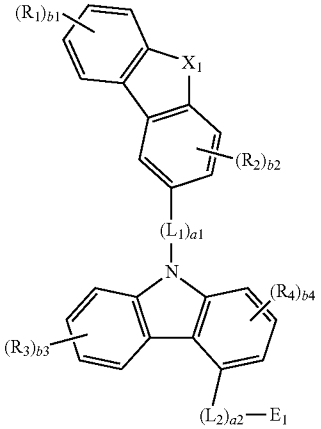
Formula 4(1)
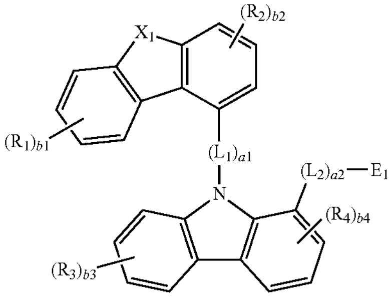
Formula 4(2)
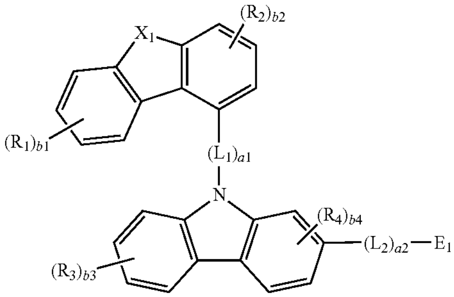
Formula 4(3)
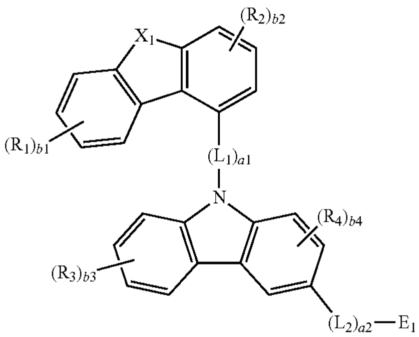

-continued

Formula 4(4)

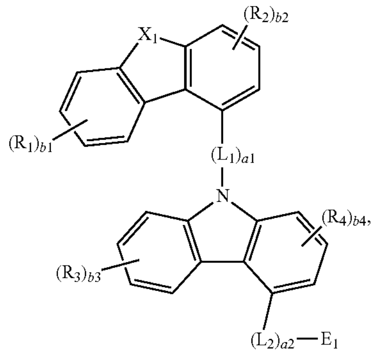

wherein $X_1$, $L_1$, $L_2$, $L_{11}$, $R_1$ to $R_4$, $R_{11}$ to $R_{13}$, a1, a2, a11, b1, b2, b3, b4, b11, and $E_1$ in Formulae 1(1) to 1(4), 2(1) to 2(4), 3(1) to 3(4), and 4(1) to 4(4) are as defined in claim 1.

14. The carbazole compound of claim 1, wherein the carbazole compound is represented by one of Formulae 1A, 1B, 1C, and 1D below:

Formula 1A

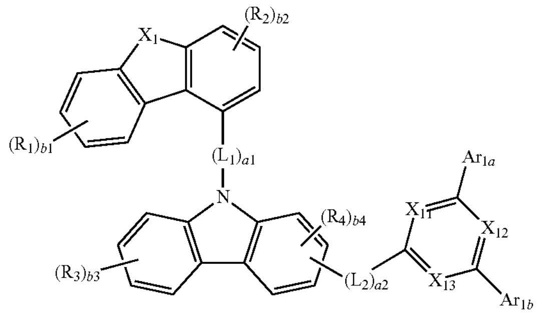

Formula 1B

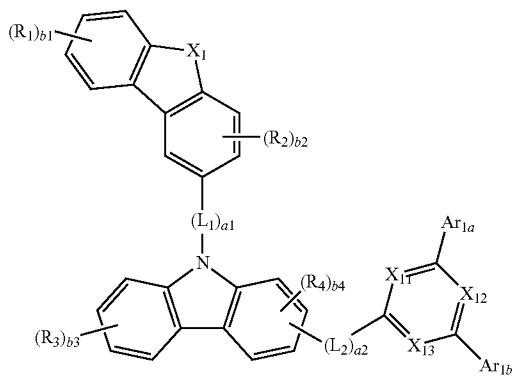

-continued

Formula 1C

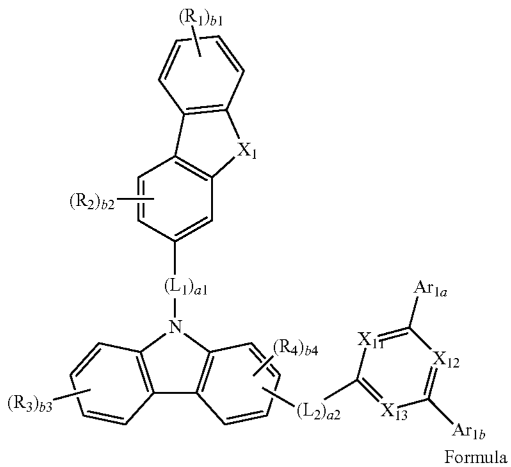

Formula 1D

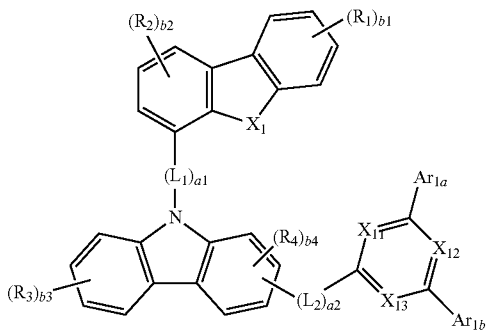

wherein in Formulae 1A, 1B, 1C, and 1D, $X_1$, $L_1$, $L_2$, $L_{11}$, $R_1$ to $R_4$, $R_{11}$ to $R_{13}$, a1, a2, a11, b1, b2, b3, b4, and b11 are as defined in claim 1, $X_{11}$ is N or $C(R_{21})$, $X_{12}$ is N or $C(R_{22})$, $X_{13}$ is N or $C(R_{23})$, and at least one of $X_{11}$ to $X_{13}$ is N;

$R_{21}$ to $R_{23}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(═O)—O-$Q_{11}$, —C(═O)-$Q_{12}$, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, and a substituted or unsubstituted monovalent non-aromatic heterocondensed polycyclic group, —N($Q_{13}$)($Q_{14}$), —Si($Q_{15}$)($Q_{16}$)($Q_{17}$), and —B($Q_{18}$)($Q_{19}$); and $Ar_{1a}$ and $Ar_{1b}$ are selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, and a substituted or unsubstituted monovalent non-aromatic heterocondensed polycyclic group.

15. The carbazole compound of claim 14, wherein $L_1$, $L_2$, and $L_{11}$ are each independently selected from a $C_1$-$C_{20}$ alkylene group, a $C_2$-$C_{20}$ alkenylene group, and a $C_2$-$C_{20}$ alkynylene group;

a $C_1$-$C_{20}$ alkylene group, a $C_2$-$C_{20}$ alkenylene group, and a $C_2$-$C_{20}$ alkynylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenylene group, a naphthylene group, a phenalenylene group, a phenanthrenylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group; and a phenylene group, a naphthylene group, a phenalenylene group, a phenanthrenylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group;

a1 and a2 are each independently 1 or 2;

a11 is 0 or 1;

$R_1$ is selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(═O)—O-$Q_1$, —C(═O)-$Q_2$, a sulfonic acid group or a salt thereof, a phosphoric acid group or a salt thereof, a $C_1$-$C_{20}$ alkyl group, and a $C_1$-$C_{20}$ alkoxy group, and $Q_1$ and $Q_2$ are each independently selected from a hydrogen and a $C_1$-$C_{20}$ alkyl group;

$R_2$ to $R_4$, $R_{11}$ to $R_{13}$, and $R_{21}$ to $R_{23}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(═O)—O-$Q_{11}$, —C(═O)-$Q_{12}$, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, and a $C_1$-$C_{20}$ alkoxy group;

a phenyl group, a naphthyl group, a pyridinyl group, and a naphthyridinyl group;

a phenyl group, a naphthyl group, a pyridinyl group, and a naphthyridinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group; and —Si($Q_{15}$)($Q_{16}$)($Q_{17}$), wherein $Q_{11}$, $Q_{12}$, and $Q_{15}$ to $Q_{17}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cynolinyl group, and a quinazolinyl group;

b1 and b3 are each independently an integer selected from 1 to 4;

b2, b4, and b11 are each independently an integer selected from 1 to 3; and $Ar_{1a}$ and $Ar_{1b}$ are each independently selected from a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group.

16. The carbazole compound of claim 1, wherein the carbazole compound is represented by one of Formulae 1A-1, 1B-1, 1C-1, and 1D-1:

Formula 1A-1

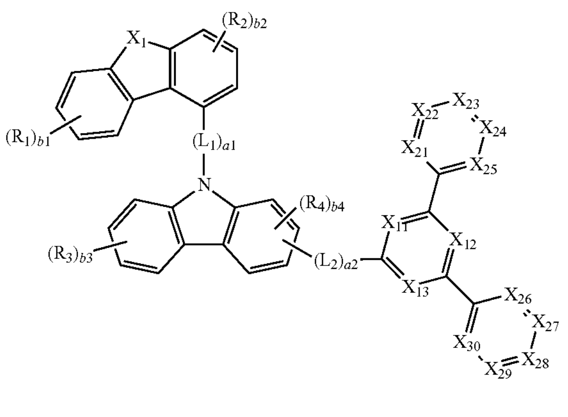

Formula 1B-1

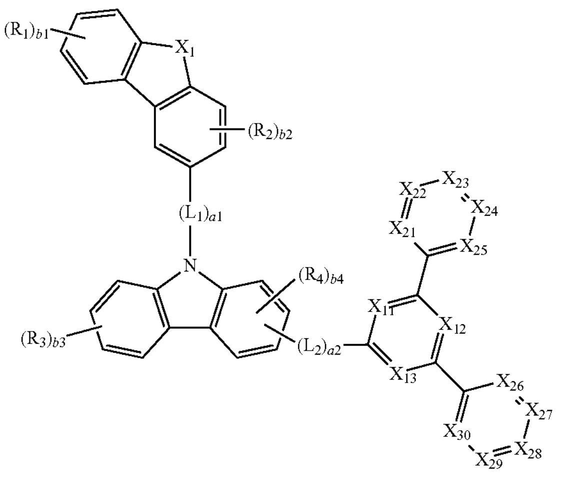

Formula 1C-1

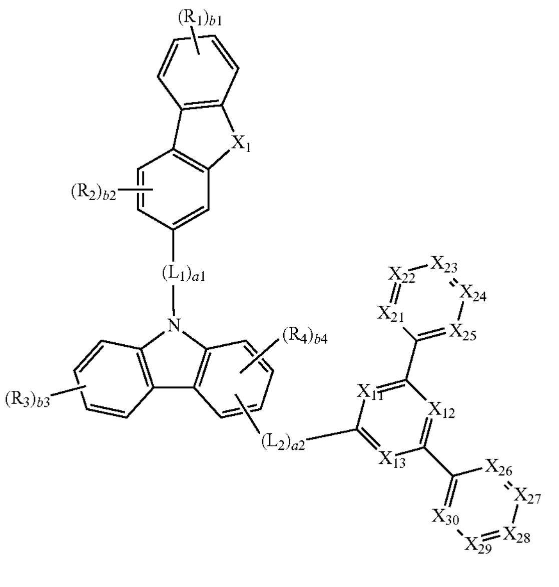

-continued

Formula 1D-1

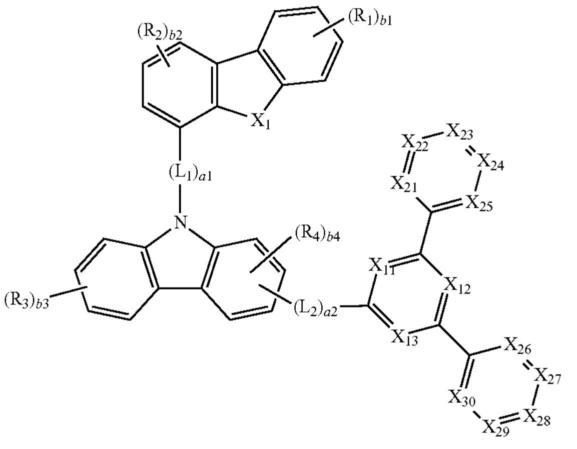

in Formulae 1A-1, 1B-1, 1C-1, and 1D-1, $X_1$, $L_1$, $L_2$, $L_{11}$, $R_1$ to $R_4$, $R_{11}$ to $R_{13}$, a1, a2, a11, b1, b2, b3, b4, and b11 are as defined in claim 1, $X_{11}$ is N or $C(R_{21})$, $X_{12}$ is N or $C(R_{22})$, $X_{13}$ is N or $C(R_{23})$, $X_{21}$ is N or $C(R_{31})$, $X_{22}$ is N or $C(R_{32})$, $X_{23}$ is N or $C(R_{33})$, $X_{24}$ is N or $C(R_{34})$, $X_{25}$ is N or $C(R_{35})$, $X_{26}$ is N or $C(R_{36})$, $X_{27}$ is N or $C(R_{37})$, $X_{28}$ is N or $C(R_{38})$, $X_{29}$ is N or $C(R_{39})$, and $X_{30}$ is N or $C(R_{40})$, wherein at least one of $X_{11}$ to $X_{13}$ is N, $R_{21}$ to $R_{23}$ and $R_{31}$ to $R_{40}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(═O)—O-$Q_{11}$, —C(═O)-$Q_{12}$, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_2$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, and a substituted or unsubstituted monovalent non-aromatic heterocondensed polycyclic group, —$N(Q_{13})(Q_{14})$, —$Si(Q_{15})(Q_{16})(Q_{17})$, and —$B(Q_{18})(Q_{19})$.

17. The carbazole compound of claim 16, wherein $L_1$, $L_2$, and $L_{11}$ are each independently selected from a $C_1$-$C_{20}$ alkylene group, a $C_2$-$C_{20}$ alkenylene group, and a $C_2$-$C_{20}$ alkynylene group;

a $C_1$-$C_{20}$ alkylene group, a $C_2$-$C_{20}$ alkenylene group, and a $C_2$-$C_{20}$ alkynylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenylene group, a naphthylene group, a phenalenylene group, a phenanthrenylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group; and a phenylene group, a naphthylene group, a phenalenylene group, a phenanthrenylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group;

a1 and a2 are each independently 1 or 2;

a11 is 0 or 1;

$R_1$ is selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(=O)—O-$Q_1$, —C(=O)-$Q_2$, a sulfonic acid group or a salt thereof, a phosphoric acid group or a salt thereof, a $C_1$-$C_{20}$ alkyl group, and a $C_1$-$C_{20}$ alkoxy group, and $Q_1$ and $Q_2$ are each independently selected from a hydrogen and a $C_1$-$C_{20}$ alkyl group;

$R_2$ to $R_4$, $R_{11}$ to $R_{13}$, $R_{21}$ to $R_{23}$, and $R_{31}$ to $R_{40}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group, —C(=O)—O-$Q_{11}$, —C(=O)-$Q_{12}$, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, and a $C_1$-$C_{20}$ alkoxy group;

a phenyl group, a naphthyl group, a pyridinyl group, and a naphthyridinyl group;

a phenyl group, a naphthyl group, a pyridinyl group, and a naphthyridinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group; and —Si($Q_{15}$)($Q_{16}$)($Q_{17}$), wherein $Q_{11}$, $Q_{12}$, and $Q_{15}$ to $Q_{17}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cynolinyl group, and a quinazolinyl group;

b1 and b3 are each independently an integer selected from 1 to 4;

b2, b4, and b11 are each independently an integer selected from 1 to 3; and $Ar_{1a}$ and $Ar_{1b}$ are each independently selected from a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cynolinyl group, and a quinazolinyl group.

18. The carbazole compound of claim 1, wherein a decomposition temperature of the carbazole compound at a vacuum degree of $10^{-8}$ torr to $10^{-3}$ torr is higher than its sublimation temperature at that vacuum degree.

19. The carbazole compound of claim 1, wherein the carbazole compound is one of Compounds 1 to 351:

1

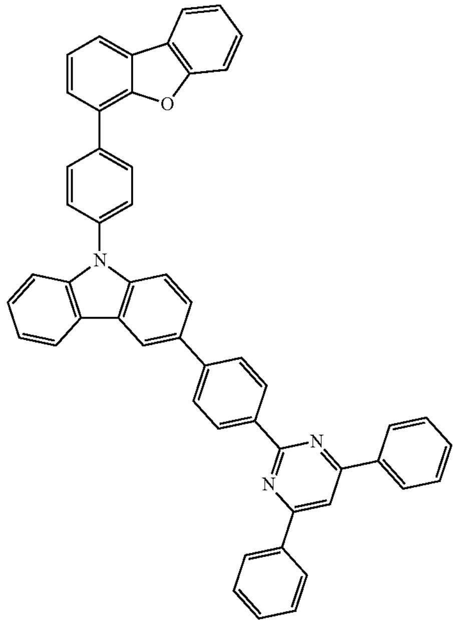

-continued
2
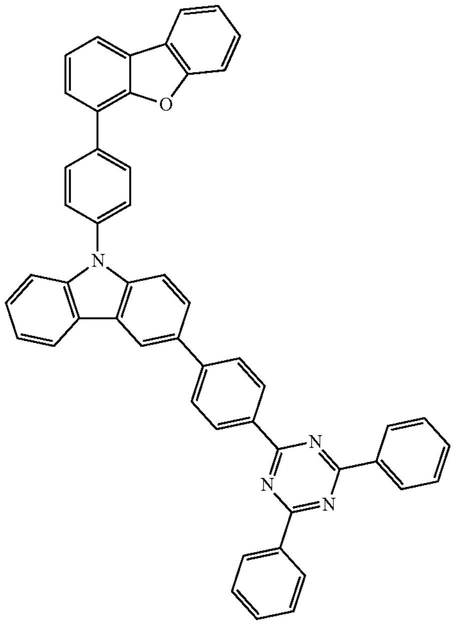
3
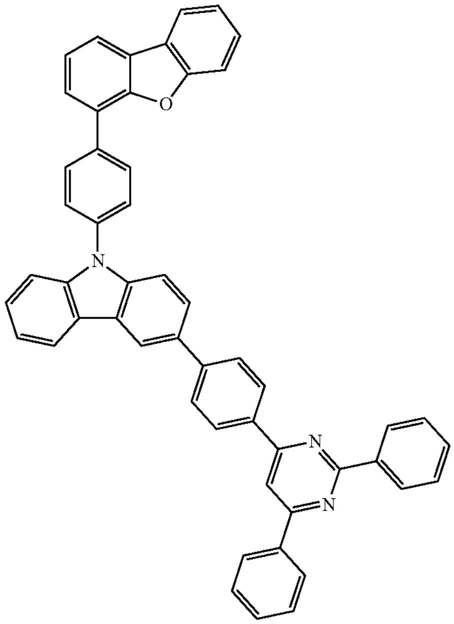
-continued
4
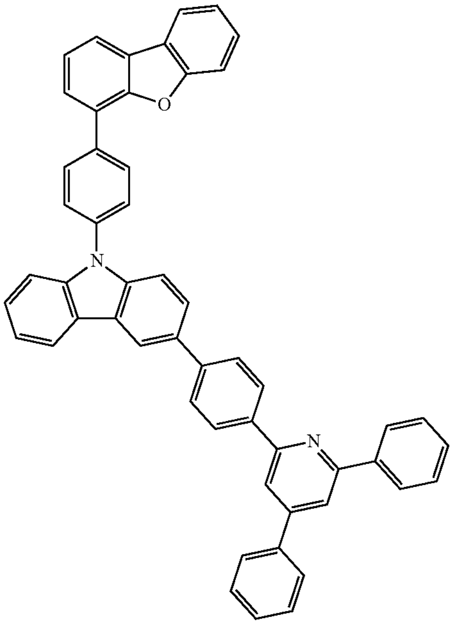
5
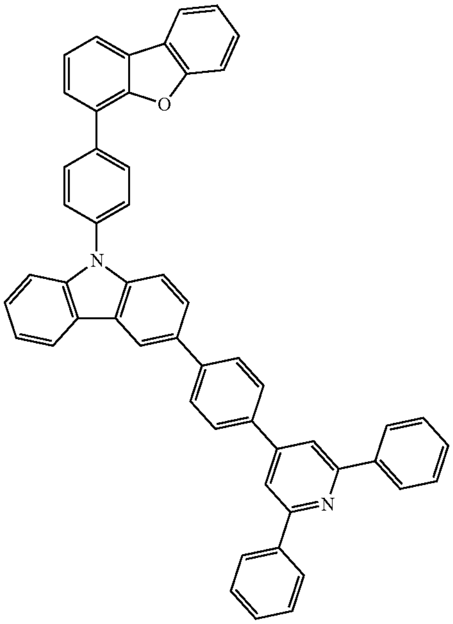

-continued
6
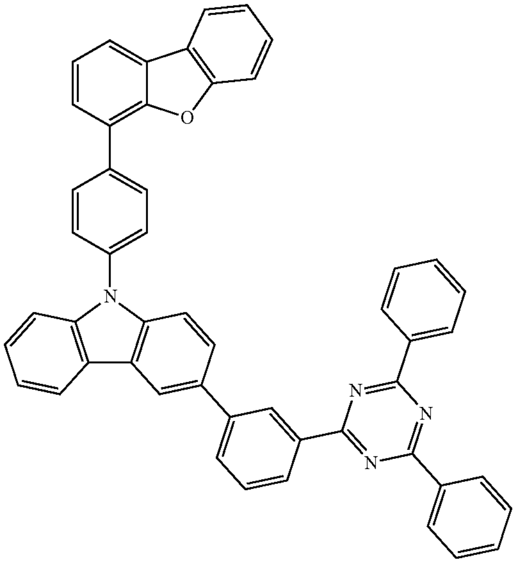
7
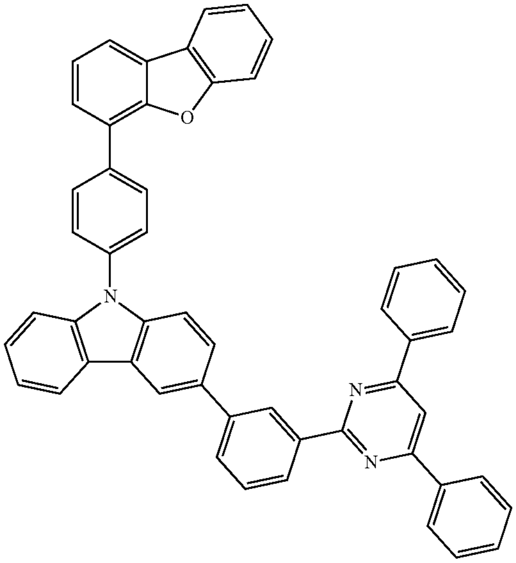
-continued
8
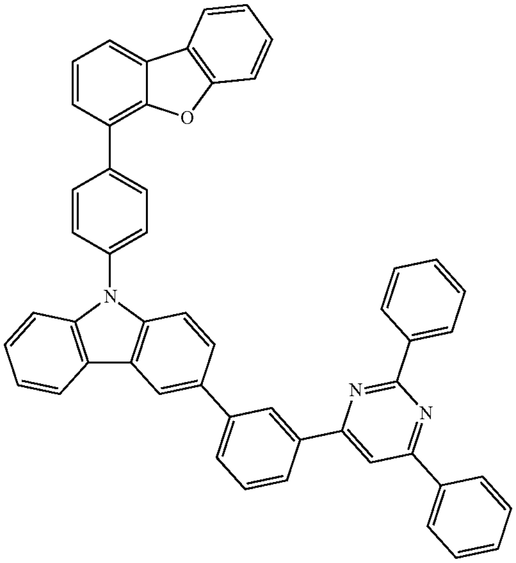
9
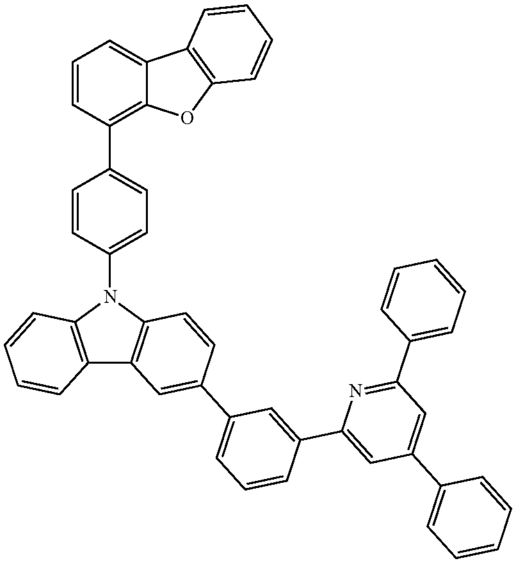

-continued
10
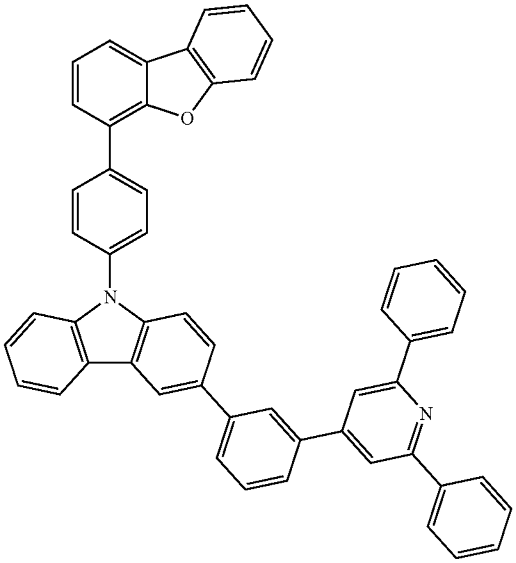
11
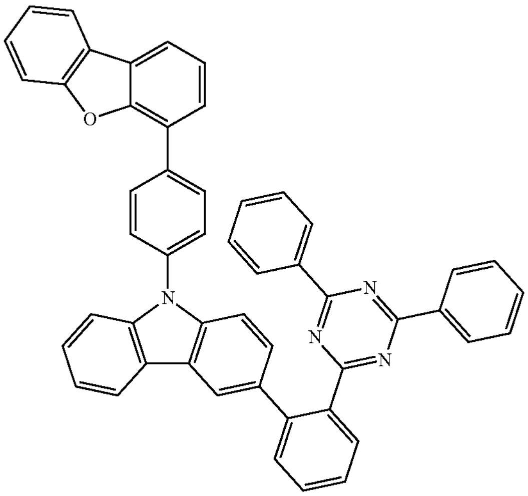
12
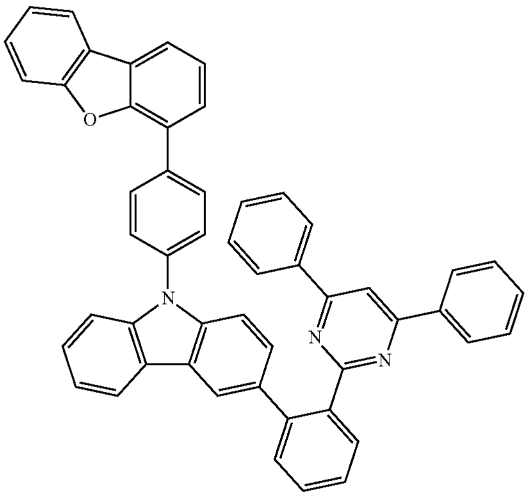
-continued
13
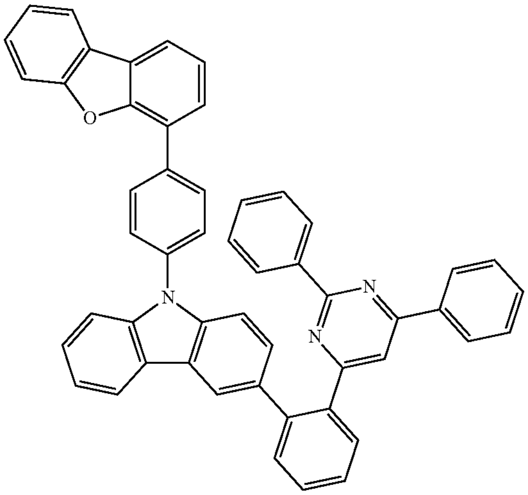
14
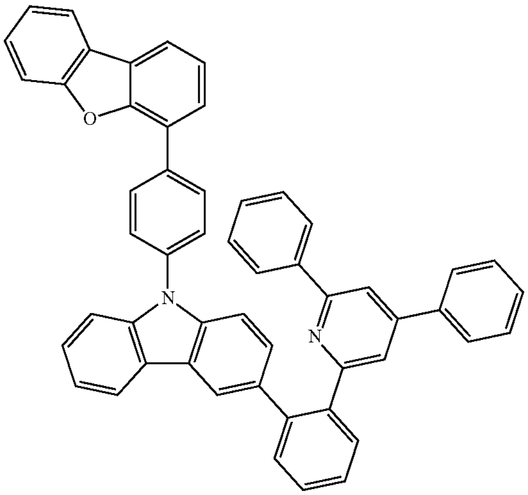
15
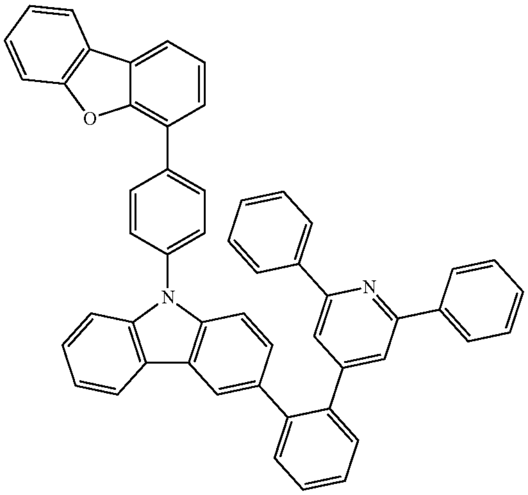

-continued
16
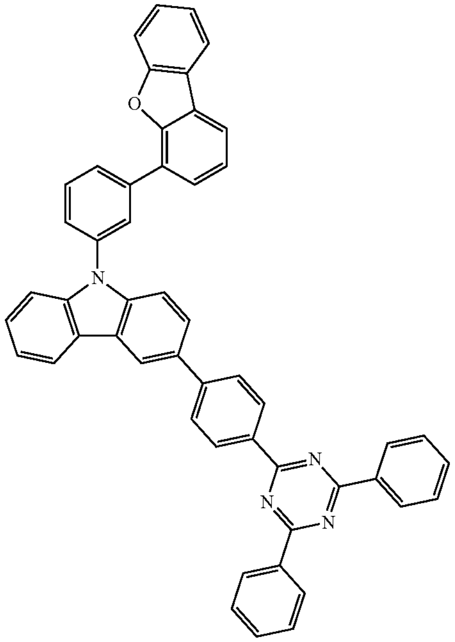
17
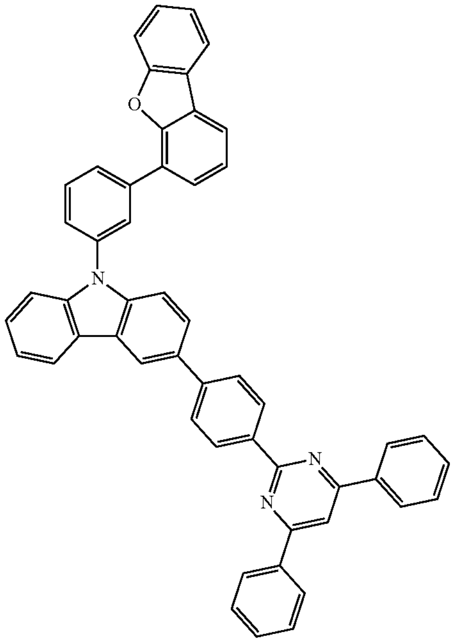
-continued
18
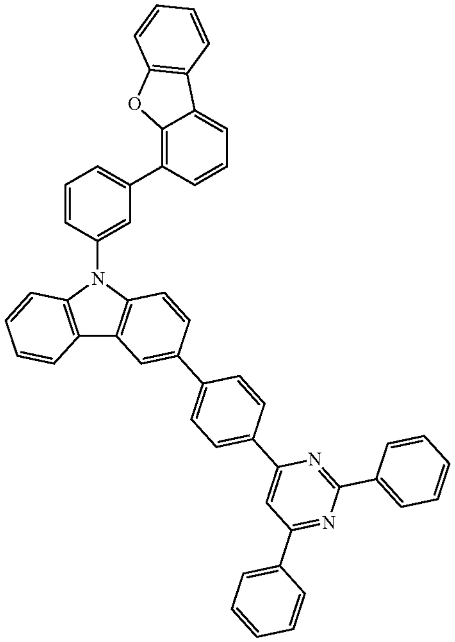
19
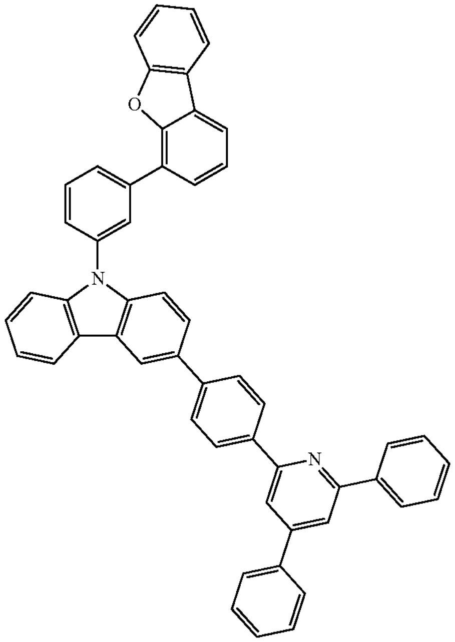

-continued
20
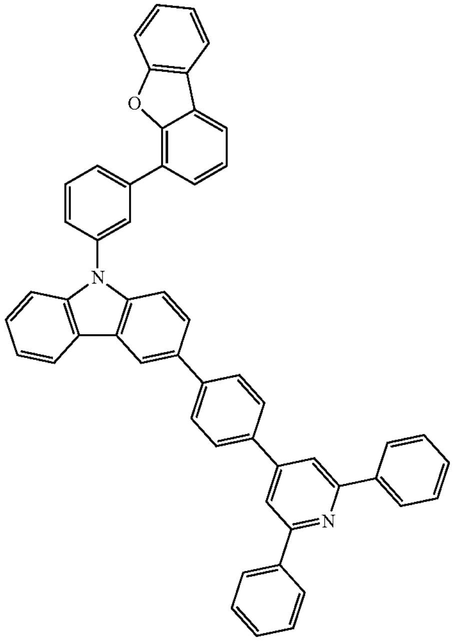
21
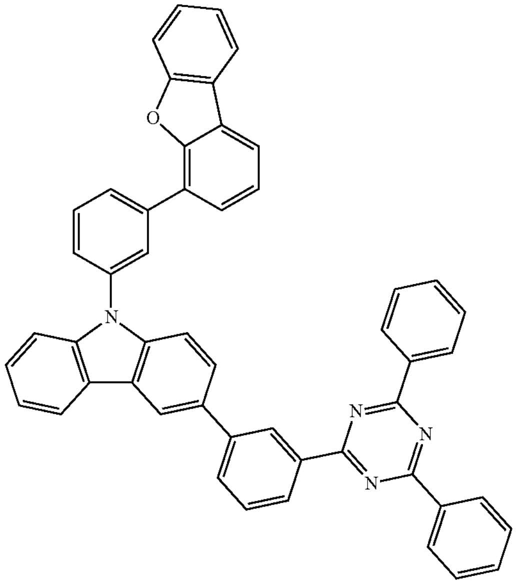
-continued
22
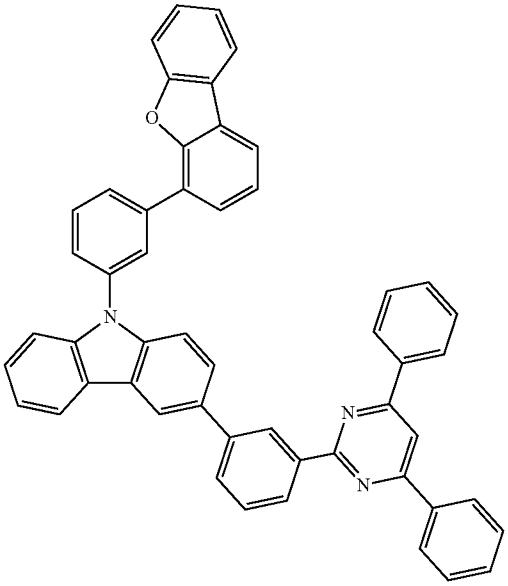
23
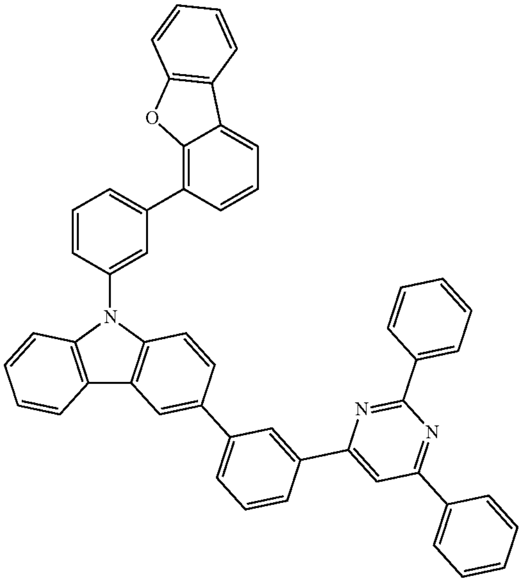

-continued
24
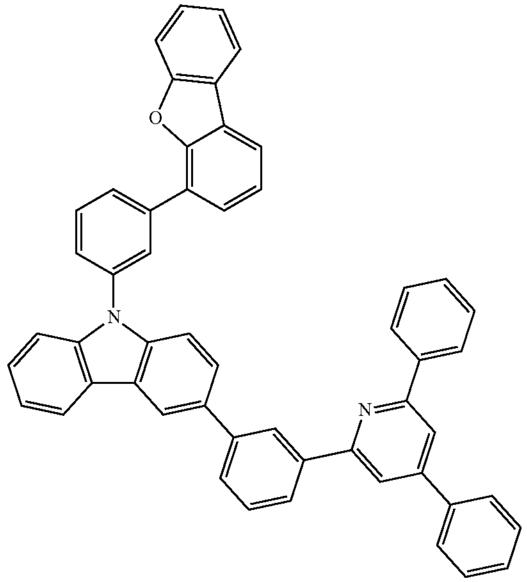
25
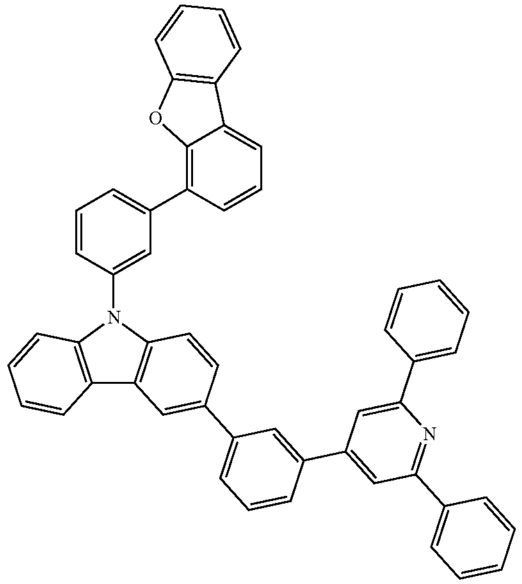
-continued
26
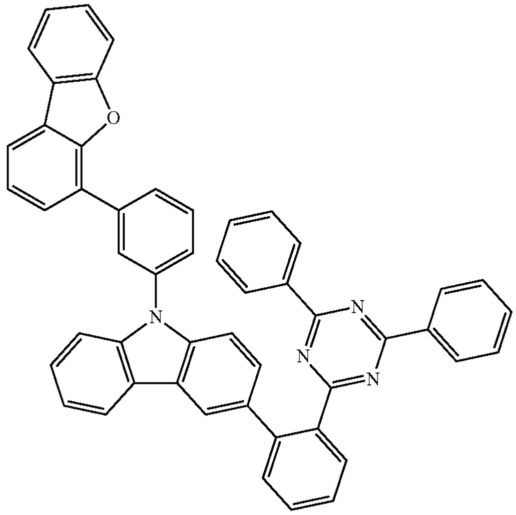
27
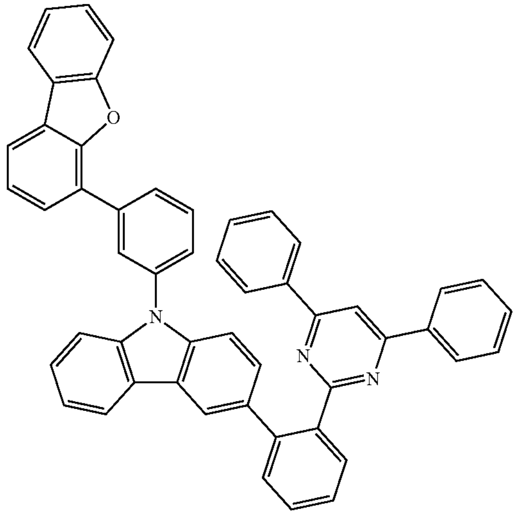
28
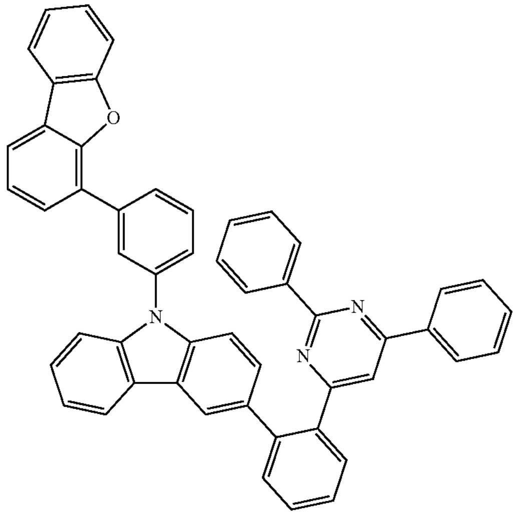

-continued
29
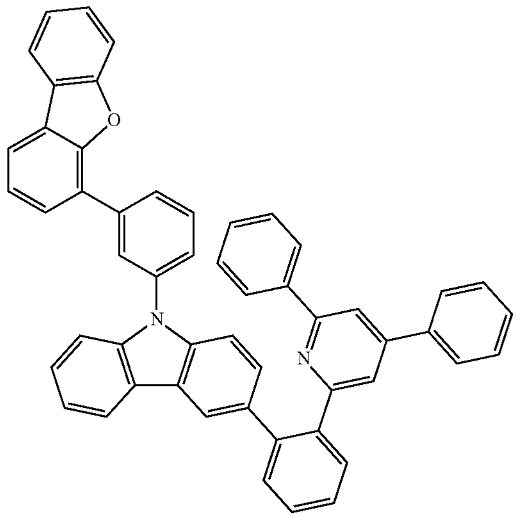
30
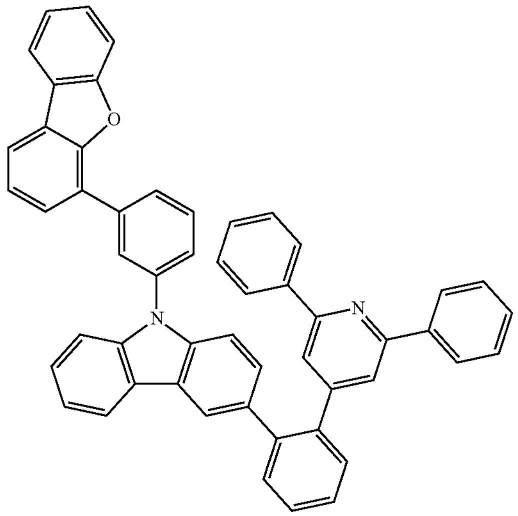
31
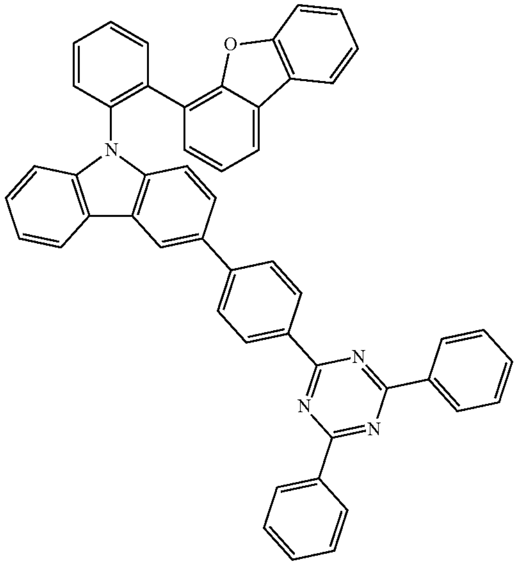
-continued
32
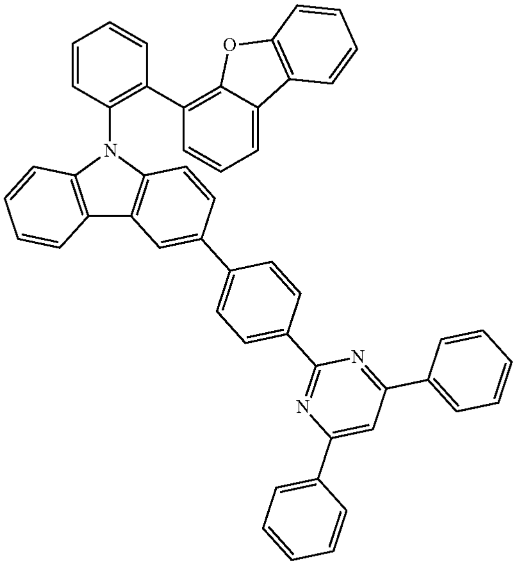
33
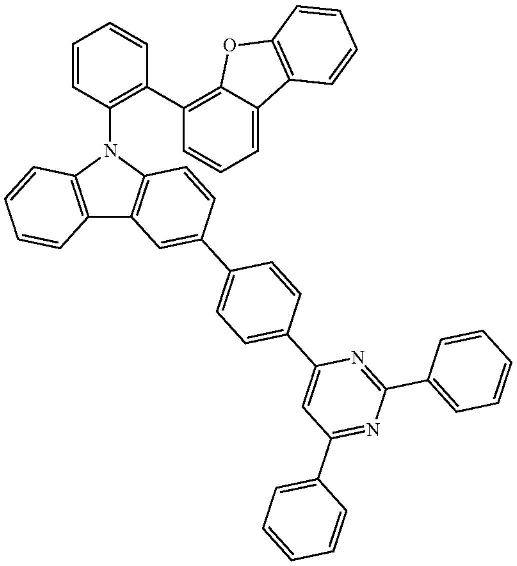

-continued
34
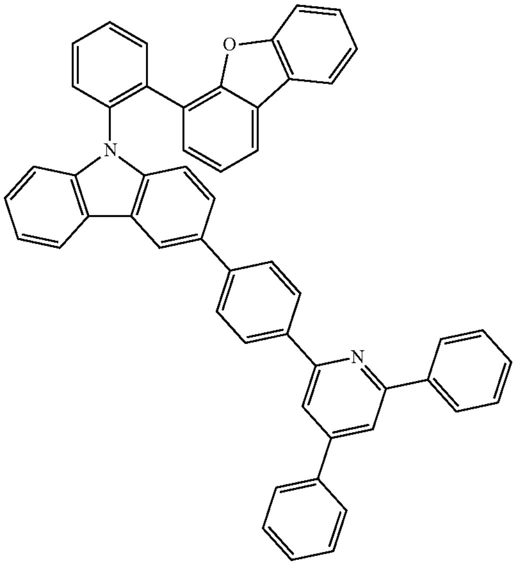
35
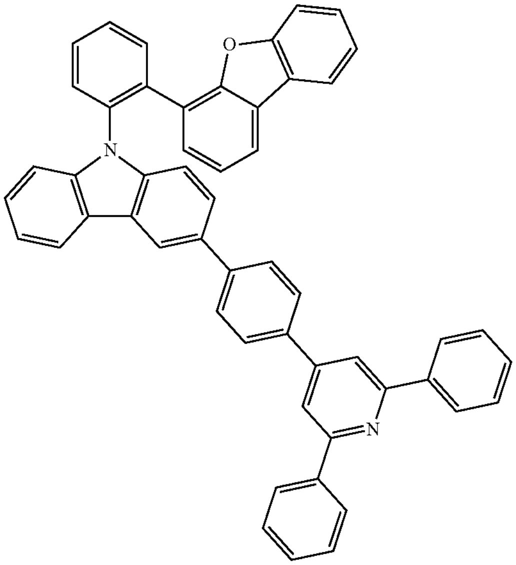
36
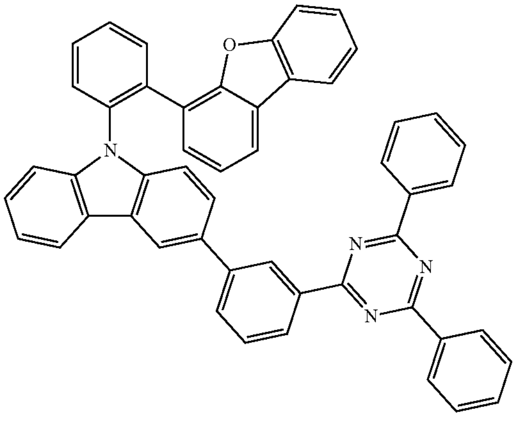
-continued
37
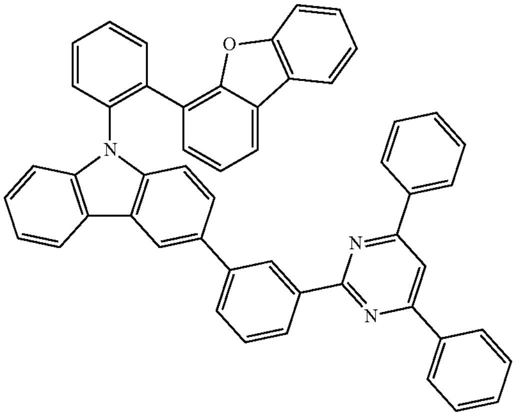
38
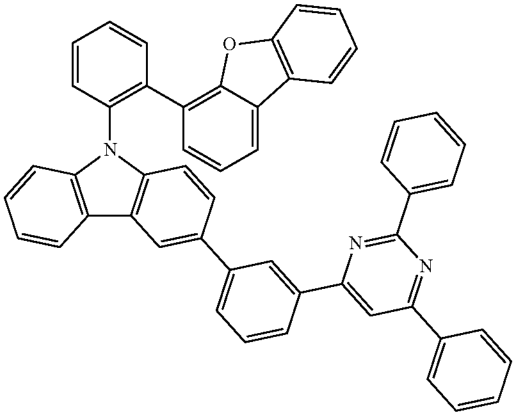
39
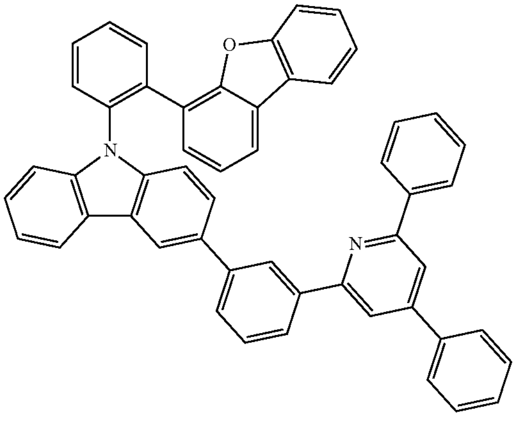

-continued
40
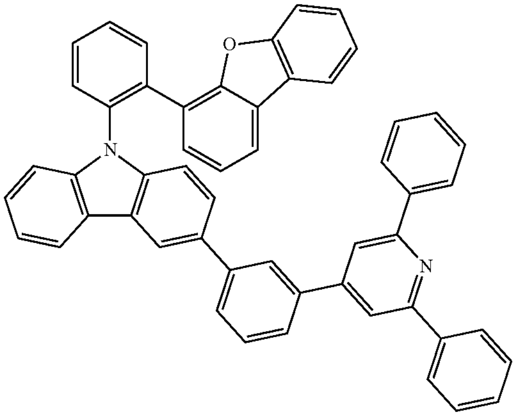
41
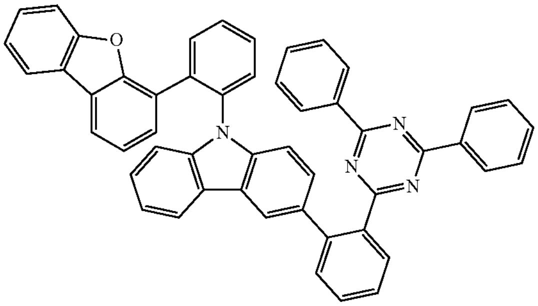
42
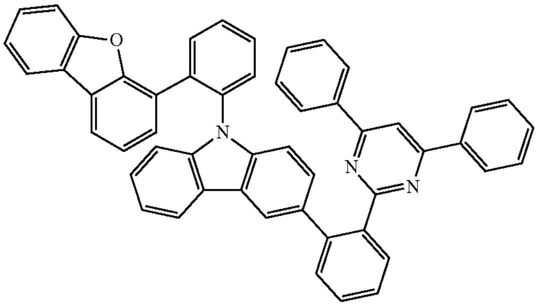
43
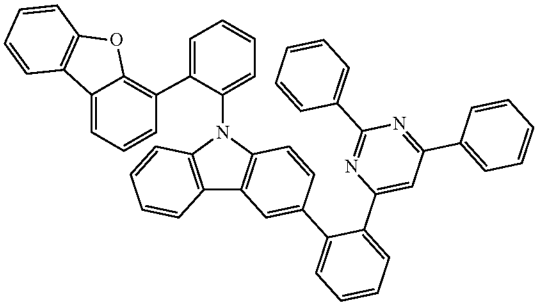
-continued
44
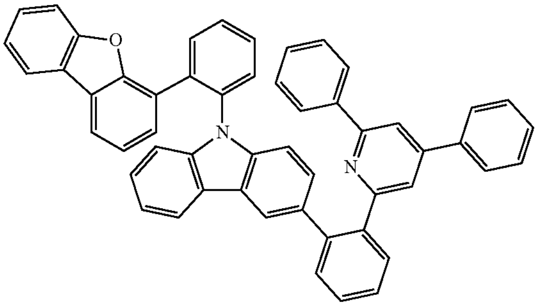
45
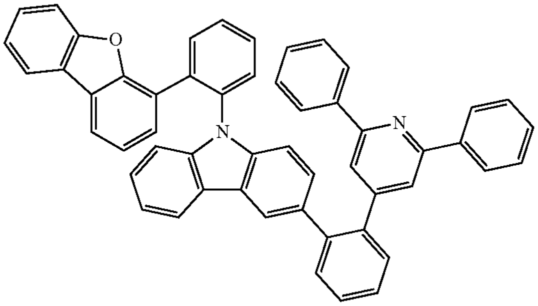
46
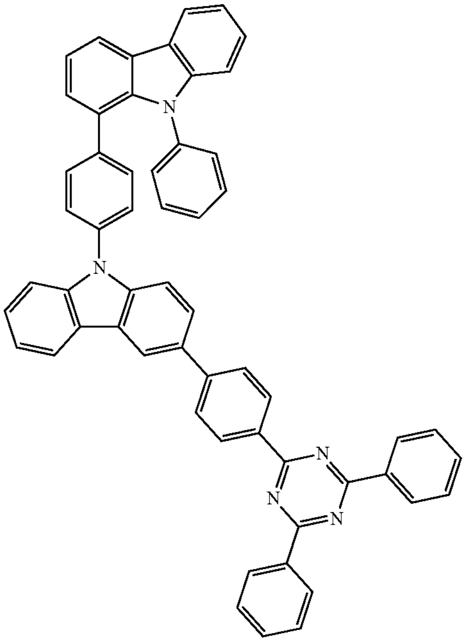

-continued
47
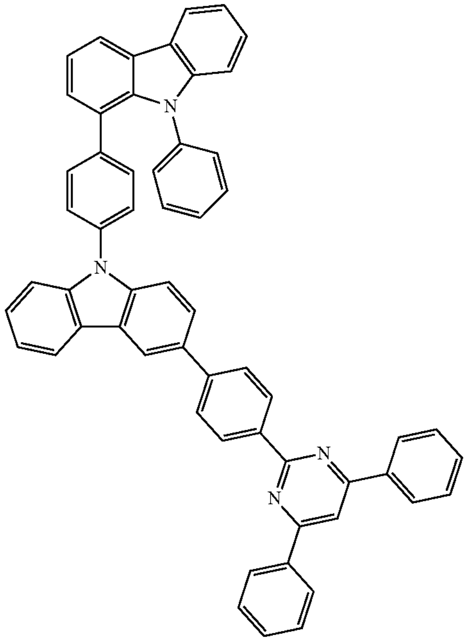
48
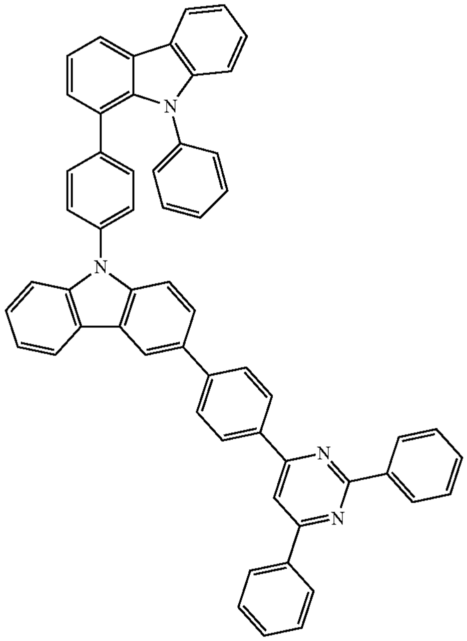
-continued
49
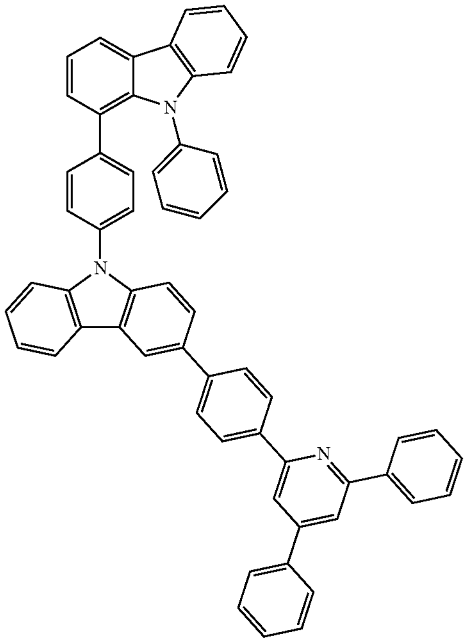
50
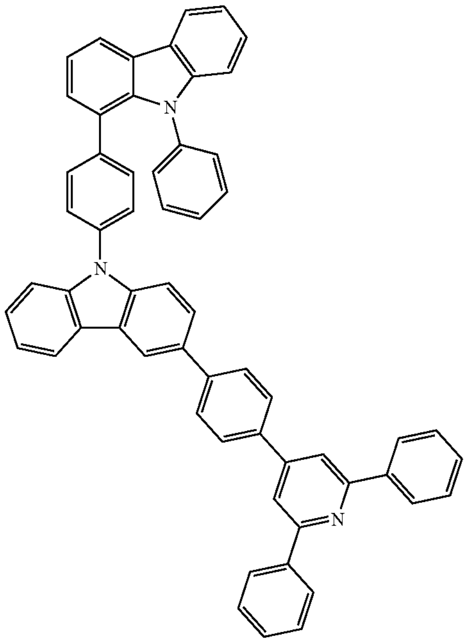

-continued
51
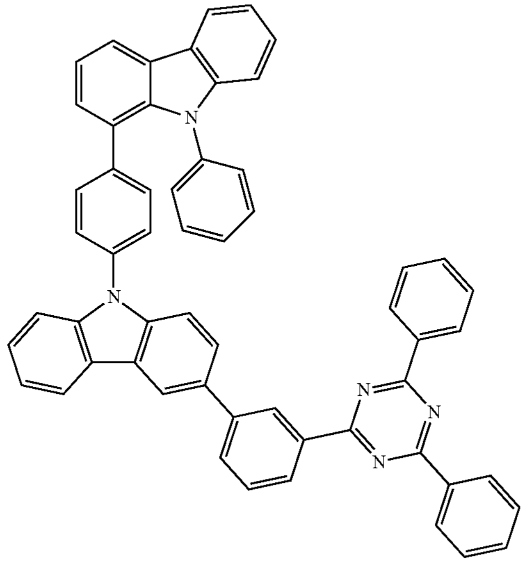
52
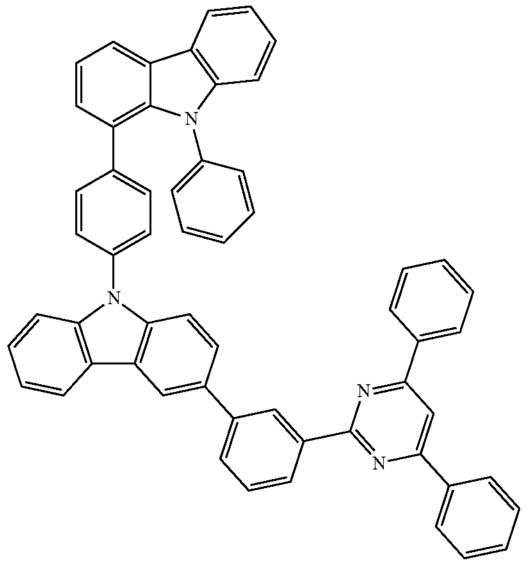
-continued
53
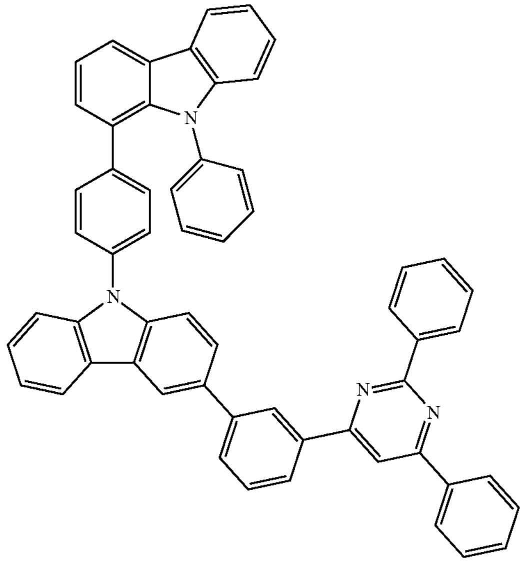
54
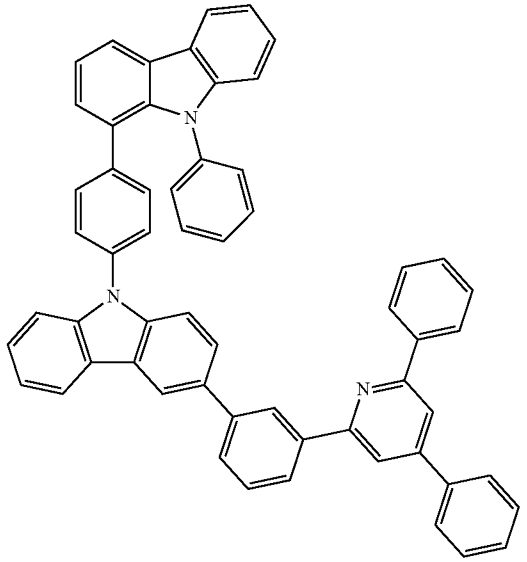

-continued
55
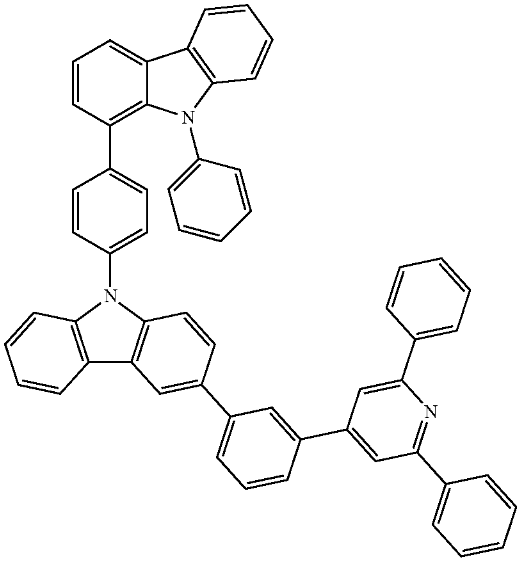
56
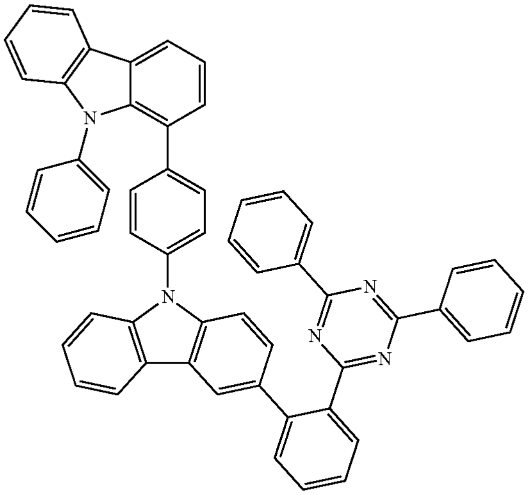
57
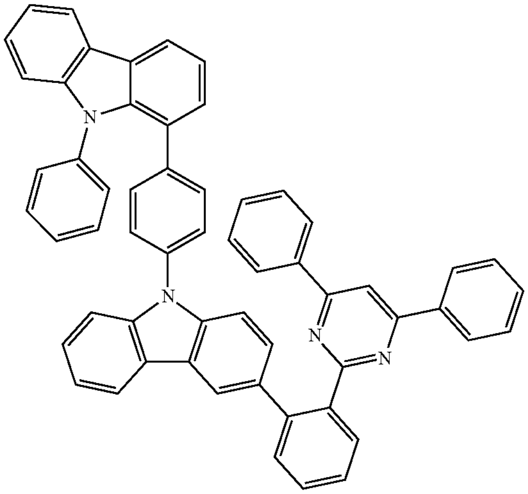
-continued
58
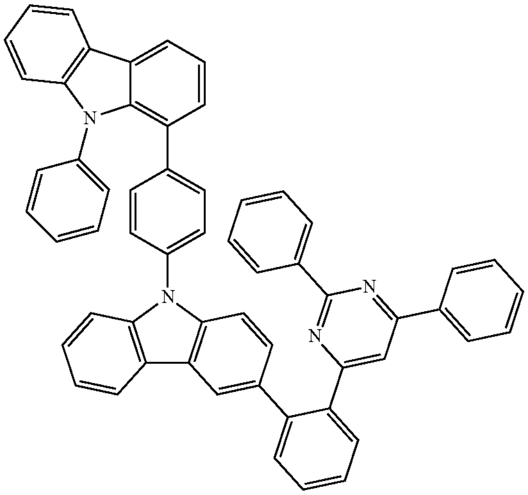
59
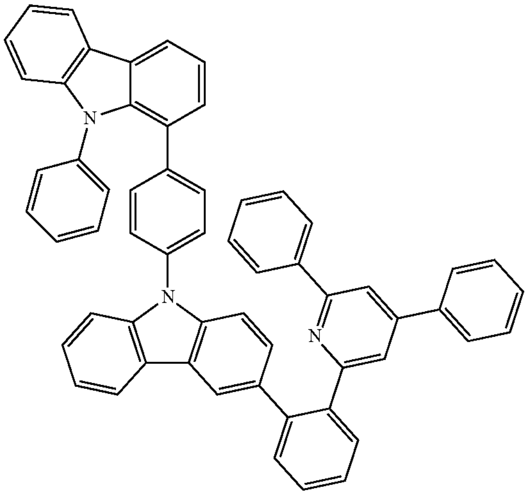
60
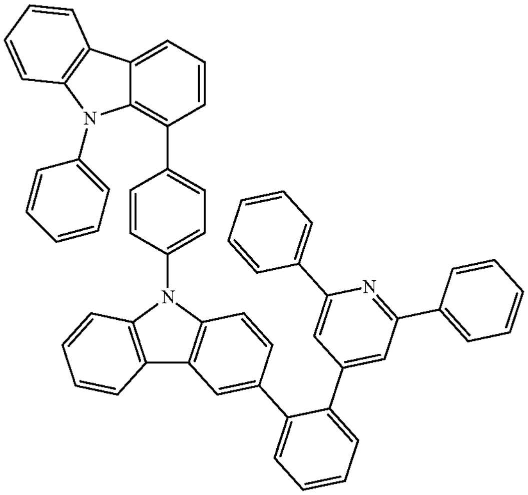

-continued
61
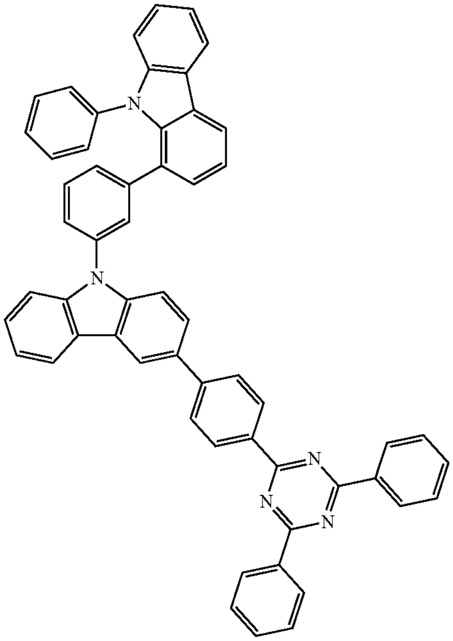
62
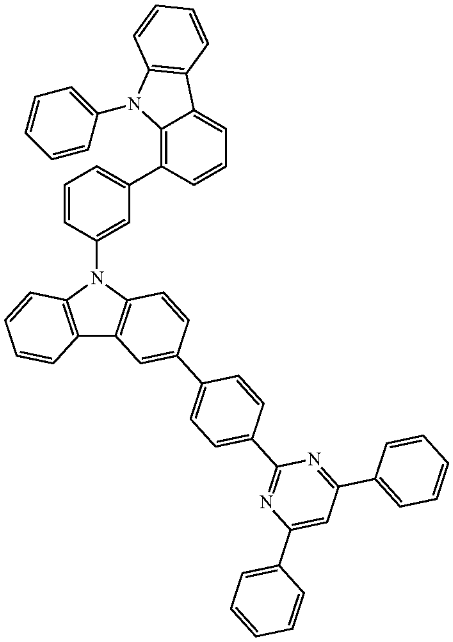
-continued
63
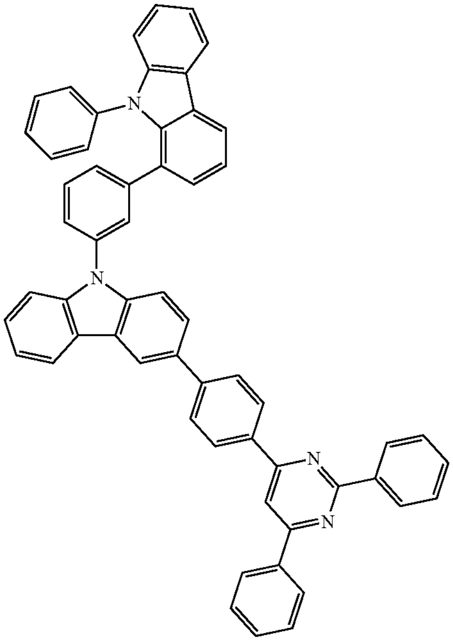
64
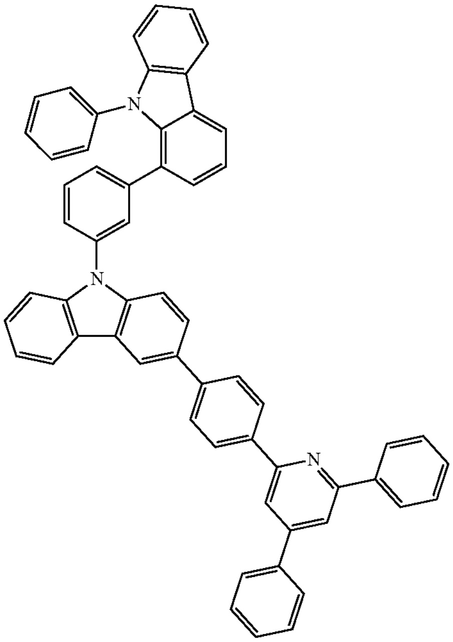

-continued
65
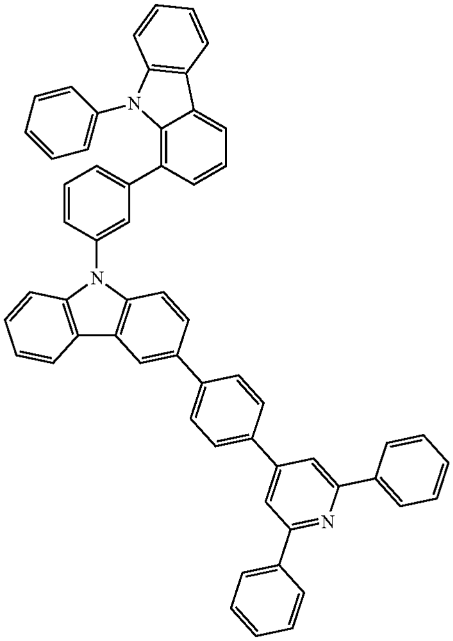
66
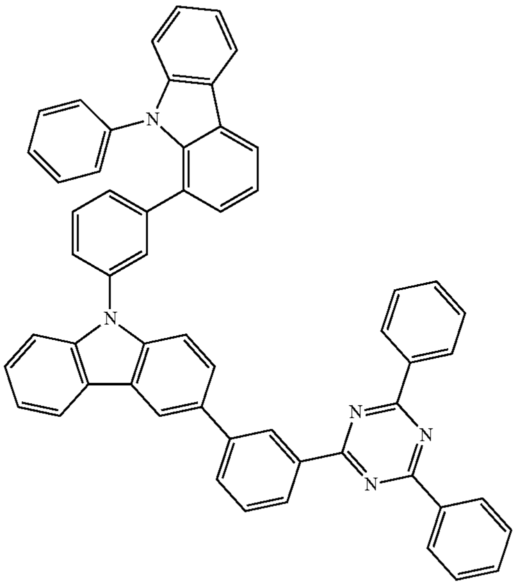
-continued
67
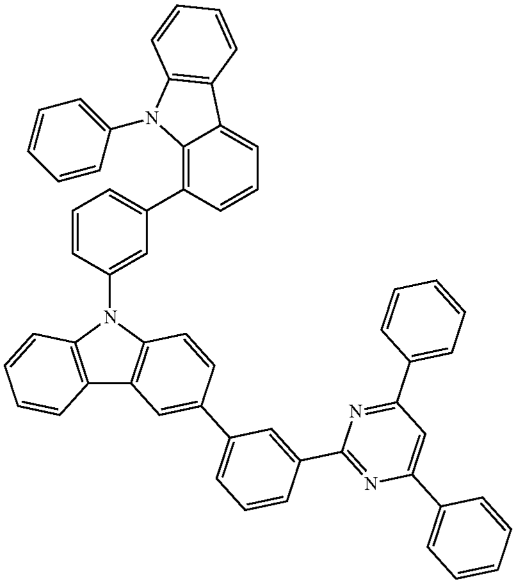
68
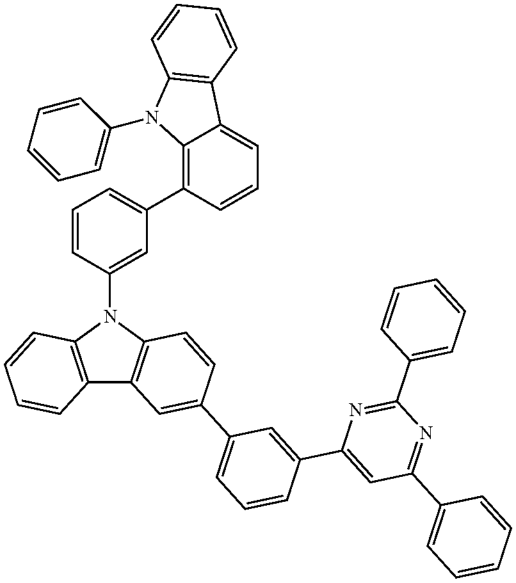

-continued
69
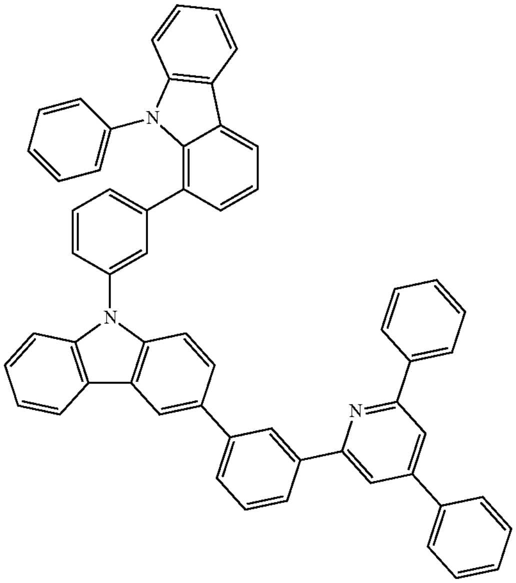
70
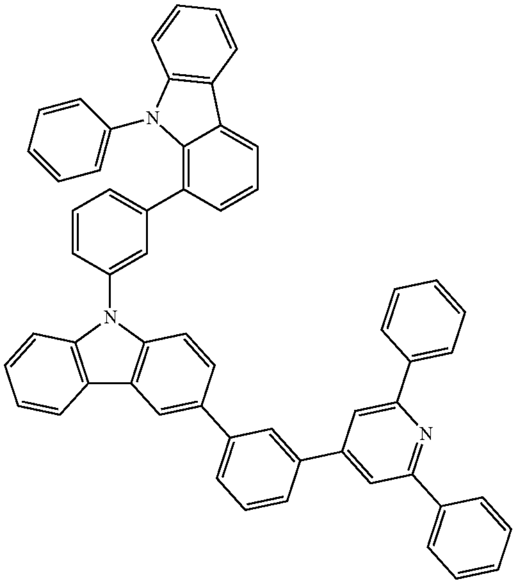
-continued
71
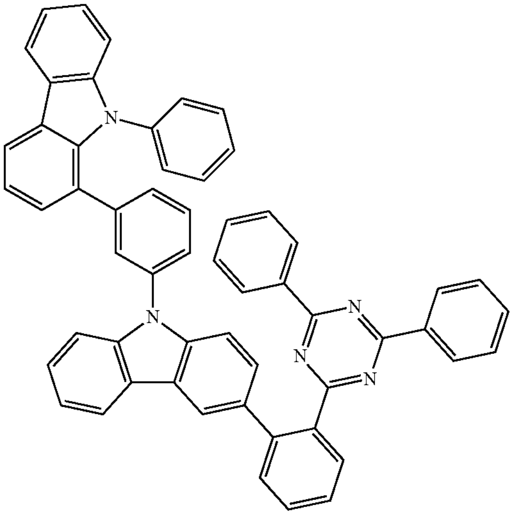
72
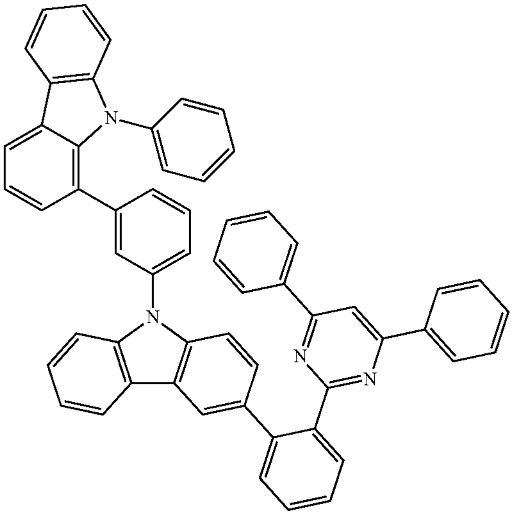
73
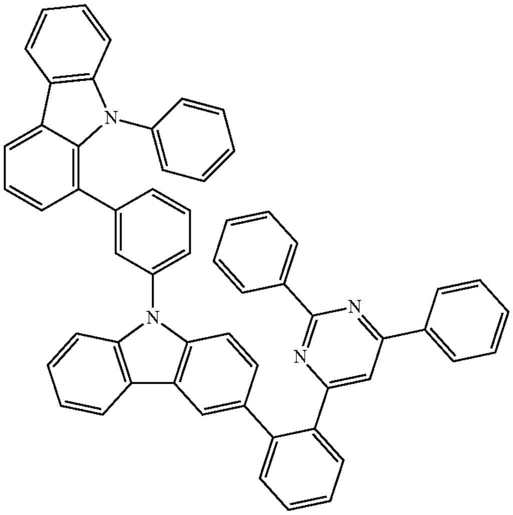

-continued
74
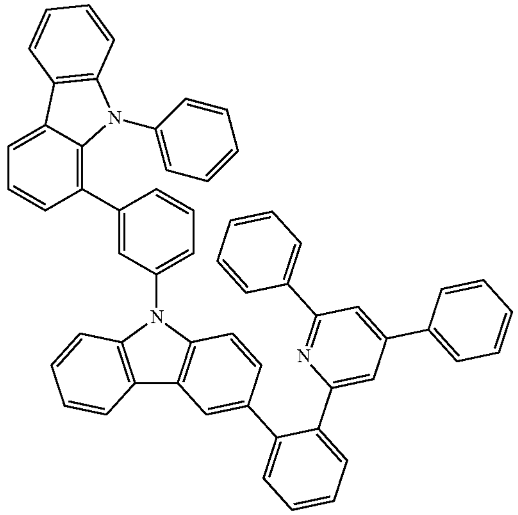
75
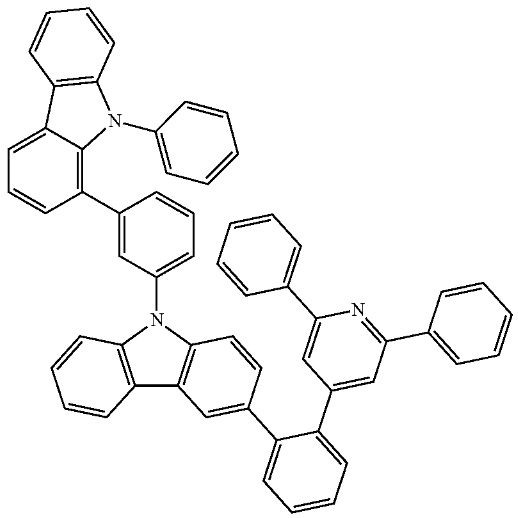
-continued
76
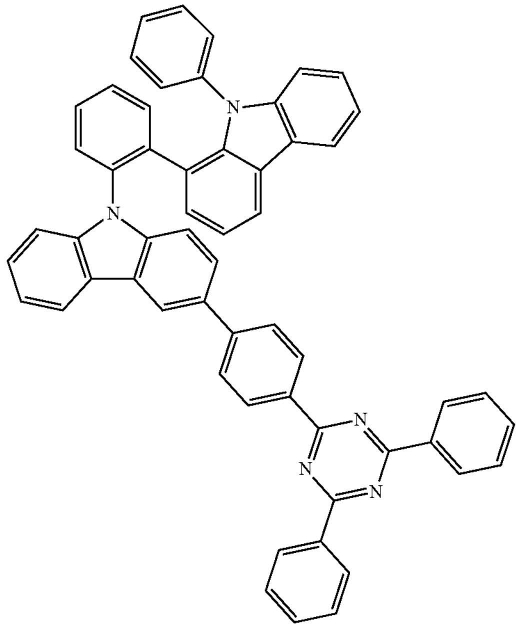
77
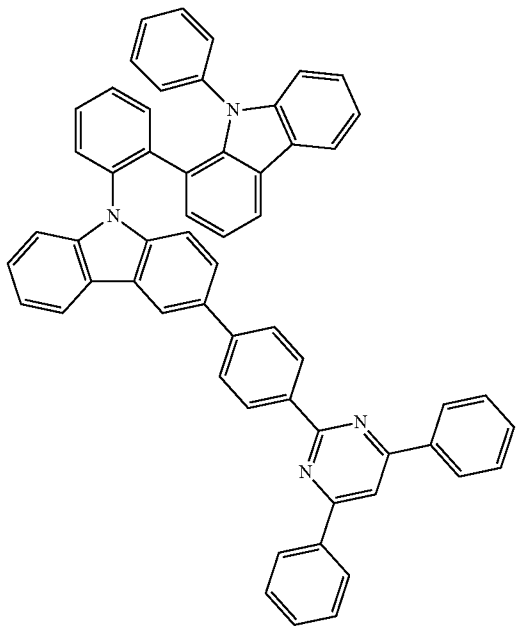

-continued
78
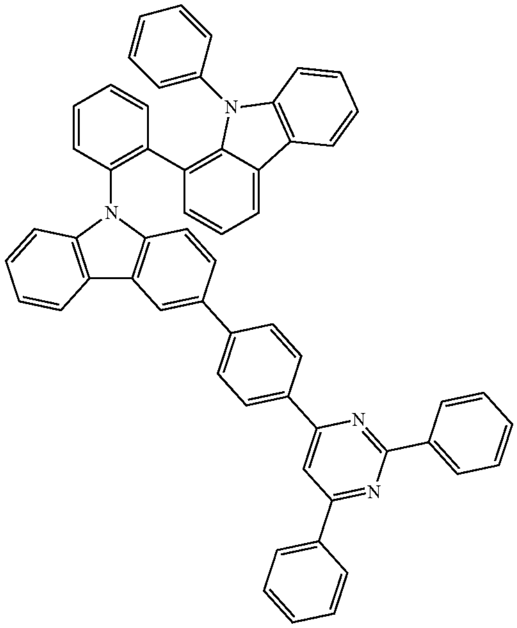
79
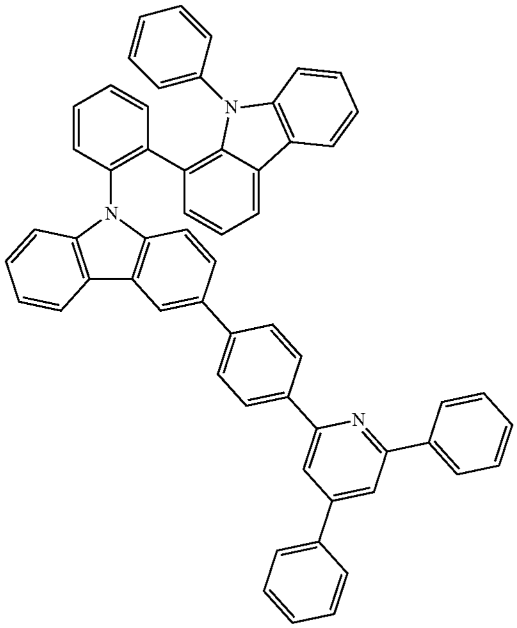
-continued
80
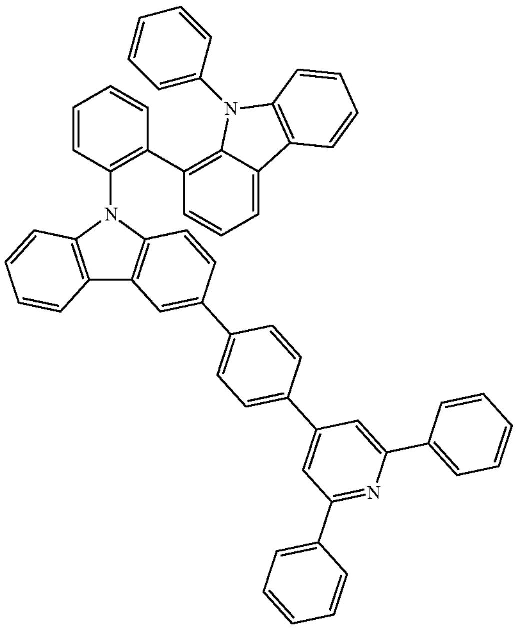
81
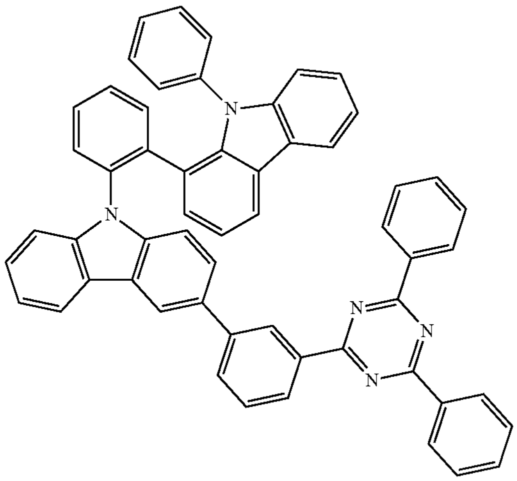
82
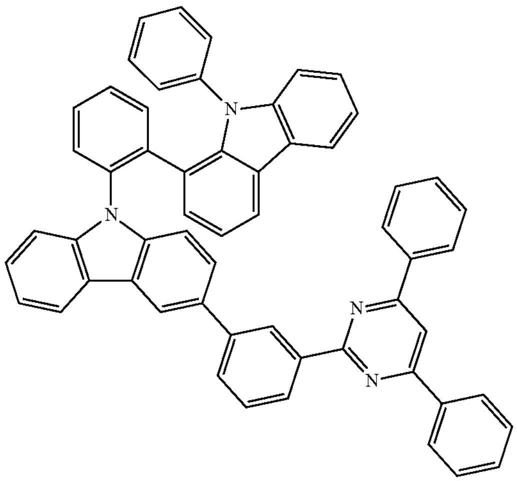

-continued
83
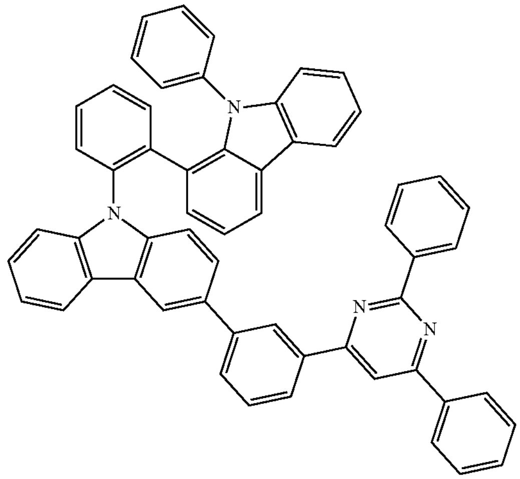
84
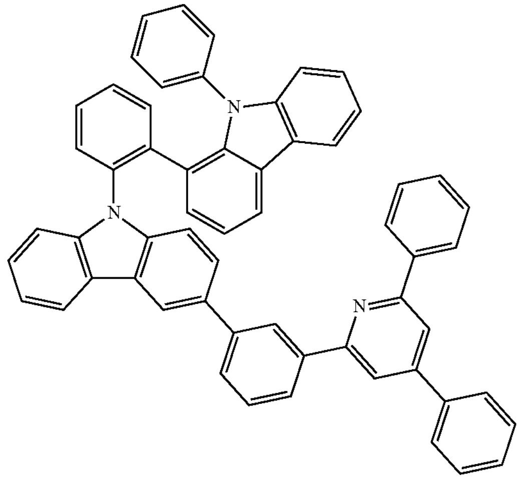
85
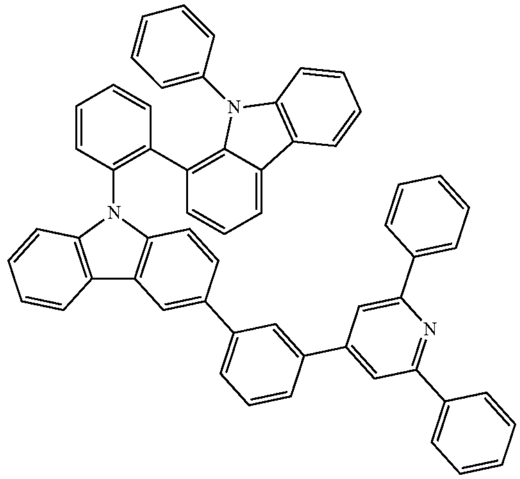
-continued
86
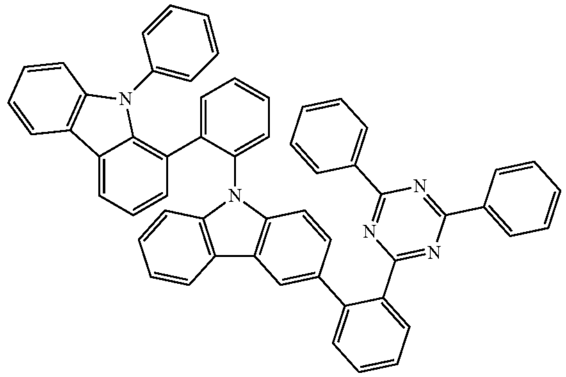
87
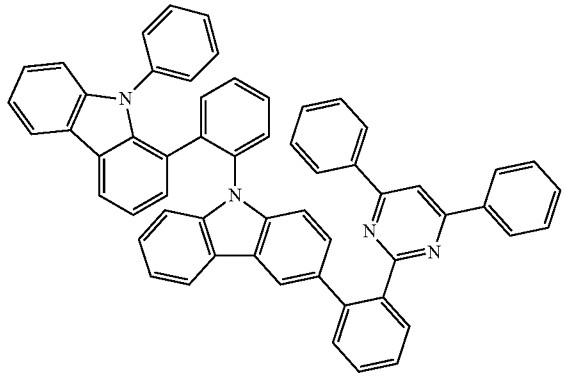
88
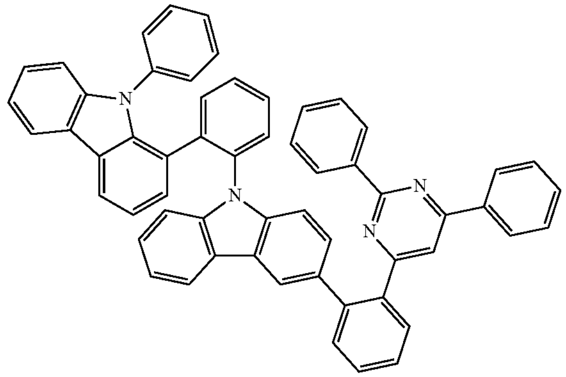
89
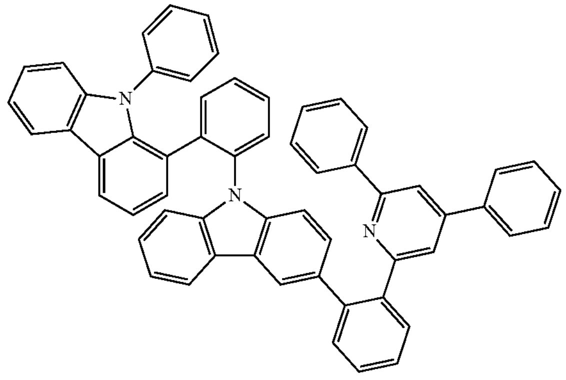

-continued
90
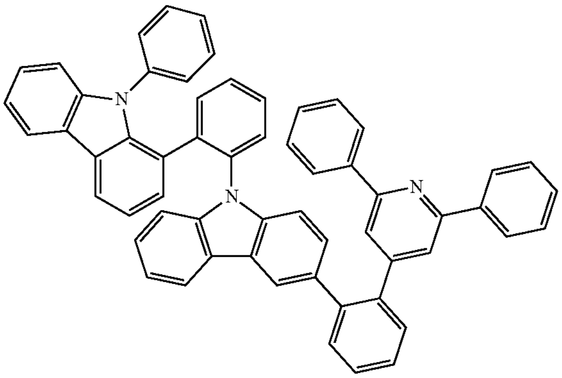
91
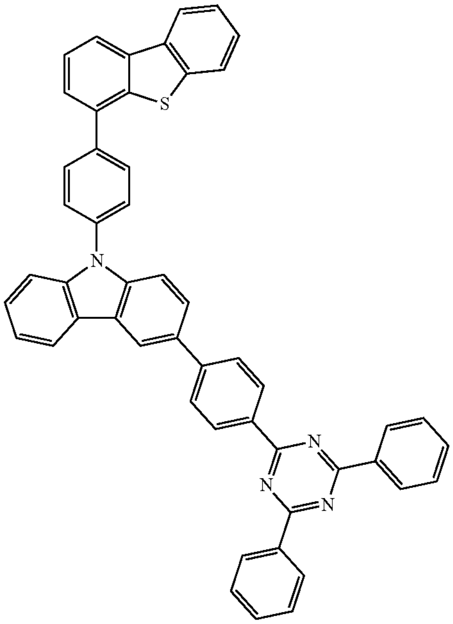
92
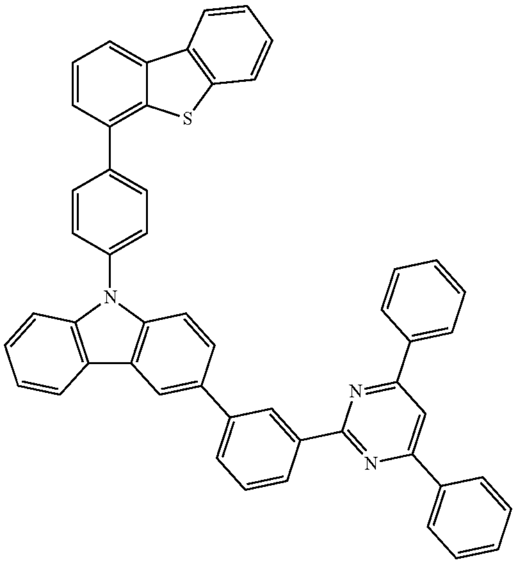
-continued
93
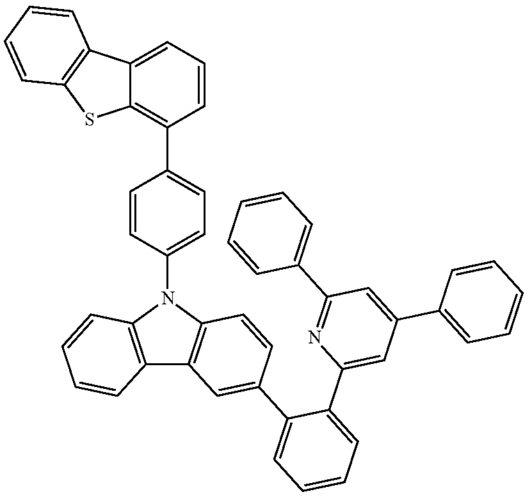
94
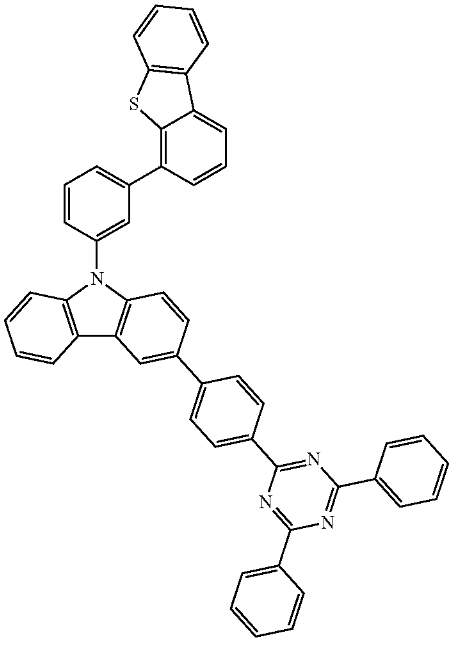

-continued
95
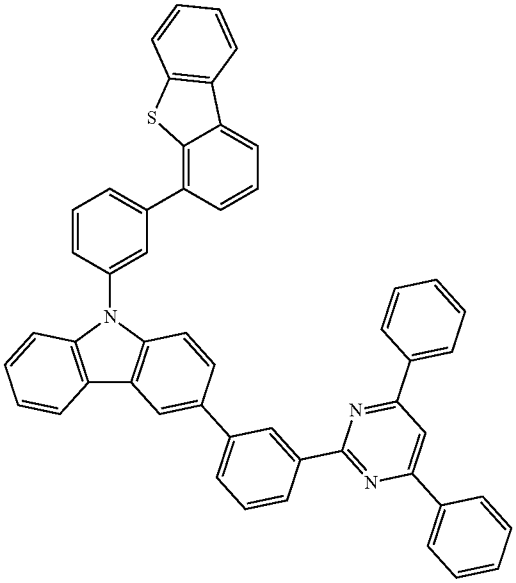
96
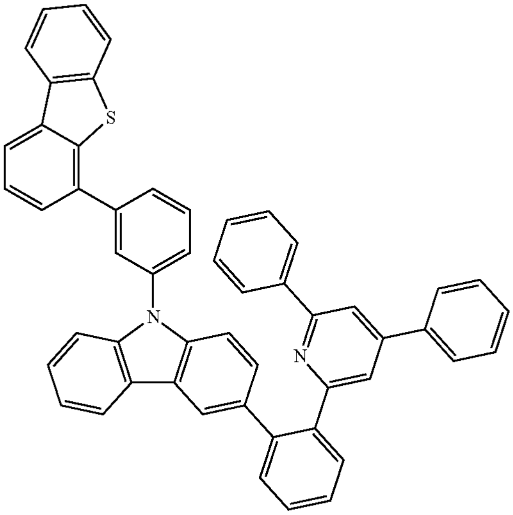
-continued
97
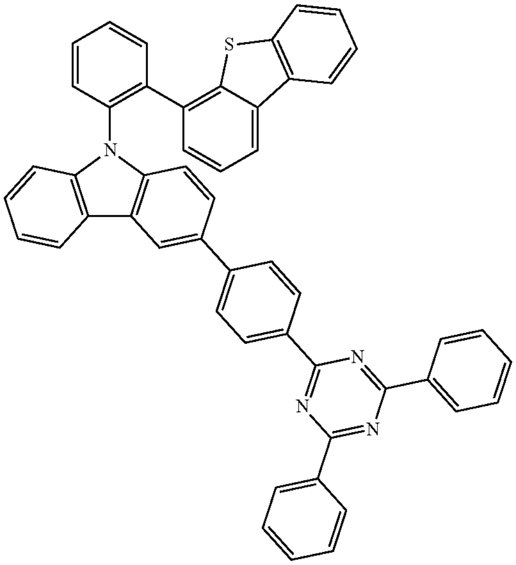
98
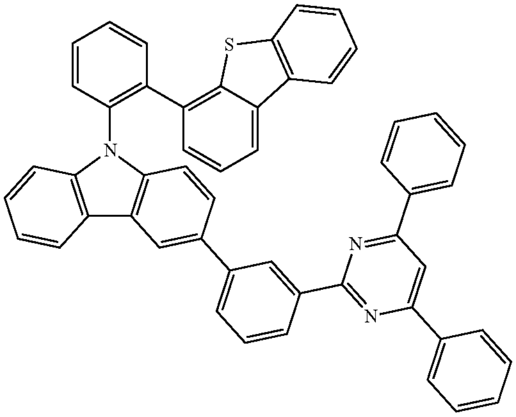
99
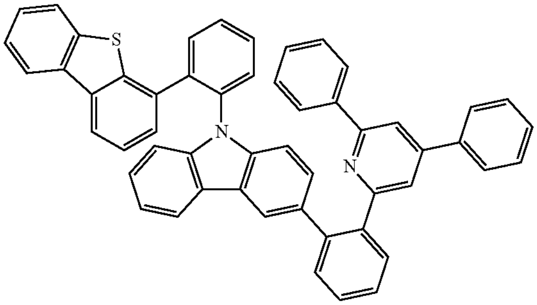

-continued
100
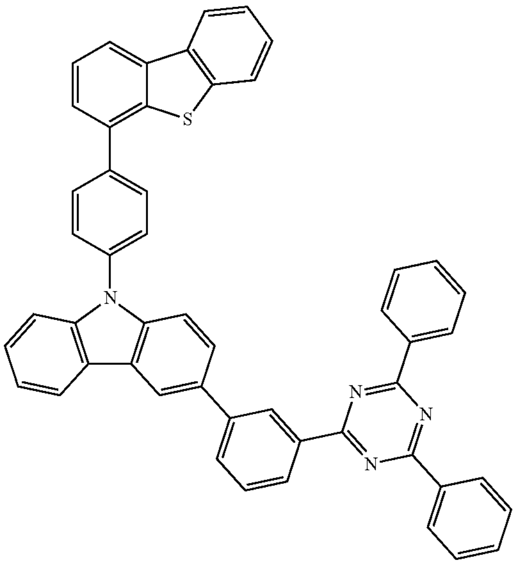
101
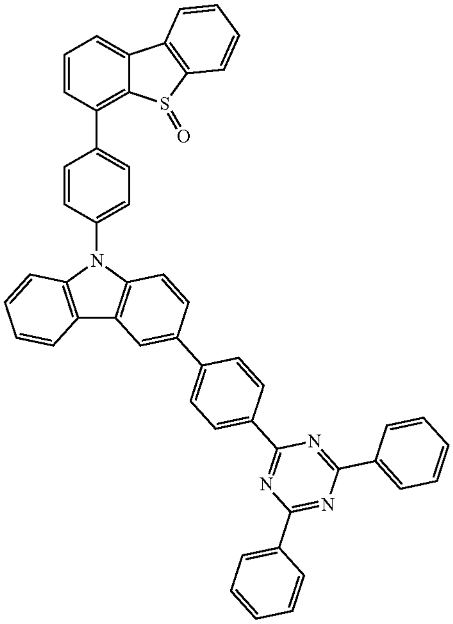
-continued
102
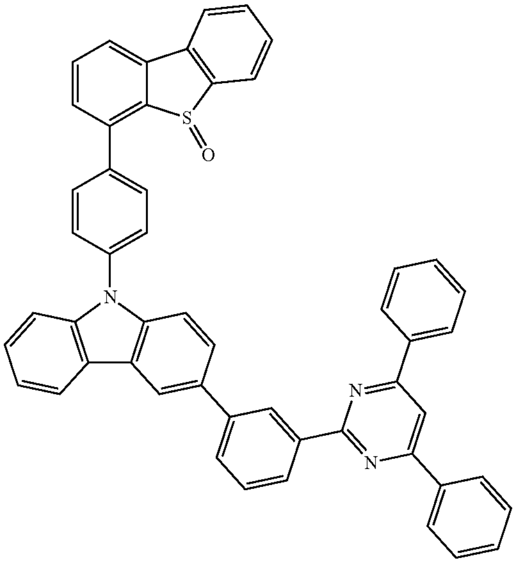
103
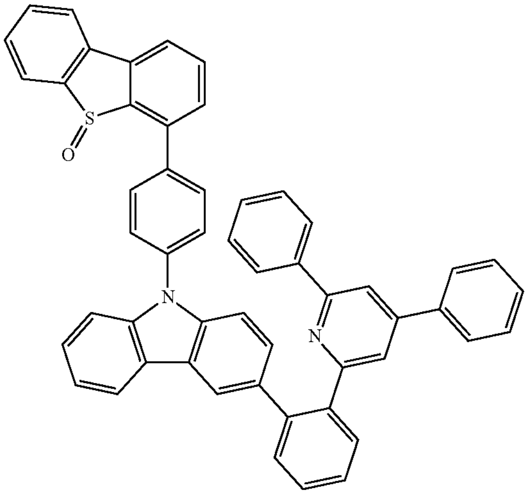

-continued
104
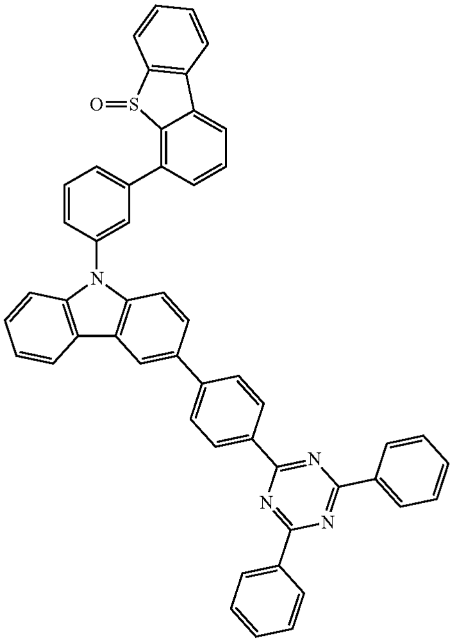
105
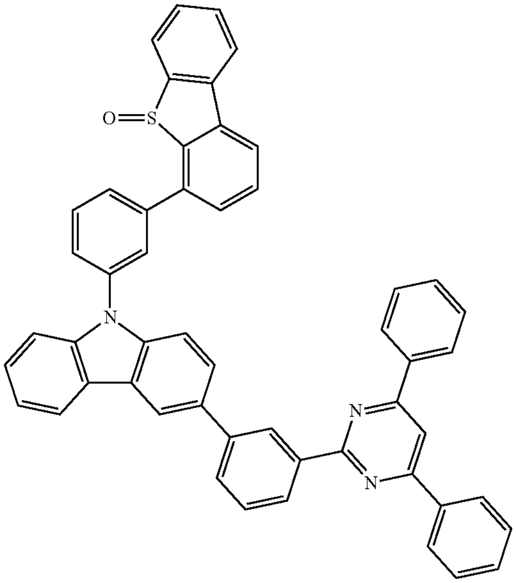
-continued
106
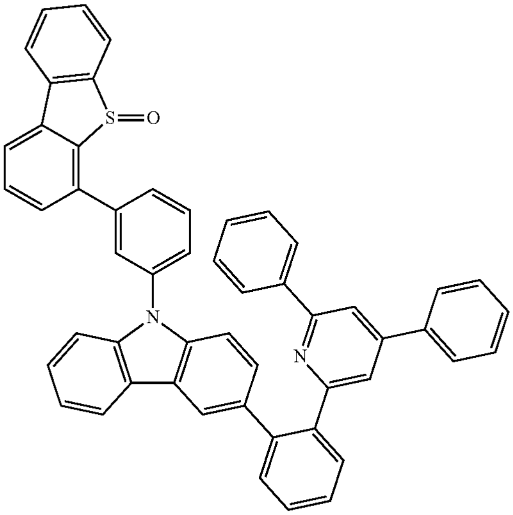
107
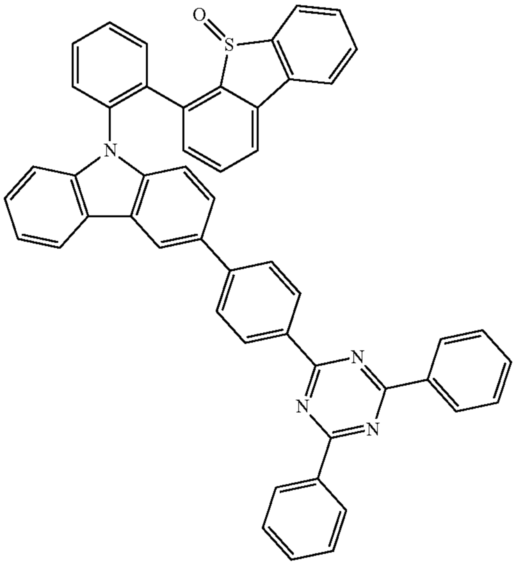
108
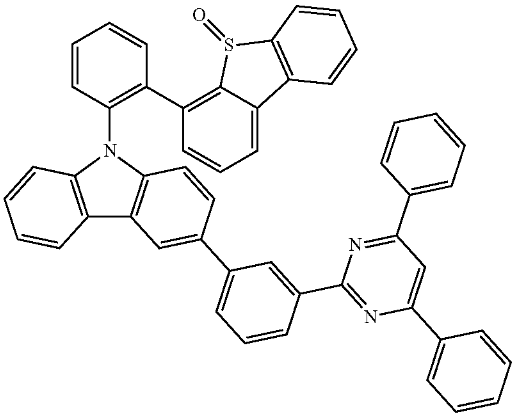

-continued
109
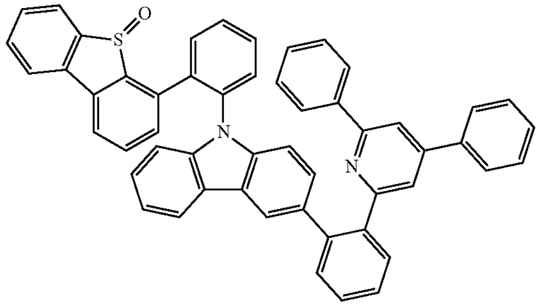
110
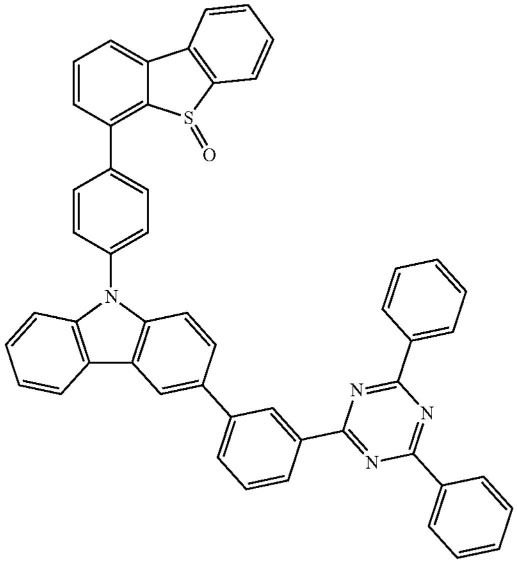
111
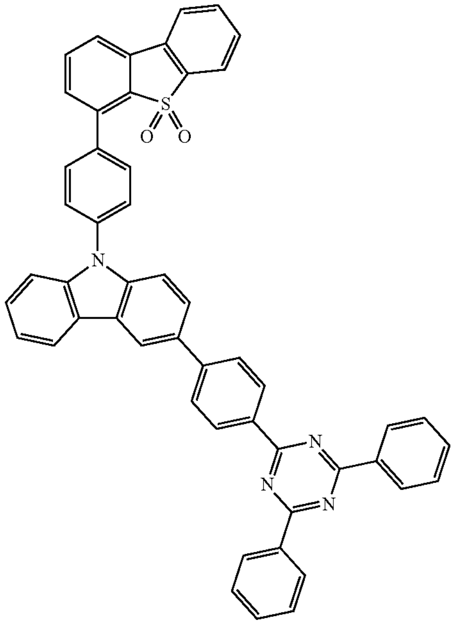
-continued
112
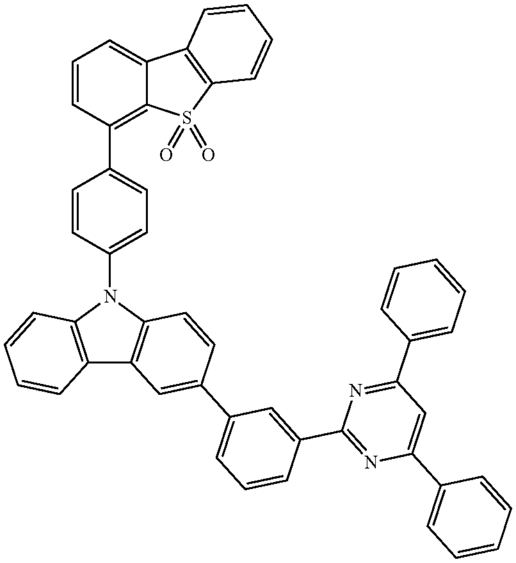
113
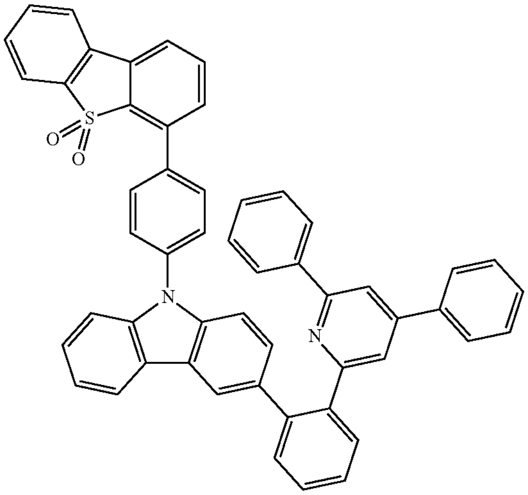

114
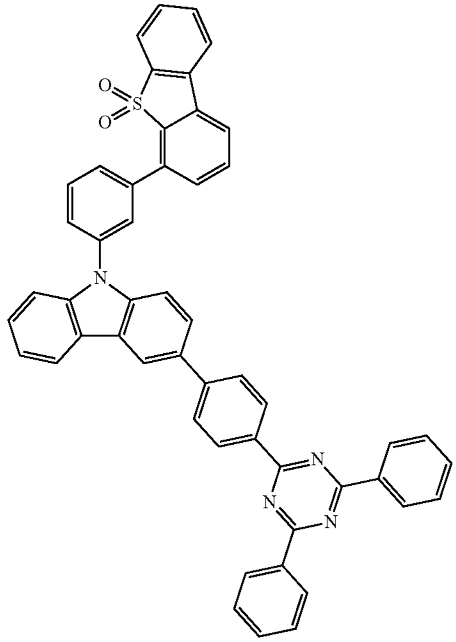
115
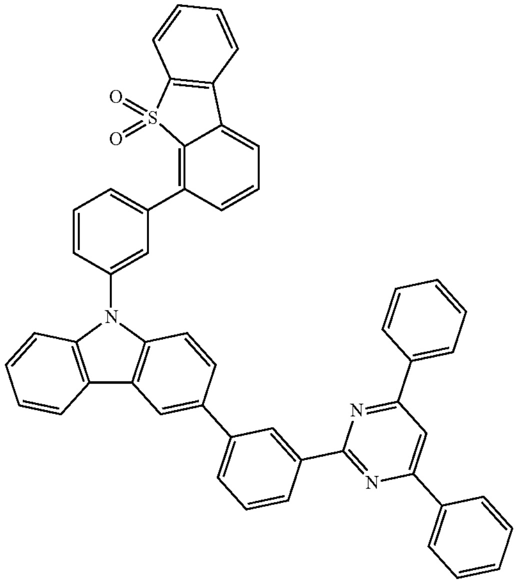
116
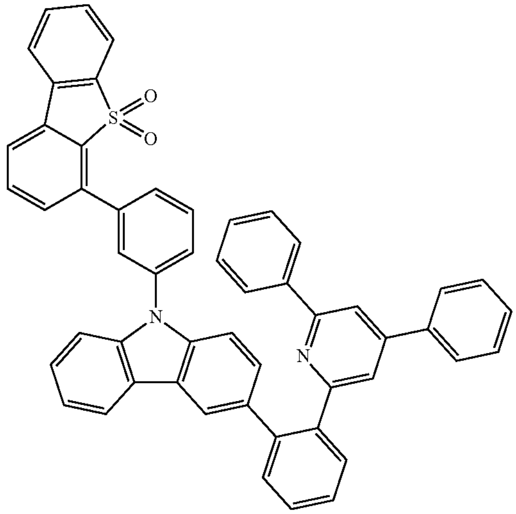
117
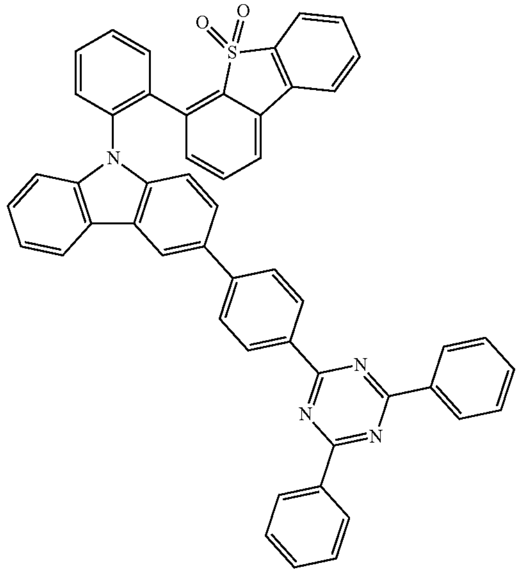
118
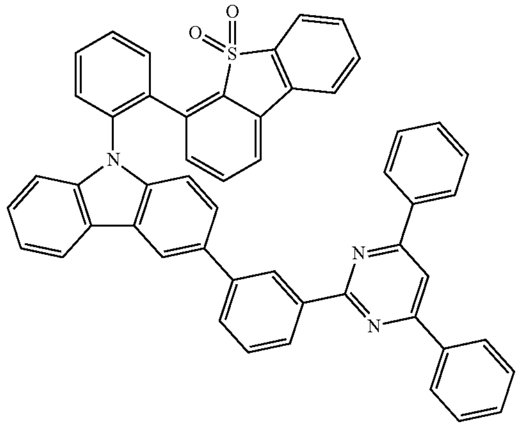

119
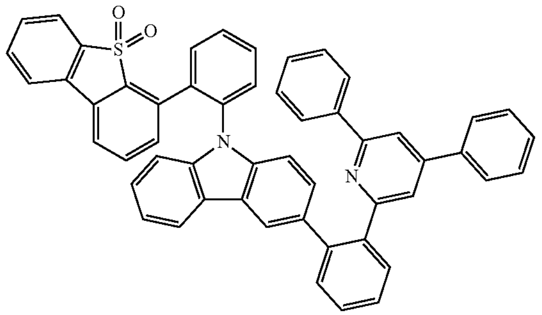
120
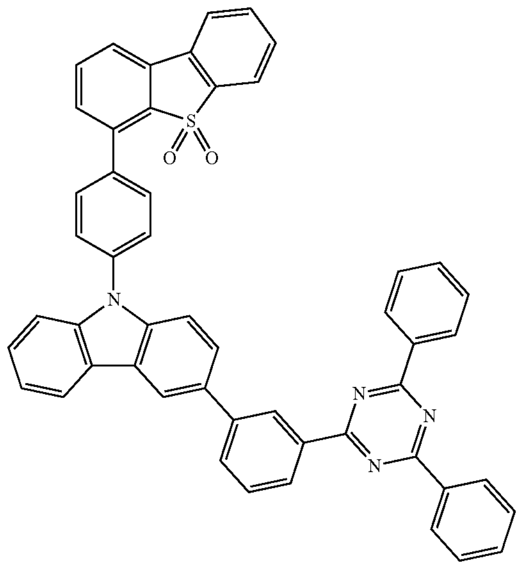
121
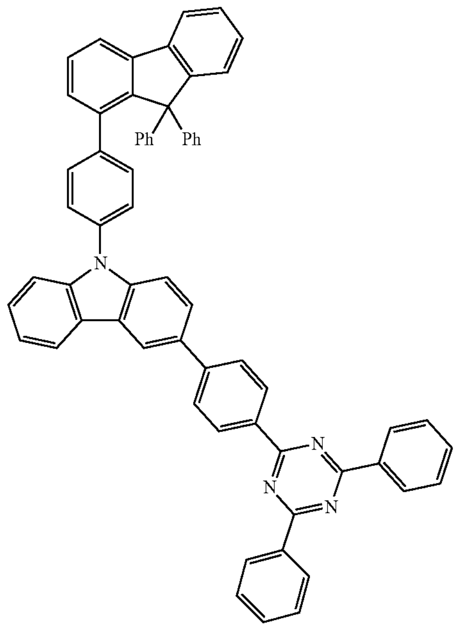
122
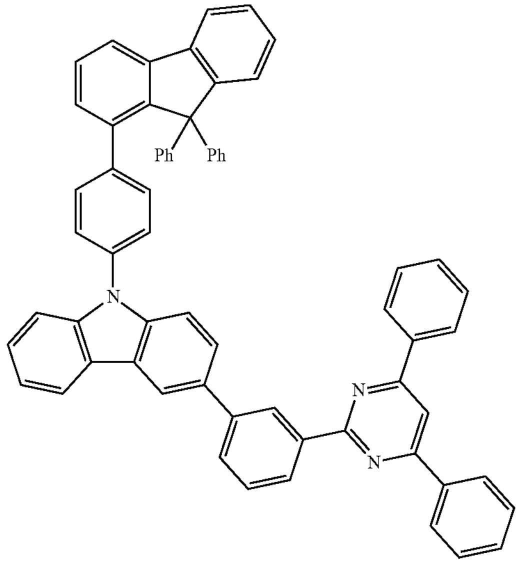
123
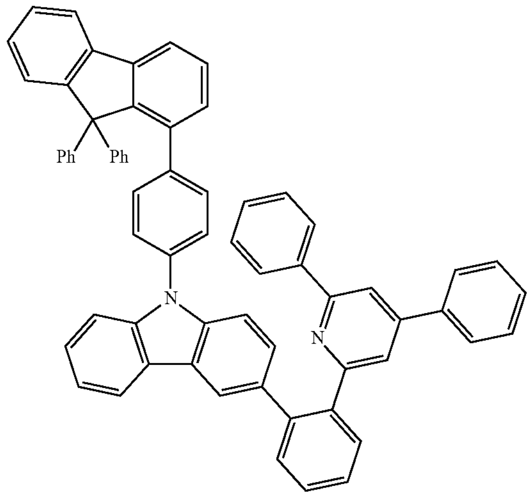

124
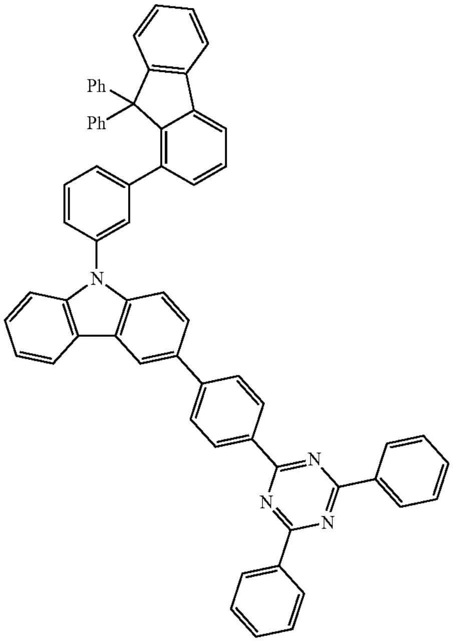
125
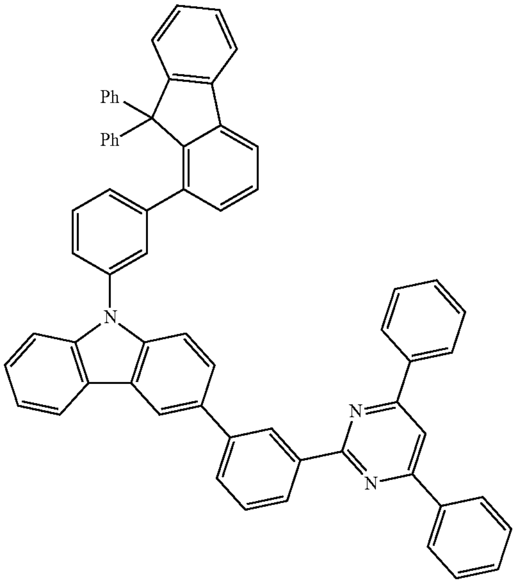
126
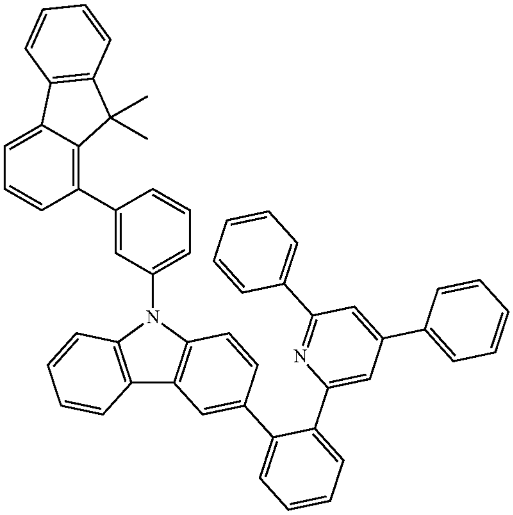
127
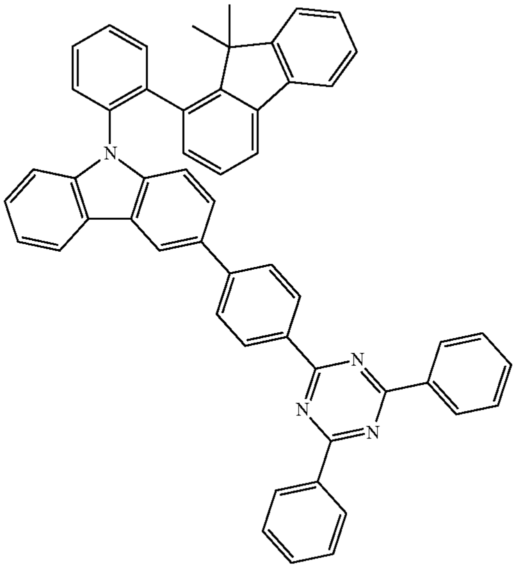
128
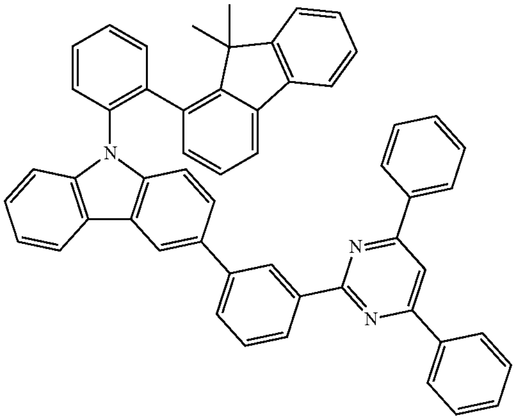

129
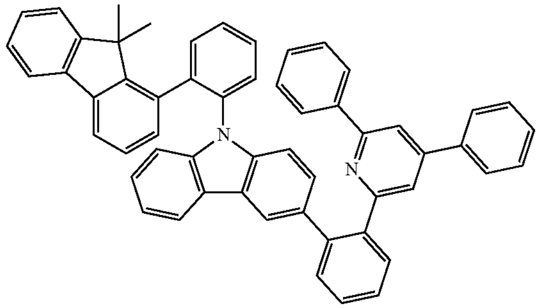
130
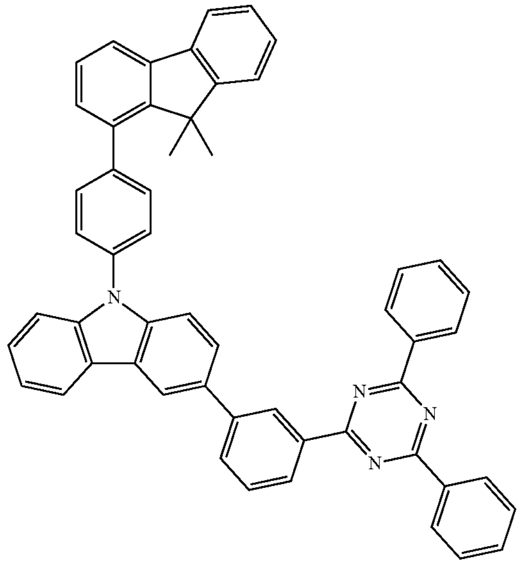
131
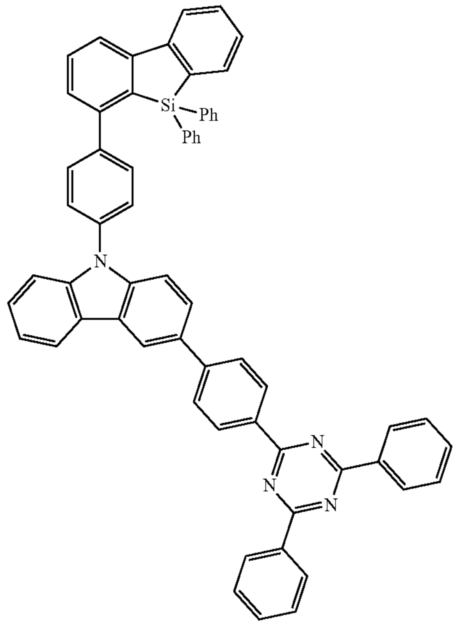
132
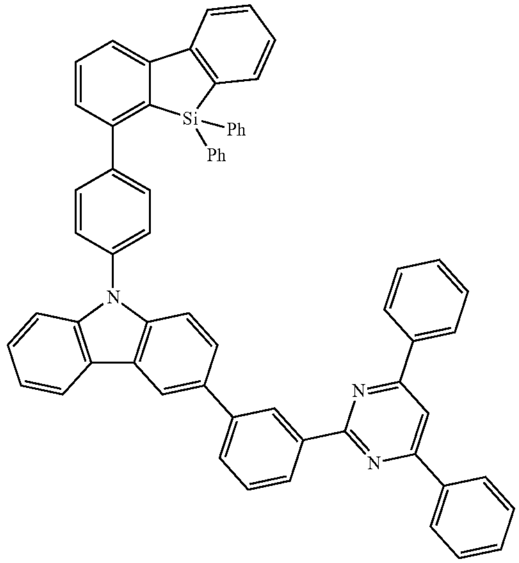
133
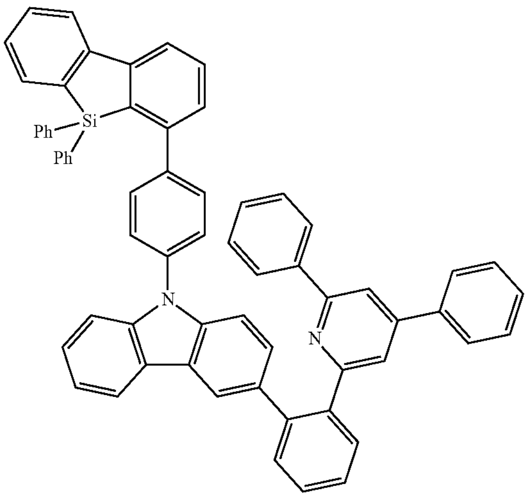

-continued
134
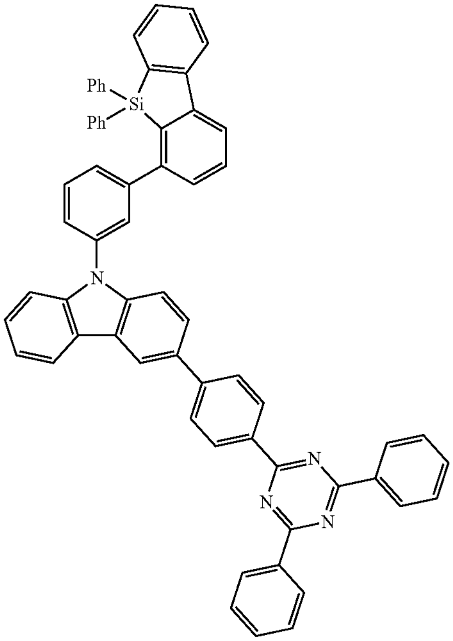
135
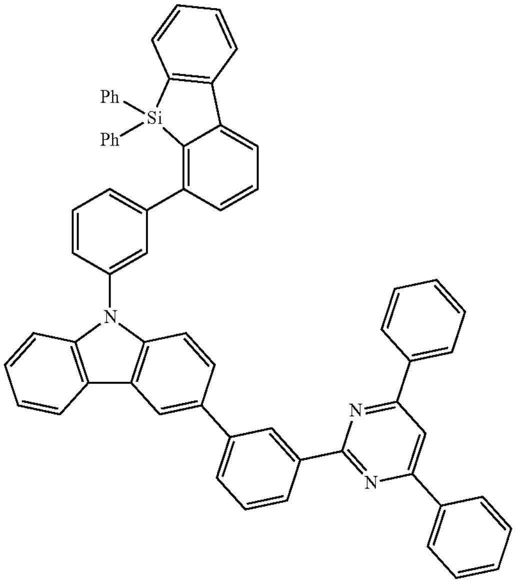
-continued
136
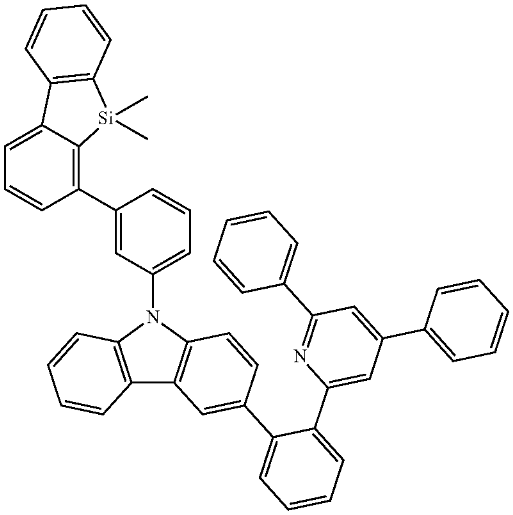
137
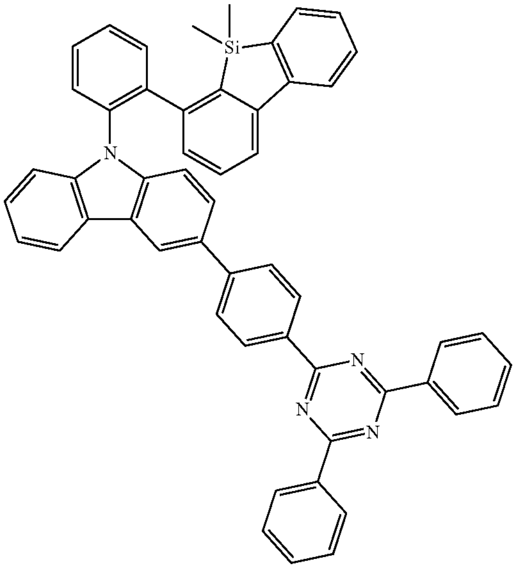
138
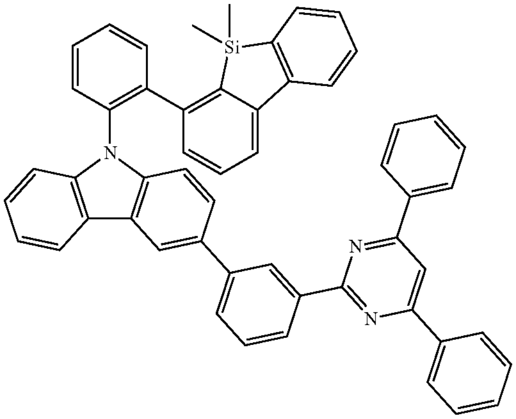

-continued
139
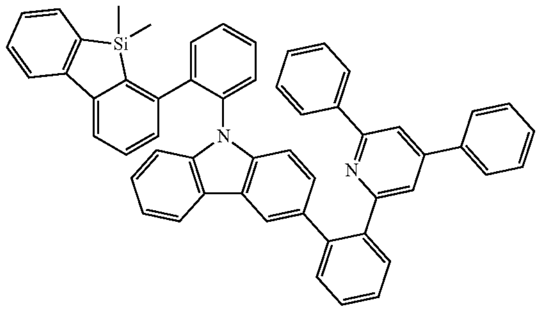
140
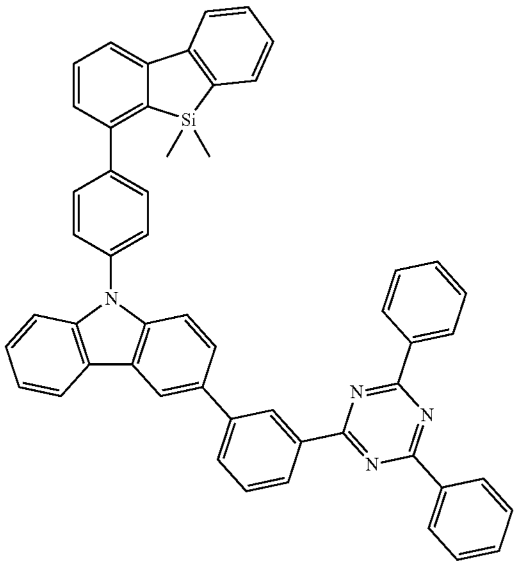
141
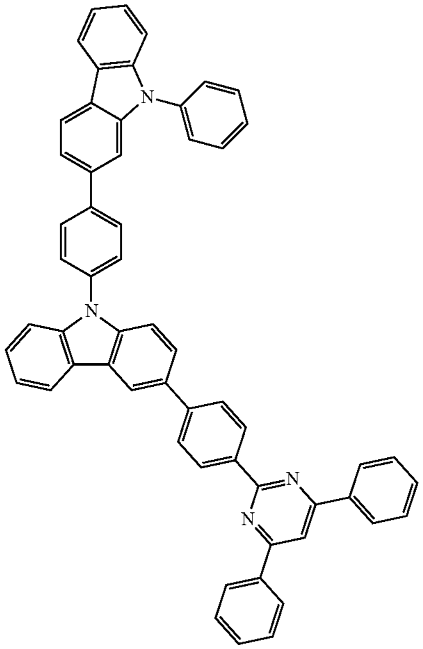
-continued
142
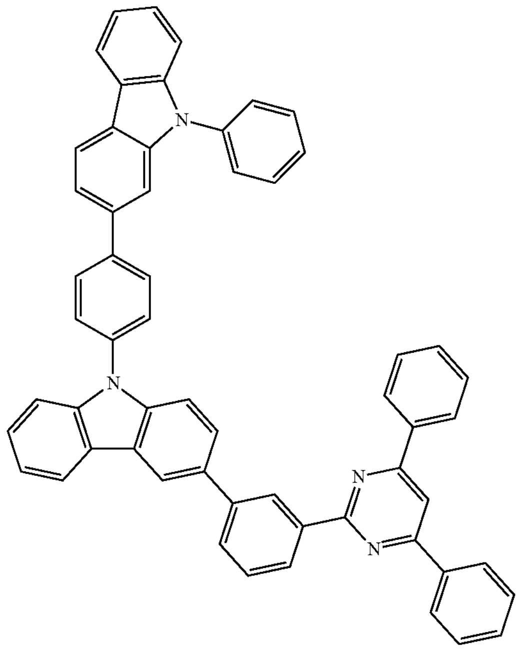
143
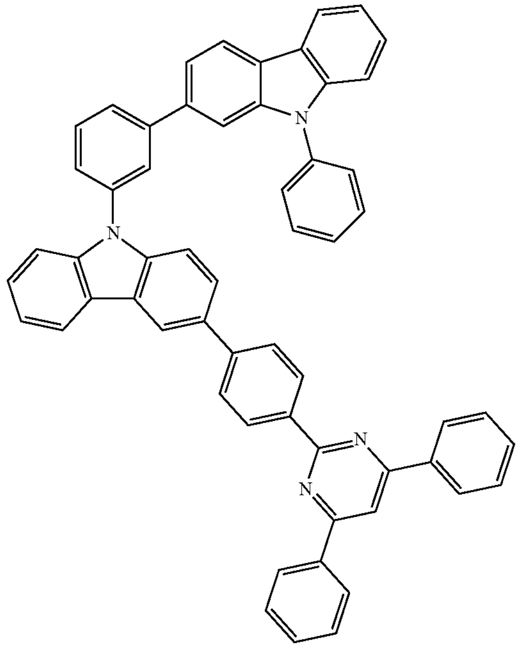

144
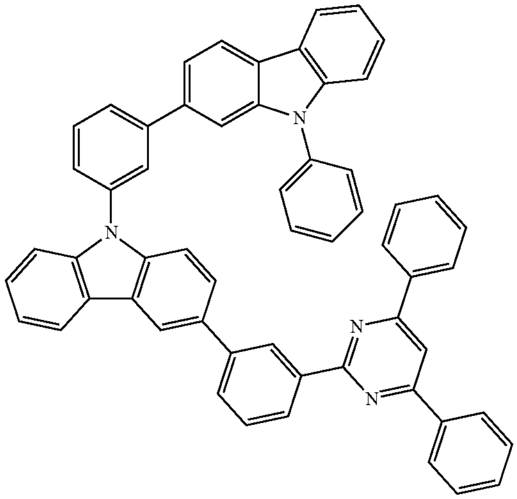
145
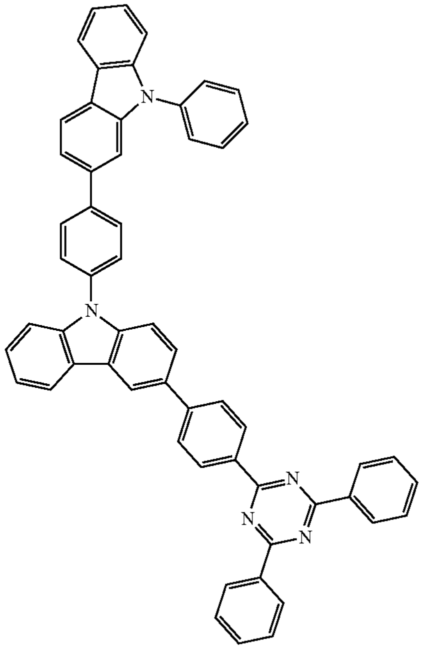
146
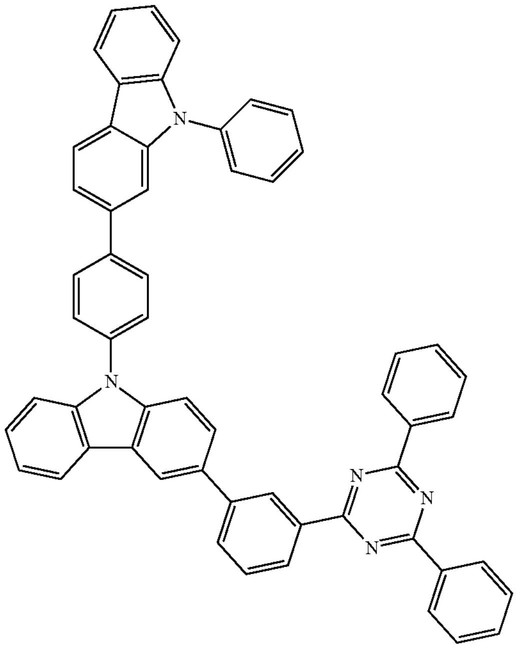
147
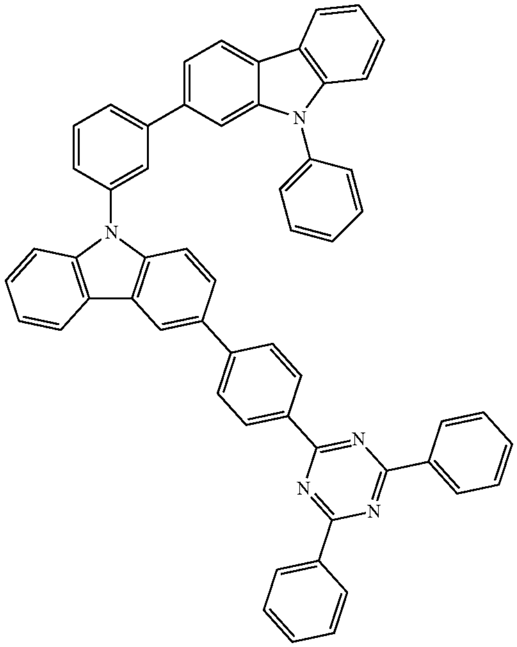

-continued
148
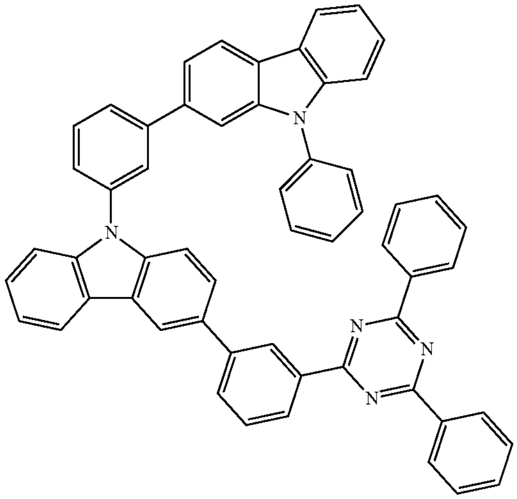
149
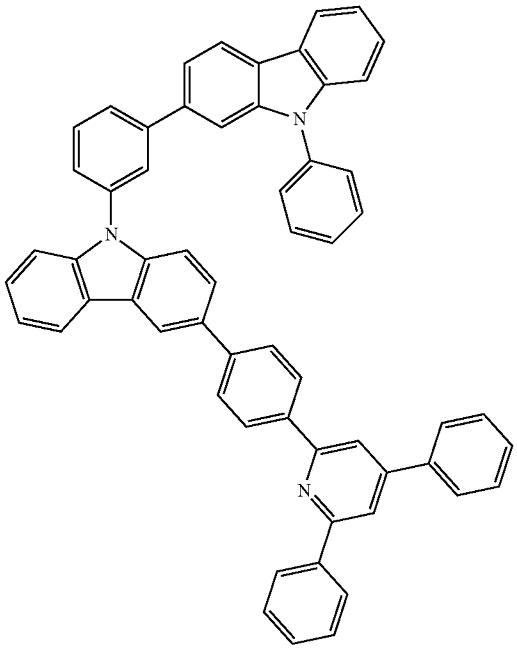
-continued
150
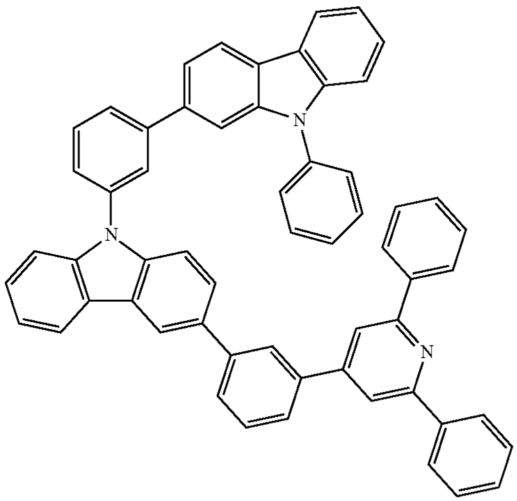
151
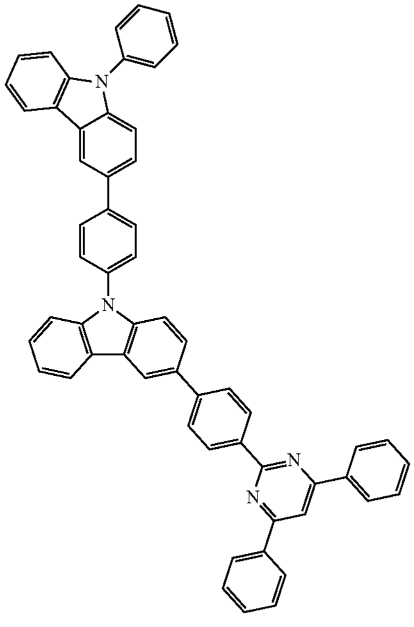

-continued
152
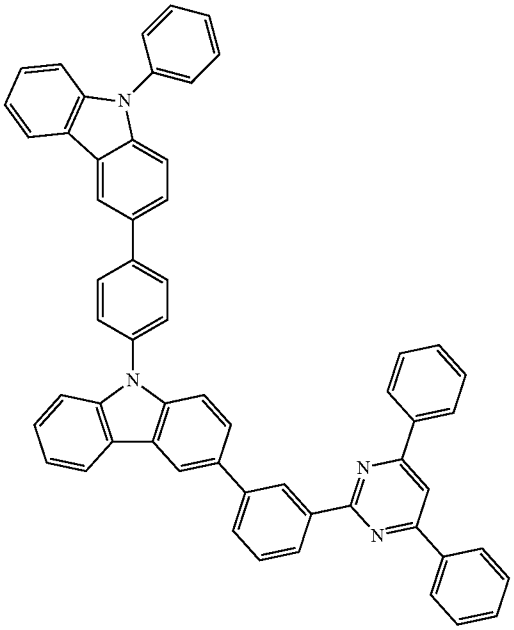
153
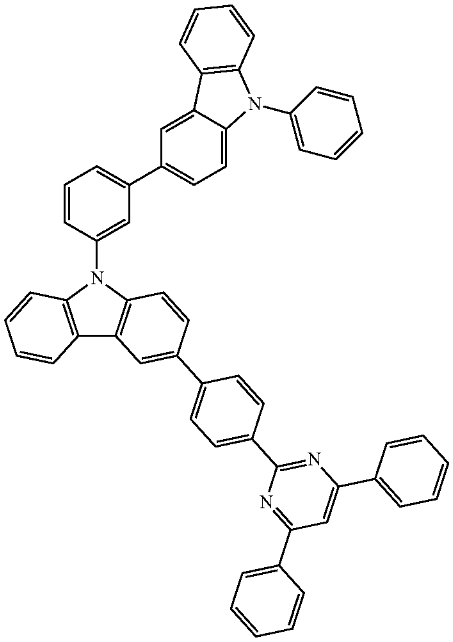
-continued
154
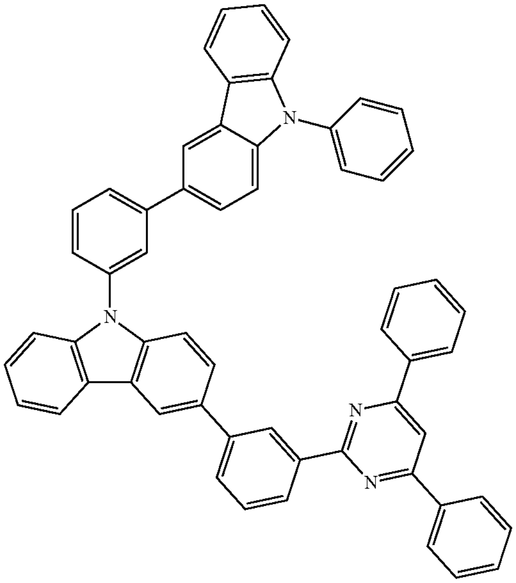
155
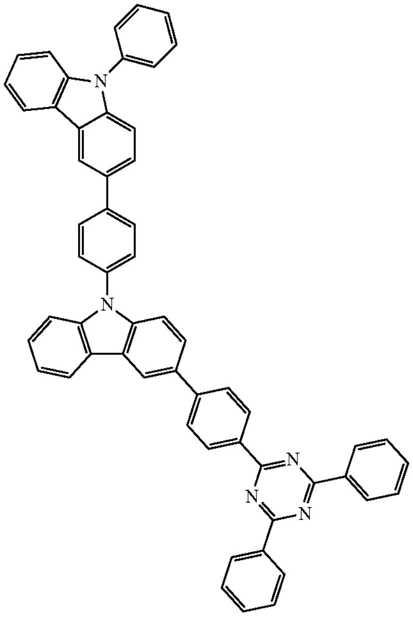

-continued
156
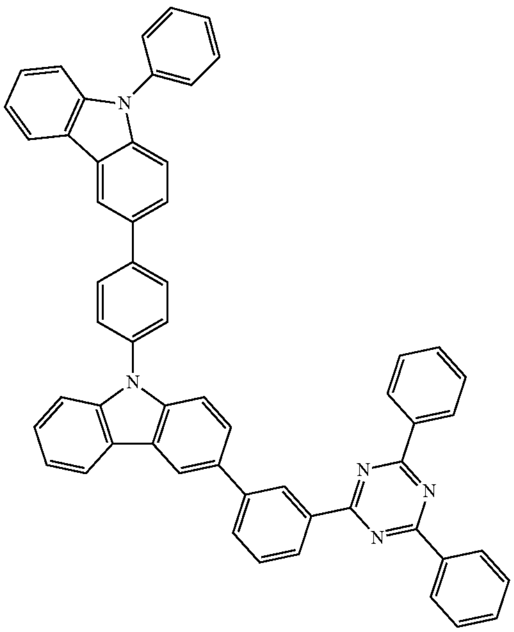
157
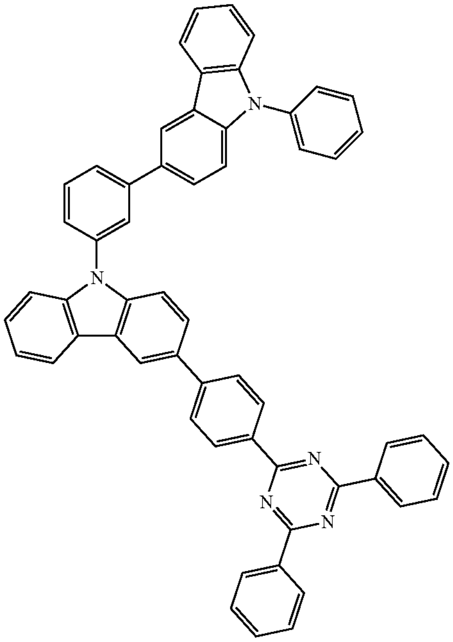
-continued
158
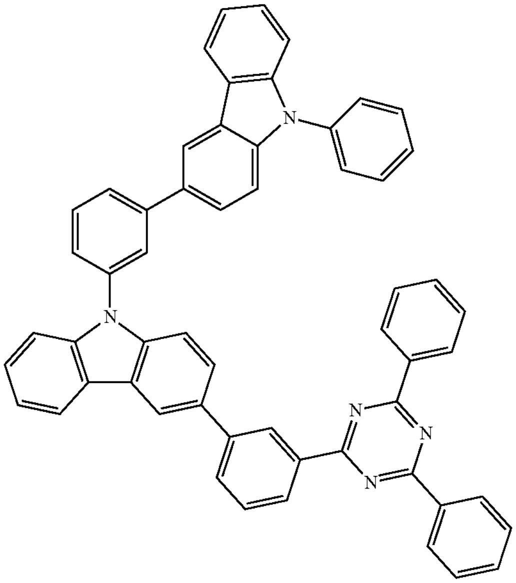
159
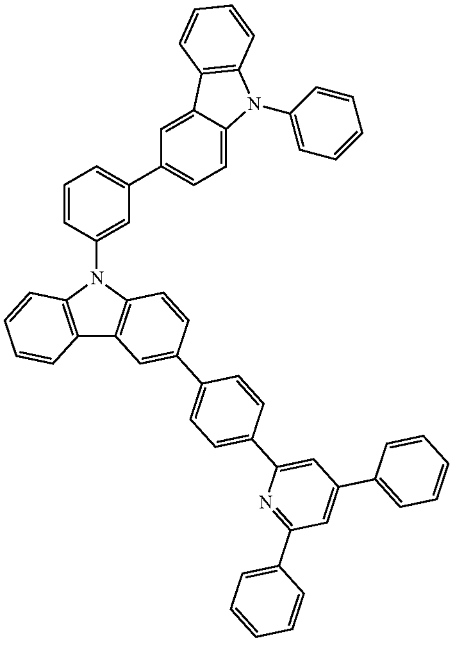

-continued
160
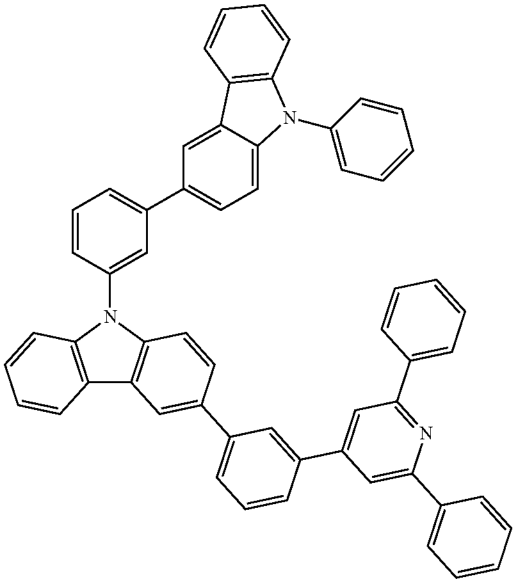
161
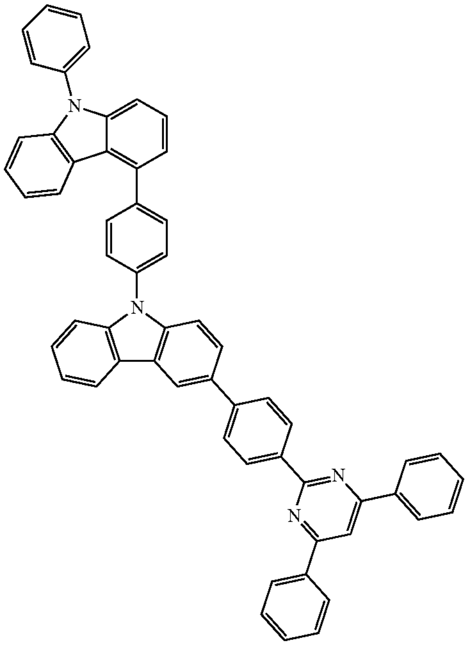
-continued
162
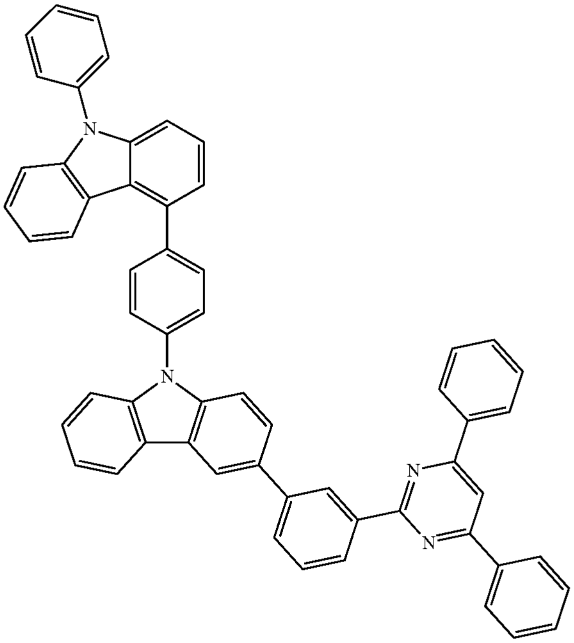
163
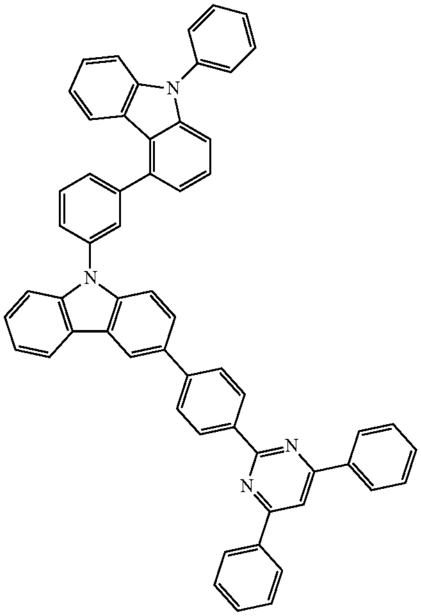

164
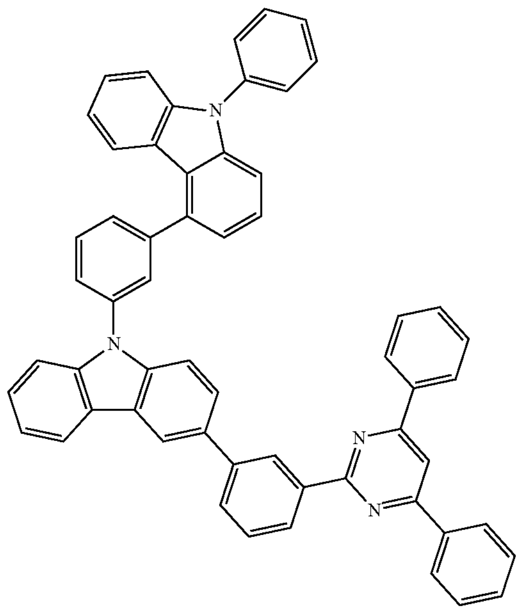
165
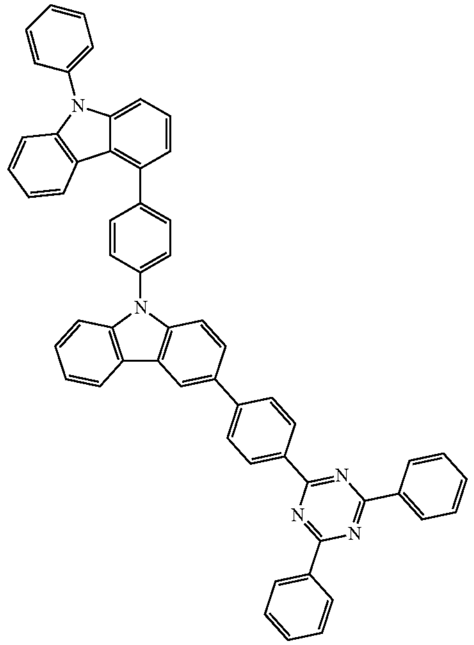
166
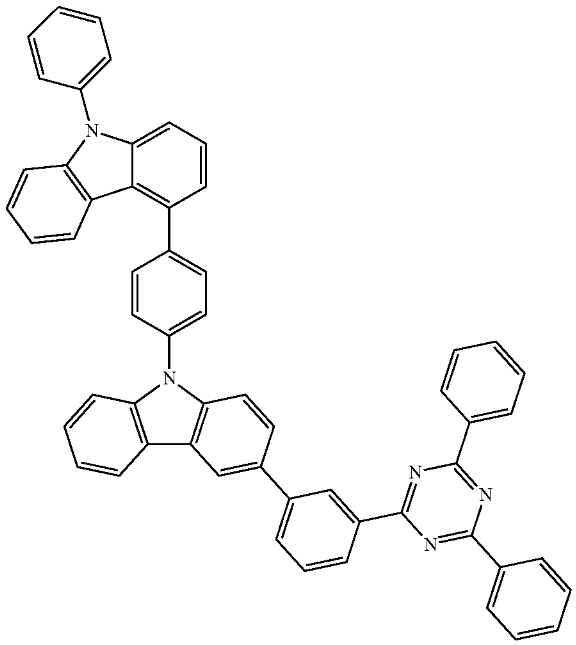
167
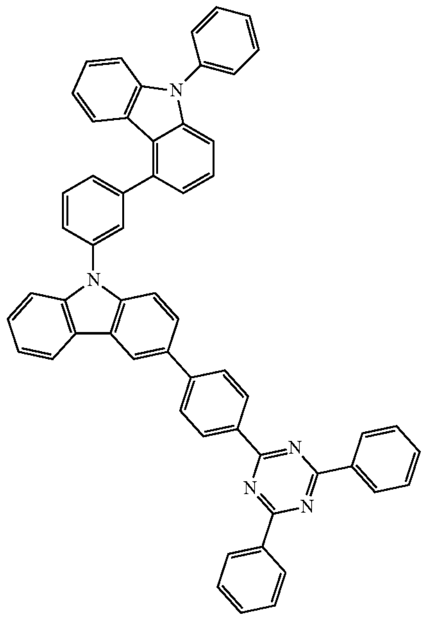

-continued
168
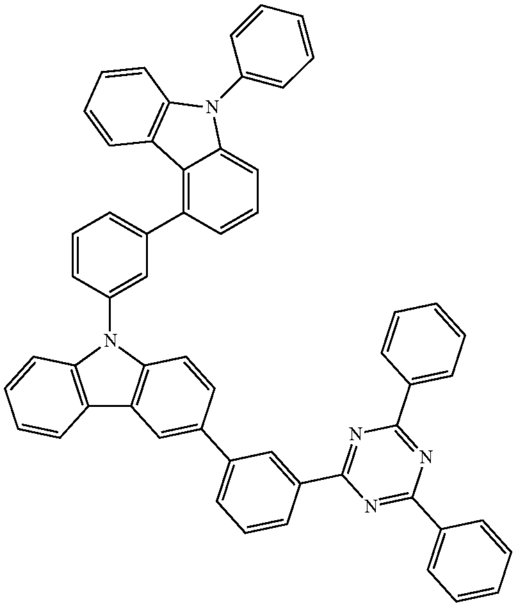
169
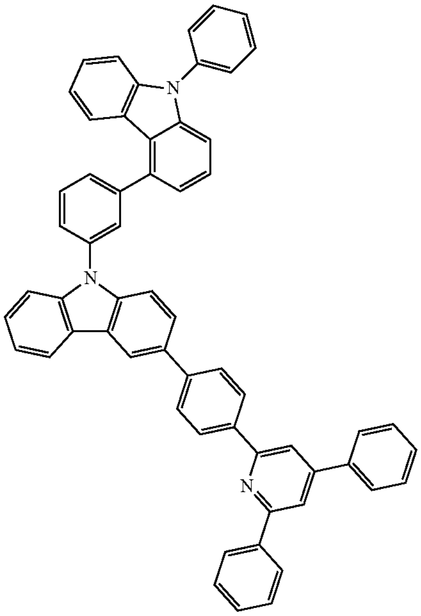
-continued
170
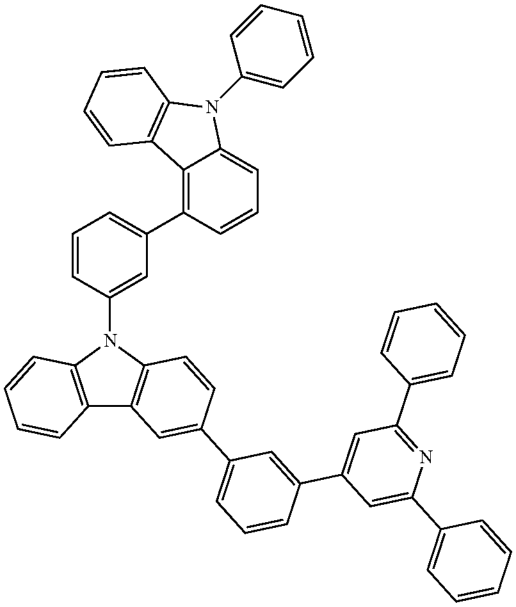
171
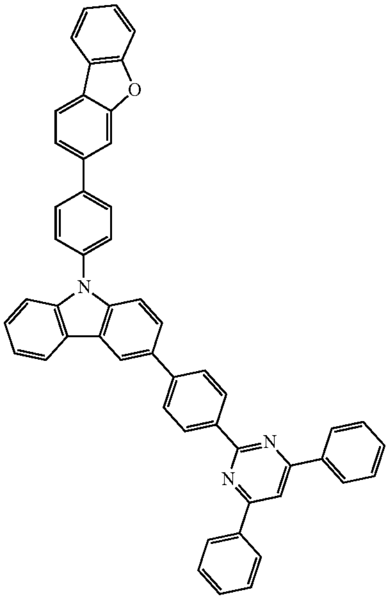

-continued
172
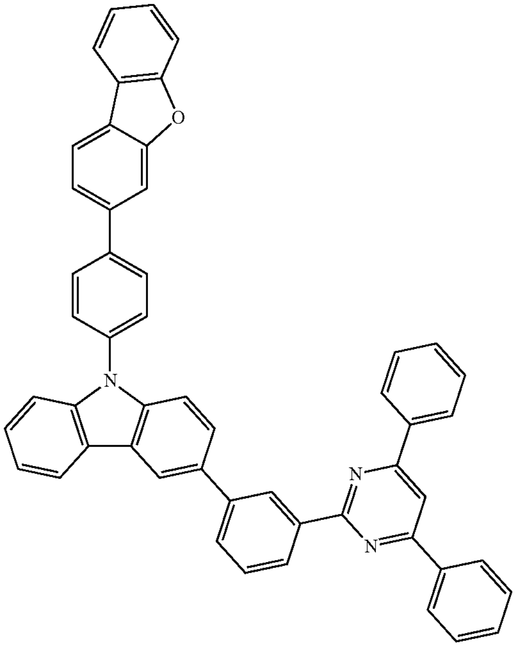
173
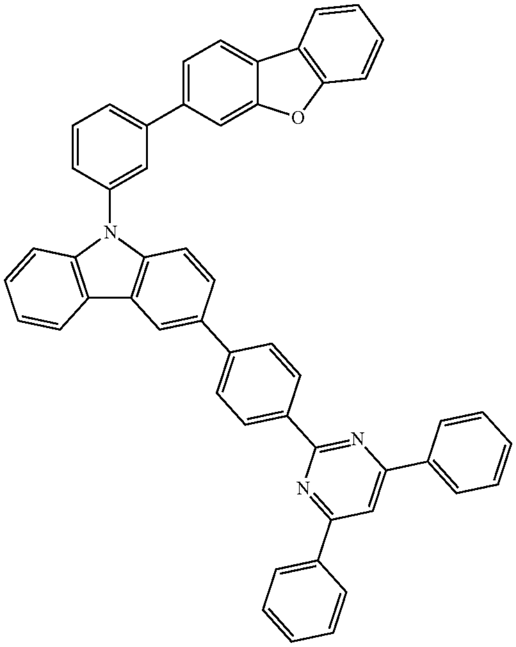
-continued
174
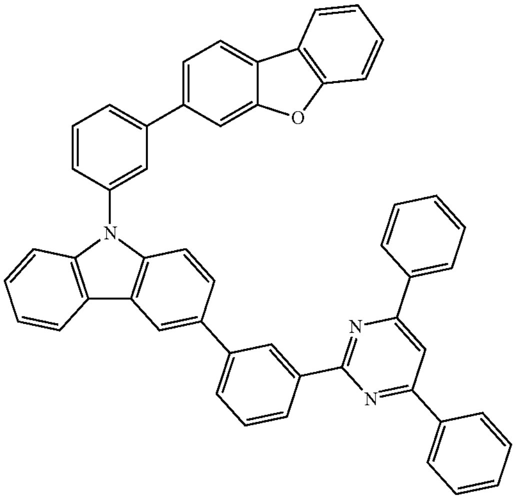
175
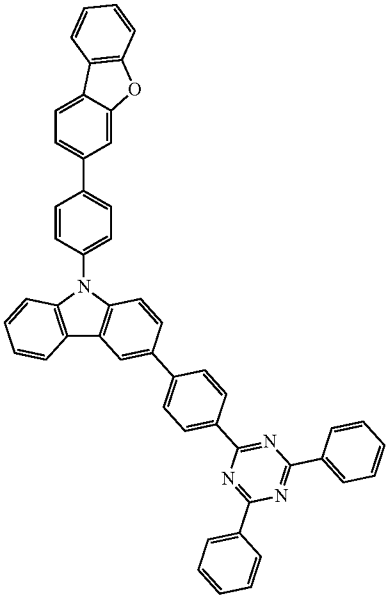

-continued
176
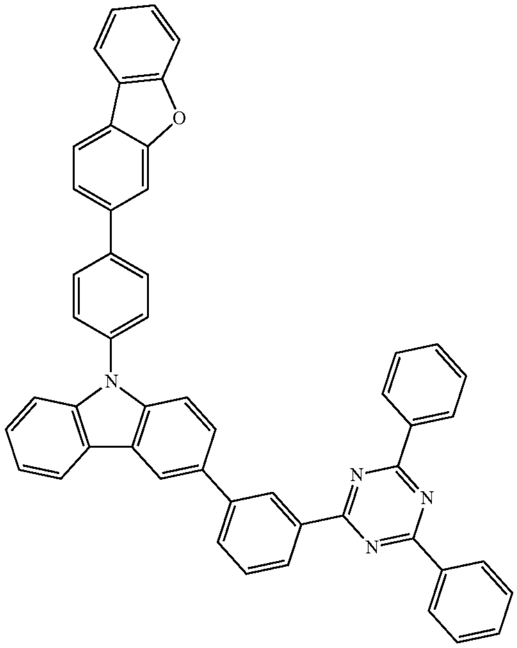
177
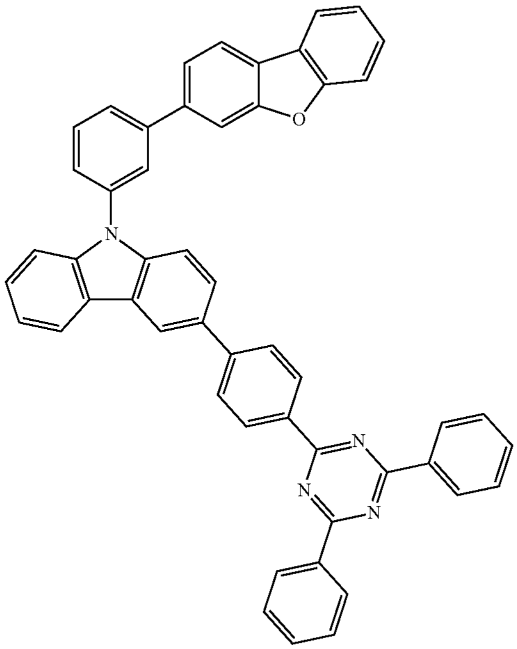
-continued
178
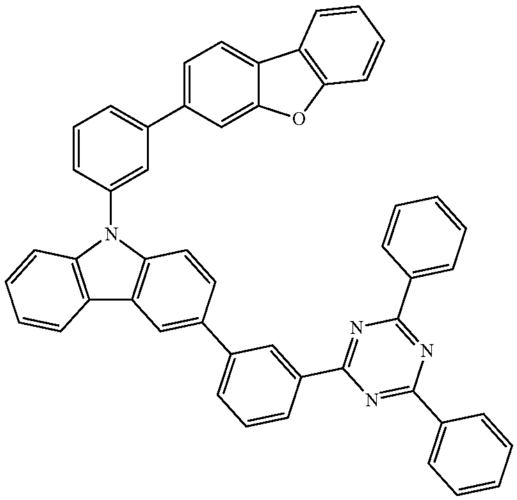
179
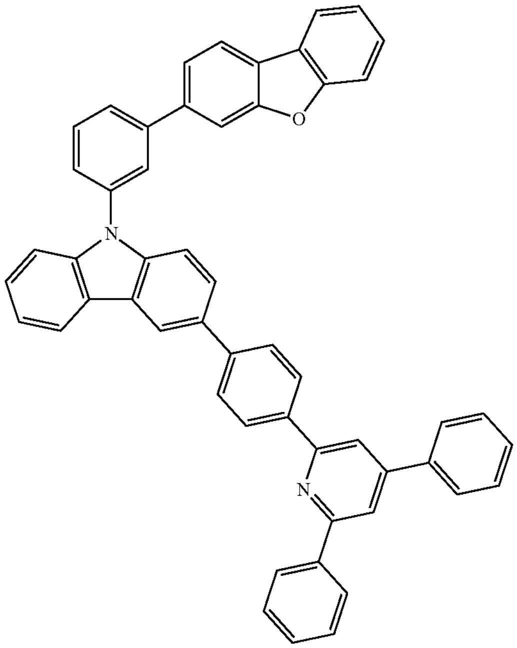

-continued
180
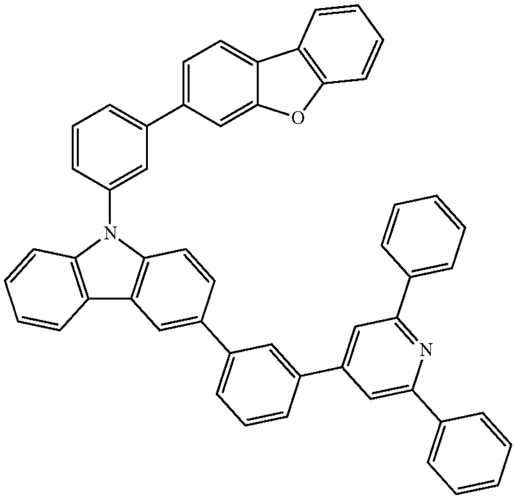
-continued
182
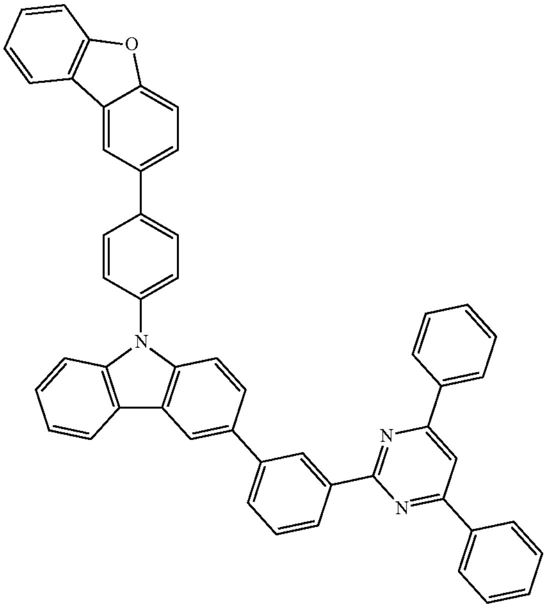
181
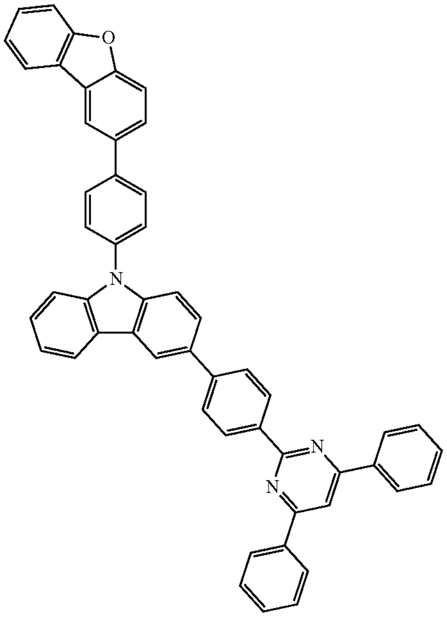
183
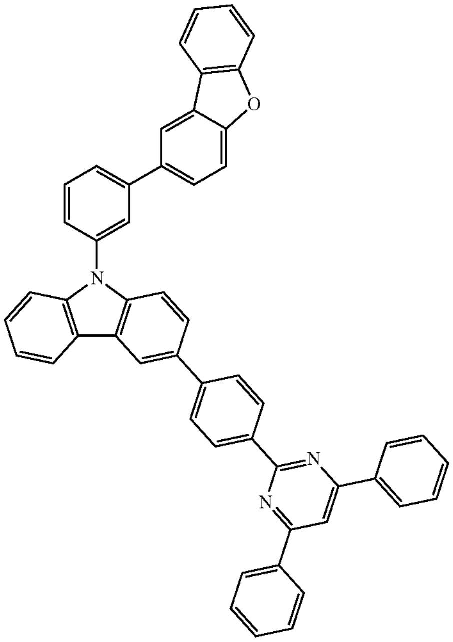

-continued
184
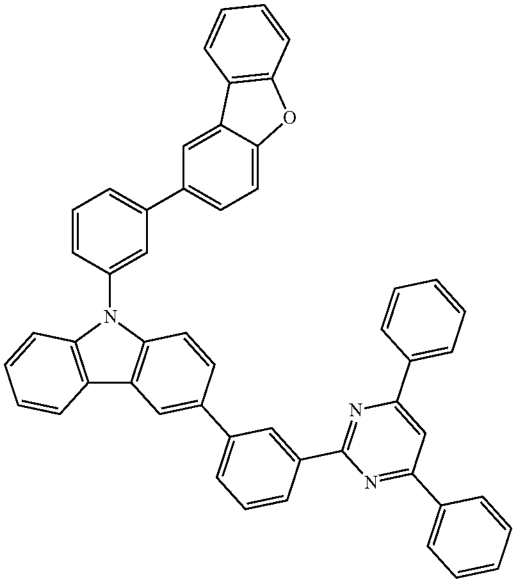
185
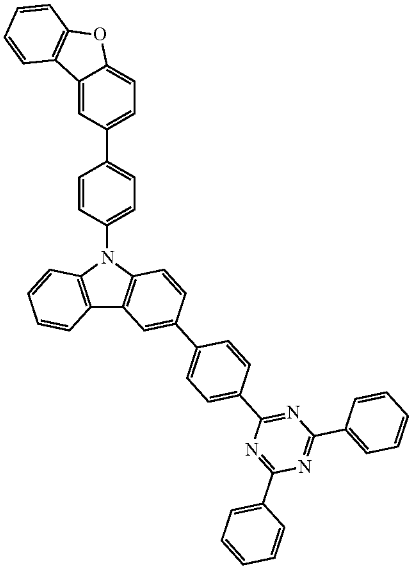
-continued
186
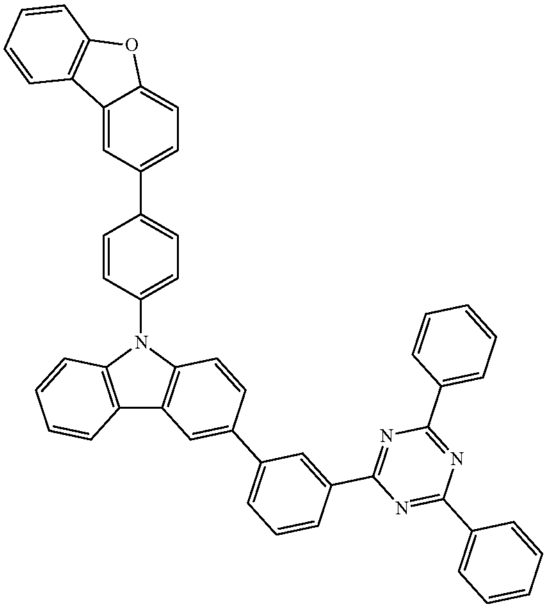
187
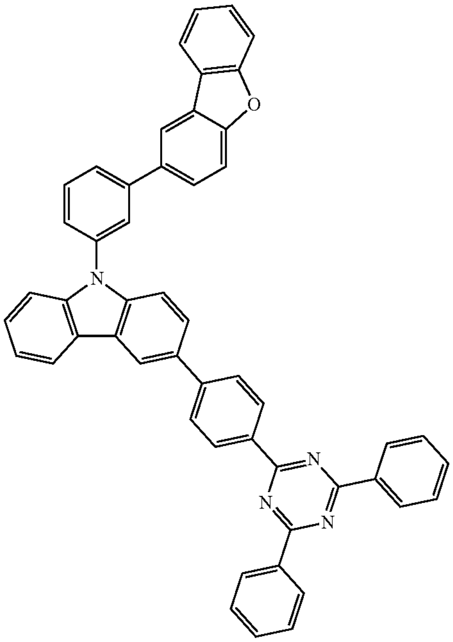

-continued
188
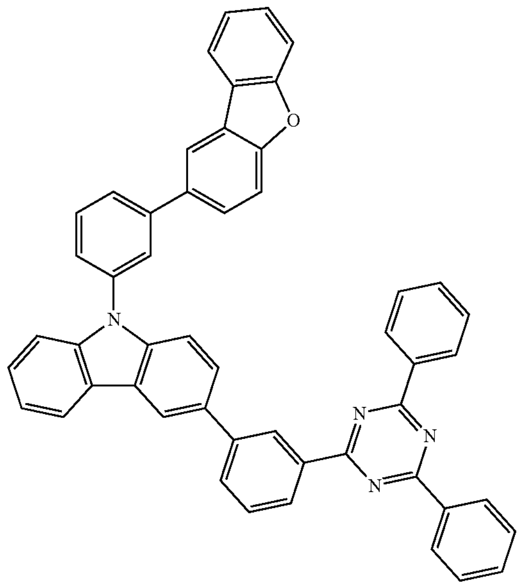
189
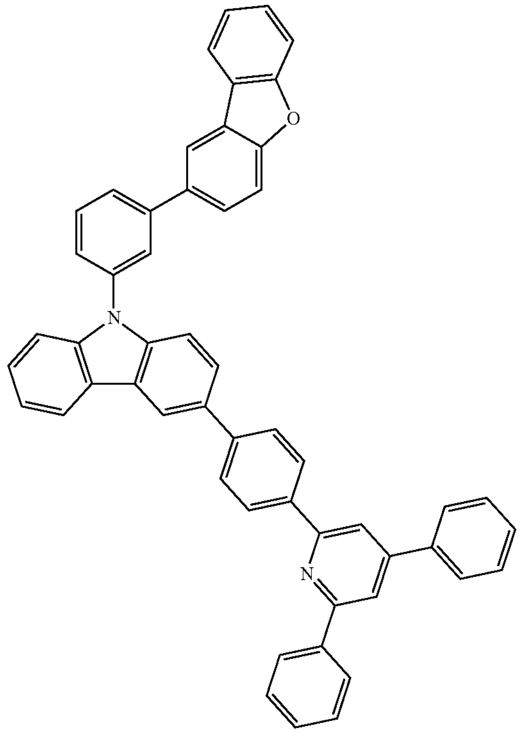
-continued
190
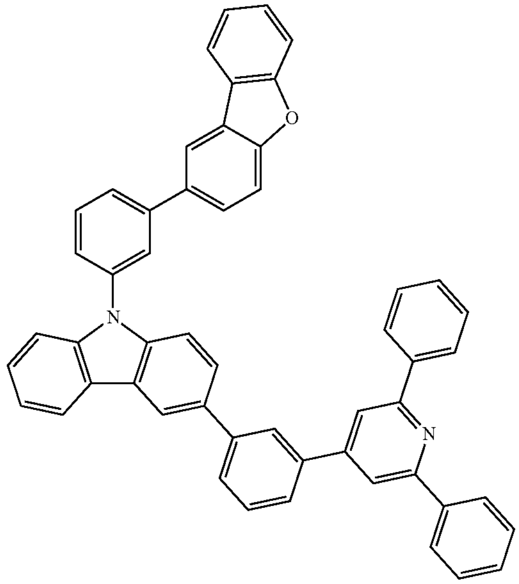
191
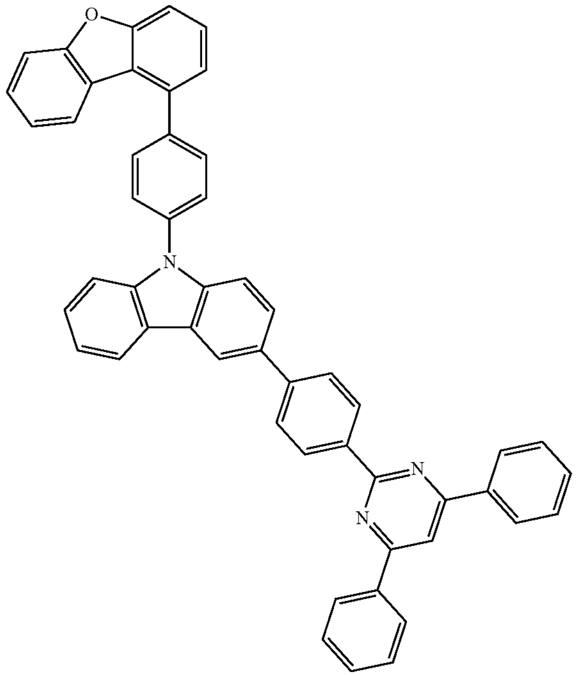

-continued
192
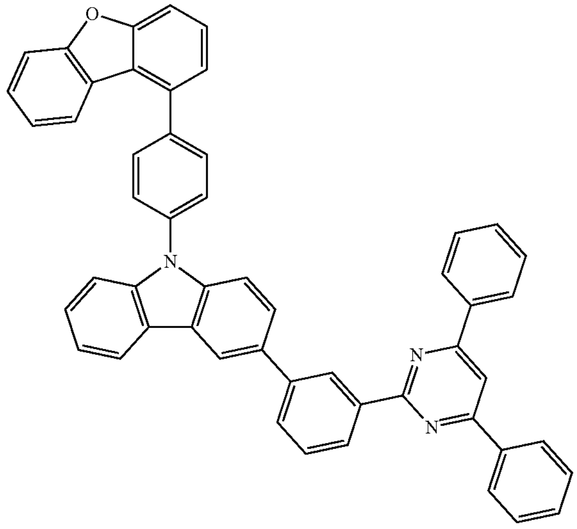
193
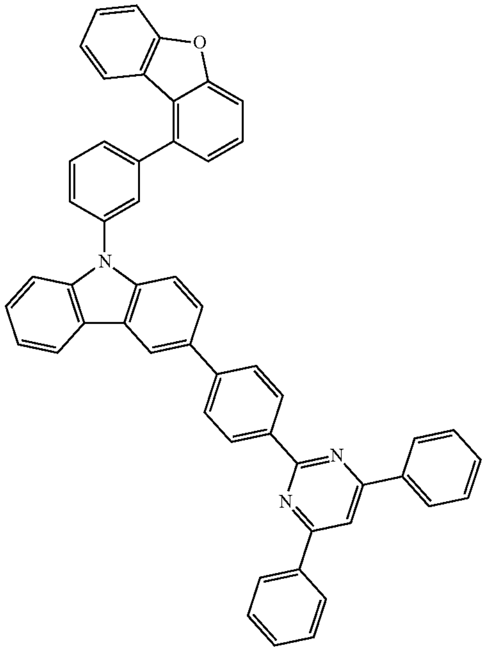
-continued
194
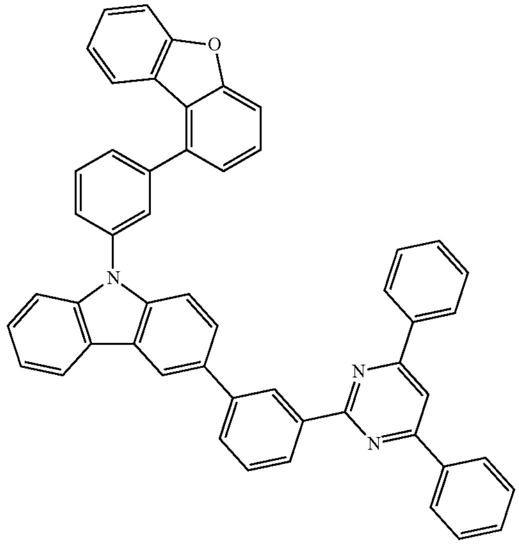
195
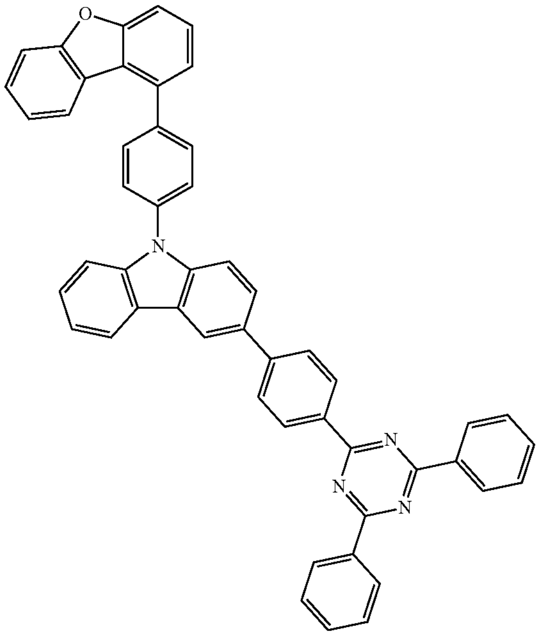

-continued
196
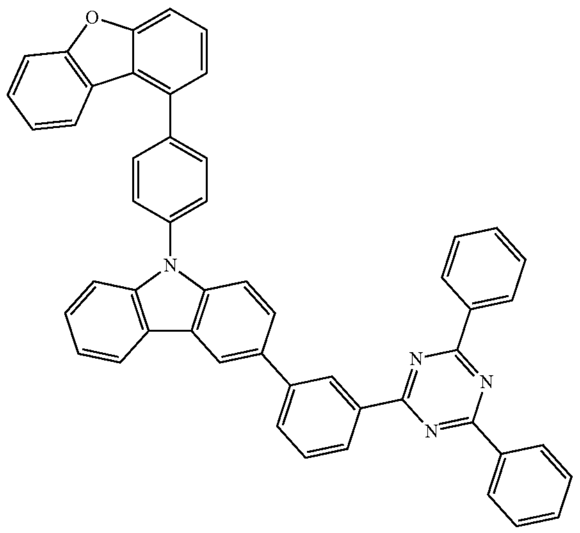
198
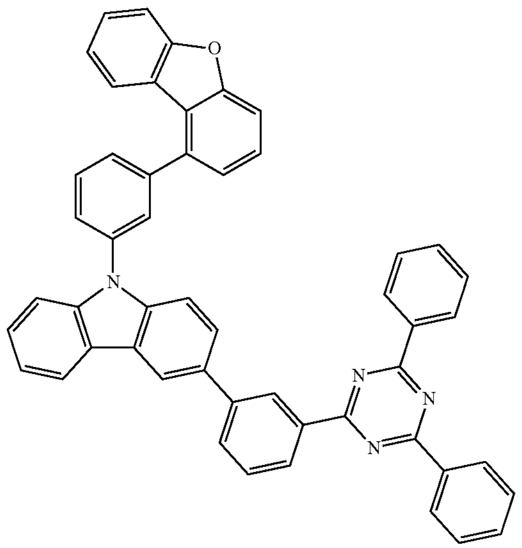
197
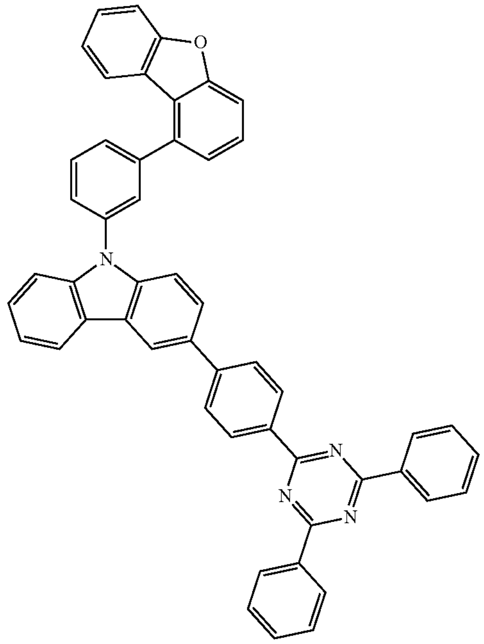
199
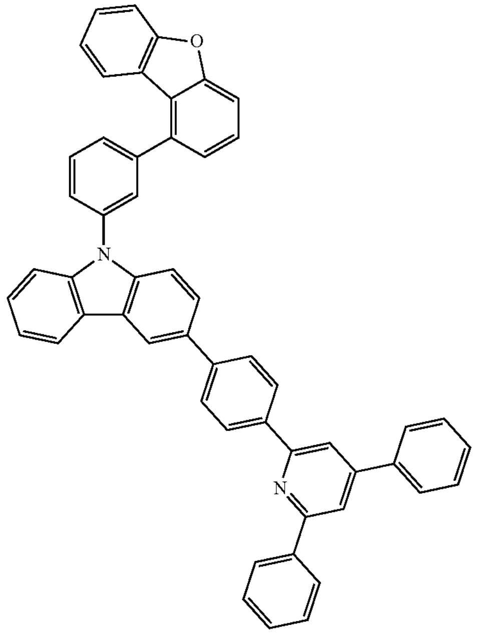

-continued
200
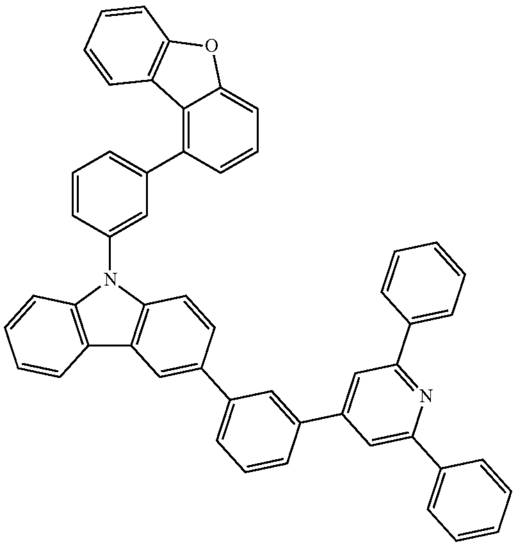
201
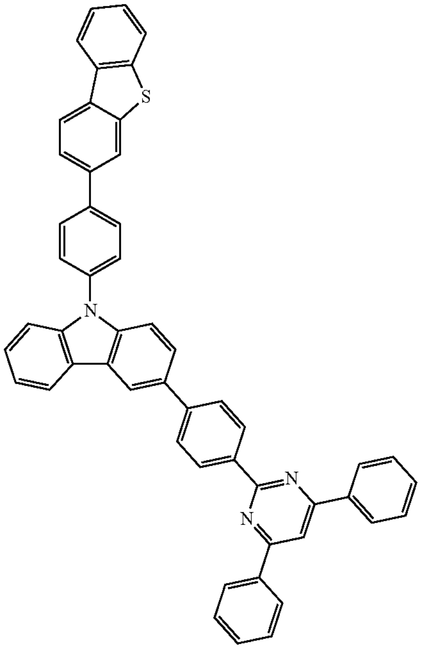
-continued
202
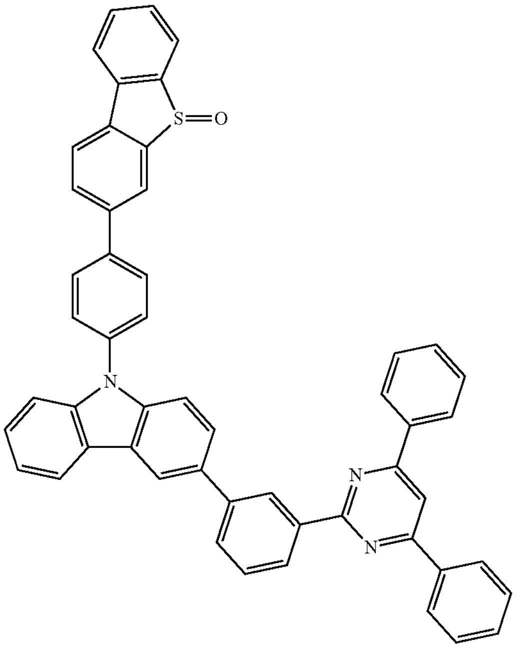
203
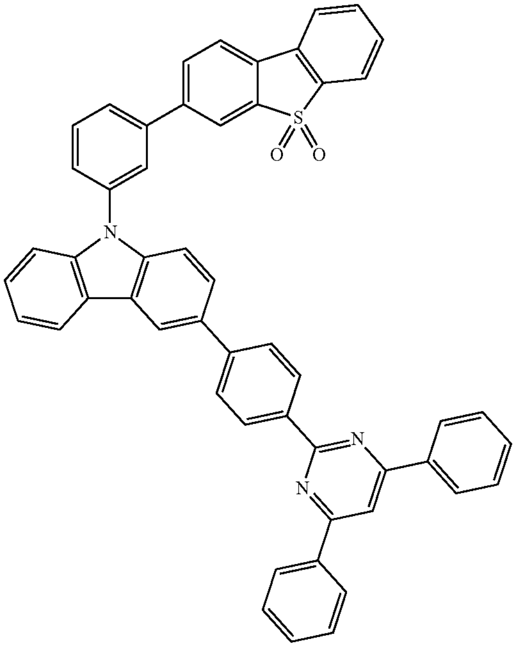

-continued
204
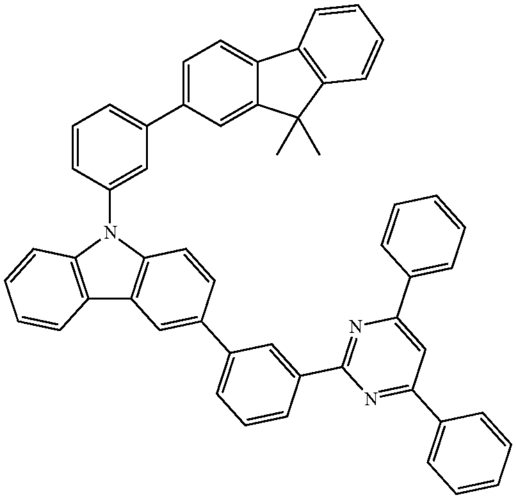
205
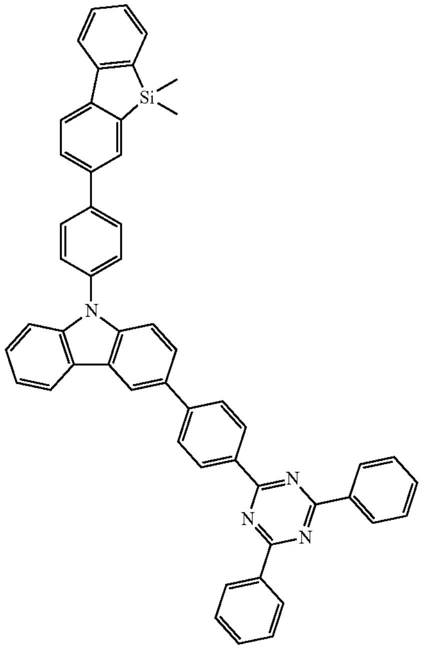
-continued
206
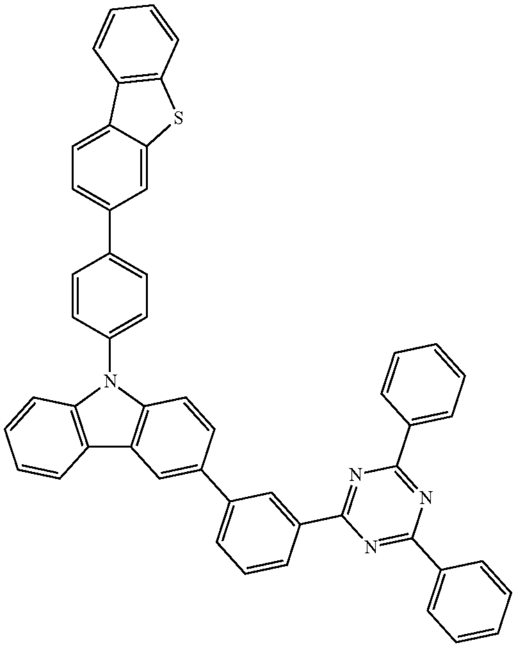
207
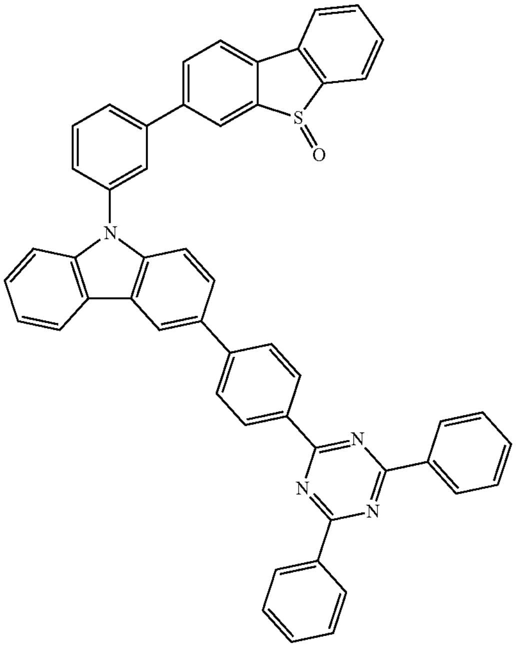

208
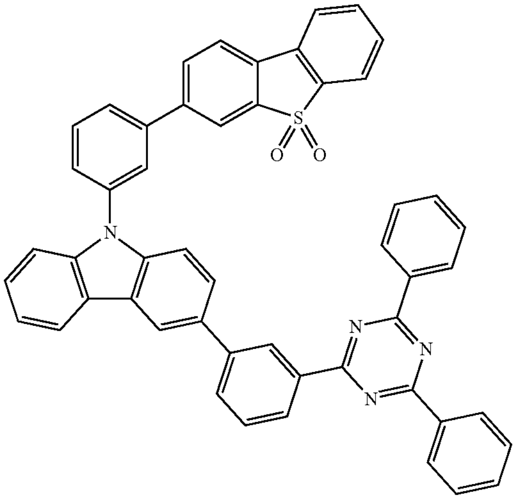
209
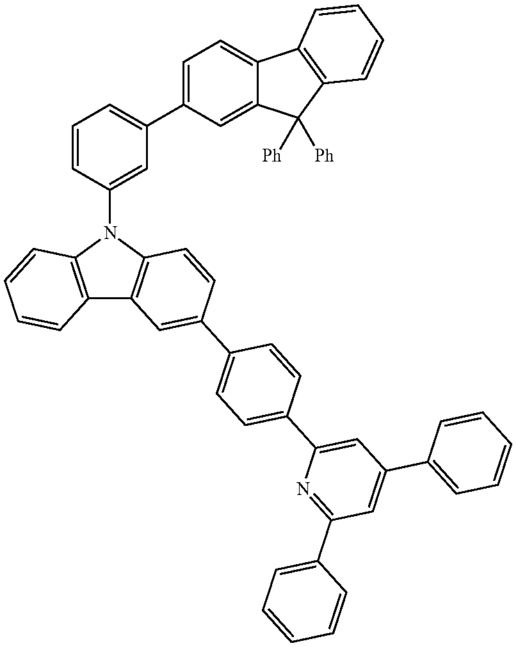
210
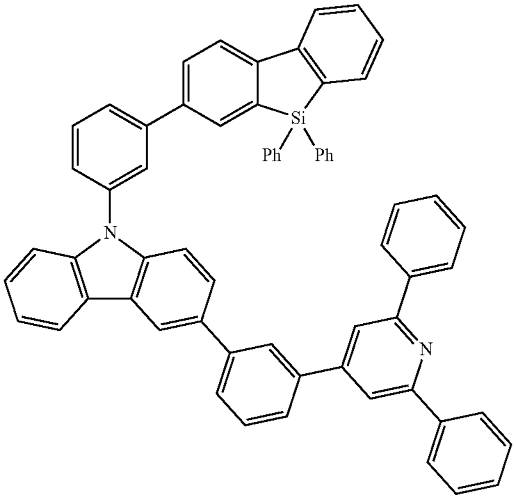
211
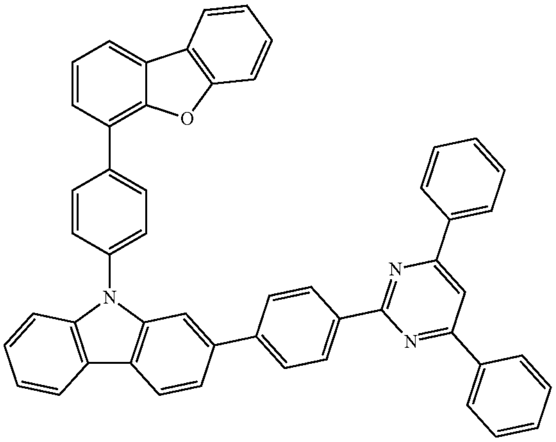
212
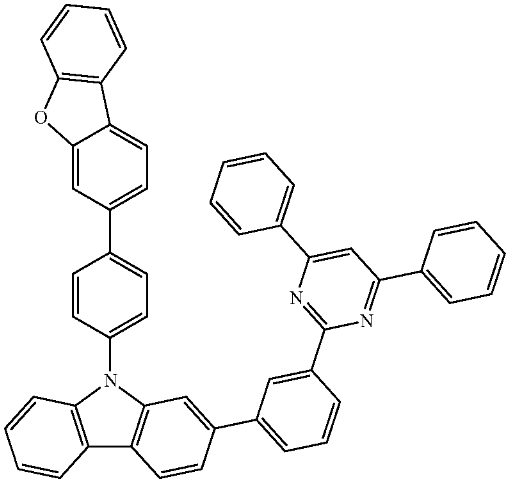

-continued
213
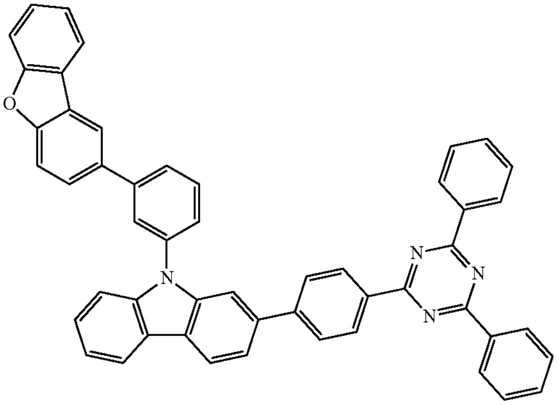
214
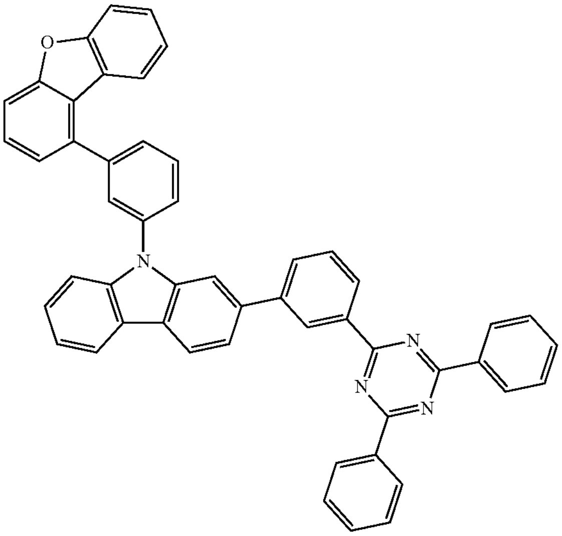
215
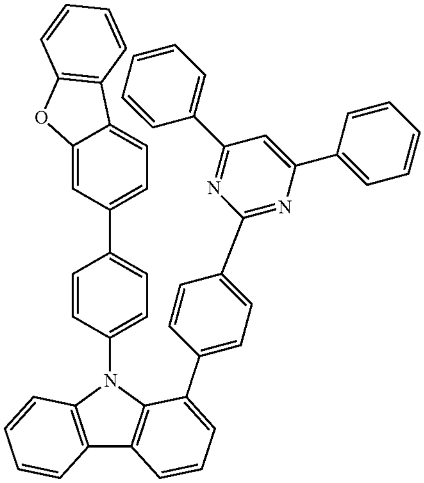
-continued
216
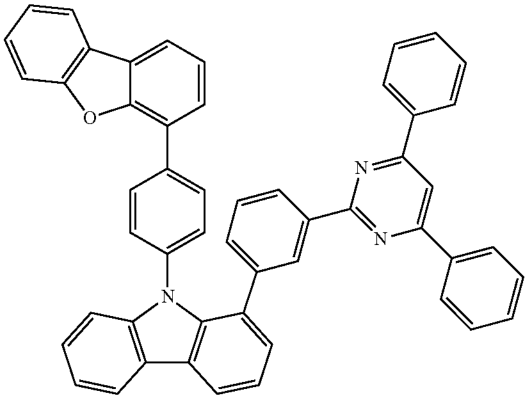
217
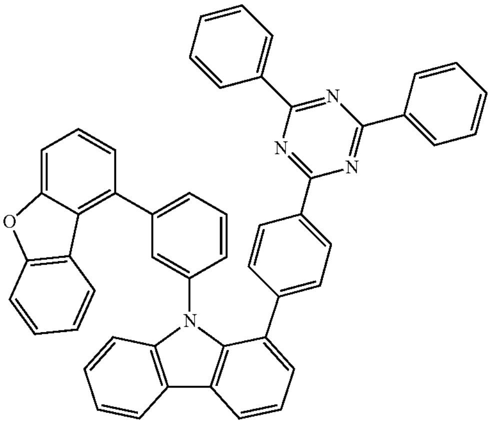
218
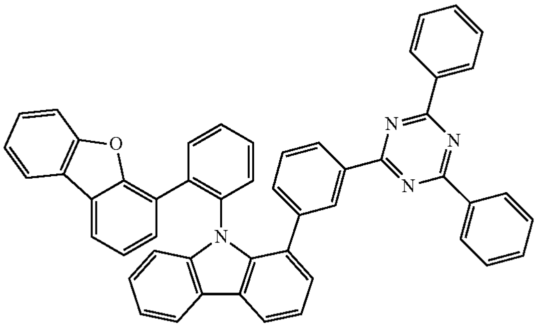

-continued
219
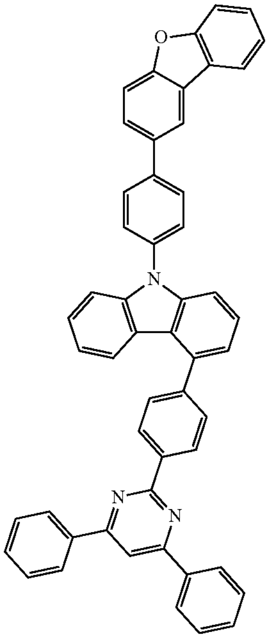
220
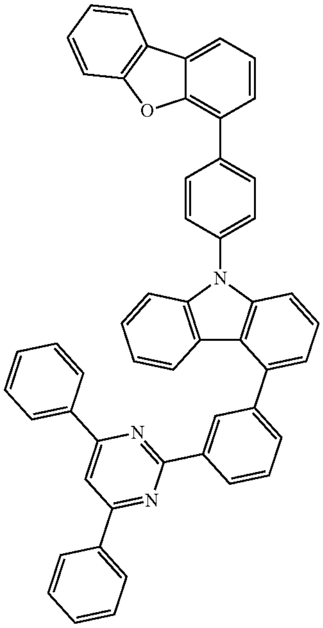
-continued
221
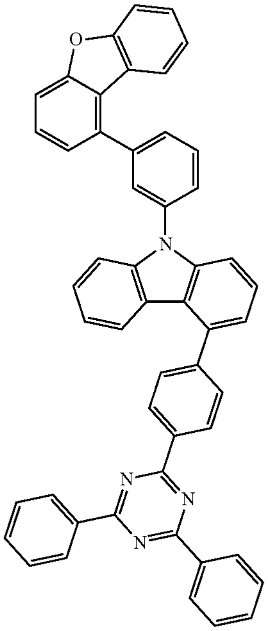
222
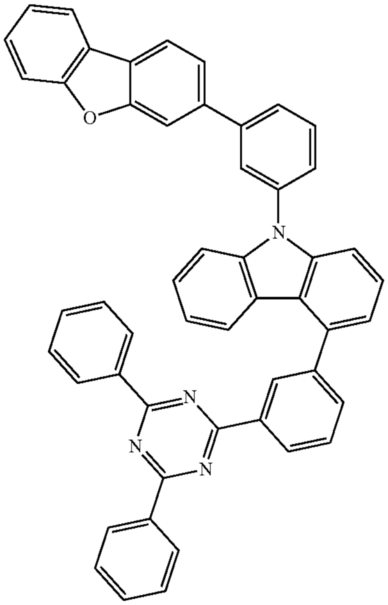

223
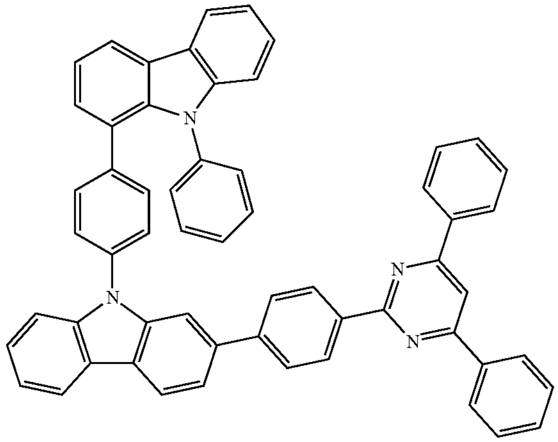
224
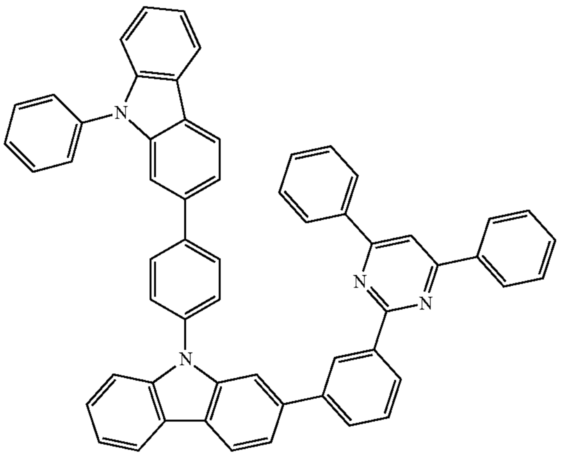
225
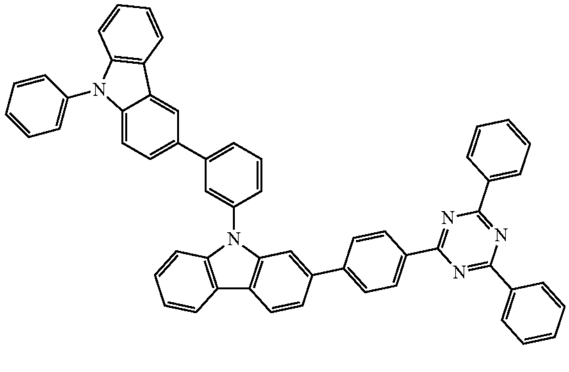
226
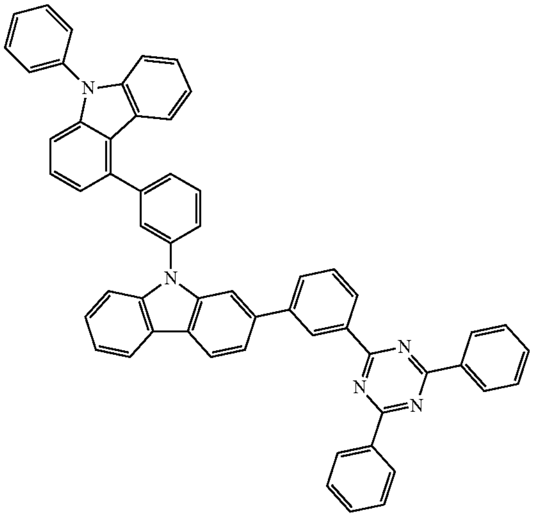
227
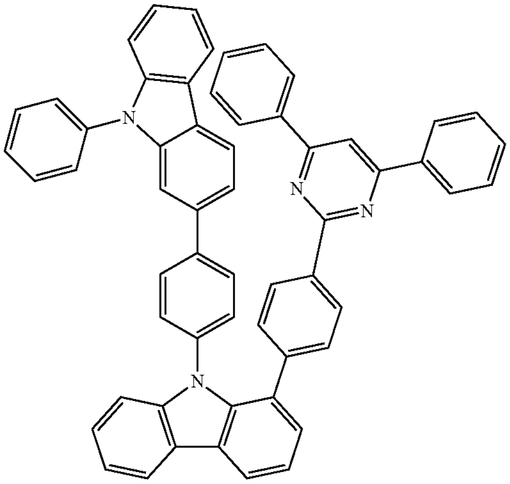
228
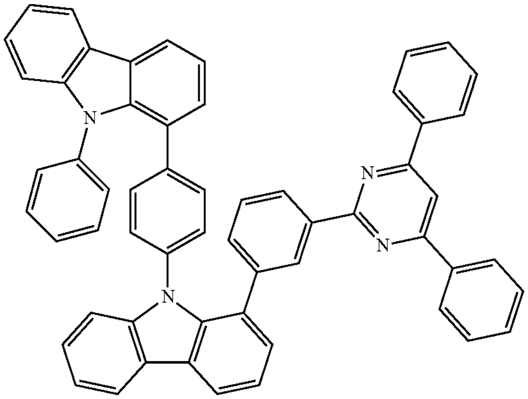

229
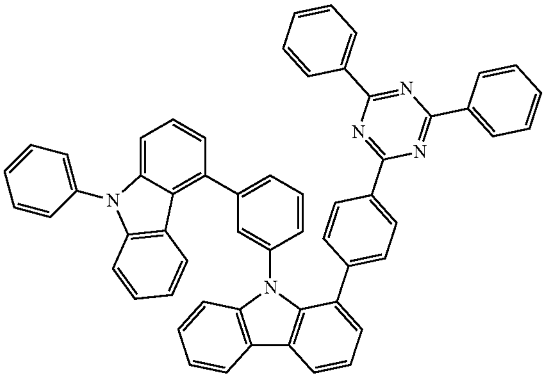
230
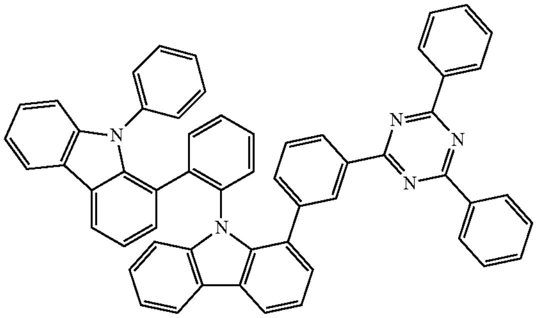
231
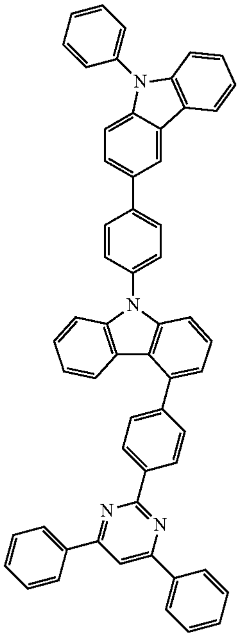
232
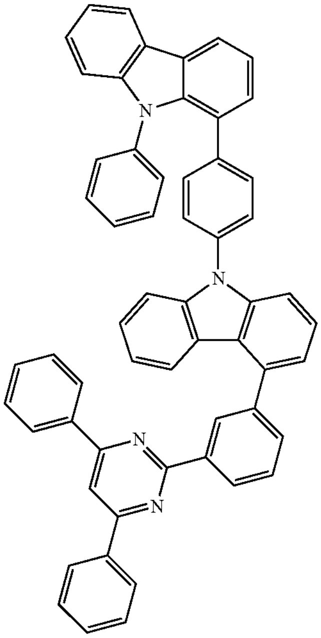
233
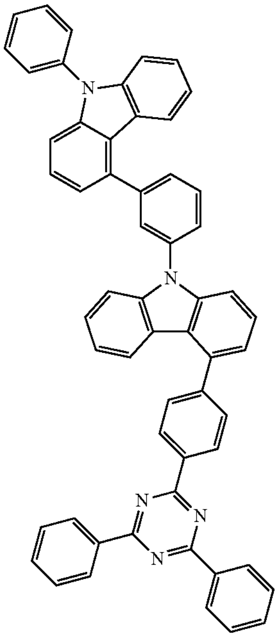

-continued
234
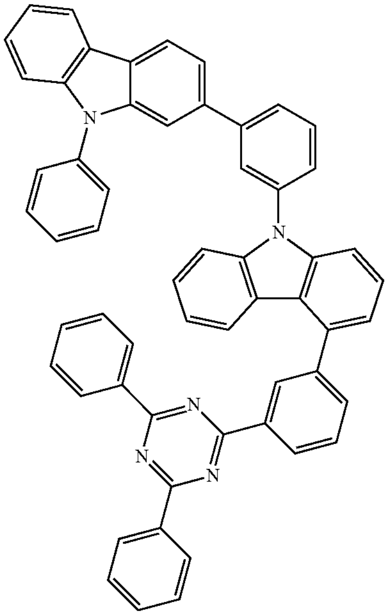
235
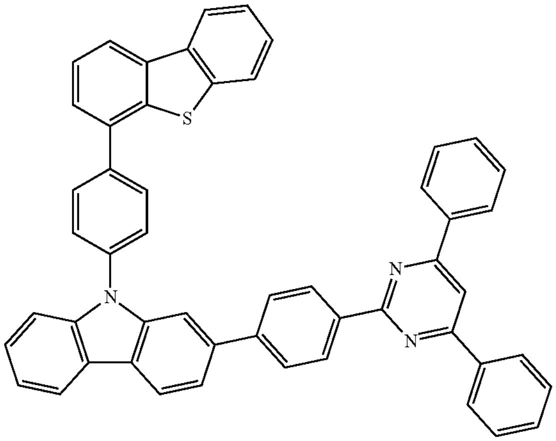
236
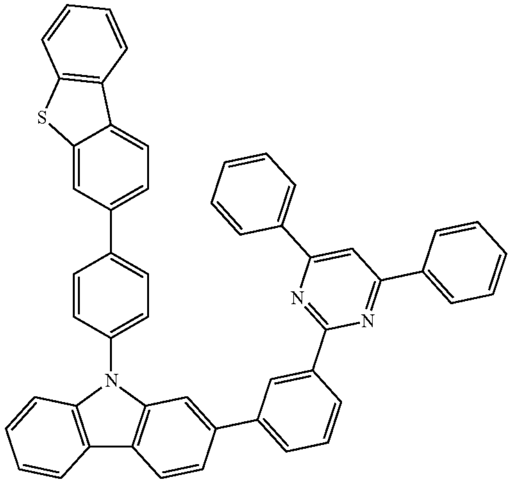
-continued
237
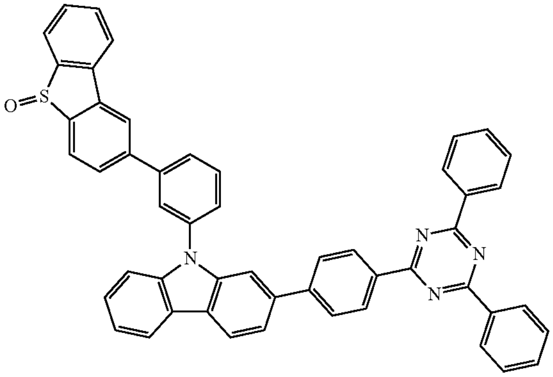
238
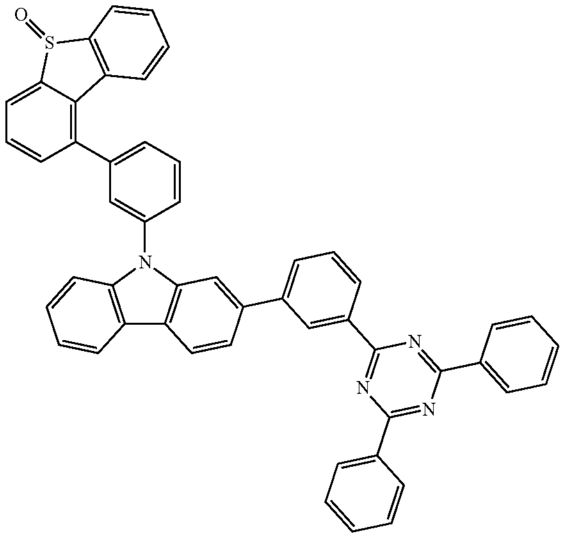
239
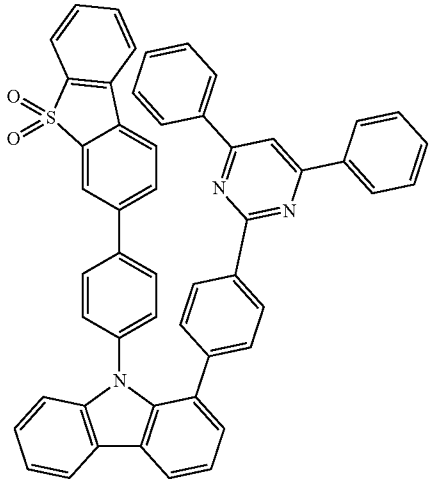

-continued
240
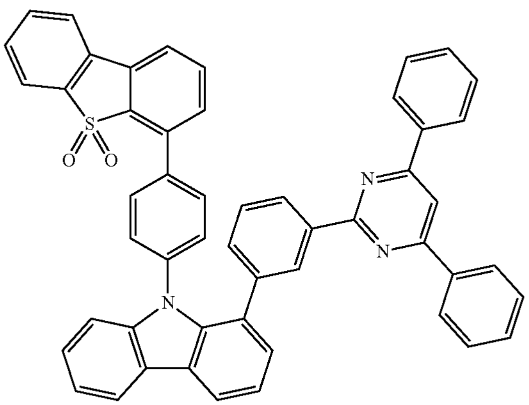
241
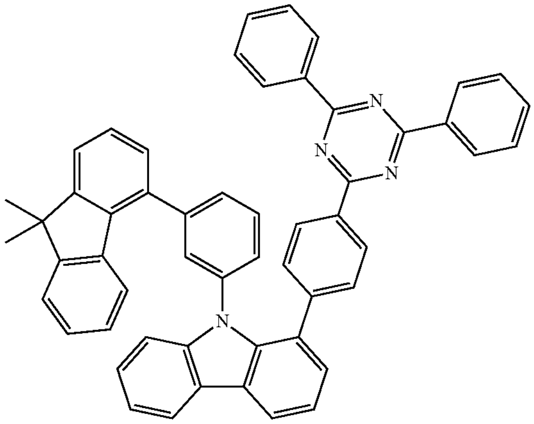
242
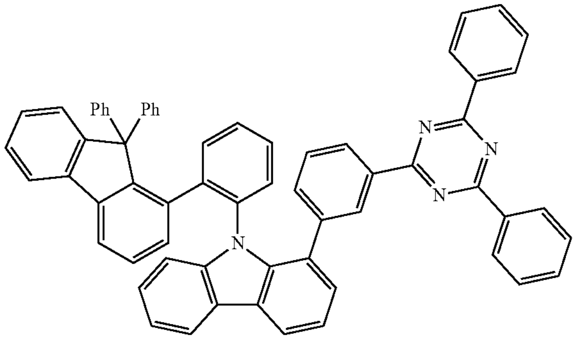
-continued
243
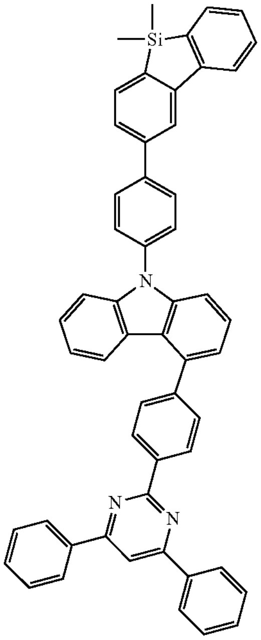
244
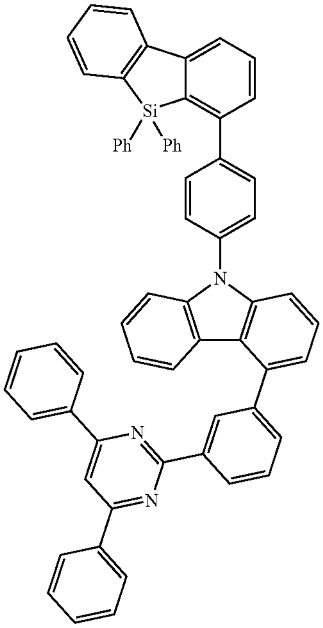

-continued
245
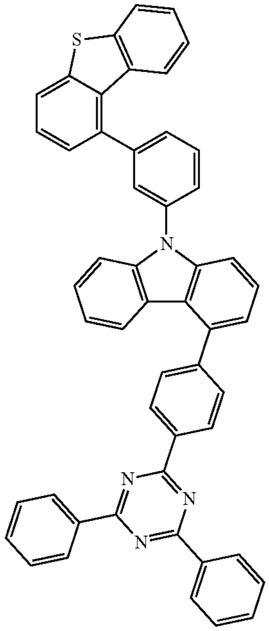
246
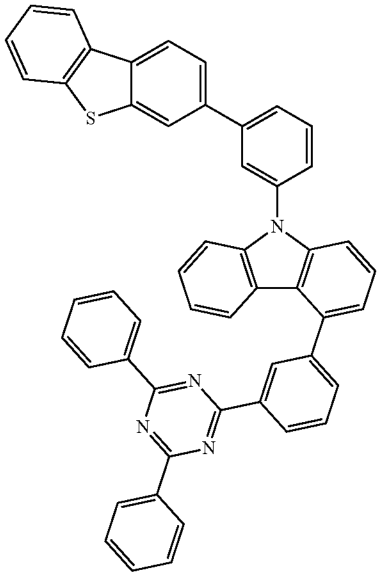
-continued
247
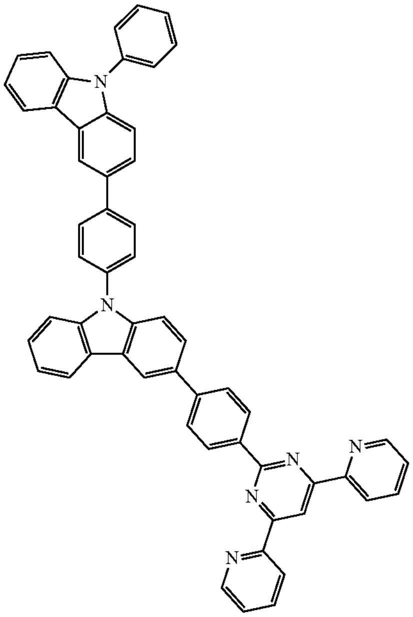
248
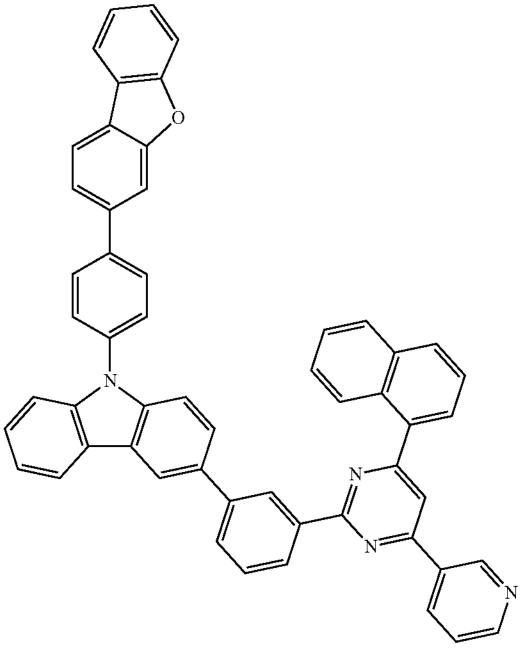

-continued
249
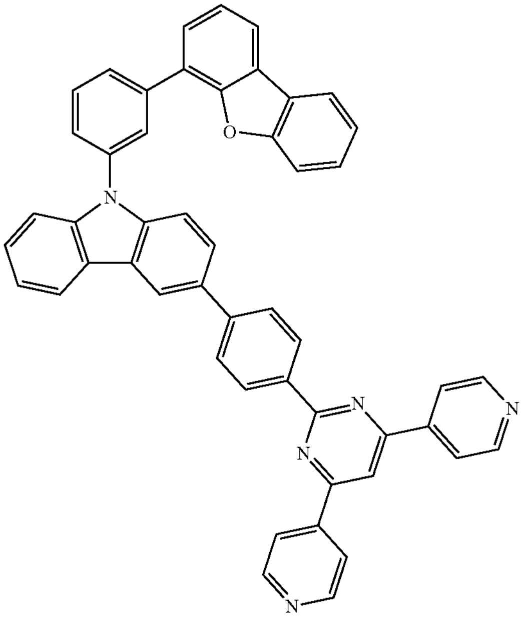
250
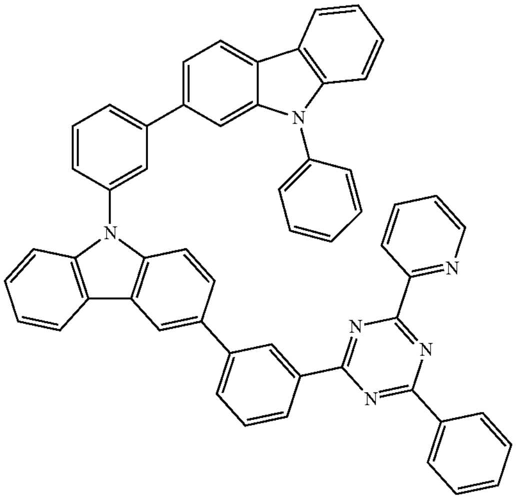
-continued
251
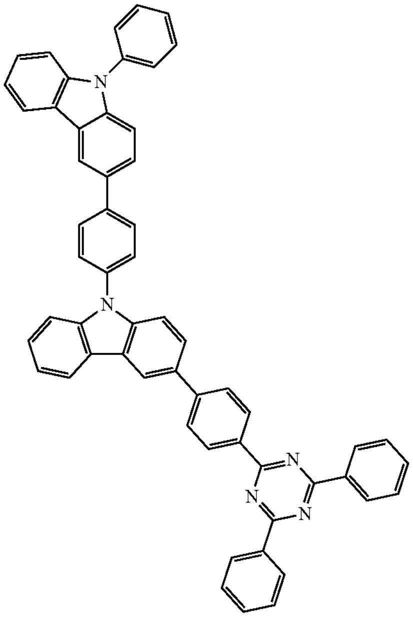
252
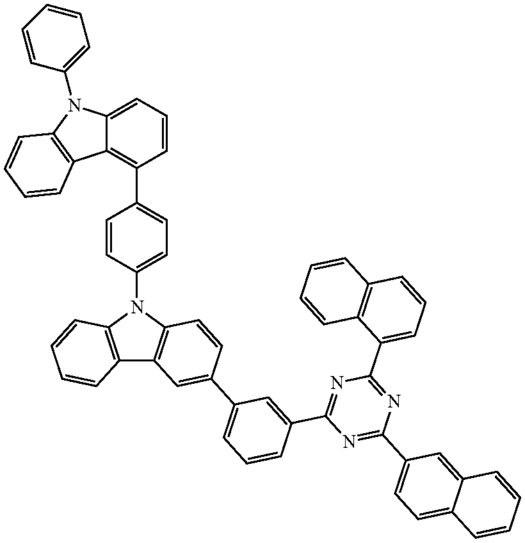

253
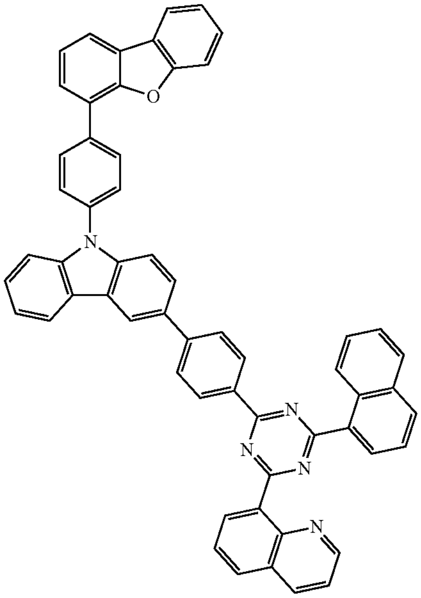
254
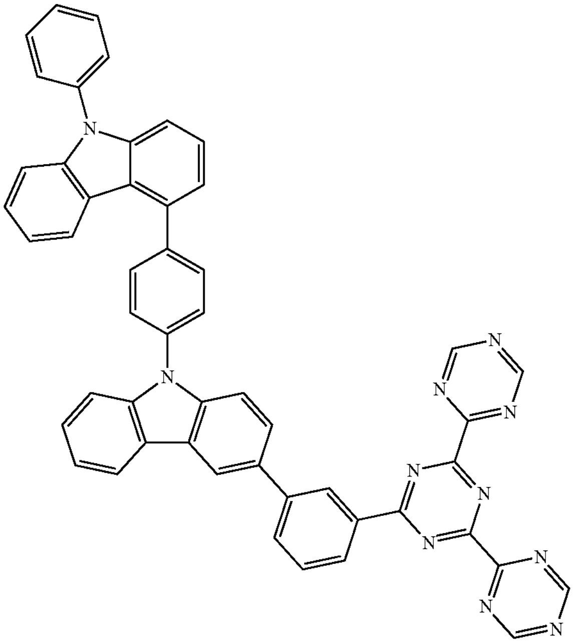
255
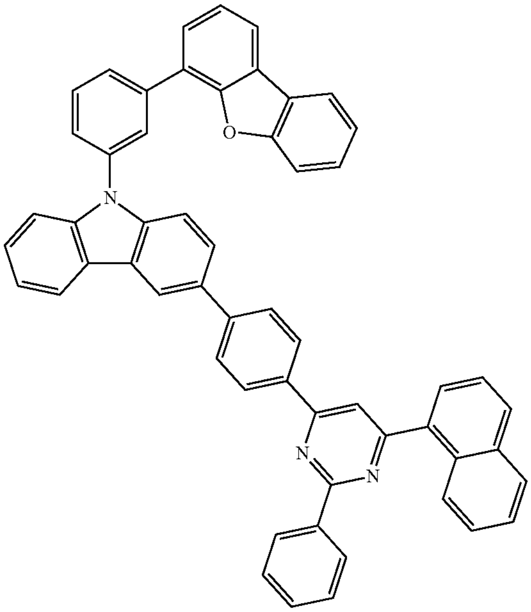
256
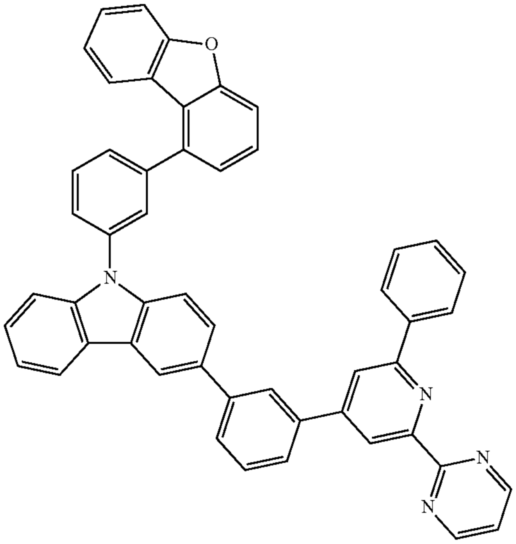

-continued
257
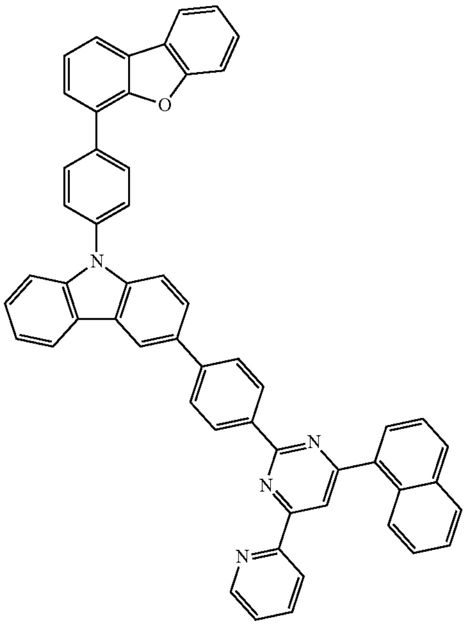
258
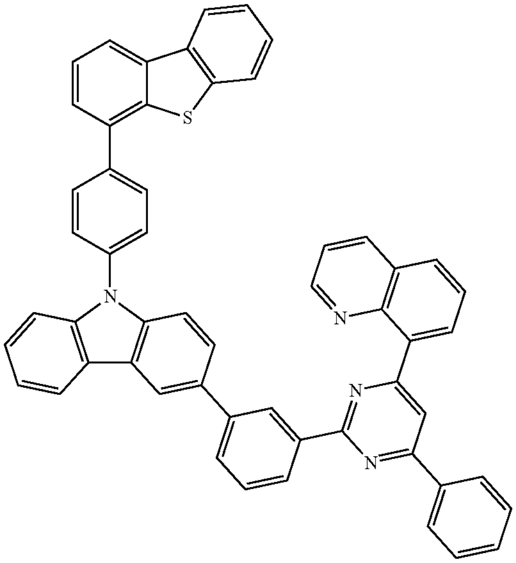
-continued
259
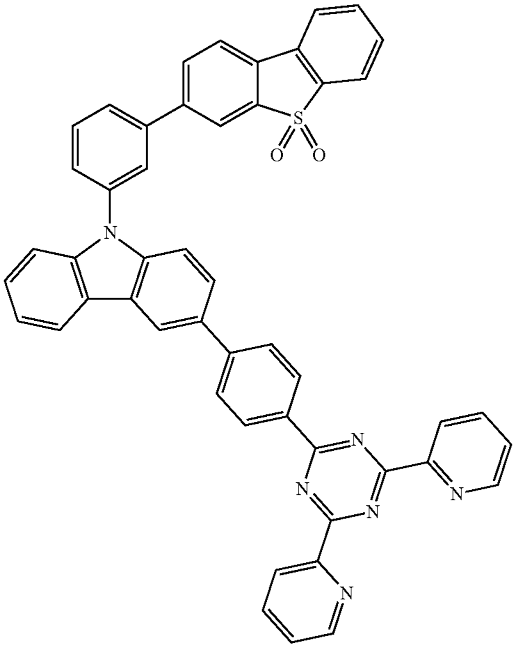
260
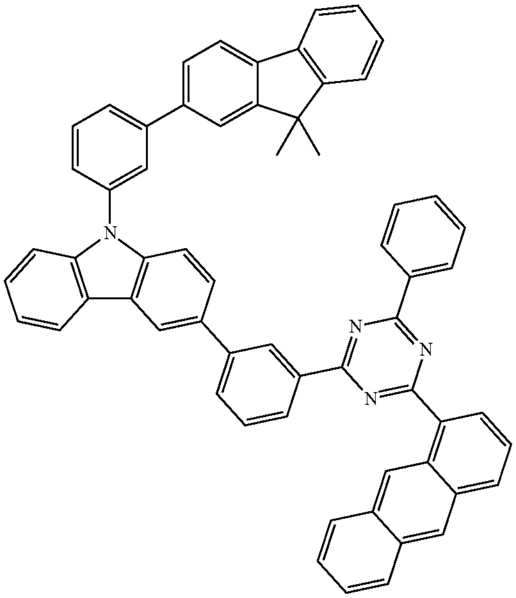

261
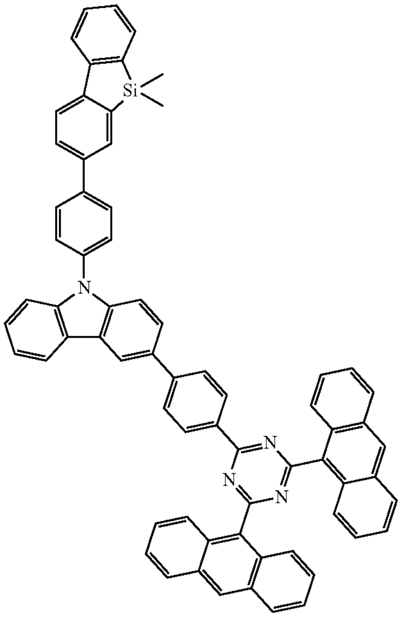
262
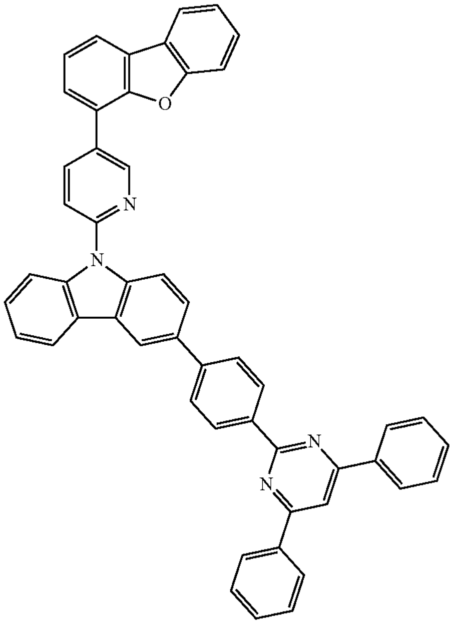
263
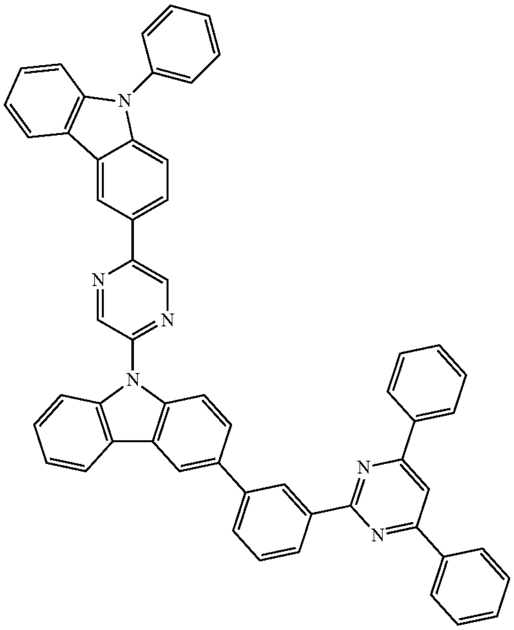
264
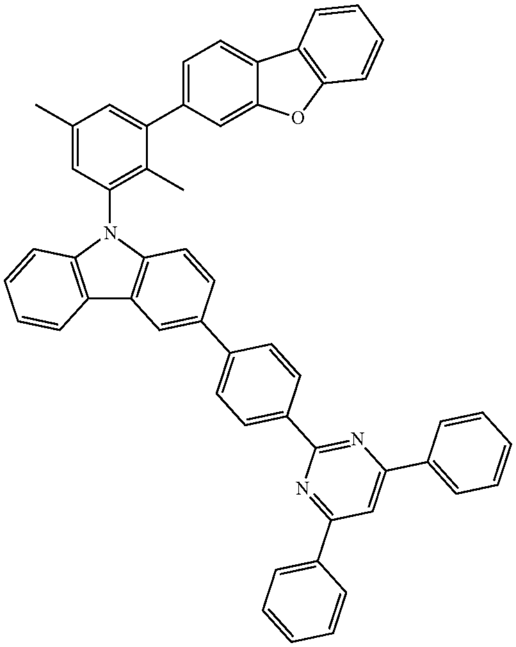

-continued
265
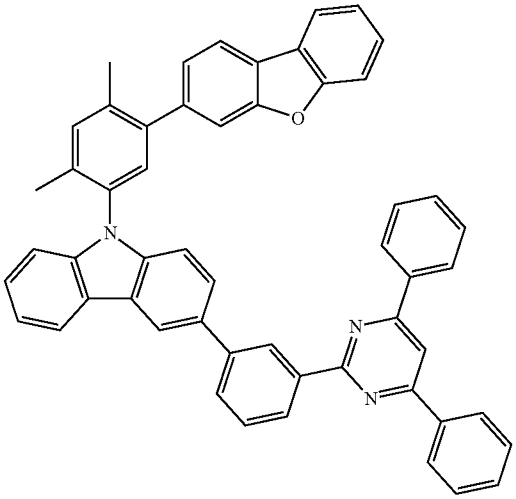
266
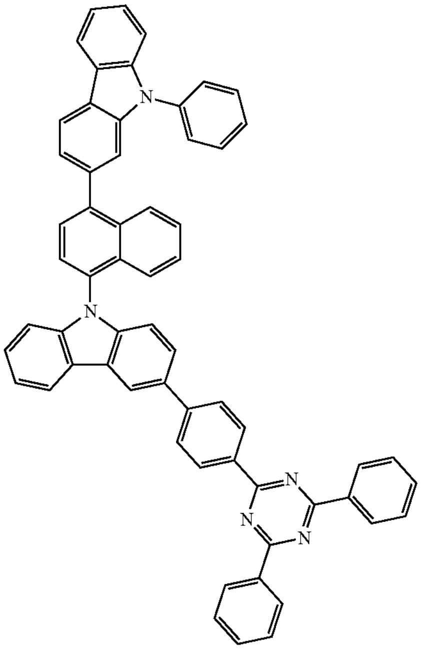
-continued
267
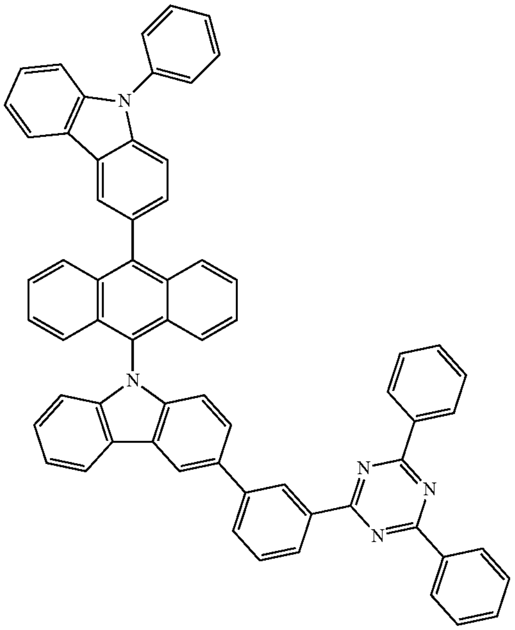
268
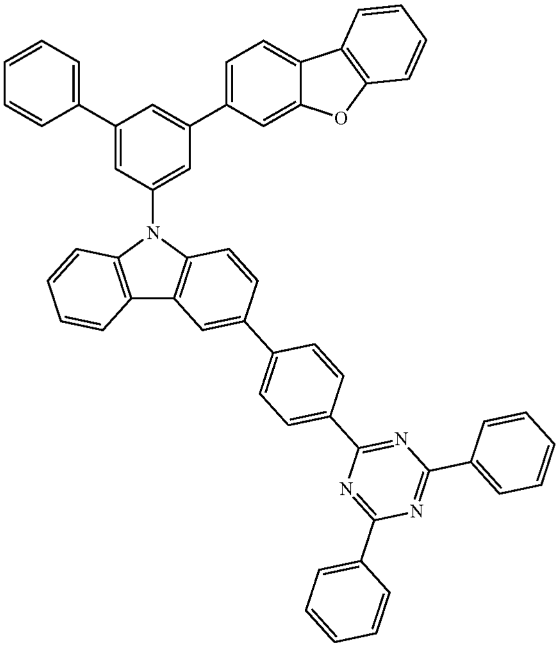

-continued
269
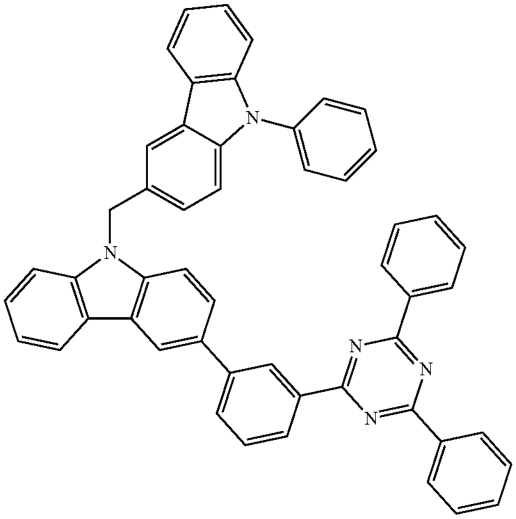
270
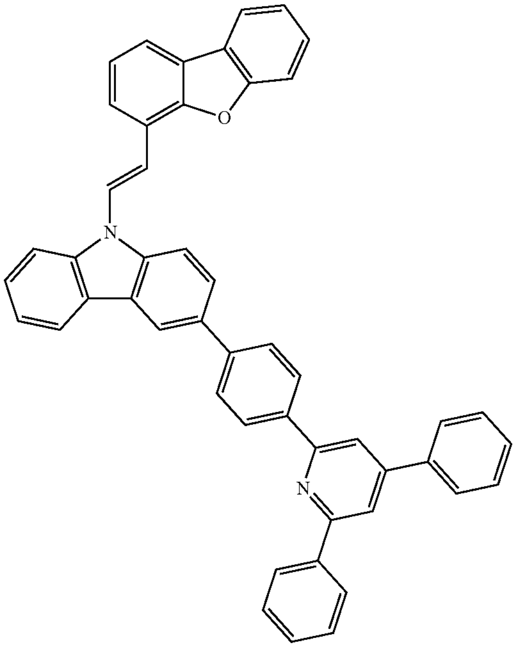
-continued
271
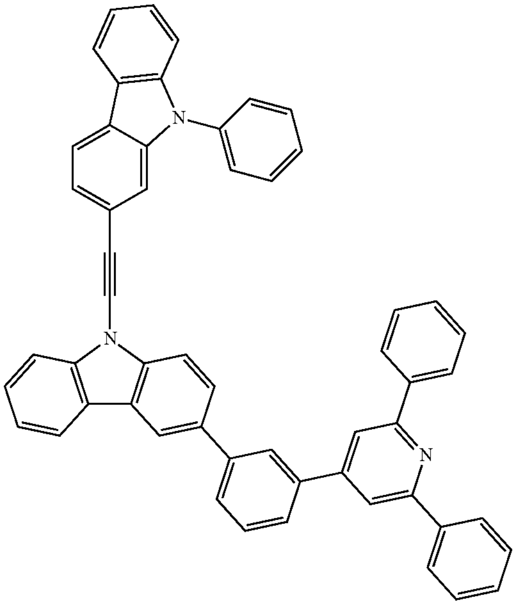
272
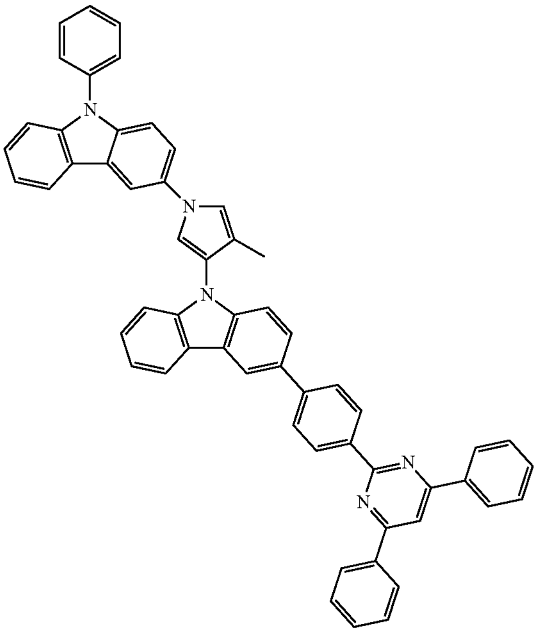

-continued
273
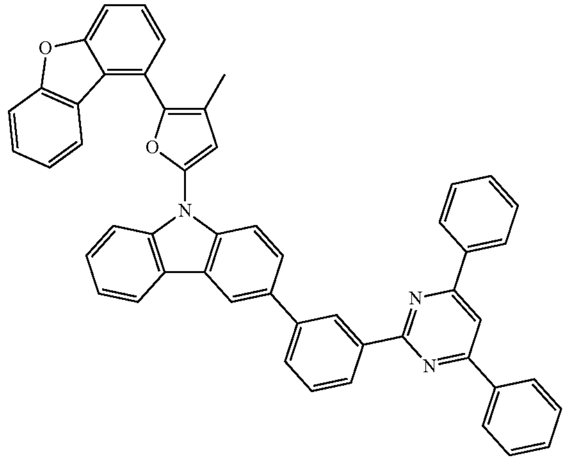
274
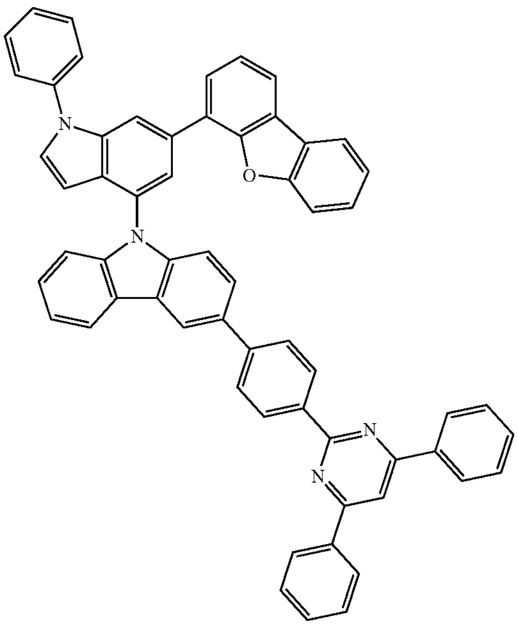
275
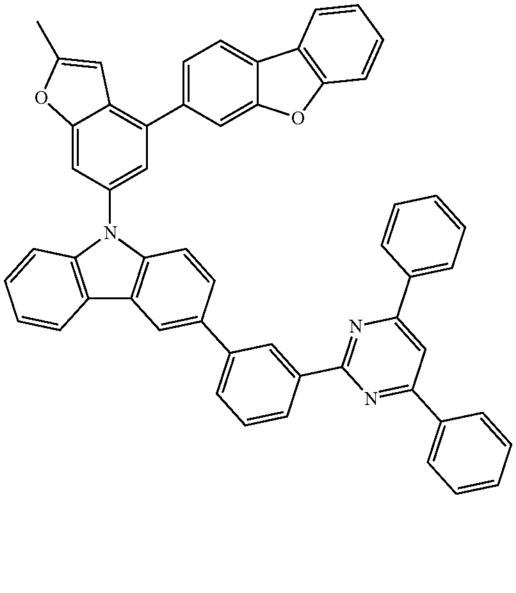
-continued
276
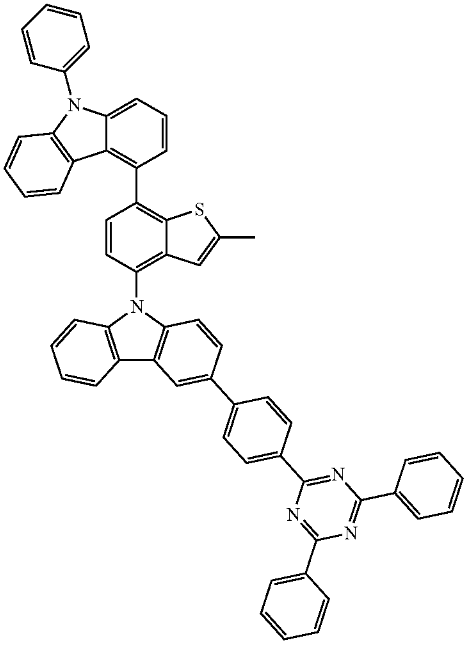
277
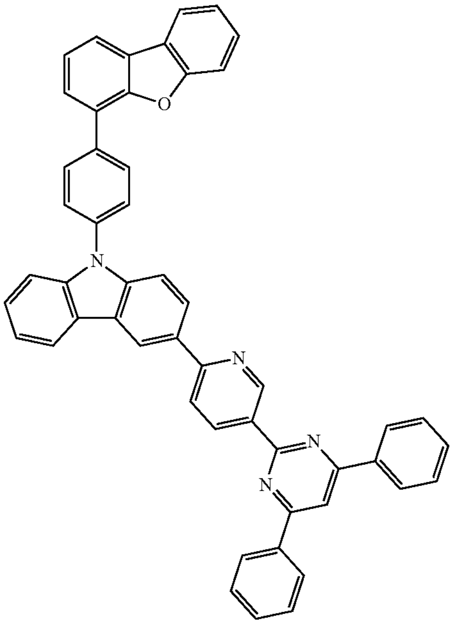

-continued
278
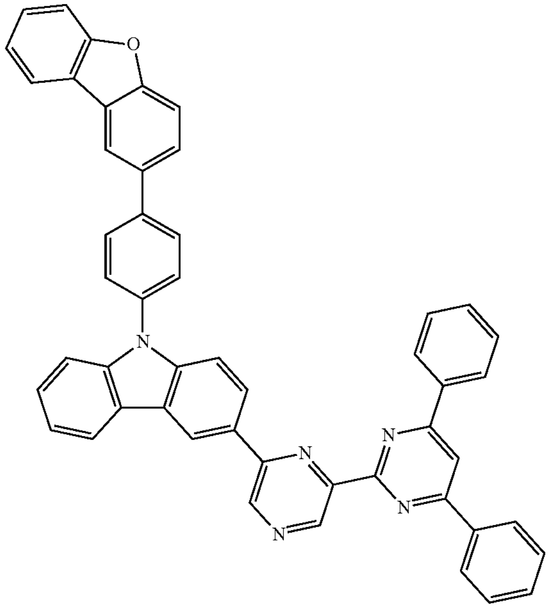
279
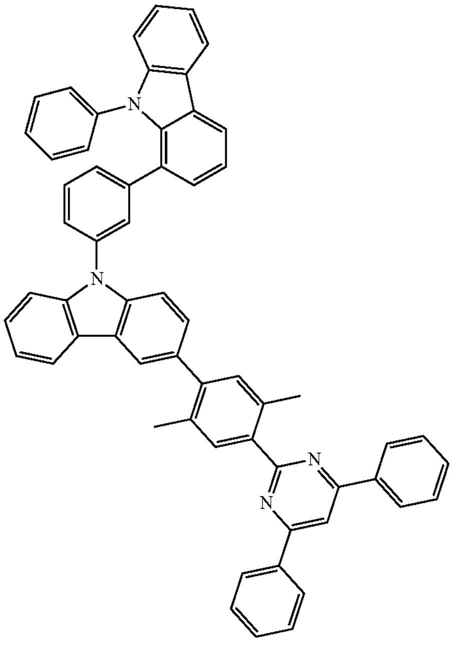
-continued
280
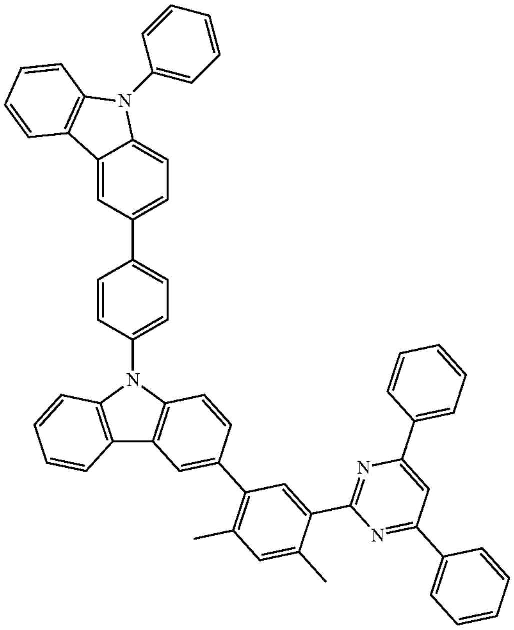
281
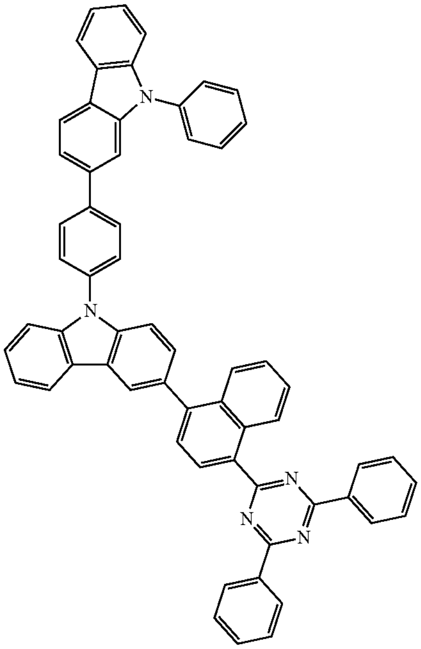

-continued
282
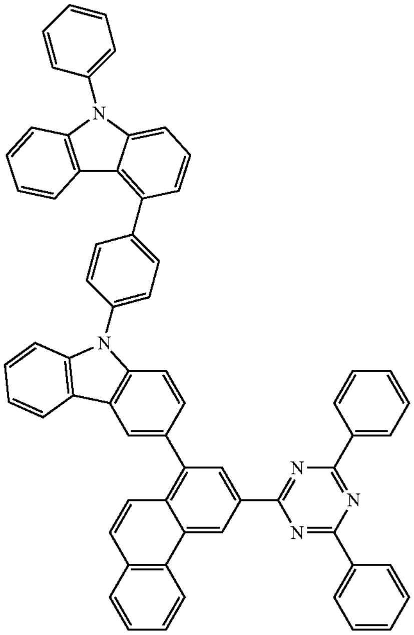
283
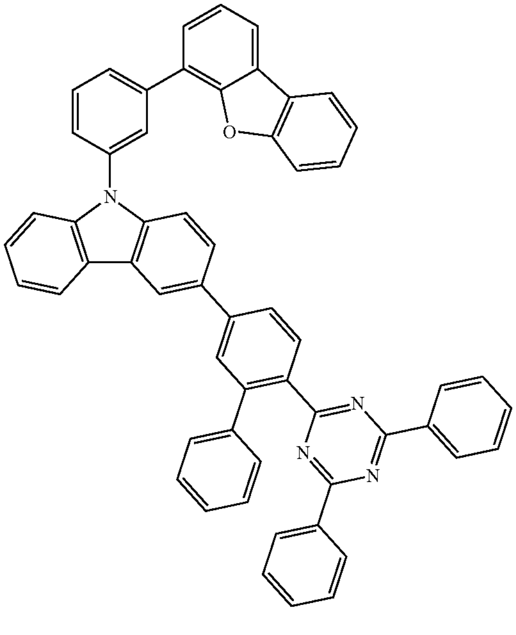
-continued
284
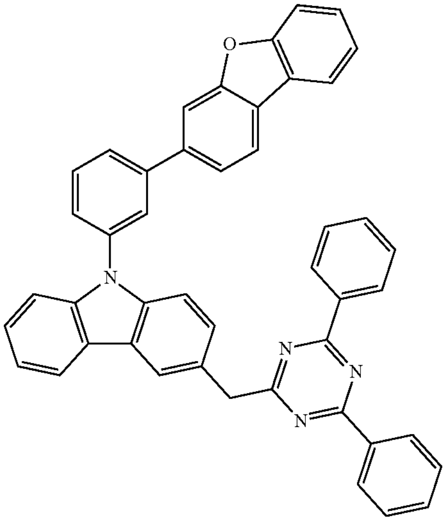
285
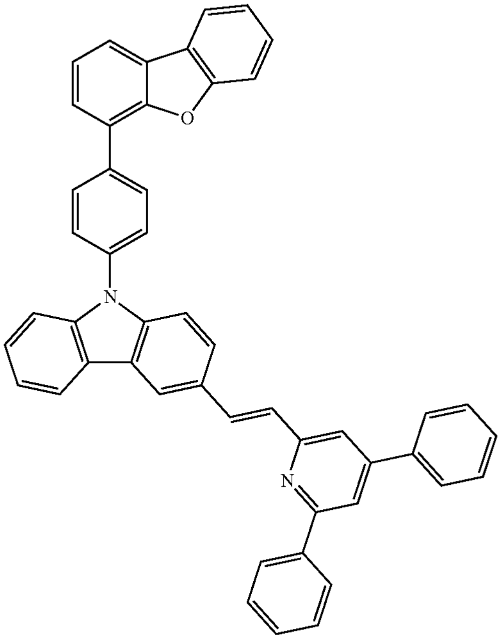

286
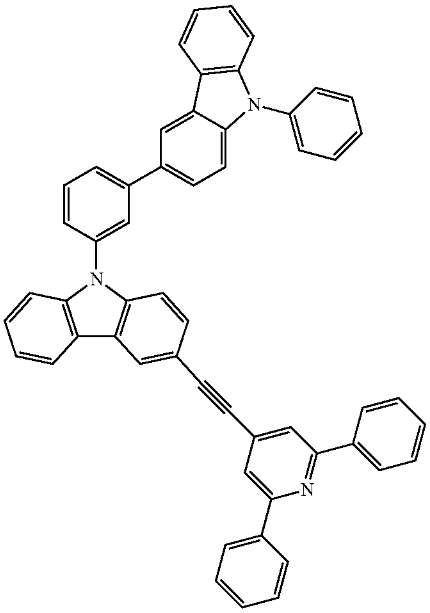
287
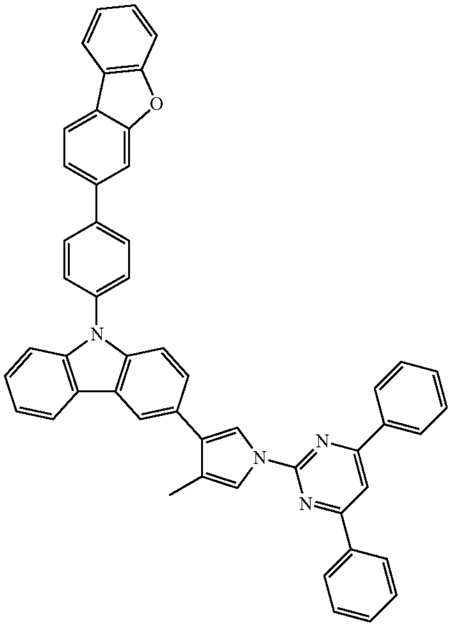
288
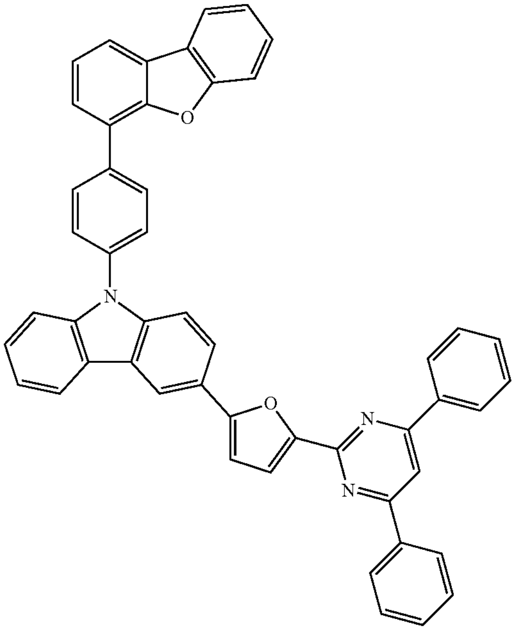
289
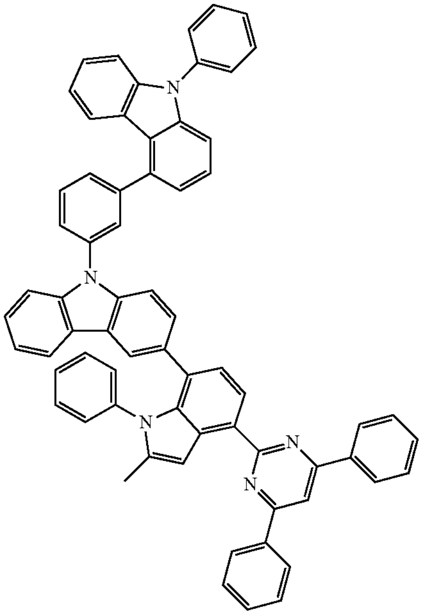

-continued
290
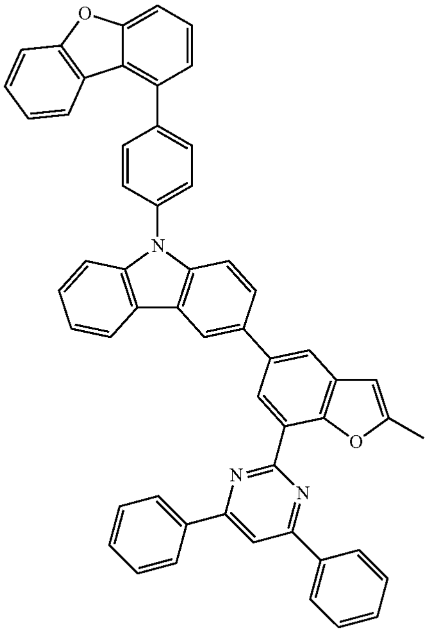
291
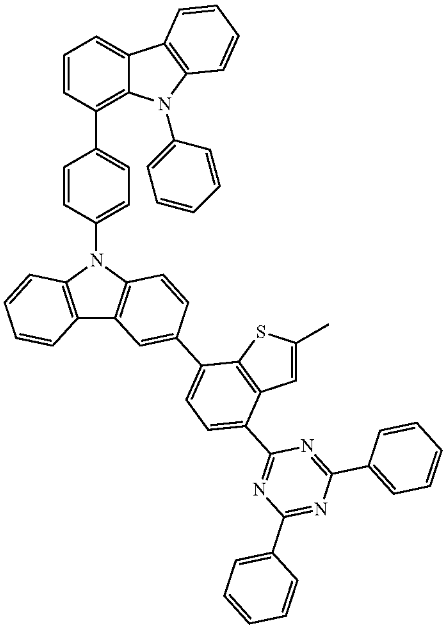
-continued
292
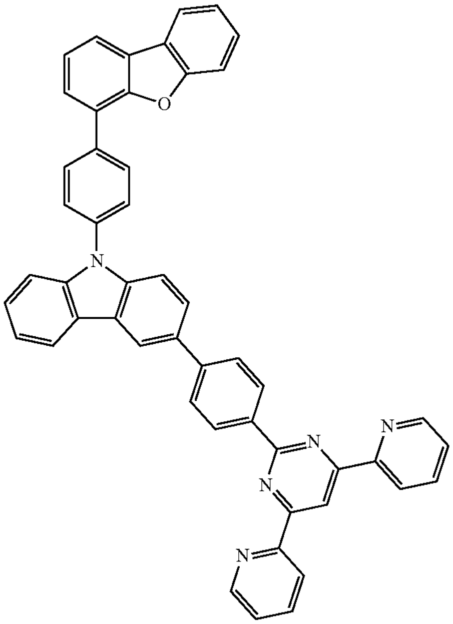
293
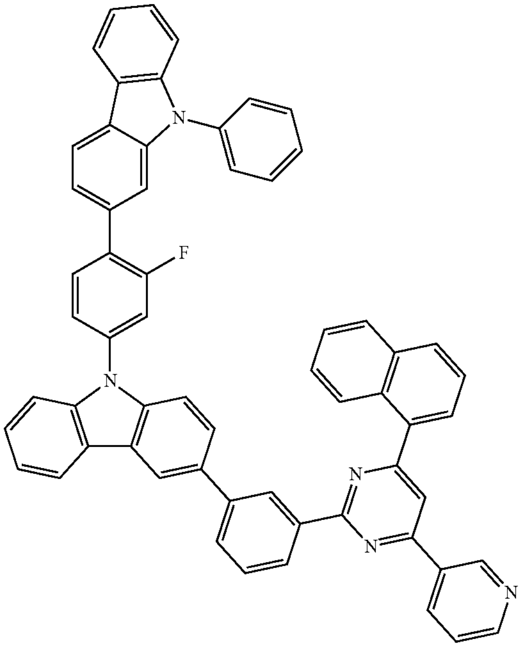

-continued
294
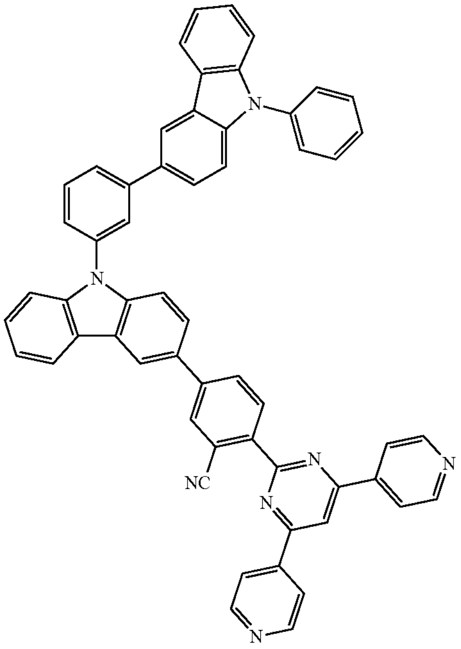
295
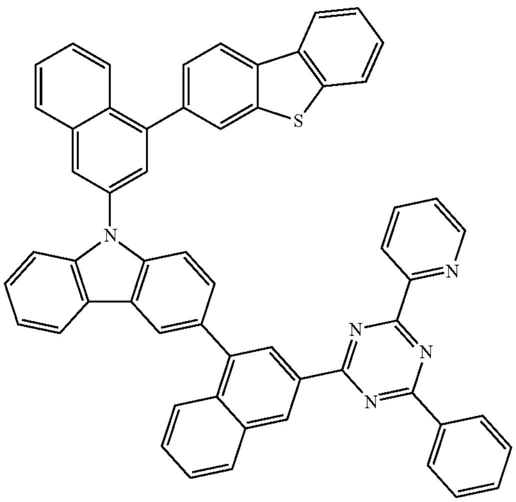
-continued
296
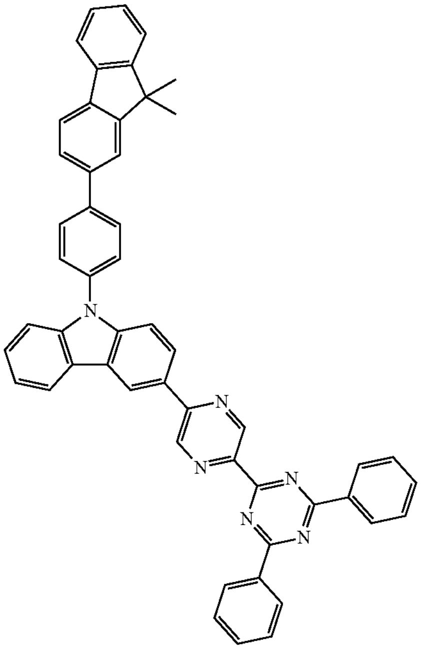
297
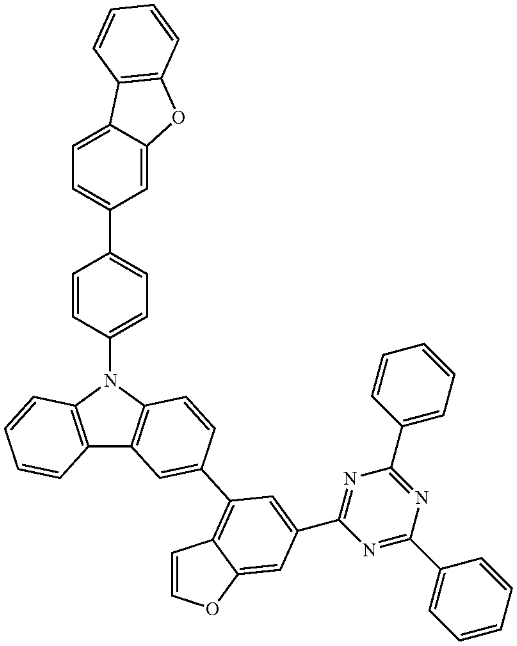

-continued
298
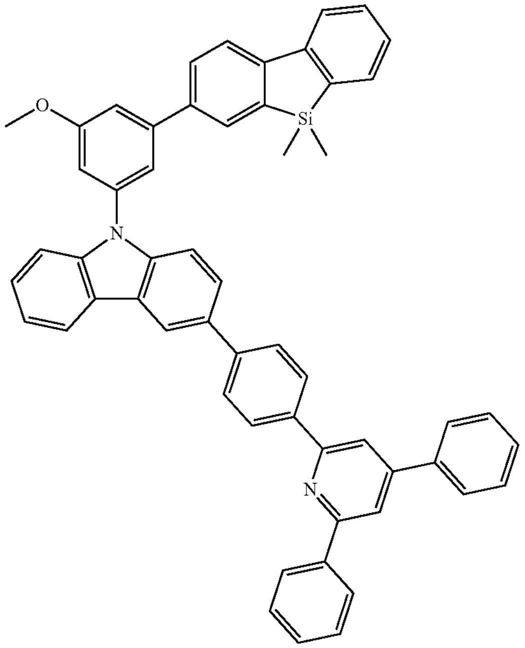
299
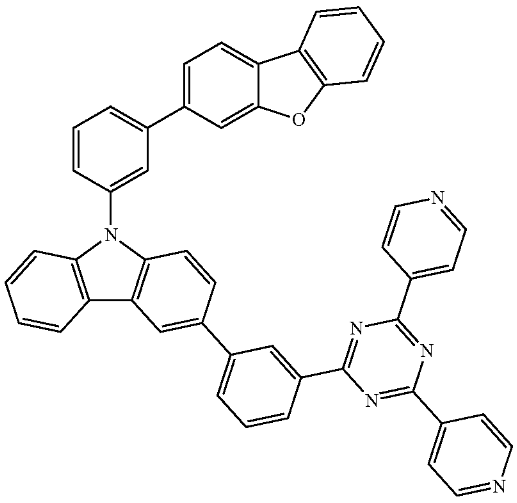
-continued
300
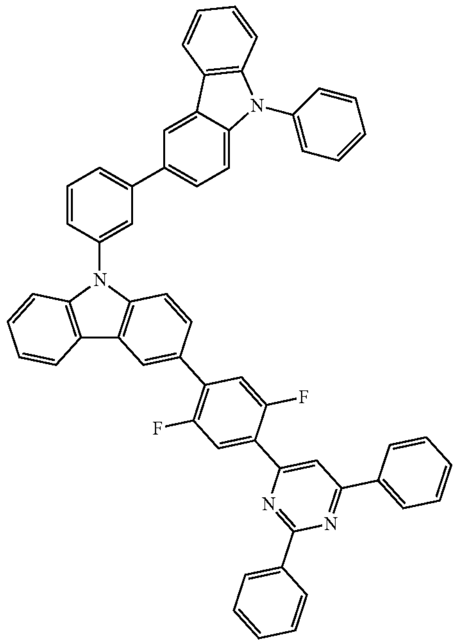
301
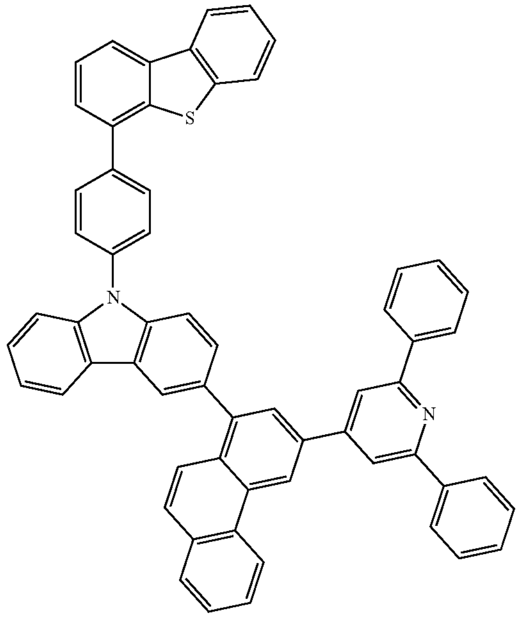

-continued
302
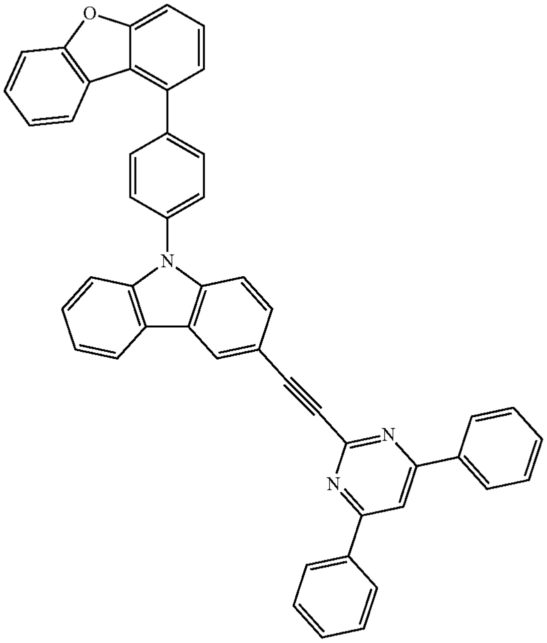
303
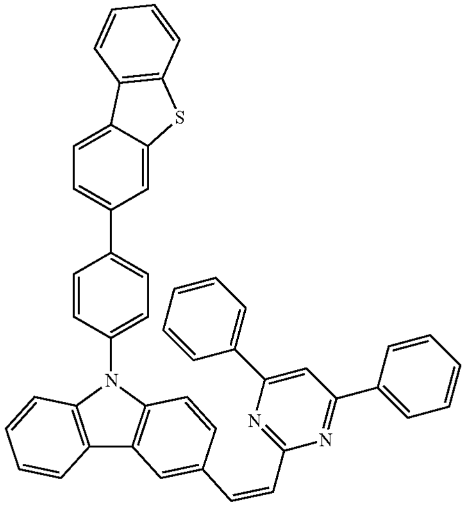
-continued
304
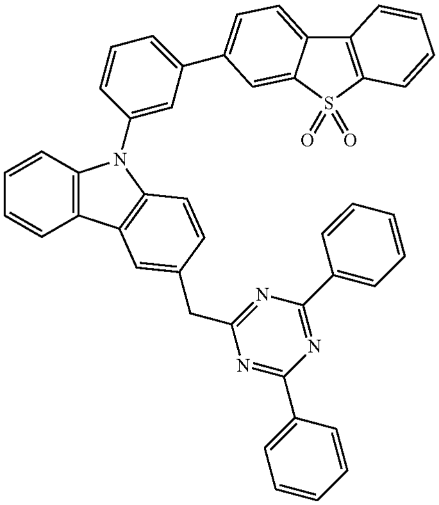
305
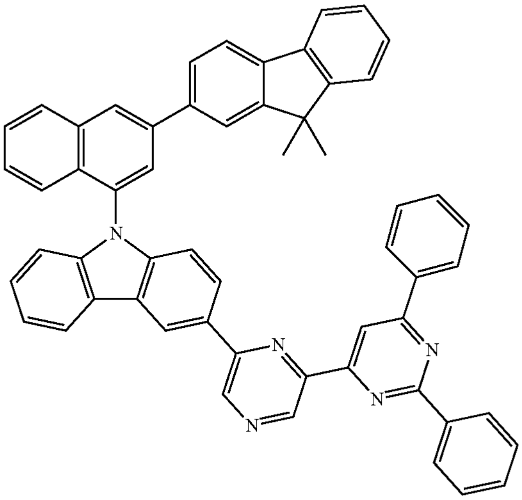
306
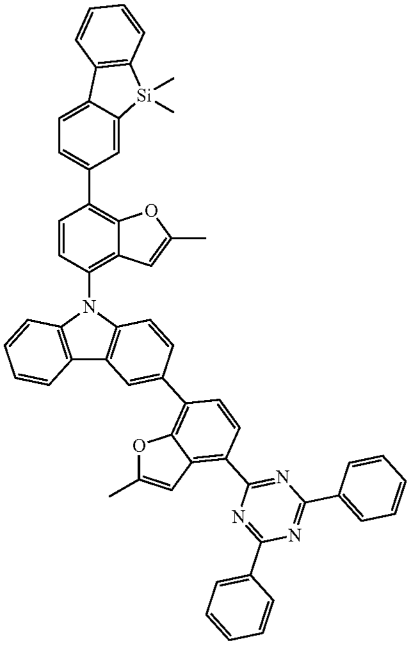

-continued
307
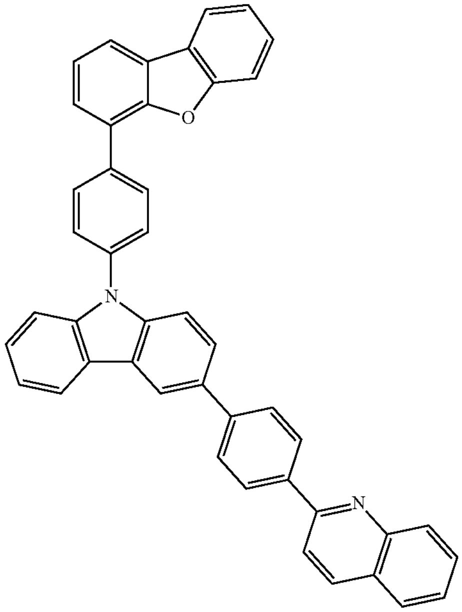
308
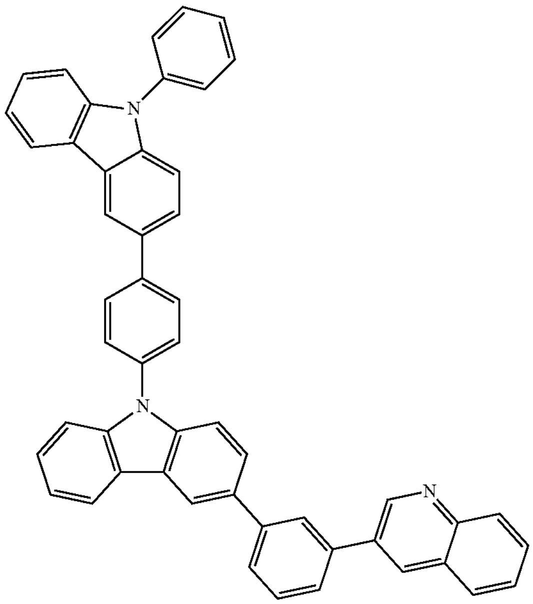
-continued
309
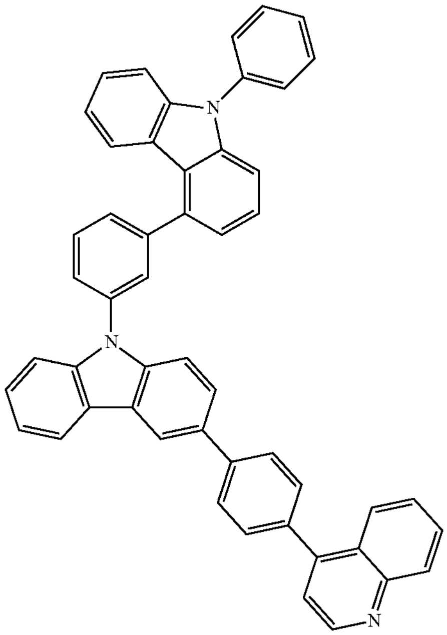
310
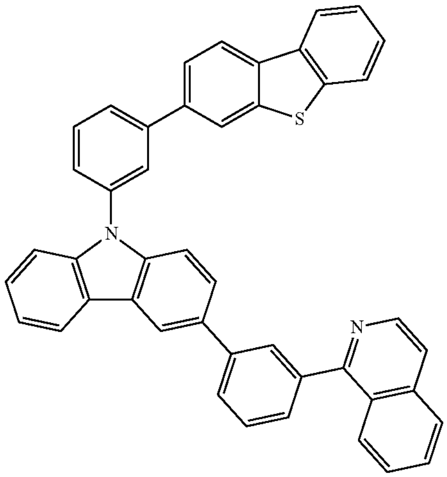

-continued
311
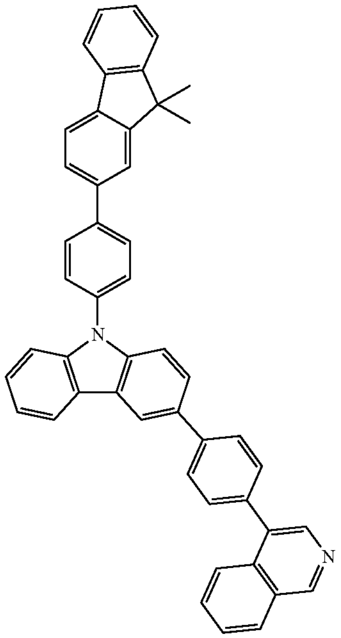
312
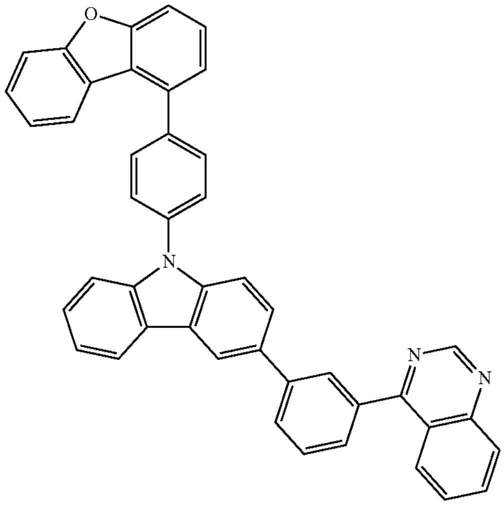
-continued
313
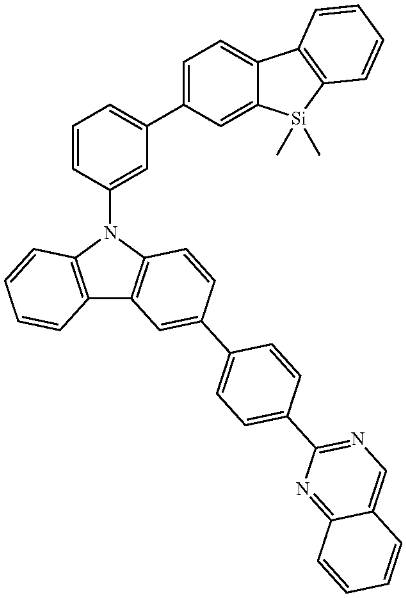
314
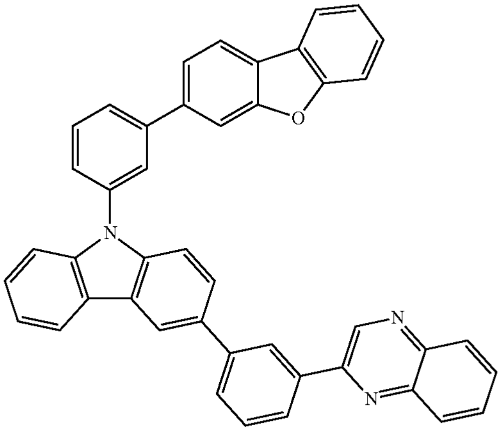
315
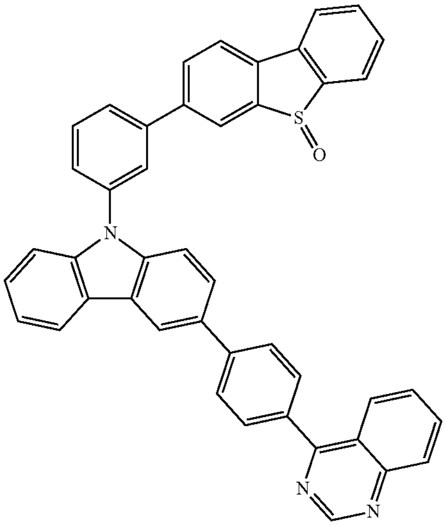

-continued
316
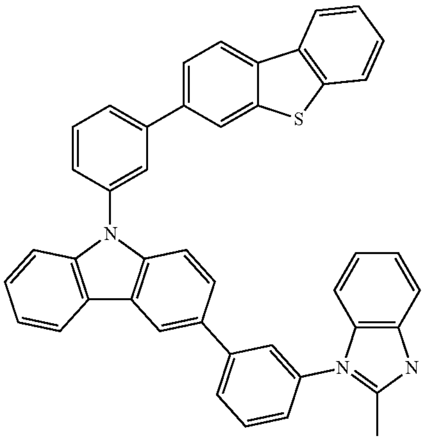
317
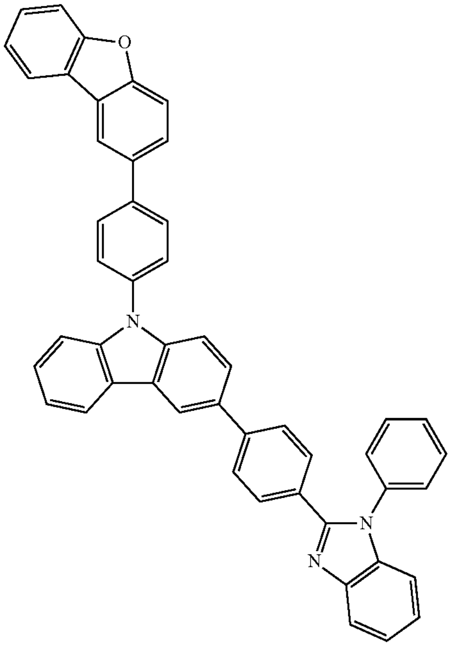
-continued
318
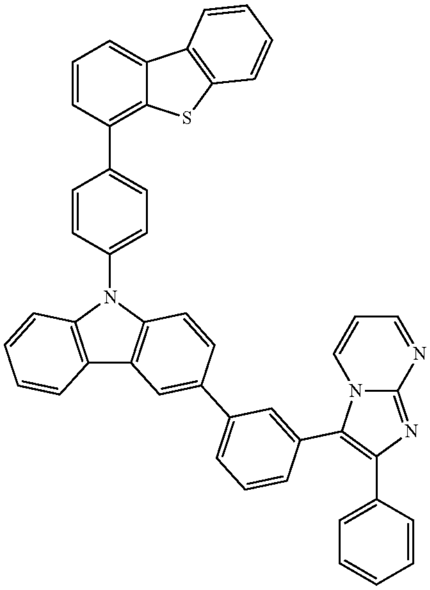
319
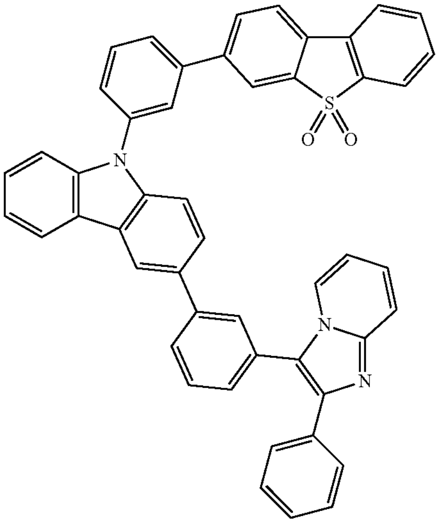
320
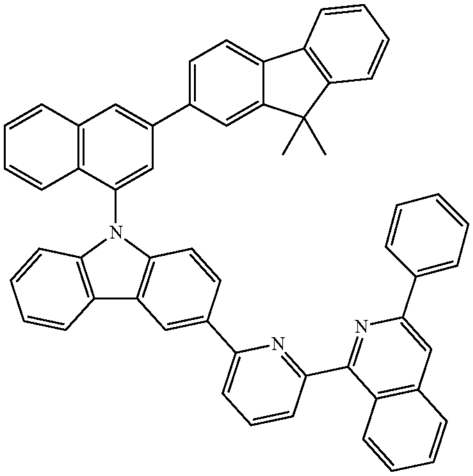

-continued
321
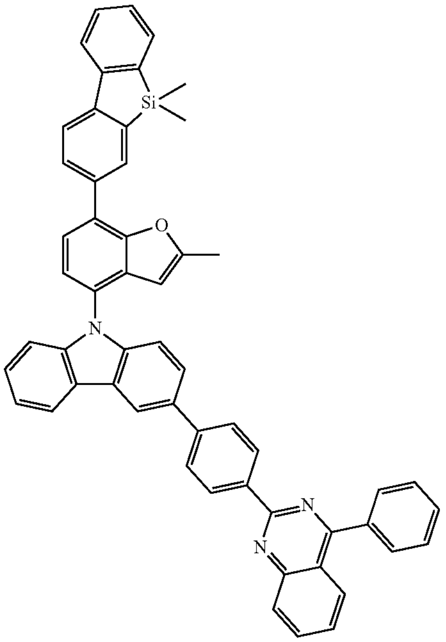
322
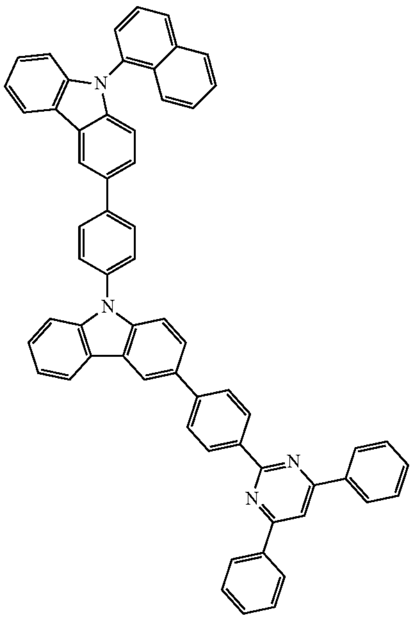
-continued
323
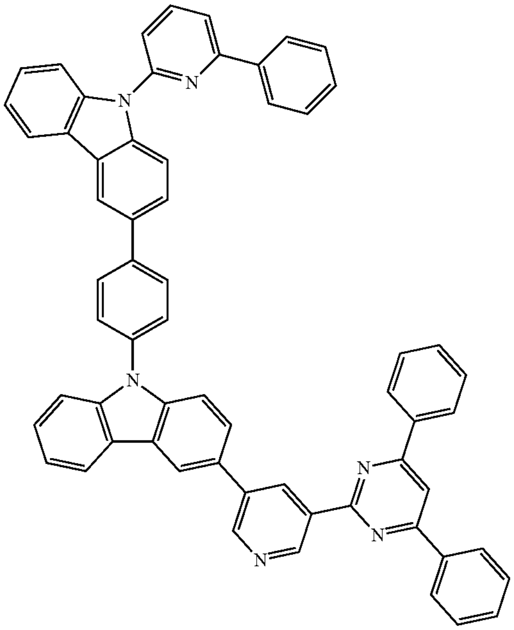
324
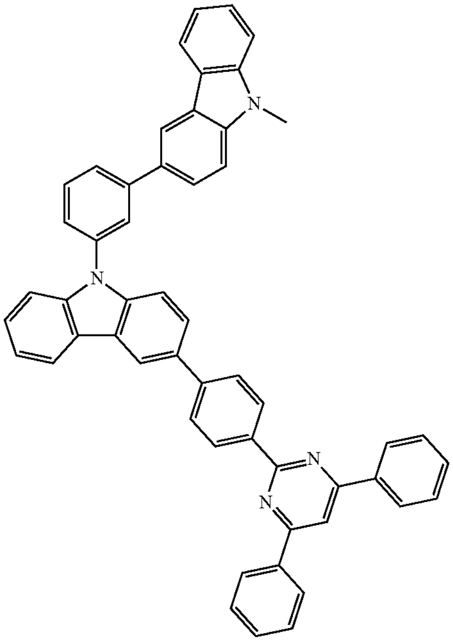

-continued
325
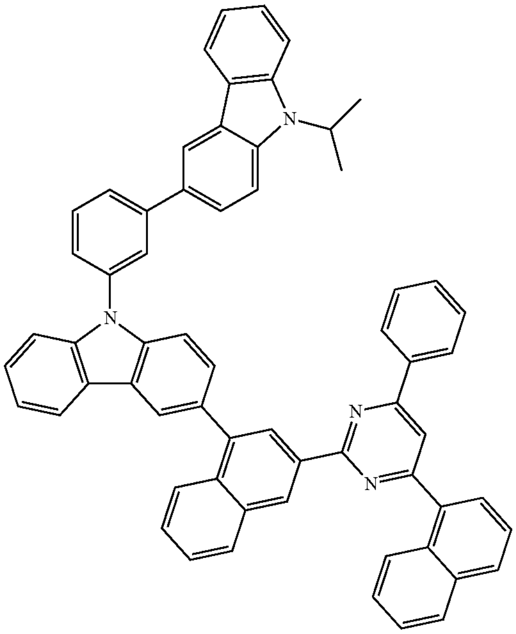
326
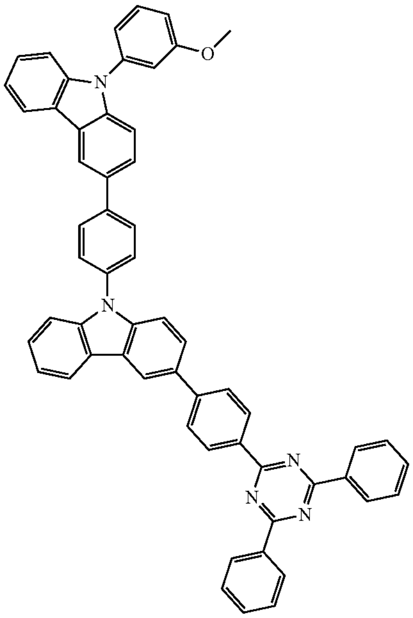
-continued
327
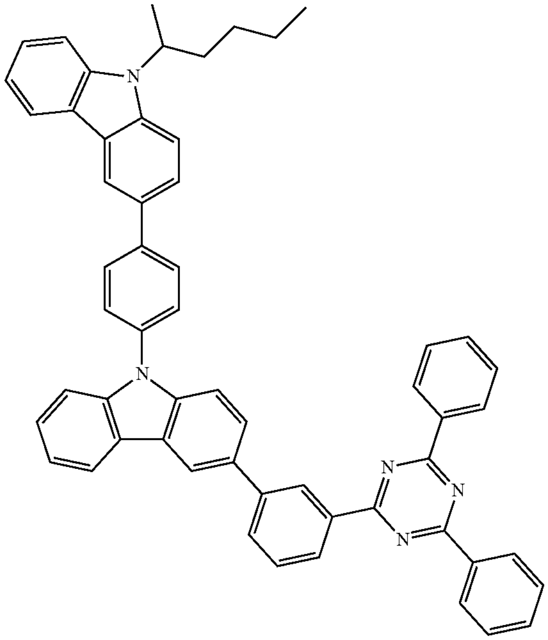
328
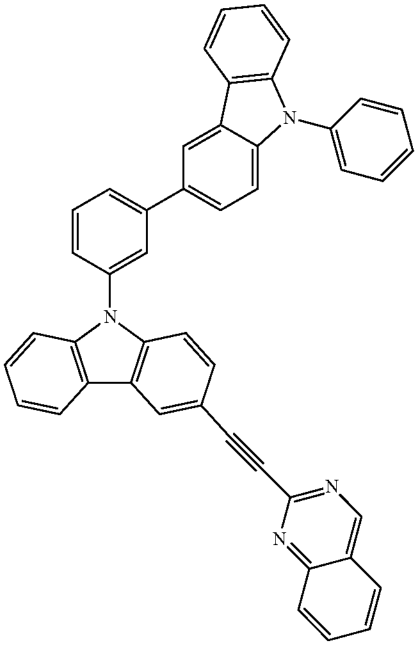

-continued
329
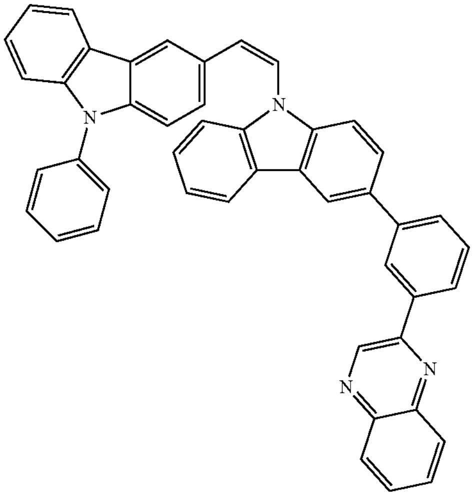
330
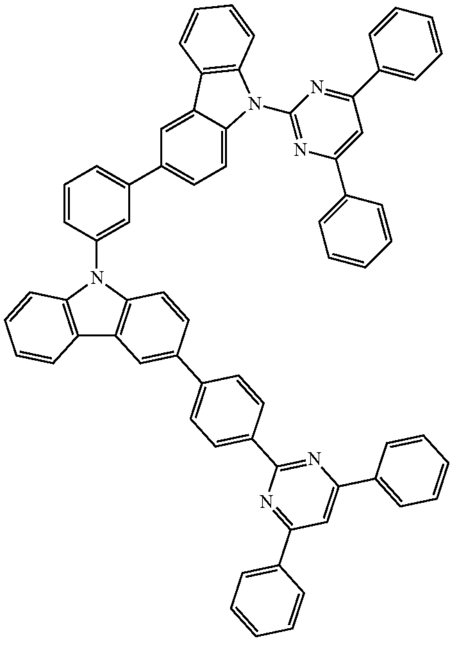
-continued
331
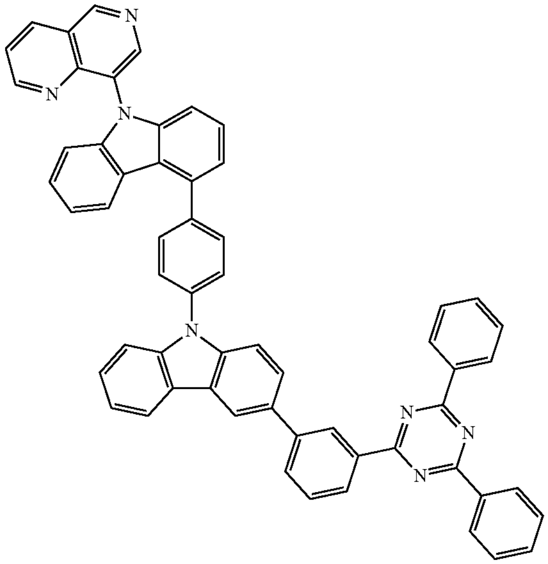
332
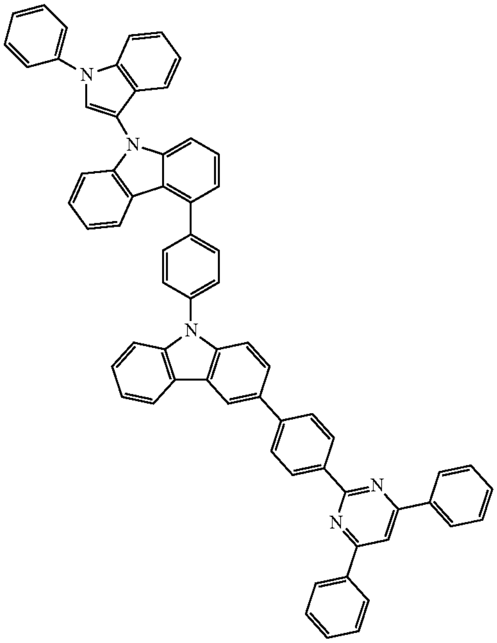

-continued
333
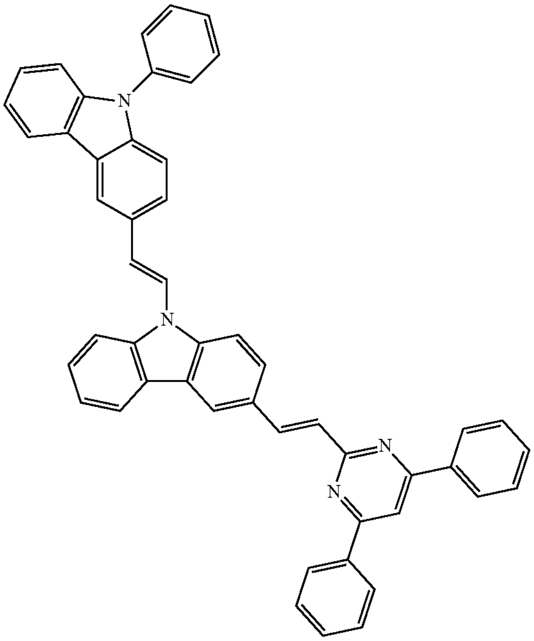
334
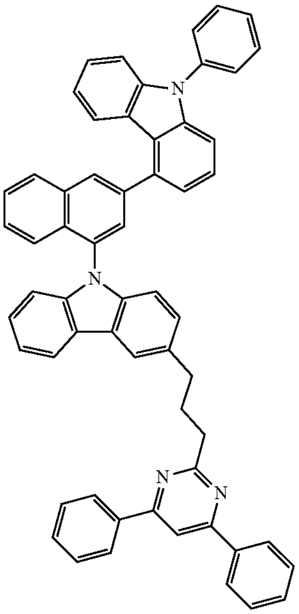
-continued
335
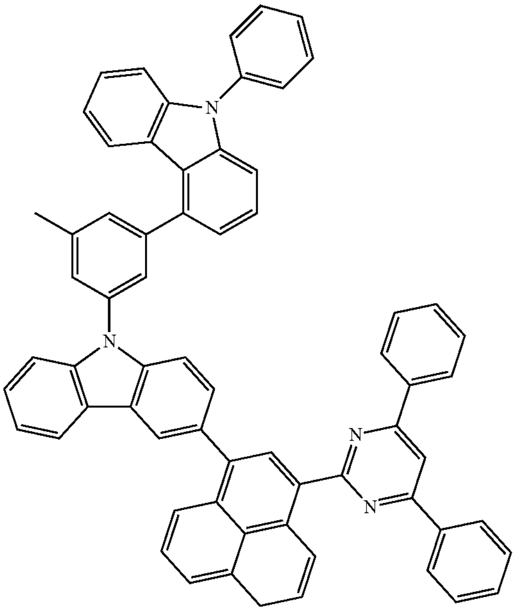
336
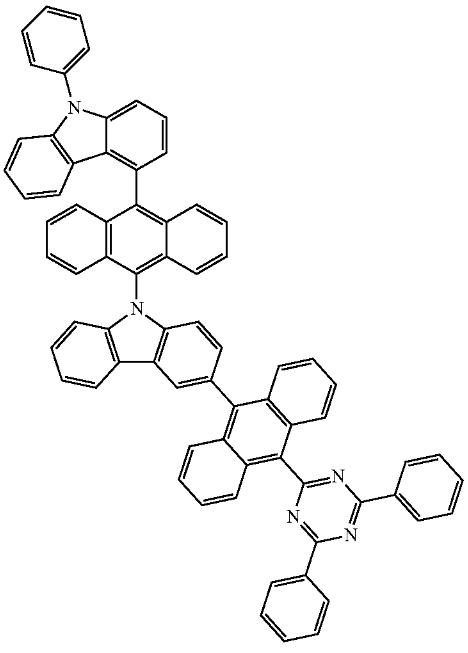

-continued
337
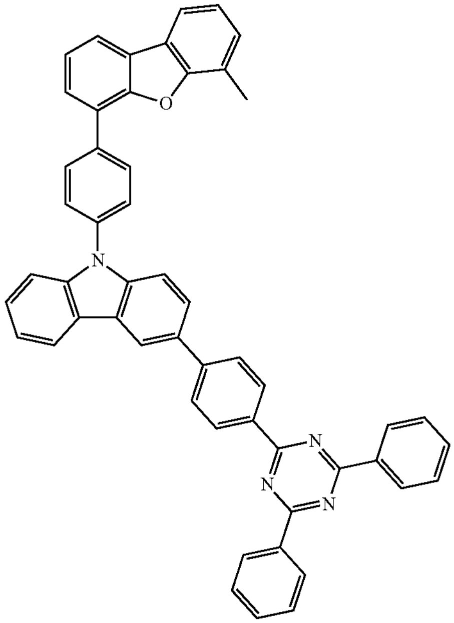
-continued
339
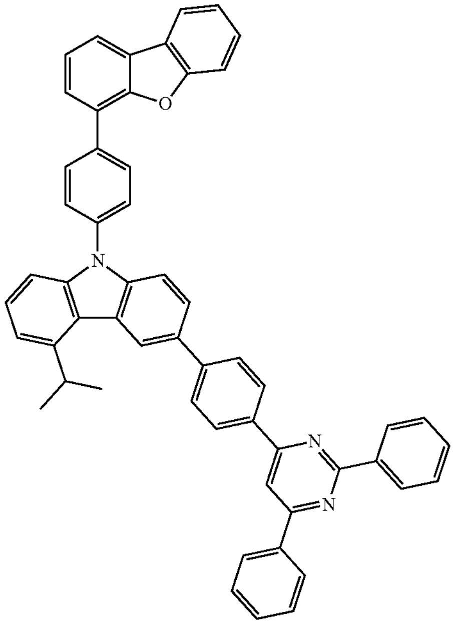
338
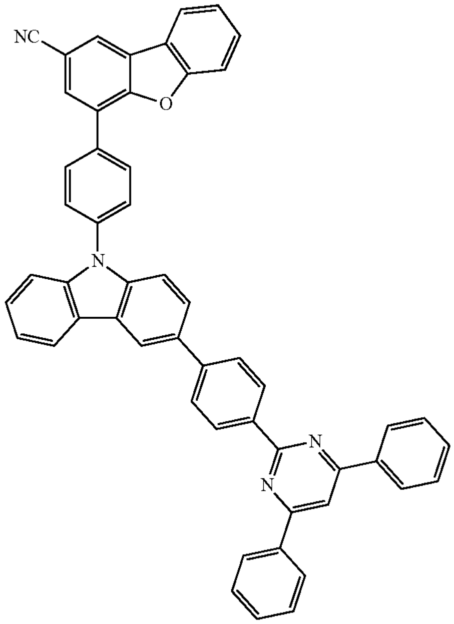
340
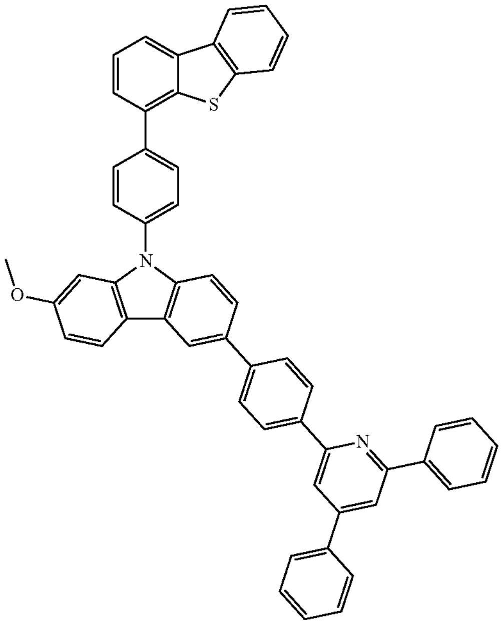

341
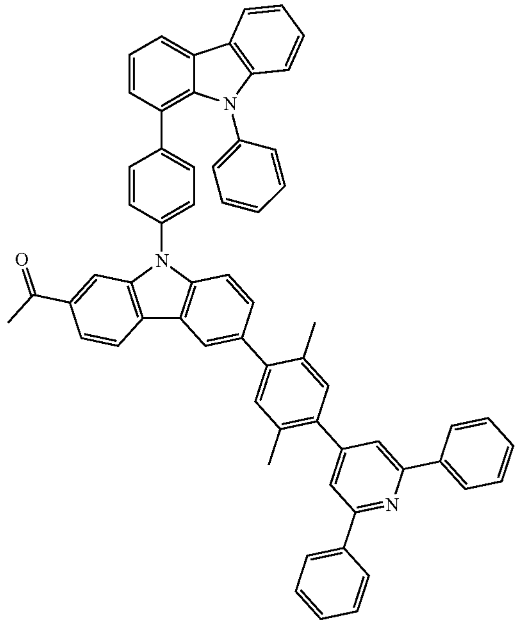
342
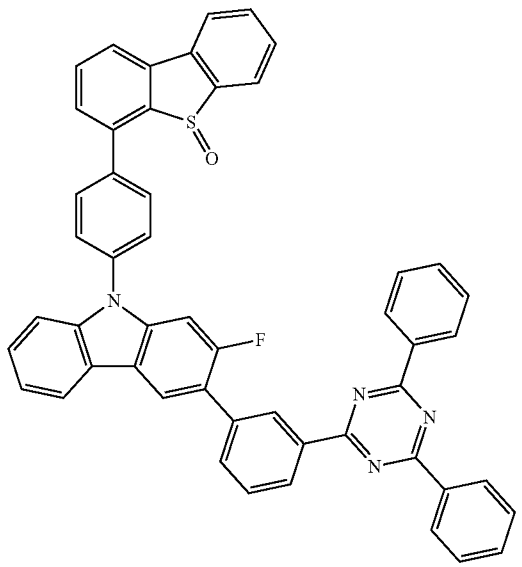
343
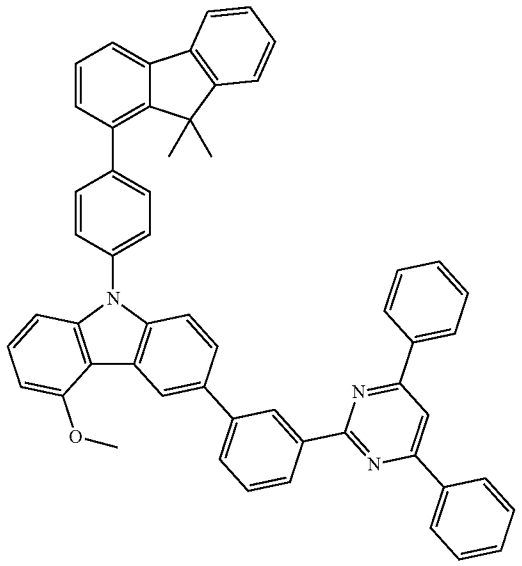
344
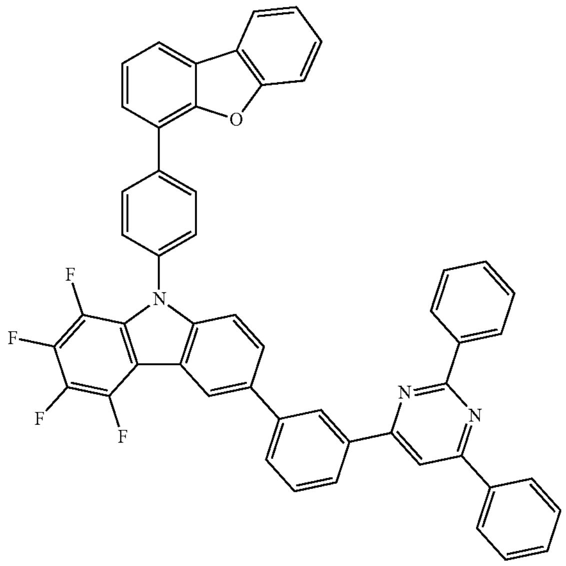

-continued
345
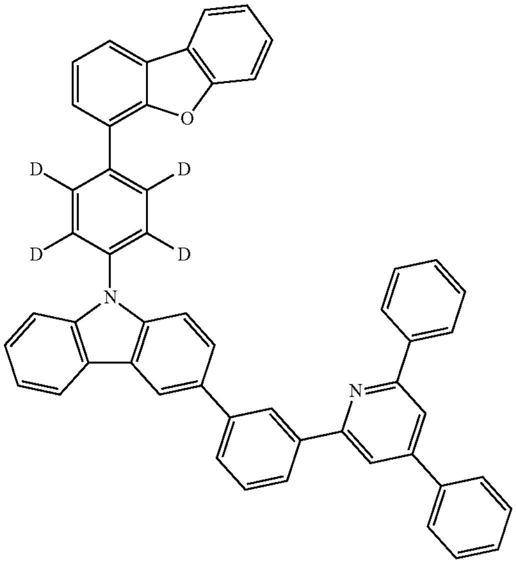
346
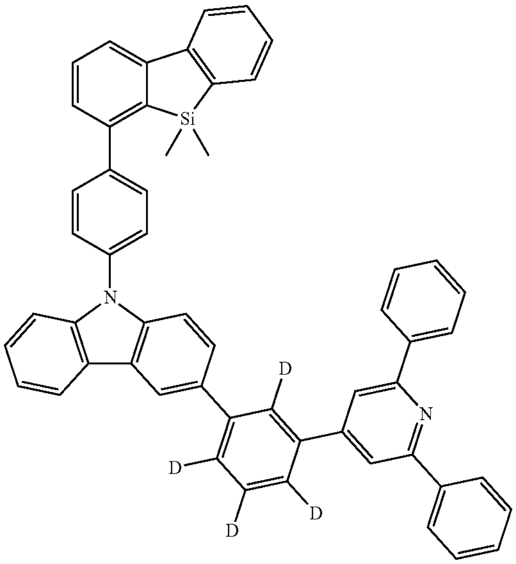
-continued
347
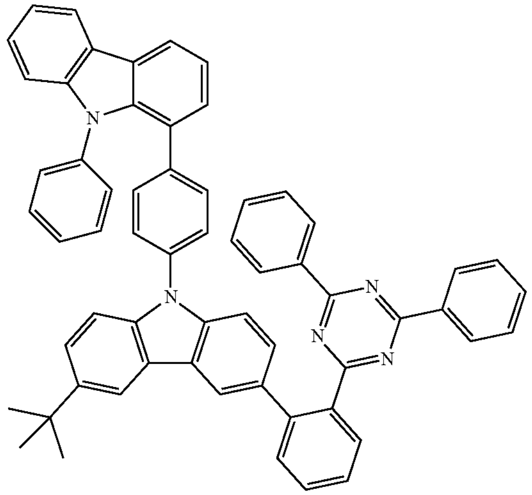
348
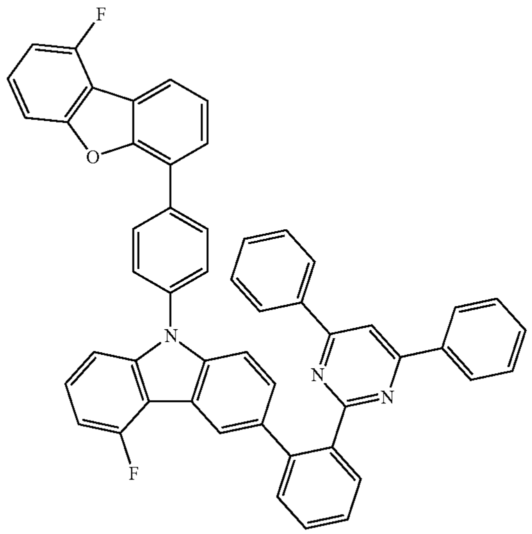
349
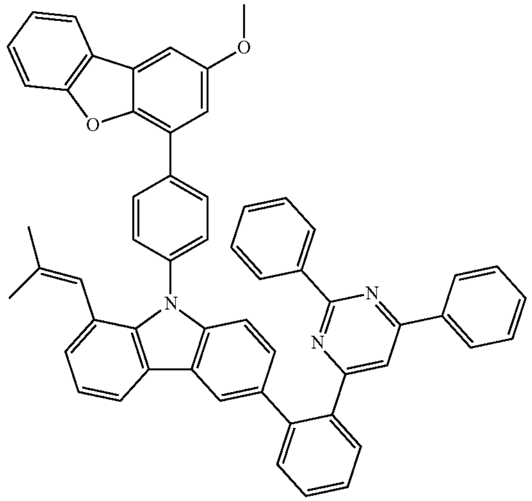

-continued

350

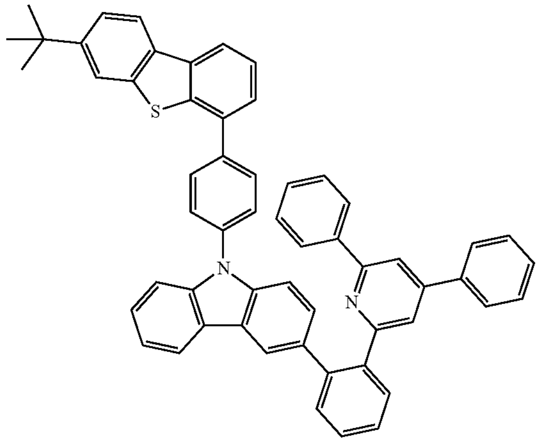

351

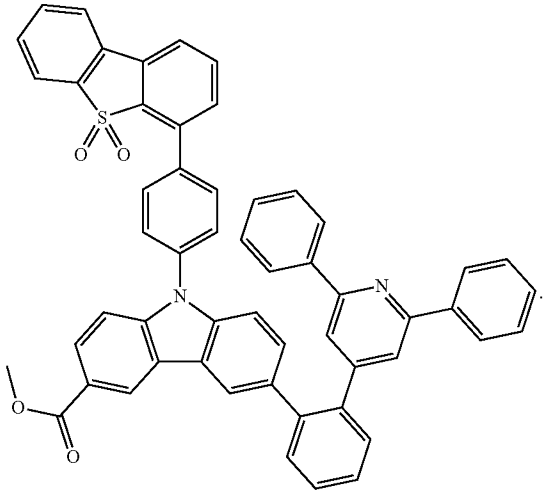

20. An organic light-emitting device comprising:

a first electrode;

a second electrode; and an organic layer disposed between the first electrode and the second electrode, wherein the organic layer comprises an emission layer and at least one of the carbazole compounds of claim 1.

21. The organic light-emitting device of claim 20, wherein the first electrode is an anode, the second electrode is a cathode, and the organic layer comprises i) a hole transport region disposed between the first electrode and the emission layer, wherein the hole transport region comprises at least one of a hole injection layer, a hole transport layer, and an electron blocking layer, and ii) an electron transport region disposed between the emission layer and the second electrode, wherein the electron transport region comprises at least one layer selected from a hole blocking layer, an electron transport layer, and an electron injection layer.

22. The organic light-emitting device of claim 20, wherein the emission layer comprises the carbazole compound.

23. The organic light-emitting device of claim 22, wherein the emission layer further comprises a phosphorescent dopant, and the carbazole compound is a host.

* * * * *